United States Patent
Amberg et al.

(10) Patent No.: US 9,067,871 B2
(45) Date of Patent: *Jun. 30, 2015

(54) AMINOTETRALINE DERIVATIVES, PHARMACEUTICAL COMPOSITIONS CONTAINING THEM, AND THEIR USE IN THERAPY

(71) Applicants: ABBVIE DEUTSCHLAND GMBH & CO KG, Wiesbaden (DE); ABBOTT LABORATORIES, Abbott Park, IL (US)

(72) Inventors: Wilhelm Amberg, Wiesbaden (DE); Michael Ochse, Wiesbaden (DE); Udo Lange, Wiesbaden (DE); Andreas Kling, Wiesbaden (DE); Berthold Behl, Wiesbaden (DE); Wilfried Hornberger, Wiesbaden (DE); Mario Mezler, Wiesbaden (DE); Charles W. Hutchins, Green Oaks, IL (US)

(73) Assignees: AbbVie Deutschland GmbH & Co. KG, Wiesbaden (DE); AbbVie Inc., North Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/031,265

(22) Filed: Sep. 19, 2013

(65) Prior Publication Data
US 2014/0031331 A1 Jan. 30, 2014

Related U.S. Application Data

(62) Division of application No. 12/706,326, filed on Feb. 16, 2010, now Pat. No. 8,563,617.

(60) Provisional application No. 61/152,825, filed on Feb. 16, 2009.

(51) Int. Cl.
*A61K 31/16* (2006.01)
*C07C 215/70* (2006.01)
*C07C 311/05* (2006.01)
(Continued)

(52) U.S. Cl.
CPC ............. *C07C 311/05* (2013.01); *C07C 215/64* (2013.01); *C07C 217/74* (2013.01); *C07C 233/18* (2013.01); *C07C 233/19* (2013.01); *C07C 233/69* (2013.01); *C07C 255/58* (2013.01); *C07C 271/24* (2013.01); *C07C 307/06* (2013.01); *C07C 309/65* (2013.01); *C07C 311/07* (2013.01); *C07C 311/09* (2013.01); *C07C 311/10* (2013.01); *C07C 311/14* (2013.01); *C07C 311/17* (2013.01); *C07C 311/18* (2013.01); *C07C 311/20* (2013.01); *C07C 311/24* (2013.01); *C07C 317/18* (2013.01); *C07C 317/28* (2013.01); *C07C 2101/02* (2013.01); *C07C 2101/04* (2013.01); *C07C 2102/10* (2013.01); *C07D 205/04* (2013.01); *C07D 207/10* (2013.01); *C07D 207/12* (2013.01); *C07D 207/27* (2013.01); *C07D 207/36* (2013.01); *C07D 207/48* (2013.01); *C07D 213/71* (2013.01); *C07D 231/18* (2013.01); *C07D 233/84* (2013.01); *C07D 249/12* (2013.01); *C07D 261/08* (2013.01); *C07D 275/02* (2013.01); *C07D 295/096* (2013.01); *C07D 305/08* (2013.01); *C07D 333/34* (2013.01); *C07D 403/12* (2013.01); *C07F 7/0818* (2013.01); *C07D 401/12* (2013.01); *C07D 409/12* (2013.01)

(58) Field of Classification Search
USPC .................. 564/308; 514/647, 403; 548/356.1
See application file for complete search history.

(56) References Cited

U.S. PATENT DOCUMENTS

| 4,927,838 A | 5/1990 | Guthrie et al. |
| 5,506,246 A | 4/1996 | Junge et al. |

(Continued)

FOREIGN PATENT DOCUMENTS

| DE | 10315570 | 10/2004 |
| EP | 0091241 | 10/1983 |

(Continued)

OTHER PUBLICATIONS

Copending U.S. Appl. No. 13/207,030, commonly assigned.*
(Continued)

Primary Examiner — Kamal Saeed
Assistant Examiner — Janet L Coppins
(74) Attorney, Agent, or Firm — Lisa V. Mueller; Michael Best & Friedrich LLP

(57) ABSTRACT

The present invention relates to aminotetraline derivatives of the formula (I)

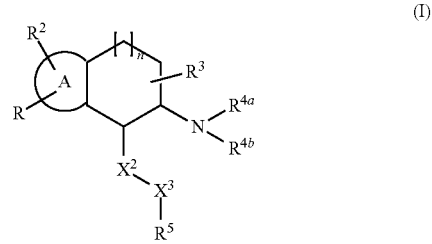

or a physiologically tolerated salt thereof.
The invention relates to pharmaceutical compositions comprising such aminotetraline derivatives, and the use of such aminotetraline derivatives for therapeutic purposes. The aminotetraline derivatives are GlyT1 inhibitors.

6 Claims, No Drawings

(51) Int. Cl.

| | | |
|---|---|---|
| C07C 215/64 | (2006.01) | |
| C07C 217/74 | (2006.01) | |
| C07C 233/18 | (2006.01) | |
| C07C 233/19 | (2006.01) | |
| C07C 233/69 | (2006.01) | |
| C07C 255/58 | (2006.01) | |
| C07C 271/24 | (2006.01) | |
| C07C 307/06 | (2006.01) | |
| C07C 309/65 | (2006.01) | |
| C07C 311/07 | (2006.01) | |
| C07C 311/09 | (2006.01) | |
| C07C 311/10 | (2006.01) | |
| C07C 311/14 | (2006.01) | |
| C07C 311/17 | (2006.01) | |
| C07C 311/18 | (2006.01) | |
| C07C 311/20 | (2006.01) | |
| C07C 311/24 | (2006.01) | |
| C07C 317/18 | (2006.01) | |
| C07C 317/28 | (2006.01) | |
| C07D 205/04 | (2006.01) | |
| C07D 207/10 | (2006.01) | |
| C07D 207/12 | (2006.01) | |
| C07D 207/27 | (2006.01) | |
| C07D 207/36 | (2006.01) | |
| C07D 207/48 | (2006.01) | |
| C07D 213/71 | (2006.01) | |
| C07D 231/18 | (2006.01) | |
| C07D 233/84 | (2006.01) | |
| C07D 249/12 | (2006.01) | |
| C07D 261/08 | (2006.01) | |
| C07D 275/02 | (2006.01) | |
| C07D 295/096 | (2006.01) | |
| C07D 305/08 | (2006.01) | |
| C07D 333/34 | (2006.01) | |
| C07D 403/12 | (2006.01) | |
| C07F 7/08 | (2006.01) | |
| C07D 401/12 | (2006.01) | |
| C07D 409/12 | (2006.01) | |

(56) References Cited

U.S. PATENT DOCUMENTS

| | | | |
|---|---|---|---|
| 5,519,034 A | | 5/1996 | Kozlik et al. |
| 5,545,755 A | | 8/1996 | Lin et al. |
| 6,057,357 A | * | 5/2000 | Horwell et al. ............... 514/422 |
| 6,331,636 B1 | | 12/2001 | Romero et al. |
| 6,426,346 B1 | | 7/2002 | Pruitt et al. |
| 7,189,850 B2 | | 3/2007 | Ceccarelli et al. |
| 7,427,612 B2 | | 9/2008 | Alberati-giani et al. |
| 7,462,617 B2 | | 12/2008 | Alberati-giani et al. |
| 7,511,013 B2 | | 3/2009 | Molino et al. |
| 7,514,068 B2 | | 4/2009 | Tung |
| 7,521,421 B2 | | 4/2009 | Naicker et al. |
| 7,528,131 B2 | | 5/2009 | Persichetti et al. |
| 7,531,685 B2 | | 5/2009 | Czarnik |
| 7,534,814 B2 | | 5/2009 | Ascher et al. |
| 7,538,189 B2 | | 5/2009 | Naicker et al. |
| 8,420,670 B2 | | 4/2013 | Amberg et al. |
| 8,642,587 B2 | | 2/2014 | Lange et al. |
| 8,653,100 B2 | | 2/2014 | Amberg et al. |
| 2002/0169197 A1 | | 11/2002 | Egle et al. |
| 2003/0083359 A1 | | 5/2003 | Lee et al. |
| 2004/0026364 A1 | | 2/2004 | Kihara |
| 2005/0124627 A1 | | 6/2005 | Schadt et al. |
| 2005/0153963 A1 | | 7/2005 | Dargazanli et al. |
| 2005/0153980 A1 | | 7/2005 | Schadt et al. |
| 2005/0159450 A1 | | 7/2005 | Dargazanli et al. |
| 2005/0267152 A1 | | 12/2005 | Bloomfield et al. |
| 2006/0074105 A1 | | 4/2006 | Ware et al. |
| 2006/0223802 A1 | | 10/2006 | Dargazanli et al. |
| 2006/0223861 A1 | | 10/2006 | Dargazanli et al. |
| 2006/0223885 A1 | | 10/2006 | Dargazanli et al. |
| 2006/0223886 A1 | | 10/2006 | Dargazanli et al. |
| 2007/0021408 A1 | | 1/2007 | Molino et al. |
| 2007/0155753 A1 | | 7/2007 | Ye et al. |
| 2007/0214087 A1 | | 9/2007 | Kawaguchi et al. |
| 2008/0070941 A1 | | 3/2008 | Dargazanli et al. |
| 2008/0119486 A1 | | 5/2008 | Jolidon et al. |
| 2009/0082471 A1 | | 3/2009 | Czarnik |
| 2009/0088416 A1 | | 4/2009 | Czarnik |
| 2009/0093422 A1 | | 4/2009 | Tung et al. |
| 2009/0105147 A1 | | 4/2009 | Masse |
| 2009/0105307 A1 | | 4/2009 | Galley et al. |
| 2009/0105338 A1 | | 4/2009 | Czarnik |
| 2009/0111840 A1 | | 4/2009 | Herold et al. |
| 2009/0118238 A1 | | 5/2009 | Czarnik |
| 2009/0131363 A1 | | 5/2009 | Harbeson |
| 2009/0131485 A1 | | 5/2009 | Liu et al. |
| 2009/0137457 A1 | | 5/2009 | Harbeson |
| 2010/0273739 A1 | | 10/2010 | Amberg et al. |
| 2012/0040947 A1 | | 2/2012 | Pohlki et al. |
| 2012/0040948 A1 | | 2/2012 | Pohlki et al. |
| 2012/0077796 A1 | | 3/2012 | Pohlki et al. |
| 2012/0088790 A1 | | 4/2012 | Pohlki et al. |
| 2012/0295881 A1 | | 11/2012 | Lange et al. |
| 2012/0316153 A1 | | 12/2012 | Amberg et al. |
| 2013/0035323 A1 | | 2/2013 | Amberg et al. |
| 2013/0131132 A1 | | 5/2013 | Amberg et al. |
| 2013/0184238 A1 | | 7/2013 | Amberg et al. |
| 2013/0203749 A1 | | 8/2013 | Amberg et al. |
| 2013/0210880 A1 | | 8/2013 | Amberg et al. |

FOREIGN PATENT DOCUMENTS

| | | |
|---|---|---|
| EP | 0258755 | 3/1988 |
| EP | 0303961 | 2/1989 |
| EP | 0420064 | 4/1991 |
| EP | 1199306 | 4/2002 |
| EP | 1254662 | 11/2002 |
| EP | 1284257 | 2/2003 |
| EP | 2246331 | 11/2010 |
| WO | 81/03491 | 12/1981 |
| WO | WO 90/15047 | 12/1990 |
| WO | WO 92/06967 | 4/1992 |
| WO | WO 92/19234 | 11/1992 |
| WO | WO 92/22533 | 12/1992 |
| WO | WO 93/13073 | 7/1993 |
| WO | WO 95/07271 | 3/1995 |
| WO | WO 97/10223 | 3/1997 |
| WO | WO 97/45115 | 12/1997 |
| WO | WO 98/04521 | 2/1998 |
| WO | WO 98/56757 | 12/1998 |
| WO | WO 00/07978 | 2/2000 |
| WO | WO 00/20376 | 4/2000 |
| WO | WO 01/09120 | 2/2001 |
| WO | 02/076979 | 10/2002 |
| WO | WO 03/031435 | 4/2003 |
| WO | WO 03/045924 | 6/2003 |
| WO | WO 03/053942 | 7/2003 |
| WO | WO 03/055478 | 7/2003 |
| WO | WO 03/076420 | 9/2003 |
| WO | WO 03/087086 | 10/2003 |
| WO | WO 03/089411 | 10/2003 |
| WO | WO 03/097586 | 11/2003 |
| WO | WO 2004/007468 | 1/2004 |
| WO | WO 2004/013100 | 2/2004 |
| WO | WO 2004/013101 | 2/2004 |
| WO | WO 2004/022528 | 3/2004 |
| WO | WO 2004/071445 | 8/2004 |
| WO | WO 2004/072034 | 8/2004 |
| WO | WO 2004/080968 | 9/2004 |
| WO | WO 2004/096761 | 11/2004 |
| WO | WO 2004/110149 | 12/2004 |
| WO | WO 2004/112787 | 12/2004 |
| WO | WO 2004/113280 | 12/2004 |
| WO | WO 2004/113301 | 12/2004 |
| WO | WO 2005/014563 | 2/2005 |
| WO | WO 2005/023260 | 3/2005 |

(56) References Cited

FOREIGN PATENT DOCUMENTS

| WO | WO 2005/037781 | 4/2005 |
|---|---|---|
| WO | WO 2005/037782 | 4/2005 |
| WO | WO 2005/037783 | 4/2005 |
| WO | WO 2005/037785 | 4/2005 |
| WO | WO 2005/037792 | 4/2005 |
| WO | WO 2005/023261 | 5/2005 |
| WO | WO 2005/040166 | 5/2005 |
| WO | WO 2005/046601 | 5/2005 |
| WO | WO 2005/049023 | 6/2005 |
| WO | WO 2005/058317 | 6/2005 |
| WO | WO 2005/058882 | 6/2005 |
| WO | WO 2005/058885 | 6/2005 |
| WO | WO 2005/099353 | 10/2005 |
| WO | WO 2005/123681 | 12/2005 |
| WO | WO 2006/008754 | 1/2006 |
| WO | WO 2006/034235 | 3/2006 |
| WO | WO 2006/063709 | 6/2006 |
| WO | WO 2006/082001 | 8/2006 |
| WO | WO 2006/102760 | 10/2006 |
| WO | WO 2006/121767 | 11/2006 |
| WO | WO 2007/143823 | 12/2007 |
| WO | WO 2008/038053 | 4/2008 |
| WO | WO 2008/148755 | 12/2008 |
| WO | WO 2009/024611 | 2/2009 |
| WO | WO 2009/121872 | 10/2009 |
| WO | WO 2010/020548 | 2/2010 |
| WO | WO 2010/025856 | 3/2010 |
| WO | WO 2010/029180 | 8/2010 |
| WO | WO 2010/092181 | 8/2010 |
| WO | WO 2010/138901 | 12/2010 |
| WO | WO 2012/020130 | 2/2012 |
| WO | WO 2012/020131 | 2/2012 |
| WO | WO 2012/020133 | 2/2012 |
| WO | WO 2012/152915 | 11/2012 |

OTHER PUBLICATIONS

Harsing, L.G. et al., "Glycine transporter Type-1 and its inhibitors," Curr. Med. Chem. (2006) 13:1017-1044.
Hashimoto, K., "Glycine transporter inhibitors as therapeutic agents for schizophrenia," Recent Patents on CNS Drug Discovery (2006) 1:43-53.
International Search Report for Application No. PCT/EP2010/051903, mailed May 26, 2010.
Javitt, D.C., "Glutamate as a therapeutic target in psychiatric disorders," Mol. Psychiatry (2004) 9:984-997.
Lindsley, C.W. et al., "Design, synthesis, and in vivo efficacy of glycine transporter-1 (GlyT1) inhibitors derived from a series of [4-phenyl-1-(propylsulfonyl)piperidin-4-yl]methyl benzamides," Chem. Med. Chem. (2006) 1(8):807-811.
Lindsley, C.W. et al., "Progress in the preparation and testing of glycine transporter type-1 (glyT1) inhibitors," Curr. Top. Med. Chem. (2006) 6:1883-1896.
Lindsley, C.W. et al., "Progress towards validating the NMDA receptor hypofunction hypothesis of schizophrenia," Cur. Top. Med. Chem. (2006) 6:771-785.
Lowe, J. et al., "A novel-nonsubstrate-based series of glycine type 1 transporter inhibitors derived from high-throughput screening," Bioorg. Med. Chem. Lett. (2007) 17(6):1675-1678.
Nunez, E. et al., "Differential effects of the tricyclic antidepressant amoxapine on glycine uptake mediated by the recombinant GLYT1 and CLYT2 glycine transporters," Br. J. Pharm. (2000) 129(1):200-206.
Written Opinion for Application No. PCT/EP2010/051903, mailed Aug. 16, 2011.
Zhao, Z. et al., "Synthesis and SAR of GlyT1 inhibitors derived from a series of N-((4-(morpholine-4-carbonyl)-1-(propylsulfonyl) piperidin-4-yl) methyl) benzamindes," Bioorg. Med. Chem. Lett. (2006) 16(23):5968-5972.
United States Patent Office Notice of Allowance for U.S. Appl. No. 12/706,326 dated Jun. 11, 2013 (10 pages).
United States Patent Office Notice of Allowance for U.S. Appl. No. 12/706,326 dated Feb. 21, 2013 (9 pages).
United States Patent Office Action for U.S. Appl. No. 12/706,326 dated Sep. 21, 2012 (7 pages).
United States Patent Office Action for U.S. Appl. No. 13/546,434 dated Apr. 14, 2014 (12 pages).
United States Patent Office Action for U.S. Appl. No. 13/792,105 dated Apr. 16, 2014 (6 pages).
United States Patent Office Action for U.S. Appl. No. 13/789,967 dated Apr. 1, 2014 (11 pages).
United States Patent Office Notice of Allowance for U.S. Appl. No. 13/207,030 dated May 13, 2015 (9 pages).
United States Patent Office Notice of Allowance for U.S. Appl. No. 13/680,488 dated Apr. 28, 2014 (13 pages).
United States Patent Office Notice of Allowance for U.S. Appl. No. 13/206,937 dated May 15, 2014 (9 pages).
Ashby, E.C. et al., "Single electron transfer in reactions of alkyl halides with lithium thiolates," J. Org. Chem. (1985) 50(25):5184-5193.
Barbasiewicz, M. et al., "Intermolecular reactions of chlorohydrine anions: acetalization of carbonyl compounds under basic conditions," Org. Lett. (2006) 8(17):3745-3748.
Belliotti, T.R. et al., "Structure-activity relationships of pregabalin and analogues that target the alpha(2)-delta protein," J. Med. Chem. (2005) 48(7):2294-2307.
Bermejo, A. et al., "Syntheses and antitumor targeting G1 phase of the cell cycle of benzoyldihydroisoquinolines and related 1-substituted isoquinolines," J. Med. Chem. (2002) 45:5058-5068.
Beylot, M. et al., "In vivo studies of intrahepatic metabolic pathways," Diabetes Metabolism (1997) 23(3):251-257.
Bishop, D.C., "Analgetics based on the azetidine ring," Azetidine Analgetics (1968) 11:466-470.
Blagojevic, N. et al., "Role of heavy water in boron neutron capture therapy," Topics in Dosimetry and Treatment Planning for Neutron Capture Thearpy (1994) 125-134.
Blake, M.I. et al., "Studies with deuterated drugs," J. Pharm. Sci. (1975) 64(3):367-391.
Boulay, D. et al., "Characterization of SSR103800, a selective inhibitor of the glycine transporter-1 in models predictive of therapeutic activity in schizophrenia," Pharmacology, Biochemistry and Behavior (2008) 91:47-58.
Brickner, S.J. et al., "Synthesis and antibacterial activity of U-100592 and U-100766, two oxazolidinone antibacterial agents for the potential treatment of multidrug-resistant gram-positive bacterial infections," J. Med. Chem. (1996) 39(3):673-679.
Burn, D., "Alkylation with the vilsmeier reagent," Chem. and Industry (1973) 870-873.
Burns, N.Z. et al., "Total synthesis of haouamine A: the indenotetrahydropyridine core," Tetrahedron (2009) 65(33):6600-6610.
Butte, N.F. et al., "Measurement of milk intake: tracer-to-infant deuterium dilution method," Br. J. Nutrition (1991) 65:3-14.
Cheng, Y. et al., "Relationship between the inhibition constant (KI) and the concentration of inhibitor which causes 50 percent inhibition (I.sub.50) of an enzymatic reaction," Biochem. Pharmacol. (1973) 22:3099-3108.
Cheung, F.K. et al., "The use of a [4+2] cycloadditional reaction for the preparation of a series of 'tethered' Ru(II)diamine and aminoalcohol complexes," Org. & Biomol. Chem. (2007) 5(7):1093-1103.
Chrzanowska, M. et al., "Asymmetric synthesis of isoquinoline alkaloids," Chem. Rev. (2004) 104(7):3341-3370.
Clayden et al., Tetra. Lett. (2003) 44(15):3059-3062.
Clezy, P.S. et al., "Preparation of a deuterated analogue of tetrahydropapaveroline suitable for use as an internal standard for G.C./M.S. analysis of this alkaloid: retro pictet-spengler condensation," Australian J. Chem. (1998) 41:483-491.
Colandrea, V.J. et al., "Synthesis and regioselective alkylation of 1.6- and 1.7-naphthyridines," Tetra. Lett. (2000) 41:8053-8057.
Coward, W.A. et al., "New method for measuring milk intakes in breast-fed babies," The Lancet (1979) 13-14.
Czajka, D.M. et al., "Effect of deuterium oxide on the reproductive potential of mice," Annals of the New York Academy of Sciences (1960) 84:770-779.

(56) References Cited

OTHER PUBLICATIONS

Czajka, D.M. et al., "Physiological effects of deuterium on dogs," Am. J. Physiology (1961) 201(2):357-362.
Denkewalter, R.G. et al., Progress of Pharmaceutical Research, Drug Research (1966) 10:223-226.
Di, L. et al., "Optimization of a higher throughput microsomal stability screening assay for profiling drug discovery candidates," J. Biomol. Screening (2003) 8(4):453-462.
Dohi, T. et al., "Glycine transporter inhibitors as a novel drug discovery strategy for neuropathic pain," Pharma. & Therapeutics (2009) 123(1):54-79.
Duan, Z.C. et al., "Highly enantioselective Rh-catalyzed hydrogenation of beta gamma-unsaturated phosphonates with chiral ferrocene-based monophosphoramidite ligands," J. Org. Chem. (2009) 74(23):9191-9194.
Erhunmwunse, M.O. et al., "A novel rearrangement reaction of beta-diaxo-alpha-ketoacetals," Tetra. Lett. (2009) 50:3568-3570.
Ferles, M. et al., "Reduction of 1-isoquinolyl-dimethylmethanol and 1-(1-isoquinolyl)cyclohexanon," Collection of Czechoslovak Chem. Comm. (1981) 46(1):262-265.
Fiedler, H.B., "Lexikon der hilfsstoffe fur pharmazie, Kosmetik und angrenzende Gebiete," (1996) 4th Edition, Table of Contents.
Foster, A.B. et al., "Deuterium isotope effects in the metabolism of drugs and xenobiotics: implications for drug design," Advances in Drug Research (1985) 14:2-36.
Fraser et al., Canadian Journal of Chemistry (1971) 49(5):800-802.
Grant & Hackh's Chemical Dictionary, 5th Edition (1987), p. 148.
Green, G.M. et al., "Polystyrene-supported benzenesulfonyl azide: a diazo transfer reagent that is both efficient and safe," J. Org. Chem. (2001) 66(7):2509-2511.
Greene, T.W. et al., In Protective Groups in Organic Synthesis, 2nd Edition, John Wiley & Sons, Inc., (1991) Table of Contents.
Greene, T.W. et al., In Protective Groups in Organic Synthesis, 3rd Edition, John Wiley & Sons, Inc., (1999) Preface, Table of Contents and Abbreviations.
Guillonneau, C. et al., "Synthesis of 9-O-substituted derivatives of 9-hydroxy-5, 6-dimethyl-6H-pyrido[4,3-b]carbazole-1-carboxylic acid (2-(dimethylamino)ethyl)amide and their 10- and 11-methyl analogues with improved antitumor activity," J. Med. Chem. (1999) 42(12):2191-2203.
Gupta, A. et al., "Simple and efficient synthesis of steroidal hybrids of estrogen and vitamin D3," Synthetic Comm. (2009) 39:61-69.
Hashimoto, K. "Glycerine transport inhibitors for the treatment of schizophrenia," The Open Medicinal Chemistry Journal (2010) 4:10-19.
Hashimoto, K. et al., "Phencyclidine-induced cognitive deficits in mice are improved by subsequent subchronic administration of the glycine transporter-1 inhibitor NFPS and D-serine," Eurp. Neuropsychopharmacology (2008) 18:414-421.
Hillier, M.C. et al., "A one-pot preparation of 1,3-disubstituted azetidines," J. Org. Chem. (2006) 71(20):7885-7887.
Ikunaka, M. et al., "The highly selective equatorial hydride delivery by biocatalysis: chemoenzymatic synthesis of trans-2-(4-propylcyclohexyl)-1,3-propanediol via cis-4-propylcyclohexanol," Organic Process Research and Development (2004) 8(3):389-395.
Jellimann, C. et al., "Synthesis of phenalene and acenaphthene derivatives as new conformationally restricted ligands for melatonin receptors," J. Med. Chem. (2000) 43(22):4051-4062.
Jensen, B.L. et al., "Total synthesis of 4,5,7a,8-tetrahydro-1,2-dimethoxyphenantluo[10,1-bc]-azepin-6(7H)-one: a photochemical approach," J. Heterocyclic Chem. (1986) 23:343-347.
Jetter, M.C. et al., "Heteroaryl beta-tetralin ureas as novel antagonists of human TRPV1," Bioorg. Med. Chem. Lett. (2007) 17(22):6160-6163.
Jutz, C. et al., "The Vilsmeier-Haackarnold acylations. C—C bond-forming reactions of chloromethyleniminium ions," Adv. Org. Chem. (1976) 9(1):225-342.
Kaiser, C. et al., "6,7-dichloro-1-(3,4,5-trimethyoxygenzyl)-1,2,3,4-tetrahydroisoquinoline. A structurally novel beta-adrenergic receptor blocking agent," J. Med. Chem. (1986) 29(11):2381-2384.

Kato, S. et al., "Synthesis of deuterated mosapride citrate," J. Labelled Compounds and Radiopharmaceuticals (1995) 36(10):927-932.
King, F.D., editor "Bioisosteres, conformational restriction and pro-drugs—case history: an example of a conformational restriction approach," Medical Chemistry: Principles and Practice (1994), Chapter 14, 206-209.
Kinney, G.G. et al., "The glycerine transporter type 1 inhibitor N-[3-(4'-fluorophenyl)-3-(4'-phenylphenoxy) propyl] sarcosine potentiates NMDA receptor-mediated responses in vivo and produces an antipsychotic profile in rodent behavior," The Journal of Neurosci. (2003) 23(20):7586-7591.
Kocienski, P.J., Protective Groups, Georg Thieme Verlag Stuttgart, Germany, Table of Contents (1994).
Kreher, R.P., Hetarene II, Georg Thieme Verlag Stuttgart, Germany (1991) 583-726.
Kuhakarn, C. et al., "Synthesis of alkylated indolizidine alkaloids via pummerer mediated cyclization: synthesis of indolizidine 167B, 5-butylindolizidine and monomorine I," Tetrahedron (2008) 64(8):1663-1670.
Kushner et al., "Pharmacological uses and perspectives of heavy water and deuterated compounds," Canadian J. Physiol. Pharmacol. (1999) 77(2):79-88.
Lizondo, J. et al., "Linezolid: oxazolindinone antibacterial," Drugs of the Future (1996) 21(11):1116-1123.
MacLennan, A.H. et al., "Neonatal body water turnover: a putative index of perinatal morbidity," Amer. J. Obstetrics & Gynecology (1981) 139(8):948-952.
Mai, K. et al., "A fast n-substituted alpha-aminonitrile synthesis," Synthetic Commun. (1985) 15(2):157-163.
Mallesham, B. et al., "Highly efficient cul-catalyzed coupline of aryl bromides with oxazolidinones using Buchwald's protocol: a short route to linezolid and toloxatone," Org. Lett. (2003) 5(7):963-965.
McOmie, J.F.W., ed., Protective Groups in Organic Chemistry, Plenum Press (1973) Table of Contents.
Meek, J.S. et al., "Diels-Alder reactions of 9-substituted anthracenes.1 II. 9-cyanoanthracene," J. Amer. Chem. Soc. (1956) 78(20):5413-5416.
Memetzidis, G. et al., "Synthesis of aromatic chloroberbines," Heterocycles (1990) 31(2):341-351.
Mezler, M. et al., "Inhibitors of GlyT1 affect glycine transport via discrete binding sites," Mol. Pharmacol. (2008) 74(6):1705-1715.
Munson, P.J. et al., "Ligand: a versatile computerized approach for characterization of ligand-binding systems," Anal. Biochem. (1980) 107(1):220-239.
Obach, R.S., "Prediction of human clearance of twenty-nine drugs from hepatic microsomal intrinsic clearance data: an examination of in vitro half-life approach and nonspecific binding to microsomes," Drug Metabolism and Disposition (1999) 27(11):1350-1359.
Obach, R.S., "The prediction of human clearance from hepatic microsomal metabolism data," Curr. Opin. Drug Disc. & Development (2001) 4(1):36-44.
Paal, T.A. et al., "Lipase-catalyzed kinetic and dynamic kinetic resolution of 1,2,3,4-tetrahydroisoquinoline-1-carboxylic acid," Tetrahedron: asymmetry (2007) 18(12):1428-1433.
Papageorgiou, C. et al., "163 synthesis of hydroxy- and methoxy-substituted octahydrobenzo[g]isoquinolines as potential ligands for serotonin receptors," Helvetica Chimica Acta (1989) 72:1463-1470.
Pinard, E. et al., "Selective gly T1 inhibitors: discovery of [4-(3-fluoro-5-trifluoremethylpyridin-2-yl)piperazin-1-yl]-]-[5-methanesulfonyl-2-((S)-2,2,2-trifluoro-1-methylethoxy)phenyl)methanone (RG1678), a promising novel medicine to treat schizophrenia," J. Med. Chem. (2010) 53:4603-4614.
Pitts, M.R. et al., "Indium metal as a reducing agent in organic synthesis," J. Chem Soc. Perkin Transactions (2001) 1:955-977.
Pons, G. et al., "Stable isotopes labeling of drugs in pediatric clinical pharmacology," Pediatrics (1999) 104(32):633-639.
Prout, F.S. et al., "3-Benzyl-3-Methylpentanoic acid," Organic Syntheses, Coll. (1963) 4:93; (1955) 35:6.
Quirante, J. et al., "Synthesis of diazatricyclic core of magangamines from Cis-perhydroisoquinolines," J. Org. Chem. (2008) 73(7):768-771.

(56) References Cited

OTHER PUBLICATIONS

Ranu et al., "Indium (III) chloride-promoted rearrangement of epoxides: a selective synthesis of substituted benzylic aldehydes and ketones," J. Org. Chem. (1998) 8212-8216.
Reddy, K.S. et al., "Synthesis of a 9-fluorenone derived beta-amino alcohol ligand depicting high catalytic activity and pronounced non-linear stereochemical effects," Synthesis (2000) 1:165-176.
Reddy, M.P. et al., "Applications of the Vilsmeier reaction. 13. Vilsmeier approach to polycyclic aromatic hydrocarbons," J. Org. Chem. (1981) 46:5371-5373.
Reimann, E. et al., "A convenient synthesis of 1-benzyl-1,2,3,4-tetrahydroisoquinolines by combined Strecker/Bruylants reaction," Monatshefte fur Chemie/Chemical Monthly (2004) 135(10):1289-1295.
Rodewald, L.E. et al., "Deuterium oxide as a tracer for measurement of compliance in pediatric clinical drug trials," J. Pediatrics (1989) 114(5):885-891.
Schwarcz, H.P., "Use of stable isotopes to determine compliance," Controlled Clinical Trials (1984) 5(Supp 4):573-575.
Schwarz, J.B. et al., "Novel cyclopropyl beta-amino acid analogues of pregabalin and gabapentin that target the alpha2-delta protein," J. Med. Chem. (2005) 48(8):3026-3035.
Sharma, S.D. et al., "Phosphorous oxychloride (POCl3): a key molecule in organic synthesis," Indian J. Chem. (1998) 37B:965-978.
Sur, C. et al., "Glycine transporter 1 inhibitors and modulation of NMDA receptor-mediated excitatory neurotransmission," Curr. Drug Targets (2007) 8:643-649.
Taber, D.F. et al., "Enantioselective ring construction: synthesis of (+)-alpha-cuparenone," J. Amer. Chem. Soc. (1985) 107:196-199.
Tavares, F.X. et al., "Potent, selective, and orally efficacious antagonists of melanin-concentrating hormone receptor 1," J. Med. Chem. (2006) 49(24):7095-7107.
Thompson, H.W. et al., "Stereochemical control of reductions. 9. Haptophilicity studies with 1,1-disubstituted 2-methyleneacenaphthenes," J. Org. Chem. (2002) 67(9):2813-2825.
Thomson, J.F., "Physiological effects of D20 in mammals," Annals of the N.Y. Academy of Sci. (1960) 84:736-744.
Ting, P.C. et al., "The synthesis of substituted bipiperidine amide compounds as CCR3 antagonists," Bioorg. Med. Chem. Lett. (2005) 15(5):1375-1378.
Tsai, G. et al., "Gene knockout of glycine transporter 1: characterization of the behavioral phenotype," PNAS (2004) 101(22):8485-8490.
Vogel, S. et al., "Palladium-catalyzed intramolecular allylic alkylation of alpha-sulfinyl carbanions: a new asymmetric route to enantiopure gamma-lactams," Tetra. Lett. (2010) 51(11):1459-1461.
White, J.D. et al., "Catalyzed asymmetric diels-alder reaction of benzoquinone. Total synthesis of (−)-ibogamine," Org. Lett. (2000) 2(15):2373-2376.
Zhou, D. et al., "Studies toward the discovery of the next generation of antidepressants. Part 5: 3,4-dihydro-2H-benzo[1,4]oxazine derivatives with dual 5-HT1A receptor and serotonin transporter affinity," Bioorg. Med. Chem. Lett. (2006) 16(5):1338-1341.
United States Patent Office Notice of Allowance for U.S. Appl. No. 12/666,629 dated Dec. 11, 2012 (5 pages).
United States Patent Office Action for U.S. Appl. No. 12/666,629 dated Jul. 5, 2012 (11 pages).
United States Patent Office Notice of Allowance for U.S. Appl. No. 12/706,321 dated Sep. 30, 2013 (10 pages).
United States Patent Office Action for U.S. Appl. No. 12/706,321 dated Jul. 19, 2012 (7 pages).
United States Patent Office Action for U.S. Appl. No. 12/706,321 dated Mar. 27, 2012 (11 pages).
United States Patent Office Notice of Allowance for U.S. Appl. No. 12/933,326 dated Jan. 9, 2014 (2 pages).
United States Patent Office Notice of Allowance for U.S. Appl. No. 12/933,326 dated Dec. 9, 2013 (4 pages).
United States Patent Office Notice of Allowance for U.S. Appl. No. 12/933,326 dated Oct. 1, 2013 (8 pages).
United States Patent Office Notice of Allowance for U.S. Appl. No. 12/933,326 dated Jan. 11, 2013 (5 pages).
United States Patent Office Action for U.S. Appl. No. 12/933,326 dated Oct. 29, 2012 (6 pages).
United States Patent Office Notice of Allowance for U.S. Appl. No. 13/206,937 dated Feb. 21, 2014 (9 pages).
United States Patent Office Action for U.S. Appl. No. 13/206,937 dated Aug. 28, 2013 (6 pages).
United States Patent Office Action for U.S. Appl. No. 13/206,750 dated Feb. 19, 2014 (6 pages).
United States Patent Office Notice of Allowance for U.S. Appl. No. 13/207,160 dated Mar. 17, 2014 (9 pages).
United States Patent Office Notice of Allowance for U.S. Appl. No. 13/207,030 dated Mar. 11, 2014 (9 pages).
United States Patent Office Action for U.S. Appl. No. 13/566,051 dated Sep. 16, 2013 (15 pages).
United States Patent Office Action for U.S. Appl. No. 13/680,488 dated Dec. 5, 2013 (17 pages).
United States Patent Office Action for U.S. Appl. No. 13/680,488 dated Jun. 21, 2013 (43 pages).
International Search Report for Application No. PCT/EP2008/061007 dated Aug. 10, 2009 (6 pages).
International Search Report for Application No. PCT/EP2009/053800 dated Nov. 20, 2009 (6 pages).
International Search Report for Application No. PCT/EP2012/058760 dated Aug. 27, 2012 (4 pages).
International Search Report for Application No. PCT/EP2012/065294 dated Sep. 21, 2012 (4 pages).
Written Opinion for Application No. PCT/EP2008/061007 dated Aug. 10, 2009 (7 pages).
Written Opinion for Application No. PCT/EP2009/053800 dated Nov. 20, 2009 (7 pages).
Written Opinion for Application No. PCT/EP2012/058760 dated Aug. 27, 2012 (4 pages).
Kamitani, T. et al., "Studies on the syntheses of heterocyclic compounds. Part DLXXVII. Synthesis of 2,3,4,5-tetrahydro-1H-benzazepine derivatives by phenolic cyclisation," J. Chem. Soc. Perkin Trans. (1974) 22:2602-2604.
Registry No. 1025812-32-1; entered in STN Jun. 5, 2008, "4-morpholineacetamide, N-[2-[[1-[2,4-dihydroxy-5-(1-methylethyl)benzoyl]-2,3-dihydro-1H-isoindol-5-y]]oxy]ethyl]".
United States Patent Office Action for U.S. Appl. No. 14/317,104 dated Nov. 5, 2014 (11 pages).
United States Patent Office Action for U.S. Appl. No. 14/282,712 dated Oct. 3, 2014 (12 pages).
United States Patent Office Action for U.S. Appl. No. 13/468,682 dated Sep. 10, 2014 (12 pages).
United States Patent Office Action for U.S. Appl. No. 13/764,454 dated Sep. 30, 2014 (11 pages).
United States Patent Office Notice of Allowance for U.S. Appl. No. 13/792,105 dated Oct. 2, 2014 (10 pages).
United States Patent Office Notice of Allowance for U.S. Appl. No. 13/206,750 dated Nov. 7, 2014 (8 pages).
United States Patent Office Notice of Allowance for U.S. Appl. No. 13/207,160 dated Jun. 6, 2014 (9 pages).
United States Patent Office Notice of Allowance for U.S. Appl. No. 13/566,051 dated May 29, 2014 (8 pages).
United States Patent Office Corrected Notice of Allowance for U.S. Appl. No. 13/680,488 dated Jun. 12, 2014 (7 pages).
United States Patent Office Notice of Allowance for U.S. Appl. No. 13/546,434 dated Jan. 16, 2015 (9 pages).

* cited by examiner

AMINOTETRALINE DERIVATIVES, PHARMACEUTICAL COMPOSITIONS CONTAINING THEM, AND THEIR USE IN THERAPY

CROSS-REFERENCE TO RELATED APPLICATIONS

This is a divisional of U.S. patent application Ser. No. 12/706,326, filed on Feb. 16, 2010, now U.S. Patent No. 8,563,617, which claims priority to U.S. Provisional Patent Application No. 61/152,825, filed on Feb. 16, 2009, the entire contents of all of which are fully incorporated herein by reference.

FIELD OF THE INVENTION

The present invention relates to aminotetraline derivatives, pharmaceutical compositions comprising such aminotetraline derivatives, and the use of such aminotetraline derivatives for therapeutic purposes. The aminotetraline derivatives are GlyT1 inhibitors.

BACKGROUND OF THE INVENTION

Dysfunction of glutamatergic pathways has been implicated in a number of disease states in the human central nervous system (CNS) including but not limited to schizophrenia, cognitive deficits, dementia, Parkinson disease, Alzheimer disease and bipolar disorder. A large number of studies in animal models lend support to the NMDA hypofunction hypothesis of schizophrenia.

NMDA receptor function can be modulated by altering the availability of the co-agonist glycine. This approach has the critical advantage of maintaining activity-dependent activation of the NMDA receptor because an increase in the synaptic concentration of glycine will not produce an activation of NMDA receptors in the absence of glutamate. Since synaptic glutamate levels are tightly maintained by high affinity transport mechanisms, an increased activation of the glycine site will only enhance the NMDA component of activated synapses.

Two specific glycine transporters, GlyT1 and GlyT2 have been identified and shown to belong to the Na/Cl-dependent family of neurotransmitter transporters which includes taurine, gamma-aminobutyric acid (GABA), proline, monoamines and orphan transporters. GlyT1 and GlyT2 have been isolated from different species and shown to have only 50% identity at the amino acid level. They also have a different pattern of expression in mammalian central nervous system, with GlyT2 being expressed in spinal cord, brainstem and cerebellum and GlyT1 present in these regions as well as forebrain areas such as cortex, hippocampus, septum and thalamus. At the cellular level, GlyT2 has been reported to be expressed by glycinergic nerve endings in rat spinal cord whereas GlyT1 appears to be preferentially expressed by glial cells. These expression studies have led to the suggestion that GlyT2 is predominantly responsible for glycine uptake at glycinergic synapses whereas GlyT1 is involved in monitoring glycine concentration in the vicinity of NMDA receptor expressing synapses. Recent functional studies in rat have shown that blockade of GlyT1 with the potent inhibitor (N-[3-(4'-fluorophenyl)-3-(4'-phenylphenoxy)propyl])sarcosine (NFPS) potentiates NMDA receptor activity and NMDA receptor-dependent long-term potentiation in rat.

Molecular cloning has further revealed the existence of three variants of GlyT1, termed GlyT-1a, GlyT-1b and GlyT-1c, each of which displays a unique distribution in the brain and peripheral tissues. The variants arise by differential splicing and exon usage, and differ in their N-terminal regions.

The physiological effects of GlyT1 in forebrain regions together with clinical reports showing the beneficial effects of GlyT1 inhibitor sarcosine in improving symptoms in schizophrenia patients suggest that selective GlyT1 inhibitors represent a new class of antipsychotic drugs.

Glycine transporter inhibitors are already known in the art, for example:

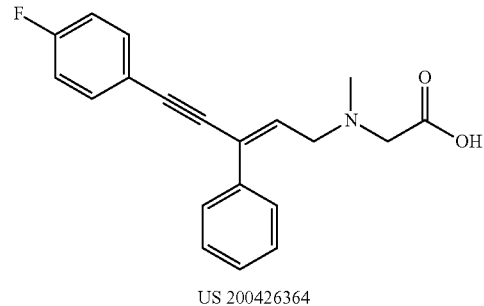

US 200426364

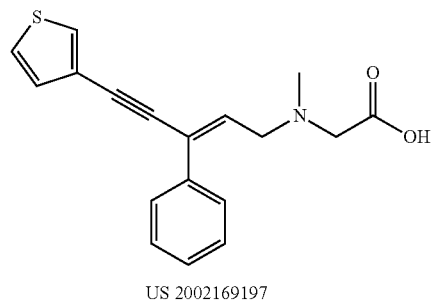

US 2002169197

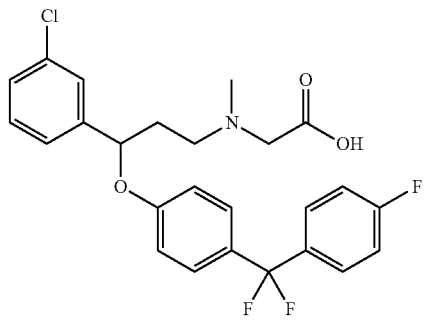

EP 1 284 257

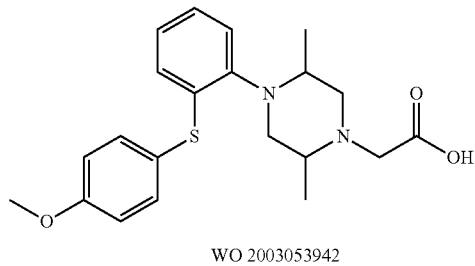

WO 2003053942

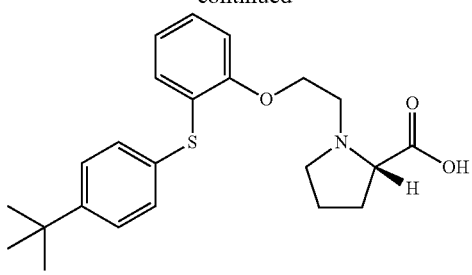
WO 2004096761
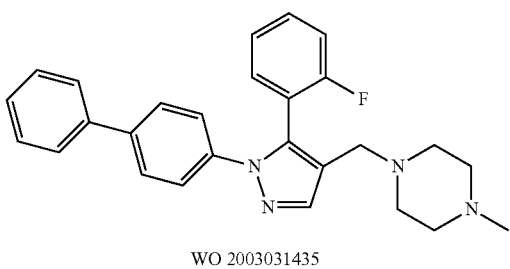
WO 2003031435
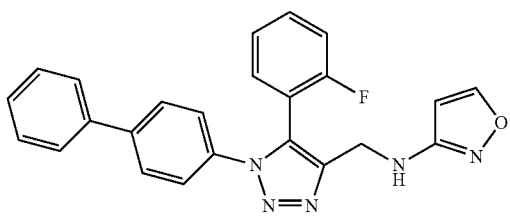
DE 10315570
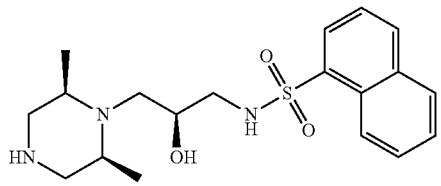
WO 2003055478
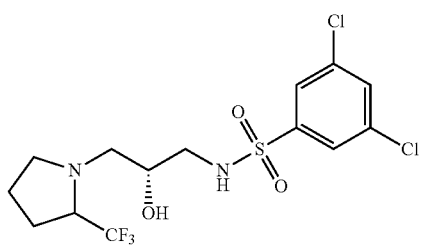
WO 2004113280
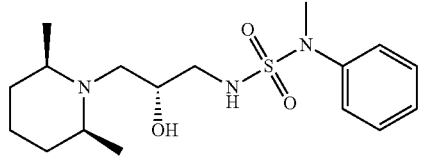
WO 2004112787
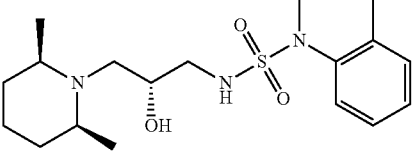
WO 2004113301
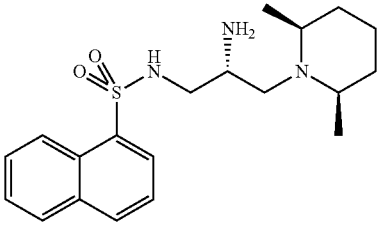
WO 2005049023
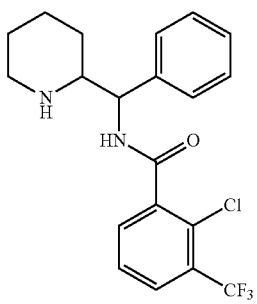
WO 2003089411
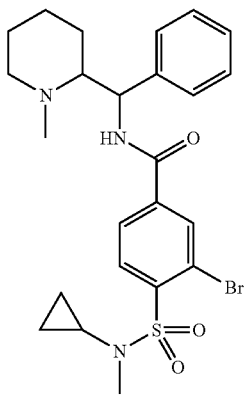
WO 2004013100
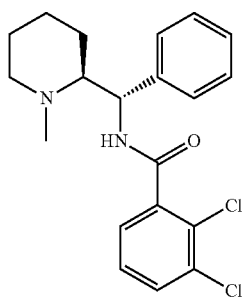
WO 2004013101

-continued
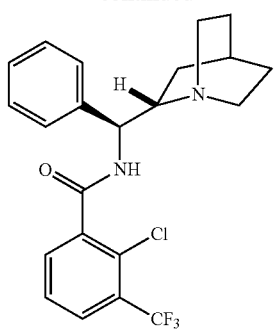
WO 2005037783
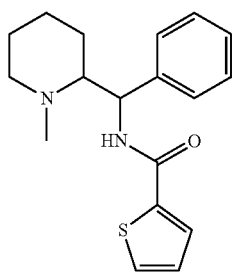
WO 2005037792
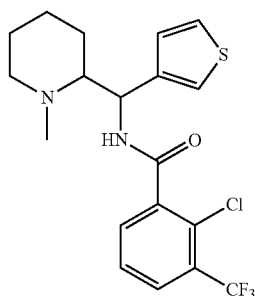
WO 2005037781
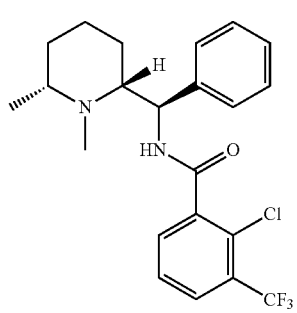
WO 2005037782
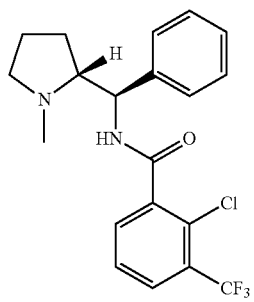
WO 2005037785
-continued
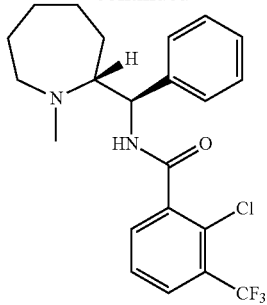
WO 2005037785
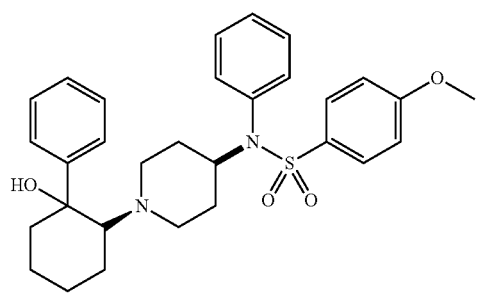
WO 2004072034
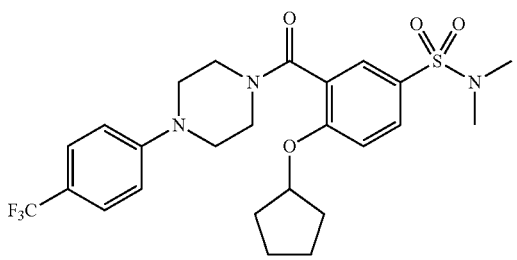
WO 2005014563
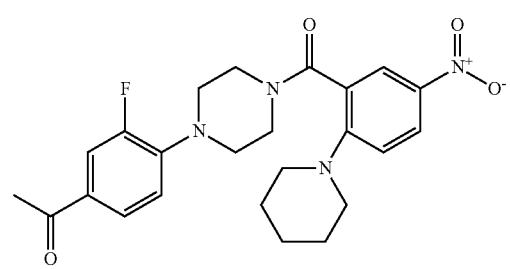
WO 2005023260
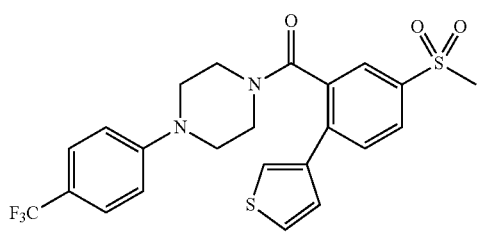
WO 2005023261

-continued

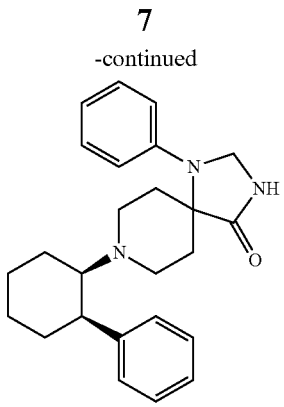

WO 2005040166

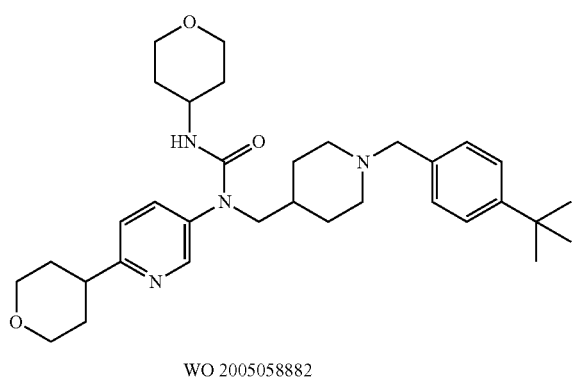

WO 2005058882

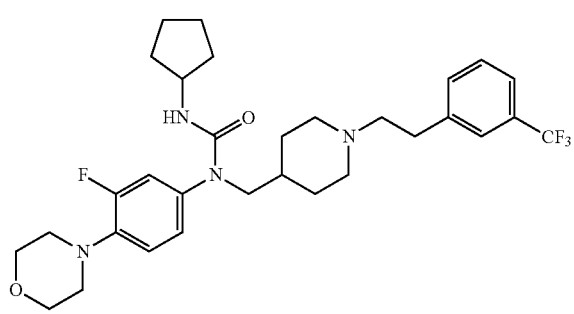

WO 2005058885

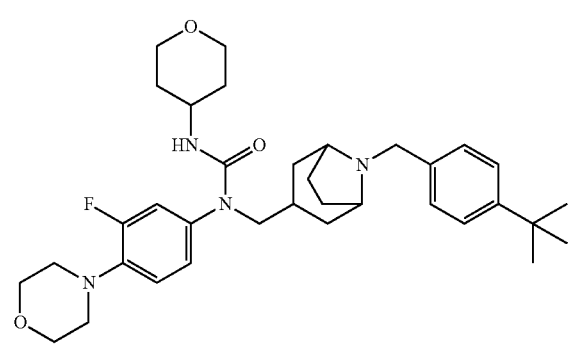

WO 2005058317

-continued

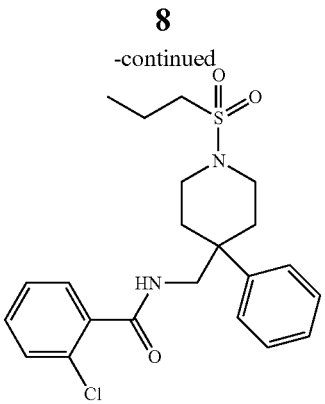

WO 2005046601

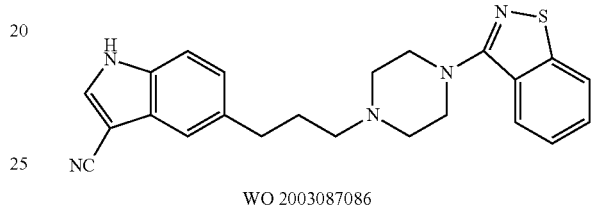

WO 2003087086

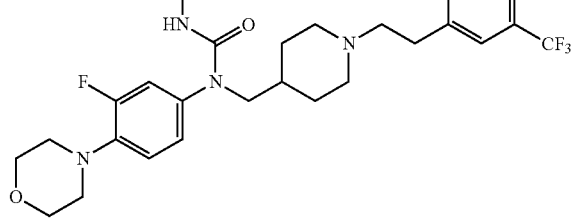

WO 2003076420

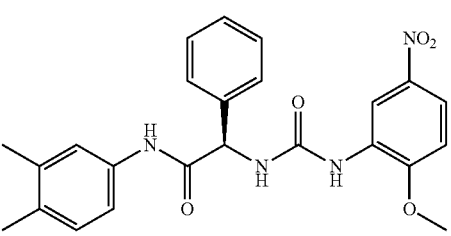

WO 2004022528

(see also Hashimoto K., Recent Patents on CNS Drug Discovery, 2006, 1, 43-53; Harsing L. G. et al., Current Medicinal Chemistry, 2006, 13, 1017-1044; Javitt D. C., Molecular Psychiatry (2004) 9, 984-997; Lindsley, C. W. et al., Current Topics in Medicinal Chemistry, 2006, 6, 771-785; Lindsley C. W. et al., Current Topics in Medicinal Chemistry, 2006, 6, 1883-1896).

It was one object of the present invention to provide further glycine transporter inhibitors.

SUMMARY OF THE INVENTION

The present invention relates to aminotetraline derivatives of the formula (I)

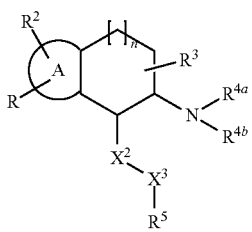

(I)

wherein

A is a 5- or 6-membered ring;

R is $R^1$—W—$A^1$—Q—Y—$A^2$—$X^1$—;

$R^1$ is hydrogen, alkyl, cycloalkylalkyl, halogenated alkyl, trialkylsilylalkyl, hydroxyalkyl, alkoxyalkyl, aminoalkyl, alkylaminoalkyl, dialkylaminoalkyl, alkylcarbonylaminoalkyl, alkyloxycarbonylaminoalkyl, alkylaminocarbonylaminoalkyl, dialkylaminocarbonylaminoalkyl, alkylsulfonylaminoalkyl, (optionally substituted arylalkyl), aminoalkyl, optionally substituted arylalkyl, optionally substituted heterocyclylalkyl, cycloalkyl, alkylcarbonyl, alkoxycarbonyl, halogenated alkoxycarbonyl, aryloxycarbonyl, aminocarbonyl, alkylaminocarbonyl, (halogenated alkyl)aminocarbonyl, arylaminocarbonyl, alkenyl, alkynyl, optionally substituted aryl, hydroxy, alkoxy, halogenated alkoxy, hydroxyalkoxy, alkoxyalkoxy, aminoalkoxy, alkylaminoalkoxy, dialkylam inoalkoxy, alkylcarbonylaminoalkoxy, arylcarbonylaminoalkoxy, alkoxycarbonylaminoalkoxy, arylalkoxy, alkylsulfonylaminoalkoxy, (halogenated alkyl)sulfonylaminoalkoxy, arylsulfonylaminoalkoxy, (arylalkyl)sulfonylaminoalkoxy, heterocyclylsulfonylaminoalkoxy, heterocyclylalkoxy, aryloxy, heterocyclyloxy, alkylthio, halogenated alkylthio, alkylamino, (halogenated alkyl)amino, dialkylamino, di(halogenated alkyl)amino, alkylcarbonylamino, (halogenated alkyl)carbonylamino, arylcarbonylamino, alkylsulfonylamino, (halogenated alkyl)sulfonylamino, arylsulfonylamino or optionally substituted heterocyclyl;

W is —$NR^8$— or a bond;

$A^1$ is optionally substituted alkylene or a bond;

Q is —$S(O)_2$— or —C(O)—;

Y is —$NR^9$— or a bond;

$A^2$ is optionally substituted alkylene, alkylene-CO—, —CO-alkylene, alkylene-O-alkylene, alkylene-$NR^{10}$-alkylene, optionally substituted alkenylen, optionally substituted alkynylene, optionally substituted arylene, optionally substituted heteroarylene or a bond;

$X^1$ is —O—, —$NR^{11}$—, —S—, optionally substituted alkylene, optionally substituted alkenylen, optionally substituted alkynylene;

$R^2$ is hydrogen, halogen, alkyl, halogenated alkyl, hydroxyalkyl, —CN, alkenyl, alkynyl, optionally substituted aryl, hydroxy, alkoxy, halogenated alkoxy, alkoxycarbonyl, alkenyloxy, arylalkoxy, alkylcarbonyloxy, alkylthio, alkylsulfinyl, alkylsulfonyl, aminosulfonyl, amino, alkylamino, alkenylamino, nitro or optionally substituted heterocyclyl, or two radicals $R^2$ together with the ring atoms of A to which they are bound form a 5- or 6-membered ring;

$R^3$ is hydrogen, halogen, alkyl or alkoxy, or two radicals $R^3$ together with the carbon atom to which they are attached form a carbonyl group;

$R^{4a}$ is hydrogen, alkyl, cycloalkylalkyl, halogenated alkyl, hydroxyalkyl, alkoxyalkyl, aminoalkyl, $CH_2CN$, —CHO, alkylcarbonyl, (halogenated alkyl)carbonyl, arylcarbonyl, alkoxycarbonyl, aryloxycarbonyl, alkylaminocarbonyl, alkenyl, —C(=NH)$NH_2$, —C(=NH)NHCN, alkylsulfonyl, arylsulfonyl, amino, —NO or heterocyclyl;

$R^{4b}$ is hydrogen, alkyl, halogenated alkyl, hydroxyalkyl, alkoxyalkyl, aminoalkyl, $CH_2CN$, —CHO, alkylcarbonyl, (halogenated alkyl)carbonyl, arylcarbonyl, alkoxycarbonyl, aryloxycarbonyl, alkylaminocarbonyl, alkenyl, —C(=NH)$NH_2$, —C(=NH)NHCN, alkylsulfonyl, arylsulfonyl, amino, —NO or heterocyclyl; or $R^{4a}$, $R^{4b}$ together are optionally substituted alkylene, wherein one —$CH_2$— of alkylene may be replaced by an oxygen atom or —$NR^{16}$;

$X^2$ is —O—, —$NR^6$—, —S—, >$CR^{12a}R^{12b}$ or a bond;

$X^3$ is —O—, —$NR^7$—, —S—, >$CR^{13a}R^{13b}$ or a bond;

$R^5$ is optionally substituted aryl, optionally substituted cycloalkyl or optionally substituted heterocyclyl;

n is 0, 1 or 2;

$R^6$ is hydrogen or alkyl;

$R^7$ is hydrogen or alkyl;

$R^8$ is hydrogen or alkyl;

$R^9$ is hydrogen, alkyl, cycloalkyl, aminoalkyl, optionally substituted arylalkyl or heterocyclyl; or $R^9$, $R^1$ together are alkylene; or $R^9$ is alkylene that is bound to a carbon atom in $A^2$ and $A^2$ is alkylene or to a carbon atom in $X^1$ and $X^1$ is alkylene;

$R^{10}$ is hydrogen, alkyl or alkylsulfonyl;

$R^{11}$ is hydrogen or alkyl, or $R^9$, $R^{11}$ together are alkylene, $R^{12a}$ is hydrogen, optionally substituted alkyl, alkylaminoalkyl, dialkylaminoalkyl, heterocyclylalkyl, optionally substituted aryl or hydroxy;

$R^{12b}$ is hydrogen or alkyl, or $R^{12a}$, $R^{12b}$ together are carbonyl or optionally substituted alkylene, wherein one —$CH_2$— of alkylene may be replaced by an oxygen atom or —$NR^{14}$—;

$R^{13a}$ is hydrogen, optionally substituted alkyl, alkylaminoalkyl, dialkylaminoalkyl, heterocyclylalkyl, optionally substituted aryl or hydroxy;

$R^{13b}$ is hydrogen or alkyl, or $R^{13a}R^{13b}$ together are carbonyl or optionally substituted alkylene, wherein one —$CH_2$— of alkylene may be replaced by an oxygen atom or —$NR^{15}$—;

$R^{14}$ is hydrogen or alkyl;

$R^{15}$ is hydrogen or alkyl; and $R^{16}$ is hydrogen or alkyl, or a physiologically tolerated salt thereof.

Thus, the present invention relates to aminotetraline derivatives having the formula (Ia)

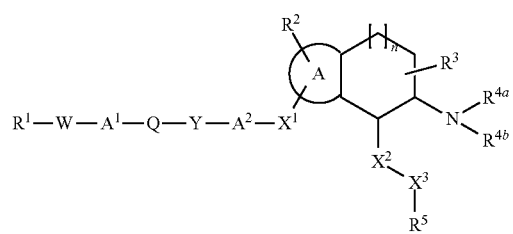

(Ia)

wherein A, $R^1$, W, $A^1$, Q, Y, $A^2$, $X^1$, $R^2$, $R^3$, $R^{4a}$, $R^{4b}$, $X^2$, $X^3$, $R^5$, n are as defined herein.

Further, the present invention relates to aminotetraline derivatives of formula (I) wherein R is —CN, i.e. aminotetraline derivatives having the formula (Ib)

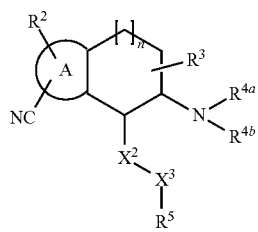

(Ib)

wherein A, $R^2$, $R^3$, $R^{4a}$, $R^{4b}$, $X^2$, $X^3$, $R^5$, n are as defined herein.

Thus, the term aminotetraline derivative is used herein to denote in particular aminotetralines (n=1) and fused cyclohexanes (n=1) wherein the benzene ring is replaced by a 5- or 6-membered heterocyclic ring as well as homologous bicyclic compounds wherein n is 0 or 2.

Said compounds of formula (I), i.e., the aminotetraline derivatives of formula (I) and their physiologically tolerated acid addition salts, are glycine transporter inhibitors and thus useful as pharmaceuticals.

The present invention thus further relates to the compounds of formula (I) for use in therapy.

The present invention also relates to pharmaceutical compositions which comprise a carrier and a compound of formula (I).

In particular, said compounds, i.e., the aminotetraline derivatives and their physiologically tolerated acid addition salts, are inhibitors of the glycine transporter GlyT1.

The present invention thus further relates to the compounds of formula (I) for use in inhibiting the glycine transporter.

The present invention also relates to the use of the compounds of formula (I) in the manufacture of a medicament for inhibiting the glycine transporter GlyT1 and corresponding methods of inhibiting the glycine transporter GlyT1.

Glycine transport inhibitors and in particular inhibitors of the glycine transporter GlyT1 are known to be useful in treating a variety of neurologic and psychiatric disorders.

The present invention thus further relates to the compounds of formula (I) for use in treating a neurologic or psychiatric disorder.

The present invention further relates to the compounds of formula (I) for use in treating pain.

The present invention also relates to the use of the compounds of formula (I) in the manufacture of a medicament for treating a neurologic or psychiatric disorder and corresponding methods of treating said disorders. The present invention also relates to the use of the compounds of formula (I) in the manufacture of a medicament for treating pain and corresponding methods of treating pain.

The present invention further relates to aminotetraline derivatives of formula (II)

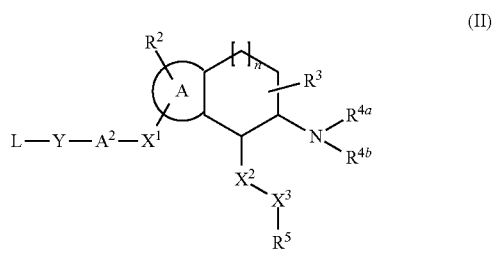

(II)

wherein L is an amino-protecting group, Y is $NR^9$, and $A^2$, $X^1$, $R^2$, $R^3$, $R^{4a}$, $R^{4b}$, $X^2$, $X^3$, $R^5$, n and $R^9$ are defined as above.

The aminotetraline derivatives of formula (II) are useful as intermediates in the preparation of GlyT1 inhibitors, in particular those of formula (I).

DETAILED DESCRIPTION OF THE INVENTION

Provided that the aminotetraline derivatives of the formula (I) or (II) of a given constitution may exist in different spatial arrangements, for example if they possess one or more centers of asymmetry, polysubstituted rings or double bonds, or as different tautomers, it is also possible to use enantiomeric mixtures, in particular racemates, diastereomeric mixtures and tautomeric mixtures, preferably, however, the respective essentially pure enantiomers, diastereomers and tautomers of the compounds of formula (I) or (II) and/or of their salts.

According to one embodiment, an enantiomer of the aminotetraline derivatives of the present invention has the following formula:

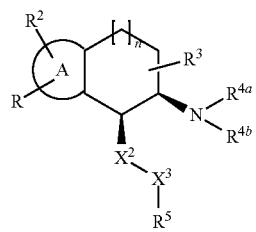

wherein A, R, $R^2$, $R^3$, $R^{4a}$, $R^{4b}$, $X^2$, $X^3$, $R^5$, n are as defined herein.

According to another embodiment, an enantiomer of the aminotetraline derivatives of the present invention has the following formula:

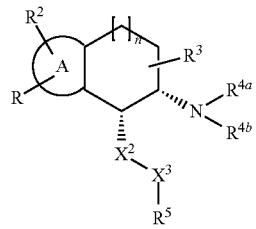

wherein A, R, $R^2$, $R^3$, $R^{4a}$, $R^{4b}$, $X^2$, $X^3$, $R^5$, n are as defined herein.

According to one embodiment, an enantiomer of the aminotetraline derivatives of the present invention has the following formula:

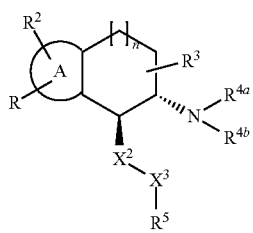

wherein A, R, $R^2$, $R^3$, $R^{4a}$, $R^{4b}$, $X^2$, $X^3$, $R^5$, n are as defined herein.

According to another embodiment, an enantiomer of the aminotetraline derivatives of the present invention has the following formula:

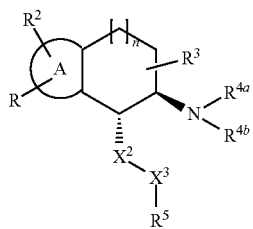

wherein A, R, $R^2$, $R^3$, $R^{4a}$, $R^{4b}$, $X^2$, $X^3$, $R^5$, n are as defined herein.

The physiologically tolerated salts of the aminotetraline derivatives of the formula (I) or (II) are especially acid addition salts with physiologically tolerated acids. Examples of suitable physiologically tolerated organic and inorganic acids are hydrochloric acid, hydrobromic acid, phosphoric acid, sulfuric acid, $C_1$-$C_4$-alkylsulfonic acids, such as methanesulfonic acid, cycloaliphatic sulfonic acids, such as S-(+)-10-campher sulfonic acid, aromatic sulfonic acids, such as benzenesulfonic acid and toluenesulfonic acid, di- and tricarboxylic acids and hydroxycarboxylic acids having 2 to 10 carbon atoms, such as oxalic acid, malonic acid, maleic acid, fumaric acid, lactic acid, tartaric acid, citric acid, glycolic acid, adipic acid and benzoic acid. Other utilizable acids are described, e.g., in Fortschritte der Arzneimittelforschung [Advances in drug research], Volume 10, pages 224 ff., Birkhäuser Verlag, Basel and Stuttgart, 1966.

The present invention moreover relates to compounds of formula (I) or (II) as defined herein, wherein at least one of the atoms has been replaced by its stable, non-radioactive isotope (e.g., hydrogen by deuterium, $^{12}C$ by $^{13}C$, $^{14}N$ by $^{15}N$, $^{16}O$ by $^{18}O$) and preferably wherein at least one hydrogen atom has been replaced by a deuterium atom.

Of course, such compounds contain more of the respective isotope than this naturally occurs and thus is anyway present in the compounds (I) or (II).

Stable isotopes (e.g., deuterium, $^{13}C$, $^{15}N$, $^{18}O$) are nonradioactive isotopes which contain one or more additional neutron than the normally abundant isotope of the respective atom. Deuterated compounds have been used in pharmaceutical research to investigate the in vivo metabolic fate of the compounds by evaluation of the mechanism of action and metabolic pathway of the non deuterated parent compound (Blake et al. *J. Pharm. Sci.* 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al., J. *Labelled Comp. Radiopharmaceut.*, 36(10):927-932 (1995); Kushner et al., *Can. J. Physiol. Pharmacol.*, 77, 79-88 (1999)).

Incorporation of a heavy atom particularly substitution of deuterium for hydrogen, can give rise to an isotope effect that could alter the pharmacokinetics of the drug. This effect is usually insignificant if the label is placed at a metabolically inert position of the molecule.

Stable isotope labeling of a drug can alter its physico-chemical properties such as pKa and lipid solubility. These changes may influence the fate of the drug at different steps along its passage through the body. Absorption, distribution, metabolism or excretion can be changed. Absorption and distribution are processes that depend primarily on the molecular size and the lipophilicity of the substance. These effects and alterations can affect the pharmacodynamic response of the drug molecule if the isotopic substitution affects a region involved in a ligand-receptor interaction.

Drug metabolism can give rise to large isotopic effect if the breaking of a chemical bond to a deuterium atom is the rate limiting step in the process. While some of the physical properties of a stable isotope-labeled molecule are different from those of the unlabeled one, the chemical and biological properties are the same, with one important exception: because of the increased mass of the heavy isotope, any bond involving the heavy isotope and another atom will be stronger than the same bond between the light isotope and that atom. In any reaction in which the breaking of this bond is the rate limiting step, the reaction will proceed slower for the molecule with the heavy isotope due to "kinetic isotope effect". A reaction involving breaking a C-D bond can be up to 700 percent slower than a similar reaction involving breaking a C—H bond. If the C-D bond is not involved in any of the steps leading to the metabolite, there may not be any effect to alter the behavior of the drug. If a deuterium is placed at a site involved in the metabolism of a drug, an isotope effect will be observed only if breaking of the C-D bond is the rate limiting step. There is evidence to suggest that whenever cleavage of an aliphatic C—H bond occurs, usually by oxidation catalyzed by a mixed-function oxidase, replacement of the hydrogen by deuterium will lead to observable isotope effect. It is also important to understand that the incorporation of deuterium at the site of metabolism slows its rate to the point where another metabolite produced by attack at a carbon atom not substituted by deuterium becomes the major pathway a process called "metabolic switching".

Deuterium tracers, such as deuterium-labeled drugs and doses, in some cases repeatedly, of thousands of milligrams of deuterated water, are also used in healthy humans of all ages, including neonates and pregnant women, without reported incident (e.g. Pons G and Rey E, Pediatrics 1999 104: 633; Coward W A et al., Lancet 1979 7: 13; Schwarcz H P, Control. Clin. Trials 1984 5(4 Suppl): 573; Rodewald L E et al., J. Pediatr. 1989 114: 885; Butte N F et al. Br. J. Nutr. 1991 65: 3; MacLennan A H et al. Am. J. Obstet. Gynecol. 1981 139: 948). Thus, it is clear that any deuterium released, for instance, during the metabolism of compounds of this invention poses no health risk.

The weight percentage of hydrogen in a mammal (approximately 9%) and natural abundance of deuterium (approximately 0.015%) indicates that a 70 kg human normally contains nearly a gram of deuterium. Furthermore, replacement of up to about 15% of normal hydrogen with deuterium has been effected and maintained for a period of days to weeks in mammals, including rodents and dogs, with minimal observed adverse effects (Czajka D M and Finkel A J, Ann.

N.Y. Acad. Sci. 1960 84: 770; Thomson J F, Ann. New York Acad. Sci. 1960 84: 736; Czakja D M et al., Am. J. Physiol. 1961 201: 357). Higher deuterium concentrations, usually in excess of 20%, can be toxic in animals. However, acute replacement of as high as 15%-23% of the hydrogen in humans' fluids with deuterium was found not to cause toxicity (Blagojevic N et al. in "Dosimetry & Treatment Planning for Neutron Capture Therapy", Zamenhof R, Solares G and Harling 0 Eds. 1994. Advanced Medical Publishing, Madison Wis. pp. 125-134; Diabetes Metab. 23: 251 (1997)).

Increasing the amount of deuterium present in a compound above its natural abundance is called enrichment or deuterium-enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %.

The hydrogens present on a particular organic compound have different capacities for exchange with deuterium. Certain hydrogen atoms are easily exchangeable under physiological conditions and, if replaced by deuterium atoms, it is expected that they will readily exchange for protons after administration to a patient. Certain hydrogen atoms may be exchanged for deuterium atoms by the action of a deuteric acid such as $D_2SO_4/D_2O$. Alternatively, deuterium atoms may be incorporated in various combinations during the synthesis of compounds of the invention. Certain hydrogen atoms are not easily exchangeable for deuterium atoms. However, deuterium atoms at the remaining positions may be incorporated by the use of deuterated starting materials or intermediates during the construction of compounds of the invention.

Deuterated and deuterium-enriched compounds of the invention can be prepared by using known methods described in the literature. Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure. Relevant procedures and intermediates are disclosed, for instance in Lizondo, J et al., *Drugs Fut,* 21(11), 1116 (1996); Brickner, S J et al., *J Med Chem,* 39(3), 673 (1996); Mallesham, B et al., *Org Lett,* 5(7), 963 (2003); PCT publications WO1997010223, WO2005099353, WO1995007271, WO2006008754; U.S. Pat. Nos. 7,538,189; 7,534,814; 7,531,685; 7,528,131; 7,521,421; 7,514,068; 7,511,013; and US Patent Application Publication Nos. 20090137457; 20090131485; 20090131363; 20090118238; 20090111840; 20090105338; 20090105307; 20090105147; 20090093422; 20090088416; 20090082471, the methods are hereby incorporated by reference.

The organic moieties mentioned in the above definitions of the variables are—like the term halogen—collective terms for individual listings of the individual group members. The prefix $C_n$—$C_m$ indicates in each case the possible number of carbon atoms in the group.

Unless indicated otherwise, the term "substituted" means that a radical is substituted with 1, 2 or 3, especially 1, substituent which are in particular selected from the group consisting of halogen, $C_1$-$C_4$-alkyl, hydroxy-$C_1$-$C_4$-alkyl, $C_3$-$C_{12}$-heterocyclyl-alkyl, $C_1$-$C_4$-alkoxy$C_1$-$C_4$-alkyl, amino-$C_1$-$C_4$-alkyl, $C_1$-$C_4$-alkenyl, OH, SH, CN, $CF_3$, O—$CF_3$, COOH, O—$CH_2$—COOH, $C_1$-$C_6$-alkoxy, $C_1$-$C_6$-alkylthio, $C_3$-$C_7$-cycloalkyl, COO—$C_1$-$C_6$-alkyl, $CONH_2$, CONH—$C_1$-$C_6$-alkyl, $SO_2NH$—$C_1$-$C_6$-alkyl, CON—($C_1$-$C_6$-alkyl)$_2$, $SO_2N$—($C_1$-$C_6$-alkyl)$_2$, $NH_2$, NH—$C_1$-$C_6$-alkyl, N—($C_1$-$C_6$-alkyl)$_2$, NH—($C_1$-$C_4$-alkyl-$C_6$-$C_{12}$-aryl), NH—CO—$C_1$-$C_6$-alkyl, NH—$SO_2$—$C_1$-$C_6$-alkyl, $SO_2$—$C_1$-$C_6$-alkyl, $C_6$-$C_{12}$-aryl, O—$C_6$-$C_{12}$-aryl, O—$CH_2$—$C_6$-$C_{12}$-aryl, CONH—$C_6$-$C_{12}$-aryl, $SO_2NH$—$C_6$-$C_{12}$-aryl, CONH—$C_3$-$C_{12}$-heterocyclyl, $SO_2NH$—$C_3$-$C_{12}$-heterocyclyl, $SO_2$—$C_6$-$C_{12}$ aryl, NH—$SO_2$—$C_6$-$C_{12}$-aryl, NH—CO—$C_6$-$C_{12}$-aryl, NH—$SO_2$—$C_3$-$C_{12}$-heterocyclyl, NH—CO—$C_3$-$C_{12}$-heterocyclyl and $C_3$-$C_{12}$-heterocyclyl, wherein aryl and heterocyclyl in turn may be unsubstituted or substituted with 1, 2 or 3 substituents selected from the group consisting of halogen, $C_1$-$C_4$-alkyl, $C_1$-$C_4$-haloalkyl, $C_1$-$C_4$-alkoxy and $C_1$-$C_4$-haloalkoxy.

The term halogen denotes in each case fluorine, bromine, chlorine or iodine, in particular fluorine or chlorine.

$C_1$-$C_4$-Alkyl is a straight-chain or branched alkyl group having from 1 to 4 carbon atoms. Examples of an alkyl group are methyl, $C_2$-$C_4$-alkyl such as ethyl, n-propyl, iso-propyl, n-butyl, 2-butyl, iso-butyl or tert-butyl. $C_1$-$C_2$-Alkyl is methyl or ethyl, $C_1$-$C_3$-alkyl is additionally n-propyl or iso-propyl.

$C_1$-$C_6$-Alkyl is a straight-chain or branched alkyl group having from 1 to 6 carbon atoms. Examples include methyl, $C_2$-$C_4$-alkyl as mentioned herein and also pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

Halogenated $C_1$-$C_4$-alkyl is a straight-chain or branched alkyl group having 1 to 4 carbon atoms, preferably 1 to 3 carbon atoms, more preferably 1 or 2 carbon atoms, wherein at least one, e.g. 1, 2, 3, 4 or all of the hydrogen atoms are replaced by 1, 2, 3, 4 or a corresponding number of identical or different halogen atoms, such as in halogenomethyl, dihalogenomethyl, trihalogenomethyl, (R)-1-halogenoethyl, (S)-1-halogenoethyl, 2-halogenoethyl, 1,1-dihalogenoethyl, 2,2-dihalogenoethyl, 2,2,2-trihalogenoethyl, (R)-1-halogenopropyl, (S)-1-halogenopropyl, 2-halogenopropyl, 3-halogenopropyl, 1,1-dihalogenopropyl, 2,2-dihalogenopropyl, 3,3-dihalogenopropyl, 3,3,3-trihalogenopropyl, (R)-2-halogeno-1-methylethyl, (S)-2-halogeno-1-methylethyl, (R)-2,2-dihalogeno-1-methylethyl, (S)-2,2-dihalogeno-1-methylethyl, (R)-1,2-dihalogeno-1-methylethyl, (S)-1,2-dihalogeno-1-methylethyl, (R)-2,2,2-trihalogeno-1-methylethyl, (S)-2,2,2-trihalogeno-1-methylethyl, 2-halogeno-1-(halogenomethyl)ethyl, 1-(dihalogenomethyl)-2,2-dihalogenoethyl, (R)-1-halogenobutyl, (S)-1-halogenobutyl, 2-halogenobutyl, 3-halogenobutyl, 4-halogenobutyl, 1,1-dihalogenobutyl, 2,2-dihalogenobutyl, 3,3-dihalogenobutyl, 4,4-dihalogenobutyl, 4,4,4-trihalogenobutyl, etc. Particular examples include the fluorinated $C_1$-$C_4$ alkyl groups as defined, such as trifluoromethyl.

$C_6$-$C_{12}$-Aryl-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by $C_6$-$C_{12}$-aryl, such as in benzyl.

Hydroxy-$C_1$-$C_4$-alkyl is a straight-chain or branched alkyl group having 1 to 4 carbon atoms, preferably 1 to 3 carbon atoms, more preferably 1 or 2 carbon atoms, wherein one or two hydrogen atoms are replaced by one or two hydroxyl groups, such as in hydroxymethyl, (R)-1-hydroxyethyl, (S)-1-hydroxyethyl, 2-hydroxyethyl, (R)-1-hydroxypropyl, (S)-1-hydroxypropyl, 2-hydroxypropyl, 3-hydroxypropyl, (R)-2-hydroxy-1-methylethyl, (S)-2-hydroxy-1-methylethyl, 2-hydroxy-1-(hydroxymethyl)ethyl, (R)-1-hydroxybutyl, (S)-1-hydroxybutyl, 2-hydroxybutyl, 3-hydroxybutyl, 4-hydroxybutyl.

$C_1$-$C_6$-Alkoxy-$C_1$-$C_4$-alkyl is a straight-chain or branched alkyl group having 1 to 4 carbon atoms, preferably 1 to 3 carbon atoms, more preferably 1 or 2 carbon atoms, wherein one or two hydrogen atoms are replaced by one or two alkoxy groups having 1 to 6, preferably 1 to 4, in particular 1 or 2 carbon atoms, such as in methoxymethyl, (R)-1-methoxyethyl, (S)-1-methoxyethyl, 2-methoxyethyl, (R)-1-methoxypropyl, (S)-1-methoxypropyl, 2-methoxypropyl, 3-methoxypropyl, (R)-2-methoxy-1-methylethyl, (S)-2-methoxy-1-methylethyl, 2-methoxy-1-(methoxymethyl)ethyl, (R)-1-methoxybutyl, (S)-1-methoxybutyl, 2-methoxybutyl, 3-methoxybutyl, 4-methoxybutyl, ethoxymethyl, (R)-1-ethoxyethyl, (S)-1-ethoxyethyl, 2-ethoxyethyl, (R)-1-ethoxypropyl, (S)-1-ethoxypropyl, 2-ethoxypropyl, 3-ethoxypropyl, (R)-2-ethoxy-1-methylethyl, (S)-2-ethoxy-1-methylethyl, 2-ethoxy-1-(ethoxymethyl)ethyl, (R)-1-ethoxybutyl, (S)-1-ethoxybutyl, 2-ethoxybutyl, 3-ethoxybutyl, 4-ethoxybutyl.

Amino-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by an amino group, such as in aminomethyl, 2-aminoethyl.

$C_1$-$C_6$-Alkylamino-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a $C_1$-$C_6$-alkylamino group, in particular by a $C_1$-$C_4$-alkylamino group, such as in methylaminomethyl, ethylaminomethyl, n-propylaminomethyl, iso-propylaminomethyl, nbutylaminomethyl, 2-butylaminomethyl, iso-butylaminomethyl or tert-butylaminomethyl.

Di-$C_1$-$C_6$-Alkylamino-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a di-$C_1$-$C_6$-Alkylamino group, in particular by a di-$C_1$-$C_4$-alkylamino group, such as in dimethylaminomethyl.

$C_1$-$C_6$-Alkylcarbonylamino-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a $C_1$-$C_6$-alkylcarbonylamino group, in particular by a $C_1$-$C_4$-alkylcarbonylamino group, such as in methylcarbonylaminomethyl, ethylcarbonylaminomethyl, n-propylcarbonylaminomethyl, iso-propylcarbonylaminomethyl, n-butylcarbonylaminomethyl, 2-butylcarbonylaminomethyl, iso-butylcarbonylaminomethyl or tertbutylcarbonylaminomethyl.

$C_1$-$C_6$-Alkylaminocarbonylamino-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a $C_1$-$C_6$-alkylaminocarbonylamino group, in particular by a $C_1$-$C_4$-alkylaminocarbonylamino group, such as in methylaminocarbonylaminomethyl, ethylaminocarbonylaminomethyl, npropylaminocarbonylaminomethyl, iso-propylaminocarbonylaminomethyl, nbutylaminocarbonylaminomethyl, 2-butylaminocarbonylaminomethyl, isobutylaminocarbonylaminomethyl or tert-butylaminocarbonylaminomethyl.

Di-$C_1$-$C_6$-alkylaminocarbonylamino-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a di-$C_1$-$C_6$-alkylaminocarbonylamino group, in particular by a di-$C_1$-$C_4$-alkylaminocarbonylamino group, such as in dimethylaminocarbonylaminomethyl, dimethylaminocarbonylaminoethyl, dimethylaminocarbonylaminon-propyl.

$C_1$-$C_6$-Alkylsulfonylamino-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a $C_1$-$C_6$-alkylsulfonylamino group, in particular by a $C_1$-$C_4$-alkylsulfonylamino group, such as in methylsulfonylaminomethyl, ethylsulfonylaminomethyl, n-propylsulfonylaminomethyl, isopropylsulfonylaminomethyl, n-butylsulfonylaminomethyl, 2-butylsulfonylaminomethyl, isobutylsulfonylaminomethyl or tert-butylsulfonylaminomethyl.

($C_6$-$C_{12}$-Aryl-$C_1$-$C_6$-alkyl)amino-$C_1$-$C_4$ alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a ($C_6$-$C_{12}$-aryl-$C_1$-$C_6$-alkyl)amino group, in particular a ($C_6$-$C_{12}$-aryl-$C_1$-$C_2$-alkyl) amino group, such as in benzylaminomethyl.

$C_3$-$C_{12}$-Heterocyclyl-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by $C_3$-$C_{12}$-heterocyclyl, such as in N-pyrrolidinylmethyl, N-piperidinylmethyl, N-morpholinylmethyl.

$C_3$-$C_{12}$-Cycloalkyl is a cycloaliphatic radical having from 3 to 12 carbon atoms. In particular, 3 to 6 carbon atoms form the cyclic structure, such as cyclopropyl, cyclobutyl, cyclopentyl and cyclohexyl. The cyclic structure may be unsubstituted or may carry 1, 2, 3 or 4 $C_1$-$C_4$ alkyl radicals, preferably one or more methyl radicals.

Carbonyl is >C=O.

$C_1$-$C_6$-Alkylcarbonyl is a radical of the formula R—C(O)—, wherein R is an alkyl radical having from 1 to 6, preferably from 1 to 4, in particular 1 or 2 carbon atoms as defined herein. Examples include acetyl, propionyl, n-butyryl, 2-methylpropionyl, pivaloyl.

Halogenated $C_1$-$C_6$-alkylcarbonyl is $C_1$-$C_6$-alkylcarbonyl as defined herein, wherein at least one, e.g. 1, 2, 3, 4 or all of the hydrogen atoms are replaced by 1, 2, 3, 4 or a corresponding number of identical or different halogen atoms. Examples include fluoromethylcarbonyl, difluoromethylcarbonyl, trifluoromethylcarbonyl. Further examples are 1,1,1-trifluoroeth-2-ylcarbonyl, 1,1,1-trifluoroprop-3-ylcarbonyl.

$C_6$-$C_{12}$-Arylcarbonyl is a radical of the formula R—C(O)—, wherein R is an aryl radical having from 6 to 12 carbon atoms as defined herein. Examples include benzoyl.

$C_1$-$C_6$-Alkoxycarbonyl is a radical of the formula R—O—C(O)—, wherein R is an alkyl radical having from 1 to 6, preferably from 1 to 4, in particular 1 or 2 carbon atoms as defined herein. Examples include methoxycarbonyl and tert-butyloxycarbonyl.

Halogenated $C_1$-$C_6$-alkoxycarbonyl is a $C_1$-$C_6$-alkoxycarbonyl as defined herein, wherein at least one, e.g. 1, 2, 3, 4 or all of the hydrogen atoms are replaced by 1, 2, 3, 4 or a corresponding number of identical or different halogen atoms.

$C_6$-$C_{12}$-Aryloxycarbonyl is a radical of the formula R—O—C(O)—, wherein R is an aryl radical having from 6 to 12 carbon atoms as defined herein. Examples include phenoxycarbonyl.

Cyano is —C≡N.

Aminocarbonyl is $NH_2C(O)$—.

$C_1$-$C_6$-Alkylaminocarbonyl is a radical of the formula R—NH—C(O)—, wherein R is an alkyl radical having from 1 to 6, preferably from 1 to 4, in particular 1 or 2 carbon atoms as defined herein. Examples include methylaminocarbonyl.

(Halogenated $C_1$-$C_4$-alkyl)aminocarbonyl is a $C_1$-$C_4$-alkylaminocarbonyl as defined herein, wherein at least one, e.g. 1, 2, 3, 4 or all of the hydrogen atoms are replaced by 1, 2, 3, 4 or a corresponding number of identical or different hydrogen atoms.

$C_6$-$C_{12}$-Arylaminocarbonyl is a radical of the formula R—NH—C(O)—, wherein R is an aryl radical having from 6 to 12 carbon atoms as defined herein. Examples include phenylaminocarbonyl.

$C_2$-$C_6$-Alkenyl is a singly unsaturated hydrocarbon radical having 2, 3, 4, 5 or 6 carbon atoms, e.g. vinyl, allyl(2-propen-1-yl), 1-propen-1-yl, 2-propen-2-yl, methallyl(2-methylprop-2-en-1-yl) and the like. $C_3$-$C_5$-Alkenyl is, in particular, allyl, 1-methylprop-2-en-1-yl, 2-buten-1-yl, 3-buten-1-yl, methallyl, 2-penten-1-yl, 3-penten-1-yl, 4-penten-1-yl, 1-methylbut-2-en-1-yl or 2-ethylprop-2-en-1-yl.

$C_2$-$C_6$-Alkynyl is a singly unsaturated hydrocarbon radical having 2, 3, 4, 5 or 6 carbon atoms, e.g. ethynyl, 2-propyn-1-yl, 1-propyn-1-yl, 2-propyn-2-yl and the like. $C_3$-$C_5$-Alkynyl is, in particular, 2-propyn-1-yl, 2-butyn-1-yl, 3-butyn-1-yl, 2-pentyn-1-yl, 3-pentyn-1-yl, 4-pentyn-1-yl.

$C_1$-$C_4$-Alkylene is straight-chain or branched alkylene group having from 1 to 4 carbon atoms. Examples include methylene and ethylene. A further example is propylene.

$C_2$-$C_4$-Alkenylene is straight-chain or branched alkenylene group having from 2 to 4 carbon atoms.

$C_2$-$C_4$-Alkynylene is straight-chain or branched alkynylene group having from 2 to 4 carbon atoms. Examples include propynylene.

$C_6$-$C_{12}$-Aryl is a 6- to 12-membered, in particular 6- to 10-membered, aromatic cyclic radical. Examples include phenyl and naphthyl.

$C_3$-$C_{12}$-Arylene is an aryl diradical. Examples include phen-1,4-ylene and phen-1,3-ylene.

Hydroxy is —OH.

$C_1$-$C_6$-Alkoxy is a radical of the formula R—O—, wherein R is a straight-chain or branched alkyl group having from 1 to 6, in particular 1 to 4 carbon atoms. Examples include methoxy, ethoxy, n-propoxy, isopropoxy, n-butoxy, 2-butoxy, iso-butoxy(2-methylpropoxy), tert.-butoxy pentyloxy, 1-methylbutoxy, 2-methylbutoxy, 3-methylbutoxy, 2,2-dimethylpropoxy, 1-ethylpropoxy, hexyloxy, 1,1-dimethylpropoxy, 1,2-dimethylpropoxy, 1-methylpentyloxy, 2-methylpentyloxy, 3-methylpentyloxy, 4-methylpentyloxy, 1,1-dimethylbutyloxy, 1,2-dimethylbutyloxy, 1,3-dimethylbutyloxy, 2,2-dimethylbutyloxy, 2,3-dimethylbutyloxy, 3,3-dimethylbutyloxy, 1-ethylbutyloxy, 2-ethylbutyloxy, 1,1,2-trimethylpropoxy, 1,2,2-trimethylpropoxy, 1-ethyl-1-methylpropoxy and 1-ethyl-2-methylpropoxy.

Halogenated $C_1$-$C_6$-alkoxy is a straight-chain or branched alkoxy group having from 1 to 6, preferably from 1 to 4, in particular 1 or 2 carbon atoms, wherein at least one, e.g. 1, 2, 3, 4 or all of the hydrogen atoms are replaced by 1, 2, 3, 4 or a corresponding number of identical or different halogen atoms, such as in halogenomethoxy, dihalogenomethoxy, trihalogenomethoxy, (R)-1-halogenoethoxy, (S)-1-halogenoethoxy, 2-halogenoethoxy, 1,1-dihalogenoethoxy, 2,2-dihalogenoethoxy, 2,2,2-trihalogenoethoxy, (R)-1-halogenopropoxy, (S)-1-halogenopropoxy, 2-halogenopropoxy, 3-halogenopropoxy, 1,1-dihalogenopropoxy, 2,2-dihalogenopropoxy, 3,3-dihalogenopropoxy, 3,3,3-trihalogenopropoxy, (R)-2-halogeno-1-methylethoxy, (S)-2-halogeno-1-methylethoxy, (R)-2,2-dihalogeno-1-methylethoxy, (S)-2,2-dihalogeno-1-methylethoxy, (R)-1,2-dihalogeno-1-methylethoxy, (S)-1,2-dihalogeno-1-methylethoxy, (R)-2,2,2-trihalogeno-1-methylethoxy, (S)-2,2,2-trihalogeno-1-methylethoxy, 2-halogeno-1-(halogenomethyl)ethoxy, 1-(dihalogenomethyl)-2,2-dihalogenoethoxy, (R)-1-halogenobutoxy, (S)-1-halogenobutoxy, 2-halogenobutoxy, 3-halogenobutoxy, 4-halogenobutoxy, 1,1-dihalogenobutoxy, 2,2-dihalogenobutoxy, 3,3-dihalogenobutoxy, 4,4-dihalogenobutoxy, 4,4,4-trihalogenobutoxy, etc. Particular examples include the fluorinated $C_1$-$C_4$ alkoxy groups as defined, such as trifluoromethoxy.

$C_1$-$C_6$-Hydroxyalkoxy is an alkoxy radical having from 1 to 6, preferably from 1 to 4 carbon atoms as defined herein, wherein one or two hydrogen atoms are replaced by hydroxy. Examples include 2-hydroxyethoxy, 3-hydroxypropoxy, 2-hydroxypropoxy, 1-methyl-2-hydroxyethoxy and the like.

$C_1$-$C_6$-Alkoxy-$C_1$-$C_4$-alkoxy is an alkoxy radical having from 1 to 4 carbon atoms, preferably 1 or 2 carbon atoms as defined herein, wherein one or two hydrogen atoms are replaced by one or two alkoxy radicals having from 1 to 6, preferably from 1 to 4 carbon atoms as defined herein. Examples include methoxymethoxy, 2-methoxyethoxy, 1-methoxyethoxy, 3-methoxypropoxy, 2-methoxypropoxy, 1-methyl-1-methoxyethoxy, ethoxymethoxy, 2-ethoxyethoxy, 1-ethoxyethoxy, 3-ethoxypropoxy, 2-ethoxypropoxy, 1-methyl-1-ethoxyethoxy and the like.

Amino-$C_1$-$C_4$-alkoxy is an alkoxy radical having from 1 to 4, preferably 1 or 2 carbon atoms as defined herein, wherein one hydrogen atom is replaced by an amino group. Examples include 2-aminoethoxy.

$C_1$-$C_6$-Alkylamino-$C_1$-$C_4$-alkoxy is an alkoxy radical having from 1 to 4, preferably 1 or 2 carbon atoms as defined herein, wherein one hydrogen atom is replaced by an alkylamino group having from 1 to 6, preferably from 1 to 4 carbon atoms as defined herein. Examples include methylaminomethoxy, ethylaminomethoxy, n-propylaminomethoxy, isopropylaminomethoxy, n-butylaminomethoxy, 2-butylaminomethoxy, isobutylaminomethoxy, tert-butylaminomethoxy, 2-(methylamino)ethoxy, 2-(ethylamino)ethoxy, 2-(n-propylamino)ethoxy, 2-(iso-propylamino)ethoxy, 2-(nbutylamino)ethoxy, 2-(2-butylamino)ethoxy, 2-(iso-butylamino)ethoxy, 2-(tert-butylamino)ethoxy.

Di-$C_1$-$C_6$-alkylamino-$C_1$-$C_4$-alkoxy is an alkoxy radical having from 1 to 4, preferably 1 or 2 carbon atoms as defined herein, wherein one hydrogen atom is replaced by a dialkylamino group having from 1 to 6, preferably from 1 to 4 carbon atoms as defined herein. Examples include dimethylaminomethoxy, diethylaminomethoxy, N-methyl-N-ethylamino)ethoxy, 2-(dimethylamino)ethoxy, 2-(diethylamino)ethoxy, 2-(N-methyl-N-ethylamino)ethoxy.

$C_1$-$C_6$-Alkylcarbonylamino-$C_1$-$C_4$-alkoxy is an alkoxy radical having from 1 to 4, preferably 1 or 2 carbon atoms as defined herein, wherein one hydrogen atom is replaced by an alkylcarbonylamino group wherein the alkyl group has from 1 to 6, preferably from 1 to 4 carbon atoms as defined herein. Examples include methylcarbonylaminomethoxy, ethylcarbonylaminomethoxy, n-propylcarbonylaminomethoxy, isopropylcarbonylaminomethoxy, n-butylcarbonylaminomethoxy, 2-butylcarbonylaminomethoxy, isobutylcarbonylaminomethoxy, tert-butylcarbonylaminomethoxy, 2-(methylcarbonylamino)ethoxy, 2-(ethylcarbonylamino)ethoxy, 2-(npropylcarbonylamino)ethoxy, 2-(iso-propylcarbonylamino)ethoxy, 2-(nbutylcarbonylamino)ethoxy, 2-(2-butylcarbonylamino)ethoxy, 2-(iso-butylcarbonylamino)ethoxy, 2-(tert-butylcarbonylamino)ethoxy.

$C_6$-$C_{12}$-Arylcarbonylamino-$C_1$-$C_4$-alkoxy is an alkoxy radical having from 1 to 4, preferably 1 or 2 carbon atoms as defined herein, wherein one hydrogen atom is replaced by a $C_6$-$C_{12}$-arylcarbonylamino group as defined herein. Examples include 2-(benzoylamino)ethoxy.

$C_1$-$C_6$-Alkoxycarbonylamino-$C_1$-$C_4$-alkoxy is an alkoxy radical having from 1 to 4, preferably 1 or 2 carbon atoms as defined herein, wherein one hydrogen atom is replaced by an alkoxycarbonylamino group wherein the alkoxy group has from 1 to 6, preferably from 1 to 4 carbon atoms as defined herein. Examples include methoxycarbonylaminomethoxy, ethoxycarbonylaminomethoxy, n-propoxycarbonylaminomethoxy, isopropoxycarbonylaminomethoxy, n-butoxycarbonylaminomethoxy, 2-butoxycarbonylaminomethoxy, iso-butoxycarbonylaminomethoxy, tertbutoxycarbonylaminomethoxy, 2-(methoxycarbonylamino)ethoxy, 2-(ethoxycarbonylamino)ethoxy, 2-(n-propoxycarbonylamino)ethoxy, 2-(iso-propoxycarbonylamino)ethoxy, 2-(n-butoxycarbonylamino)ethoxy, 2-(2-butoxycarbonylamino)ethoxy, 2-(isobutoxycarbonylamino)ethoxy, 2-(tert-butoxycarbonylamino)ethoxy.

$C_2$-$C_6$-Alkenyloxy is a radical of the formula R—O—, wherein R is a straight-chain or branched alkenyl group having from 2 to 6, in particular 2 to 4 carbon atoms. Examples include vinyloxy, allyloxy(2-propen-1-yloxy), 1-propen-1-yloxy, 2-propen-2-yloxy, methallyloxy(2-methylprop-2-en-1-yloxy) and the like. $C_3$-$C_5$-Alkenyloxy is, in particular, allyloxy, 1-methylprop-2-en-1-yloxy, 2-buten-1-yloxy, 3-buten-1-yloxy, methallyloxy, 2-penten-1-yloxy, 3-penten-1-yloxy, 4-penten-1-yloxy, 1-methylbut-2-en-1-yloxy or 2-ethylprop-2-en-1-yloxy.

$C_6$-$C_{12}$-Aryl-$C_1$-$C_4$-alkoxy is an alkoxy radical having from 1 to 4, preferably 1 or 2 carbon atoms as defined herein, wherein one hydrogen atom is replaced by a $C_6$-$C_{12}$-aryl group as defined herein. Examples include benzyloxy.

$C_1$-$C_6$-Alkylsulfonylamino-$C_1$-$C_4$-alkoxy is an alkoxy radical having from 1 to 4, preferably 1 or 2 carbon atoms as defined herein, wherein one hydrogen atom is replaced by an alkylsulfonylamino group having from 1 to 6, preferably from 1 to 4 carbon atoms as defined herein. Examples include 2-(methylsulfonylamino)ethoxy, 2-(ethylsulfonylamino)ethoxy, 2-[(2-methylpropyl)sulfonylamino]ethoxy.

(Halogenated $C_1$-$C_6$-alkyl)sulfonylamino-$C_1$-$C_4$-alkoxy is an alkoxy radical having from 1 to 4, preferably 1 or 2 carbon atoms as defined herein, wherein one hydrogen atom is replaced by an alkylsulfonylamino group having from 1 to 6, preferably from 1 to 4 carbon atoms as defined herein, wherein the alkyl group is halogenated. Examples include 2-(trifluoromethylsulfonylamino)ethoxy.

$C_6$-$C_{12}$-Arylsulfonylamino-$C_1$-$C_4$-alkoxy is an alkoxy radical having from 1 to 4, preferably 1 or 2 carbon atoms as defined herein, wherein one hydrogen atom is replaced by a $C_6$-$C_{12}$-arylsulfonylamino group as defined herein. Examples include 2-(phenylsulfonylamino)ethoxy, 2-(naphthylsulfonylamino)ethoxy.

($C_6$-$C_{12}$-Aryl-$C_1$-$C_6$-alkyl)sulfonylamino-$C_1$-$C_4$-alkoxy is an alkoxy radical having from 1 to 4, preferably 1 or 2 carbon atoms as defined herein, wherein one hydrogen atom is replaced by a ($C_6$-$C_{12}$-aryl-$C_1$-$C_6$-alkyl)sulfonylamino group, preferably by a ($C_6$-$C_{12}$-aryl-$C_1$-$C_2$-alkyl)sulfonylamino group. Examples include 2-(benzylsulfonylamino)ethoxy.

$C_3$-$C_{12}$-Heterocyclylsulfonylamino-$C_1$-$C_4$-alkoxy is an alkoxy radical having from 1 to 4, preferably 1 or 2 carbon atoms as defined herein, wherein one hydrogen atom is replaced by a $C_3$-$C_{12}$-heterocyclylsulfonylamino group as defined herein. Examples include 2-(pyridin-3-yl-sulfonylamino)ethoxy.

$C_3$-$C_{12}$-Heterocyclyl-$C_1$-$C_4$-alkoxy is an alkoxy radical having from 1 to 4, preferably 1 or 2 carbon atoms as defined herein, wherein one hydrogen atom is replaced by a $C_3$-$C_{12}$-heterocyclyl group as defined herein. Examples include 2-(N-pyrrolidinyl)ethoxy, 2-(Nmorpholinyl)ethoxy and 2-(N-imidazolyl)ethoxy.

$C_1$-$C_2$-Alkylenedioxo is a radical of the formula —O—R—O—, wherein R is a straight-chain or branched alkylene group having from 1 or 2 carbon atoms as defined herein. Examples include methylenedioxo.

$C_6$-$C_{12}$-Aryloxy is a radical of the formula R—O—, wherein R is an aryl group having from 6 to 12, in particular 6 carbon atoms as defined herein. Examples include phenoxy.

$C_3$-$C_{12}$-Heterocyclyloxy is a radical of the formula R—O—, wherein R is a $C_3$-$C_{12}$-heterocyclyl group having from 3 to 12, in particular from 3 to 7 carbon atoms as defined herein. Examples include pyridin-2-yloxy.

$C_1$-$C_6$-Alkylthio is a radical of the formula R—S—, wherein R is an alkyl radical having from 1 to 6, preferably from 1 to 4 carbon atoms as defined herein. Examples include methylthio, ethylthio, propylthio, butylthio, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropyl and 1-ethyl-2-methylpropyl.

Halogenated $C_1$-$C_6$-alkylthio is a radical of the formula R—S—, wherein R is a halogenated alkyl radical from 1 to 6, preferably from 1 to 4 carbon atoms as defined herein. Examples include halogenomethylthio, dihalogenomethylthio, trihalogenomethylthio, (R)-1-halogenoethylthio, (S)-1-halogenoethylthio, 2-halogenoethylthio, 1,1-dihalogenoethylthio, 2,2-dihalogenoethylthio, 2,2,2-trihalogenoethylthio, (R)-1-halogenopropylthio, (S)-1-halogenopropylthio, 2-halogenopropylthio, 3-halogenopropylthio, 1,1-dihalogenopropylthio, 2,2-dihalogenopropylthio, 3,3-dihalogenopropylthio, 3,3,3-trihalogenopropylthio, (R)-2-halogeno-1-methylethylthio, (S)-2-halogeno-1-methylethylthio, (R)-2,2-dihalogeno-1-methylethylthio, (S)-2,2-dihalogeno-1-methylethylthio, (R)-1,2-dihalogeno-1-methylethylthio, (S)-1,2-dihalogeno-1-methylethylthio, (R)-2,2,2-trihalogeno-1-methylethylthio, (S)-2,2,2-trihalogeno-1-methylethylthio, 2-halogeno-1-(halogenomethyl)ethylthio, 1-(dihalogenomethyl)-2,2-dihalogenoethylthio, (R)-1-halogenobutylthio, (S)-1-halogenobutylthio, 2-halogenobutylthio, 3-halogenobutylthio, 4-halogenobutylthio, 1,1-dihalogenobutylthio, 2,2-dihalogenobutylthio, 3,3-dihalogenobutylthio, 4,4-dihalogenobutylthio, 4,4,4-trihalogenobutylthio, etc. Particular examples include the fluorinated $C_1$-$C_4$ alkylthio groups as defined, such as trifluoromethylthio.

$C_1$-$C_6$-Alkylsulfinyl is a radical of the formula R—S(O)—, wherein R is an alkyl radical having from 1 to 6, preferably from 1 to 4 carbon atoms as defined herein. Examples include methylsulfinyl, ethylsulfinyl, propylsulfinyl, butylsulfinyl, pentylsulfinyl, 1-methylbutylsulfinyl, 2-methylbutylsulfinyl, 3-methylbutylsulfinyl, 2,2-dimethylpropylsulfinyl, 1-ethylpropylsulfinyl, hexylsulfinyl, 1,1-dimethylpropylsulfinyl, 1,2-dimethylpropylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropyl and 1-ethyl-2-methylpropyl.

$C_1$-$C_6$-Alkylsulfonyl is a radical of the formula R—S(O)$_2$—, wherein R is an alkyl radical having from 1 to 6, preferably from 1 to 4 carbon atoms as defined herein. Examples include methylsulfonyl, ethylsulfonyl, propylsulfonyl, butylsulfonyl, pentylsulfonyl, 1-methylbutylsulfonyl, 2-methylbutylsulfonyl, 3-methylbutylsulfonyl, 2,2-dimethylpropylsulfonyl, 1-ethylpropylsulfonyl, hexylsulfonyl, 1,1-dimethylpropylsulfonyl, 1,2-dimethylpropylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropyl and 1-ethyl-2-methylpropyl.

(Halogenated $C_1$-$C_6$-alkyl)sulfonyl is a $C_1$-$C_6$-alkylsulfonyl as defined herein, wherein at least one, e.g. 1, 2, 3, 4 or all of the hydrogen atoms are replaced by 1, 2, 3, 4 or a corresponding number of identical or different halogen atoms.

$C_6$-$C_{12}$-Arylsulfonyl is a radical of the formula R—S(O)$_2$—, wherein R is an aryl radical having from 6 to 12 carbon atoms as defined herein. Examples include phenylsulfonyl.

($C_6$-$C_{12}$-Aryl-$C_1$-$C_4$-alkyl)sulfonyl is a radical of the formula R—S(O)$_2$—, wherein R is a $C_6$-$C_{12}$-aryl-$C_1$-$C_4$-alkyl radical, in particular a $C_6$-$C_{12}$-aryl-$C_1$-$C_2$-alkyl radical as defined herein. Examples include benzylsulfonyl.

$C_3$-$C_{12}$-Heterocyclylsulfonyl is a radical of the formula R—S(O)$_2$—, wherein R is $C_3$-$C_{12}$-heterocyclyl as defined herein.

Aminosulfonyl is NH$_2$—S(O)$_2$—.

$C_1$-$C_6$-Alkylaminosulfonyl is a radical of the formula R—NH—S(O)$_2$— wherein R is an alkyl radical having from 1 to 6, preferably from 1 to 4 carbon atoms as defined herein. Examples include methylaminosulfonyl, ethylaminosulfonyl, n-propylaminosulfonyl, isopropylaminosulfonyl, n-butylaminosulfonyl, 2-butylaminosulfonyl, iso-butylaminosulfonyl, tert-butylaminosulfonyl.

Di-$C_1$-$C_6$-alkylaminosulfonyl is a radical of the formula RR'N—S(O)$_2$— wherein R and R' are independently of each other an alkyl radical having from 1 to 6, preferably from 1 to 4 carbon atoms as defined herein. Examples include dimethylaminosulfonyl, diethylaminosulfonyl, N-methyl-N-ethylaminosulfonyl.

$C_6$-$C_{12}$-Arylaminosulfonyl is a radical of the formula R—NH—S(O)$_2$— wherein R is an aryl radical having from 6 to 12, preferably 6 carbon atoms as defined herein.

Amino is NH$_2$.

$C_1$-$C_6$-Alkylamino is a radical of the formula R—NH— wherein R is an alkyl radical having from 1 to 6, in particular from 1 to 4 carbon atoms as defined herein. Examples include methylamino, ethylamino, n-propylamino, iso-propylamino, n-butylamino, 2-butylamino, iso-butylamino, tert-butylamino.

(Halogenated $C_1$-$C_6$-alkyl)amino is a $C_1$-$C_6$-alkylamino as defined herein, wherein at least one, e.g. 1, 2, 3, 4 or all of the hydrogen atoms are replaced by 1, 2, 3, 4 or a corresponding number of identical or different halogen atoms.

Di-$C_1$-$C_6$-alkylamino is a radical of the formula RR'N— wherein R and R' are independently of each other an alkyl radical having from 1 to 6, in particular from 1 to 4 carbon atoms as defined herein. Examples include dimethylamino, diethylamino, N-methyl-N-ethylamino. Di-(halogenated $C_1$-$C_6$-alkyl)amino is a di-$C_1$-$C_6$-alkylamino as defined herein, wherein at least one, e.g. 1, 2, 3, 4 or all of the hydrogen atoms are replaced by 1, 2, 3, 4 or a corresponding number of identical or different halogen atoms.

$C_1$-$C_6$-Alkylcarbonylamino is a radical of the formula R—C(O)—NH—, wherein R is an alkyl radical having from 1 to 6, in particular from 1 to 4 carbon atoms as defined herein. Examples include acetamido(methylcarbonylamino), propionamido, n-butyramido, 2-methylpropionamido(isopropylcarbonylamino), 2,2-dimethylpropionamido and the like.

(Halogenated $C_1$-$C_6$-alkyl)carbonylamino is a $C_1$-$C_6$-alkylcarbonylamino as defined herein, wherein at least one, e.g. 1, 2, 3, 4 or all of the hydrogen atoms are replaced by 1, 2, 3, 4 or a corresponding number of identical or different halogen atoms.

$C_6$-$C_{12}$-Arylcarbonylamino is a radical of the formula R—C(O)—NH—, wherein R is an aryl radical having from 6 to 12 carbon atoms as defined herein. Examples include phenylcarbonylamino.

$C_2$-$C_6$-Alkenylamino is a radical of the formula R—NH—, wherein R is a straight-chain or branched alkenyl group having from 2 to 6, in particular 2 to 4 carbon atoms. Examples include vinylamino, allylamino (2-propen-1-ylamino), 1-propen-1-ylamino, 2-propen-2-ylamino, methallylamino (2-methylprop-2-en-1-ylamino) and the like. $C_3$-$C_5$-Alkenylamino is, in particular, allylamino, 1-methylprop-2-en-1-ylamino, 2-buten-1-ylamino, 3-buten-1-ylamino, methallylamino, 2-penten-1-ylamino, 3-penten-1-ylamino, 4-penten-1-ylamino, 1-methylbut-2-en-1-ylamino or 2-ethylprop-2-en-1-ylamino.

$C_1$-$C_6$-Alkylsulfonylamino is a radical of the formula R—S(O)$_2$—NH—, wherein R is an alkyl radical having from 1 to 6, in particular from 1 to 4 carbon atoms as defined herein. Examples include methylsulfonylamino, ethylsulfonylamino, n-propylsulfonylamino, isopropylsulfonylamino, n-butylsulfonylamino, 2-butylsulfonylamino, iso-butylsulfonylamino, tert-butylsulfonylamino.

(Halogenated $C_1$-$C_6$ alkyl)sulfonylamino is a $C_1$-$C_6$-alkylsulfonylamino as defined herein, wherein at least one, e.g. 1, 2, 3, 4 or all of the hydrogen atoms are replaced by 1, 2, 3, 4 or a corresponding number of identical or different halogen atoms.

$C_6$-$C_{12}$-Arylsulfonylamino is a radical of the formula R—S(O)$_2$—NH—, wherein R is an aryl radical having from 6 to 12 carbon atoms as defined herein. Examples include phenylsulfonylamino.

Nitro is —NO$_2$.

$C_3$-$C_{12}$-Heterocyclyl is a 3- to 12-membered heterocyclic radical including a saturated heterocyclic radical, which generally has 3, 4, 5, 6, or 7 ring forming atoms (ring members), an unsaturated non-aromatic heterocyclic radical, which generally has 5, 6 or 7 ring forming atoms, and a heteroaromatic radical (hetaryl), which generally has 5, 6 or 7 ring forming atoms. The heterocyclic radicals may be bound via a carbon atom (C-bound) or a nitrogen atom (N-bound). Preferred heterocyclic radicals comprise 1 nitrogen atom as ring member atom and optionally 1, 2 or 3 further heteroatoms as ring members, which are selected, independently of each other from O, S and N. Likewise preferred heterocyclic radicals comprise 1 heteroatom as ring member, which is selected from O, S and N, and optionally 1, 2 or 3 further nitrogen atoms as ring members.

Examples of $C_3$-$C_{12}$-heterocyclyl include:

C- or N-bound 3-4-membered, saturated rings, such as 2-oxiranyl, 2-oxetanyl, 3-oxetanyl, 2-aziridinyl, 3-thiethanyl, 1-azetidinyl, 2-azetidinyl, 3-azetidinyl;

C-bound, 5-membered, saturated rings, such as tetrahydrofuran-2-yl, tetrahydrofuran-3-yl, tetrahydrothien-2-yl, tetrahydrothien-3-yl, tetrahydropyrrol-2-yl, tetrahydropyrrol-3-yl, tetrahydropyrazol-3-yl, tetrahydro-pyrazol-4-yl, tetrahydroisoxazol-3-yl, tetrahydroisoxazol-4-yl, tetrahydroisoxazol-5-yl, 1,2-oxathiolan-3-yl, 1,2-oxathiolan-4-yl, 1,2-oxathiolan-5-yl, tetrahydroisothiazol-3-yl, tetrahydroisothiazol-4-yl, tetrahydroisothiazol-5-yl, 1,2-dithiolan-3-yl, 1,2-dithiolan-4-yl, tetrahydroimidazol-2-yl, tetrahydroimidazol-4-yl, tetrahydrooxazol-2-yl, tetrahydrooxazol-4-yl, tetrahydrooxazol-5-yl, tetrahydrothiazol-2-yl, tetrahydrothiazol-4-yl, tetrahydrothiazol-5-yl, 1,3-dioxolan-2-yl, 1,3-dioxolan-4-yl, 1,3-oxathiolan-2-yl, 1,3-oxathiolan-4-yl, 1,3-oxathiolan-5-yl, 1,3-dithiolan-2-yl, 1,3-dithiolan-4-yl, 1,3,2-dioxathiolan-4-yl;

C-bound, 6-membered, saturated rings, such as tetrahydropyran-2-yl, tetrahydropyran-3-yl, tetrahydropyran-4-yl, piperidin-2-yl, piperidin-3-yl, piperidin-4-yl, tetrahydrothiopyran-2-yl, tetrahydrothiopyran-3-yl, tetrahydrothiopyran-4-yl, 1,3-dioxan-2-yl, 1,3-dioxan-4-yl, 1,3-dioxan-5-yl, 1,4-dioxan-2-yl, 1,3-dithian-2-yl, 1,3-dithian-4-yl, 1,3-dithian-5-yl, 1,4-dithian-2-yl, 1,3-oxathian-2-yl, 1,3-oxathian-4-yl, 1,3-oxathian-5-yl, 1,3-oxathian-6-yl, 1,4-oxathian-2-yl, 1,4-oxathian-3-yl, 1,2-dithian-3-yl, 1,2-dithian-4-yl, hexahydropyrimidin-2-yl, hexahydropyrimidin-4-yl, hexahydropyrimidin-5-yl, hexahydropyrazin-2-yl, hexahydropyridazin-3-yl, hexahydropyridazin-4-yl, tetrahydro-1,3-oxazin-2-yl, tetrahydro-1,3-oxazin-4-yl, tetrahydro-1,3-oxazin-5-yl, tetrahydro-1,3-oxazin-6-yl, tetrahydro-1,3-thiazin-2-yl, tetrahydro-1,3-thiazin-4-yl, tetrahydro-1,3-thiazin-5-yl, tetrahydro-1,3-thiazin-6-yl, tetrahydro-1,4-thiazin-2-yl, tetrahydro-1,4-thiazin-3-yl, tetrahydro-1,4-oxazin-2-yl, tetrahydro-1,4-oxazin-3-yl, tetrahydro-1,2-oxazin-3-yl, tetrahydro-1,2-oxazin-4-yl, tetrahydro-1,2-oxazin-5-yl, tetrahydro-1,2-oxazin-6-yl;

N-bound, 5-membered, saturated rings, such as tetrahydropyrrol-1-yl(pyrrolidin-1-yl), tetrahydropyrazol-1-yl, tetrahydroisoxazol-2-yl, tetrahydroisothiazol-2-yl, tetrahydroimidazol-1-yl, tetrahydrooxazol-3-yl, tetrahydrothiazol-3-yl;

N-bound, 6-membered, saturated rings, such as piperidin-1-yl, hexahydropyrimidin-1-yl, hexahydropyrazin-1-yl(piperazin-1-yl), hexahydropyridazin-1-yl, tetrahydro-1,3-oxazin-3-yl, tetrahydro-1,3-thiazin-3-yl, tetrahydro-1,4-thiazin-4-yl, tetrahydro-1,4-oxazin-4-yl(morpholin-1-yl), tetrahydro-1,2-oxazin-2-yl;

C-bound, 5-membered, partially unsaturated rings, such as 2,3-dihydrofuran-2-yl, 2,3-dihydrofuran-3-yl, 2,5-dihydrofuran-2-yl, 2,5-di-hydrofuran-3-yl, 4,5-dihydrofuran-2-yl, 4,5-dihydrofuran-3-yl, 2,3-dihydro-thien-2-yl, 2,3-dihydrothien-3-yl, 2,5-dihydrothien-2-yl, 2,5-dihydrothien-3-yl, 4,5-dihydrothien-2-yl, 4,5-dihydrothien-3-yl, 2,3-dihydro-1H-pyrrol-2-yl, 2,3-dihydro-1H-pyrrol-3-yl, 2,5-dihydro-1H-pyrrol-2-yl, 2,5-dihydro-1H-pyrrol-3-yl, 4,5-dihydro-1H-pyrrol-2-yl, 4,5-dihydro-1H-pyrrol-3-yl, 3,4-dihydro-2H-pyrrol-2-yl, 3,4-dihydro-2H-pyrrol-3-yl, 3,4-dihydro-5H-pyrrol-2-yl, 3,4-dihydro-5H-pyrrol-3-yl, 4,5-dihydro-1H-pyrazol-3-yl, 4,5-dihydro-1H-pyrazol-4-yl, 4,5-dihydro-1H-pyrazol-5-yl, 2,5-dihydro-1H-pyrazol-3-yl, 2,5-dihydro-1H-pyrazol-4-yl, 2,5-dihydro-1H-pyrazol-5-yl, 4,5-dihydroisoxazol-3-yl, 4,5-dihydroisoxazol-4-yl, 4,5-dihydroisoxazol-5-yl, 2,5-dihydroisoxazol-3-yl, 2,5-dihydroisoxazol-4-yl, 2,5-dihydroisoxazol-5-yl, 2,3-dihydroisoxazol-3-yl, 2,3-dihydroisoxazol-4-yl, 2,3-dihydroisoxazol-5-yl, 4,5-dihydroisothiazol-3-yl, 4,5-dihydroisothiazol-4-yl, 4,5-dihydroisothiazol-5-yl, 2,5-dihydroisothiazol-3-yl, 2,5-dihydroisothiazol-4-yl, 2,5-dihydroisothiazol-5-yl, 2,3-dihydroisothiazol-3-yl, 2,3-dihydroisothiazol-4-yl, 2,3-dihydroisothiazol-5-yl, 4,5-dihydro-1H-imidazol-2-yl, 4,5-dihydro-1H-imidazol-4-yl, 4,5-dihydro-1H-imidazol-5-yl, 2,5-dihydro-1H-imidazol-2-yl, 2,5-dihydro-1H-imidazol-4-yl, 2,5-dihydro-1H-imidazol-5-yl, 2,3-dihydro-1H-imidazol-2-yl, 2,3-dihydro-1H-imidazol-4-yl, 4,5-dihydro-oxazol-2-yl, 4,5-dihydrooxazol-4-yl, 4,5-dihydrooxazol-5-yl, 2,5-dihydrooxazol-2-yl, 2,5-dihydrooxazol-4-yl, 2,5-dihydrooxazol-5-yl, 2,3-dihydrooxazol-2-yl, 2,3-dihydrooxazol-4-yl, 2,3-dihydrooxazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydrothiazol-2-yl, 2,3-dihydrothiazol-4-yl, 2,3-dihydrothiazol-5-yl, 1,3-dioxol-2-yl, 1,3-dioxol-4-yl, 1,3-dithiol-2-yl, 1,3-dithiol-4-yl, 1,3-oxathiol-2-yl, 1,3-oxathiol-4-yl, 1,3-oxathiol-5-yl;

C-bound, 6-membered, partially unsaturated rings, such as 2H-3,4-dihydropyran-6-yl, 2H-3,4-dihydropyran-5-yl, 2H-3,4-dihydropyran-4-yl, 2H-3,4-dihydropyran-3-yl, 2H-3,4-dihydropyran-2-yl, 2H-3,4-dihydrothiopyran-6-yl, 2H-3,4-dihydrothiopyran-5-yl, 2H-3,4-dihydrothiopyran-4-yl, 2H-3,4-dihydrothiopyran-3-yl, 2H-3,4-dihydrothiopyran-2-yl, 1,2,3,4-tetrahydropyridin-6-yl, 1,2,3,4-tetrahydropyridin-5-yl, 1,2,3,4-tetrahydropyridin-4-yl, 1,2,3,4-tetrahydropyridin-3-yl, 1,2,3,4-tetrahydropyridin-2-yl, 2H-5,6-dihydropyran-2-yl, 2H-5,6-dihydropyran-3-yl, 2H-5,6-dihydropyran-4-yl, 2H-5,6-dihydropyran-5-yl, 2H-5,6-dihydropyran-6-yl, 2H-5,6-dihydrothiopyran-2-yl, 2H-5,6-dihydrothiopyran-3-yl, 2H-5,6-dihydrothiopyran-4-yl, 2H-5,6-dihydrothiopyran-5-yl, 2H-5,6-dihydrothiopyran-6-yl, 1,2,5,6-tetrahydropyridin-2-yl, 1,2,5,6-tetrahydropyridin-3-yl, 1,2,5,6-tetrahydropyridin-4-yl, 1,2,5,6-tetrahydropyridin-5-yl, 1,2,5,6-tetrahydropyridin-6-yl, 2,3,4,5-tetrahydropyridin-2-yl, 2,3,4,5-tetrahydropyridin-3-yl, 2,3,4,5-tetrahydropyridin-4-yl, 2,3,4,5-tetrahydropyridin-5-yl, 2,3,4,5-tetrahydropyridin-6-yl, 4H-pyran-2-yl, 4H-pyran-3-yl, 4H-pyran-4-yl, 4H-thiopyran-2-yl, 4H-thiopyran-3-yl, 4H-thiopyran-4-yl, 1,4-dihydropyridin-2-yl, 1,4-dihydropyridin-3-yl, 1,4-dihydropyridin-4-yl, 2H-pyran-2-yl, 2H-pyran-3-yl, 2H-pyran-4-yl, 2H-pyran-5-yl, 2H-pyran-6-yl, 2H-thiopyran-2-yl, 2H-thiopyran-3-yl, 2H-thiopyran-4-yl, 2H-thiopyran-5-yl, 2H-thiopyran-6-yl, 1,2-dihydropyridin-2-yl, 1,2-dihydro-pyridin-3-yl, 1,2-dihydropyridin-4-yl, 1,2-dihydropyridin-5-yl, 1,2-dihydro-pyridin-6-yl, 3,4-dihydropyridin-2-yl, 3,4-dihydropyridin-3-yl, 3,4-dihydro-pyridin-4-yl, 3,4-dihydropyridin-5-yl, 3,4-dihydropyridin-6-yl, 2,5-dihydropyridin-2-yl, 2,5-dihydropyridin-3-yl, 2,5-dihydropyridin-4-yl, 2,5-dihydropyridin-5-yl, 2,5-dihydropyridin-6-yl, 2,3-dihydropyridin-2-yl, 2,3-dihydropyridin-3-yl, 2,3-dihydropyridin-4-yl, 2,3-dihydropyridin-5-yl, 2,3-dihydropyridin-6-yl, 2H-5,6-dihydro-1,2-oxazin-3-yl, 2H-5,6-dihydro-1,2-oxazin-4-yl, 2H-5,6-dihydro-1,2-oxazin-5-yl, 2H-5,6-dihydro-1,2-oxazin-6-yl, 2H-5,6-dihydro-1,2-thiazin-3-yl, 2H-5,6-dihydro-1,2-thiazin-4-yl, 2H-5,6-dihydro-1,2-thiazin-5-yl, 2H-5,6-dihydro-1,2-thiazin-6-yl, 4H-5,6-dihydro-1,2-oxazin-3-yl, 4H-5,6-dihydro-1,2-oxazin-4-yl, 4H-5,6-dihydro-1,2-oxazin-5-yl, 4H-5,6-dihydro-1,2-oxazin-6-yl, 4H-5,6-dihydro-1,2-thiazin-3-yl, 4H-5,6-dihydro-1,2-thiazin-4-yl, 4H-5,6-dihydro-1,2-thiazin-5-yl, 4H-5,6-dihydro-1,2-thiazin-6-yl, 2H-3,6-dihydro-1,2-oxazin-3-yl, 2H-3,6-dihydro-1,2-oxazin-4-yl, 2H-3,6-dihydro-1,2-oxazin-5-yl, 2H-3,6-dihydro-1,2-oxazin-6-yl, 2H-3,6-dihydro-1,2-thiazin-3-yl, 2H-3,6-dihydro-1,2-thiazin-4-yl, 2H-3,6-dihydro-1,2-thiazin-5-yl, 2H-3,6-dihydro-1,2-thiazin-6-yl, 2H-3,4-dihydro-1,2-oxazin-3-yl, 2H-3,4-dihydro-1,2-oxazin-4-yl, 2H-3,4-dihydro-1,2-oxazin-5-yl, 2H-3,4-dihydro-1,2-oxazin-6-yl, 2H-3,4- dihydro-1,2-thiazin-3-yl, 2H-3,4-dihydro-1,2-thiazin-4-yl, 2H-3,4-dihydro-1,2-thiazin-5-yl, 2H-3,4-dihydro-1,2-thiazin-6-yl, 2,3,4,5-tetrahydropyridazin-3-yl, 2,3,4,5-tetrahydropyridazin-4-yl, 2,3,4,5-tetrahydropyridazin-5-yl, 2,3,4,5-tetrahydropyridazin-6-yl, 3,4,5,6-tetrahydropyridazin-3-yl, 3,4,5,6-tetrahydropyridazin-4-yl, 1,2,5,6-tetrahydropyridazin-3-yl, 1,2,5,6-tetrahydropyridazin-4-yl, 1,2,5,6-tetrahydropyridazin-5-yl, 1,2,5,6-tetrahydropyridazin-6-yl, 1,2,3,6-tetrahydro-pyridazin-3-yl, 1,2,3,6-tetrahydropyridazin-4-yl, 4H-5,6-dihydro-1,3-oxazin-2-yl, 4H-5,6-dihydro-1,3-oxazin-4-yl, 4H-5,6-dihydro-1,3-oxazin-5-yl, 4H-5,6-dihydro-1,3-oxazin-6-yl, 4H-5,6-dihydro-1,3-thiazin-2-yl, 4H-5,6-dihydro-1,3-thiazin-4-yl, 4H-5,6-dihydro-1,3-thiazin-5-yl, 4H-5,6-dihydro-1,3-thiazin-6-yl, 3,4,5-6-tetrahydropyrimidin-2-yl, 3,4,5,6-tetrahydropyrimidin-4-yl, 3,4,5,6-tetrahydropyrimidin-5-yl, 3,4,5,6-tetrahydropyrimidin-6-yl, 1,2,3,4-tetrahydropyrazin-2-yl, 1,2,3,4-tetrahydropyrazin-5-yl, 1,2,3,4-tetrahydro-pyrimidin-2-yl, 1,2,3,4-tetrahydropyrimidin-4-yl, 1,2,3,4-tetrahydropyrimidin-5-yl, 1,2,3,4-tetrahydropyrimidin-6-yl, 2,3-dihydro-1,4-thiazin-2-yl, 2,3-dihydro-1,4-thiazin-3-yl, 2,3-dihydro-1,4-thiazin-5-yl, 2,3-dihydro-1,4-thiazin-6-yl, 2H-1,3-oxazin-2-yl, 2H-1,3-oxazin-4-yl, 2H-1,3-oxazin-5-yl, 2H-1,3-oxazin-6-yl, 2H-1,3-thiazin-2-yl, 2H-1,3-thiazin-4-yl, 2H-1,3-thiazin-5-yl, 2H-1,3-thiazin-6-yl, 4H-1,3-oxazin-2-yl, 4H-1,3-oxazin-4-yl, 4H-1,3-oxazin-5-yl, 4H-1,3-oxazin-6-yl, 4H-1,3-thiazin-2-yl, 4H-1,3-thiazin-4-yl, 4H-1,3-thiazin-5-yl, 4H-1,3-thiazin-6-yl, 6H-1,3-oxazin-2-yl, 6H-1,3-oxazin-4-yl, 6H-1,3-oxazin-5-yl, 6H-1,3-oxazin-6-yl, 6H-1,3-thiazin-2-yl, 6H-1,3-oxazin-4-yl, 6H-1,3-oxazin-5-yl, 6H-1,3-thiazin-6-yl, 2H-1,4-oxazin-2-yl, 2H-1,4-oxazin-3-yl, 2H-1,4-oxazin-5-yl, 2H-1,4-oxazin-6-yl, 2H-1,4-thiazin-2-yl, 2H-1,4-thiazin-3-yl, 2H-1,4-thiazin-5-yl, 2H-1,4-thiazin-6-yl, 4H-1,4-oxazin-2-yl, 4H-1,4-oxazin-3-yl, 4H-1,4-thiazin-2-yl, 4H-1,4-thiazin-3-yl, 1,4-dihydropyridazin-3-yl, 1,4-dihydropyridazin-4-yl, 1,4-dihydropyridazin-5-yl, 1,4-dihydropyridazin-6-yl, 1,4-dihydropyrazin-2-yl, 1,2-dihydropyrazin-2-yl, 1,2-dihydropyrazin-3-yl, 1,2-dihydropyrazin-5-yl, 1,2-dihydropyrazin-6-yl, 1,4-dihydropyrimidin-2-yl, 1,4-dihydropyrimidin-4-yl, 1,4-dihydropyrimidin-5-yl, 1,4-dihydropyrimidin-6-yl, 3,4-dihydropyrimidin-2-yl, 3,4-dihydropyrimidin-4-yl, 3,4-dihydropyrimidin-5-yl or 3,4-dihydropyrimidin-6-yl;

N-bound, 5-membered, partially unsaturated rings, such as 2,3-dihydro-1H-pyrrol-1-yl, 2,5-dihydro-1H-pyrrol-1-yl, 4,5-dihydro-1H-pyrazol-1-yl, 2,5-dihydro-1H-pyrazol-1-yl, 2,3-dihydro-1H-pyrazol-1-yl, 2,5-dihydroisoxazol-2-yl, 2,3-dihydroisoxazol-2-yl, 2,5-dihydroisothiazol-2-yl, 2,3-dihydroisoxazol-2-yl, 4,5-dihydro-1H-imidazol-1-yl, 2,5-dihydro-1H-imidazol-1-yl, 2,3-dihydro-1H-imidazol-1-yl, 2,3-dihydrooxazol-3-yl, 2,3-dihydrothiazol-3-yl;

N-bound, 6-membered, partially unsaturated rings, such as 1,2,3,4-tetrahydropyridin-1-yl, 1,2,5,6-tetrahydropyridin-1-yl, 1,4-dihydro-pyridin-1-yl, 1,2-dihydropyridin-1-yl, 2H-5,6-dihydro-1,2-oxazin-2-yl, 2H-5,6-dihydro-1,2-thiazin-2-yl, 2H-3,6-dihydro-1,2-oxazin-2-yl, 2H-3,6-dihydro-1,2-thiazin-2-yl, 2H-3,4-dihydro-1,2-oxazin-2-yl, 2H-3,4-dihydro-1,2-thiazin-2-yl, 2,3,4,5-tetrahydropyridazin-2-yl, 1,2,5,6-tetrahydropyridazin-1-yl, 1,2,5,6-tetrahydropyridazin-2-yl, 1,2,3,6-tetrahydropyridazin-1-yl, 3,4,5,6-tetrahydropyrimidin-3-yl, 1,2,3,4-tetrahydropyrazin-1-yl, 1,2,3,4-tetrahydropyrimidin-1-yl, 1,2,3,4-tetrahydropyrimidin-3-yl, 2,3-dihdro-1,4-thiazin-4-yl, 2H-1,2-oxazin-2-yl, 2H-1,2-thiazin-2-yl, 4H-1,4-oxazin-4-yl, 4H-1,4-thiazin-4-yl, 1,4-dihydropyridazin-1-yl, 1,4-dihydropyrazin-1-yl, 1,2-dihydropyrazin-1-yl, 1,4-dihydropyrimidin-1-yl or 3,4-dihydropyrimidin-3-yl;

C-bound, 5-membered, heteroaromatic rings, such as 2-furyl, 3-furyl, 2-thienyl, 3-thienyl, pyrrol-2-yl, pyrrol-3-yl, pyrazol-3-yl, pyrazol-4-yl, isoxazol-3-yl, isoxazol-4-yl, isoxazol-5-yl, isothiazol-3-yl, isothiazol-4-yl, isothiazol-5-yl, imidazol-2-yl, imidazol-4-yl, oxazol-2-yl, oxazol-4-yl, oxazol-5-yl, thiazol-2-yl, thiazol-4-yl, thiazol-5-yl, 1,2,3-oxadiazol-4-yl, 1,2,3-oxadiazol-5-yl, 1,2,4-oxadiazol-3-yl, 1,2,4-oxadiazol-5-yl, 1,3,4-oxadiazol-2-yl, 1,2,3-thiadiazol-4-yl, 1,2,3-thiadiazol-5-yl, 1,2,4-thiadiazol-3-yl, 1,2,4-thiadiazol-5-yl, 1,3,4-thiadiazolyl-2-yl, 1,2,3-triazol-4-yl, 1,2,4-triazol-3-yl, tetrazol-5-yl;

C-bound, 6-membered, heteroaromatic rings, such as pyridin-2-yl, pyridin-3-yl, pyridin-4-yl(4-pyridyl), pyridazin-3-yl, pyridazin-4-yl, pyrimidin-2-yl, pyrimidin-4-yl, pyrimidin-5-yl, pyrazin-2-yl, 1,3,5-triazin-2-yl, 1,2,4-triazin-3-yl, 1,2,4-triazin-5-yl, 1,2,4-triazin-6-yl, 1,2,4,5-tetrazin-3-yl;

N-bound, 5-membered, heteroaromatic rings, such as pyrrol-1-yl, pyrazol-1-yl, imidazol-1-yl, 1,2,3-triazol-1-yl, 1,2,4-triazol-1-yl, tetrazol-1-yl.

Heterocyclyl also includes bicyclic heterocycles, which comprise one of the described 5- or 6-membered heterocyclic rings and a further anellated, saturated or unsaturated or aromatic carbocycle, such as a benzene, cyclohexane, cyclohexene or cyclohexadiene ring, or a further anellated 5- or 6-membered heterocyclic ring, this heterocyclic ring being saturated or unsaturated or aromatic. These include quinolinyl, isoquinolinyl, indolyl, indolizinyl, isoindolyl, indazolyl, benzofuryl, benzthienyl, benzo[b]thiazolyl, benzoxazolyl, benzthiazolyl and benzimidazolyl. Examples of 5- or 6-membered heteroaromatic compounds comprising an anellated cycloalkenyl ring include dihydroindolyl, dihydroindolizinyl, dihydroisoindolyl, dihydrochinolinyl, dihydroisoquinolinyl, chromenyl and chromanyl.

$C_3$-$C_{12}$-Heteroarylene is a heteroaryl diradical. Examples include pyrid-2,5-ylene and pyrid-2,4-ylene.

With respect to the compounds' capability of inhibiting glycine transporter 1, the variables A, R, $R^1$, W, $A^1$, Q, Y, $A^2$, $X^1$, $R^2$, $R^3$, $R^4$, $X^2$, $X^3$, $R^5$, $R^6$, $R^7$, $R^8$, $R^9$, $R^{10}$, $R^{11}$, $R^{12}$, $R^{13}$, $R^{14}$, $R^{15}$, $R^{16}$, n preferably have the following meanings which, when taken alone or in combination, represent particular embodiments of the aminotetraline derivatives of the formula (I), (II) or any other formula disclosed herein.

In said formula (I) or (II), there may be one or more than one substituent R, $R^2$ and/or $R^3$. More particularly, there may be up to 3 substituents $R^2$, and up to 6 substituents $R^3$. Preferably there is one substituent R and 1, 2 or 3 substituents $R^2$. Formula (I) may thus be depicted as follows:

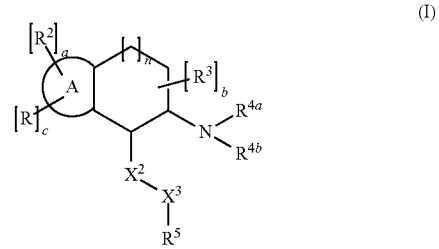

(I)

wherein a is 1, 2 or 3, b is 1, 2, 3, 4, 5 or 6 and c is 1. If there is more than one radical $R^2$, these may be the same or different radicals. If there is more than one radical $R^3$, these may be the same or different radicals.

A is a 5- or 6-membered ring which includes two carbon atoms from the cyclopentane, cyclohexane or cycloheptane moiety to which A is fused. A may be a homocyclic or heterocyclic ring. The ring may be saturated, unsaturated non-aromatic or aromatic. According to a particular embodiment, A is a benzene ring. As a heterocyclic ring, A may include 1, 2 or 3 heteroatoms as ring member atoms, which are selected, independently of each other from N, S and O. Preferred heterocyclic rings comprise 1 nitrogen atom as ring member atom and optionally 1 or 2 further heteroatoms as ring members, which are selected, independently of each other from O, S and N. Likewise preferred heterocyclic radicals comprise 1 heteroatom as ring member atom, which is selected from O, S and N, and optionally 1 or 2 further nitrogen atoms as ring member atoms. According to a particular embodiment, A is a heterocyclic ring selected from the group consisting of the following 5- or 6-membered heterocyclic rings:

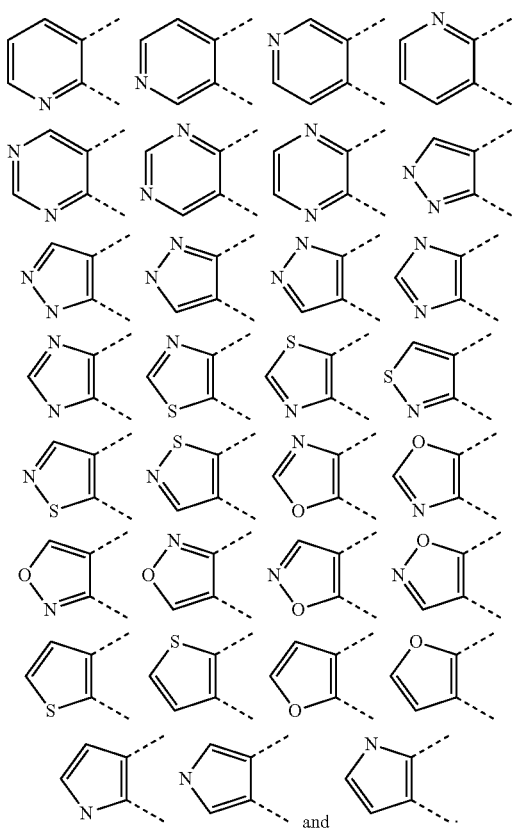

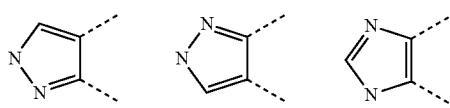

In said formulae, hydrogen atoms are not depicted. This is meant to illustrate that the free valency of a carbon or nitrogen atom may be either bound to a hydrogen atom, to R or to $R^2$. Accordingly, R and $R^2$ may be C- or N-bound at any position of ring A.

The skilled person will appreciate that some of the rings depicted above may be represented with a different structure, e.g. with hydrogen atoms having other positions than those shown above, for instance as given in the following structures:

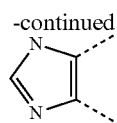

Preferably, A is a heterocyclic ring selected from the group consisting of the following 5- or 6-membered heterocyclic rings:

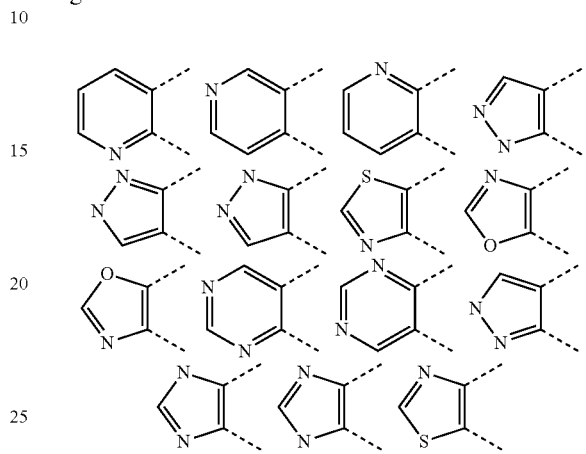

According to a further particular embodiment, A is a heterocyclic ring selected from the group consisting of the following 5- or 6-membered heterocyclic rings:

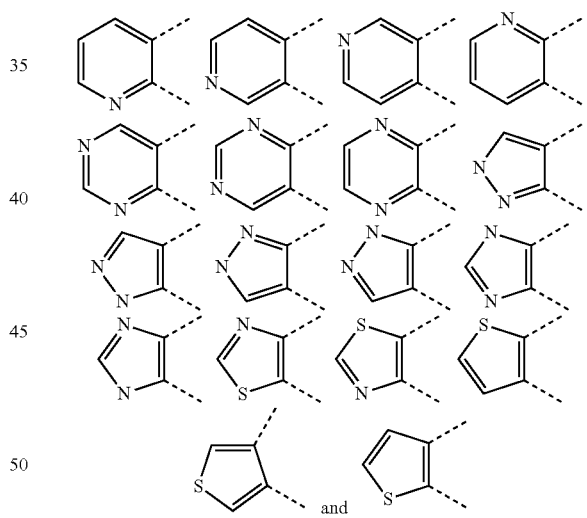

According to a preferred embodiment, A is a heterocyclic ring selected from the group consisting of the following 5- or 6-membered heterocyclic rings:

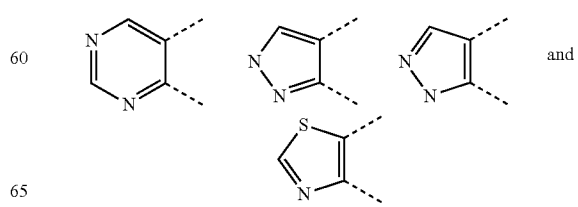

If ring A is a 5-membered heterocyclic ring it is preferred that R is bound to $G^1$ or $G^2$, in particular $G^2$:

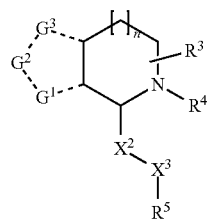

In said formula, $G^1$, $G^2$ and $G^3$ independently are —CH=, —CH$_2$—, —N=, —NH—, S or O, the dotted line represents a single or a double bond and $R^3$, $R^4$, $X^2$, $X^3$, $R^5$ are as defined herein.

If ring A is 6-membered heterocyclic ring it is preferred that R is bound to $G^1$ or $G^2$, in particular $G^2$:

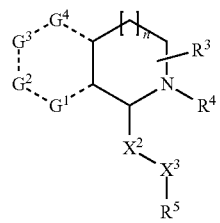

In said formula, $G^1$, $G^2$, $G^3$ and $G^4$ independently are —CH=, —CH$_2$—, —N=, —NH—, S or O, the dotted line represents a single or a double bond and $R^3$, $R^4$, $X^2$, $X^3$, $R^5$ are as defined herein.

Heterocyclic compounds having the following partial structures are preferred:

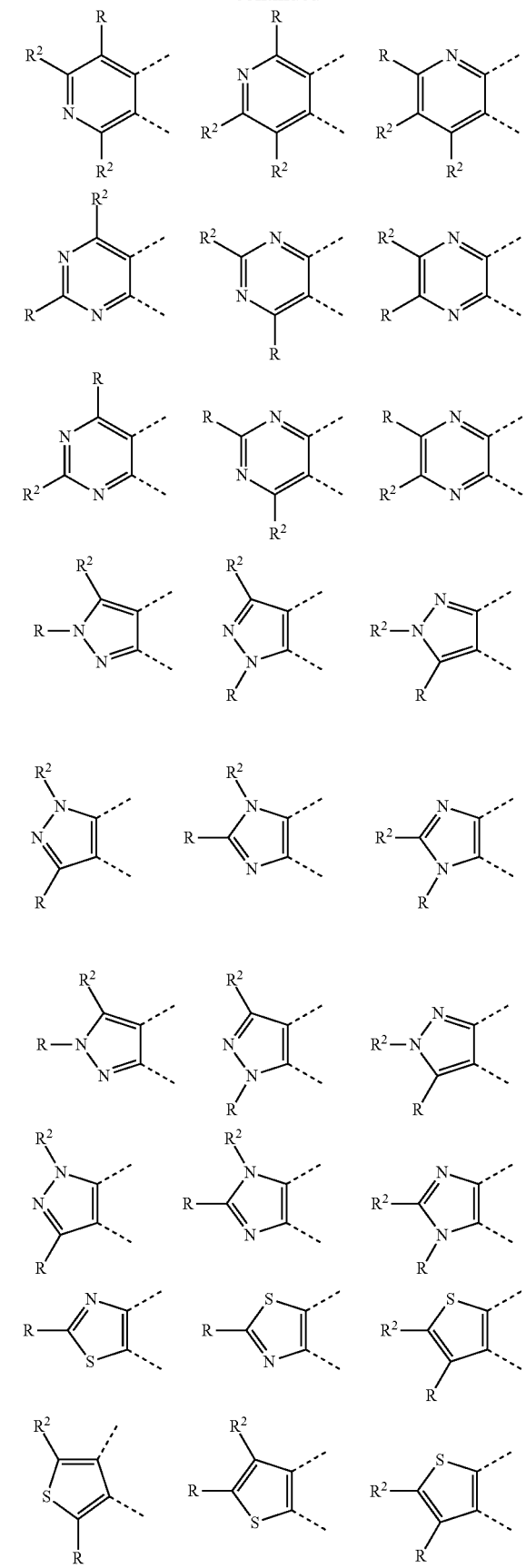

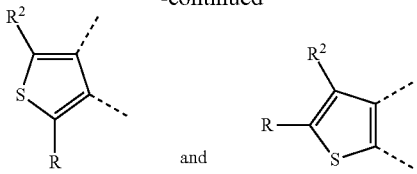

and

Heterocyclic compounds having the following partial structures are particularly preferred:

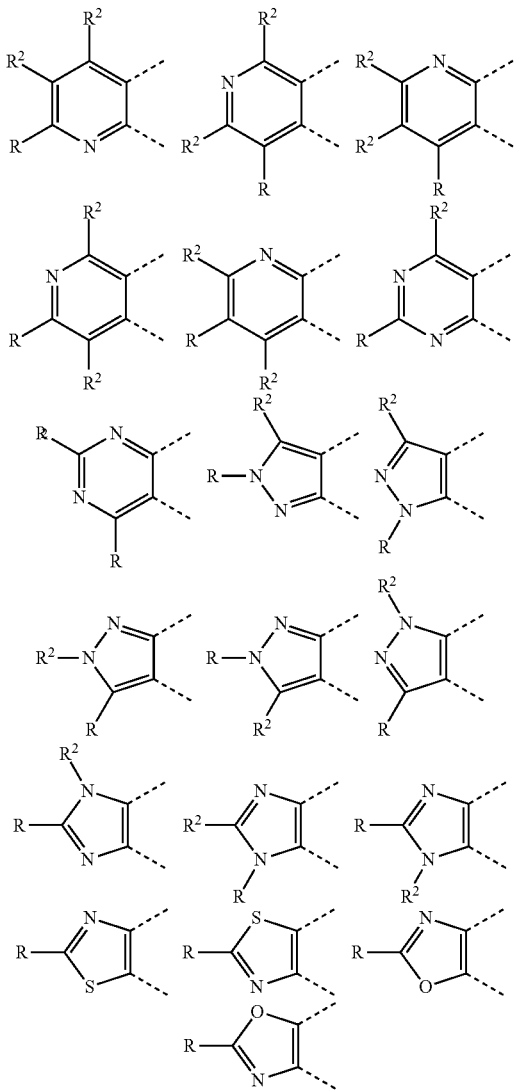

In said formulae, R and R² are as defined herein. If there is more than one radical R², these may be the same or different radicals.

According to a particular embodiment, the partial structures depicted above are fused with a cyclohexane moiety (i.e., n is 1). The same applies to the preferred and particular embodiments disclosed for ring A.

According to one embodiment, R is cyano.

Preferably, R is R¹—W-A¹-Q-Y-A²-X¹— and A, R¹, W, A¹, Q, Y, A², X¹, R², R³, R⁴ᵃ, R⁴ᵇ, X², X³, R⁵ are as defined herein.

R¹ is hydrogen, $C_1$-$C_6$-alkyl (e.g. methyl, ethyl, n-propyl, isopropyl or sec-butyl, a further example being n-butyl or n-pentyl), $C_3$-$C_{12}$-cycloalkyl-$C_1$-$C_4$-alkyl (e.g. cyclopentylmethyl or cyclohexylmethyl, a further example being cyclopropylmethyl), halogenated $C_1$-$C_6$-alkyl (e.g. 3-fluoroprop-1-yl, 3-chloroprop-1-yl or 3,3,3-trifluoroprop-1-yl), hydroxy-$C_1$-$C_4$-alkyl, $C_1$-$C_6$-alkoxy-$C_1$-$C_4$-alkyl (e.g. ethoxyethyl), amino-$C_1$-$C_4$-alkyl, $C_1$-$C_6$-alkylamino-$C_1$-$C_4$-alkyl, di-$C_1$-$C_6$-alkylamino-$C_1$-$C_4$-alkyl, $C_1$-$C_6$-alkylcarbonylamino-$C_1$-$C_4$-alkyl, $C_1$-$C_6$-alkyloxycarbonylamino-$C_1$-$C_4$-alkyl, $C_1$-$C_6$-alkylaminocarbonylamino-$C_1$-$C_4$-alkyl, di-$C_1$-$C_6$-alkylaminocarbonylamino-$C_1$-$C_4$-alkyl, $C_1$-$C_6$-alkylsulfonylamino-$C_1$-$C_4$-alkyl, (optionally substituted $C_6$-$C_{12}$-aryl-$C_1$-$C_6$-alkyl)amino-$C_1$-$C_4$-alkyl, optionally substituted $C_6$-$C_{12}$-aryl$C_1$-$C_4$-alkyl, optionally substituted $C_3$-$C_{12}$-heterocyclyl-$C_1$-$C_4$-alkyl, $C_3$-$C_{12}$-cycloalkyl (e.g. cyclopropyl or cyclobutyl), $C_1$-$C_6$-alkylcarbonyl, $C_1$-$C_6$-alkoxycarbonyl, halogenated $C_1$-$C_6$-alkoxycarbonyl, $C_6$-$C_{12}$-aryloxycarbonyl, aminocarbonyl, $C_1$-$C_6$-alkylaminocarbonyl, (halogenated $C_1$-$C_4$-alkyl)aminocarbonyl, $C_6$-$C_{12}$-arylaminocarbonyl, $C_2$-$C_6$-alkenyl (e.g. prop-1,2-en-1-yl), $C_2$-$C_6$-alkynyl, optionally substituted $C_6$-$C_{12}$-aryl (e.g. phenyl, a further example being 2-methylphenyl), hydroxy, $C_1$-$C_6$-alkoxy (e.g. tert-butyloxy), halogenated $C_1$-$C_6$-alkoxy, $C_1$-$C_6$-hydroxyalkoxy, $C_1$-$C_6$-alkoxy-$C_1$-$C_4$-alkoxy, amino-$C_1$-$C_4$-alkoxy, $C_1$-$C_6$-alkylamino-$C_1$-$C_4$-alkoxy, di-$C_1$-$C_6$-alkylamino-$C_1$-$C_4$-alkoxy, $C_1$-$C_6$-alkylcarbonylamino-$C_1$-$C_4$-alkoxy, $C_6$-$C_{12}$-arylcarbonylamino-$C_1$-$C_4$-alkoxy, $C_1$-$C_6$-alkoxycarbonylamino-$C_1$-$C_4$-alkoxy, $C_6$-$C_{12}$-aryl-$C_1$-$C_4$-alkoxy, $C_1$-$C_6$-alkylsulfonylamino-$C_1$-$C_4$-alkoxy, (halogenated $C_1$-$C_6$-alkyl)sulfonylamino-$C_1$-$C_4$-alkoxy, $C_6$-$C_{12}$-arylsulfonylamino-$C_1$-$C_4$-alkoxy, ($C_6$-$C_{12}$-aryl$C_1$-$C_6$-alkyl)sulfonylamino-$C_1$-$C_4$-alkoxy, $C_3$-$C_{12}$-heterocyclylsulfonylamino-$C_1$-$C_4$-alkoxy, $C_3$-$C_{12}$-heterocyclyl-$C_1$-$C_4$-alkoxy, $C_6$-$C_{12}$-aryloxy, $C_3$-$C_{12}$-heterocyclyloxy, $C_1$-$C_6$-alkylthio, halogenated $C_1$-$C_6$-alkylthio, $C_1$-$C_6$-alkylamino, (halogenated $C_1$-$C_6$-alkyl)amino, di-$C_1$-$C_6$-alkylamino (e.g. dimethylamino), di-(halogenated $C_1$-$C_6$-alkyl)amino, $C_1$-$C_6$-alkylcarbonylamino, (halogenated $C_1$-$C_6$-alkyl)carbonylamino, $C_6$-$C_{12}$-arylcarbonylamino, $C_1$-$C_6$-alkylsulfonylamino, (halogenated $C_1$-$C_6$-alkyl)sulfonylamino, $C_6$-$C_{12}$-arylsulfonylamino or optionally substituted $C_3$-$C_{12}$-heterocyclyl (e.g. 3-pyridyl, 2-thienyl, 4-methyl-2-thienyl, 5-methyl-2-thienyl, 5-chloro-2-thienyl, 2,5-dimethyl-3-thienyl, 1,2-diazol-4-yl, 1-methyl-1,2-diazol-4-yl, 1-ethyl-1,2-diazol-4-yl, 1-difluormethyl-1,2-diazol-4-yl, 2-methyl-1,3-diazol-4-yl, 1-methyl-1,3-diazol-4-yl, 2-methyl-1,3-thiazol-5-yl, 2,4-dimethyl-1,3-thiazol-5-yl or 3-pyrrolidinyl, a further example being 1-methyl-pyrrol-3-yl, 2-pyridyl, 1-methyl-1,2-diazol-3-yl, 1-methyl-3-trifluoromethyl-1,2-diazol-4-yl, 1,2-dimethyl-1,3-diazol-4-yl, 5-methylisoxazol-3-yl or 1-methyl-1,2,4-triazol-3-yl). Additionally, R¹ may also be tri($C_1$-$C_4$-alkyl)-silyl-$C_1$-$C_4$-alkyl (e.g. trimethylsilylethyl).

Preferably, R¹ is $C_1$-$C_6$-alkyl (e.g. methyl, ethyl, n-propyl, isopropyl or sec-butyl, a further example being n-butyl or n-pentyl), $C_3$-$C_{12}$-cycloalkyl-$C_1$-$C_4$-alkyl (e.g. cyclopentylmethyl or cyclohexylmethyl, a further example being cyclopropylmethyl), halogenated $C_1$-$C_6$-alkyl (e.g. 3-fluoroprop-1-yl, 3-chloroprop-1-yl or 3,3,3-trifluoroprop-1-yl), $C_1$-$C_6$-alkoxy-$C_1$-$C_4$-alkyl (e.g. ethoxyethyl), amino-$C_1$-$C_4$-alkyl, $C_1$-$C_6$-alkylamino-$C_1$-$C_4$-alkyl, di-$C_1$-$C_6$-alkylamino-$C_1$-$C_4$-alkyl, $C_1$-$C_6$-alkyloxycarbonylamino-$C_1$-$C_4$-alkyl, $C_1$-$C_6$-alkylaminocarbonylamino-$C_1$-$C_4$-alkyl, $C_6$-$C_{12}$-aryl-$C_1$-$C_4$-alkyl, $C_3$-$C_{12}$-cycloalkyl (e.g. cyclopropyl or cyclobutyl), $C_2$-$C_6$-alkenyl (e.g. prop-1,2-en-1-yl), optionally substituted $C_6$-$C_{12}$-aryl (e.g. phenyl), hydroxy, $C_1$-$C_6$-alkylamino, (halogenated $C_1$-$C_6$-alkyl)amino, di-$C_1$-$C_6$-alkylamino or optionally substituted $C_3$-$C_{12}$-heterocyclyl (e.g. 3-pyridyl, 2-thienyl, 4-methyl-2-thienyl, 5-methyl-2-thienyl, 5-chloro-2-thienyl, 2,5-dimethyl-3-thienyl, 1,2-diazol-4-yl, 1-methyl-1,2-diazol-4-yl, 1-ethyl-1,2-diazol-4-yl, 1-difluormethyl-1,2-diazol-4-yl, 2-methyl-1,3-diazol-4-yl, 1-methyl-1,3-diazol-4-yl, 2-methyl-1,3-thiazol-5-yl, 2,4-dimethyl-1,3-thiazol-5-yl or 3-pyrrolidinyl). It is further preferred if $R^1$ is tri-($C_1$-$C_4$-alkyl)-silyl-$C_1$-$C_4$-alkyl (e.g. trimethylsilylethyl).

In particular, $R^1$ is $C_1$-$C_6$-alkyl (e.g. methyl, ethyl, n-propyl, isopropyl or sec-butyl, a further example being n-butyl or n-pentyl), $C_3$-$C_{12}$-cycloalkyl-$C_1$-$C_4$-alkyl (e.g. cyclopentylmethyl or cyclohexylmethyl, a further example being cyclopropylmethyl), halogenated $C_1$-$C_6$-alkyl (e.g. 3-fluoroprop-1-yl, 3-chloroprop-1-yl or 3,3,3-trifluoroprop-1-yl), $C_3$-$C_{12}$-cycloalkyl (e.g. cyclopropyl or cyclobutyl), $C_2$-$C_6$-alkenyl (e.g. prop-1,2-en-1-yl), optionally substituted $C_6$-$C_{12}$-aryl (e.g. phenyl), or optionally substituted $C_3$-$C_{12}$-heterocyclyl (e.g. 3-pyridyl, 2-thienyl, 4-methyl-2-thienyl, 5-methyl-2-thienyl, 5-chloro-2-thienyl, 2,5-dimethyl-3-thienyl, 1,2-diazol-4-yl, 1-methyl-1,2-diazol-4-yl, 1-ethyl-1,2-diazol-4-yl, 1-difluormethyl-1,2-diazol-4-yl, 2-methyl-1,3-diazol-4-yl, 1-methyl-1,3-diazol-4-yl, 2-methyl-1,3-thiazol-5-yl, 2,4-dimethyl-1,3-thiazol-5-yl or 3-pyrrolidinyl). In particular, $R^1$ may also be tri-($C_1$-$C_4$-alkyl)silyl-$C_1$-$C_4$-alkyl (e.g. trimethylsilylethyl).

In connection with $R^1$, substituted $C_6$-$C_{12}$-aryl in particular includes $C_6$-$C_{12}$-aryl, such as phenyl or naphthyl, substituted with 1, 2 or 3 substituents selected from the group consisting of halogen, $C_1$-$C_4$-alkyl, $C_1$-$C_4$-haloalkyl, cyano, $C_1$-$C_4$-alkoxy, $C_1$-$C_4$-haloalkoxy, amino, $C_1$-$C_4$-alkylamino, $C_1$-$C_4$-dialkylamino, morpholino and piperidinyl. The same applies to substituted $C_6$-$C_{12}$-aryl in substituted $C_6$-$C_{12}$-aryl-$C_1$-$C_4$-alkyl.

In connection with $R^1$, substituted $C_3$-$C_{12}$-heterocyclyl in particular includes $C_3$-$C_{12}$-heterocyclyl, such as pyridyl, thienyl, diazolyl, quinolinyl, piperidinyl, piperazinyl or morpholinyl(pyrrolyl, isoxazolyl and triazolyl being further examples of such $C_3$-$C_{12}$-heterocyclyl), substituted with 1, 2 or 3 substituents selected from the group consisting of halogen, $C_1$-$C_4$-alkyl, $C_1$-$C_4$-haloalkyl, $C_1$-$C_4$-alkoxycarbonyl, cyano, $C_1$-$C_4$-alkoxy, $C_1$-$C_4$-haloalkoxy, $C_1$-$C_4$-alkylsulfonyl, amino, $C_1$-$C_4$-alkylamino, $C_1$-$C_4$-dialkylamino, $C_6$-$C_{12}$-arylamino and $C_3$-$C_{12}$-heterocyclyl (e.g., morpholino or piperidinyl). The same applies to substituted $C_3$-$C_{12}$-heteroaryl in substituted $C_3$-$C_{12}$-heteroaryl-$C_1$-$C_4$-alkyl.

According to one embodiment, W is —$NR^8$— and Y is a bond. According to an alternative embodiment, W is a bond and Y is —$NR^9$—. According to a further alternative embodiment, W is a bond and Y is a bond, especially if $R^1$ is a nitrogen-bound radical, e.g. nitrogen-bound heterocyclyl such as piperazinyl or morpholinyl.

According to one embodiment, Q is —$S(O)_2$—. According to an alternative embodiment, Q is —C(O)—.

According to a particular embodiment, —W-$A^1$-Q-Y— is —W-$A^1$-$S(O)_2$—$NR^9$—, —$NR^8$—$S(O)_2$—, -$A^1$-$S(O)_2$— or —$S(O)_2$—. According to a further particular embodiment, —W-$A^1$-Q-Y— is —W-$A^1$-$CONR^9$— or —$NR^8$—CO—.

$A^1$ is optionally substituted $C_1$-$C_4$-alkylene or a bond. In connection with $A^1$, substituted $C_1$-$C_4$-alkylene in particular includes $C_1$-$C_4$-alkylene substituted with 1, 2 or 3 substituents selected from the group consisting of halogen, $C_1$-$C_4$-alkyl and cyano. Preferably, $A^1$ is a bond. If $A^1$ is $C_1$-$C_4$-alkylene, W is preferably —$NR^8$—.

$A^2$ is optionally substituted $C_1$-$C_4$-alkylene (e.g. 1,2-ethylene or 1,3-propylene), $C_1$-$C_4$-alkylene-CO—, —CO—$C_1$-$C_4$-alkylene, $C_1$-$C_4$-alkylene-O—$C_1$-$C_4$-alkylene, $C_1$-$C_4$-alkylene-$NR^{10}$—$C_1$-$C_4$-alkylene, optionally substituted $C_6$-$C_{12}$-arylene, optionally substituted $C_6$-$C_{12}$-heteroarylene or a bond. Additionally, $A^2$ may be optionally substituted $C_2$-$C_4$-alkenylen or optionally substituted $C_2$-$C_4$-alkynylene. Preferably, $A^2$ is optionally substituted $C_1$-$C_4$-alkylene (e.g. 1,2-ethylene or 1,3-propylene). More preferably, $A^2$ is $C_1$-$C_4$-alkylene (e.g. 1,2-ethylene or 1,3-propylene). Alternatively, it is preferred that $A^2$ is optionally substituted $C_6$-$C_{12}$-arylene, in particular $C_6$-$C_{12}$-arylene selected from the group consisting of phen-1,4-ylene and phen-1,3-ylene, or optionally substituted $C_6$-$C_{12}$-heteroarylene, in particular $C_6$-$C_{12}$-heteroarylene selected from the group consisting of pyrid-2,5-ylene and pyrid-2,4-ylene. If $A^2$ is a bond, $X^1$ is preferably optionally substituted $C_1$-$C_4$-alkylene. Alternatively, if $A^2$ is a bond, $X^1$ is in particular optionally substituted $C_2$-$C_4$-alkenylene or optionally substituted $C_2$-$C_4$-alkynylene.

In connection with $A^2$, substituted $C_1$-$C_4$-alkylene in particular includes $C_1$-$C_4$-alkylene substituted with 1, 2 or 3 substituents selected from the group consisting of halogen, $C_1$-$C_4$-alkyl, $C_1$-$C_4$-haloalkyl and cyano.

In connection with $A^2$, substituted $C_2$-$C_4$-alkenylene or substituted $C_2$-$C_4$-alkynylene in particular includes $C_2$-$C_4$-alkenylene or $C_2$-$C_4$-alkynylene substituted with 1, 2 or 3 substituents selected from the group consisting of halogen, $C_1$-$C_4$-alkyl, $C_1$-$C_4$-haloalkyl and cyano.

In connection with $A^2$, substituted $C_6$-$C_{12}$-arylene in particular includes $C_6$-$C_{12}$-arylene substituted with 1, 2 or 3 substituents selected from the group consisting of $C_1$-$C_4$-alkyl, $C_1$-$C_4$-haloalkyl, $C_1$-$C_4$-alkoxycarbonyl, cyano, $C_1$-$C_4$-alkoxy, $C_1$-$C_4$-haloalkoxy, $C_1$-$C_4$-alkylsulfonyl, amino, $C_1$-$C_4$-alkylamino, $C_1$-$C_4$-dialkylamino, $C_6$-$C_{12}$-arylamino and $C_3$-$C_{12}$-heterocyclyl (e.g., morpholino or piperidinyl).

In connection with $A^2$, substituted $C_6$-$C_{12}$-heteroarylene in particular includes $C_6$-$C_{12}$-heteroarylene substituted with 1, 2 or 3 substituents selected from the group consisting of $C_1$-$C_4$-alkyl, $C_1$-$C_4$-haloalkyl, $C_1$-$C_4$-alkoxycarbonyl, cyano, $C_1$-$C_4$-alkoxy, $C_1$-$C_4$-haloalkoxy, $C_1$-$C_4$-alkylsulfonyl, amino, $C_1$-$C_4$-alkylamino, $C_1$-$C_4$-dialkylamino, $C_6$-$C_{12}$-arylamino and $C_3$-$C_{12}$-heterocyclyl (e.g., morpholino or piperidinyl).

$X^1$ is —O—, —$NR^{11}$—, —S— or optionally substituted $C_1$-$C_4$-alkylene (e.g. —$CH_2$—, a further example being 1,2-ethylene and 1,3-popylene). In connection with $X^1$, substituted $C_1$-$C_4$-alkylene in particular includes $C_1$-$C_4$-alkylene substituted with 1, 2 or 3 substituents selected from the group consisting of halogen, $C_1$-$C_4$-alkyl, $C_1$-$C_4$-haloalkyl and cyano. Additionally, $X^1$ may be optionally substituted $C_2$-$C_4$-alkenylen or optionally substituted $C_2$-$C_4$-alkynylene (e.g. propynylene). In connection with $X^1$, substituted $C_2$-$C_4$-alkenylene or substituted $C_2$-$C_4$-alkynylene in particular includes $C_2$-$C_4$-alkenylene or $C_2$-$C_4$-alkynylene substituted with 1, 2 or 3 substituents selected from the group consisting of halogen, $C_1$-$C_4$-alkyl, $C_1$-$C_4$-haloalkyl and cyano. Preferably, $X^1$ is —O—, —$NR^{11}$—, —S—. More preferably, $X^1$ is —O—. Alternatively, it is preferred if $X^1$ is optionally substituted $C_1$-$C_4$-alkylene (e.g. —$CH_2$—, 1,2-ethylene and 1,3-popylene).

According to a particular embodiment, $A^2$ is a bond and $X^1$ is optionally substituted $C_1$-$C_4$-alkylene, optionally substituted $C_2$-$C_4$-alkenylene or optionally substituted $C_2$-$C_4$-alkynylene.

According to a particular embodiment, $R^1$—W-$A^1$-Q-Y-$A^2$-$X^1$— is $R^1$—$S(O)_2$—NH-$A^2$-$X^1$—, $R^1$—NH—$S(O)_2$-$A^2$-$X^1$—, $R^1$—C(O)—NH-$A^2$-$X^1$— or $R^1$—NH—C(O)-$A^2$-$X^1$—.

According to a particular embodiment, the structural element —Y-A²-X¹— comprises at least 2, 3 or 4 atoms in the main chain. According to further particular embodiments the structural element —Y-A²-X¹— has up to 4, 5 or 6 atoms in the main chain, such as 2 to 6, 2 to 5 or 2 to 4 atoms in the main chain, especially 2, 3 or 4 atoms in the main chain.

According to a further particular embodiment, —Y-A²-X¹— is —$C_1$-$C_4$-alkylene-O— or —$NR^9$—$C_1$-$C_4$-alkylene-O—, with —Y-A²-X¹— preferably having 2 to 6, 3 to 5 and especially 4 atoms in the main chain. Particular examples of —Y-A²-X¹— include —$(CH_2)_3$—O— and —$NR^9$—$(CH_2)_2$—O—. In this particular embodiment, $R^9$ is as defined herein and preferably $R^9$ is hydrogen, $C_1$-$C_6$-alkyl (e.g. methyl or ethyl) or $C_3$-$C_{12}$-cycloalkyl (e.g. cyclopropyl), or $R^9$ is $C_1$-$C_4$-alkylene that is bound to a carbon atom in $A^2$ which is $C_1$-$C_4$-alkylene.

According to a further particular embodiment, —Y-A²-X¹— is —$NR^9$—$C_1$-$C_4$-alkylene- (e.g. —NH—$CH_2$—, a further example being —NH—$(CH_2)_2$— or —NH—$(CH_2)_3$—), with —Y-A²-X¹— preferably having 2 to 6, 2 to 5, 2 to 4 and especially 2, 3 or 4 atoms in the main chain. In this particular embodiment, $R^9$ is as defined herein and preferably $R^9$ is hydrogen, $C_1$-$C_6$-alkyl (e.g. methyl or ethyl) or $C_3$-$C_{12}$-cycloalkyl (e.g. cyclopropyl); or $R^9$ is $C_1$-$C_4$-alkylene that is bound to a carbon atom in $X^1$ which is $C_1$-$C_4$-alkylene. If A is a heterocyclic ring, this embodiment of —Y-A²-X¹— is particularly suitable.

According to a further particular embodiment, —Y-A²-X¹— is —$NR^9$—$C_2$-$C_4$-alkenylene- or —$NR^9$—$C_2$-$C_4$-alkynylene- (e.g.—NH—$CH_2$—C≡C—), with —Y-A²-X¹— preferably having 2 to 6, 3 to 5 and especially 4 atoms in the main chain. In this particular embodiment, $R^9$ is as defined herein and preferably is $R^9$ is hydrogen, $C_1$-$C_6$-alkyl (e.g. methyl or ethyl) or $C_3$-$C_{12}$-cycloalkyl (e.g. cyclopropyl or cyclobutyl). If A is a heterocyclic ring, this embodiment of —Y-A²-X¹— is particularly suitable.

According to a further particular embodiment, —Y-A²-X¹— is —$C_1$-$C_4$-alkylene- (e.g. —$(CH_2)_2$—), with —Y-A²-X¹— preferably having 2 to 6, 2 to 5, 2 to 4 and especially 2 atoms in the main chain. If A is a heterocyclic ring, this embodiment of —Y-A²-X¹— is particularly suitable.

According to a further particular embodiment, the structural motif —Y-A²-X¹ as disclosed herein is bound to Q being —$S(O)_2$— or —C(O)—. Particular examples for this embodiment include heterocyclic compounds of the invention wherein R is $R^1$—$S(O)_2$—Y-A²-X¹ or $R^1$—C(O)Y-A²-X¹.

The radical R and in particular the radical $R^1$—W-$A^1$-Q-Y-A²-X¹— may, in principle, be bound to the 5-, 6-, 7- or 8-position of the aminotetraline skeleton:

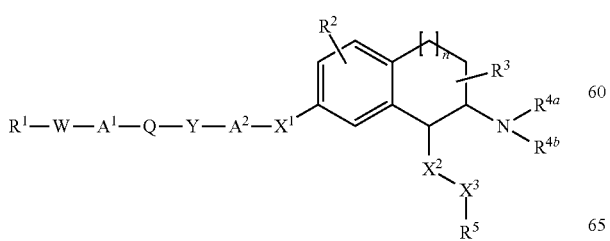

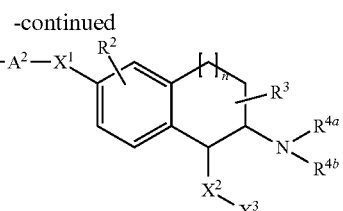

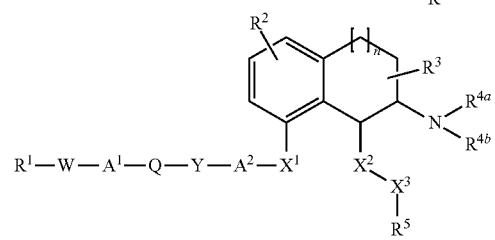

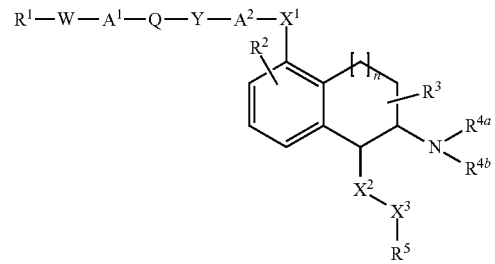

In said formulae, $R^1$, W, $A^1$, Q, Y, $A^2$, $X^1$, $R^2$, $R^3$, $R^{4a}$, $R^{4b}$, $X^2$, $X^3$, $R^5$, n are as defined herein.

Further particular examples include heterocyclic compounds of the above formulae wherein the radical $R^1$—W-$A^1$-Q-Y-$A^2$-$X^1$— is replaced by the radical —CN.

Aminotetraline derivatives having the radical $R^1$—W-$A^1$-Q-Y-$A^2$-$X^1$— (or the radical —CN) in the 5-, 6-, 7-position are preferred.

Particularly preferred are aminotetraline derivatives having the radical $R^1$—W-$A^1$-Q-Y-$A^2$-$X^1$— (or the radical —CN) in the 7-position.

In addition to the radical $R^1$-$A^1$-Q-Y-$A^2$-$X^1$— (or the radical —CN), the aminotetraline derivatives of the invention may have one or more than one further substituent bound to the ring A. In these positions, the skeleton of the aminotetraline derivatives may thus be substituted with one or more than one radical $R^2$. If there is more than one radical $R^2$, these may be the same or different radicals. In particular, in 5-, 6-, 7- and/or 8-position, the aminotetraline skeleton may be substituted with one or more than one radical $R^2$. The aminotetraline derivatives of the invention may therefore be represented by one of the following formulae:

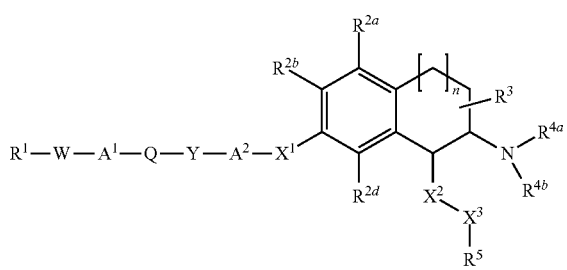

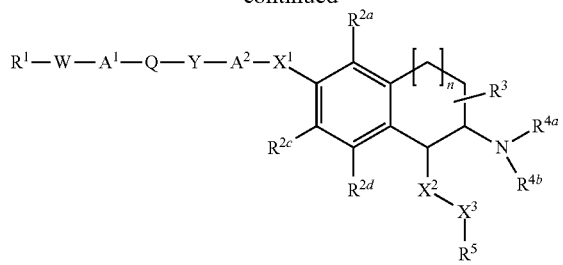

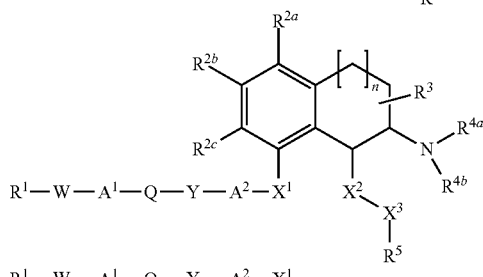

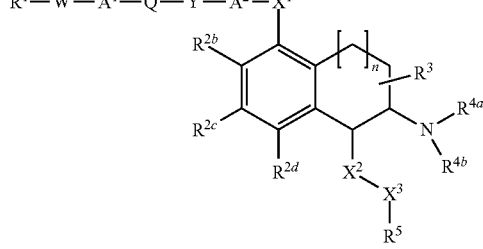

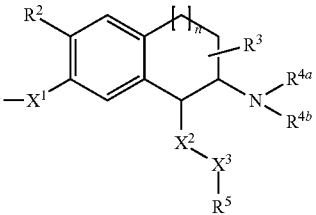

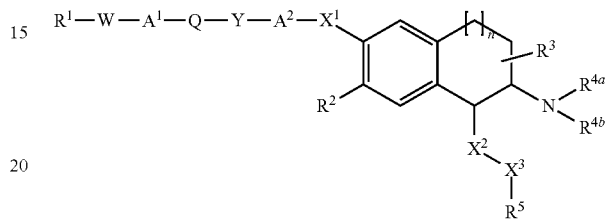

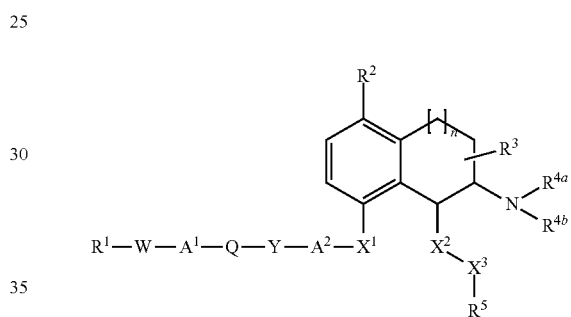

or by corresponding formulae wherein the radical $R^1$—W-$A^1$-Q-Y-$A^2$-$X^1$— is replaced by the radical —CN, wherein $R^{2a}$, $R^{2b}$, $R^{2c}$, $R^{2d}$ independently have one of the meanings given for $R^2$, and $R^1$, W, $A^1$, Q, Y, $A^2$, $X^1$, $R^2$, $R^3$, $R^{4a}$, $R^{2b}$, $X^2$, $X^3$, $R^5$, n are as defined herein.

$R^2$ is hydrogen, halogen, $C_1$-$C_6$-alkyl, halogenated $C_1$-$C_4$-alkyl, hydroxy-$C_1$-$C_4$-alkyl, —CN, $C_2$-$C_6$-alkenyl, $C_2$-$C_6$-alkynyl, optionally substituted $C_6$-$C_{12}$-aryl, hydroxy, $C_1$-$C_6$-alkoxy, halogenated $C_1$-$C_6$-alkoxy, $C_1$-$C_6$-alkoxycarbonyl, $C_2$-$C_6$-alkenyloxy, $C_6$-$C_{12}$-aryl-$C_1$-$C_4$-alkoxy, $C_1$-$C_6$-alkylcarbonyloxy, $C_1$-$C_6$-alkylthio, $C_1$-$C_6$-alkylsulfinyl, $C_1$-$C_6$-alkylsulfonyl, aminosulfonyl, amino, $C_1$-$C_6$-alkylamino, $C_2$-$C_6$-alkenylamino, nitro or optionally substituted $C_3$-$C_{12}$-heterocyclyl, or two radicals $R^2$ together with the ring atoms of A to which they are bound form a 5- or 6 membered ring.

An optionally substituted 5- or 6-membered ring that is formed by two radicals $R^2$ together with the ring atoms of A to which they are bound is, for instance, a benzene ring.

In connection with $R^2$, substituted $C_6$-$C_{12}$-aryl in particular includes $C_6$-$C_{12}$-aryl, such as phenyl, substituted with 1, 2 or 3 substituents selected from the group consisting of halogen and $C_1$-$C_4$-alkyl, $C_1$-$C_4$-haloalkyl, cyano, $C_1$-$C_4$-alkoxy and $C_1$-$C_4$-haloalkoxy.

In connection with $R^2$, substituted $C_3$-$C_{12}$-heterocyclyl in particular includes $C_3$-$C_{12}$-heterocyclyl, such as morpholinyl, pyrrolidinyl and piperidinyl, substituted with 1, 2 or 3 substituents selected from the group consisting of halogen, $C_1$-$C_4$-alkyl, $C_1$-$C_4$-haloalkyl, cyano, $C_1$-$C_4$-alkoxy and $C_1$-$C_4$-haloalkoxy.

Preferably, $R^2$ is hydrogen, halogen or $C_1$-$C_6$-alkoxy. In particular, $R^2$ is hydrogen.

According to a particular embodiment, the aminotetraline derivatives of the invention have one of the following formulae:

or by corresponding formulae wherein the radical $R^1$—W-$A^1$-Q-Y-$A^2$-$X^1$— is replaced by the radical —CN, wherein $R^1$, W, $A^1$, Q, Y, $A^2$, $X^1$, $R^2$, $R^3$, $R^{4a}$, $R^{4b}$, $X^2$, $X^3$, $R^5$, n are as defined herein.

In 1-, 2-, 3-, 4- and/or 5-position, the aminotetraline derivatives of the invention may be substituted with one or more than one radical $R^3$. If there is more than one radical $R^3$, these may be the same or different radicals. The aminotetraline derivatives of the invention may therefore be represented by the following formula:

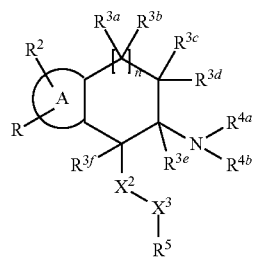

wherein $R^{3a}$, $R^{3b}$, $R^{3c}$, $R^{3d}$, $R^{3e}$, $R^{3f}$ independently have one of the meanings given for $R^3$, and A, R, $R^2$, $R^3$, $R^{4a}$, $R^{4b}$, $X^2$, $X^3$, $R^5$, n are as defined herein.

According to a particular embodiment, the aminotetraline derivatives of the invention have one of the following formulae:

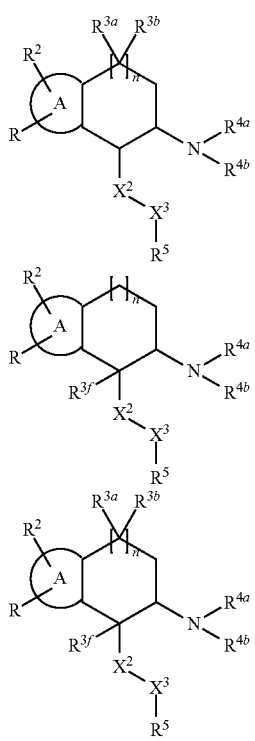

wherein $R^{3a}$, $R^{3b}$, $R^{3f}$ independently have the meaning of $R^3$ and A, R, $R^2$, $R^3$, $R^{4a}$, $R^{4b}$, $X^2$, $X^3$, $R^5$, n are as defined herein.

$R^3$ is hydrogen, halogen, $C_1$-$C_6$-alkyl, $C_1$-$C_6$-alkoxy, or two radicals $R^3$ together with the carbon atom to which they are attached form a carbonyl group.

Preferably, $R^3$ is hydrogen or $C_1$-$C_6$-alkyl. In particular, $R^3$ is hydrogen.

$R^{4a}$ is hydrogen, $C_1$-$C_6$-alkyl (e.g. methyl, ethyl, n-propyl or isopropyl), $C_3$-$C_{12}$-cycloalkyl-$C_1$-$C_4$-alkyl (e.g. cyclopropylmethyl), halogenated $C_1$-$C_4$-alkyl (e.g. 2-fluoroethyl or 2,2,2-trifluoroethyl), hydroxy-$C_1$-$C_4$-alkyl, $C_1$-$C_6$-alkoxy-$C_1$-$C_4$-alkyl, amino-$C_1$-$C_4$-alkyl, $CH_2CN$, —CHO, $C_1$-$C_4$-alkylcarbonyl (e.g. methylcarbonyl or isopropylcarbonyl, a further example being ethylcarbonyl), (halogenated $C_1$-$C_4$-alkyl)carbonyl (e.g. fluoromethylcarbonyl, difluoromethylcarbonyl or trifluoromethylcarbonyl, a further example being 1,1,1-trifluoroeth-2-ylcarbonyl or 1,1,1-trifluoroprop-3-ylcarbonyl), $C_6$-$C_{12}$-arylcarbonyl (e.g. phenylcarbonyl), $C_1$-$C_4$-alkoxycarbonyl (e.g. ethoxycarbonyl or tert-butyloxycarbonyl), $C_6$-$C_{12}$-aryloxycarbonyl (e.g. phenoxycarbonyl), $C_1$-$C_6$-alkylaminocarbonyl, $C_2$-$C_6$-alkenyl, C(=NH)NH$_2$, —C(=NH)NHCN, $C_1$-$C_6$-alkylsulfonyl, $C_6$-$C_{12}$-arylsulfonyl, amino, —NO or $C_3$-$C_{12}$-heterocyclyl.

Preferably, $R^{4a}$ is hydrogen, $C_1$-$C_6$-alkyl (e.g. methyl, ethyl, n-propyl or isopropyl), $C_3$-$C_{12}$-cycloalkyl-$C_1$-$C_4$-alkyl (e.g. cyclopropylmethyl), halogenated $C_1$-$C_4$-alkyl (e.g. 2-fluoroethyl or 2,2,2-trifluoroethyl), amino-$C_1$-$C_4$-alkyl, $CH_2CN$, $C_1$-$C_4$-alkylcarbonyl (e.g. methylcarbonyl or isopropylcarbonyl), (halogenated $C_1$-$C_4$-alkyl)carbonyl (e.g. fluoromethylcarbonyl, difluoromethylcarbonyl or trifluoromethylcarbonyl), $C_6$-$C_{12}$-arylcarbonyl (e.g. phenylcarbonyl), $C_1$-$C_4$-alkoxycarbonyl (e.g. ethoxycarbonyl or tert-butyloxycarbonyl), $C_6$-$C_{12}$-aryloxycarbonyl (e.g. phenoxycarbonyl), —C(=NH)NH$_2$, —C(=NH)NHCN, $C_1$-$C_6$-alkylsulfonyl, amino, —NO or $C_3$-$C_{12}$-heterocyclyl. It is further preferred if $R^1$ is —CHO.

In particular, $R^{4a}$ is hydrogen, $C_1$-$C_6$-alkyl (e.g. methyl, ethyl, n-propyl or isopropyl), $C_3$-$C_{12}$-cycloalkyl-$C_1$-$C_4$-alkyl (e.g. cyclopropylmethyl), halogenated $C_1$-$C_4$-alkyl (e.g. 2-fluoroethyl or 2,2,2-trifluoroethyl), $C_1$-$C_4$-alkylcarbonyl (e.g. methylcarbonyl or isopropylcarbonyl), (halogenated $C_1$-$C_4$-alkyl)carbonyl (e.g. fluoromethylcarbonyl, difluoromethylcarbonyl or trifluoromethylcarbonyl), $C_6$-$C_{12}$-arylcarbonyl (e.g. phenylcarbonyl), $C_1$-$C_4$-alkoxycarbonyl (e.g. ethoxycarbonyl or tert-butyloxycarbonyl), $C_6$-$C_{12}$-aryloxycarbonyl (e.g. phenoxycarbonyl). In particular, $R^{4a}$ may also be —CHO.

$R^{4b}$ is hydrogen, $C_1$-$C_6$-alkyl (e.g. methyl, a further example being ethyl), halogenated $C_1$-$C_4$-alkyl, hydroxy-$C_1$-$C_4$-alkyl, $C_1$-$C_6$-alkoxy-$C_1$-$C_4$-alkyl, amino-$C_1$-$C_4$-alkyl, $CH_2CN$, —CHO, $C_1$-$C_4$-alkylcarbonyl, (halogenated $C_1$-$C_4$-alkyl)carbonyl, $C_6$-$C_{12}$-arylcarbonyl, $C_1$-$C_4$-alkoxycarbonyl, $C_6$-$C_{12}$-aryloxycarbonyl, $C_1$-$C_6$-alkylaminocarbonyl, $C_2$-$C_6$-alkenyl, —C(=NH)NH$_2$, —C(=NH)NHCN, $C_1$-$C_6$-alkylsulfonyl, $C_6$-$C_{12}$-arylsulfonyl, amino, —NO or $C_3$-$C_{12}$-heterocyclyl.

Preferably, $R^{4b}$ is hydrogen, $C_1$-$C_6$-alkyl (e.g. methyl, a further example being ethyl).

Alternatively, $R^{4a}$, $R^{4b}$ together are optionally substituted $C_1$-$C_6$-alkylene (e.g. 1,4-butylene, a further example being 1,3-propylene, 2-fluoro-but-1,4-ylene or 1-oxo-but-1,4-ylene), wherein one —CH$_2$— of $C_1$-$C_4$-alkylene may be replaced by an oxygen atom (e.g. —CH$_2$—CH$_2$—O—CH$_2$—CH$_2$—) or —NR$^{16}$.

$X^2$ is —O—, —NR$^6$—, —S—, >CR$^{12a}$R$^{12b}$ or a bond. Preferably, $X^2$ is >CR$^{12a}$R$^{12b}$.

$X^3$ is —O—, —S—, >CR$^{13a}$R$^{13b}$ or a bond. Preferably, $X^3$ is a bond.

Thus, it is preferred if $X^2$ is >CR$^{12a}$R$^{12b}$ and $X^3$ is a bond.

$R^{12a}$ is hydrogen, optionally substituted $C_1$-$C_6$-alkyl, $C_1$-$C_6$-alkylamino-$C_1$-$C_4$-alkyl, di-$C_1$-$C_6$-alkylamino-$C_1$-$C_4$-alkyl, $C_3$-$C_{12}$-heterocyclyl-$C_1$-$C_6$-alkyl, optionally substituted $C_6$-$C_{12}$-aryl or hydroxy. Preferably, $R^{12a}$ is hydrogen or $C_1$-$C_6$-alkyl.

$R^{13a}$ is hydrogen, optionally substituted $C_1$-$C_6$-alkyl, $C_1$-$C_6$-alkylamino-$C_1$-$C_4$-alkyl, di-$C_1$-$C_6$-alkylamino-$C_1$-$C_4$-alkyl, $C_3$-$C_{12}$-heterocyclyl-$C_1$-$C_6$-alkyl, optionally substituted $C_6$-$C_{12}$-aryl or hydroxy. Preferably, $R^{13a}$ is hydrogen or $C_1$-$C_6$-alkyl.

In connection with $R^{12a}$ and $R^{13a}$, substituted $C_1$-$C_6$-alkyl in particular includes $C_1$-$C_6$-alkyl substituted with 1, 2 or 3 substituents selected from the group consisting of halogen, hydroxy, $C_1$-$C_4$-alkoxy and amino.

In connection with $R^{12a}$ and $R^{13a}$, substituted $C_6$-$C_{12}$-aryl in particular includes $C_6$-$C_{12}$-aryl, such as phenyl, substituted with 1, 2 or 3 substituents selected from the group consisting of $C_1$-$C_4$-alkyl, $C_1$-$C_4$-haloalkyl, cyano, $C_1$-$C_4$-alkoxy and $C_1$-$C_4$-haloalkoxy.

$R^{12b}$ is hydrogen or $C_1$-$C_6$-alkyl. According to a particular embodiment, $R^{12b}$ is hydrogen.

$R^{13b}$ is hydrogen or $C_1$-$C_6$-alkyl. According to a particular embodiment, $R^{13b}$ is hydrogen.

Alternatively, $R^{12a}$ and $R^{12b}$, or $R^{13a}$ and $R^{13b}$, together are together are carbonyl or, preferably, optionally substituted $C_1$-$C_4$-alkylene (e.g. 1,3-propylene), wherein one —CH$_2$— of $C_1$-$C_4$-alkylene may be replaced by an oxygen atom or —NR$^{14}$—.

In connection with $R^{12a}$ and $R^{12b}$, or $R^{13a}$ and $R^{13b}$, substituted $C_1$-$C_4$-alkylene in particular includes $C_1$-$C_4$-alkylene substituted with 1, 2 or 3 substituents selected from the group consisting of halogen, $C_1$-$C_4$-alkyl, $C_1$-$C_4$-haloalkyl, cyano, $C_1$-$C_4$-alkoxy and $C_1$-$C_4$-haloalkoxy.

According to a particular embodiment, $R^{12a}$ is $C_1$-$C_6$-alkyl and $R^{12b}$ is hydrogen or $C_1$-$C_6$-alkyl, or $R^{13a}$ is $C_1$-$C_6$-alkyl and $R^{13b}$ is hydrogen or $C_1$-$C_6$-alkyl.

According to a further particular embodiment, $R^{12a}$ is hydrogen and $R^{12b}$ is hydrogen, or $R^{13a}$ is hydrogen and $R^{13b}$ is hydrogen.

According to a further particular embodiment, $R^{12a}$ and $R^{12b}$ together are optionally substituted 1,3-propylene, or $R^{13a}$ and $R^{13b}$ together are optionally substituted 1,3-propylene.

$R^5$ is optionally substituted $C_6$-$C_{12}$-aryl (e.g. phenyl, 3-chlorophenyl, 3,4-dichlorophenyl or 2,4-dichlorophenyl, a further example being 2-fluorophenyl, 2-chlorophenyl, 3-fluorophenyl, 3-chlorophenyl; 3-cyanophenyl, 3-methylphenyl, 3-trifluoromethylphenyl, 3-methoxyphenyl, 4-fluorophenyl, 4-chlorophenyl, 4-methoxyphenyl, 3,4-difluorophenyl, 3,5-difluorophenyl, 3-fluoro-5-chlorophenyl, 3-chloro-4-fluorophenyl), optionally substituted $C_3$-$C_{12}$-cycloalkyl (e.g. cyclohexyl) or optionally substituted $C_3$-$C_{12}$-heterocyclyl.

In connection with $R^5$, substituted $C_3$-$C_{12}$-cycloalkyl in particular includes $C_3$-$C_{12}$-cycloalkyl, such as cyclopropyl or cyclohexyl, substituted with 1, 2 or 3 substituents selected from the group consisting of halogen, optionally substituted $C_1$-$C_6$-alkyl, halogenated $C_1$-$C_6$-alkyl, CN, hydroxy, $C_1$-$C_6$-alkoxy, halogenated $C_1$-$C_6$-alkoxy, amino, $C_1$-$C_6$-alkylamino, di-$C_1$-$C_6$-alkylamino and $C_3$-$C_{12}$-heterocyclyl.

In connection with $R^5$, substituted $C_6$-$C_{12}$-aryl in particular includes $C_6$-$C_{12}$-aryl, such as phenyl, substituted with 1, 2 or 3 substituents selected from the group consisting of halogen (e.g. F, Cl, Br), optionally substituted $C_1$-$C_6$-alkyl (e.g. methyl), halogenated $C_1$-$C_6$-alkyl (e.g. trifluoromethyl), CN, hydroxy, $C_1$-$C_6$-alkoxy (e.g. methoxy), halogenated $C_1$-$C_6$-alkoxy, amino, $C_1$-$C_6$-alkylamino, di-$C_1$-$C_6$-alkylamino and $C_3$-$C_{12}$-heterocyclyl.

In connection with $R^5$, substituted $C_3$-$C_{12}$-heterocyclyl in particular includes $C_3$-$C_{12}$-heterocyclyl substituted with 1, 2 or 3 substituents selected from the group consisting of halogen, optionally substituted $C_1$-$C_6$-alkyl, halogenated $C_1$-$C_6$-alkyl, CN, hydroxy, $C_1$-$C_6$-alkoxy, halogenated $C_1$-$C_6$-alkoxy, amino, $C_1$-$C_6$-alkylamino, di-$C_1$-$C_6$-alkylamino and $C_3$-$C_{12}$-heterocyclyl.

In connection with $R^5$, $C_3$-$C_{12}$-heterocyclyl in particular is $C_3$-$C_{12}$-heteroaryl.

Preferably, $R^5$ is optionally substituted $C_6$-$C_{12}$-aryl, in particular as in the aminotetraline derivatives of the formula:

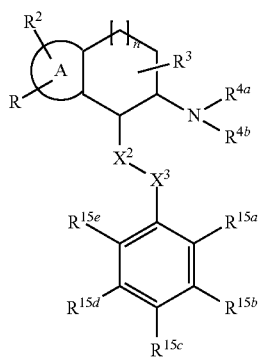

wherein A, R, $R^2$, $R^3$, $R^{4a}$, $R^{4b}$, $X^2$, $X^3$, n are as defined herein, and $R^{15a}$, $R^{15b}$, $R^{15c}$, $R^{15d}$, $R^{15e}$ independently are hydrogen, halogen (e.g. F, Cl or Br), optionally substituted $C_1$-$C_6$-alkyl (e.g. methyl), halogenated $C_1$-$C_6$-alkyl (e.g. trifluoromethyl), CN, hydroxy, $C_1$-$C_6$-alkoxy (e.g. methoxy), amino, $C_1$-$C_6$-alkylamino, di-$C_1$-$C_6$-alkylamino or $C_3$-$C_{12}$-heterocyclyl.

According to a particular embodiment, the invention relates to aminotetralin derivatives of the formula:

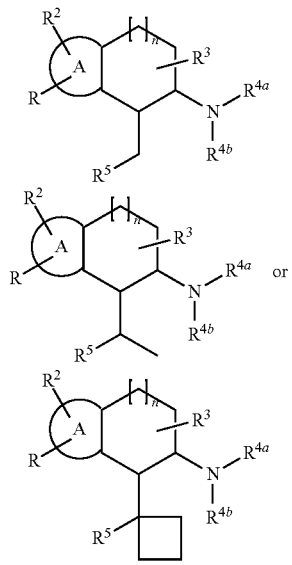

wherein A, R, $R^2$, $R^3$, $R^{4a}$, $R^{4b}$, $R^5$, n are as defined herein, $R^5$ preferably being optionally substituted aryl and in particular optionally substituted phenyl as disclosed herein.

In connection with $R^5$ or $R^{15a}$, $R^{15b}$, $R^{15c}$, $R^{15d}$, $R^{15e}$, substituted $C_1$-$C_6$-alkyl in particular includes $C_1$-$C_6$-alkyl, especially $C_1$-$C_4$-alkyl, substituted with 1, 2 or 3 substituents selected from the group consisting of hydroxy, $C_1$-$C_6$-alkoxy, amino, $C_1$-$C_6$-alkylamino, di-$C_1$-$C_6$-alkylamino and $C_3$-$C_{12}$-heterocyclyl (e.g. morpholinyl or piperidinyl).

According to a particular embodiment, $R^{15a}$, $R^{15b}$, $R^{15d}$, $R^{15e}$ are hydrogen and $R^{15c}$ is different from hydrogen (para-mono-substitution).

According to a further particular embodiment, $R^{15a}$, $R^{15c}$, $R^{15d}$, $R^{15e}$ are hydrogen and $R^{15b}$ is different from hydrogen (meta-mono-substitution).

In connection with $R^{15a}$, $R^{15b}$, $R^{15c}$, $R^{15d}$, $R^{15e}$, $C_3$-$C_{12}$-heterocyclyl in particular includes morpholinyl, imidazolyl and pyrazolyl.

The index n is 0, 1 or 2. According to a particular embodiment, n is 1.

$R^6$ is hydrogen or $C_1$-$C_6$-alkyl. Preferably, $R^6$ is hydrogen.
$R^7$ is hydrogen or $C_1$-$C_6$-alkyl. Preferably, $R^7$ is hydrogen.
$R^8$ is hydrogen or $C_1$-$C_6$-alkyl. Preferably, $R^8$ is hydrogen.
$R^9$ is hydrogen, $C_1$-$C_6$-alkyl (e.g. methyl or ethyl), $C_3$-$C_{12}$-cycloalkyl (e.g. cyclopropyl), amino-$C_1$-$C_6$-alkyl, optionally substituted $C_6$-$C_{12}$-aryl-$C_1$-$C_4$-alkyl or $C_3$-$C_{12}$-heterocyclyl (e.g. 3-azetidinyl). Preferably, $R^9$ is hydrogen or $C_1$-$C_6$-alkyl (e.g. methyl or ethyl).

According to a particular embodiment, $R^9$ and $R^1$ together are $C_1$-$C_4$-alkylene (e.g. 1,3-propylene, a further example being 1,2-ethylene) so as that $R^9$ and $R^1$ together with the atom in Q to which $R^1$ is bound and the nitrogen atom to which $R^9$ is bound form an heterocyclic ring having, in particular, 4, 5 or 6 ring member atoms (including the nitrogen atom and Q). With W and $A^1$ both being a bond, such a ring may be represented by the following partial structure:

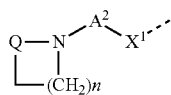

wherein Q is as defined herein (e.g. S(O)$_2$) and n is 0, 1, 2, 3 or 4.

According to a further particular embodiment, R$^9$ is C$_1$-C$_4$-alkylene (e.g. methylene or 1,3-propylene) that is bound to a carbon atom in A$^2$ and A$^2$ is C$_1$-C$_4$-alkylene so that R$^9$ and at least part of A$^2$ together with the nitrogen atom to which R$^9$ is bound form an N-containing heterocyclic ring having, in particular, 4, 5, 6 or 7 ring member atoms (including the nitrogen atom). Such a ring may be represented by the following partial structure:

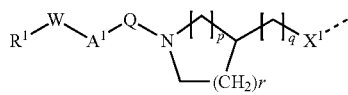

wherein R$^1$, W, A$^1$, Q and X$^1$ are as defined herein, p is 1 or 2, r is 0, 1 or 2 and q is 0, 1 or 2. In this particular embodiment, X$^1$ preferably is —O—. Particular combinations of p, r and q include p=1, r=0, q=1; and p=1, r=0, q=0. Alternatively, p is 0, r is 3 and q is 1, with X$^1$ preferably being —O—.

According to a further particular embodiment, R$^9$ is C$_1$-C$_4$-alkylene (e.g. methylene or 1,3-propylene) that is bound to a carbon atom in X$^1$ and X$^1$ is C$_1$-C$_4$-alkylene (e.g. 1,2-ethylene) so that R$^9$ and at least part of X$^1$ together with the nitrogen atom to which R$^9$ is bound form an N-containing heterocyclic ring having, in particular, 4, 5, 6 or 7 ring member atoms (including the nitrogen atom). With A$^2$ being a bond, such a ring may be represented by the following partial structure:

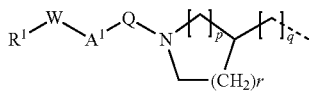

wherein R$^1$, W, A$^1$, Q and X$^1$ are as defined herein, p is 1 or 2, r is 0, 1 or 2 and q is 0, 1 or 2. Particular combinations of p, r and q include p=1, r=0, q=0.

R$^{10}$ is hydrogen, C$_1$-C$_6$-alkyl or C$_1$-C$_6$-alkylsulfonyl. Preferably, R$^{10}$ is hydrogen.

R$^{11}$ is hydrogen or C$_1$-C$_6$-alkyl. Preferably, R$^{11}$ is hydrogen.

Alternatively, R$^9$, R$^{11}$ together are C$_1$-C$_4$-alkylene (e.g. ethylene).

R$^{14}$ is hydrogen or C$_1$-C$_6$-alkyl. Preferably, R$^{14}$ is hydrogen.

R$^{15}$ is hydrogen or C$_1$-C$_6$-alkyl. Preferably, R$^{15}$ is hydrogen.

R$^{16}$ is hydrogen or C$_1$-C$_6$-alkyl. Preferably, R$^{16}$ is hydrogen.

Particular embodiments of aminotetraline derivatives of the invention result if

A is a 5- or 6-membered ring;
R is R$^1$—W—A$^1$-Q-Y-A$^2$-X$^1$— or —CN;
R$^1$ is hydrogen, C$_1$-C$_6$-alkyl, C$_3$-C$_{12}$-cycloalkyl-C$_1$-C$_4$-alkyl, halogenated C$_1$-C$_6$-alkyl, hydroxy-C$_1$-C$_4$-alkyl, C$_1$-C$_6$-alkoxy-C$_1$-C$_4$-alkyl, amino-C$_1$-C$_4$-alkyl, C$_1$-C$_6$-alkylamino-C$_1$-C$_4$-alkyl, di-C$_1$-C$_6$-alkylamino-C$_1$-C$_4$-alkyl, C$_1$-C$_6$-alkylcarbonylamino-C$_1$-C$_4$-alkyl, C$_1$-C$_6$-alkyloxycarbonylamino-C$_1$-C$_4$-alkyl, C$_1$-C$_6$-alkylaminocarbonylamino-C$_1$-C$_4$-alkyl, di-C$_1$-C$_6$-alkylaminocarbonylamino-C$_1$-C$_4$-alkyl, C$_1$-C$_6$-alkylsulfonylamino-C$_1$-C$_4$-alkyl, (optionally substituted C$_6$-C$_{12}$-aryl-C$_1$-C$_6$-alkyl)amino-C$_1$-C$_4$-alkyl, optionally substituted C$_6$-C$_{12}$-aryl-C$_1$-C$_4$-alkyl, optionally substituted C$_3$-C$_{12}$-heterocyclyl-C$_1$-C$_4$-alkyl, C$_3$-C$_{12}$-cycloalkyl, C$_1$-C$_6$-alkylcarbonyl, C$_1$-C$_6$-alkoxycarbonyl, halogenated C$_1$-C$_6$-alkoxycarbonyl, C$_6$-C$_{12}$-aryloxycarbonyl, aminocarbonyl, C$_1$-C$_6$-alkylaminocarbonyl, (halogenated C$_1$-C$_4$-alkyl)aminocarbonyl, C$_6$-C$_{12}$-arylaminocarbonyl, C$_2$-C$_6$-alkenyl, C$_2$-C$_6$-alkynyl, optionally substituted C$_6$-C$_{12}$-aryl, hydroxy, C$_1$-C$_6$-alkoxy, halogenated C$_1$-C$_6$-alkoxy, C$_1$-C$_6$-hydroxyalkoxy, C$_1$-C$_6$-alkoxy-C$_1$-C$_4$-alkoxy, amino-C$_1$-C$_4$-alkoxy, C$_1$-C$_6$-alkylamino-C$_1$-C$_4$-alkoxy, di-C$_1$-C$_6$-alkylamino-C$_1$-C$_4$-alkoxy, C$_1$-C$_6$-alkylcarbonylamino-C$_1$-C$_4$-alkoxy, C$_6$-C$_{12}$-arylcarbonylamino-C$_1$-C$_4$-alkoxy, C$_1$-C$_6$-alkoxycarbonylamino-C$_1$-C$_4$-alkoxy, C$_6$-C$_{12}$-aryl-C$_1$-C$_4$-alkoxy, C$_1$-C$_6$-alkylsulfonylamino-C$_1$-C$_4$-alkoxy, (halogenated C$_1$-C$_6$-alkyl)sulfonylamino-C$_1$-C$_4$-alkoxy, C$_6$-C$_{12}$-arylsulfonylamino-C$_1$-C$_4$-alkoxy, (C$_6$-C$_{12}$-aryl-C$_1$-C$_6$-alkyl)sulfonylamino-C$_1$-C$_4$-alkoxy, C$_3$-C$_{12}$-heterocyclylsulfonylamino-C$_1$-C$_4$-alkoxy, C$_3$-C$_{12}$-heterocyclyl-C$_1$-C$_4$-alkoxy, C$_6$-C$_{12}$-aryloxy, C$_3$-C$_{12}$-heterocyclyloxy, C$_1$-C$_6$-alkylthio, halogenated C$_1$-C$_6$-alkylthio, C$_1$-C$_6$-alkylamino, (halogenated C$_1$-C$_6$-alkyl)amino, di-C$_1$-C$_6$-alkylamino, di-(halogenated C$_1$-C$_6$-alkyl)amino, C$_1$-C$_6$-alkylcarbonylamino, (halogenated C$_1$-C$_6$-alkyl)carbonylamino, C$_6$-C$_{12}$-arylcarbonylamino, C$_1$-C$_6$-alkylsulfonylamino, (halogenated C$_1$-C$_6$-alkyl)sulfonylamino, C$_6$-C$_{12}$-arylsulfonylamino or optionally substituted C$_3$-C$_{12}$-heterocyclyl;

W is —NR$^8$— or a bond;
A$^1$ is optionally substituted C$_1$-C$_4$-alkylene or a bond;
Q is —S(O)$_2$— or —C(O)—;
Y is —NR$^9$— or a bond;
A$^2$ is optionally substituted C$_1$-C$_4$-alkylene, C$_1$-C$_4$-alkylene-CO—, —CO—C$_1$-C$_4$-alkylene, C$_1$-C$_4$-alkylene-O—C$_1$-C$_4$-alkylene, C$_1$-C$_4$-alkylene-NR$^{10}$—C$_1$-C$_4$-alkylene, optionally substituted C$_6$-C$_{12}$-arylene, optionally substituted C$_6$-C$_{12}$-heteroarylene or a bond;
X$^1$ is —O—, —NR$^{11}$—, —S—, optionally substituted C$_1$-C$_4$-alkylene;
R$^2$ is hydrogen, halogen, C$_1$-C$_6$-alkyl, halogenated C$_1$-C$_4$-alkyl, hydroxy-C$_1$-C$_4$-alkyl, CN, C$_2$-C$_6$-alkenyl, C$_2$-C$_6$-alkynyl, optionally substituted C$_6$-C$_{12}$-aryl, hydroxy, C$_1$-C$_6$-alkoxy, halogenated C$_1$-C$_6$-alkoxy, C$_1$-C$_6$-alkoxycarbonyl, C$_2$-C$_6$-alkenyloxy, C$_6$-C$_{12}$-aryl-C$_1$-C$_4$-alkoxy, C$_1$-C$_6$-alkylcarbonyloxy, C$_1$-C$_6$-alkylthio, C$_1$-C$_6$-alkylsulfinyl, C$_1$-C$_6$-alkylsulfonyl, aminosulfonyl, amino, C$_1$-C$_6$-alkylamino, C$_2$-C$_6$-alkenylamino, nitro or optionally substituted C$_3$-C$_{12}$-heterocyclyl, or two radicals R$^2$ together with the ring atoms of A to which they are bound form a 5- or 6 membered ring;
R$^3$ is hydrogen, halogen, C$_1$-C$_6$-alkyl or C$_1$-C$_6$-alkoxy, or two radicals R$^3$ together with the carbon atom to which they are attached form a carbonyl group;
R$^{4a}$ is hydrogen, C$_1$-C$_6$-alkyl, C$_3$-C$_{12}$-cycloalkyl-C$_1$-C$_4$-alkyl, halogenated C$_1$-C$_4$-alkyl, hydroxy-C$_1$-C$_4$-alkyl, C$_1$-C$_6$-alkoxy-C$_1$-C$_4$-alkyl, amino-C$_1$-C$_4$-alkyl, CH$_2$CN, —CHO, C$_1$-C$_4$-alkylcarbonyl, (halogenated C$_1$-C$_4$-alkyl) carbonyl, C$_6$-C$_{12}$-arylcarbonyl, C$_1$-C$_4$-alkoxycarbonyl, C$_6$-C$_{12}$-aryloxycarbonyl, C$_1$-C$_6$-alkylaminocarbonyl, $C_2$-$C_6$-alkenyl, —C(=NH)NH$_2$, —C(=NH)NHCN, $C_1$-$C_6$-alkylsulfonyl, $C_6$-$C_{12}$-arylsulfonyl, amino, —NO or $C_3$-$C_{12}$-heterocyclyl;

$R^{4b}$ is hydrogen, $C_1$-$C_6$-alkyl, halogenated $C_1$-$C_4$-alkyl, hydroxy-$C_1$-$C_4$-alkyl, $C_1$-$C_6$-alkoxy-$C_1$-$C_4$-alkyl, amino-$C_1$-$C_4$-alkyl, CH$_2$CN, —CHO, $C_1$-$C_4$-alkylcarbonyl, (halogenated $C_1$-$C_4$-alkyl)carbonyl, $C_6$-$C_{12}$-arylcarbonyl, $C_1$-$C_4$-alkoxycarbonyl, $C_6$-$C_{12}$-aryloxycarbonyl, $C_1$-$C_6$-alkylaminocarbonyl, $C_2$-$C_6$-alkenyl, —C(=NH)NH$_2$, —C(=NH)NHCN, $C_1$-$C_6$-alkylsulfonyl, $C_6$-$C_{12}$-arylsulfonyl, amino, —NO or $C_3$-$C_{12}$-heterocyclyl; or $R^{4a}R^{4b}$, together are optionally substituted $C_1$-$C_6$-alkylene, wherein one —CH$_2$— of $C_1$-$C_4$-alkylene may be replaced by an oxygen atom or —NR$^{16}$;

$X^2$ is —O—, —NR$^6$—, —S—, >CR$^{12a}$R$^{12b}$ or a bond;

$X^3$ is —O—, —NR$^7$—, —S—, >CR$^{13a}$R$^{13b}$ or a bond;

$R^5$ is optionally substituted $C_6$-$C_{12}$-aryl, optionally substituted $C_3$-$C_{12}$-cycloalkyl or optionally substituted $C_3$-$C_{12}$-heterocyclyl;

n is 0, 1 or 2;

$R^6$ is hydrogen or $C_1$-$C_6$-alkyl;

$R^7$ is hydrogen or $C_1$-$C_6$-alkyl;

$R^8$ is hydrogen or $C_1$-$C_6$-alkyl;

$R^9$ is hydrogen, $C_1$-$C_6$-alkyl, $C_3$-$C_{12}$-cycloalkyl, amino-$C_1$-$C_6$-alkyl, optionally substituted $C_6$-$C_{12}$-aryl-$C_1$-$C_4$-alkyl; or $R^9$, $R^1$ together are $C_1$-$C_4$-alkylene; or $R^9$ is $C_1$-$C_4$-alkylene that is bound to a carbon atom in $A^2$ and $A^2$ is $C_1$-$C_4$-alkylene or to a carbon atom in $X^1$ and $X^1$ is $C_1$-$C_4$-alkylene;

$R^{10}$ is hydrogen, $C_1$-$C_6$-alkyl or $C_1$-$C_6$-alkylsulfonyl;

$R^{11}$ is hydrogen or $C_1$-$C_6$-alkyl, or $R^9$, $R^{11}$ together are $C_1$-$C_4$-alkylene, $R^{12a}$ is hydrogen, optionally substituted $C_1$-$C_6$-alkyl, $C_1$-$C_6$-alkylamino-$C_1$-$C_4$-alkyl, di-$C_1$-$C_6$-alkylamino-$C_1$-$C_4$-alkyl, $C_3$-$C_{12}$-heterocyclyl-$C_1$-$C_6$-alkyl, optionally substituted $C_6$-$C_{12}$-aryl or hydroxy;

$R^{12b}$ is hydrogen or $C_1$-$C_6$-alkyl, or $R^{12a}$, $R^{12b}$ together are carbonyl or optionally substituted $C_1$-$C_4$-alkylene, wherein one —CH$_2$— of $C_1$-$C_4$-alkylene may be replaced by an oxygen atom or —NR$^{14}$—;

$R^{13a}$ is hydrogen, optionally substituted $C_1$-$C_6$-alkyl, $C_1$-$C_6$-alkylamino-$C_1$-$C_4$-alkyl, di-$C_1$-$C_6$-alkylamino-$C_1$-$C_4$-alkyl, $C_3$-$C_{12}$-heterocyclyl-$C_1$-$C_6$-alkyl, optionally substituted $C_6$-$C_{12}$-aryl or hydroxy;

$R^{13b}$ is hydrogen or $C_1$-$C_6$-alkyl, or $R^{13a}$, $R^{13b}$ together are carbonyl or optionally substituted $C_1$-$C_4$-alkylene, wherein one —CH$_2$— of $C_1$-$C_4$-alkylene may be replaced by an oxygen atom or —NR$^{15}$—;

$R^{14}$ is hydrogen or $C_1$-$C_6$-alkyl;

$R^{15}$ is hydrogen or $C_1$-$C_6$-alkyl; and $R^{16}$ is hydrogen or $C_1$-$C_6$-alkyl, or if one or more of said variables A, R, $R^1$, W, $A^1$, Q, Y, $A^2$, $X^1$, $R^2$, $R^3$, $R^4$, $X^2$, $X^3$, $R^5$, $R^6$, $R^7$, $R^8$, $R^9$, $R^{10}$, $R^{11}$, $R^{12}$, $R^{13}$, $R^{14}$, $R^{15}$, $R^{16}$, n are defined more precidely as disclosed herein.

Further particular embodiments of aminotetraline derivatives of the invention result if A is a benzene ring;

R is $R^1$—W-$A^1$-Q-Y-$A^2$-$X^1$—;

$R^1$ is $C_1$-$C_6$-alkyl (e.g. methyl, ethyl, n-propyl, isopropyl, n-butyl, sec-butyl, n-pentyl), $C_3$-$C_{12}$-cycloalkyl-$C_1$-$C_4$-alkyl (e.g. cyclopropylmethyl, cyclopentylmethyl, cyclohexylmethyl), halogenated $C_1$-$C_6$-alkyl (e.g. 3-fluoroprop-1-yl, 3-chloroprop-1-yl, 3,3,3-trifluoroprop-1-yl), tri-($C_1$-$C_4$-alkyl)-silyl-$C_1$-$C_4$-alkyl (e.g. trimethylsilylethyl), $C_1$-$C_6$-alkoxy-$C_1$-$C_4$-alkyl (e.g. ethoxyethyl), $C_3$-$C_{12}$-cycloalkyl (e.g. cyclopropyl, cyclobutyl, cyclohexyl), $C_2$-$C_6$-alkenyl (e.g. prop-1,2-en-1-yl), optionally substituted $C_6$-$C_{12}$-aryl (e.g. phenyl, 2-methylphenyl), or optionally substituted $C_3$-$C_{12}$-heterocyclyl (e.g. 1-methyl-pyrrol-3-yl, 2-pyridyl, 3-pyridyl, 2-thienyl, 4-methyl-2-thienyl, 5-methyl-2-thienyl, 5-chloro-2-thienyl, 2,5-dimethyl-3-thienyl, 1,2-diazol-4-yl, 1-methyl-1,2-diazol-3-yl, 1-methyl-1,2-diazol-4-yl, 1-ethyl-1,2-diazol-4-yl, 1-difluormethyl-1,2-diazol-4-yl, 1-methyl-3-trifluoromethyl-1,2-diazol-4-yl, 2-methyl-1,3-diazol-4-yl, 1-methyl-1,3-diazol-4-yl, 1,2-dimethyl-1,3-diazol-4-yl, 5-methylisoxazol-3-yl, 2-methyl-1,3-thiazol-5-yl, 2,4-dimethyl-1,3-thiazol-5-yl, 1-methyl-1,2,4-triazol-3-yl, 3-pyrrolidinyl);

W is a bond;

$A^1$ is a bond;

Q is —S(O)$_2$— or —C(O)—;

Y is —NR$^9$— or a bond;

$A^2$ is $C_1$-$C_4$-alkylene (e.g. 1,2-ethylene, 1,3-propylene) or a bond;

$X^1$ is —O— or optionally substituted $C_1$-$C_4$-alkylene (e.g. methylene, 1,2-ethylene, 1,3-propylene) or $C_2$-$C_4$-alkynylene (e.g. prop-1,2-yn-1,3-ylene);

$R^2$ is hydrogen;

$R^3$ is hydrogen;

$R^{4a}$ is hydrogen, $C_1$-$C_6$-alkyl (e.g. methyl, ethyl, n-propyl, isopropyl), $C_3$-$C_{12}$-cycloalkyl-$C_1$-$C_4$-alkyl (e.g. cyclopropylmethyl), halogenated $C_1$-$C_4$-alkyl (e.g. 2-fluoroethyl, 2,2,2-trifluoroethyl), —CHO, $C_1$-$C_4$-alkylcarbonyl (e.g. methylcarbonyl, ethylcarbonyl, isopropylcarbonyl), (halogenated $C_1$-$C_4$-alkyl)carbonyl (e.g. fluoromethylcarbonyl, difluoromethylcarbonyl, trifluoromethylcarbonyl, 1,1,1-trifluoroeth-2-ylcarbonyl, 1,1,1-trifluoroprop-3-ylcarbonyl), $C_6$-$C_{12}$-arylcarbonyl (e.g. phenylcarbonyl), $C_1$-$C_4$-alkoxycarbonyl (e.g. ethoxycarbonyl, tert-butyloxycarbonyl), $C_6$-$C_{12}$-aryloxycarbonyl (e.g. phenoxycarbonyl);

$R^{4b}$ is hydrogen or $C_1$-$C_6$-alkyl (e.g. methyl, ethyl); or $R^{4a}$, $R^{4b}$ together are optionally substituted $C_1$-$C_6$-alkylene (e.g. 1,3-propylene, 1,4-butylene, 2-fluoro-but-1,4-ylene, 1-oxo-but-1,4-ylene), wherein one —CH$_2$— of $C_1$-$C_4$-alkylene may be replaced by an oxygen atom (e.g. —CH$_2$—CH$_2$—O—CH$_2$—CH$_2$—);

$X^2$ is CR$^{12a}$R$^{12b}$;

$X^3$ is a bond;

$R^5$ is optionally substituted phenyl (e.g. phenyl, 2-fluorophenyl, 2-chlorophenyl, 3-fluorophenyl, 3-chlorophenyl, 3-cyanophenyl, 3-methylphenyl, 3-trifluoromethylphenyl, 3-methoxyphenyl, 4-fluorophenyl, 4-chlorophenyl, 4-methoxyphenyl, 3,4-difluorophenyl, 3,5-difluorophenyl, 3-fluoro-5-chlorophenyl, 3-chloro-4-fluorophenyl, 3,4-dichlorophenyl, 2,4-dichlorophenyl) or optionally substituted $C_3$-$C_{12}$-cycloalkyl (e.g. cyclohexyl);

n is 1;

$R^9$ is hydrogen, $C_1$-$C_6$-alkyl (e.g. methyl, ethyl) or $C_3$-$C_{12}$-cycloalkyl [cyclopropyl], or $R^9$, $R^1$ together are $C_1$-$C_4$-alkylene (e.g. 1,3-propylene); or $R^9$ is $C_1$-$C_4$-alkylene (e.g. methylene, 1,3-propylene) that is bound to a carbon atom in $A^2$ and $A^2$ is $C_1$-$C_4$-alkylene (e.g.

1,2-ethylene, 1,3-propylene) or to a carbon atom in $X^1$ and $X^1$ is $C_1$-$C_4$-alkylene (e.g. 1,2-ethylene);
$R^{12a}$ is hydrogen; and
$R^{12b}$ is hydrogen.

Further particular embodiments of aminotetraline derivatives of the invention result if
A is a benzene ring;
R is $R^1$—W-$A^1$-Q-Y-$A^2$-$X^1$—;
$R^1$ is $C_1$-$C_6$-alkyl (e.g. methyl, ethyl, n-propyl, isopropyl or sec-butyl), $C_3$-$C_{12}$-cycloalkyl-$C_1$-$C_4$-alkyl (e.g. cyclopentylmethyl or cyclohexylmethyl), halogenated $C_1$-$C_6$-alkyl (e.g. 3-fluoroprop-1-yl, 3-chloroprop-1-yl or 3,3,3-trifluoroprop-1-yl), $C_3$-$C_{12}$-cycloalkyl (e.g. cyclopropyl or cyclobutyl), $C_2$-$C_6$-alkenyl (e.g. prop-1,2-en-1-yl), optionally substituted $C_6$-$C_{12}$-aryl (e.g. phenyl), or optionally substituted $C_3$-$C_{12}$-heterocyclyl (e.g. 3-pyridyl, 2-thienyl, 4-methyl-2-thienyl, 5-methyl-2-thienyl, 5-chloro-2-thienyl, 2,5-dimethyl-3-thienyl, 1,2-diazol-4-yl, 1-methyl-1,2-diazol-4-yl, 1-ethyl-1,2-diazol-4-yl, 1-difluormethyl-1,2-diazol-4-yl, 2-methyl-1,3-diazol-4-yl, 1-methyl-1,3-diazol-4-yl, 2-methyl-1,3-thiazol-5-yl, 2,4-dimethyl-1,3-thiazol-5-yl or 3-pyrrolidinyl);
W is a bond;
$A^1$ is a bond;
Q is —S(O)$_2$— or —C(O)—;
Y is —NR$^9$— or a bond;
$A^2$ is $C_1$-$C_4$-alkylene (e.g. methylene or 1,3-propylene) or a bond;
$X^1$ is —O— or optionally substituted $C_1$-$C_4$-alkylene (e.g. methylene);
$R^2$ is hydrogen;
$R^3$ is hydrogen;
$R^{4a}$ is hydrogen, $C_1$-$C_6$-alkyl (e.g. methyl, ethyl, n-propyl or isopropyl), $C_3$-$C_{12}$-cycloalkyl-$C_1$-$C_4$-alkyl (e.g. cyclopropylmethyl), halogenated $C_1$-$C_4$-alkyl (e.g. 2-fluoroethyl or 2,2,2-trifluoroethyl), $C_1$-$C_4$-alkylcarbonyl (e.g. methylcarbonyl or, isopropylcarbonyl), (halogenated $C_1$-$C_4$-alkyl) carbonyl (e.g. fluoromethylcarbonyl, difluoromethylcarbonyl or trifluoromethylcarbonyl), $C_6$-$C_{12}$-arylcarbonyl (e.g. phenylcarbonyl), $C_1$-$C_4$-alkoxycarbonyl (e.g. ethoxycarbonyl or tert-butyloxycarbonyl), $C_6$-$C_{12}$-aryloxycarbonyl (e.g. phenoxycarbonyl);
$R^{4b}$ is hydrogen or $C_1$-$C_6$-alkyl (e.g. methyl);
$X^2$ is $CR^{12a}R^{12b}$;
$X^3$ is a bond;
$R^5$ is optionally substituted phenyl (e.g. phenyl, 3-chlorophenyl, 3,4-dichlorophenyl or 2,4-dichlorophenyl);
n is 1;
$R^6$ is hydrogen;
$R^7$ is hydrogen;
$R^8$ is hydrogen;
$R^9$ is hydrogen or alkyl (e.g. methyl or ethyl); or
$R^9$, $R^1$
together are $C_1$-$C_4$-alkylene (e.g. 1,3-propylene); or
$R^9$ is $C_1$-$C_4$-alkylene (e.g. methylene or 1,3-propylene) that is bound to a carbon atom in $A^2$ and $A^2$ is $C_1$-$C_4$-alkylene;
$R^{10}$ is hydrogen;
$R^{11}$ is hydrogen;
$R^{12a}$ is hydrogen; and
$R^{12b}$ is hydrogen.

Particular compounds of the present invention are the aminotetraline derivatives disclosed in preparation examples and physiologically tolerated acid addition salts thereof. These include for each preparation example the exemplified compound as well as the corresponding free base and any other physiologically tolerated acid addition salts of the free base (if the exemplified compound is a salt), or any physiologically tolerated acid addition salt of the free base (if the exemplified compound is a free base). These further include enantiomers, diastereomers, tautomers and any other isomeric forms of said compounds, be they explicitly or implicitly disclosed.

The compounds of the formula (I) can be prepared by analogy to methods which are well known in the art. Suitable methods for the preparation of compounds of formula (I) is outlined in the following schemes.

The process depicted in scheme 1 is useful for obtaining aminotetralines, wherein $X^1$ is —O— or —S—.

Scheme 1:

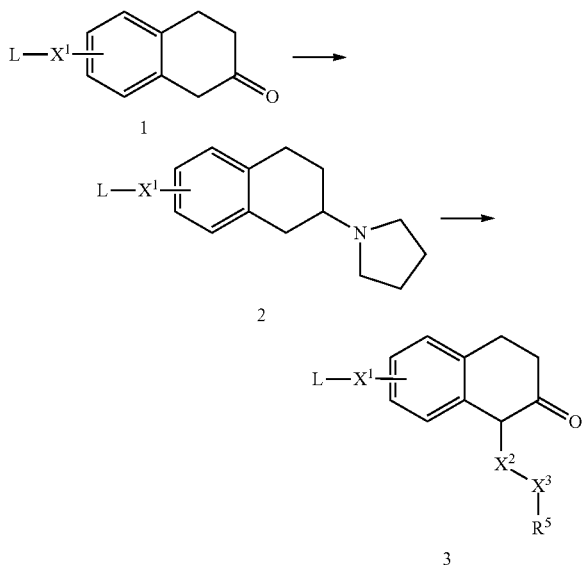

As shown in scheme 1, the compound of general formula 1 readily undergoes enamine alkylation to give the compound of general formula 3.

In scheme 1, the variables $X^2$, $X^3$, $R^5$ are as defined herein and L a suitable protecting group (e.g. L=Me). The process depicted in scheme 1 is also useful for obtaining aminotetralines, wherein X is optionally substituted alkylene. In this case, L is a group that represents, or can be converted into, the desired side chain $R^1$—W-$A^1$-Q-Y-$A^2$-.

Alternatively, compounds of formula 3 can be prepared as described in scheme 2.

Scheme 2:

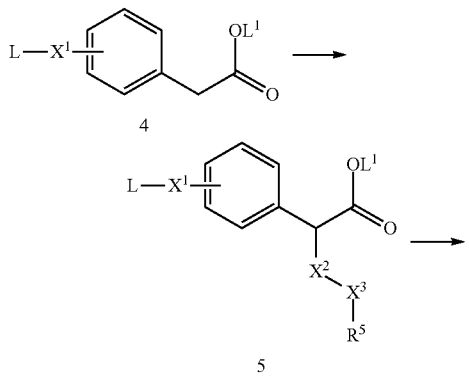

-continued

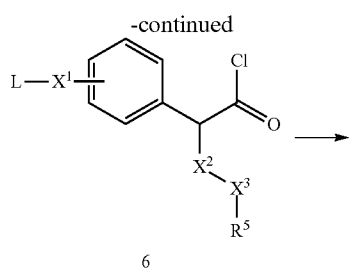
6

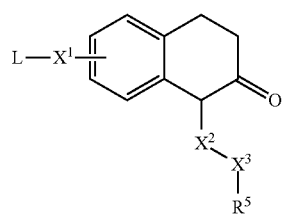
3

As shown in scheme 2, the compound of general formula 4 readily undergoes alkylation to give the compound of general formula 5. Conversion to the acid chloride and subsequent ring closure with ethylene in the presence of a Lewis acid (e.g. $AlCl_3$) affords compound 3 (e.g. J. Het. Chem., 23 (2), 343, 1986 and Bioorg. Med. Chem. Let, 17 (22), 6160, 2007)

The variables $X^2$, $X^3$, $R^5$ are as defined herein and L, $L^1$ are a suitable protecting group (e.g. L, $L^1$=Me). Compounds 3 can be further converted to compounds of the general formula (I).

The process depicted in scheme 3 is useful for obtaining aminotetralines, wherein $X^1$ is —O— or —S—, $A^2$ is optionally substituted alkylene, Y is —$NR^9$—, and Q is —$S(O)_2$.

Scheme 3:

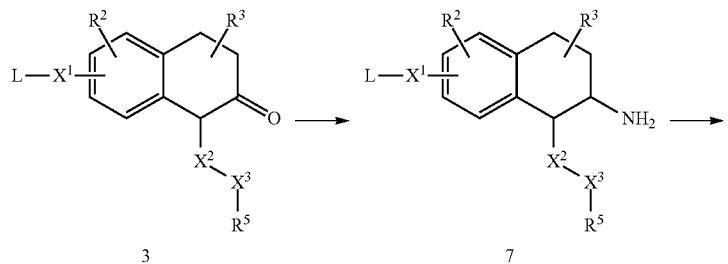

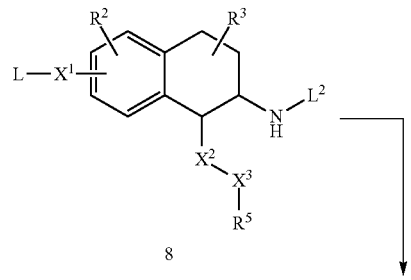
8

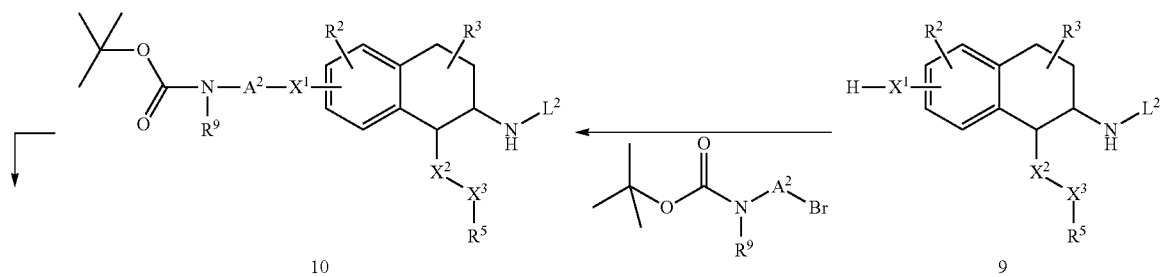

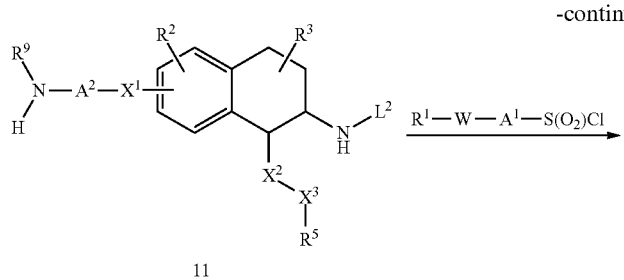
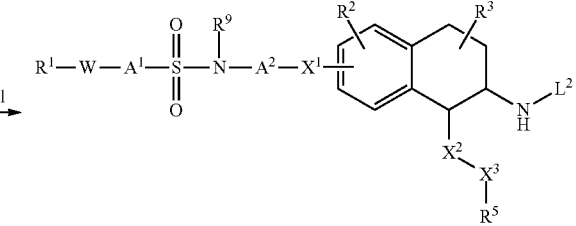
11 → 12
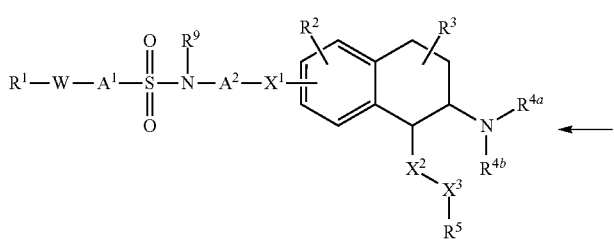
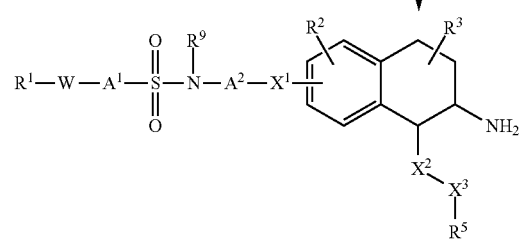
14 ← 13
In scheme 3, the variables $R^1$, W, $A^1$, $R^2$, $R^3$, $R^{4a}$, $R^{4b}$, $R^5$, $R^9$, $X^2$, $X^3$ are as defined herein and $L^2$ is a suitable protecting group (e.g. $L^2$=COOEt).
The process depicted in scheme 4 is useful for obtaining aminotetralines, wherein $X^1$ is methylene, $A^2$ is a bond, Y is —$NR^9$—, and Q is —$S(O)_2$—.
Scheme 4:
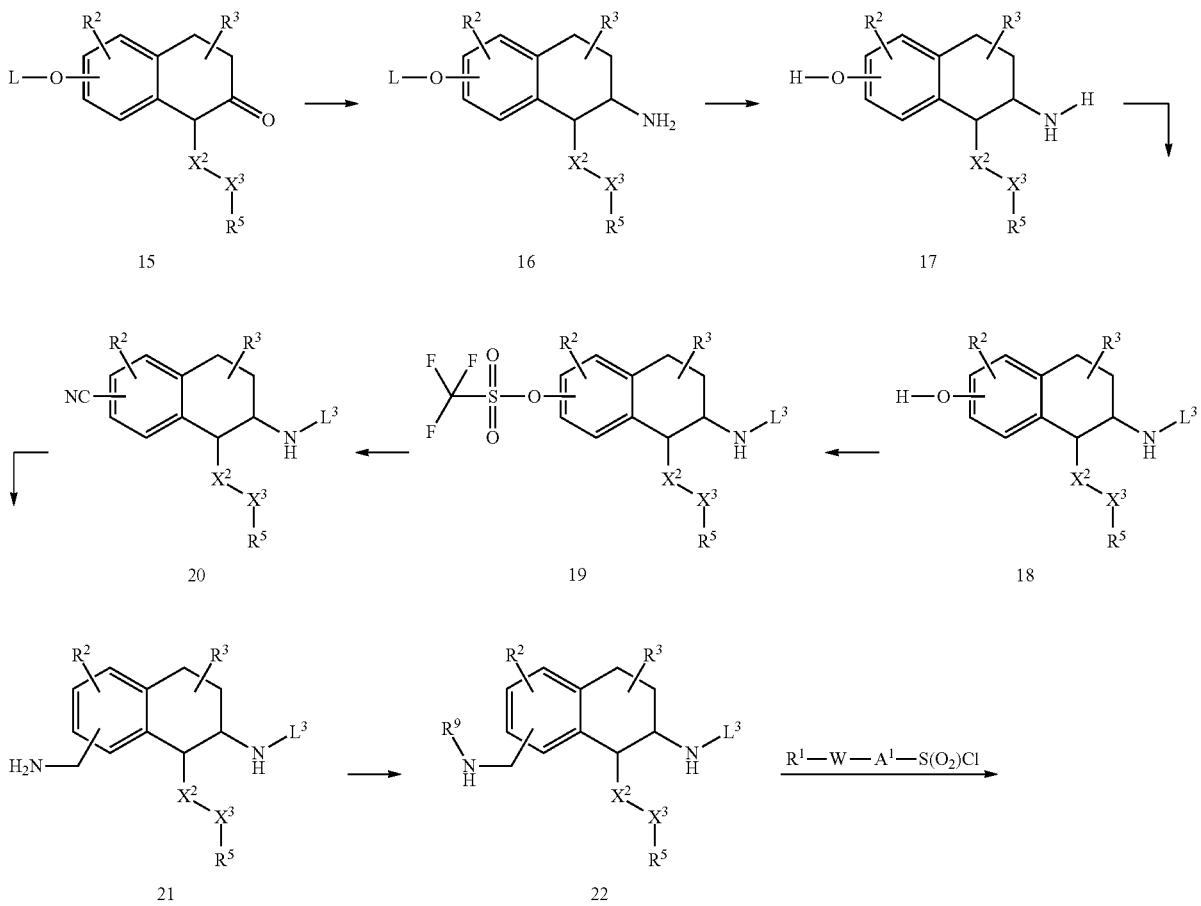

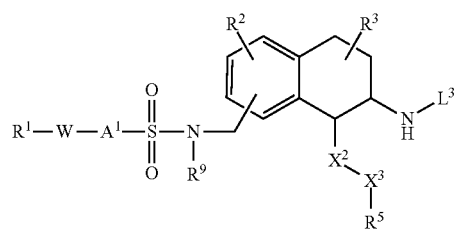

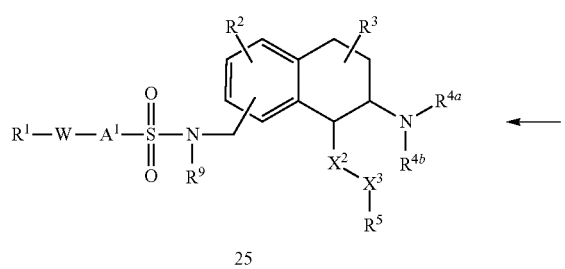

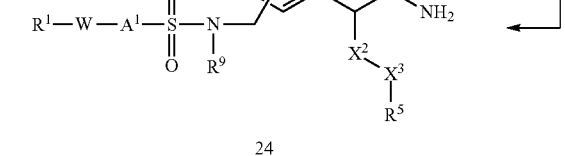

Alternatively to triflate 19, the corresponding bromide or iodide can be used to prepare compound 20.

In scheme 4, the variables $R^1$, W, $A^1$, $R^2$, $R^3$, $R^{4a}$, $R^{4b}$, $R^5$, $R^9$, $X^2$, $X^3$ are as defined herein, and $L^3$ is a suitable protecting group (e.g. $L^3$=COO$^t$Bu).

The process depicted in scheme 5 is useful for obtaining aminotetralines, wherein $X^1$ is optionally substituted alkylene, $A^2$ is optionally substituted alkylene or a bond, Y is —$NR^9$—, and Q is —$S(O)_2$.

Scheme 5:

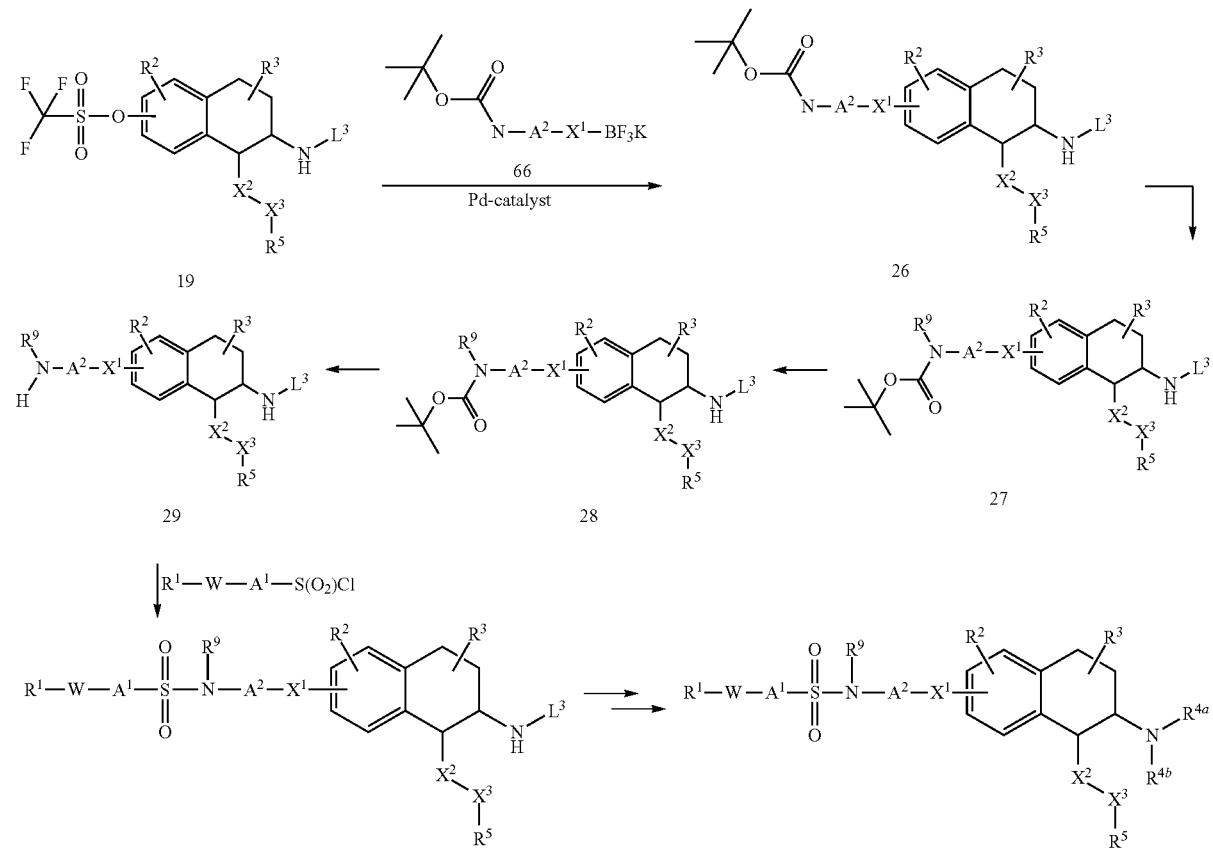

Instead of the trifluoroborate 66, the corresponding 9-borabicyclo[3.3.1]non-9-yl derivative can be used to prepare compound 26.

In scheme 5, the variables $R^1$, W, $A^1$, $R^2$, $R^3$, $R^{4a}$, $R^{4b}$, $R^5$, $R^9$, $X^2$, $X^3$, $A^2$ are as defined herein, and $L^3$ is a suitable protecting group (e.g. $L^3$=COO$^t$Bu).

The process depicted in scheme 6 is useful for obtaining aminotetralines, wherein X is —$NR^{11}$—, $A^2$ is optionally substituted alkylene, Y is —$NR^9$—, and Q is —$S(O)_2$.

Scheme 6:

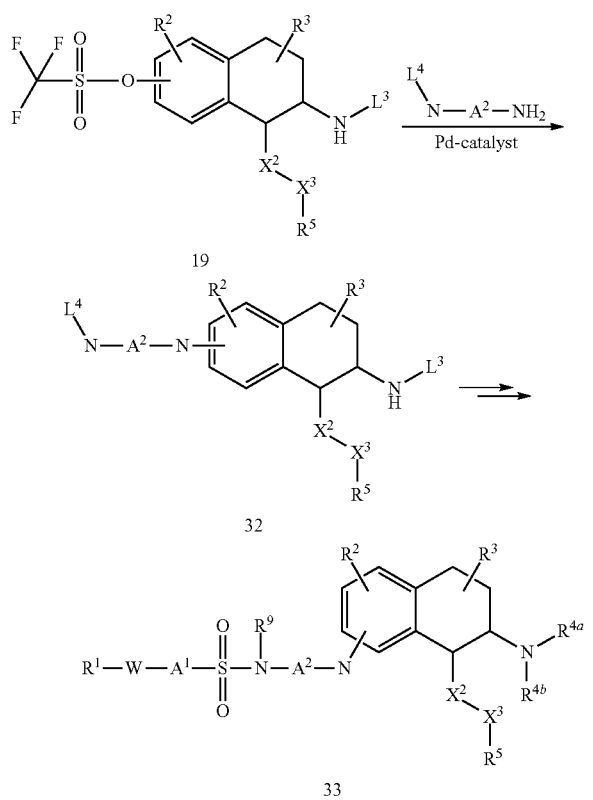

In scheme 5, the variables $R^1$, W, $A^1$, $R^2$, $R^3$, $R^{4a}$, $R^{4b}$, $R^5$, $R^9$, $X^2$, $X^3$, $A^2$ are as defined herein, and $L^4$ is a suitable protecting group.

The process depicted in the following schemes is useful for obtaining compounds of the general formula (I) in which A is a heterocycle.

Scheme 7:

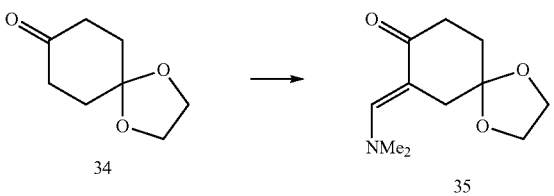

As shown in scheme 7, the compound of general formula 34 readily undergoes condensation with dimethylformamide dimethyl acetal to give the compound of general formula 35.

Scheme 8:

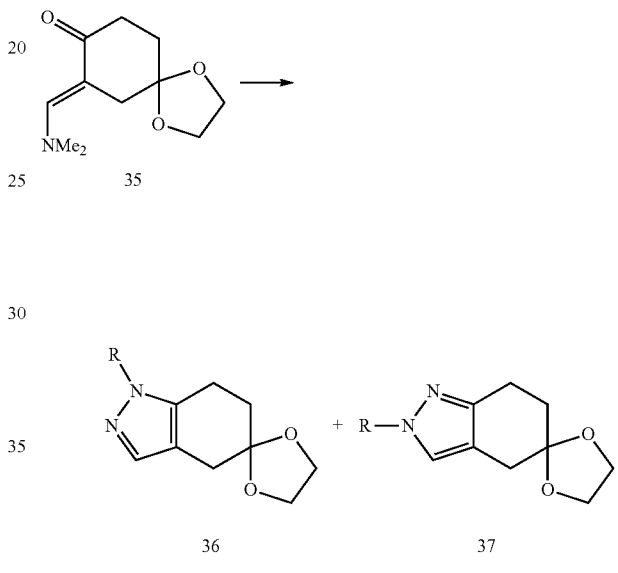

As shown in the above scheme 8, the intermediate of general formula 35 reacts with various nucleophiles of general formula $H_2N$—NH—R in an alcoholic solvent preferably methanol or ethanol at a temperature of about 20° to 80° C. to obtain the compounds of general formulae 36 and 37. In case of monosubstituted hydrazines regioisomeric products are formed. Compounds 36 and 37 can be transformed to compounds of the general formula (I) as depicted in Scheme 9.

In scheme 8, the variable R is as defined herein.

Scheme 9:

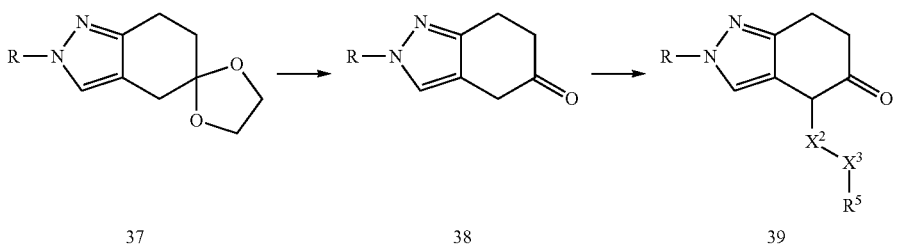

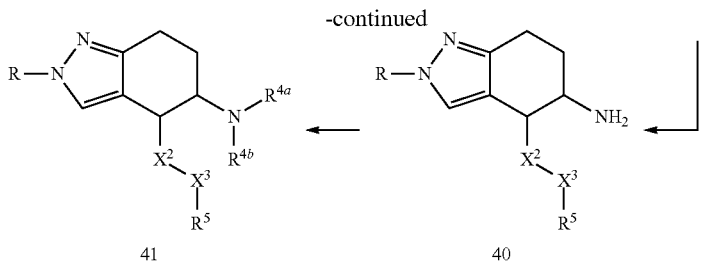

Alkylation of 38 can proceed via an enamine as described in scheme 1, or via an enolate. Reductive amination of 39 leads to 40. Alkylation or acylation of 40 affords 41. In scheme 9, the variables R, $R^{4a}$, $R^{4b}$, $R^5$, $X^2$, $X^3$ are as defined herein.

Scheme 10:

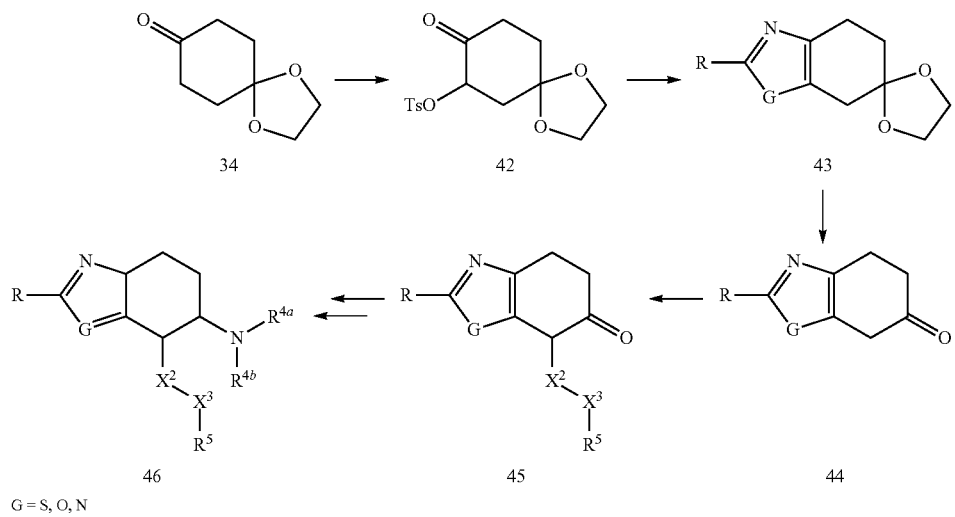

G = S, O, N

As shown in scheme 10, the reaction of compound of general formula 34 with hydroxyl(tosyloxy)iodobenzene gives the compound of formula 42. Reaction of compound of general formula 42 with 1,3-nucleophiles under appropriate conditions yield the compound of general formula 43. Further transformation to compounds of general formula 46 occurs as described in Scheme 9.

In scheme 10, the variables R, $R^{4a}$, $R^{4b}$, $R^5$, $X^2$, $X^3$ are as defined herein.

Scheme 11:

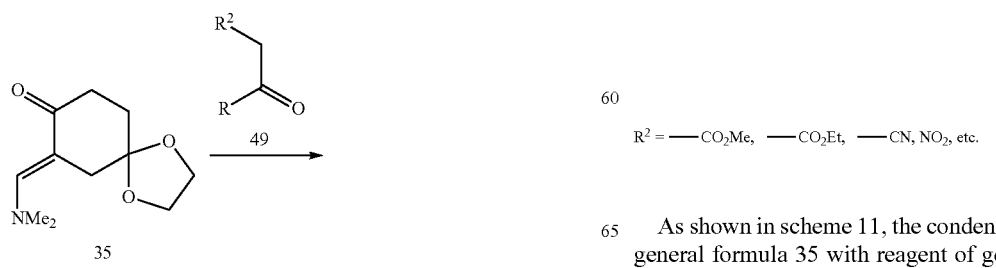

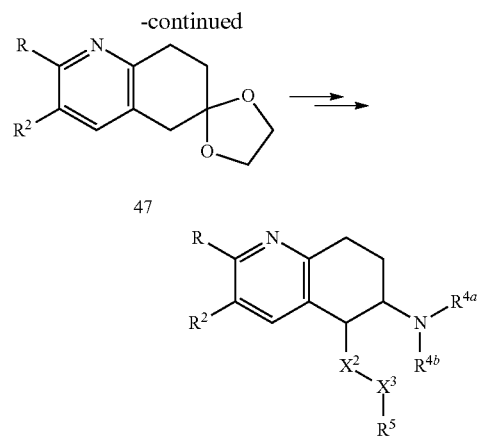

$R^2 =$ —$CO_2Me$, —$CO_2Et$, —CN, $NO_2$, etc.

As shown in scheme 11, the condensation of compound of general formula 35 with reagent of general formula 49 and ammonia acetate in refluxing acetic acid give compound of general formula 47, which can be further transformed to compounds of general formula 48.

In scheme 11, the variables R, $R^{4a}$, $R^{4b}$, $R^5$, $X^2$, $X^3$ are as defined herein.

Scheme 12:

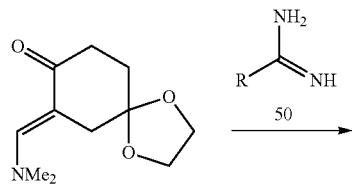

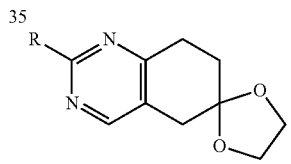

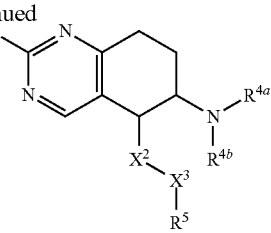

As shown in scheme 12, the cyclocondensation of intermediate of general formula 35 with the 1,3-nucleophiles of general formula 50 in the presence of suitable organic or inorganic bases such as KOH, NaOH, NaHCO$_3$, sodium ethoxide, sodium methoxide, triethyl amine and diisopropyl ethyl amine in an alcoholic solvent, preferably ethanol or methanol, at a temperature of about 20° to 80° C. yield the compound of general formula 51, which can be transformed further to give compounds of general formula 52.

In scheme 12, the variables R, $R^{4a}$, $R^{4b}$, $R^5$, $X^2$, $X^3$ are as defined herein.

Scheme 13:

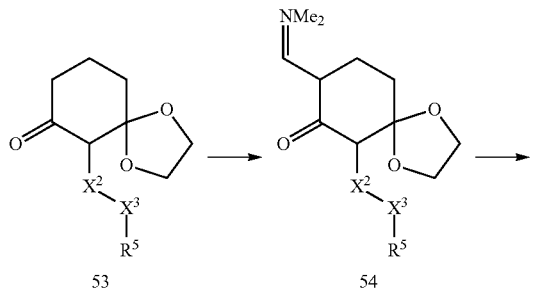

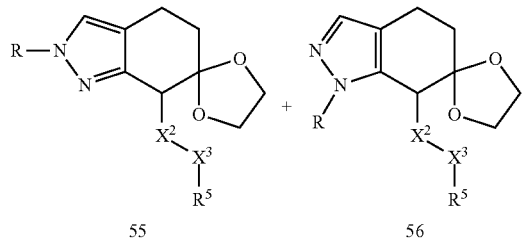

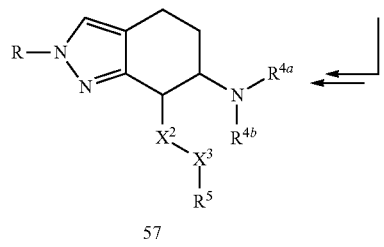

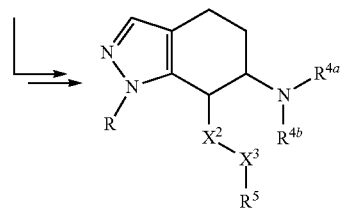

As shown in scheme 13, the intermediate of general formula 53 readily can undergo condensation with dimethylformamide dimethyl acetal to give the compound of general formula 54, which reacts with various nucleophiles of general formula H₂N—NH—R in an alcoholic solvent, preferably methanol or ethanol, at a temperature of about 20° to 80° C. to afford the compound of general formula 55 and 56. Compounds 55 and 56 can be transformed to compounds of the general formula (I) as depicted in the previous schemes.

In scheme 13, the variables R, $R^{4a}$, $R^{4b}$, $R^5$, $X^2$, $X^3$ are as defined herein.

Scheme 14:

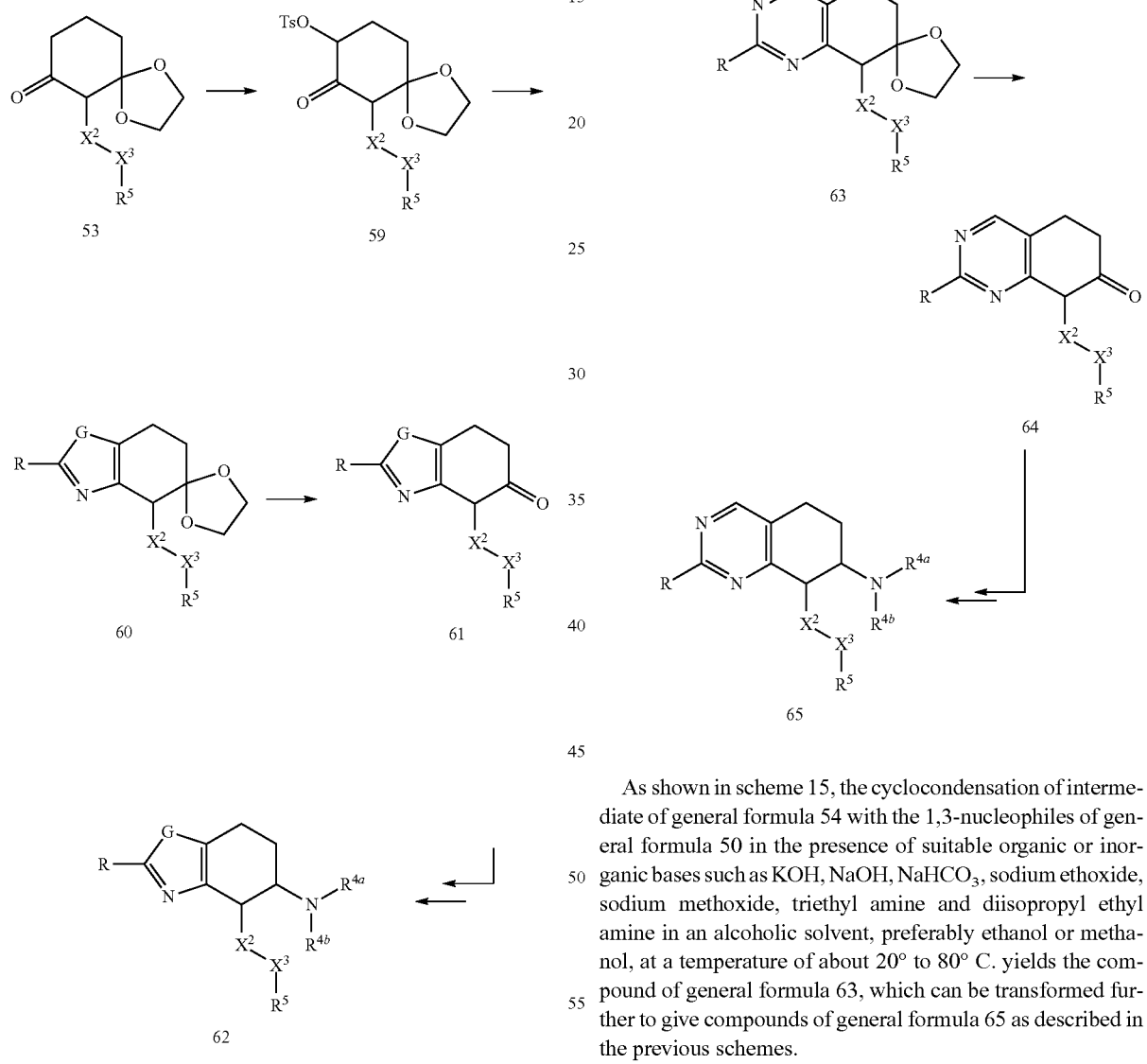

As shown in scheme 14, the reaction of compound of general formula 53 with hydroxyl(tosyloxy)iodobenzene gives the compound of formula 59, which reacts with 1,3-nucleophiles under appropriate conditions to yield the compound of general formula 60. Further transformation to compounds of general formula 62 occurs as described in the previous schemes.

In scheme 14, the variables R, $R^{4a}$, $R^{4b}$, $R^5$, $X^2$, $X^3$ are as defined herein.

Scheme 15:

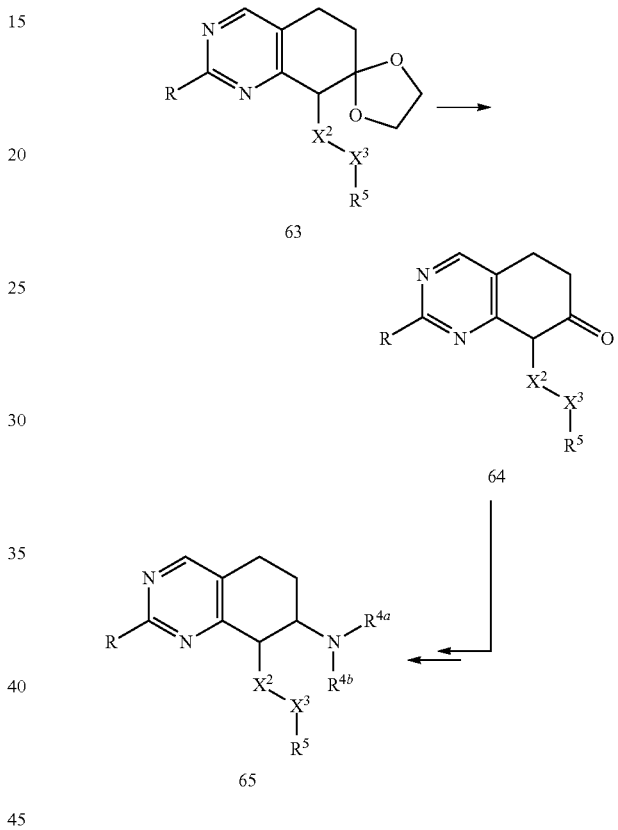

As shown in scheme 15, the cyclocondensation of intermediate of general formula 54 with the 1,3-nucleophiles of general formula 50 in the presence of suitable organic or inorganic bases such as KOH, NaOH, NaHCO₃, sodium ethoxide, sodium methoxide, triethyl amine and diisopropyl ethyl amine in an alcoholic solvent, preferably ethanol or methanol, at a temperature of about 20° to 80° C. yields the compound of general formula 63, which can be transformed further to give compounds of general formula 65 as described in the previous schemes.

In scheme 15, the variables R, $R^{4a}$, $R^{4b}$, $R^5$, $X^2$, $X^3$ are as defined herein.

The acid addition salts of the aminotetraline derivatives of formula (I) are prepared in a customary manner by mixing the free base with a corresponding acid, optionally in solution in an organic solvent, for example a lower alcohol, such as methanol, ethanol or propanol, an ether, such as methyl tert-butyl ether or diisopropyl ether, a ketone, such as acetone or methyl ethyl ketone, or an ester, such as ethyl acetate.

The aminotetraline derivatives of formula (II)

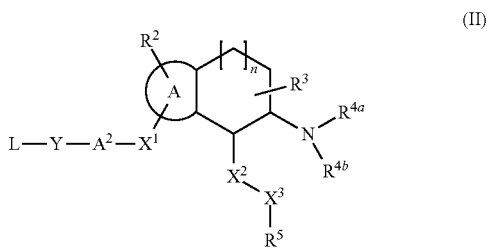

wherein L is an amino-protecting group, Y is NR9, and $A^2$, $X^1$, $R^2$, $R^3$, $R^{4a}$, $R^{4b}$, $X^2$, $X^3$, $R^5$, n are defined as above are useful as intermediates in the preparation of GlyT1 inhibitors, in particular those of formula (I).

Suitable amino-protecting groups are well known in the art such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991.

According to a particular embodiment, L is optionally substituted alkylcarbonyl (e.g., tertbutylcarbonyl), optionally substituted arylcarbonyl, optionally substituted arylalkycarbonyl (e.g., benzylcarbonyl), optionally substituted alkoxycarbonyl (e.g., methoxycarbonyl or tert-butyloxycarbonyl), optionally substituted aryloxycarbonyl (e.g. phenoxycarbonyl) or optionally substituted arylalkoxycarbonyl.

The compounds of the formula (I) are capable of inhibiting the activity of glycine transporter, in particular glycine transporter 1 (GlyT1).

The utility of the compounds in accordance with the present invention as inhibiting the glycine transporter activity, in particular GlyT1 activity, may be demonstrated by methodology known in the art. For instance, human GlyT1c expressing recombinant hGlyT1c_5_CHO cells can be used for measuring glycine uptake and its inhibition ($IC_{50}$) by a compound of formula (I).

Amongst the compounds of the formula (I) those are preferred which achieve effective inhibition at low concentrations. In particular, compounds of the formula (I) are preferred which inhibit glycine transporter 1 (GlyT1) at a level of $IC_{50} < 1$ μMol, more preferably at a level of $IC_{50} < 0.5$ μMol, particularly preferably at a level of $IC_{50} < 0.2$ μMol and most preferably at a level of $IC_{50} < 0.1$ μMol.

The compounds of the formula (I) according to the present invention are thus useful as pharmaceuticals.

The present invention therefore also relates to pharmaceutical compositions which comprise an inert carrier and a compound of the formula (I).

The present invention also relates to the use of the compounds of the formula (I) in the manufacture of a medicament for inhibiting the glycine transporter GlyT1, and to corresponding methods of inhibiting the glycine transporter GlyT1.

The NMDA receptor is central to a wide range of CNS processes, and its role in a variety of diseases in humans or other species has been described. GlyT1 inhibitors slow the removal of glycine from the synapse, causing the level of synaptic glycine to rise. This in turn increases the occupancy of the glycine binding site on the NMDA receptor, which increases activation of the NMDA receptor following glutamate release from the presynaptic terminal. Glycine transport inhibitors and in particular inhibitors of the glycine transporter GlyT1 are thus known to be useful in treating a variety of neurologic and psychiatric disorders. Further, glycine A receptors play a role in a variety of diseases in humans or other species. Increasing extracellular glycine concentrations by inhibiting glycine transport may enhance the activity of glycine A receptors. Glycine transport inhibitors and in particular inhibitors of the glycine transporter GlyT1 are thus useful in treating a variety of neurologic and psychiatric disorders.

The present invention thus further relates to the use of the compounds of the formula (I) for the manufacture of a medicament for treating a neurologic or psychiatric disorder, and to corresponding methods of treating said disorders.

According to a particular embodiment, the disorder is associated with glycinergic or glutamatergic neurotransmission dysfunction.

According to a further particular embodiment, the disorder is one or more of the following conditions or diseases: schizophrenia or a psychotic disorder including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced psychotic disorder, including both the positive and the negative symptoms of schizophrenia and other psychoses; cognitive disorders including dementia (associated with Alzheimer's disease, ischemia, multi-infarct dementia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or cognitive impairment including age related cognitive decline; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; substance-related disorders and addictive behaviors (including substance-induced delirium, persisting dementia, persisting amnestic disorder, psychotic disorder or anxiety disorder; tolerance, dependence or withdrawal from substances including alcohol, amphetamines, cannabis, cocaine, hallucinogens, inhalants, nicotine, opioids, phencyclidine, sedatives, hypnotics or anxiolytics); obesity, bulimia nervosa and compulsive eating disorders; bipolar disorders, mood disorders including depressive disorders; depression including unipolar depression, seasonal depression and post-partum depression, premenstrual syndrome (PMS) and premenstrual dysphoric disorder (PDD), mood disorders due to a general medical condition, and substance-induced mood disorders; learning disorders, pervasive developmental disorder including autistic disorder, attention deficit disorders including attention-deficit hyperactivity disorder (ADHD) and conduct disorder; movement disorders, including akinesias and akinetic-rigid syndromes (including Parkinson's disease, drug-induced parkinsonism, postencephalitic parkinsonism, progressive supranuclear palsy, multiple system atrophy, corticobasal degeneration, parkinsonism-ALS dementia complex and basal ganglia calcification), medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, epilepsy, muscular spasms and disorders associated with muscular spasticity or weakness including tremors; dyskinesias [including tremor (such as rest tremor, postural tremor and intention tremor), chorea (such as Sydenham's chorea, Huntington's disease, benign hereditary chorea, neuroacanthocytosis, symptomatic chorea, drug-induced chorea and hemiballism), myoclonus (including generalised myoclonus and focal myoclonus), tics (including simple tics, complex tics and symptomatic tics), and dystonia (including generalised dystonia such as iodiopathic dystonia, drug-induced dystonia, symptomatic dystonia and paroxymal dystonia, and focal dystonia such as blepharospasm, oromandibular dystonia, spasmodic dysphonia, spasmodic torticollis, axial dystonia, dystonic writers cramp and hemiplegic dystonia)]; urinary incontinence; neuronal damage including ocular damage, retinopathy or macular degeneration of the eye, tinnitus, hearing impairment and loss, and brain edema; emesis; and sleep disorders including insomnia and narcolepsy.

According to a further particular embodiment, the disorder is pain, in particular chronic pain and especially neuropathic pain.

Pain can be classified as acute and chronic pain. Acute pain and chronic pain differ in their etiology, pathophysiology, diagnosis and treatment.

Acute pain, which occurs following tissue injury, is self-limiting, serves as an alert to ongoing tissue damage and following tissue repair it will usually subside. There are minimal psychological symptoms associated with acute pain apart from mild anxiety. Acute pain is nociceptive in nature and occurs following chemical, mechanical and thermal stimulation of A-delta and C-polymodal pain receptors.

Chronic pain, on the other hand, serves no protective biological function. Rather than being the symptom of tissue damage it is a disease in its own right. Chronic pain is unrelenting and not self-limiting and can persist for years, perhaps decades after the initial injury. Chronic pain can be refractory to multiple treatment regimes. Psychological symptoms associated with chronic pain include chronic anxiety, fear, depression, sleeplessness and impairment of social interaction. Chronic non-malignant pain is predominantly neuropathic in nature and involves damage to either the peripheral or central nervous systems.

Acute pain and chronic pain are caused by different neurophysiological processes and therefore tend to respond to different types of treatments. Acute pain can be somatic or visceral in nature. Somatic pain tends to be a well localised, constant pain and is described as sharp, aching, throbbing or gnawing. Visceral pain, on the other hand, tends to be vague in distribution, paroxysmal in nature and is usually described as deep, aching, squeezing or colicky in nature. Examples of acute pain include post-operative pain, pain associated with trauma and the pain of arthritis. Acute pain usually responds to treatment with opioids or non-steroidal anti-inflammatory drugs.

Chronic pain, in contrast to acute pain, is described as burning, electric, tingling and shooting in nature. It can be continuous or paroxysmal in presentation. The hallmarks of chronic pain are chronic allodynia and hyperalgesia. Allodynia is pain resulting from a stimulus that normally does not ellicit a painful response, such as a light touch. Hyperalgesia is an increased sensitivity to normally painful stimuli. Primary hyperalgesia occurs immediately within the area of the injury. Secondary hyperalgesia occurs in the undamaged area surrounding the injury. Examples of chronic pain include complex regional pain syndrome, pain arising from peripheral neuropathies, post-operative pain, chronic fatigue syndrome pain, tension-type headache, pain arising from mechanical nerve injury and severe pain associated with diseases such as cancer, metabolic disease, neurotropic viral disease, neurotoxicity, inflammation, multiple sclerosis or any pain arising as a consequence of or associated with stress or depressive illness.

Although opioids are cheap and effective, serious and potentially life-threatening side effects occur with their use, most notably respiratory depression and muscle rigidity. In addition the doses of opioids which can be administered are limited by nausea, emesis, constipation, pruritis and urinary retention, often resulting in patients electing to receive sub-optimal pain control rather than suffer these distressing side-effects. Furthermore, these side-effects often result in patients requiring extended hospitalisation. Opioids are highly addictive and are scheduled drugs in many territories.

The compounds of formula (I) are particularly useful in the treatment of schizophrenia, bipolar disorder, depression including unipolar depression, seasonal depression and post-partum depression, premenstrual syndrome (PMS) and premenstrual dysphoric disorder (PDD), learning disorders, pervasive developmental disorder including autistic disorder, attention deficit disorders including Attention-Deficit/Hyperactivity Disorder, tic disorders including Tourette's disorder, anxiety disorders including phobia and post traumatic stress disorder, cognitive disorders associated with dementia, AIDS dementia, Alzheimer's, Parkinson's, Huntington's disease, spasticity, myoclonus, muscle spasm, tinnitus and hearing impairment and loss are of particular importance.

Particular cognitive disorders are dementia, delirium, amnestic disorders and cognitive impartment including age-related cognitive decline.

Particular anxiety disorders are generalized anxiety disorder, obsessive-compulsive disorder and panic attack.

Particular schizophrenia or psychosis pathologies are paranoid, disorganized, catatonic or undifferentiated schizophrenia and substance-induced psychotic disorder.

Particular neurologic disorders that can be treated with the compounds of the formula (I) include in particular a cognitive disorder such as dementia, cognitive impairment, attention deficit hyperactivity disorder.

Particular psychiatric disorders that can be treated with the compounds of the formula (I) include in particular an anxiety disorder, a mood disorder such as depression or a bipolar disorder, schizophrenia, a psychotic disorder.

Within the context of the treatment, the use according to the invention of the compounds of the formula (I) involves a method. In this method, an effective quantity of one or more compounds or the formula (I), as a rule formulated in accordance with pharmaceutical and veterinary practice, is administered to the individual to be treated, preferably a mammal, in particular a human being. Whether such a treatment is indicated, and in which form it is to take place, depends on the individual case and is subject to medical assessment (diagnosis) which takes into consideration signs, symptoms and/or malfunctions which are present, the risks of developing particular signs, symptoms and/or malfunctions, and other factors.

As a rule, the treatment is effected by means of single or repeated daily administration, where appropriate together, or alternating, with other drugs or drug-containing preparations.

The invention also relates to the manufacture of pharmaceutical compositions for treating an individual, preferably a mammal, in particular a human being. Thus, the compounds of the formula (I) are customarily administered in the form of pharmaceutical compositions which comprise an inert carrier (e.g. a pharmaceutically acceptable excipient) together with at least one compound according to the invention and, where appropriate, other drugs. These compositions can, for example, be administered orally, rectally, transdermalty, subcutaneously, intravenously, intramuscularly or intranasally.

Examples of suitable pharmaceutical formulations are solid medicinal forms, such as powders, granules, tablets, in particular film tablets, lozenges, sachets, cachets, sugar-coated tablets, capsules, such as hard gelatin capsules and soft gelatin capsules, suppositories or vaginal medicinal forms, semisolid medicinal forms, such as ointments, creams, hydrogels, pastes or plasters, and also liquid medicinal forms, such as solutions, emulsions, in particular oil-in-water emulsions, suspensions, for example lotions, injection preparations and infusion preparations, and eyedrops and eardrops. Implanted release devices can also be used for administering inhibitors according to the invention. In addition, it is also possible to use liposomes or microspheres.

When producing the compositions, the compounds according to the invention are optionally mixed or diluted with one or more carriers (excipients). Carriers (excipients) can be solid, semisolid or liquid materials which serve as vehicles, carriers or medium for the active compound.

Suitable carriers (excipients) are listed in the specialist medicinal monographs. In addition, the formulations can comprise pharmaceutically acceptable auxiliary substances, such as wetting agents; emulsifying and suspending agents; preservatives; antioxidants; antiirritants; chelating agents; coating auxiliaries; emulsion stabilizers; film formers; gel formers; odor masking agents; taste corrigents; resin; hydrocolloids; solvents; solubilizers; neutralizing agents; diffusion accelerators; pigments; quaternary ammonium compounds; refatting and overfatting agents; raw materials for ointments, creams or oils; silicone derivatives; spreading auxiliaries; stabilizers; sterilants; suppository bases; tablet auxiliaries, such as binders, fillers, glidants, disintegrants or coatings; propellants; drying agents; opacifiers; thickeners; waxes; plasticizers and white mineral oils. A formulation in this regard is based on specialist knowledge as described, for example, in Fiedler, H. P., Lexikon der Hilfsstoffe für Pharmazie, Kosmetik and angrenzende Gebiete [Encyclopedia of auxiliary substances for pharmacy, cosmetics and related fields], 4$^{th}$ edition, Aulendorf: ECVEditio-Cantor-Verlag, 1996.

The compounds of formula (I) may also be suitable for combination with other therapeutic agents.

Thus, the present invention also provides:
i) a combination comprising a compound of formula (I) with one or more further therapeutic agents;
ii) a pharmaceutical composition comprising a combination product as defined in i) above and at least one carrier, diluent or excipient;
iii) the use of a combination as defined in i) above in the manufacture of a medicament for treating or preventing a disorder, disease or condition as defined herein;
iv) a combination as defined in i) above for use in treating or preventing a disorder, disease or condition as defined herein;
v) a kit-of-parts for use in the treatment of a disorder, disease or condition as defined herein, comprising a first dosage form comprising a compound of formula (I) and one or more further dosage forms each comprising one or more further therapeutic agents for simultaneous therapeutic administration,
vi) a combination as defined in i) above for use in therapy;
vii) a method of treatment or prevention of a disorder, disease or condition as defined herein comprising administering an effective amount of a combination as defined in i) above;
viii) a combination as defined in i) above for treating or preventing a disorder, disease or condition as defined herein.

The combination therapies of the invention may be administered adjunctively. By adjunctive administration is meant the coterminous or overlapping administration of each of the components in the form of separate pharmaceutical compositions or devices. This regime of therapeutic administration of two or more therapeutic agents is referred to generally by those skilled in the art and herein as adjunctive therapeutic administration; it is also known as add-on therapeutic administration. Any and all treatment regimes in which a patient receives separate but coterminous or overlapping therapeutic administration of the compounds of formula (I) and at least one further therapeutic agent are within the scope of the current invention. In one embodiment of adjunctive therapeutic administration as described herein, a patient is typically stabilised on a therapeutic administration of one or more of the components for a period of time and then receives administration of another component.

The combination therapies of the invention may also be administered simultaneously. By simultaneous administration is meant a treatment regime wherein the individual components are administered together, either in the form of a single pharmaceutical composition or device comprising or containing both components, or as separate compositions or devices, each comprising one of the components, administered simultaneously. Such combinations of the separate individual components for simultaneous combination may be provided in the form of a kit-of-parts.

In a further aspect, the invention provides a method of treatment of a psychotic disorder by adjunctive therapeutic administration of compounds of formula (I) to a patient receiving therapeutic administration of at least one antipsychotic agent. In a further aspect, the invention provides the use of compounds of formula (I) in the manufacture of a medicament for adjunctive therapeutic administration for the treatment of a psychotic disorder in a patient receiving therapeutic administration of at least one antipsychotic agent. The invention further provides compounds of formula (I) for use for adjunctive therapeutic administration for the treatment of a psychotic disorder in a patient receiving therapeutic administration of at least one antipsychotic agent.

In a further aspect, the invention provides a method of treatment of a psychotic disorder by adjunctive therapeutic administration of at least one antipsychotic agent to a patient receiving therapeutic administration of compounds of formula (I). In a further aspect, the invention provides the use of at least one antipsychotic agent in the manufacture of a medicament for adjunctive therapeutic administration for the treatment of a psychotic disorder in a patient receiving therapeutic administration of compounds of formula (I). The invention further provides at least one antipsychotic agent for adjunctive therapeutic administration for the treatment of a psychotic disorder in a patient receiving therapeutic administration of compounds of formula (I).

In a further aspect, the invention provides a method of treatment of a psychotic disorder by simultaneous therapeutic administration of compounds of formula (I) in combination with at least one antipsychotic agent. The invention further provides the use of a combination of compounds of formula (I) and at least one antipsychotic agent in the manufacture of a medicament for simultaneous therapeutic administration in the treatment of a psychotic disorder. The invention further provides a combination of compounds of formula (I) and at least one antipsychotic agent for simultaneous therapeutic administration in the treatment of a psychotic disorder. The invention further provides the use of compounds of formula (I) in the manufacture of a medicament for simultaneous therapeutic administration with at least one antipsychotic agent in the treatment of a psychotic disorder. The invention further provides compounds of formula (I) for use for simultaneous therapeutic administration with at least one antipsychotic agent in the treatment of a psychotic disorder. The invention further provides the use of at least one antipsychotic agent in the manufacture of a medicament for simultaneous therapeutic administration with compounds of formula (I) in the treatment of a psychotic disorder. The invention further provides at least one antipsychotic agent for simultaneous therapeutic administration with compounds of formula (I) in the treatment of a psychotic disorder.

In further aspects, the invention provides a method of treatment of a psychotic disorder by simultaneous therapeutic administration of a pharmaceutical composition comprising compounds of formula (I) and at least one mood stabilising or antimanic agent, a pharmaceutical composition comprising compounds of formula (I) and at least one mood stabilising or antimanic agent, the use of a pharmaceutical composition comprising compounds of formula (I) and at least one mood stabilising or antimanic agent in the manufacture of a medicament for the treatment of a psychotic disorder, and a pharmaceutical composition comprising compounds of formula (I) and at least one mood stabilising or antimanic agent for use in the treatment of a psychotic disorder.

Antipsychotic agents include both typical and atypical antipsychotic drugs. Examples of antipsychotic drugs that are useful in the present invention include, but are not limited to: butyrophenones, such as haloperidol, pimozide, and droperidol; phenothiazines, such as chlorpromazine, thioridazine, mesoridazine, trifluoperazine, perphenazine, fluphenazine, thiflupromazine, prochlorperazine, and acetophenazine; thioxanthenes, such as thiothixene and chlorprothixene; thienobenzodiazepines; dibenzodiazepines; benzisoxazoles; dibenzothiazepines; imidazolidinones; benziso-thiazolylpiperazines; triazine such as lamotrigine; dibenzoxazepines, such as loxapine; dihydroindolones, such as molindone; aripiprazole; and derivatives thereof that have antipsychotic activity.

Examples of tradenames and suppliers of selected antipsychotic drugs are as follows: clozapine (available under the tradename CLOZARIL®, from Mylan, Zenith Goldline, UDL, Novartis); olanzapine (available under the tradename ZYPREX®, from Lilly); ziprasidone (available under the tradename GEODON®, from Pfizer); risperidone (available under the tradename RISPERDAL®, from Janssen); quetiapine fumarate (available under the tradename SEROQUEL®, from AstraZeneca); haloperidol (available under the tradename HALDOL®, from Ortho-McNeil); chlorpromazine (available under the tradename THORAZINE®, from SmithKline Beecham (GSK)); fluphenazine (available under the tradename PROLIXIN®, from Apothecon, Copley, Schering, Teva, and American Pharmaceutical Partners, Pasadena); thiothixene (available under the tradename NAVANE®, from Pfizer); trifluoperazine (10-[3-(4-methyl-1-piperazinyl)propyl]-2-(trifluoromethyl)phenothiazine dihydrochloride, available under the tradename STELAZINE®, from Smith Klein Beckman); perphenazine (available under the tradename TRILAFON®; from Schering); thioridazine (available under the tradename MELLARIL®; from Novartis, Roxane, HiTech, Teva, and Alpharma); molindone (available under the tradename MOBAN®, from Endo); and loxapine (available under the tradename LOXITANE (D; from Watson). Furthermore, benperidol (Glianimon®), perazine (Taxilan®) or melperone (Eunerpan®) may be used. Other antipsychotic drugs include promazine (available under the tradename SPARINE®), triflurpromazine (available under the tradename VESPRI N®), chlorprothixene (available under the tradename TARACTAN®), droperidol (available under the tradename INAPSINE®), acetophenazine (available under the tradename TINDAL®), prochlorperazine (available under the tradename COMPAZINE®), methotrimeprazine (available under the tradename NOZINAN®), pipotiazine (available under the tradename PIPOTRIL®), ziprasidone, and hoperidone.

In a further aspect, the invention provides a method of treatment of a neurodegenerative disorder such as Alzheimer Disease by adjunctive therapeutic administration of compounds of formula (I) to a patient receiving therapeutic administration of at least one agent suitable for the treatment of a neurodegenerative disorder such as Alzheimer Disease. In a further aspect, the invention provides the use of compounds of formula (I) in the manufacture of a medicament for adjunctive therapeutic administration for the treatment of a neurodegenerative disorder such as Alzheimer Disease in a patient receiving therapeutic administration of at least one agent suitable for the treatment of a neurodegenerative disorder such as Alzheimer Disease. The invention further provides compounds of formula (I) for use for adjunctive therapeutic administration for the treatment of a neurodegenerative disorder such as Alzheimer Disease in a patient receiving therapeutic administration of at least one agent suitable for the treatment of a neurodegenerative disorder such as Alzheimer Disease.

In a further aspect, the invention provides a method of treatment of a neurodegenerative disorder such as Alzheimer Disease by adjunctive therapeutic administration of at least one agent suitable for the treatment of a neurodegenerative disorder such as Alzheimer Disease to a patient receiving therapeutic administration of compounds of formula (I). In a further aspect, the invention provides the use of at least one agent suitable for the treatment of a neurodegenerative disorder such as Alzheimer Disease in the manufacture of a medicament for adjunctive therapeutic administration for the treatment of a neurodegenerative disorder such as Alzheimer Disease in a patient receiving therapeutic administration of compounds of formula (I). The invention further provides at least one agent suitable for the treatment of a neurodegenerative disorder such as Alzheimer Disease for adjunctive therapeutic administration for the treatment of a neurodegenerative disorder such as Alzheimer Disease in a patient receiving therapeutic administration of compounds of formula (I).

In a further aspect, the invention provides a method of treatment of a neurodegenerative disorder such as Alzheimer Disease by simultaneous therapeutic administration of compounds of formula (I) in combination with at least one agent suitable for the treatment of a neurodegenerative disorder such as Alzheimer Disease. The invention further provides the use of a combination of compounds of formula (I) and at least one agent suitable for the treatment of a neurodegenerative disorder such as Alzheimer Disease in the manufacture of a medicament for simultaneous therapeutic administration in the treatment of a neurodegenerative disorder such as Alzheimer Disease. The invention further provides a combination of compounds of formula (I) and at least one agent suitable for the treatment of a neurodegenerative disorder such as Alzheimer Disease for simultaneous therapeutic administration in the treatment of a neurodegenerative disorder such as Alzheimer Disease. The invention further provides the use of compounds of formula (I) in the manufacture of a medicament for simultaneous therapeutic administration with at least one agent suitable for the treatment of a neurodegenerative disorder such as Alzheimer Disease in the treatment of a neurodegenerative disorder such as Alzheimer Disease. The invention further provides compounds of formula (I) for use for simultaneous therapeutic administration with at least one agent suitable for the treatment of a neurodegenerative disorder such as Alzheimer Disease in the treatment of a neurodegenerative disorder such as Alzheimer Disease. The invention further provides the use of at least one agent suitable for the treatment of a neurodegenerative disorder such as Alzheimer Disease in the manufacture of a medicament for simultaneous therapeutic administration with compounds of formula (I) in the treatment of a neurodegenerative disorder such as Alzheimer Disease. The invention further provides at least one agent suitable for the treatment of a neurodegenerative disorder such as Alzheimer Disease for simultaneous therapeutic administration with compounds of formula (I) in the treatment of a neurodegenerative disorder such as Alzheimer Disease.

Examples of agents suitable for the treatment of a neurodegenerative disorder such as Alzheimer Disease that are useful in the present invention include, but are not limited to: cholinesterase inhibitors, agents targeting nicotinic or muscarinic acetylcholine receptors, NMDA receptors, amyloid formation, mitochondrial dysfunctions, disease associated calpain activity, neuroinflamation, tumor necrosis factor receptors, NF-kappaB, peroxisome proliferator activator receptor gamma, Apolipoprotein E variant 4 (ApoE4), diseaseassociated increase of the HPA axis, epileptic discharges, vascular dysfunction, vascular risk factors, and oxidative stress.

Suitable cholinesterase inhibitors which may be used in combination with the compounds of the inventions include for example tacrine, donepezil, galantamine and rivastigmine.

Suitable NMDA receptors targeting agents which may be used in combination with the compounds of the inventions include for example memantine.

Suitable agents affecting increased HPA axis activity which may be used in combination with the compounds of the inventions include for example CRF1 antagonists or V1b antagonists.

In a further aspect therefore, the invention provides a method of treatment of pain by adjunctive therapeutic administration of compounds of formula (I) to a patient receiving therapeutic administration of at least one agent suitable for the treatment of pain. In a further aspect, the invention provides the use of compounds of formula (I) in the manufacture of a medicament for adjunctive therapeutic administration for the treatment of pain in a patient receiving therapeutic administration of at least one agent suitable for the treatment of pain. The invention further provides compounds of formula (I) for use for adjunctive therapeutic administration for the treatment of pain in a patient receiving therapeutic administration of at least one agent suitable for the treatment of pain.

In a further aspect, the invention provides a method of treatment of pain by adjunctive therapeutic administration of at least one agent suitable for the treatment of pain to a patient receiving therapeutic administration of compounds of formula (I). In a further aspect, the invention provides the use of at least one agent suitable for the treatment of pain in the manufacture of a medicament for adjunctive therapeutic administration for the treatment of pain in a patient receiving therapeutic administration of compounds of formula (I). The invention further provides at least one agent suitable for the treatment of pain for adjunctive therapeutic administration for the treatment of pain in a patient receiving therapeutic administration of compounds of formula (I).

In a further aspect, the invention provides a method of treatment of pain by simultaneous therapeutic administration of compounds of formula (I) in combination with at least one agent suitable for the treatment of pain. The invention further provides the use of a combination of compounds of formula (I) and at least one agent suitable for the treatment of pain in the manufacture of a medicament for simultaneous therapeutic administration in the treatment of pain. The invention further provides a combination of compounds of formula (I) and at least one agent suitable for the treatment of pain for simultaneous therapeutic administration in the treatment of pain. The invention further provides the use of compounds of formula (I) in the manufacture of a medicament for simultaneous therapeutic administration with at least one agent suitable for the treatment of pain in the treatment of pain. The invention further provides compounds of formula (I) for use for simultaneous therapeutic administration with at least one agent suitable for the treatment of pain in the treatment of pain. The invention further provides the use of at least one agent suitable for the treatment of pain in the manufacture of a medicament for simultaneous therapeutic administration with compounds of formula (I) in the treatment of pain. The invention further provides at least one agent suitable for the treatment of pain for simultaneous therapeutic administration with compounds of formula (I) in the treatment of pain.

Examples of agents suitable for the treatment of pain that are useful in the present invention include, but are not limited to: NSAIDs (Nonsteroidal Antiinflammatory Drugs), anticonvulsant drugs such as carbamazepine and gabapentin, sodium channel blockers, antidepressant drugs, cannabinoids and local anaesthetics.

Suitable agents used in combination with the compounds of the inventions include for example celecoxib, etoricoxib, lumiracoxib, paracetamol, tramadol, methadone, venlafaxine, imipramine, duloxetine, bupropion, gabapentin, pregabalin, lamotrigine, fentanyl, parecoxib, nefopam, remifentanil, pethidine, diclofenac, rofecoxib, nalbuphine, sufentanil, pethidine, diamorphine and butorphanol.

It will be appreciated by those skilled in the art that the compounds according to the invention may advantageously be used in conjunction with one or more other therapeutic agents, for instance, antidepressant agents such as 5HT3 antagonists, serotonin agonists, NK-1 antagonists, selective serotonin reuptake inhibitors (SSRI), noradrenaline re-uptake inhibitors (SNRI), tricyclic antidepressants, dopaminergic antidepressants, H3 antagonists, 5HT1A antagonists, 5HT1 B antagonists, 5HT1 D antagonists, D1 agonists, M1 agonists and/or anticonvulsant agents, as well as cognitive enhancers.

Suitable 5HT3 antagonists which may be used in combination of the compounds of the inventions include for example ondansetron, granisetron, metoclopramide.

Suitable serotonin agonists which may be used in combination with the compounds of the invention include sumatriptan, rauwolscine, yohimbine, metoclopramide.

Suitable SSRIs which may be used in combination with the compounds of the invention include fluoxetine, citalopram, femoxetine, fluvoxamine, paroxetine, indalpine, sertraline, zimeldine.

Suitable SNRIs which may be used in combination with the compounds of the invention include venlafaxine and reboxetine.

Suitable tricyclic antidepressants which may be used in combination with a compound of the invention include imipramine, amitriptiline, chlomipramine and nortriptiline.

Suitable dopaminergic antidepressants which may be used in combination with a compound of the invention include bupropion and amineptine.

Suitable anticonvulsant agents which may be used in combination of the compounds of the invention include for example divalproex, carbamazepine and diazepam.

The following examples serve to explain the invention without limiting it.

The compounds were characterized by mass spectrometry, generally recorded via HPLCMS in a fast gradient on C18-material (electrospray-ionisation (ESI) mode).

PREPARATION EXAMPLES

All final compounds have cis configuration at the tetrahydronaphthalen core if not otherwise noted.

Example 1

[7-(2-tert-Butoxycarbonylamino-ethoxy)-1-(3,4-dichloro-benzyl)-1,2,3,4-tetrahydro-naphthalen-2-yl]-carbamic acid ethyl ester 1.1 1-(3,4-Dichlorobenzyl)-7-methoxy-3,4-dihydronaphthalen-2(1H)-one

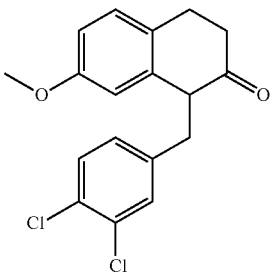 [SMILES: COc1ccc2c(c1)C(Cc1ccc(Cl)c(Cl)c1)C(=O)CC2]

15 g (85 mmol) of 7-methoxy-3,4-dihydronaphthalen-2 (1H)-one were dissolved in 200 ml of dry MeOH under nitrogen. Then 6.66 g (94 mmol) of pyrrolidine were added dropwise and slowly and the colour changes. The mixture is stirred for one h. The solvent was reduced under vacuo and the residue was dissolved in MeCN. At 5° C. 22.5 g (94 mmol) 4-(bromomethyl)-1,2-dichlorobenzene dissolved in MeCN were added and the mixture was stirred over night at RT. The solvent was reduced under vacuo and the residue was mixed with MeOH/CH$_2$Cl$_2$/H$_2$O 1:1:1 (50 ml, 50 ml, 50 ml) and 10 ml of glacial acid were added. The mixture was stirred over night. Work-up: The reaction mixture was put on ice water and extracted 3× with CH$_2$Cl$_2$. The combined organic layers were washed 1× with NaHCO$_3$ solution and 1× with saturated NaCl solution. The organic phase was dried on MgSO$_4$ and the solvent was evaporated. The residue (31.5 g) was purified by flash-chromatography on silica gel with heptane/EtOAc 2:1. 24.1 g (71.7 mmol, 84%) of the product were obtained.

ESI-MS [M+H$^+$]=335.1 Calculated for C$_{18}$H$_{16}$Cl$_2$O$_2$=334.05.

1.2 1-(3,4-Dichlorobenzyl)-7-methoxy-1,2,3,4-tetrahydronaphthalen-2-amine hydrochloride

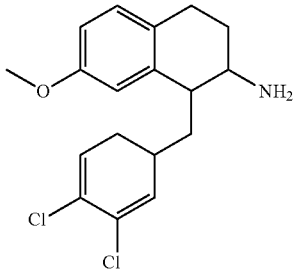 [SMILES: COc1ccc2c(c1)C(CC1C=C(Cl)C(Cl)=CC1)C(N)CC2]

To 1-(3,4-dichlorobenzyl)-7-methoxy-3,4-dihydronaphthalen-2(1H)-one 5.2 g (15.5 mmol) in MeOH reactant ammonium acetate (12.0 g, 155 mmol) and sodium cyanoborohydride (1.46 g, 23.3 mmol) were added under nitrogen. The mixture was stirred for 4d at RT. The solvent was reduced under vacuo and extracted with EtOAc after addition of water. The organic layer was washed with NaCl, dried on MgSO$_4$ and the solvent was removed. The residue was dissolved in iPrOH and HCl in iPrOH (6N) was added. After crystallization over night the HCl-salt was separated from the mother liquor and transferred to the free base with NaOH (1N). An oil was obtained that after treatment with HCl gave the cis product (1.95 g, 5.80 mmol, 37.4%) after crystallization. The mother liquor contained a cis/trans mixture of the product.

ESI-MS [M+H$^+$]+=336.2 Calculated for C$_{18}$H$_{19}$Cl$_2$NO=336.26.

1.3 Ethyl 1-(3,4-dichlorobenzyl)-7-methoxy-1,2,3,4-tetrahydronaphthalen-2-ylcarbamate To 1-(3,4-dichlorobenzyl)-7-methoxy-1,2,3,4-tetrahydronaphthalen-2-amine hydrochloride (1.95 g, 5.80 mmol) in pyridine 10 ml) the ethylchloroformate (1.00 g, 9.28 mmol) was added slowly under nitrogen. The mixture was stirred over night at RT. The solvent was reduced under vacuo and extracted with CH$_2$Cl$_2$ after addition of HCl (1N). The organic layer was washed with HCl (1N), NaHCO$_3$ solution, and NaCl solution, then dried on MgSO$_4$ and the solvent was removed. The product was obtained as an orange oil that precipitates after a few hours (2.10 g, 5.14 mmol, 89%).

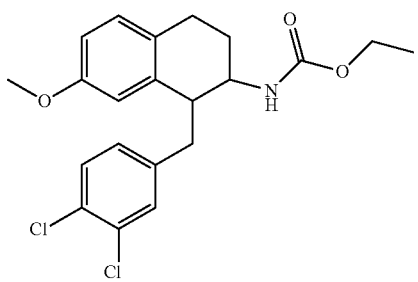 [SMILES: CCOC(=O)NC1CCc2ccc(OC)cc2C1Cc1ccc(Cl)c(Cl)c1]

ESI-MS [M+H⁺]+=408.2 Calculated for $C_{21}H_{23}ClN_2O_3$=407.11.

1.4 Ethyl 1-(3,4-dichlorobenzyl)-7-hydroxy-1,2,3,4-tetrahydronaphthalen-2-ylcarbamate

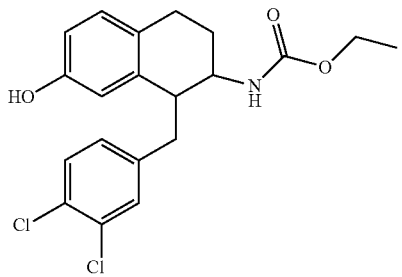 [SMILES: CCOC(=O)NC1CCc2ccc(O)cc2C1Cc1ccc(Cl)c(Cl)c1]

Ethyl 1-(3,4-dichlorobenzyl)-7-methoxy-1,2,3,4-tetrahydronaphthalen-2-ylcarbamate (2.1 g, 5.14 mmol) was dissolved in $CH_2Cl_2$ (50 ml) and $BBr_3$ (3.87 g, 15.4 mmol) was added at −10° C. The reaction mixture was slowly warmed to RT and stirred for 2 h. The reaction mixture was added to ice water and extracted with $CH_2Cl_2$. The organic layer was washed with $NaHCO_3$ solution and NaCl solution, then dried on $MgSO_4$ and the solvent was removed. The product was obtained as a brown oil (2.05 g, 5.14 mmol, 100%).

ESI-MS [M+H⁺]+=394.1 Calculated for $C_{20}H_{21}Cl_2NO_3$=393.09.

1.5 7-(2-tert-Butoxycarbonylamino-ethoxy)-1-(3,4-dichloro-benzyl)-1,2,3,4-tetrahydronaphthalen-2-yl]-carbamic acid ethyl ester

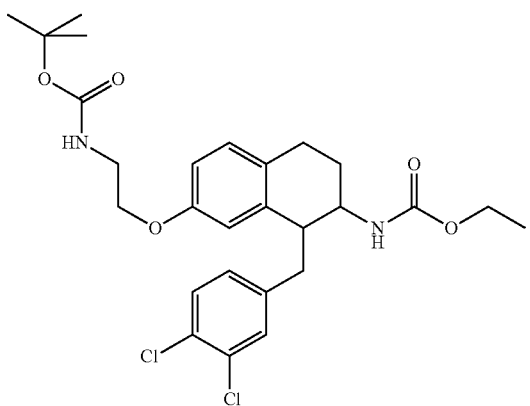 [SMILES: CCOC(=O)NC1CCc2ccc(OCCNC(=O)OC(C)(C)C)cc2C1Cc1ccc(Cl)c(Cl)c1]

NaH (55% in paraffin, 34.5 mmol) was suspended in DMA (80 ml) and ethyl 1-(3,4-dichlorobenzyl)-7-hydroxy-1,2,3,4-tetrahydronaphthalen-2-ylcarbamate (6.80 g, 17.3 mmol) dissolved in DMA (40 ml) was added. The mixture was stirred for another h. Then the bromide was added in portions and the mixture was stirred for 3d at RT. The reaction mixture was added to half concentrated NaCl and extracted with EtOAc. The organic layer was washed with $H_2O$, NaCl solution, then dried on $MgSO_4$ and the solvent was removed. Some DMA was removed on an oil pump. The residue was purified by flash chromatography using silica gel and $CH_2Cl_2$/MeOH 98:2. The product was obtained as an yellow oil (9.27 g, 17.3 mmol, 100%) that becomes solid after a few hours.

ESI-MS [M+H⁺]=481.1 Calculated for $C_{27}H_{34}Cl_2N_2O_5$=536.18

Example 2

Ethyl 1-(3,4-dichlorobenzyl)-7-(2-(1-methyl-1H-imidazole-4-sulfonamido)ethoxy)-1,2,3,4-tetrahydronaphthalen-2-ylcarbamate

2.1 Ethyl 7-(2-aminoethoxy)-1-(3,4-dichlorobenzyl)-1,2,3,4-tetrahydronaphthalen-2-ylcarbamate hydrochloride

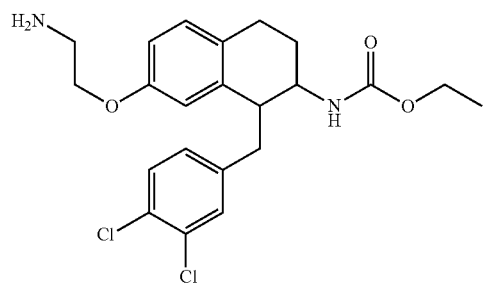 [SMILES: CCOC(=O)NC1CCc2ccc(OCCN)cc2C1Cc1ccc(Cl)c(Cl)c1]

[7-(2-tert-Butoxycarbonylamino-ethoxy)-1-(3,4-dichloro-benzyl)-1,2,3,4-tetrahydronaphthalen-2-yl]-carbamic acid ethyl ester (9.27 g, 17.3 mmol) example 1 was dissolved in $CH_2Cl_2$ (200 ml) and HCl in iPrOH (6N) was added. The reaction was stirred at RT over night after which a solid precipitates. To the reaction mixture diethyl ether was added and the precipitating HCl salt was separated by filtration to give the final product as a solid (5.85 g, 12.3 mmol, 72%).

ESI-MS [M+H⁺]=437.1 Calculated for $C_{22}H_{26}Cl_2N_2O_3$=436.13

2.2 Ethyl 1-(3,4-dichlorobenzyl)-7-(2-(1-methyl-1H-imidazole-4-sulfonamido)ethoxy)-1,2,3,4-tetrahydronaphthalen-2-ylcarbamate

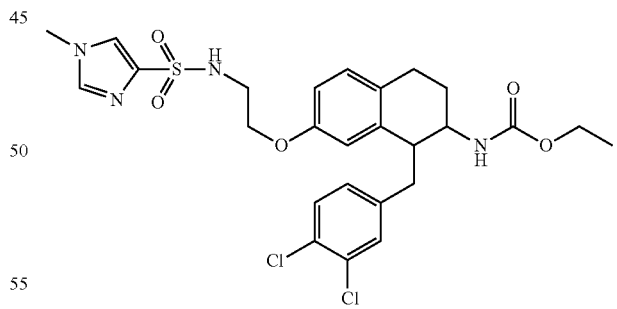

Ethyl 7-(2-aminoethoxy)-1-(3,4-dichlorobenzyl)-1,2,3,4-tetrahydronaphthalen-2-ylcarbamate hydrochloride (100 mg, 0.229 mmol) and DMAP (27.9 mg, 0.229 mmol) were dissolved in $CH_2Cl_2$ (15 ml) and 1-methyl-1H-imidazole-4-sulfonyl chloride (41.3 mg, 0.229 mmol) dissolved in $CH_2Cl_2$ (15 ml) was added. The reaction mixture was stirred over night at RT. After addition of $H_2O$ the phases were separated and the aqueous phase was extracted with $CH_2Cl_2$. The organic layer was washed with HCl (1N), $NaHCO_3$ solution and NaCl solution, then dried on $MgSO_4$ and the solvent was removed. To the residue EtOAc/diethylether (1:1) was added, stirred, and the precipitate was separated by filtration to obtain a brown solid of product (100 mg).

ESI-MS [M+H$^+$]=581.5 Calculated for C$_{26}$H$_{30}$Cl$_2$N$_4$O$_5$S=580.13

Example 3

N-(2-(7-Amino-8-(3,4-dichlorobenzyl)-5,6,7,8-tetrahydronaphthalen-2-yloxy)ethyl)-1-methyl-1H-imidazole-4-sulfonamide hydrochloride

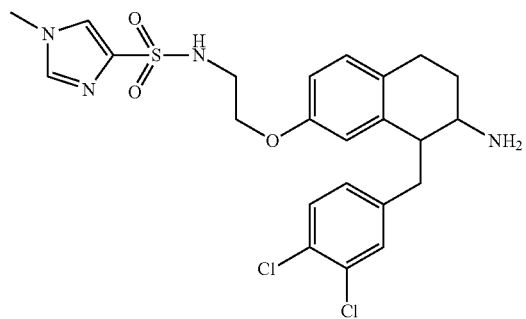 [SMILES: Cn1cnc(S(=O)(=O)NCCOc2ccc3c(c2)C(Cc2ccc(Cl)c(Cl)c2)C(N)CC3)c1]

Ethyl 1-(3,4-dichlorobenzyl)-7-(2-(1-methyl-1H-imidazole-4-sulfonamido)ethoxy)-1,2,3,4-tetrahydronaphthalen-2-ylcarbamate (1.00 g, 1.72 mmol) example 2 was refluxed in 25 g of EtOH/20% KOH for 2 h. To the reaction mixture half concentrated NaCl solution was added and the mixture was extracted with ethyl acetate. The organic layers were combined and washed with NaCl solution, then dried on MgSO$_4$ and the solvent was removed. A significant amount was found to be bound on MgSO$_4$ and so additional separation/extraction with H$_2$O/CH$_2$Cl$_2$ and drying on Na$_2$SO$_4$ resulted in a yellow oil (830 mg). This residue was dissolved in little MeOH, HCl (1N) was added, and the final product (650 mg, 1.19 mmol, 69%) was separated by filtration.

ESI-MS [M+H$^+$]=509.1 Calculated for C$_{23}$H$_{26}$Cl$_2$N$_4$O$_3$S=508.11

Example 4

1-Methyl-1H-pyrazole-4-sulfonic acid {2-[7-amino-8-(3,4-dichloro-benzyl)-5,6,7,8-tetrahydro-naphthalen-2-yloxy]-ethyl}-amide hydrochloride

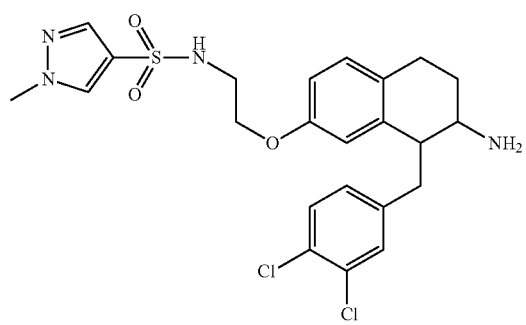 [SMILES: Cn1cc(S(=O)(=O)NCCOc2ccc3c(c2)C(Cc2ccc(Cl)c(Cl)c2)C(N)CC3)cn1]

1-Methyl-1H-pyrazole-4-sulfonic acid {2-[7-amino-8-(3,4-dichloro-benzyl)-5,6,7,8-tetrahydro-naphthalen-2-yloxy]-ethyl}-amide hydrodrochloride was prepared analogously to example 3 using 1-methyl-1H-pyrazole-4-sulfonyl chloride in place of 1-methyl-1H-imidazole-4-sulfonyl chloride.

ESI-MS [M+H$^+$]=509.1 Calculated for C$_{23}$H$_{26}$Cl$_2$N$_4$O$_3$S=508.11

Example 5

Pyridine-3-sulfonic acid {2-[7-amino-8-(3,4-dichloro-benzyl)-5,6,7,8-tetrahydro-naphthalen-2-yloxy]-ethyl}-amide hydrochloride

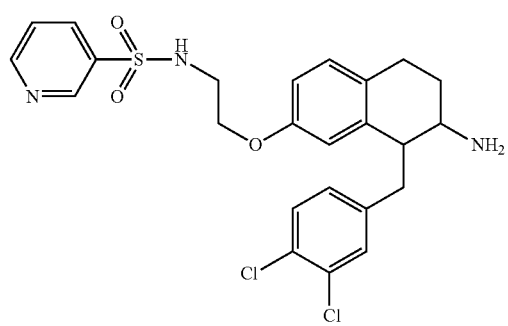 [SMILES: NC1CCc2ccc(OCCNS(=O)(=O)c3cccnc3)cc2C1Cc1ccc(Cl)c(Cl)c1]

Pyridine-3-sulfonic acid {2-[7-amino-8-(3,4-dichloro-benzyl)-5,6,7,8-tetrahydro-naphthalen-2-yloxy]-ethyl}-amide hydrochloride was prepared analogously to example 3 using pyridyl-3-sulfonyl chloride in place of 1-methyl-1H-imidazole-4-sulfonyl chloride.

ESI-MS [M+H$^+$]=506.1 Calculated for C$_{24}$H$_{25}$Cl$_2$N$_3$O$_3$S=505

Example 6

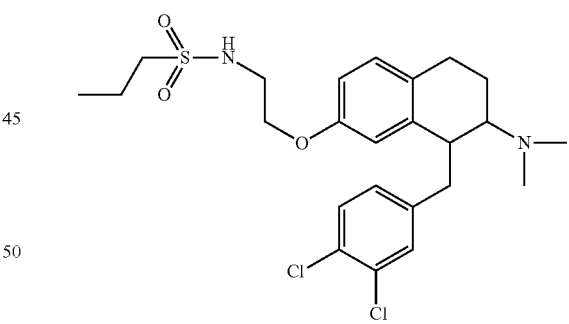

N-(2-(7-Amino-8-(3,4-dichlorobenzyl)-5,6,7,8-tetrahydronaphthalen-2-yloxy)ethyl)propane-1-sulfonamide (example 8) (66.0 mg, 0.140 mmol), paraformaldehyde (7.63 mg, 0.254 mmol), and formic acid (21.6 mg, 0.469 mmol) were dissolved in ethanol (5 ml) and refluxed for 4 h. The solvent was reduced and to the residue NaOH (1N) was added. After extraction with CH$_2$Cl$_2$ the organic layers were washed with water and saturated NaCl solution, dried with Na$_2$SO$_4$, filtered, and the solvent was removed. The residue was purified by column chromatography (CH$_2$Cl$_2$/MeOH 97:7→95:5). The final product (15.0 mg, 0.028 mmol, 20%) was obtained as a brown, solid HCl salt from isopropanol treated with HCl in isopropanol (6N).

ESI-MS [M+H⁺]=499.1 Calculated for $C_{24}H_{32}Cl_2N_2O_3S$=498

Example 7

1-(3,4-Dichloro-benzyl)-7-[2-(propane-1-sulfonylamino)-ethoxy]-1,2,3,4-tetrahydro-naphthalen-2-yl}-carbamic acid ethyl ester

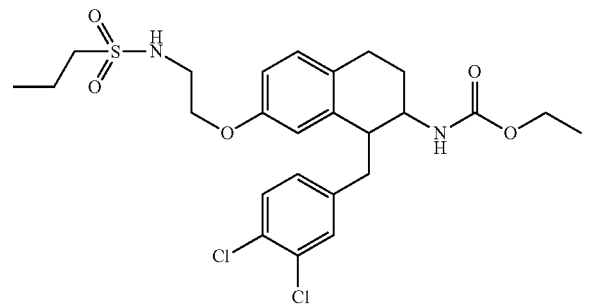 [SMILES: CCCS(=O)(=O)NCCOc1ccc2c(c1)C(Cc1ccc(Cl)c(Cl)c1)C(NC(=O)OCC)CC2]

{1-(3,4-Dichloro-benzyl)-7-[2-(propane-1-sulfonylamino)-ethoxy]-1,2,3,4-tetrahydronaphthalen-2-yl}-carbamic acid ethyl ester was prepared analogously to example example 3 using propane-1-sulfonyl chloride in place of 1-methyl-1H-imidazole-4-sulfonyl chloride. ESI-MS [M+H⁺]=543.2 Calculated for $C_{25}H_{32}Cl_2N_2O_5S$=542

Example 8

Propane-1-sulfonic acid {2-[7-amino-8-(3,4-dichloro-benzyl)-5,6,7,8-tetrahydronaphthalen-2-yloxy]-ethyl}-amide hydrochloride

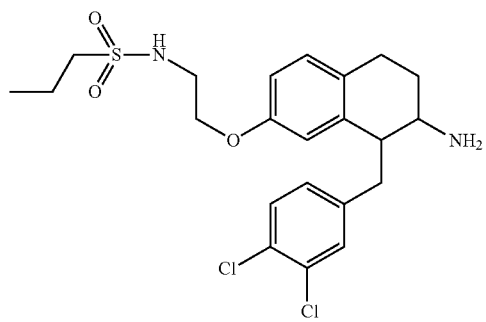

Propane-1-sulfonic acid {2-[7-amino-8-(3,4-dichloro-benzyl)-5,6,7,8-tetrahydronaphthalen-2-yloxy]-ethyl}-amide hydrochloride was prepared analogously to example 3 using propane-1-sulfonyl chloride in place of 1-methyl-1H-imidazole-4-sulfonyl chloride.

ESI-MS [M+H⁺]=471.1 Calculated for $C_{22}H_{28}Cl_2N_2O_3S$=470

Example 9

{1-(3,4-Dichloro-benzyl)-7-[2-(1-methyl-1H-pyrazole-4-sulfonylamino)-ethoxy]-1,2,3,4-tetrahydro-naphthalen-2-yl}-carbamic acid ethyl ester

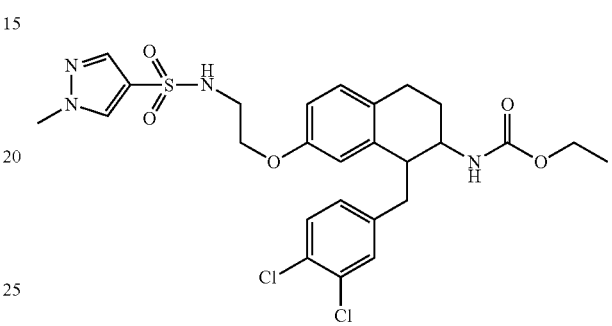

{1-(3,4-Dichloro-benzyl)-7-[2-(1-methyl-1H-pyrazole-4-sulfonylamino)-ethoxy]-1,2,3,4-tetrahydro-naphthalen-2-yl}-carbamic acid ethyl ester was prepared analogously to example example 3 using 1-methyl-1H-pyrazole-4-sulfonyl chloride in place of 1-methyl-1H-imidazole-4-sulfonyl chloride.

ESI-MS [M+H⁺]=581.2 Calculated for $C_{26}H_{30}Cl_2N_4O_5S$=580

Example 10

{1-(3,4-Dichloro-benzyl)-7-[2-(pyridine-3-sulfonylamino)-ethoxy]-1,2,3,4-tetrahydronaphthalen-2-yl}-carbamic acid ethyl ester

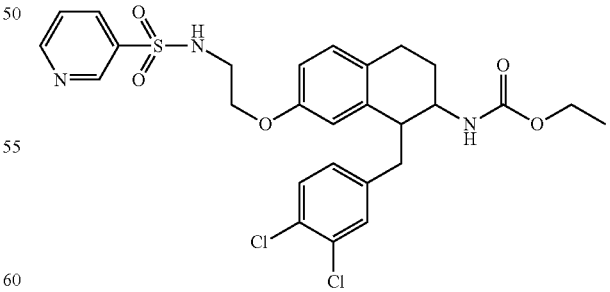

{1-(3,4-Dichloro-benzyl)-7-[2-(pyridine-3-sulfonylamino)-ethoxy]-1,2,3,4-tetrahydronaphthalen-2-yl}-carbamic acid ethyl ester was prepared analogously to example 3 using pyridine-3-sulfonyl chloride in place of 1-methyl-1H-imidazole-4-sulfonyl chloride.

ESI-MS [M+H$^+$]=578.2 Calculated for C$_{27}$H$_{29}$Cl$_2$N$_3$O$_5$S=577

Example 11

N-(2-(7-Amino-8-(3,4-dichlorobenzyl)-5,6,7,8-tetrahydronaphthalen-2-yloxy)ethyl)-N-methylpropane-1-sulfonamide hydrochloride

11.1 N-(1-(3,4-Dichlorobenzyl)-7-(2-(propylsulfonamido)ethoxy)-1,2,3,4-tetrahydronaphthalen-2-yl)-2,2,2-trifluoroacetamide

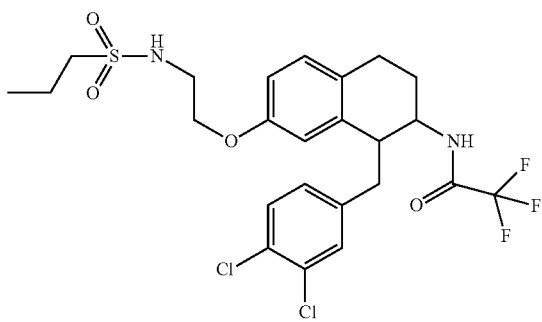 [SMILES: CCCS(=O)(=O)NCCOc1ccc2c(c1)C(Cc1ccc(Cl)c(Cl)c1)C(NC(=O)C(F)(F)F)CC2]

N-(2-(7-Amino-8-(3,4-dichlorobenzyl)-5,6,7,8-tetrahydronaphthalen-2-yloxy)ethyl)propane-1-sulfonamide (example 3, 150 mg, 0.318 mmol) and triethylamine (32.2 mg, 0.318 mmol) were dissolved in THF (10 ml) and trifluoro acetic anhydride (66.8 mg, 0.318 mmol) was added. The mixture was stirred at RT for 48 h. Ethyl acetate was added and the mixture was extracted with water and then washed with a NaHCO$_3$ solution and a saturated NaCl solution. After drying with MgSO$_4$ and removal of the solvent the residue was purified by chromatography on silica gel using CH$_2$Cl$_2$/MeOH 98:2 to give the final product as a colourless oil that becomes solid after a while (80.0 mg, 0.141 mmol, 44%).

11.2 N-(2-(7-Amino-8-(3,4-dichlorobenzyl)-5,6,7,8-tetrahydronaphthalen-2-yloxy)ethyl)N-methylpropane-1-sulfonamide hydrochloride

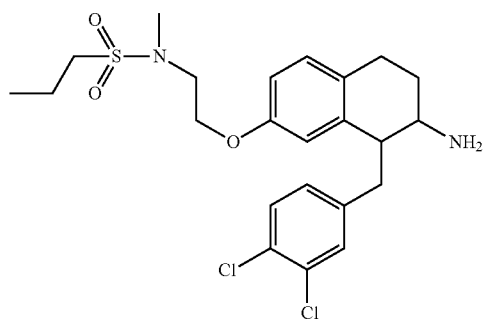 [SMILES: CCCS(=O)(=O)N(C)CCOc1ccc2c(c1)C(Cc1ccc(Cl)c(Cl)c1)C(N)CC2]

NaH (3.38 mg, 0.078 mmol, 55% in oil) was suspended in DMA (5 ml) and N-(1-(3,4-dichlorobenzyl)-7-(2-(propylsulfonamido)ethoxy)-1,2,3,4-tetrahydronaphthalen-2-yl)-2,2,2-trifluoroacetamide (40 mg, 0.07 mmol) dissolved in DMA (4 ml) was added dropwise. After stirring for 1 h iodomethane (10.5 mg, 0.074 mmol) dissolved in DMA (1 ml) was added. After stirring for another 14 h the reaction mixture was added to a halfconcentrated solution of NaCl. Extraction with ethyl acetate, washing of the organic layers with water and saturated NaCl solution followed by drying with Na$_2$SO$_4$ gave a residue that was washed with diisopropyl ether. Cleavage of the amide bond was achieved by stirring the residue with concentrated NaOH in water and subsequent extraction with ethyl acetate. The organic layer was dried with MgSO$_4$ and evaporated. The residue was purified by preparative HPLC (RP-18, acetonitrile/water, 0.01% TFA). After transferring the product into the HCl salt a yellow solid (11.0 mg, 0.021 mmol, 30%) was obtained.

ESI-MS [M+H$^+$]=485.2 Calculated for C$_{23}$H$_{30}$Cl$_2$N$_2$O$_3$S=484

Example 12

[1-(3,4-Dichloro-benzyl)-7-(2-methanesulfonylamino-ethoxy)-1,2,3,4-tetrahydronaphthalen-2-yl]-carbamic acid ethyl ester

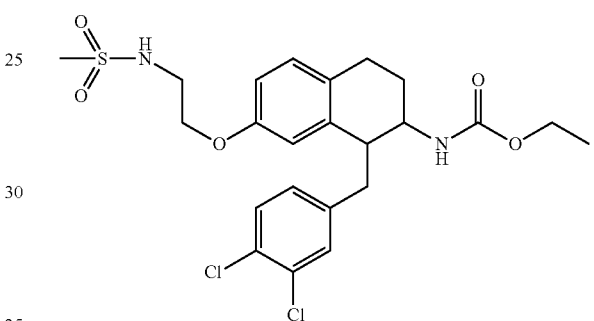

[1-(3,4-Dichloro-benzyl)-7-(2-methanesulfonylaminoethoxy)-1,2,3,4-tetrahydronaphthalen-2-yl]-carbamic acid ethyl ester was prepared analogously to example 3 using methyl sulfonyl chloride in place of 1-methyl-1H-imidazole-4-sulfonyl chloride.

ESI-MS [M+H$^+$]=515.1 Calculated for C$_{23}$H$_{28}$Cl$_2$N$_2$O$_5$S=514

Example 13

[7-(2-Benzenesulfonylamino-ethoxy)-1-(3,4-dichloro-benzyl)-1,2,3,4-tetrahydronaphthalen-2-yl]-carbamic acid ethyl ester

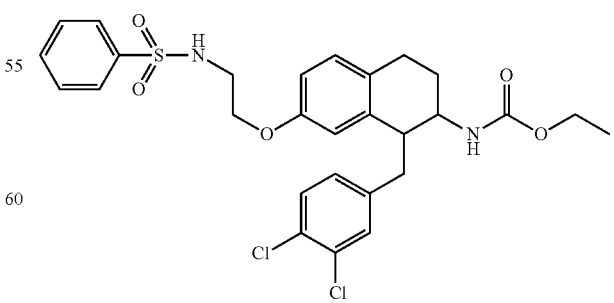

[7-(2-Benzenesulfonylamino-ethoxy)-1-(3,4-dichloro-benzyl)-1,2,3,4-tetrahydronaphthalen-2-yl]-carbamic acid ethyl ester was prepared analogously to example 3 using phenyl sulfonyl chloride in place of 1-methyl-1H-imidazole-4-sulfonyl chloride.

ESI-MS [M+H$^+$]=577.2 Calculated for C$_{28}$H$_{30}$Cl$_2$N$_2$O$_5$S=576

Example 14

{1-(3,4-Dichloro-benzyl)-7-[2-(thiophene-2-sulfonylamino)-ethoxy]-1,2,3,4-tetrahydronaphthalen-2-yl}-carbamic acid ethyl ester

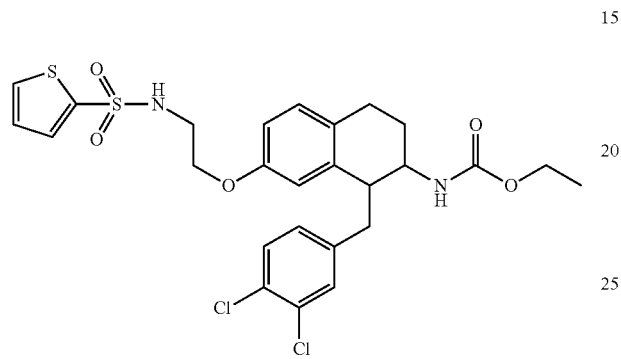

{1-(3,4-Dichloro-benzyl)-7-[2-(thiophene-2-sulfonylamino)-ethoxy]-1,2,3,4-tetrahydronaphthalen-2-yl}-carbamic acid ethyl ester was prepared analogously to example 3 using phenyl sulfonyl chloride in place of 1-methyl-1H-imidazole-4-sulfonyl chloride.

ESI-MS [M+H$^+$]=583.1 Calculated for C$_{26}$H$_{28}$Cl$_2$N$_2$O$_5$S$_2$=582

Example 15

N-{2-[7-Amino-8-(3,4-dichloro-benzyl)-5,6,7,8-tetrahydro-naphthalen-2-yloxy]-ethyl}-methanesulfonamide hydrochloride

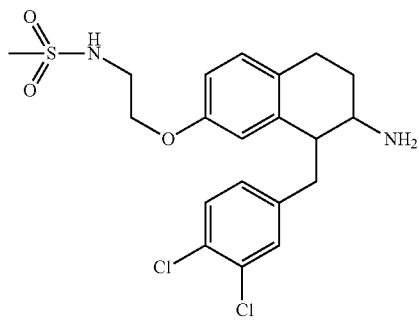 [SMILES: CS(=O)(=O)NCCOc1ccc2c(c1)C(Cc1ccc(Cl)c(Cl)c1)C(N)CC2]

N-{2-[7-Amino-8-(3,4-dichloro-benzyl)-5,6,7,8-tetrahydro-naphthalen-2-yloxy]-ethyl}-methanesulfonamide was prepared analogously to example 3 using methyl sulfonyl chloride in place of 1-methyl-1H-imidazole-4-sulfonyl chloride.

ESI-MS [M+H$^+$]=443.1 Calculated for C$_{20}$H$_{24}$Cl$_2$N$_2$O$_3$S=442

Example 16

N-{2-[7-Amino-8-(3,4-dichloro-benzyl)-5,6,7,8-tetrahydro-naphthalen-2-yloxy]-ethyl}-benzenesulfonamide hydrochloride

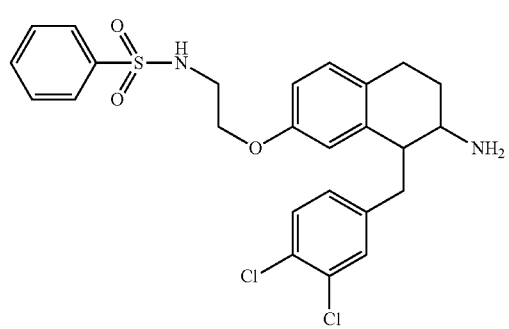

N-{2-[7-Amino-8-(3,4-dichloro-benzyl)-5,6,7,8-tetrahydro-naphthalen-2-yloxy]-ethyl}-benzenesulfonamide was prepared analogously to example 3 using phenyl sulfonyl chloride in place of 1-methyl-1H-imidazole-4-sulfonyl chloride.

ESI-MS [M+H$^+$]=505.1 Calculated for C$_{25}$H$_{26}$Cl$_2$N$_2$O$_3$S=504

Example 17

Thiophene-2-sulfonic acid {2-[7-amino-8-(3,4-dichloro-benzyl)-5,6,7,8-tetrahydro-naphthalen-2-yloxy]-ethyl}-amide hydrochloride

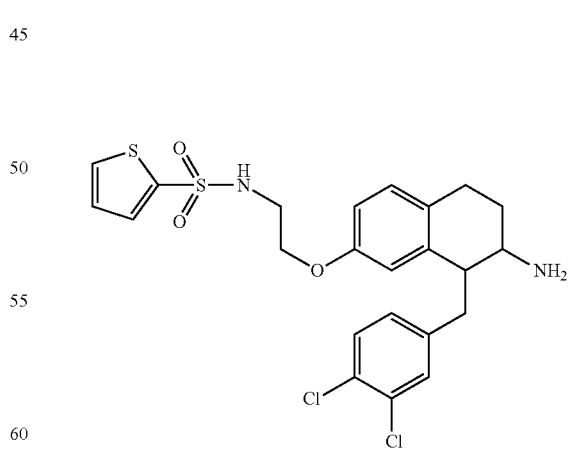

Thiophene-2-sulfonic acid {2-[7-amino-8-(3,4-dichloro-benzyl)-5,6,7,8-tetrahydronaphthalen-2-yloxy]-ethyl}-amide was prepared analogously to example 3 using thiophene sulfonyl chloride in place of 1-methyl-1H-imidazole-4-sulfonyl chloride.

ESI-MS [M+H$^+$]=511.1 Calculated for C$_{23}$H$_{24}$Cl$_2$N$_2$O$_3$S$_2$=510

Example 18

N-{1-(3,4-Dichloro-benzyl)-7-[2-(1-methyl-1 imidazole-4-sulfonylamino)-ethoxy]-1,2,3,4-tetrahydro-naphthalen-2-yl}-2,2,2-trifluoro-acetamide

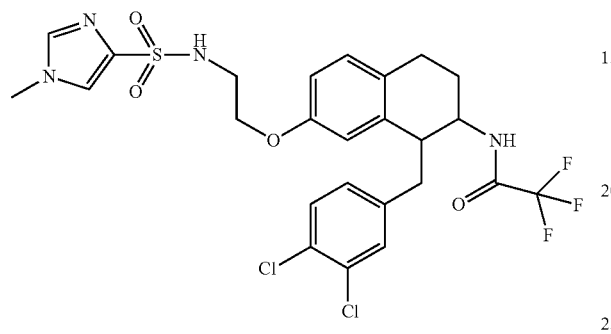

N-{1-(3,4-Dichloro-benzyl)-7-[2-(1-methyl-1H-imidazole-4-sulfonylamino)-ethoxy]-1,2,3,4-tetrahydro-naphthalen-2-yl}-2,2,2-trifluoro-acetamide was prepared analogously to example 11 using the product of example 3 in place of example 8.

ESI-MS [M+H$^+$]=605.1 Calculated for C$_{25}$H$_{25}$Cl$_2$F$_3$N$_4$O$_4$S=604

Example 19

Pyrrolidine-3-sulfonic acid {2-[7-amino-8-(3,4-dichloro-benzyl)-5,6,7,8-tetrahydronaphthalen-2-yloxy]-ethyl}-amide hydrochloride

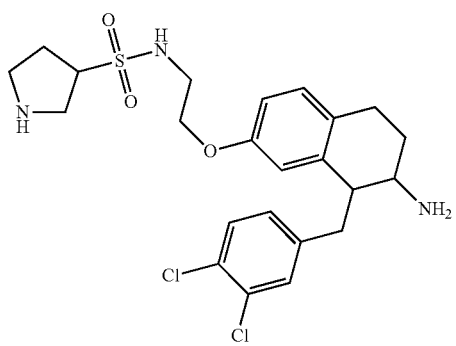 [SMILES: NC1CCc2ccc(OCCNS(=O)(=O)C3CCNC3)cc2C1Cc1ccc(Cl)c(Cl)c1]

Pyrrolidine-3-sulfonic acid {2-[7-amino-8-(3,4-dichloro-benzyl)-5,6,7,8-tetrahydronaphthalen-2-yloxy]-ethyl}-amide hydrochloride was prepared analogously to example 3 using benzyl 3-(chlorosulfonyl)pyrrolidine-1-carboxylate (synthesis described in WO2008075070) in place of 1-methyl-1H-imidazole-4-sulfonyl chloride.

ESI-MS [M+H$^+$]=498.2 Calculated for C$_{23}$H$_{29}$Cl$_2$N$_3$O$_3$S=497

Example 20

1-Methyl-1H-imidazole-4-sulfonic acid {2-[8-(3,4-dichloro-benzyl)-7-formylamino-5,6,7,8-tetrahydro-naphthalen-2-yloxy]-ethyl}-amide

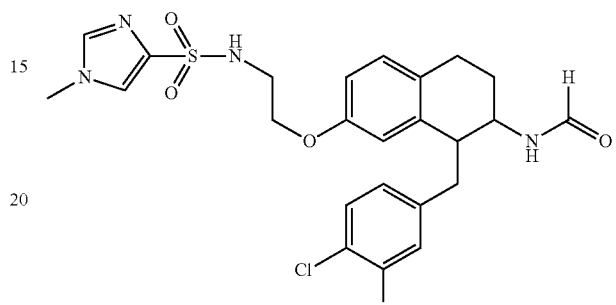

Ethyl 1-(3,4-dichlorobenzyl)-7-(2-(1-methyl-1H-imidazole-4-sulfonamido)ethoxy)-1,2,3,4-tetrahydronaphthalen-2-ylcarbamate (example 3, 60.0 mg, 0.103 mmol) was dissolved in THF (5 ml) and LiAlH$_4$ (7.83 mg, 0.206 mmol) was added at RT. The residue was added to 2N NaOH and extracted with dichloromethane. The organic layer was washed with saturated NaHCO$_3$ solution and then with saturated NaCl solution, dried and evaporated. The product was precipitated as an HCl salt from 6N HCl in isopropanol and isopropylether to obtain the product as a white salt (36 mg, 61%).

ESI-MS [M+H$^+$]=537.1 Calculated for C$_{24}$H$_{26}$Cl$_2$N$_4$O$_4$S=536

Example 21

1-(3,4-Dichloro-benzyl)-7-[2-(4-methyl-thiophene-2-sulfonylamino)-ethoxy]-1,2,3,4-tetrahydro-naphthalen-2-yl}-carbamic acid ethyl ester

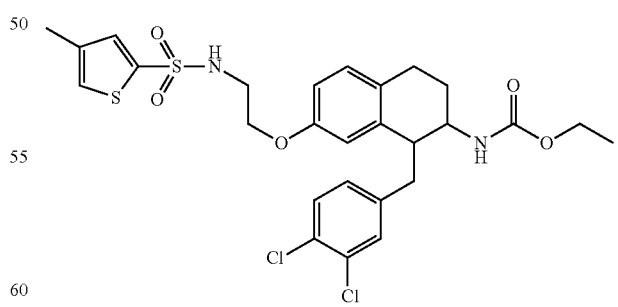

1-(3,4-Dichloro-benzyl)-7-[2-(4-methyl-thiophene-2-sulfonylamino)-ethoxy]-1,2,3,4-tetrahydro-naphthalen-2-yl}-carbamic acid ethyl ester was prepared analogously to example 3 using 4-methylthiophene-2-sulfonyl chloride in place of 1-methyl-1H-imidazole-4-sulfonyl chloride.

ESI-MS [M+H$^+$]=597.1 Calculated for C$_{27}$H$_{30}$Cl$_2$N$_2$O$_5$S$_2$=596

Example 22

{1-(3,4-Dichloro-benzyl)-7-[2-(3-fluoro-propane-1-sulfonylamino)-ethoxy]-1,2,3,4-tetrahydro-naphthalen-2-yl}-carbamic acid ethyl ester

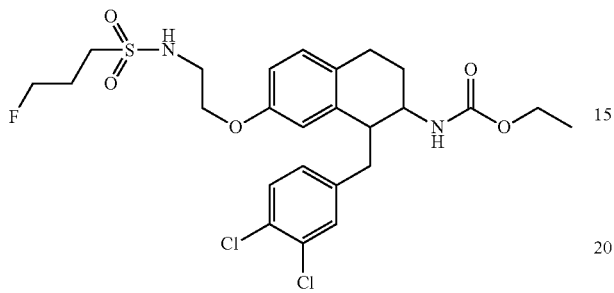

{1-(3,4-Dichloro-benzyl)-7-[2-(3-fluoro-propane-1-sulfonylamino)-ethoxy]-1,2,3,4-tetrahydro-naphthalen-2-yl}-carbamic acid ethyl ester was prepared analogously to example 3 using 3-fluoropropane-1-sulfonyl chloride in place of 1-methyl-1H-imidazole-4-sulfonyl chloride.

ESI-MS [M+H$^+$]=561.2 Calculated for C$_{25}$H$_{31}$Cl$_2$FN$_2$O$_5$S=560

Example 23

1-Methyl-1H-imidazole-4-sulfonic acid {2-[8-(3,4-dichloro-benzyl)-7-ethylamino-5,6,7,8-tetrahydro-naphthalen-2-yloxy]-ethyl}-amide

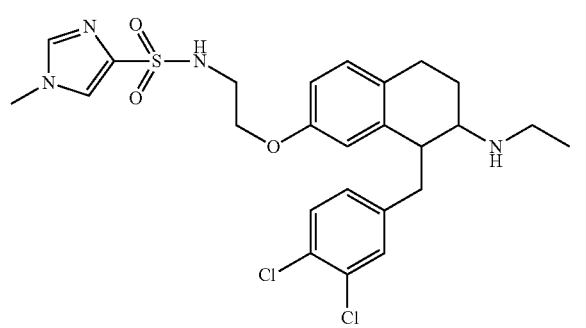 [SMILES: CCNC1CCc2ccc(OCCNS(=O)(=O)c3cn(C)cn3)cc2C1Cc1ccc(Cl)c(Cl)c1]

Ethyl 1-(3,4-dichlorobenzyl)-7-(2-(1-methyl-1H-imidazole-4-sulfonamido)ethoxy)-1,2,3,4-tetrahydronaphthalen-2-ylcarbamate (example 3, 60.0 mg, 0.103 mmol) was dissolved in dichloromethane (5 ml) and acetaldehyde (5.45 mg, 0.124 mmol µl) and molsieve 3 Å were added and the mixture was stirred for 3 h. Acetic acid (7.07 mg, 0.118 mmol) was added and the mixture was stirred for another 3 h. MeOH (5 ml) and sodium cyanoborohydride (14.8 mg, 0.236 mmol) were added and it was stirred for another 14 h. Water was added and it was extracted with dichloromethane. The organic layer was washed with saturated NaHCO$_3$ solution, washed and evaporated. The residue was purified by column chromatography using SiO$_2$ and CH$_2$Cl$_2$/MeOH 95:5→90:10. The product was precipitated as an HCl salt from 6N HCl in isopropanol and isopropylether to obtain the product as a white salt (17 mg, 25%).

ESI-MS [M+H$^+$]=537.2 Calculated for C$_{25}$H$_{30}$Cl$_2$N$_4$O$_3$S=536

Example 24

4-Methyl-thiophene-2-sulfonic acid {2-[7-amino-8-(3,4-dichloro-benzyl)-5,6,7,8-tetrahydronaphthalen-2-yloxy]-ethyl}-amide hydrochloride

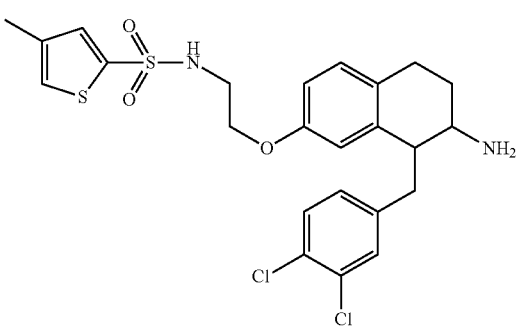 [SMILES: Cc1csc(S(=O)(=O)NCCOc2ccc3c(c2)C(Cc2ccc(Cl)c(Cl)c2)C(N)CC3)c1]

4-Methyl-thiophene-2-sulfonic acid {2-[7-amino-8-(3,4-dichloro-benzyl)-5,6,7,8-tetrahydronaphthalen-2-yloxy]-ethyl}-amide hydrochloride was prepared analogously to example 3 using 4-methylthiophene-2-sulfonyl chloride in place of 1-methyl-1H-imidazole-4-sulfonyl chloride.

ESI-MS [M+H$^+$]=525.1 Calculated for C$_{24}$H$_{26}$Cl$_2$N$_2$O$_3$S$_2$=524

Example 25

N'-(2-{[7-amino-8-(3,4-dichlorobenzyl)-5,6,7,8-tetrahydronaphthalen-2-yl]oxy}ethyl)-N,N-dimethyl-sulfuric diamide hydrochloride

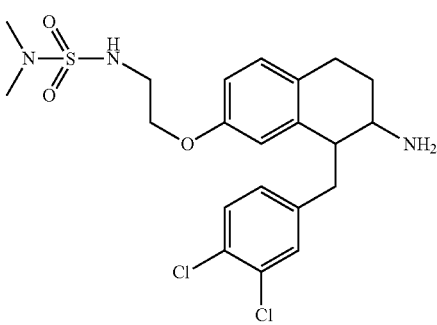 [SMILES: CN(C)S(=O)(=O)NCCOc1ccc2c(c1)C(Cc1ccc(Cl)c(Cl)c1)C(N)CC2]

N'-(2-{[7-Amino-8-(3,4-dichlorobenzyl)-5,6,7,8-tetrahydronaphthalen-2-yl]oxy}ethyl)-N,N-dimethylsulfuric diamide hydrochloride was prepared analogously to example 3 using dimethylsulfamoyl chloride in place of 1-methyl-1H-imidazole-4-sulfonyl chloride.

ESI-MS [M+H$^+$]=472.1 Calculated for C$_{21}$H$_{27}$Cl$_2$N$_3$O$_3$S=471

Example 26

{1-(3,4-Dichloro-benzyl)-7-[2-(3,3,3-trifluoro-propane-1-sulfonylamino)-ethoxy]-1,2,3,4-tetrahydronaphthalen-2-yl}-carbamic acid ethyl ester

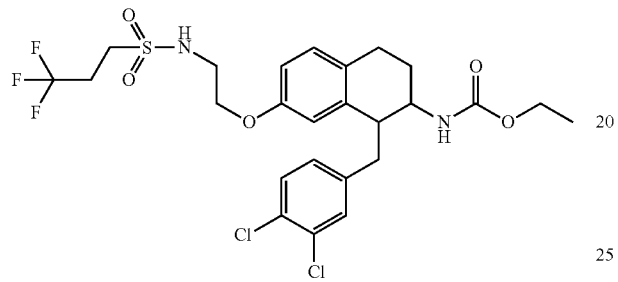

{1-(3,4-Dichloro-benzyl)-7-[2-(3,3,3-trifluoro-propane-1-sulfonylamino)-ethoxy]-1,2,3,4-tetrahydro-naphthalen-2-yl}-carbamic acid ethyl ester was prepared analogously to example 3 using dimethylsulfamoyl chloride in place of 1-methyl-1H-imidazole-4-sulfonyl chloride.

ESI-MS [M+H$^+$]=597.1 Calculated for C$_{25}$H$_{29}$Cl$_2$F$_3$N$_2$O$_5$S=596

Example 27

1-Methyl-1H-imidazole-4-sulfonic acid {2-[7-amino-8-(4-chloro-benzyl)-5,6,7,8-tetrahydronaphthalen-2-yloxy]-ethyl}-amide hydrochloride

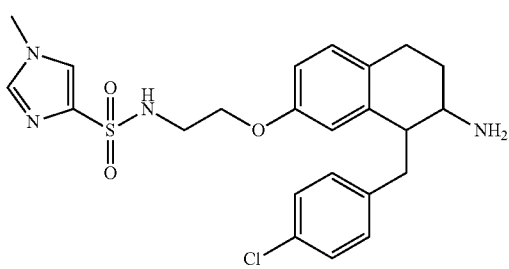 [SMILES: Cn1cnc(S(=O)(=O)NCCOc2ccc3c(c2)C(Cc2ccc(Cl)cc2)C(N)CC3)c1]

1-Methyl-1H-imidazole-4-sulfonic acid {2-[7-amino-8-(4-chloro-benzyl)-5,6,7,8-tetrahydronaphthalen-2-yloxy]-ethyl}-amide hydrochloride was prepared analogously to example 3 using 1-methyl-1H-imidazole-4-sulfonyl chloride in place of 1-methyl-1H-imidazole-4-sulfonyl chloride and 4-(bromomethyl)-1-dichlorobenzene instead of 4-(bromomethyl)-1,2-dichlorobenzene.

ESI-MS [M+H$^+$]=475.1 Calculated for C$_{23}$H$_{27}$ClN$_4$O$_3$S=474

Example 28

1-Methyl-1H-pyrazole-4-sulfonic acid {2-[7-amino-8-(4-chloro-benzyl)-5,6,7,8-tetrahydronaphthalen-2-yloxy]-ethyl}-amide hydrochloride

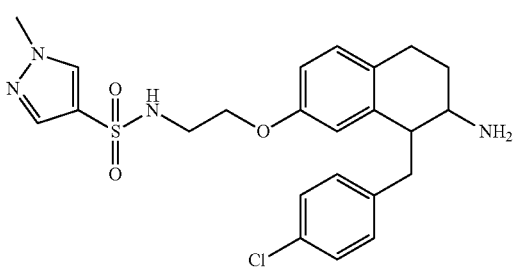 [SMILES: Cn1cc(S(=O)(=O)NCCOc2ccc3c(c2)C(Cc2ccc(Cl)cc2)C(N)CC3)cn1]

1-Methyl-1H-pyrazole-4-sulfonic acid {2-[7-amino-8-(4-chloro-benzyl)-5,6,7,8-tetrahydronaphthalen-2-yloxy]-ethyl}-amide hydrochloride was prepared analogously to example 3 using 1-methyl-1H-pyrazole-4-sulfonyl chloride in place of 1-methyl-1H-imidazole-4-sulfonyl chloride and 4-(bromomethyl)-1-dichlorobenzene instead of 4-(bromomethyl)-1,2-dichlorobenzene.

ESI-MS [M+H$^+$]=475.1 Calculated for C$_{23}$H$_{27}$ClN$_4$O$_3$S=474

Example 29

7-Amino-8-(3,4-dichlorobenzyl)-5,6,7,8-tetrahydronaphthalene-2-carbonitrile trifluoroacetate 29.1 8-(3,4-Dichlorobenzyl)-7-[(ethoxycarbonyl)amino]-5,6,7,8-tetrahydronaphthalen-2-yl trifluoromethanesulfonate

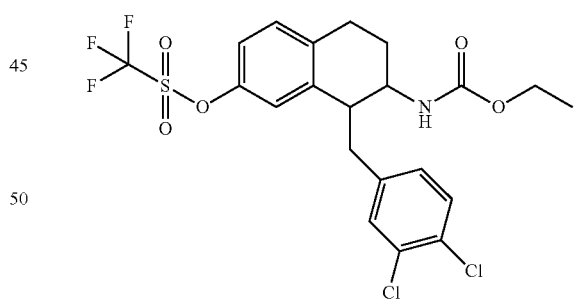

Ethyl 1-(3,4-dichlorobenzyl)-7-hydroxy-1,2,3,4-tetrahydronaphthalen-2-ylcarbamate (700 mg, 1.775 mmol, cf. example 3d) and 1,1,1-trifluoro-N-phenyl-N-(trifluoromethylsulfonyl)methanesulfonamide (761 mg, 2.13 mmol) were dissolved in dichloromethane (30 mL). The reaction mixture was cooled to 0° C. and a solution of triethylamine (0.495 mL, 3.55 mmol) in dichloromethane (5 mL) was added dropwise. The reaction mixture was allowed to warm to room temperature and stirring was continued over night. The solvent was evaporated in vacuo and the crude product was purified by flash chromatography (dichloromethane, silica gel). Yield: 934 mg (100%).

ESI-MS [M+H⁺]=526 Calculated for $C_{21}H_{20}Cl_2F_3NO_5S$=525.

29.2 Ethyl [7-cyano-1-(3,4-dichlorobenzyl)-1,2,3,4-tetrahydronaphthalen-2-yl]carbamate

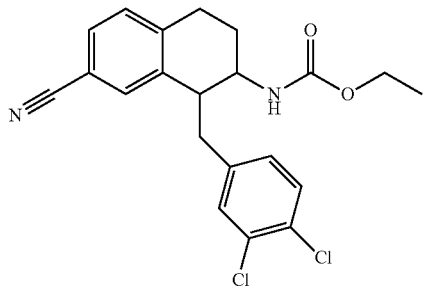 [SMILES: CCOC(=O)NC1CCc2ccc(C#N)cc2C1Cc1ccc(Cl)c(Cl)c1]

8-(3,4-Dichlorobenzyl)-7-[(ethoxycarbonyl)amino]-5,6,7,8-tetrahydronaphthalen-2-yl trifluoromethanesulfonate (250 mg, 0.475 mmol), zinc cyanide (139 mg, 1.187 mmol) and tetrakistriphenyl palladium (82 mg, 0.071 mmol) in dimethylformamide (5 mL) were heated in the microwave at 120° C. (100 W) under stirring for 35 min. The solvent was evaporated in vacuo and the crude product was partitioned between ethyl acetate (40 mL) and water (30 mL). The aqueous layer was extracted with ethyl acetate one more time (20 mL) and the combined organic extracts were dried (Na₂SO₄) and concentrated in vacuo. The crude product (460 mg) was purified by flash chromatography (dichloromethane:methanol=100:1, silica gel). Yield: 109 mg (0.270 mmol, 57%, colorless solid).

ESI-MS [M+H⁺]=403 Calculated for $C_{21}H_{20}Cl_2N_2O_2$=402.

29.3 7-Amino-8-(3,4-dichlorobenzyl)-5,6,7,8-tetrahydronaphthalene-2-carbonitrile trifluoroacetate

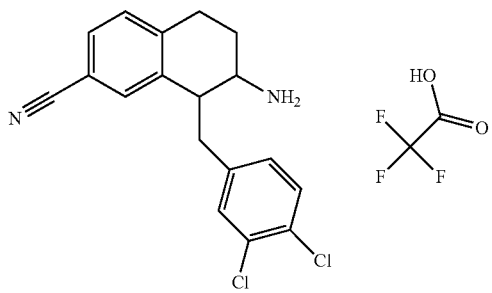 [SMILES: N#Cc1ccc2c(c1)C(Cc1ccc(Cl)c(Cl)c1)C(N)CC2 ; O=C(O)C(F)(F)F]

Ethyl [7-cyano-1-(3,4-dichlorobenzyl)-1,2,3,4-tetrahydronaphthalen-2-yl]carbamate (50 mg, 0.124 mmol) was dissolved in 10% potassium hydroxide in ethanol (1.5 mL) and the reaction mixture was stirred at 80° C. for 2.5 h. The solvent was evaporated in vacuo. To the crude product brine (5 mL) and 2N hydrochloric acid were added until pH 7 was reached. The aqueous layer was extracted with dichloromethane three times. The combined organic extracts were dried (Na₂SO₄) and concentrated in vacuo. The crude product (60 mg) was purified by preparative HPLC (xTerra prep MS C18 column, 19×150 mm, 5 μm; gradient: water, acetonitrile with 0.1% trifluoroacetic acid, flow: 20 mL/min). Yield: 6 mg (0.013 mmol, 11%).

ESI-MS [M+H⁺]=331 Calculated for $C_{18}H_{16}Cl_2N_2$=330.

Example 30

7-Amino-8-(4-chlorobenzyl)-5,6,7,8-tetrahydronaphthalene-2-carbonitrile hydrochloride

30.1 7-Amino-8-(4-chlorobenzyl)-5,6,7,8-tetrahydronaphthalen-2-ol

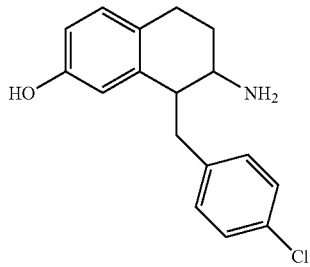 [SMILES: NC1CCc2ccc(O)cc2C1Cc1ccc(Cl)cc1]

1-(4-chlorobenzyl)-7-methoxy-1,2,3,4-tetrahydronaphthalen-2-amine (13.18 g, 43.7 mmol, prepared analogously to 1-(3,4-dichlorobenzyl)-7-methoxy-1,2,3,4-tetrahydronaphthalen-2-amine cf. example 3) was dissolved in dichloromethane (200 mL). The solution was cooled to −10° C. and a 1 M solution of borontribromide in dichloromethane (131 mL, 131 mmol) was slowly added. The reaction mixture was allowed to warm to room temperature and stirring was continued for 2 h. The reaction mixture was poured on ice water and sodium hydroxide was added until pH 8 was reached. The aqueous layer was extracted with dichloromethane. The combined organic extracts were dried (Na₂SO₄) and concentrated in vacuo. The crude product was used for the next step without further purification. Yield: 8.89 g (30.9 mmol, 71%, colorless solid).

ESI-MS [M+H⁺]=288 Calculated for $C_{17}H_{18}ClNO$=287.

30.2 Tert-butyl[1-(4-chlorobenzyl)-7-hydroxy-1,2,3,4-tetrahydronaphthalen-2-yl]carbamate

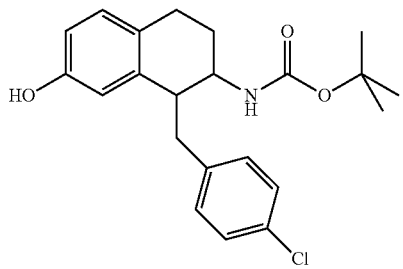 [SMILES: CC(C)(C)OC(=O)NC1CCc2ccc(O)cc2C1Cc1ccc(Cl)cc1]

7-Amino-8-(4-chlorobenzyl)-5,6,7,8-tetrahydronaphthalen-2-ol (2.0 g, 6.95 mmol) was dissolved in dry tetrahydrofurane and di-tertiar butyl carbonate (1.517 g, 6.95 mmol) and triethylamine (2.91 mL, 20.85 mmol) were added. The reaction mixture was stirred at room temperature for 3 h. The solvent was evaporated in vacuo. Water was added and the aqueous layer was extracted with dichloromethane. The combined organic extracts were dried (Na₂SO₄) and concentrated in vacuo. The crude product was recrystallized from n-hexane. Yield: 2.2 g (5.67 mmol, 82%).

ESI-MS [M-isobutene+H$^+$]=332 Calculated for C$_{22}$H$_{26}$ClNO$_3$=387.

30.3 7-[(Tert-butoxycarbonyl)amino]-8-(4-chlorobenzyl)-5,6,7,8-tetrahydronaphthalen-2-yl trifluoromethanesulfonate

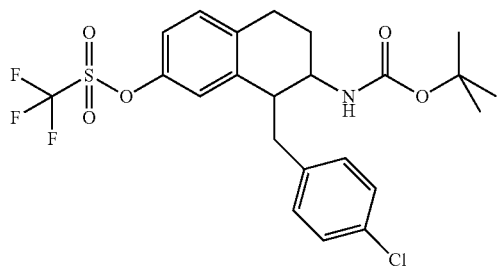 [SMILES: CC(C)(C)OC(=O)NC1CCc2ccc(OS(=O)(=O)C(F)(F)F)cc2C1Cc1ccc(Cl)cc1]

Tert-butyl[1-(4-chlorobenzyl)-7-hydroxy-1,2,3,4-tetrahydronaphthalen-2-yl]carbamate (850 mg, 2.191 mmol) and 1,1,1-trifluoro-N-phenyl-N-(trifluoromethylsulfonyl)methanesulfonamide (939 mg, 2.63 mmol) were dissolved in dichloromethane (45 mL). The pale yellow solution was cooled to 0° C. and a solution of triethylamine (0.611 mL, 4.38 mmol) in dichloromethane (5 mL) was added dropwise. The reaction mixture was allowed to warm to room temperature and stirring was continued over night. The solvent was evaporated in vacuo and the crude product was purified by flash chromatography (dichloromethane, silica gel). Yield: 1.03 g (1.981 mmol, 90%, colorless solid).

ESI-MS [M-isobutene+CH$_3$CN+H$^+$]=505 Calculated for C$_{23}$H$_{25}$ClF$_3$NO$_5$S=519.

30.4 Tert-butyl[1-(4-chlorobenzyl)-7-cyano-1,2,3,4-tetrahydronaphthalen-2-yl]carbamate

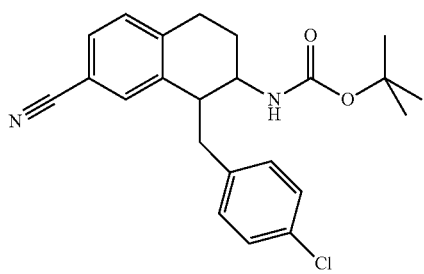 [SMILES: CC(C)(C)OC(=O)NC1CCc2ccc(C#N)cc2C1Cc1ccc(Cl)cc1]

DPPF (8.1 mg, 0.015 mmol) and Pd$_2$ dba$_3$ (3.35 mg, 0.00365 mmol) were suspended in dimethylformamide (0.4 mL) and after stirring at room temperature under an inert atmosphere of nitrogen for 20 min 7-[(tert-butoxycarbonyl)amino]-8-(4-chlorobenzyl)-5,6,7,8-tetrahydronaphthalen-2-yl trifluoromethanesulfonate (38 mg, 0.073 mmol) and zinc cyanide (12.87 mg, 0.110 mmol) were added. The reaction mixture was stirred at 90° C. for 1 h. The solvent was evaporated in vacuo. Water (10 mL) was added to the crude product and the aqueous layer was extracted with ethyl acetate (two times with 10 mL). The combined organic extracts were dried (Na$_2$SO$_4$) and concentrated in vacuo. The crude product was purified by flash chromatography (dichloromethane, silica gel). Yield: 16 mg (0.040 mmol, 55%).

ESI-MS [M-isobutene+CH$_3$CN++H$^+$]=382 Calculated for C$_{23}$H$_{25}$ClN$_2$O$_2$=396.

30.5 7-Amino-8-(4-chlorobenzyl)-5,6,7,8-tetrahydronaphthalene-2-carbonitrile hydrochloride

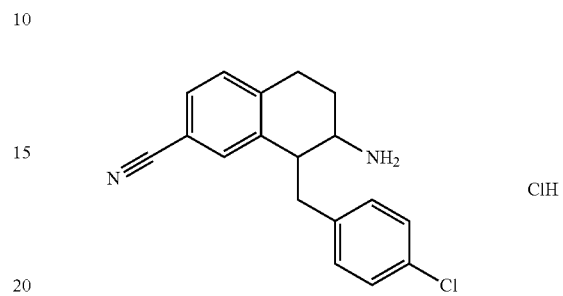

Tert-butyl[1-(4-chlorobenzyl)-7-cyano-1,2,3,4-tetrahydronaphthalen-2-yl]carbamate (15 mg, 0.038 mmol) was dissolved in dichloromethane (1.5 mL) and 5 M hydrochloric acid in isopropanol (0.3 mL) was added. The reaction mixture was stirred for 3 h at room temperature. The solvent and the excess hydrochloric acid were evaporated in vacuo. Yield: 11 mg (0.033 mmol, 87%, colorless solid).

ESI-MS [M+H$^+$]+=297 Calculated for C$_{18}$H$_{17}$ClN$_2$=296.

Example 31

N-[(7-amino-8-benzyl-5,6,7,8-tetrahydronaphthalen-2-yl)methyl]-3-fluoropropane-1-sulfonamide trifluoroacetate

31.1 Tert-butyl[7-(aminomethyl)-1-benzyl-1,2,3,4-tetrahydronaphthalen-2-yl]carbamate

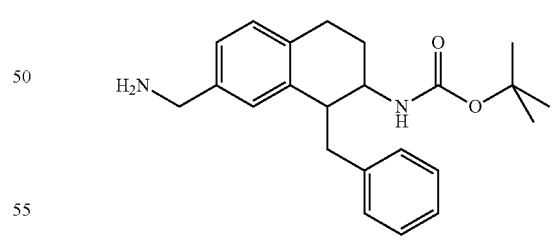

Tert-butyl[1-(4-chlorobenzyl)-7-cyano-1,2,3,4-tetrahydronaphthalen-2-yl]carbamate (52 mg, 0.131 mmol, cf. example 30d) were dissolved in methanol (5 mL). Raney nickel (about 30 mg) was added and the reaction mixture was stirred at room temperature for 4 h under an atmosphere of hydrogen. The catalyst was removed by filtration. The solvent was evaporated in vacuo. The crude product was used without further purification for the next step. Yield: 32 mg (0.087 mmol, 67%).

ESI-MS [M-isobutene+H$^+$]=311 Calculated for C$_{23}$H$_{30}$N$_2$O$_2$=366.

31.2 Tert-butyl[1-benzyl-7-({[(3-fluoropropyl)sulfonyl]amino}methyl)-1,2,3,4-tetrahydronaphthalen-2-yl]carbamate

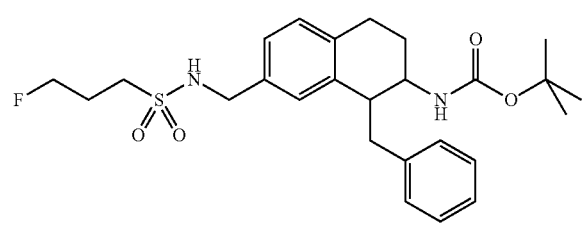 [SMILES: CC(C)(C)OC(=O)NC1CCc2ccc(CNS(=O)(=O)CCCF)cc2C1Cc1ccccc1]

Tert-butyl[7-(aminomethyl)-1-benzyl-1,2,3,4-tetrahydronaphthalen-2-yl]carbamate (32 mg, 0.87 mmol) was dissolved in dichloromethane (15 mL) and 4-dimethylaminopyridine (12 mg, 0.096 mmol) and 3-fluoropropane-1-sulfonyl chloride (14 mg, 0.087 mmol) were added. The reaction mixture was stirred at room temperature over night. The dichloromethane solution of the crude product was washed successively with 1N aqueous hydrochloric acid and aqueous NaHCO$_3$ solution, dried (Na$_2$SO$_4$) and concentrated in vacuo. The crude product was purified by flash chromatography (dichloromethane, methanol, silica gel). Yield: 9.3 mg (0.019 mmol, 22%).

ESI-MS [M-isobutene+H$^+$]=435 Calculated for C$_{26}$H$_{35}$FN$_2$O$_4$S=490.

31.3 N-{[7-Amino-8-benzyl-5,6,7,8-tetrahydronaphthalen-2-yl]methyl}-3-fluoropropane-1-sulfonamide trifluoroacetate

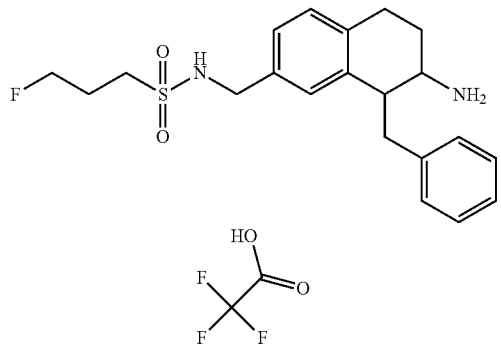

Tert-butyl[1-benzyl-7-({[(3-fluoropropyl)sulfonyl]amino}methyl)-1,2,3,4-tetrahydronaphthalen-2-yl]carbamate (9.3 mg, 0.019 mmol) was dissolved in dichloromethane (10 mL) and trifluoroacetic acid (excess) was added. The reaction mixture was stirred at room temperature for 4 h. The solvent was evaporated in vacuo and the crude product was purified by flash chromatography (silica gel, dichloromethane, methanol).

Yield: 4 mg (0.0079 mmol, 42%).

ESI-MS [M+H$^+$]=391 Calculated for C$_{21}$H$_{27}$FN$_2$O$_2$S=390.

Example 32

Ethyl [7-cyano-1-(3,4-dichlorobenzyl)-1,2,3,4-tetrahydronaphthalen-2-yl]carbamate

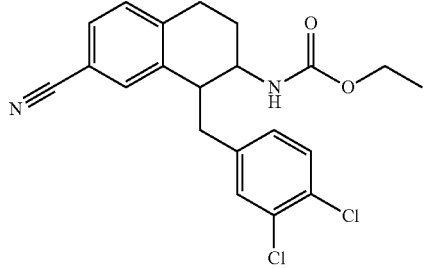 [SMILES: CCOC(=O)NC1CCc2ccc(C#N)cc2C1Cc1ccc(Cl)c(Cl)c1]

Cf. Example 29b.
ESI-MS [M+H$^+$]=403 Calculated for C$_{21}$H$_{20}$Cl$_2$N$_2$O$_2$=402.

Example 33

1-(3-chlorobenzyl)-7-[2-(1,1-dioxidoisothiazolidin-2-yl)ethoxy]-1,2,3,4-tetrahydronaphthalen-2-amine hydrochloride

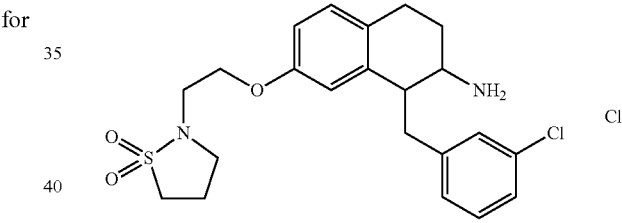

ESI-MS [M+H$^+$]=435 Calculated for C$_{22}$H$_{27}$ClN$_2$O$_3$S=434.

Example 34 tert-Butyl[7-cyano-1-(3,4-dichlorobenzyl)-1,2,3,4-tetrahydronaphthalen-2-yl]carbamate

34.1 7-Amino-8-(3,4-dichlorobenzyl)-5,6,7,8-tetrahydronaphthalen-2-ol

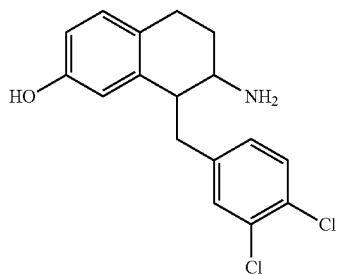 [SMILES: NC1CCc2ccc(O)cc2C1Cc1ccc(Cl)c(Cl)c1]

1-(3,4-Dichlorobenzyl)-7-methoxy-1,2,3,4-tetrahydronaphthalen-2-amine (10 g, 26.8 mmol, cf. example 3.2 were dissolved in dichloromethane (240 mL). The suspension was cooled to −10° C. and a 1 M solution of bortribromide in dichloromethane (80 mL, 80 mmol). The solution was allowed to warm to room temperature and stirring was continued for 3 h. The reaction mixture was poured on ice (1 L). The aqueous layer was made alkaline (pH 10) with 2N sodium hydroxide solution. The layers were separated. The aqueous layer was extracted with dichloromethane and the combined organic layers were washed with saturated NaHCO$_3$ solution and water. The organic layers were dried (Na$_2$SO$_4$) and concentrated in vacuo. The crude product was used without further purification for the next step. Yield: 10.8 g ESI-MS [M+H$^+$]=322 Calculated for C$_{17}$H$_{17}$Cl$_2$NO=321.

34.2 tert-Butyl[1-(3,4-dichlorobenzyl)-7-hydroxy-1,2,3,4-tetrahydronaphthalen-2-yl]carbamate

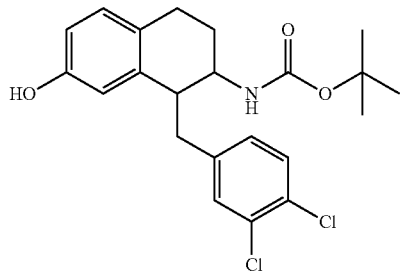 [SMILES: CC(C)(C)OC(=O)NC1CCc2ccc(O)cc2C1Cc1ccc(Cl)c(Cl)c1]

7-Amino-8-(3,4-dichlorobenzyl)-5,6,7,8-tetrahydronaphthalen-2-ol (10.8 g) and triethylamine (14.01 mL, 101 mmol) were dissolved in dry tetrahydrofuran (200 mL). Di-tert-butyl carbonate (7.31 g, 33.5 mmol) was added in small portions at room temperature. The reaction mixture was stirred over night. The solvent was evaporated in vacuo. The residue was dissolved in ethyl acetate (300 mL) and washed with water (2×200 mL). The ethyl acetate solution of the crude product was dried (Na$_2$SO$_4$). The solvent was evaporated in vacuo and the crude product was used for the next step without further purification. Yield: 12.2 g.

ESI-MS [M−isobutene+CH$_3$CN+H$^+$]=407 Calculated for C$_{22}$H$_{25}$Cl$_2$NO$_3$=421.

34.3 7-[(tert-Butoxycarbonyl)amino]-8-(3,4-dichlorobenzyl)-5,6,7,8-tetrahydronaphthalen-2-yl trifluoromethanesulfonate

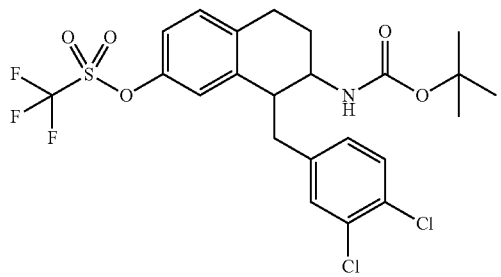 [SMILES: CC(C)(C)OC(=O)NC1CCc2ccc(OS(=O)(=O)C(F)(F)F)cc2C1Cc1ccc(Cl)c(Cl)c1]

tert-Butyl[1-(3,4-dichlorobenzyl)-7-hydroxy-1,2,3,4-tetrahydronaphthalen-2-yl]carbamate (4.06 g, 9.66 mmol) and 1,1,1-trifluoro-N-phenyl-N-(trifluoromethylsulfonyl)methanesulfonamide (4.14 g, 11.59 mmol) were dissolved in dichloromethane (190 mL). The light brown solution was cooled to 0° C. and triethylamine (2.69 mL, 19.32 mmol) in dichloromethane (10 mL) was added dropwise. The reaction mixture was allowed to warm to room temperature and stirring was continued over night. The solvent was evaporated in vacuo and the crude product was purified by flash chromatography (dichloromethane, silica gel). Yield: 3.2 g (5.77 mmol, 60%).

34.4 tert-Butyl[7-cyano-1-(3,4-dichlorobenzyl)-1,2,3,4-tetrahydronaphthalen-2-yl]carbamate

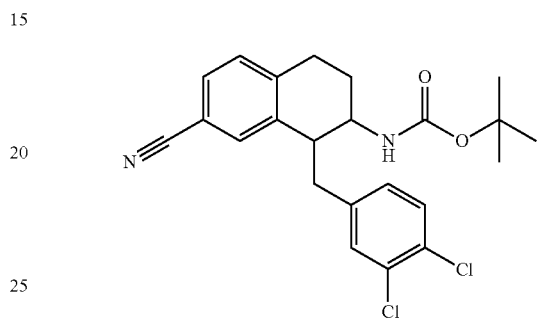

Diphenylphosphinoferrocene (100 mg, 0.18 mmol) and dipalladium trisdibenzylideneacetone (41 mg, 0.045 mmol) were suspended under an atmosphere of argon in dry dimethylformamide (5 mL). After stirring at room temperature for 40 min 7-[(tert-butoxycarbonyl)amino]-8-(3,4-dichlorobenzyl)-5,6,7,8-tetrahydronaphthalen-2-yl trifluoromethanesulfonate (0.5 g, 0.902 mmol) was added and the reaction mixture was heated to 90° C. Over 30 min zinc cyanide (159 mg, 1.353 mmol) was added in small portions. After complete addition stirring was continued at 90° C. for 2 h. The reaction mixture was cooled to room temperature diluted with dichloromethane (50 mL), washed with saturated NaHCO$_3$ (3×10 mL). The organic layer was dried (MgSO$_4$) and concentrated in vacuo. The crude product was purified by flash chromatography (dichloromethane, silica gel). Yield: 97 mg (0.225 mmol, 25%).

ESI-MS [M+Na$^+$]=453 Calculated for C$_{23}$H$_{24}$Cl$_2$N$_2$O$_2$=430.

Example 35

7-Amino-8-(3,4-dichlorobenzyl)-5,6,7,8-tetrahydronaphthalen-2-ol trifluoroacetate (salt)

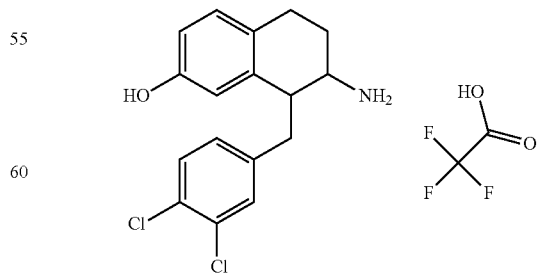

Cf. example 34a
ESI-MS [M+H$^+$]=322 Calculated for C$_{17}$H$_{17}$Cl$_2$NO=321.

Example 36

1-(4-chlorobenzyl)-7-(difluoromethoxy)-1,2,3,4-tetrahydronaphthalen-2-amine hydrochloride

36.1 tert-Butyl[1-(4-chlorobenzyl)-7-(difluoromethoxy)-1,2,3,4-tetrahydronaphthalen-2-yl]carbamate

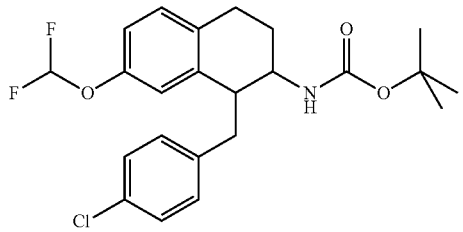 [SMILES: CC(C)(C)OC(=O)NC1CCc2ccc(OC(F)F)cc2C1Cc1ccc(Cl)cc1]

Tert-butyl[1-(4-chlorobenzyl)-7-hydroxy-1,2,3,4-tetrahydronaphthalen-2-yl]carbamate (180 mg, 0.464 mmol, prepared analogously to tert-butyl[1-(3,4-dichlorobenzyl)-7-hydroxy-1,2,3,4-tetrahydronaphthalen-2-yl]carbamate, cf. Example 34.2 and potassium hydroxide (1.4 g, 25 mmol) were suspended in acetonitrile (4 mL). After stirring the two phase system for 45 min at room temperature the reaction mixture was cooled to −15° C. and a solution of 2-chloro-2,2-difluoro-1-phenylethanone (442 mg, 2.32 mmol) in acetonitrile (1 mL) was added dropwise over 30 min. The reaction mixture was warmed to room temperature and then heated at 80° C. for 2 h. The reaction mixture was cooled to room temperature and diluted with ethyl acetate. The aqueous layer was extracted with ethyl acetate. The combined extracts were dried (MgSO$_4$) and concentrated in vacuo. The crude product was purified by flash chromatography (dichloromethane, silica gel). Yield: 30 mg (0.069 mmol, 15%).

ESI-MS [M-isobutene+CH3CN+H$^+$]=423 Calculated for C$_{23}$H$_{26}$ClF$_2$NO$_3$=437.

36.2 1-(4-Chlorobenzyl)-7-(difluoromethoxy)-1,2,3,4-tetrahydronaphthalen-2-amine hydrochloride

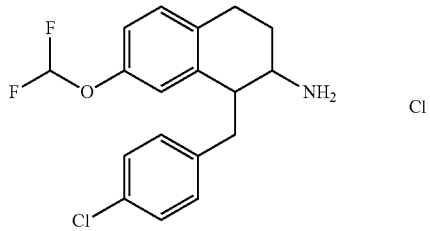 [SMILES: NC1CCc2ccc(OC(F)F)cc2C1Cc1ccc(Cl)cc1 ; Cl]

tert-Butyl[1-(4-chlorobenzyl)-7-(difluoromethoxy)-1,2,3,4-tetrahydronaphthalen-2-yl]carbamate (30 mg, 0.069 mmol) was dissolved in dichloromethane (2 mL). 5N isopropanolic hydrochloric acid (0.3 mL) were added and the reaction mixture was stirred at room temperature for 3 h. The solvents were evaporated in vacuo. Yield: 26 mg (0.069 mmol, 100%, colorless solid).

ESI-MS [M+H$^+$]+=338 Calculated for C$_{18}$H$_{18}$ClF$_2$NO=337.

Example 37

Benzyl [1-(4-chlorobenzyl)-7-hydroxy-1,2,3,4-tetrahydronaphthalen-2-yl]carbamate

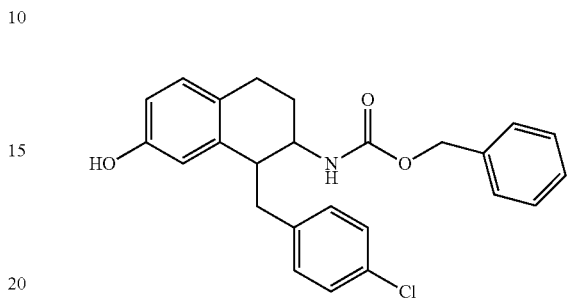

tert-Butyl[1-(4-chlorobenzyl)-7-hydroxy-1,2,3,4-tetrahydronaphthalen-2-yl]carbamate (2 g, 6.95 mmol, prepared analogously to tert-butyl[1-(3,4-dichlorobenzyl)-7-hydroxy-1,2,3,4-tetrahydronaphthalen-2-yl]carbamate, cf. example 34.2 were suspended in dimethylformamide (40 mL). Triethylamine (0.969 mL, 6.95 mmol) and benzyl carbonochloridate (1.186 g, 6.95 mmol) were added. The reaction mixture was stirred at room temperature over night. The solvent was evaporated in vacuo. To the crude product ethyl acetate and water were added. The aqueous layer was extracted with ethyl acetate. The combined organic layers were dried (MgSO$_4$) and concentrated in vacuo. The crude product was purified by flash chromatography (silica gel, dichloromethane, methanol). Yield: 393 mg (0.931 mmol, 13.4%, colorless foam).

ESI-MS [M+H$^+$]=422 Calculated for C$_{25}$H$_{24}$ClNO$_3$=421.

Example 38 tert-Butyl[7-(aminomethyl)-1-(3,4-dichlorobenzyl)-1,2,3,4-tetrahydronaphthalen-2-yl]carbamate

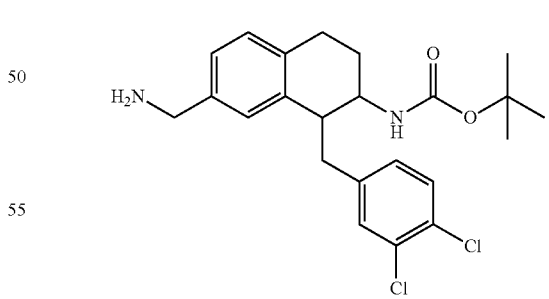

tert-Butyl[7-cyano-1-(3,4-dichlorobenzyl)-1,2,3,4-tetrahydronaphthalen-2-yl]carbamate (30 mg, 0.07 mmol, cf. example 34d) were dissolved in methanol (3 mL). Raney nickel (10 mg) was added and the reaction mixture stirred at room temperature under an atmosphere of hydrogen for 4 h. The catalyst was removed by filtration and the methanol was evaporated in vacuo. Yield: 18 mg (0.041 mmol, 59%).

ESI-MS [M+H⁺]=435 Calculated for C₂₃H₂₈Cl₂N₂O₂=434.

Example 39 tert-Butyl[1-(3,4-dichlorobenzyl)-7-{[(propylsulfonyl)amino]methyl}-1,2,3,4-tetrahydronaphthalen-2-yl]carbamate

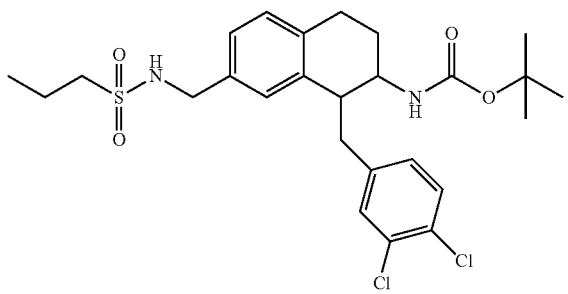 [SMILES: CCCS(=O)(=O)NCc1ccc2c(c1)C(Cc1ccc(Cl)c(Cl)c1)C(NC(=O)OC(C)(C)C)CC2]

tert-Butyl[7-(aminomethyl)-1-(3,4-dichlorobenzyl)-1,2,3,4-tetrahydronaphthalen-2-yl]carbamate (120 mg, 0.276 mmol, cf. Example 38) was dissolved in dichloromethane (5 mL). 4-Dimethylaminopyridine (35 mg, 0.289 mmol) was added. After stirring at room temperature for 5 min propane-1-sulfonyl chloride (39 mg, 0.031 mmol) was added and stirring was continued over night. The reaction mixture was diluted with dichloromethane and washed successively with 0.5 N hydrochloric acid (2×2 mL) and saturated NaHCO₃ (1×2 mL). The organic phase was dried (MgSO₄) and concentrated in vacuo. The crude product was used for the next step without further purification. Yield: 125 mg (0.231 mmol, 84%).

ESI-MS [M+Na⁺]=563 Calculated for C₂₆H₃₄Cl₂N₂O₄S=540.

Example 40

N-{[7-Amino-8-(3,4-dichlorobenzyl)-5,6,7,8-tetrahydronaphthalen-2-yl]methyl}propane-1-sulfonamide hydrochloride

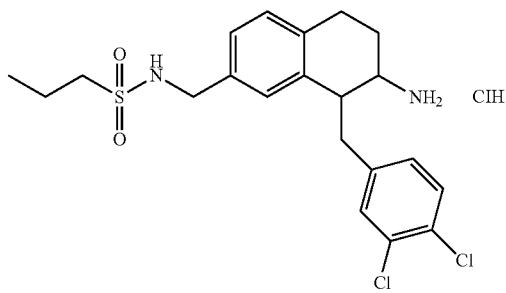

Tert-butyl[1-(3,4-dichlorobenzyl)-7-{[(propylsulfonyl)amino]methyl}-1,2,3,4-tetrahydronaphthalen-2-yl]carbamate (120 mg, 0.222 mmol, cf. example 39) was dissolved in 5 N isopropanolic hydrochloric acid (2 mL). The reaction mixture was stirred at room temperature for 1 h. The solvent was evaporated and the product was dried in vacuo. Yield: 101 mg (0.211 mmol, 95%).

ESI-MS [M+H⁺]=441 Calculated for C₂₁H₂₆Cl₂N₂O₂S=440.

Example 41

N-{[7-Amino-8-(3,4-dichlorobenzyl)-5,6,7,8-tetrahydronaphthalen-2-yl]methyl}-3-fluoropropane-1-sulfonamide hydrochloride

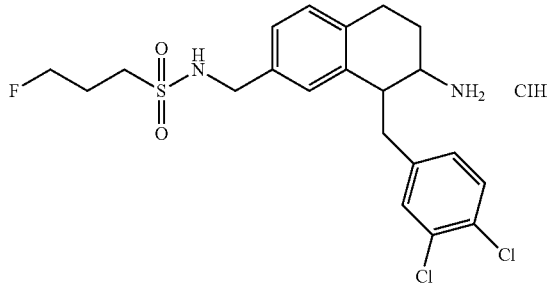

The compound was prepared analogously to example 40 using 3-fluoropropane-1-sulfonyl chloride in place of n-propane-1-sulfonyl chloride.

ESI-MS [M+H⁺]+=459 Calculated for C₂₁H₂₅Cl₂FN₂O₂S=458.

Example 42

N-{[7-Amino-8-benzyl-5,6,7,8-tetrahydronaphthalen-2-yl]methyl}propane-1-sulfonamide trifluoroacetate

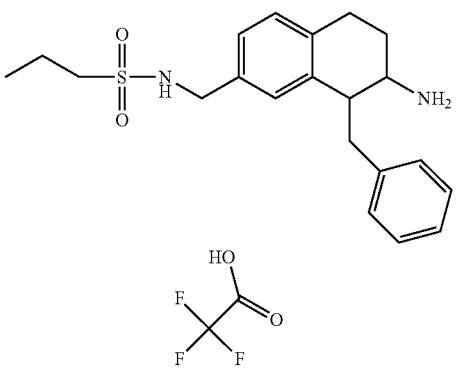

N-{[7-Amino-8-(3,4-dichlorobenzyl)-5,6,7,8-tetrahydronaphthalen-2-yl]methyl}propane-1-sulfonamide hydrochloride (40 mg, 0.084 mmol, cf. example 40) were dissolved in methanol (4 mL) and hydrogenated at the H-cube (1 h, 40° C., 30 bar, 20% Pd/C). The solvent was evaporated and the crude product was purified by preparative HPLC (xTerra prep MS C18 column, 19×150 mm, 5 μm; gradient: water, acetonitrile with 0.1% trifluoroacetic acid, flow: 20 mL/min). Yield: 4.9 mg (0.0102 mmol, 12%)

ESI-MS [M+H⁺]=373 Calculated for C₂₁H₂₈N₂O₂S=372.

Example 43

N-{[cis-7-Amino-8-benzyl-5,6,7,8-tetrahydronaphthalen-2-yl]methyl}cyclobutanesulfonamide hydrochloride

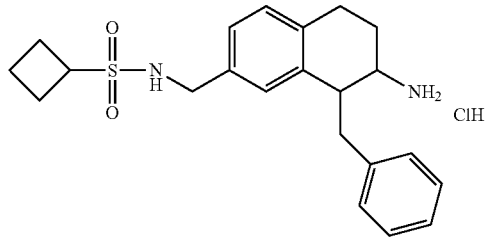 [SMILES: NC1CCc2ccc(CNS(=O)(=O)C3CCC3)cc2C1Cc1ccccc1 ; Cl]

The compound was prepared analogously to example 40 using cyclobutylsulfonyl chloride in place of n-propane-1-sulfonyl chloride.

ESI-MS [M+H$^+$]+=385 Calculated for $C_{22}H_{28}N_2O_2S$=384.

Example 44

N-{[cis-7-Amino-8-benzyl-5,6,7,8-tetrahydronaphthalen-2-yl]methyl}-1-cyclopropylmethanesulfonamide hydrochloride

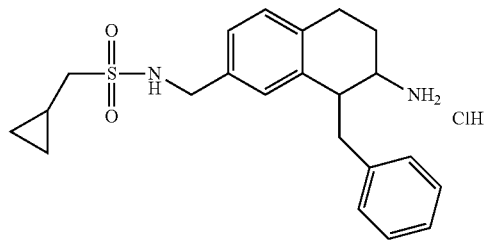 [SMILES: NC1CCc2ccc(CNS(=O)(=O)CC3CC3)cc2C1Cc1ccccc1 ; Cl]

The compound was prepared analogously to example 40 using cyclopropylmethanesulfonyl chloride in place of n-propane-1-sulfonyl chloride.

ESI-MS [M+H$^+$]=385 Calculated for $C_{22}H_{28}N_2O_2S$=384.

Example 45

N-{[cis-7-amino-8-benzyl-5,6,7,8-tetrahydronaphthalen-2-yl]methyl}-N-methylpropane-1-sulfonamide hydrochloride

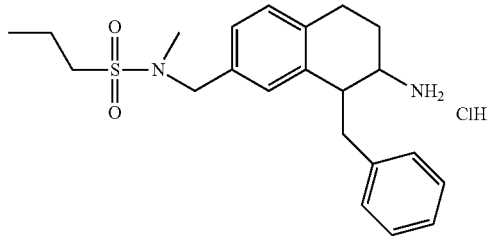 [SMILES: CCCS(=O)(=O)N(C)Cc1ccc2c(c1)C(Cc1ccccc1)C(N)CC2 ; Cl]

Tert-butyl-1-benzyl-7-(propylsulfonamidomethyl)-1,2,3,4-tetrahydronaphthalen-2-ylcarbamate (35 mg, 0.074 mmol, prepared analog to example 40) was dissolved in acetonitrile (1 mL). Cesium carbonate (29 mg, 0.09 mmol)) and methyliodide (12 µL, 0.19 mmol) were added successively and the reaction mixture was heated in the microwave to 100° C. for 3 h. The solvents were evaporated in vacuo. The residue was treated with dichloromethane and washed with water. The organic layer was dried (MgSO$_4$) and concentrated. The crude product was dissolved in isopropanol and treated with 5 M hydrochloric acid in isopropanol. The solvent was evaporated in vacuo to yield the final product as colorless solid. Yield: 18 mg (0.043 mmol, 58%).

ESI-MS [M+H$^+$]=387 Calculated for $C_{22}H_{30}N_2O_2S$=386.

Example 46

{1-(3-Chloro-benzyl)-7-[2-(1-methyl-1H-pyrazole-4-sulfonylamino)-ethoxy]-1,2,3,4-tetrahydro-naphthalen-2-yl}-carbamic acid ethyl ester 46.1 7-(2-tert-Butoxycarbonylamino-ethoxy)-1-(3-chloro-benzyl)-1,2,3,4-tetrahydronaphthalen-2-yl]-carbamic acid ethyl ester

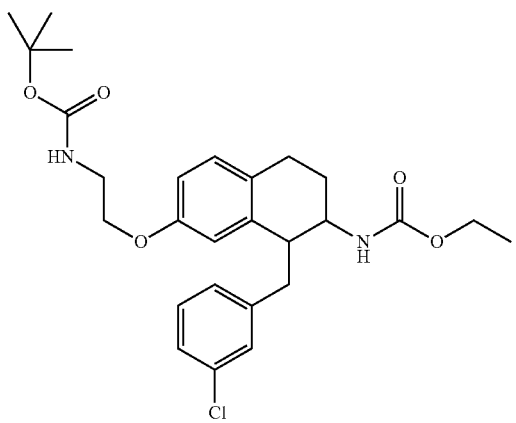 [SMILES: CCOC(=O)NC1CCc2ccc(OCCNC(=O)OC(C)(C)C)cc2C1Cc1cccc(Cl)c1]

7-(2-tert-Butoxycarbonylamino-ethoxy)-1-(3-chloro-benzyl)-1,2,3,4-tetrahydro-naphthalen-2-yl]-carbamic acid ethyl ester was prepared in analogy to example 1 using 1-bromomethyl-3-chloro-benzene in place of 4-(bromomethyl)-1,2-dichlorobenzene.

ESI-MS [M+H$^+$]=503 Calculated for $C_{27}H_{35}ClN_2O_5$=502

46.2 {1-(3-Chloro-benzyl)-7-[2-(1-methyl-1H-pyrazole-4-sulfonylamino)-ethoxy]-1,2,3,4-tetrahydro-naphthalen-2-yl}-carbamic acid ethyl ester

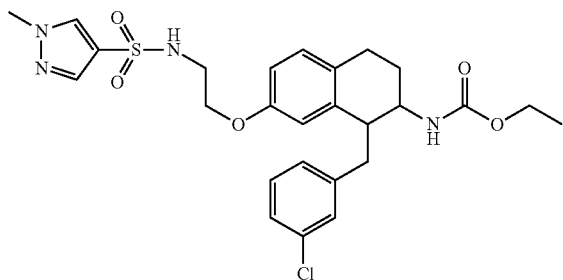 [SMILES: CCOC(=O)NC1CCc2ccc(OCCNS(=O)(=O)c3cnn(C)c3)cc2C1Cc1cccc(Cl)c1]

{1-(3-Chloro-benzyl)-7-[2-(1-methyl-1H-pyrazole-4-sulfonylamino)-ethoxy]-1,2,3,4-tetrahydro-naphthalen-2-yl}-carbamic acid ethyl ester was prepared starting from 7-(2-tertButoxycarbonylamino-ethoxy)-1-(3-chloro-benzyl)-1,2,3,4-tetrahydro-naphthalen-2-yl]-carbamic acid ethyl ester from previous step in analogy to example 2 using 1-methyl-1H-pyrazole-4-sulfonyl chloride in place of 1-methyl-1H-imidazole-4-sulfonyl chloride.

ESI-MS [M+H$^+$]=547 Calculated for $C_{26}H_{31}ClN_4O_5$=546

Example 47

1-Methyl-1H-pyrazole-4-sulfonic acid {2-[7-amino-8-(3-chloro-benzyl)-5,6,7,8-tetrahydronaphthalen-2-yloxy]-ethyl}-amide hydrochloride

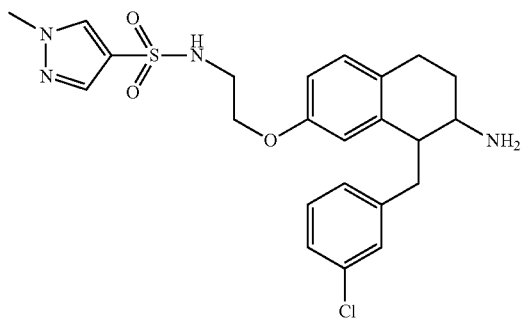 [SMILES: Cn1cc(S(=O)(=O)NCCOc2ccc3c(c2)C(Cc2cccc(Cl)c2)C(N)CC3)cn1]

1-Methyl-1H-pyrazole-4-sulfonic acid {2-[7-amino-8-(3-chloro-benzyl)-5,6,7,8-tetrahydronaphthalen-2-yloxy]-ethyl}-amide hydrochloride was prepared in analogy to example 3 starting from {1-(3-Chloro-benzyl)-7-[2-(1-methyl-1H-pyrazole-4-sulfonylamino)-ethoxy]-1,2,3,4-tetrahydro-naphthalen-2-yl}-carbamic acid ethyl ester (example 46)

ESI-MS [M+H$^+$]=475 Calculated for $C_{23}H_{27}ClN_4O_3S$=474

Example 48

1-Methyl-1H-imidazole-4-sulfonic acid {2-[7-amino-8-(3-chloro-benzyl)-5,6,7,8-tetrahydronaphthalen-2-yloxy]-ethyl}-amide hydrochloride

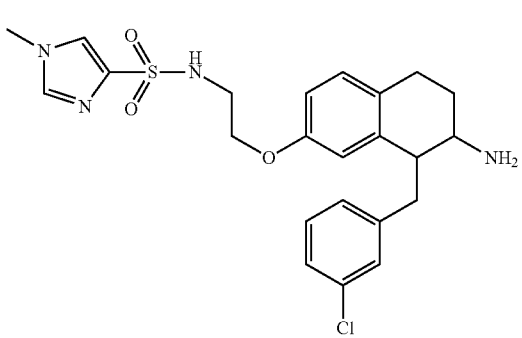 [SMILES: Cn1cnc(S(=O)(=O)NCCOc2ccc3c(c2)C(Cc2cccc(Cl)c2)C(N)CC3)c1]

1-Methyl-1H-imidazole-4-sulfonic acid {2-[7-amino-8-(3-chloro-benzyl)-5,6,7,8-tetrahydronaphthalen-2-yloxy]-ethyl}-amide hydrochloride was prepared in three steps from 7-(2-tertButoxycarbonylamino-ethoxy)-1-(3-chloro-benzyl)-1,2,3,4-tetrahydro-naphthalen-2-yl]-carbamic acid ethyl ester in analogy to example 47 using 1-Methyl-1H-imidazole-4-sulfonyl chloride.

ESI-MS [M+H$^+$]=475 Calculated for $C_{23}H_{27}ClN_4O_3S$=474

Example 49

{1-(3-Chloro-benzyl)-7-[2-(2,4-dimethyl-thiazole-5-sulfonylamino)-ethoxy]-1,2,3,4-tetrahydro-naphthalen-2-yl}-carbamic acid ethyl ester

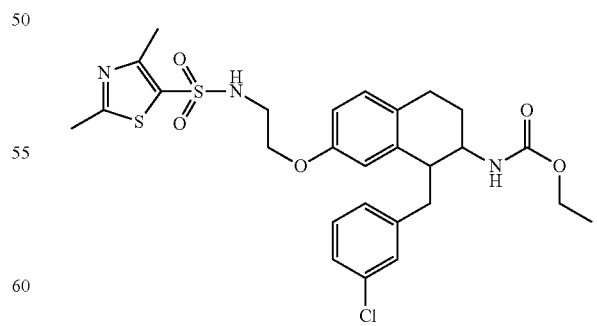

Prepared in two steps from 7-(2-tert-Butoxycarbonylamino-ethoxy)-1-(3-chloro-benzyl)-1,2,3,4-tetrahydro-naphthalen-2-yl]-carbamic acid ethyl ester in analogy to example 46 using 2,4-dimethyl-thiazole-5-sulfonyl chloride.

ESI-MS [M+H$^+$]+=578 Calculated for C$_{27}$H$_{32}$ClN$_3$O$_5$S$_2$=577

Example 50

{1-(3-Chloro-benzyl)-7-[2-(thiophene-2-sulfonylamino)-ethoxy]-1,2,3,4-tetrahydronaphthalen-2-yl}-carbamic acid ethyl ester

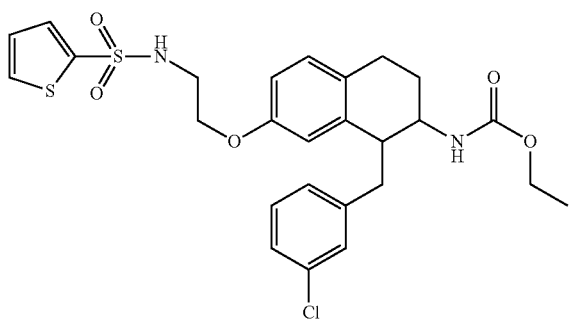 [SMILES: CCOC(=O)NC1CCc2ccc(OCCNS(=O)(=O)c3cccs3)cc2C1Cc1cccc(Cl)c1]

Prepared in two steps from 7-(2-tert-Butoxycarbonylamino-ethoxy)-1-(3-chloro-benzyl)-1,2,3,4-tetrahydronaphthalen-2-yl]-carbamic acid ethyl ester in analogy to example 46 using thiophene-2-sulfonyl chloride.

ESI-MS [M+H$^+$]+=549 Calculated for C$_{26}$H$_{29}$ClN$_2$O$_5$S$_2$=548

Example 51

{1-(3-Chloro-benzyl)-7-[2-(5-chloro-thiophene-2-sulfonylamino)-ethoxy]-1,2,3,4-tetrahydronaphthalen-2-yl}-carbamic acid ethyl ester

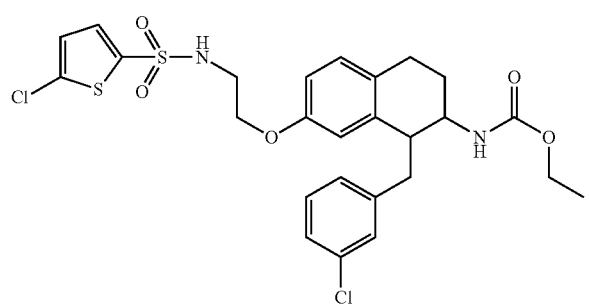 [SMILES: CCOC(=O)NC1CCc2ccc(OCCNS(=O)(=O)c3ccc(Cl)s3)cc2C1Cc1cccc(Cl)c1]

Prepared in two steps from 7-(2-tert-butoxycarbonylamino-ethoxy)-1-(3-chloro-benzyl)-1,2,3,4-tetrahydronaphthalen-2-yl]-carbamic acid ethyl ester in analogy to example 46 using 5-Chloro-thiophene-2-sulfonyl chloride.

ESI-MS [M+H$^+$]+=583 Calculated for C$_{26}$H$_{28}$Cl$_2$N$_2$O$_5$S$_2$=582

Example 52

{1-(3-Chloro-benzyl)-7-[2-(2-methyl-3H-imidazole-4-sulfonylamino)-ethoxy]-1,2,3,4-tetrahydro-naphthalen-2-yl}-carbamic acid ethyl ester

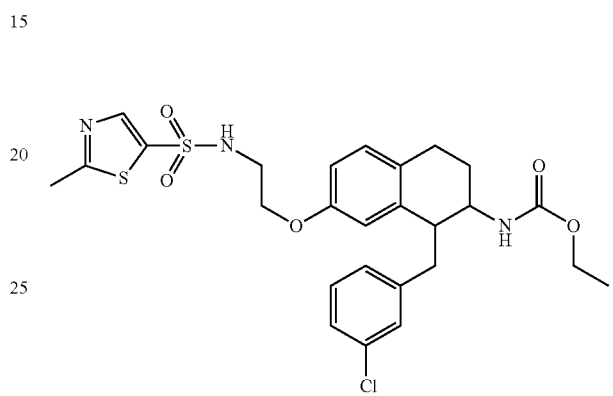

Prepared in two steps from 7-(2-tert-butoxycarbonylamino-ethoxy)-1-(3-chloro-benzyl)-1,2,3,4-tetrahydronaphthalen-2-yl]-carbamic acid ethyl ester in analogy to example 46 using 2-Methyl-3H-imidazole-4-sulfonyl chloride.

ESI-MS [M+H$^+$]=547 Calculated for C$_{26}$H$_{31}$ClN$_4$O$_5$S=546

Example 53

{1-(3-Chloro-benzyl)-7-[2-(5-methyl-thiophene-2-sulfonylamino)-ethoxy]-1,2,3,4-tetrahydro-naphthalen-2-yl}-carbamic acid ethyl ester

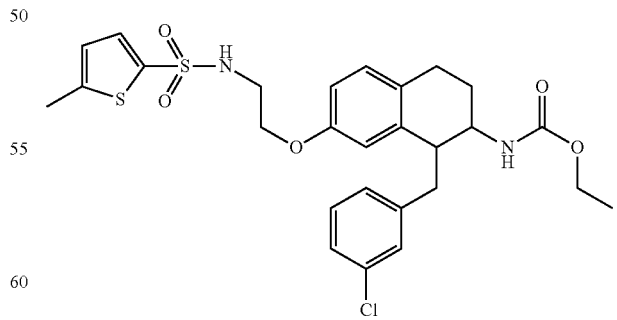

Prepared in two steps from 7-(2-tert-butoxycarbonylamino-ethoxy)-1-(3-chloro-benzyl)-1,2,3,4-tetrahydronaphthalen-2-yl]carbamic acid ethyl ester in analogy to example 46 using 5-Methyl-thiophene-2-sulfonyl chloride.

ESI-MS [M+H⁺]=563 Calculated for C₂₇H₃₁ClN₂O₅S₂=562

Example 54

{1-(3-Chloro-benzyl)-7-[2-(4-methyl-thiophene-2-sulfonylamino)-ethoxy]-1,2,3,4-tetrahydro-naphthalen-2-yl}-carbamic acid ethyl ester

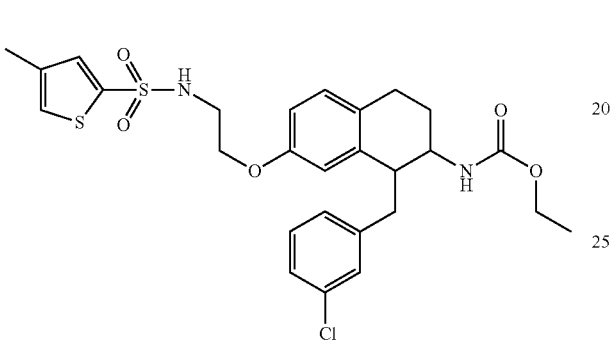

Prepared in two steps from 7-(2-tert-butoxycarbonylamino-ethoxy)-1-(3-chloro-benzyl)-1,2,3,4-tetrahydro-naphthalen-2-yl]-carbamic acid ethyl ester in analogy to example 46 using 4-Methyl-thiophene-2-sulfonyl chloride.
ESI-MS [M+H⁺]+=563 Calculated for C₂₇H₃₁ClN₂O₅S₂=562

Example 55

Propane-1-sulfonic acid {2-[7-amino-8-(3-chloro-benzyl)-5,6,7,8-tetrahydro-naphthalen-2-yloxy]-ethyl}-amide hydrochloride

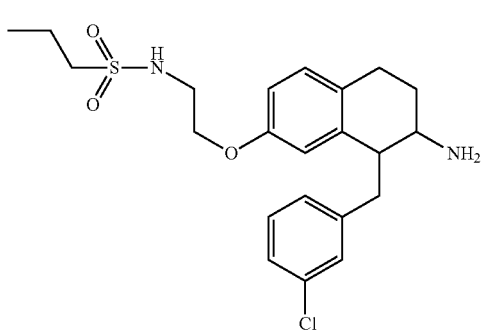

Prepared in three steps from 7-(2-tert-butoxycarbonylamino-ethoxy)-1-(3-chloro-benzyl)-1,2,3,4-tetrahydro-naphthalen-2-yl]-carbamic acid ethyl ester in analogy to example 48 using propane-1-sulfonyl chloride.

ESI-MS [M+H⁺]+=437 Calculated for C₂₂H₂₉ClN₂O₃S=436

Example 56

Thiophene-2-sulfonic acid {2-[7-amino-8-(3-chloro-benzyl)-5,6,7,8-tetrahydro-naphthalen-2-yloxy]-ethyl}-amide

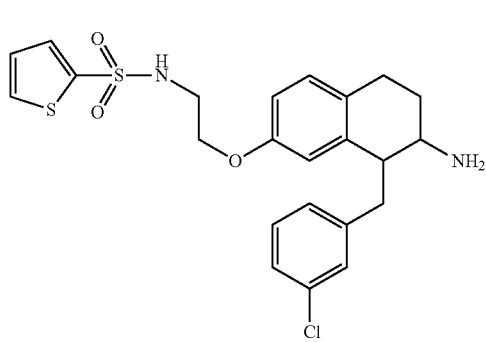 [SMILES: NC1CCc2ccc(OCCNS(=O)(=O)c3cccs3)cc2C1Cc1cccc(Cl)c1]

Prepared in one step from {1-(3-chloro-benzyl)-7-[2-(thiophene-2-sulfonylamino)-ethoxy]-1,2,3,4-tetrahydro-naphthalen-2-yl}-carbamic acid ethyl ester in analogy to example 48.
ESI-MS [M+H⁺]=477 Calculated for C₂₃H₂₅ClN₂O₃S₂=476

Example 57

2,4-Dimethyl-thiazole-5-sulfonic acid {2-[7-amino-8-(3-chloro-benzyl)-5,6,7,8-tetrahydronaphthalen-2-yloxy]-ethyl}-amide

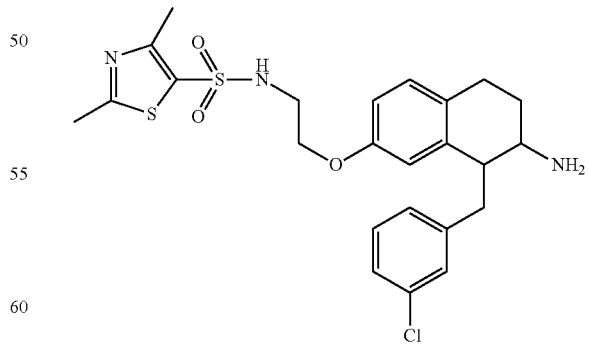

Prepared in one step from {1-(3-Chloro-benzyl)-7-[2-(2,4-dimethyl-thiazole-5-sulfonylamino)-ethoxy]-1,2,3,4-tetrahydro-naphthalen-2-yl}-carbamic acid ethyl ester (example 49) in analogy to example 48.

ESI-MS [M+H$^+$]+=506 Calculated for C$_{24}$H$_{28}$ClN$_3$O$_3$S$_2$=505

Example 58

2-Methyl-3H-imidazole-4-sulfonic acid {2-[7-amino-8-(3-chloro-benzyl)-5,6,7,8-tetrahydronaphthalen-2-yloxy]-ethyl}-amide

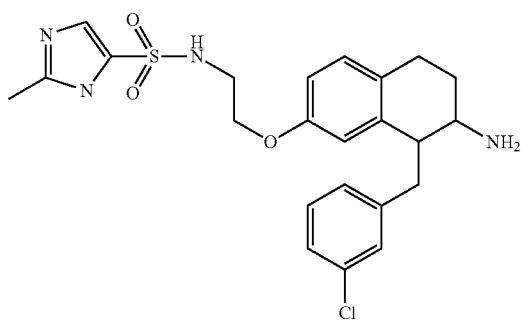 [SMILES: Cc1ncc(S(=O)(=O)NCCOc2ccc3c(c2)C(Cc2cccc(Cl)c2)C(N)CC3)[nH]1]

Prepared in one step from {1-(3-Chloro-benzyl)-7-[2-(2-methyl-3H-imidazole-4-sulfonylamino)-ethoxy]-1,2,3,4-tetrahydro-naphthalen-2-yl}-carbamic acid ethyl ester (example 52) in analogy to example 48.

ESI-MS [M+H$^+$]=475 Calculated for C$_{23}$H$_{27}$ClN$_4$O$_3$S=474

Example 59

5-Chloro-thiophene-2-sulfonic acid {2-[7-amino-8-(3-chloro-benzyl)-5,6,7,8-tetrahydronaphthalen-2-yloxy]-ethyl}-amide

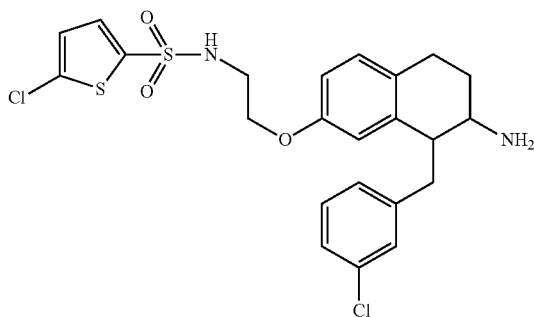 [SMILES: NC1CCc2ccc(OCCNS(=O)(=O)c3ccc(Cl)s3)cc2C1Cc1cccc(Cl)c1]

Prepared in one step from {1-(3-chloro-benzyl)-7-[2-(5-chloro-thiophene-2-sulfonylamino)ethoxy]-1,2,3,4-tetrahydro-naphthalen-2-yl}-carbamic acid ethyl ester (example 51) in analogy to example 48.

ESI-MS [M+H$^+$]=511 Calculated for C$_{23}$H$_{24}$Cl$_2$N$_2$O$_3$S$_2$=510

Example 60

{1-(3-Chloro-benzyl)-7-[2-(2,5-dimethyl-thiophene-3-sulfonylamino)-ethoxy]-1,2,3,4-tetrahydro-naphthalen-2-yl}-carbamic acid ethyl ester

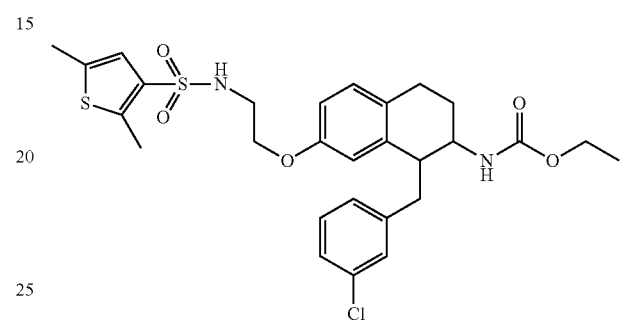

Prepared in two steps from 7-(2-tert-butoxycarbonylamino-ethoxy)-1-(3-chloro-benzyl)-1,2,3,4-tetrahydronaphthalen-2-yl]-carbamic acid ethyl ester in analogy to example 46 using 2,5-Dimethyl-thiophene-3-sulfonyl chloride.

ESI-MS [M+H$^+$]=577 Calculated for C$_{28}$H$_{33}$ClN$_2$O$_5$S$_2$=576

Example 61

{1-(3-Chloro-benzyl)-7-[2-(1-ethyl-1H-pyrazole-4-sulfonylamino)-ethoxy]-1,2,3,4-tetrahydro-naphthalen-2-yl}-carbamic acid ethyl ester

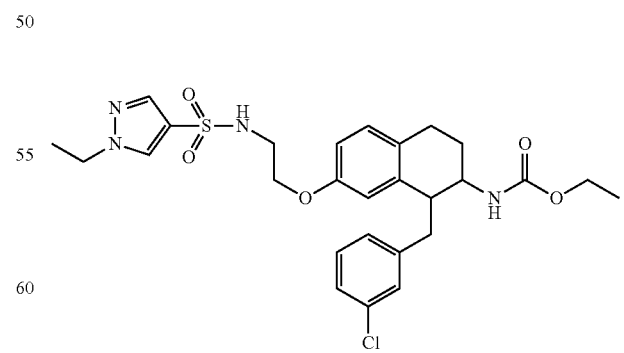

Prepared in two steps from 7-(2-tert-butoxycarbonylamino-ethoxy)-1-(3-chloro-benzyl)-1,2,3,4-tetrahydro-naphthalen-2-yl]-carbamic acid ethyl ester in analogy to example 46 using 1-Ethyl-1H-pyrazole-4-sulfonyl chloride.
ESI-MS [M+H$^+$]=561 Calculated for C$_{27}$H$_{33}$ClN$_4$O$_5$S=560

Example 62

{1-(2,4-Dichloro-benzyl)-7-[2-(1-methyl-1H-pyrazole-4-sulfonylamino)-ethoxy]-1,2,3,4-tetrahydro-naphthalen-2-yl}-carbamic acid ethyl ester

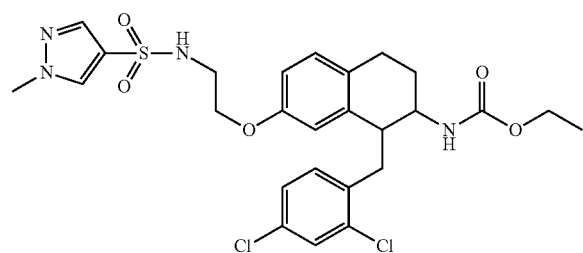 [SMILES: CCOC(=O)NC1CCc2ccc(OCCNS(=O)(=O)c3cnn(C)c3)cc2C1Cc1ccc(Cl)cc1Cl]

Prepared as described for example 46 using 1-bromomethyl-2,4-dichloro-benzene in place of 4-(bromomethyl)-3-chlorobenzene.

ESI-MS [M+H$^+$]=581 Calculated for C$_{26}$H$_{30}$Cl$_2$N$_4$O$_5$S=580

Example 63

{1-(2,4-Dichloro-benzyl)-7-[2-(thiophene-2-sulfonylamino)-ethoxy]-1,2,3,4-tetrahydronaphthalen-2-yl}-carbamic acid ethyl ester

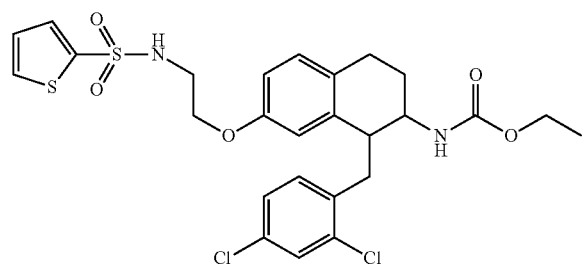 [SMILES: CCOC(=O)NC1CCc2ccc(OCCNS(=O)(=O)c3cccs3)cc2C1Cc1ccc(Cl)cc1Cl]

Prepared as described for example 62 using thiophene-2-sulfonyl chloride in place of 1-methyl-1H-pyrazole-4-sulfonyl chloride.

ESI-MS [M+H$^+$]=583 Calculated for C$_{26}$H$_{28}$Cl$_2$N$_4$O$_5$S$_2$=582

Example 64

{1-(2,4-Dichloro-benzyl)-7-[2-(5-methyl-thiophene-2-sulfonylamino)-ethoxy]-1,2,3,4-tetrahydro-naphthalen-2-yl}-carbamic acid ethyl ester

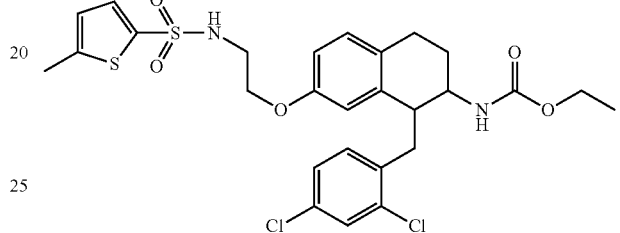

Prepared as described for example 62 using 5-methyl-thiophene-2-sulfonyl chloride in place of 1-Methyl-1H-pyrazole-4-sulfonyl chloride.

ESI-MS [M+H$^+$]=597 Calculated for C$_{27}$H$_{30}$Cl$_2$N$_2$O$_5$S$_2$=596

Example 65

[1-(3-Chloro-benzyl)-7-(2-ethanesulfonylamino-ethoxy)-1,2,3,4-tetrahydro-naphthalen-2-yl]-carbamic acid ethyl ester

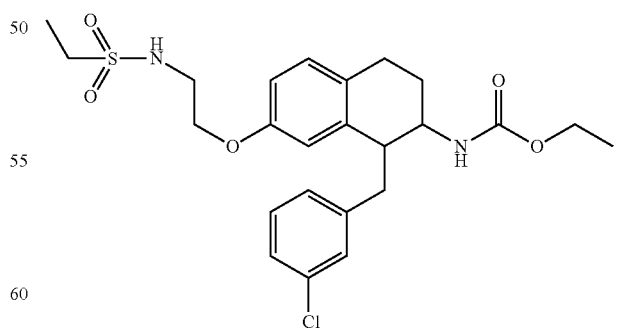

Prepared in two steps from 7-(2-tert-butoxycarbonylamino-ethoxy)-1-(3-chloro-benzyl)-1,2,3,4-tetrahydro-naphthalen-2-yl]-carbamic acid ethyl ester in analogy to example 46 using ethane-sulfonyl chloride.

ESI-MS [M+H⁺]+=495 Calculated for C$_{24}$H$_{31}$ClN$_2$O$_5$S=494

Example 66

1-Ethyl-1H-pyrazole-4-sulfonic acid {2-[7-amino-8-(3-chloro-benzyl)-5,6,7,8-tetrahydronaphthalen-2-yloxy]-ethyl}-amide hydrochloride

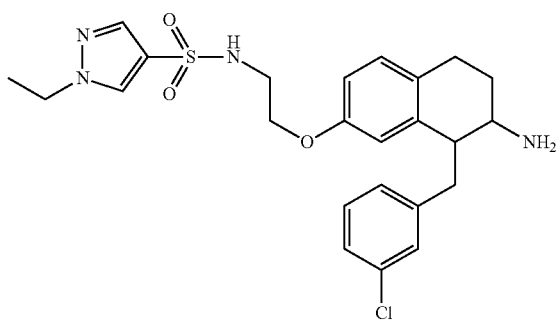 [SMILES: CCn1cc(S(=O)(=O)NCCOc2ccc3c(c2)C(Cc2cccc(Cl)c2)C(N)CC3)cn1]

Prepared in one step from {1-(3-chloro-benzyl)-7-[2-(1-ethyl-1H-pyrazole-4-sulfonylamino)-ethoxy]-1,2,3,4-tetrahydro-naphthalen-2-yl}-carbamic acid ethyl ester (example 61) in analogy to example 48. ESI-MS [M+H⁺]=489 Calculated for C$_{24}$H$_{29}$ClN$_4$O$_3$S=488

Example 67

4-Methyl-thiophene-2-sulfonic acid {2-[7-amino-8-(3-chloro-benzyl)-5,6,7,8-tetrahydronaphthalen-2-yloxy]-ethyl}-amide hydrochloride

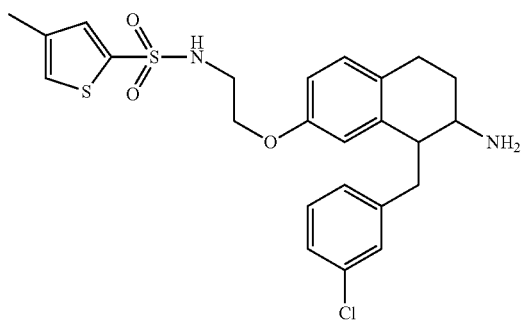 [SMILES: Cc1csc(S(=O)(=O)NCCOc2ccc3c(c2)C(Cc2cccc(Cl)c2)C(N)CC3)c1]

Prepared in one step from {1-(3-chloro-benzyl)-7-[2-(2-methyl-3H-imidazole-4-sulfonylamino)-ethoxy]-1,2,3,4-tetrahydro-naphthalen-2-yl}-carbamic acid ethyl ester (example 53) in analogy to example 48.

ESI-MS [M+H⁺]=491 Calculated for C$_{24}$H$_{27}$ClN$_2$O$_3$S$_2$=490

Example 68

5-Methyl-thiophene-2-sulfonic acid {2-[7-amino-8-(3-chloro-benzyl)-5,6,7,8-tetrahydronaphthalen-2-yloxy]-ethyl}-amide hydrochloride

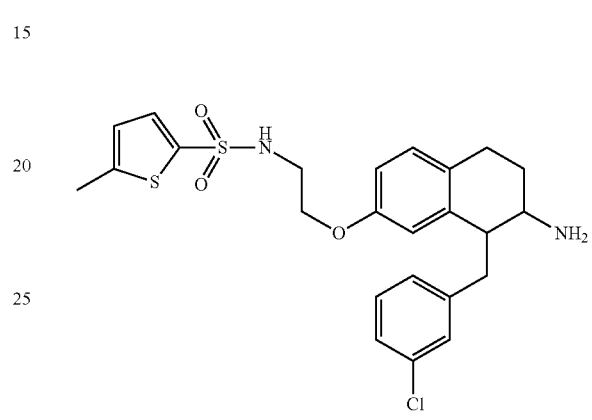

Prepared in one step from {1-(3-chloro-benzyl)-7-[2-(5-methyl-thiophene-2-sulfonylamino)ethoxy]-1,2,3,4-tetrahydro-naphthalen-2-yl}-carbamic acid ethyl ester (example 53) in analogy to example 48.

ESI-MS [M+H⁺]=491 Calculated for C$_{24}$H$_{27}$ClN$_2$O$_3$S$_2$=490

Example 69

2,5-Dimethyl-thiophene-3-sulfonic acid {2-[7-amino-8-(3-chloro-benzyl)-5,6,7,8-tetrahydronaphthalen-2-yloxy]-ethyl}-amide hydrochloride

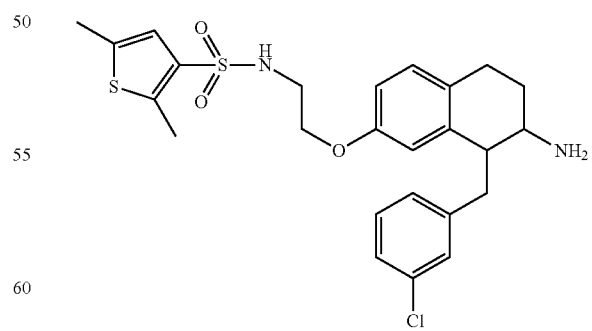

Prepared in one step from {1-(3-Chloro-benzyl)-7-[2-(2,5-dimethyl-thiophene-3-sulfonylamino)-ethoxy]-1,2,3,4-tetrahydro-naphthalen-2-yl}-carbamic acid ethyl ester (example 60) in analogy to example 48.

ESI-MS [M+H⁺]+=505 Calculated for C$_{25}$H$_{29}$ClN$_2$O$_3$S$_2$=504

Example 70

Ethanesulfonic acid {2-[7-amino-8-(3-chloro-benzyl)-5,6,7,8-tetrahydro-naphthalen-2-yloxy]-ethyl}-amide hydrochloride

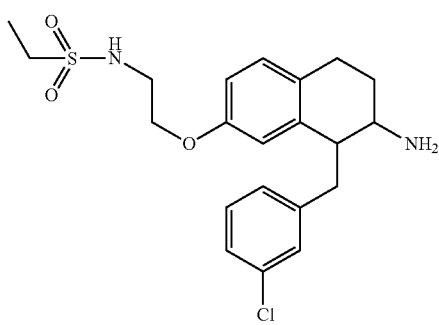 [SMILES: CCS(=O)(=O)NCCOc1ccc2c(c1)C(Cc1cccc(Cl)c1)C(N)CC2]

Prepared in one step from [1-(3-chloro-benzyl)-7-(2-ethanesulfonylamino-ethoxy)-1,2,3,4-tetrahydro-naphthalen-2-yl]-carbamic acid ethyl ester (example 65) in analogy to example 48.

ESI-MS [M+H⁺]=423 Calculated for C$_{21}$H$_{27}$ClN$_2$O$_3$S=422

Example 71

1-Methyl-1H-pyrazole-4-sulfonic acid {2-[7-amino-8-(2,4-dichloro-benzyl)-5,6,7,8-tetrahydro-naphthalen-2-yloxy]-ethyl}-amide hydrochloride

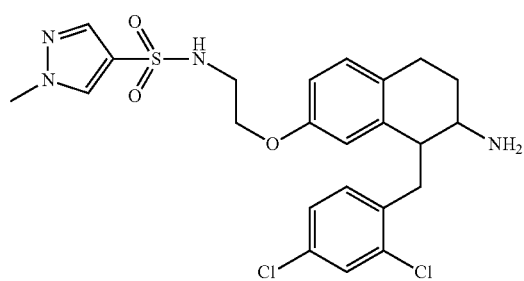 [SMILES: Cn1cc(S(=O)(=O)NCCOc2ccc3c(c2)C(Cc2ccc(Cl)cc2Cl)C(N)CC3)cn1]

Prepared in one step from {1-(2,4-dichloro-benzyl)-7-[2-(1-methyl-1H-pyrazole-4-sulfonylamino)-ethoxy]-1,2,3,4-tetrahydro-naphthalen-2-yl}-carbamic acid ethyl ester (example 62) in analogy to example 48.

ESI-MS [M+H⁺]=509 Calculated for C$_{23}$H$_{26}$Cl$_2$N$_4$O$_3$S=508

Example 72

Thiophene-2-sulfonic acid {2-[7-amino-8-(2,4-dichloro-benzyl)-5,6,7,8-tetrahydronaphthalen-2-yloxy]-ethyl}-amide hydrochloride

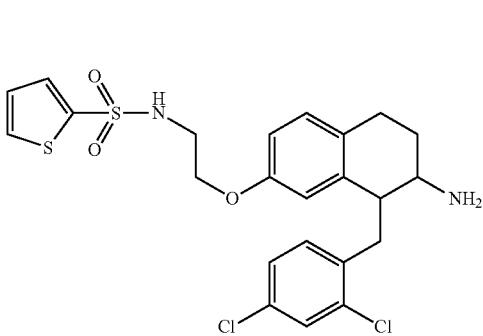 [SMILES: NC1CCc2ccc(OCCNS(=O)(=O)c3cccs3)cc2C1Cc1ccc(Cl)cc1Cl]

Prepared in one step from {1-(2,4-dichloro-benzyl)-7-[2-(thiophene-2-sulfonylamino)ethoxy]-1,2,3,4-tetrahydro-naphthalen-2-yl}-carbamic acid ethyl ester (example 63) in analogy to example 48.

ESI-MS [M+H⁺]=511 Calculated for C$_{23}$H$_{24}$Cl$_2$N$_2$O$_3$S$_2$=510

Example 73

5-Methyl-thiophene-2-sulfonic acid {2-[7-amino-8-(2,4-dichloro-benzyl)-5,6,7,8-tetrahydronaphthalen-2-yloxy]-ethyl}-amide hydrochloride

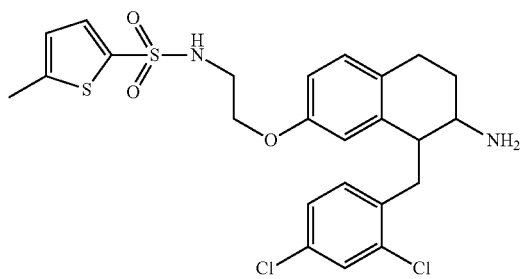 [SMILES: Cc1ccc(S(=O)(=O)NCCOc2ccc3c(c2)C(Cc2ccc(Cl)cc2Cl)C(N)CC3)s1]

Prepared in one step from {1-(2,4-dichloro-benzyl)-7-[2-(5-methyl-thiophene-2-sulfonylamino)-ethoxy]-1,2,3,4-tetrahydro-naphthalen-2-yl}-carbamic acid ethyl ester (example 64) in analogy to example 48.

ESI-MS [M+H$^+$]=525 Calculated for C$_{24}$H$_{26}$Cl$_2$N$_2$O$_3$S$_2$=524

Example 74

{1-(2,4-Dichloro-benzyl)-7-[2-(propane-1-sulfonylamino)-ethoxy]-1,2,3,4-tetrahydronaphthalen-2-yl}-carbamic acid ethyl ester

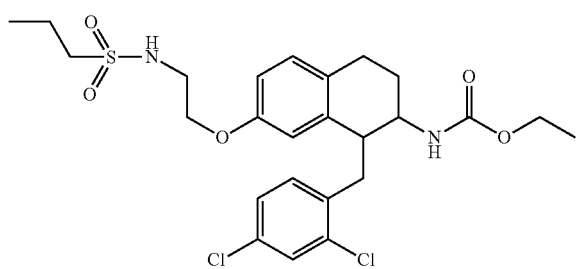 [SMILES: CCCS(=O)(=O)NCCOc1ccc2c(c1)C(Cc1ccc(Cl)cc1Cl)C(NC(=O)OCC)CC2]

Prepared as described for example 62 using propane-1-sulfonyl chloride in place of 1-methyl-1H-pyrazole-4-sulfonyl chloride.

ESI-MS [M+H$^+$]=543 Calculated for C$_{25}$H$_{32}$Cl$_2$N$_2$O$_5$S=542

Example 75

Propane-1-sulfonic acid {2-[7-amino-8-(2,4-dichloro-benzyl)-5,6,7,8-tetrahydronaphthalen-2-yloxy]-ethyl}-amide hydrochloride

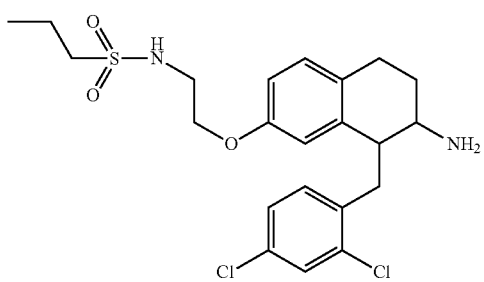 [SMILES: CCCS(=O)(=O)NCCOc1ccc2c(c1)C(Cc1ccc(Cl)cc1Cl)C(N)CC2]

Prepared in one step from {1-(2,4-dichloro-benzyl)-7-[2-(propane-1-sulfonylamino)ethoxy]-1,2,3,4-tetrahydro-naphthalen-2-yl}-carbamic acid ethyl ester (example 74) in analogy to example 48.

ESI-MS [M+H$^+$]=471 Calculated for C$_{22}$H$_{28}$Cl$_2$N$_2$O$_3$S=470

Example 76

(1-(4-Chloro-benzyl)-7-{2-[methyl-(propane-1-sulfonyl)-amino]-ethoxy}-1,2,3,4-tetrahydronaphthalen-2-yl)-carbamic acid ethyl ester

76.1 2-(N-methylpropylsulfonamido)ethyl propane-1-sulfonate

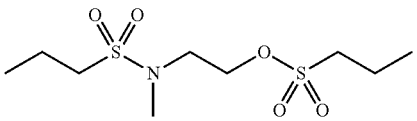 [SMILES: CCCS(=O)(=O)OCCN(C)S(=O)(=O)CCC]

To a cooled solution (0-5° C.) of 2-(methylamino)ethanol (8.56 ml, 107 mmol) in 100 ml DCM was added dropwise a solution of propane-1-sulfonyl chloride (13.1 ml, 117 mmol) in 50 ml DCM over an 1 h period. The resulting mixture was stirred at room temperature over night. Water and 10% citric acid were added and then was extracted with DCM, dried over MgSO$_4$, filtrated and evaporated to obtain a yellow/orange oil. (13.6 g) Chromatography afforded 2.75 g of product.

76.2 (1-(4-Chloro-benzyl)-7-{2-[methyl-(propane-1-sulfonyl)-amino]-ethoxy}-1,2,3,4-tetrahydro-naphthalen-2-yl)-carbamic acid ethyl ester

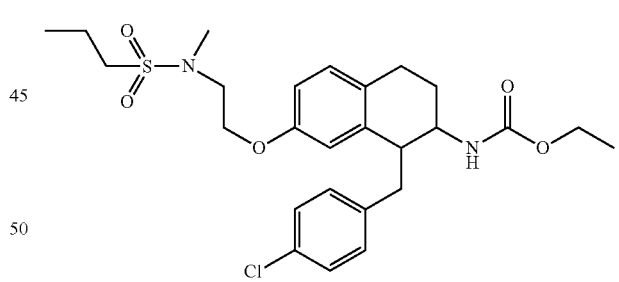

A solution of ethyl 1-(4-chlorobenzyl)-7-hydroxy-1,2,3,4-tetrahydronaphthalen-2-ylcarbamate (0.128 g, 0.355 mmol) in DMF under N$_2$ was treated with sodium hydride (0.014 g, 0.568 mmol) and the reaction was stirred for 30 minutes at room temperature. A solution of 2-(N-methylpropylsulfonamido)ethyl propane-1-sulfonate (0.102 g, 0.355 mmol) (see step 1) in DMF was added and the reaction mixture was stirred at ambient temperature over night. The mixture was portioned between ethyl acetate and water. The organic layer was washed with water, dried (MgSO$_4$), filtrated and evaporated to afford brown/white crystals. After addition of a few drops of ethyl acetate/cyclohexane (1:4) a white precipitate formed. Yield 43 mg ESI-MS [M+H$^+$]=523 Calculated for C$_{26}$H$_{35}$ClN$_2$O$_5$S=522

Example 77

Propane-1-sulfonic acid {2-[7-amino-8-(4-chloro-benzyl)-5,6,7,8-tetrahydro-naphthalen-2-yloxy]-ethyl}-methyl-amide hydrochloride

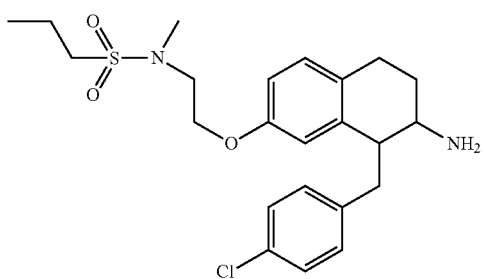 [SMILES: CCCS(=O)(=O)N(C)CCOc1ccc2c(c1)C(Cc1ccc(Cl)cc1)C(N)CC2]

Prepared in one step from (1-(4-chloro-benzyl)-7-{2-[methyl-(propane-1-sulfonyl)-amino]-ethoxy}-1,2,3,4-tetrahydro-naphthalen-2-yl)-carbamic acid ethyl ester (example 76) in analogy to example 48.

ESI-MS [M+H$^+$]=451 Calculated for C$_{23}$H$_{31}$ClN$_2$O$_3$S=450

Example 78

(1-(3-Chloro-benzyl)-7-{2-[methyl-(propane-1-sulfonyl)-amino]-ethoxy}-1,2,3,4-tetrahydronaphthalen-2-yl)-carbamic acid ethyl ester

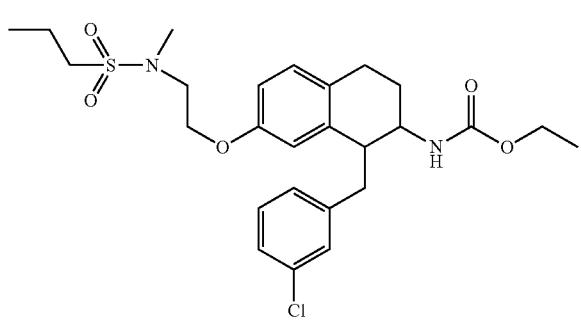 [SMILES: CCCS(=O)(=O)N(C)CCOc1ccc2c(c1)C(Cc1cccc(Cl)c1)C(NC(=O)OCC)CC2]

Prepared from [1-(3-chloro-benzyl)-7-hydroxy-1,2,3,4-tetrahydro-naphthalen-2-yl]-carbamic acid ethyl ester as described example 77.

ESI-MS [M+H$^+$]=523 Calculated for C$_{26}$H$_{35}$ClN$_2$O$_5$S=522

Example 79

Propane-1-sulfonic acid {2-[7-amino-8-(3-chloro-benzyl)-5,6,7,8-tetrahydro naphthalen-2-yloxy]-ethyl}-methyl-amide hydrochloride

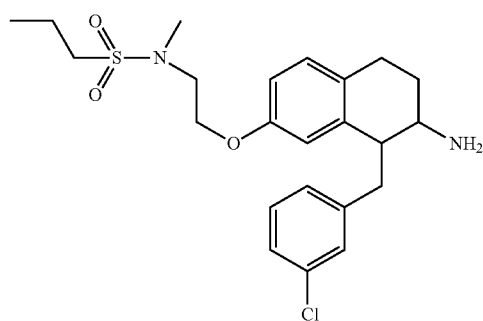 [SMILES: CCCS(=O)(=O)N(C)CCOc1ccc2c(c1)C(Cc1cccc(Cl)c1)C(N)CC2]

Prepared in one step from (1-(3-chloro-benzyl)-7-{2-[methyl-(propane-1-sulfonyl)-amino]-ethoxy}-1,2,3,4-tetrahydro-naphthalen-2-yl)-carbamic acid ethyl ester (example 78) in analogy to example 48.

ESI-MS [M+H$^+$]=451 Calculated for C$_{23}$H$_{31}$ClN$_2$O$_3$S=450

Example 80

{1-(3-Chloro-benzyl)-7-[2-(1-methyl-1H-imidazole-4-sulfonylamino)-ethoxy]-1,2,3,4-tetrahydro-naphthalen-2-yl}-carbamic acid ethyl ester

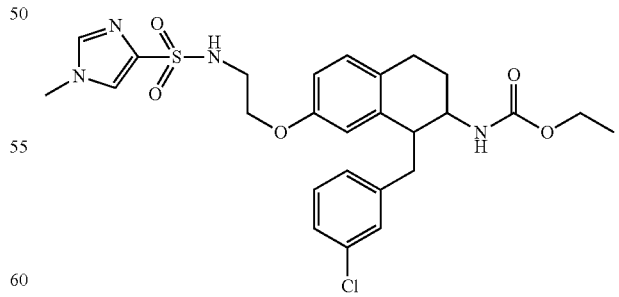

Prepared in two steps from 7-(2-tert-butoxycarbonylamino-ethoxy)-1-(3-chloro-benzyl)-1,2,3,4-tetrahydro-naphthalen-2-yl]carbamic acid ethyl ester in analogy to example 46 using 1-Methyl-1H-imidazole-4-sulfonyl chloride.

ESI-MS [M+H⁺]=547 Calculated for C$_{26}$H$_{31}$ClN$_4$O$_5$S=546

Example 81

{1-(3-Chloro-benzyl)-7-[2-(1-difluoromethyl-1H-pyrazole-4-sulfonylamino)-ethoxy]-1,2,3,4-tetrahydro-naphthalen-2-yl}-carbamic acid ethyl ester

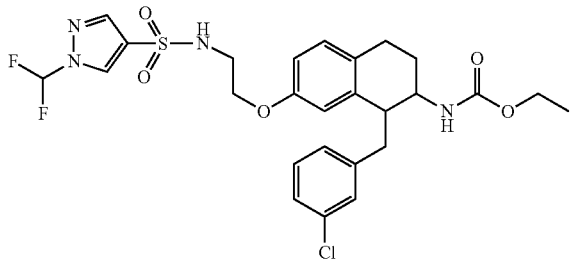 [SMILES: CCOC(=O)NC1CCc2ccc(OCCNS(=O)(=O)c3cnn(C(F)F)c3)cc2C1Cc1cccc(Cl)c1]

Prepared in two steps from 7-(2-tert-butoxycarbonylamino-ethoxy)-1-(3-chloro-benzyl)-1,2,3,4-tetrahydro-naphthalen-2-yl]-carbamic acid ethyl ester in analogy to example 46 using 1-difluoromethyl-1H-pyrazole-4-sulfonyl chloride.

ESI-MS [M+H⁺]=583 Calculated for C$_{26}$H$_{29}$CF$_2$N$_4$O$_5$S=582

Example 82

1-(3-Chloro-benzyl)-7-[(R)-1-(propane-1-sulfonyl)-pyrrolidin-2-ylmethoxy]-1,2,3,4-tetrahydro-naphthalen-2-ylamine hydrochloride 82.1 (Propane-1-sulfonic acid (R)-1-(propane-1-sulfonyl)-pyrrolidin-2-ylmethyl ester

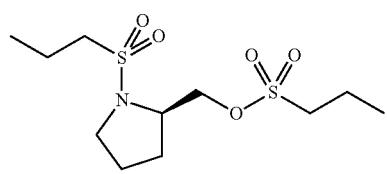 [SMILES: CCCS(=O)(=O)OC[C@H]1CCCN1S(=O)(=O)CCC]

Prepared as described for 2-(N-methylpropylsulfonamido)ethyl propane-1-sulfonate (example 76, step 1 using (R)-1-pyrrolidin-2-yl-methanol instead of 2-(methylamino)ethanol.

82.2 1-(3-Chloro-benzyl)-7-[(R)-1-(propane-1-sulfonyl)-pyrrolidin-2-ylmethoxy]-1,2,3,4-tetrahydro-naphthalen-2-ylamine hydrochloride

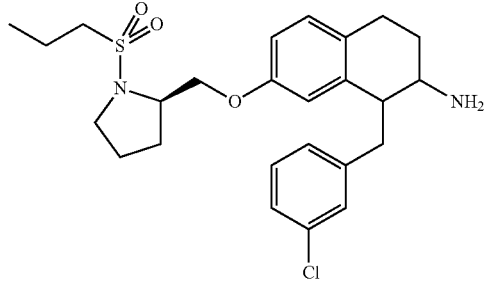 [SMILES: CCCS(=O)(=O)N1CCC[C@@H]1COc1ccc2c(c1)C(Cc1cccc(Cl)c1)C(N)CC2]

Prepared in two steps from (propane-1-sulfonic acid (R)-1-(propane-1-sulfonyl)-pyrrolidin-2-ylmethyl ester (see previous step) and ethyl 1-(4-chlorobenzyl)-7-hydroxy-1,2,3,4-tetrahydronaphthalen-2-ylcarbamate as described for example 77.

ESI-MS [M+H⁺]+=477 Calculated for C$_{25}$H$_{33}$ClN$_2$O$_3$S=476

Example 83

1-(3-Chloro-benzyl)-7-[1-(propane-1-sulfonyl)-azetidin-3-yloxy]-1,2,3,4-tetrahydronaphthalen-2-ylamine hydrochloride 83.1 1-(Propane-1-sulfonyl)-azetidin-3-ol

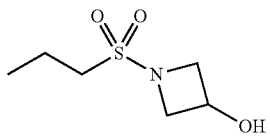

To a cooled solution (0-5° C.) of azetidin-3-ol hydrochloride (1 g, 9.13 mmol) in 10 ml dichloromethane containing diisopropyl ethyl amine (2,391 ml, 13.69 mmol) was added dropwise a solution of propane-1-sulfonyl chloride (1,126 ml, 10.04 mmol) dissolved in 5 ml dichloromethane over an 1 h period. The mixture was allowed to warm up to room temperature and was stirred over night. Citric acid (10%) was added, extracted with dichloromethane, dried over MgSO$_4$, filtered and the solvent was evaporated to obtain 597 mg of a yellow oil, which was purified by chromatography (yield 470 mg)

83.2 Methanesulfonic acid 1-(propane-1-sulfonyl)-azetidin-3-yl ester

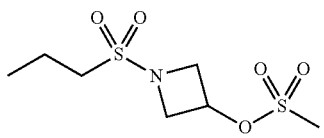

To a solution of 1-(propane-1-sulfonyl)-azetidin-3-ol (236 mg, 1.317 mmol) in pyridine was added drop wise methane sulfonyl chloride (205 µl, 2.63 mmol) at 0° C. The mixture was allowed to warm up to room temperature and was stirred for 3 h. Dichloromethane was added. The mixture was subsequently washed with water, saturated NaHCO$_3$ and brine, dried (MgSO4), and filtrated. The solvent was evaporated to obtain 293 mg of crude product which was used without further purification.

83.3 1-(3-Chloro-benzyl)-7-[1-(propane-1-sulfonyl)-azetidin-3-yloxy]-1,2,3,4-tetrahydronaphthalen-2-ylamine hydrochloride

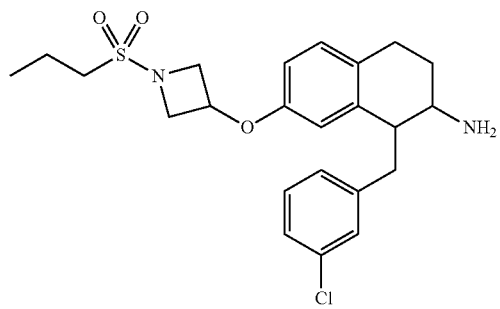 [SMILES: CCCS(=O)(=O)N1CC(Oc2ccc3c(c2)C(Cc2cccc(Cl)c2)C(N)CC3)C1]

Prepared in two steps from methanesulfonic acid 1-(propane-1-sulfonyl)-azetidin-3-yl ester (see previous step) and ethyl 1-(4-chlorobenzyl)-7-hydroxy-1,2,3,4-tetrahydronaphthalen-2-ylcarbamate as described for example 77.

ESI-MS [M+H$^+$]=449 Calculated for C$_{23}$H$_{29}$ClN$_2$O$_3$S=448

Example 84

1-(3-Chloro-benzyl)-7-(3-ethanesulfonyl-propoxy)-1,2,3,4-tetrahydro-naphthalen-2-ylamine hydrochloride

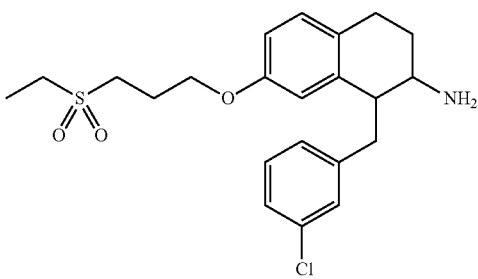 [SMILES: CCS(=O)(=O)CCCOc1ccc2c(c1)C(Cc1cccc(Cl)c1)C(N)CC2]

Prepared in two steps from 1-chloro-3-ethanesulfonyl-propane (see: Synthetic Communications, 19(9-10), 1583-91; 1989) and ethyl 1-(4-chlorobenzyl)-7-hydroxy-1,2,3,4-tetrahydronaphthalen-2-ylcarbamate in analogy to example 77.

ESI-MS [M+H$^+$]=422 Calculated for C$_{22}$H$_{28}$ClNO$_3$S=421

Example 85

Cyclohexanesulfonic acid {2-[7-amino-8-(3,4-dichloro-benzyl)-5,6,7,8-tetrahydro-naphthalen-2-yloxy]-ethyl}-amide hydrochloride

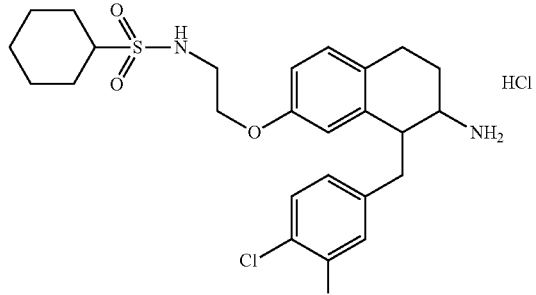

Cyclohexanesulfonic acid {2-[7-amino-8-(3,4-dichloro-benzyl)-5,6,7,8-tetrahydro-naphthalen-2-yloxy]-ethyl}-amide hydrochloride was prepared in analogy to example 3 using cyclohexyl-sulfonyl chloride in place of 1-methyl-1H-imidazole-4-sulfonyl chloride.

ESI-MS [M+H⁺]=511 Calculated for C$_{25}$H$_{32}$Cl$_2$N$_2$O$_3$S=510

Example 86

2-Trimethylsilanyl-ethanesulfonic acid {2-[7-amino-8-(3,4-dichloro-benzyl)-5,6,7,8-tetrahydro-naphthalen-2-yloxy]-ethyl}-amide hydrochloride

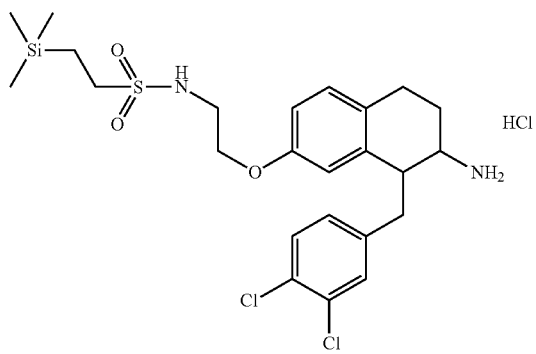 [SMILES: C[Si](C)(C)CCS(=O)(=O)NCCOc1ccc2c(c1)C(Cc1ccc(Cl)c(Cl)c1)C(N)CC2 ; Cl]

2-Trimethylsilanyl-ethanesulfonic acid {2-[7-amino-8-(3,4-dichloro-benzyl)-5,6,7,8-tetrahydro-naphthalen-2-yloxy]-ethyl}-amid hydrochloride was prepared in analogy to example 3.

ESI-MS [M+H⁺]=529 Calculated for C$_{24}$H$_{34}$Cl$_2$N$_2$O$_3$SSi=528

Example 87

N-{2-[7-Amino-8-(3,4-dichloro-benzyl)-5,6,7,8-tetrahydro-naphthalen-2-yloxy]-ethyl}-C-(5-methyl-isoxazol-3-yl)-methanesulfonamide hydrochloride

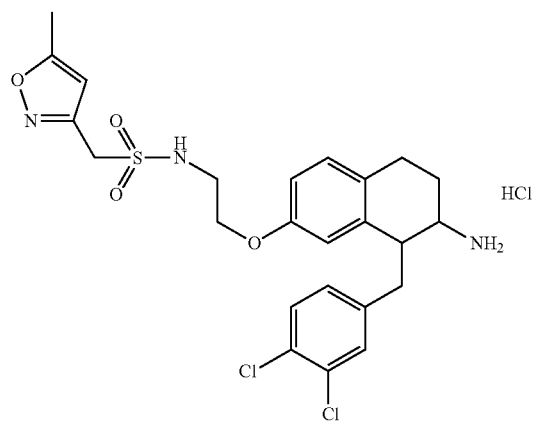 [SMILES: Cc1cc(CS(=O)(=O)NCCOc2ccc3c(c2)C(Cc2ccc(Cl)c(Cl)c2)C(N)CC3)no1 ; Cl]

N-{2-[7-Amino-8-(3,4-dichloro-benzyl)-5,6,7,8-tetrahydro-naphthalen-2-yloxy]-ethyl}-C-(5-methyl-isoxazol-3-yl)-methanesulfonamide hydrochloride was prepared in analogy to example 3.

ESI-MS [M+H⁺]=524 Calculated for C$_{24}$H$_{27}$Cl$_2$N$_3$O$_4$S=523

Example 88

Cyclobutanesulfonic acid {2-[8-(3,4-dichloro-benzyl)-7-pyrrolidin-1-yl-5,6,7,8-tetrahydronaphthalen-2-yloxy]-ethyl}-amide hydrochloride

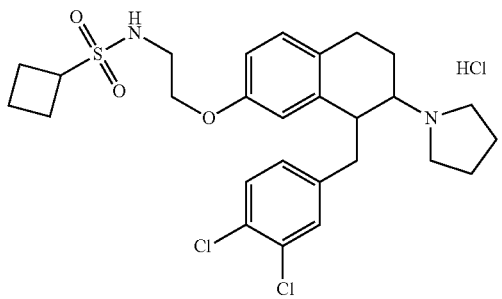 [SMILES: O=S(=O)(NCCOc1ccc2c(c1)C(Cc1ccc(Cl)c(Cl)c1)C(N1CCCC1)CC2)C1CCC1 ; Cl]

88.1 1-(1-(3,4-Dichlorobenzyl)-7-methoxy-1,2,3,4-tetrahydronaphthalen-2-yl)pyrrolidine

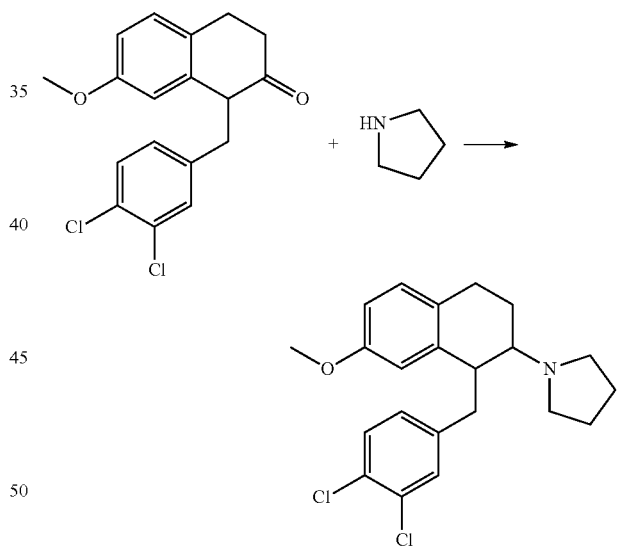

1-(3,4-Dichlorobenzyl)-7-methoxy-3,4-dihydronaphthalen-2(1H)-one (5.5 g, 16.4 mmol, example 1), pyrrolidine (1.40 g, 19.7 mmol), and p-toluenesulfonic acid monohydrate (31.0 mg, 0.164 mmol) were dissolved in toluene (100 ml) and refluxed for 2 h using a DeanStark condenser. The solvent was removed and after addition of MeOH (50 ml) and sodium cyanohydride (1.57 g, 24.6 mmol) the mixture was stirred for 4d at room temperature under nitrogen. Water was added, the organic phase separated and the aqueous phase extracted with ethyl acetate. The combined organic layers were washed with saturated NaCl solution, dried over MgSO$_4$, and concentrated to afford a residue that was purified by flash chromatography (silica gel, MeOH/CH$_2$Cl$_2$3:97→5:95). The beige solid product (1.6 g, 25%) was obtained from precipitation in ethyl acetate/diisopropylether (1:1).

88.2 8-(3,4-Dichlorobenzyl)-7-(pyrrolidin-1-yl)-5,6,7,8-tetrahydronaphthalen-2-ol

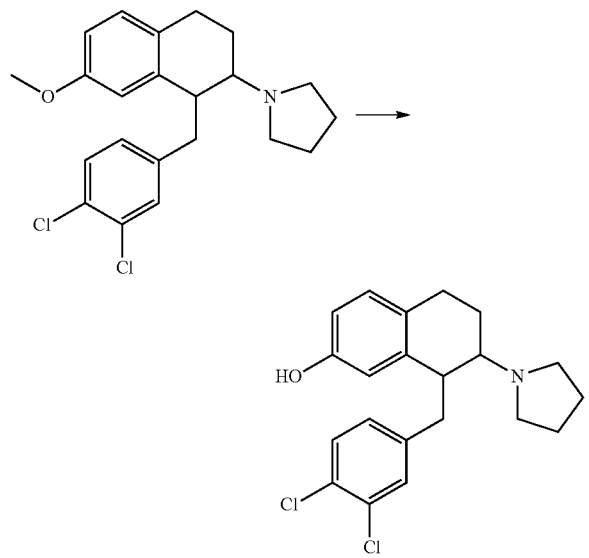

1-(1-(3,4-Dichlorobenzyl)-7-methoxy-1,2,3,4-tetrahydronaphthalen-2-yl)pyrrolidine (1.6 g, 4.10 mmol) was dissolved in CH$_2$Cl$_2$ (100 ml) and BBr$_3$ (1 molar in CH$_2$Cl$_2$, 12.3 ml, 12.3 mmol) was added at −10° C. It was stirred for 2 h after which time the temperature rose to room temperature. Ice water was added, the organic phase separated and the aqueous phase extracted with CH$_2$Cl$_2$. The combined organic layers were washed with saturated NaHCO$_3$ and NaCl solution, dried over Na$_2$SO$_4$, and concentrated to afford a residue. The beige solid product (1.2 g, 78%) was obtained from precipitation in ethyl acetate.

88.3 tert-Butyl 2-(8-(3,4-dichlorobenzyl)-7-(pyrrolidin-1-yl)-5,6,7,8-tetrahydronaphthalen-2-yloxy)ethylcarbamate

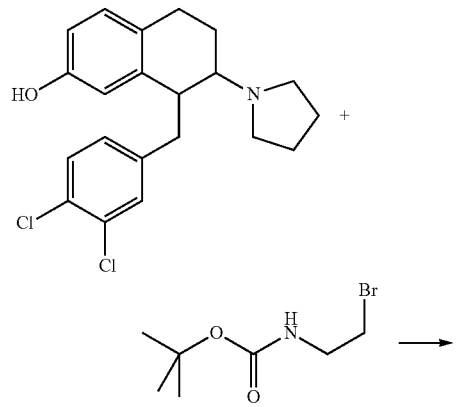

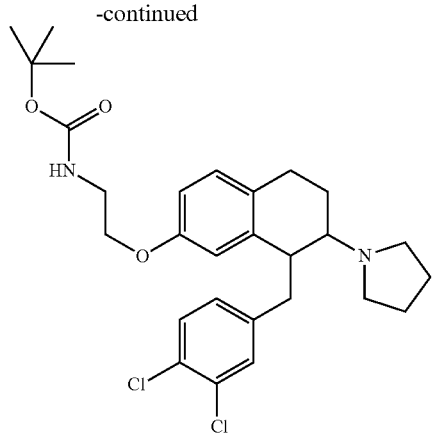

NaH in paraffin (0.278 g, 6.38 mmol, 55% in paraffin) was washed with n-hexane and suspended in DMA (30 ml). 8-(3,4-Dichlorobenzyl)-7-(pyrrolidin-1-yl)-5,6,7,8-tetrahydronaphthalen-2-ol (1.2 g, 3.19 mmol) in DMA (20 ml) was added. After stirring for 1 h at room temperature tert-butyl 2-bromoethylcarbamate (2.14 g, 6.38 mmol) was added in portions and the mixture was stirred for 48 h. Water was added and the aqueous phase was extracted with ethyl acetate. The combined organic layers were washed with saturated NaCl solution, dried over Na$_2$SO$_4$, and concentrated to afford a residue that was purified by flash chromatography (silica gel, MeOH/CH$_2$Cl$_2$ 3:97). The product (1.6 g, 97%) was obtained as a yellow oil.

88.4 2-(8-(3,4-Dichlorobenzyl)-7-(pyrrolidin-1-yl)-5,6,7,8-tetrahydronaphthalen-2-yloxy)ethanamine hydrochloride

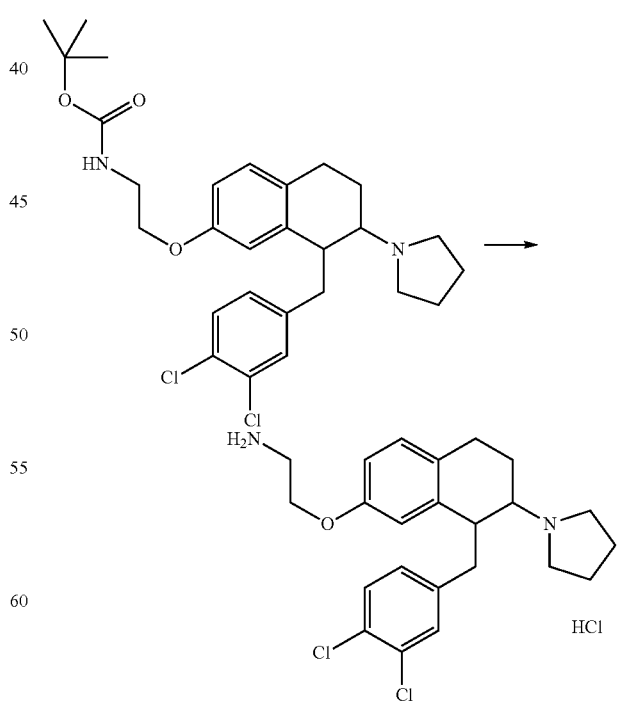

tert-Butyl 2-(8-(3,4-dichlorobenzyl)-7-(pyrrolidin-1-yl)-5,6,7,8-tetrahydronaphthalen-2-yloxy)ethylcarbamate (1.6 g, 3.08 mmol) was dissolved in CH₂Cl₂ (70 ml) and HCl in iPrOH was added. It was stirred for 14 h at room temperature after during which time the temperature rose to room temperature. The solvent was removed to obtain white salt (1.2 g, 85%).

88.5 Cyclobutanesulfonic acid {2-[8-(3,4-dichloro-benzyl)-7-pyrrolidin-1-yl-5,6,7,8-tetrahydro-naphthalen-2-yloxy]-ethyl}-amide hydrochloride

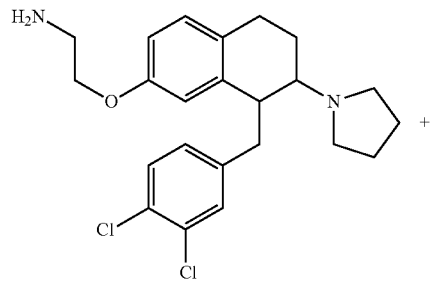

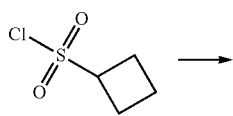

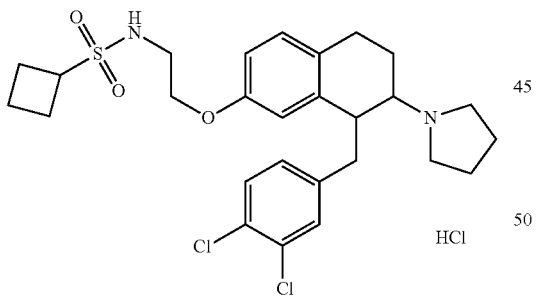

2-(8-(3,4-Dichlorobenzyl)-7-(pyrrolidin-1-yl)-5,6,7,8-tetrahydronaphthalen-2-yloxy)ethanamine (120 mg, 0.286 mmol), para-(N,N-dimethylamino) pyridine (1.40 g, 19.7 mmol), and cyclobutanesulfonyl chloride (46.5 mg, 0.30 mmol) were dissolved in CH₂Cl₂ (20 ml) and stirred for 14 h at room temperature. 0.5N HCl was added, the organic phase separated and the aqueous phase extracted with CH₂Cl₂. The combined organic layers were washed with water, NaHCO₃ solution, and saturated NaCl solution, dried over Na₂SO₄, and concentrated to afford a residue that was purified by flash chromatography (silica gel, MeOH/CH₂Cl₂ 3:97→5:95). The white solid product (164 mg, 32%) was transferred to an HCl salt and precipitated from diisopropyl ether.

ESI-MS [M+H⁺]=537 Calculated for C₂₇H₃₄Cl₂N₂O₃S=536

Example 89

1-Methyl-1H-pyrazole-4-sulfonic acid {2-[8-(3,4-dichloro-benzyl)-7-pyrrolidin-1-yl-5,6,7,8-tetrahydro-naphthalen-2-yloxy]-ethyl}-methyl-amide hydrochloride

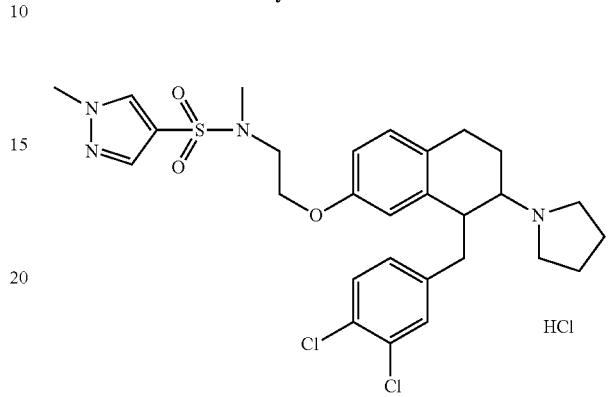

N-(2-(8-(3,4-Dichlorobenzyl)-7-(pyrrolidin-1-yl)-5,6,7,8-tetrahydronaphthalen-2-yloxy)ethyl)-1-methyl-1H-pyrazole-4-sulfonamide hydrochloride (41 mg, 0.068 mmol, Example 91, iodomethane (11.6 mg, 0.082 mmol), caesium carbonate (49.0 mg, 0.150 mmol) were dissolved in acetonitrile (3 ml) and stirred for 1 h at 100° C. in the microwave. After addition of another iodomethane (11.6 mg, 0.082 mmol) and caesium carbonate (49.0 mg, 0.150 mmol) it was stirred for another 1 h at 100° C. in the microwave. Water and CH₂Cl₂ were added, the organic phase separated and the aqueous phase extracted with CH₂Cl₂. The combined organic layers were washed with saturated NaCl solution, dried over Na₂SO₄, and concentrated to afford a residue that was purified by flash chromatography (silica gel, MeOH/CH₂Cl₂ 3:97→5:95). The white solid product (42 mg, 38%) was transferred to an HCl salt and precipitated from diisopropyl ether. ESI-MS [M+H⁺]=577

Calculated for C₂₈H₃₄Cl₂N₄O₃S=576

Example 90

Butane-1-sulfonic acid {2-[7-amino-8-(3,4-dichloro-benzyl)-5,6,7,8-tetrahydro-naphthalen-2-yloxy]-ethyl}-amide hydrochloride

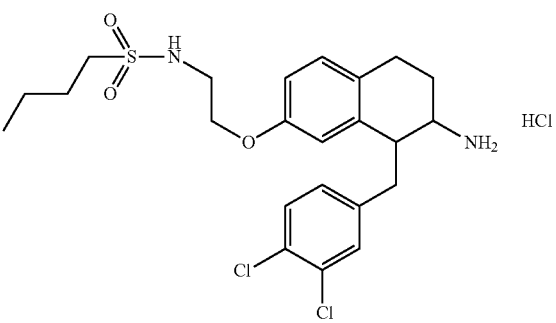 [SMILES: CCCCS(=O)(=O)NCCOc1ccc2c(c1)C(Cc1ccc(Cl)c(Cl)c1)C(N)CC2 ; Cl]

Butane-1-sulfonic acid {2-[7-amino-8-(3,4-dichloro-benzyl)-5,6,7,8-tetrahydro-naphthalen-2-yloxy]-ethyl}-amide hydrochloride was prepared in analogy to example 3.

ESI-MS [M+H$^+$]=485 Calculated for C$_{23}$H$_{30}$Cl$_2$N$_2$O$_3$S=484

Example 91

Propane-2-sulfonic acid {2-[7-amino-8-(3,4-dichloro-benzyl)-5,6,7,8-tetrahydronaphthalen-2-yloxy]-ethyl}-amide hydrochloride

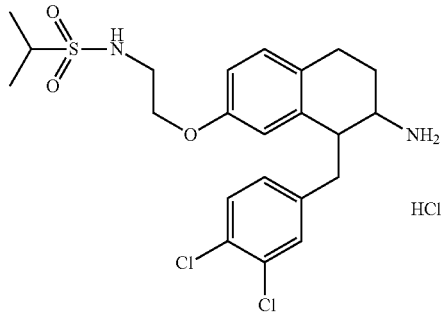 [SMILES: CC(C)S(=O)(=O)NCCOc1ccc2c(c1)C(Cc1ccc(Cl)c(Cl)c1)C(N)CC2 ; Cl]

Propane-2-sulfonic acid {2-[7-amino-8-(3,4-dichloro-benzyl)-5,6,7,8-tetrahydronaphthalen-2-yloxy]-ethyl}-amide hydrochloride was prepared in analogy to example 3.

ESI-MS [M+H$^+$]=471 Calculated for C$_{22}$H$_{28}$Cl$_2$N$_2$O$_3$S=470

Example 92

1-Methyl-1H-pyrazole-4-sulfonic acid {2-[8-(3,4-dichloro-benzyl)-7-pyrrolidin-1-yl-5,6,7,8-tetrahydro-naphthalen-2-yloxy]-ethyl}-amide hydrochloride

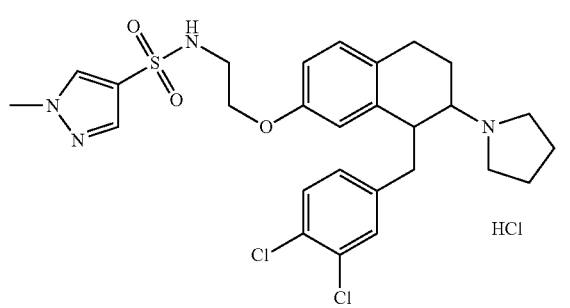 [SMILES: Cn1cc(S(=O)(=O)NCCOc2ccc3c(c2)C(Cc2ccc(Cl)c(Cl)c2)C(N2CCCC2)CC3)cn1 ; Cl]

1-Methyl-1H-pyrazole-4-sulfonic acid {2-[8-(3,4-dichloro-benzyl)-7-pyrrolidin-1-yl-5,6,7,8-tetrahydro-naphthalen-2-yloxy]-ethyl}-amide hydrochloride was prepared in analogy to example 88.

ESI-MS [M+H$^+$]=563 Calculated for C$_{27}$H$_{32}$Cl$_2$N$_4$O$_3$S=562

Example 93

2-Ethoxy-ethanesulfonic acid {2-[7-amino-8-(3,4-dichloro-benzyl)-5,6,7,8-tetrahydronaphthalen-2-yloxy]-ethyl}-amide hydrochloride

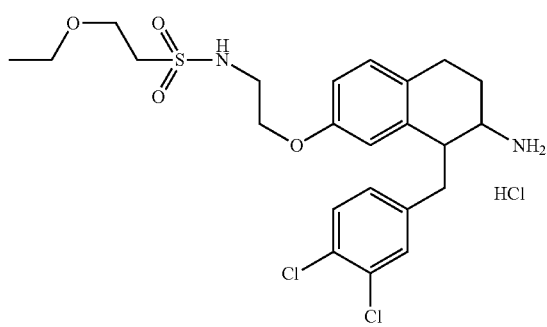 [SMILES: CCOCCS(=O)(=O)NCCOc1ccc2c(c1)C(Cc1ccc(Cl)c(Cl)c1)C(N)CC2 ; Cl]

2-Ethoxy-ethanesulfonic acid {2-[7-amino-8-(3,4-dichloro-benzyl)-5,6,7,8-tetrahydronaphthalen-2-yloxy]-ethyl}-amide hydrochloride was prepared in analogy to example 3.

ESI-MS [M+H$^+$]=501 Calculated for C$_{23}$H$_{30}$Cl$_2$N$_2$O$_4$S=500

Example 94

Cyclobutanesulfonic acid {2-[8-(3,4-dichloro-benzyl)-7-pyrrolidin-1-yl-5,6,7,8-tetrahydronaphthalen-2-yloxy]-ethyl}-methyl-amide hydrochloride

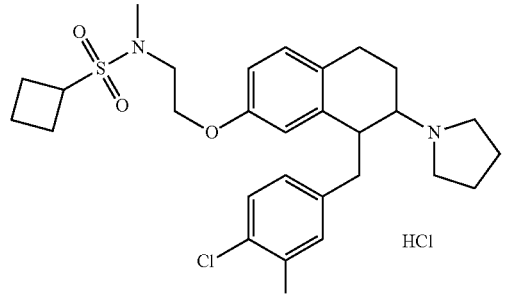

Cyclobutanesulfonic acid {2-[8-(3,4-dichloro-benzyl)-7-pyrrolidin-1-yl-5,6,7,8-tetrahydronaphthalen-2-yloxy]-ethyl}-methyl-amide hydrochloride was prepared from N-(2-(8-(3,4-dichlorobenzyl)-7-(pyrrolidin-1-yl)-5,6,7,8-tetrahydronaphthalen-2-yloxy)ethyl) cyclobutanesulfonamide hydrochloride (example 88) in analogy to example 89.

ESI-MS [M+H⁺]=551 Calculated for C$_{28}$H$_{36}$Cl$_2$N$_2$O$_3$S=550

Example 95

N-{2-[7-Amino-8-(3,4-dichloro-benzyl)-5,6,7,8-tetrahydro-naphthalen-2-yloxy]-ethyl}-C-cyclopropyl-methanesulfonamide hydrochloride

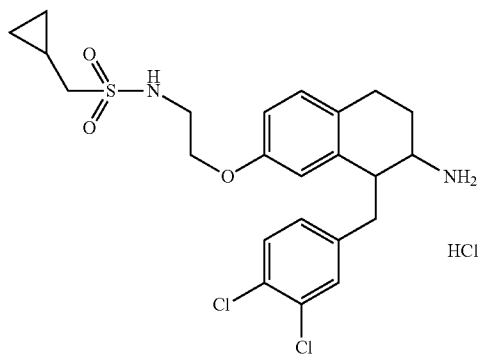 [SMILES: NC1CCc2ccc(OCCNS(=O)(=O)CC3CC3)cc2C1Cc1ccc(Cl)c(Cl)c1 ; Cl]

N-{2-[7-Amino-8-(3,4-dichloro-benzyl)-5,6,7,8-tetrahydro-naphthalen-2-yloxy]-ethyl}-C-cyclopropyl-methanesulfonamide hydrochloride was prepared in analogy to example 3.

ESI-MS [M+H⁺]=483 Calculated for C$_{23}$H$_{28}$Cl$_2$N$_2$O$_3$S=482

Example 96

Propane-1-sulfonic acid {2-[7-amino-8-(4-methoxy-benzyl)-5,6,7,8-tetrahydro-naphthalen-2-yloxy]-ethyl}-amide hydrochloride

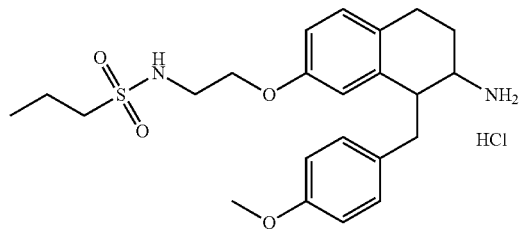 [SMILES: CCCS(=O)(=O)NCCOc1ccc2c(c1)C(Cc1ccc(OC)cc1)C(N)CC2 ; Cl]

Propane-1-sulfonic acid {2-[7-amino-8-(4-methoxy-benzyl)-5,6,7,8-tetrahydro-naphthalen-2-yloxy]-ethyl}-amide hydrochloride was prepared in analogy to example 3.

ESI-MS [M+H⁺]=433 Calculated for C$_{23}$H$_{32}$N$_2$O$_4$S=432

Example 97

N-[2-(7-Amino-8-benzyl-5,6,7,8-tetrahydro-naphthalen-2-yloxy)-ethyl]-methanesulfonamide hydrochloride

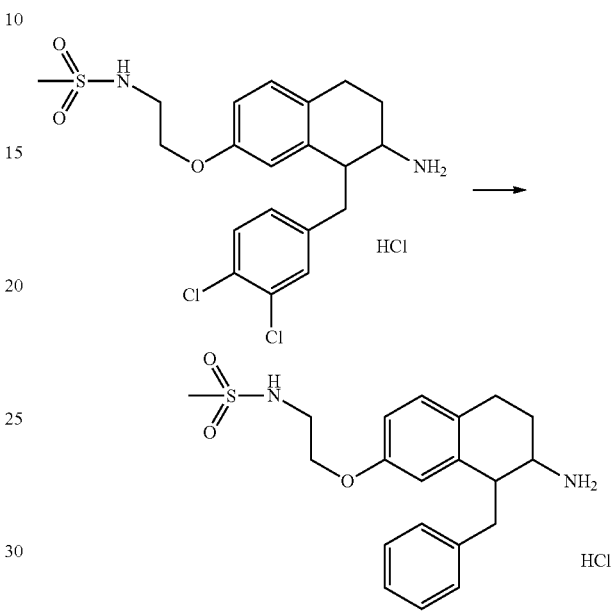

N-(2-(7-Amino-8-(3,4-dichlorobenzyl)-5,6,7,8-tetrahydronaphthalen-2-yloxy)ethylmethanesulfonamide hydrochloride (50.0 mg, 0.104 mmol), Pd—C 10% (1.10 mg), and hydrazine monohydrate (522 mg, 10.4 mmol) were suspended in ethanol (5 ml) and stirred for 4 h under reflux. Water and CH$_2$Cl$_2$ were added, the mixture filtered, and the filtrate was extracted with CH$_2$Cl$_2$. The combined organic layers were washed with water, saturated NaCl solution, dried over Na$_2$SO$_4$, and concentrated to afford a residue that was purified by precipitation from diisopropylether. The residue was transferred to an HCl salt and finally gave the product as a white solid (31 mg, 72%).

ESI-MS [M+H⁺]=375 Calculated for C$_{20}$H$_{26}$N$_2$O$_3$S=374

Example 98

1-Methyl-1H-imidazole-4-sulfonic acid [2-(7-amino-8-benzyl-5,6,7,8-tetrahydronaphthalen-2-yloxy)-ethyl]-methyl-amide hydrochloride

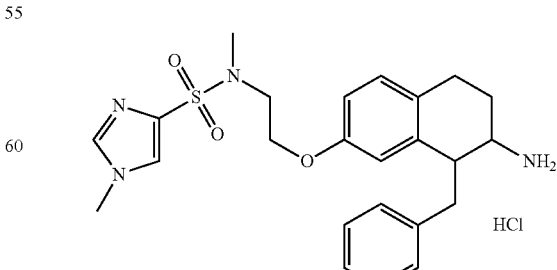

1-Methyl-1H-imidazole-4-sulfonic acid [2-(7-amino-8-benzyl-5,6,7,8-tetrahydronaphthalen-2-yloxy)-ethyl]-methyl-amide hydrochloride was prepared in analogy to example 3 and 89.

ESI-MS [M+H$^+$]=455 Calculated for $C_{24}H_{30}N_4O_3S$=454

Example 99

N-[2-(7-Amino-8-benzyl-5,6,7,8-tetrahydro-naphthalen-2-yloxy)-ethyl]-benzenesulfonamide hydrochloride

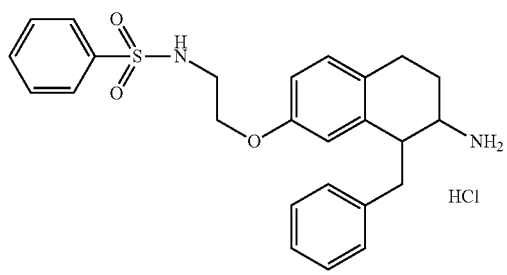 [SMILES: NC1CCc2ccc(OCCNS(=O)(=O)c3ccccc3)cc2C1Cc1ccccc1 ; Cl]

N-[2-(7-Amino-8-benzyl-5,6,7,8-tetrahydro-naphthalen-2-yloxy)-ethyl]-benzenesulfonamide hydrochloride was prepared from N-{2-[7-Amino-8-(3,4-dichloro-benzyl)-5,6,7,8-tetrahydro-naphthalen-2-yloxy]-ethyl}-benzenesulfonamide hydrochloride (example 16) in analogy to example 3 and 97.

ESI-MS [M+H$^+$]=437 Calculated for $C_{25}H_{28}N_2O_3S$=436

Example 100

3,3,3-Trifluoro-propane-1-sulfonic acid [2-(7-amino-8-benzyl-5,6,7,8-tetrahydronaphthalen-2-yloxy)-ethyl]amide hydrochloride

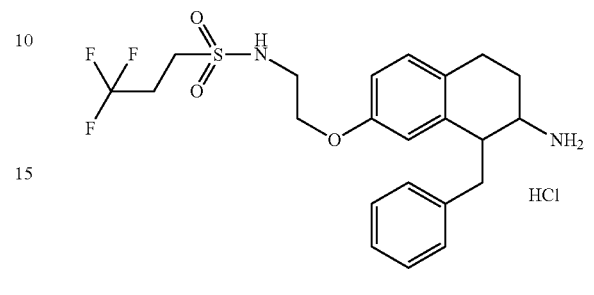

3,3,3-Trifluoro-propane-1-sulfonic acid [2-(7-amino-8-benzyl-5,6,7,8-tetrahydronaphthalen-2-yloxy)-ethyl]-amide hydrochloride was prepared in analogy to example 3 and 97.

ESI-MS [M+H$^+$]=457 Calculated for $C_{22}H_{27}F_3N_2O_3S$=456

Example 101

1-Methyl-1H-imidazole-4-sulfonic acid [2-(8-benzyl-7-pyrrolidin-1-yl-5,6,7,8-tetrahydronaphthalen-2-yloxy)-ethyl]-methyl-amide hydrochloride

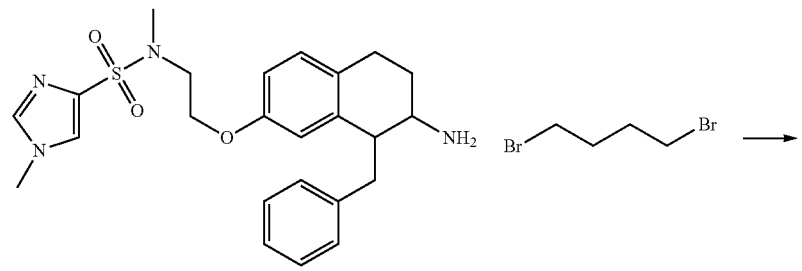

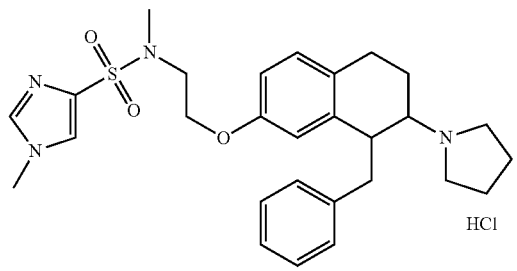

N-(2-{[7-Amino-8-benzyl-5,6,7,8-tetrahydronaphthalen-2-yl]oxy}ethyl)-N,1-dimethyl-1H-imidazole-4-sulfonamide hydrochloride (98), 1,4-dibromobutane (49.9 mg, 0.231 mmol), and triethylamine (31.2 mg, 0.308 mmol) were dissolved in acetonitrile (3 ml) and stirred for 2 h at 130° C. in the microwave. Water and ethyl acetate were added and the organic phase was separated. After extraction of the aqueous phase with ethylacetate the combined organic layers were washed with saturated NaCl solution, dried over $Na_2SO_4$, and concentrated to afford a residue a residue that was purified by flash chromatography (silica gel, $MeOH/CH_2Cl_2$ 5:95). The residue was transferred to an HCl salt and finally gave the product as a white solid (8.5 mg, 10%) after precipitation from diisopropylether.

ESI-MS $[M+H^+]+=509$ Calculated for $C_{28}H_{36}N_4O_3S=508$

Example 102

Cyclopropanesulfonic acid [2-(7-amino-8-benzyl-5,6,7,8-tetrahydro-naphthalen-2-yloxy)ethyl]-amide hydrochloride

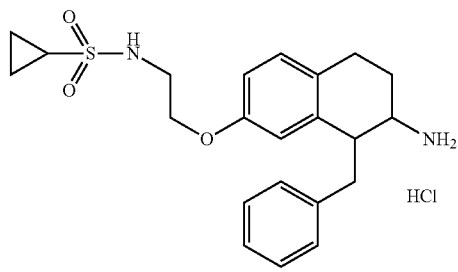 [SMILES: NC1CCc2ccc(OCCNS(=O)(=O)C3CC3)cc2C1Cc1ccccc1 ; Cl]

Cyclopropanesulfonic acid [2-(7-amino-8-benzyl-5,6,7,8-tetrahydro-naphthalen-2-yloxy)ethyl]-amide hydrochloride was prepared in analogy to example 3 and 97.

ESI-MS $[M+H^+]=401$ Calculated for $C_{22}H_{28}N_2O_3S=400$

Example 103

N-[2-(7-Amino-8-benzyl-5,6,7,8-tetrahydro-naphthalen-2-yloxy)-ethyl]-propionamide hydrochloride

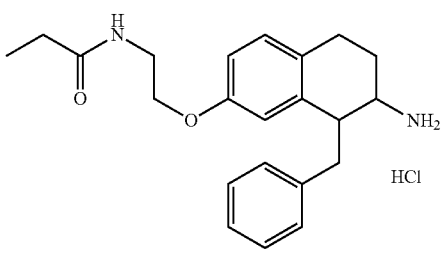 [SMILES: CCC(=O)NCCOc1ccc2c(c1)C(Cc1ccccc1)C(N)CC2 ; Cl]

Ethyl 7-(2-aminoethoxy)-1-(3,4-dichlorobenzyl)-1,2,3,4-tetrahydronaphthalen-2-ylcarbamate hydrochloride (example 2.1, 100 mg, 0.229 mmol) and N,N-dimethyl amino pyridine (30.7 mg, 0.252 mmol) were dissolved in $CH_2Cl_2$ (20 ml) and propionyl chloride (30.7 mg, 0.252 mmol) was added at RT. After stirring at RT for 14 h 0.5 N HCl was added and the mixture was extracted with $CH_2Cl_2$. The combined organic layers were washed with saturated $NaHCO_3$ and NaCl solution, dried over $Na_2SO_4$, and concentrated to afford a residue. White solid ethyl 1-(3,4-dichlorobenzyl)-7-(2-propionamidoethoxy)-1,2,3,4-tetrahydronaphthalen-2-ylcarbamate (98 mg, 87%) was obtained from precipitation in ethyl acetate. Further transformation in analogy to example 2 and 97 finally gave N-[2-(7-Amino-8-benzyl-5,6,7,8-tetrahydro-naphthalen-2-yloxy)-ethyl]-propionamide hydrochloride.

ESI-MS $[M+H^+]=353$ Calculated for $C_{22}H_{28}N_2O_2=352$

Example 104

1-Methyl-1H-[1,2,4]triazole-3-sulfonic acid {2-[7-amino-8-(3,4-dichloro-benzyl)-5,6,7,8-tetrahydro-naphthalen-2-yloxy]-ethyl}-amide

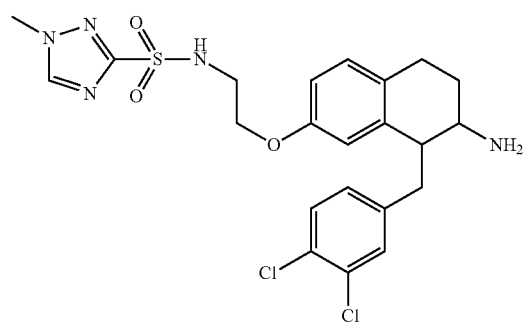 [SMILES: Cn1cnc(S(=O)(=O)NCCOc2ccc3c(c2)C(Cc2ccc(Cl)c(Cl)c2)C(N)CC3)n1]

1-Methyl-1H-[1,2,4]triazole-3-sulfonic acid {2-[7-amino-8-(3,4-dichloro-benzyl)-5,6,7,8-tetrahydro-naphthalen-2-yloxy]-ethyl}-amide was prepared in analogy to example 3.

ESI-MS $[M+H^+]=510$ Calculated for $C_{22}H_{25}Cl_2N_5O_3S=509$

Example 105

1-Methyl-1H-imidazole-4-sulfonic acid [2-(7-azetidin-1-yl-8-benzyl-5,6,7,8-tetrahydronaphthalen-2-yloxy)-ethyl]-methyl-amide

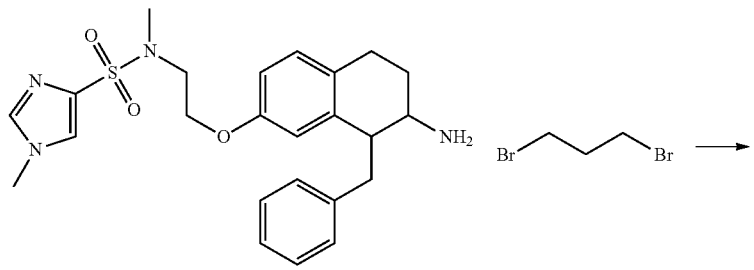

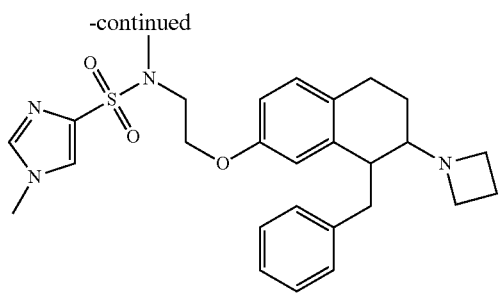

1-Methyl-1H-imidazole-4-sulfonic acid [2-(7-azetidin-1-yl-8-benzyl-5,6,7,8-tetrahydronaphthalen-2-yloxy)-ethyl]-methyl-amide was prepared in analogy to example 101.

ESI-MS [M+H$^+$]=495 Calculated for $C_{27}H_{34}N_4O_3S$=494

Example 106

N-{2-[7-Amino-8-(3,4-dichloro-benzyl)-5,6,7,8-tetrahydro-naphthalen-2-yloxy]-ethyl}-Ccyclobutyl-methanesulfonamide hydrochloride

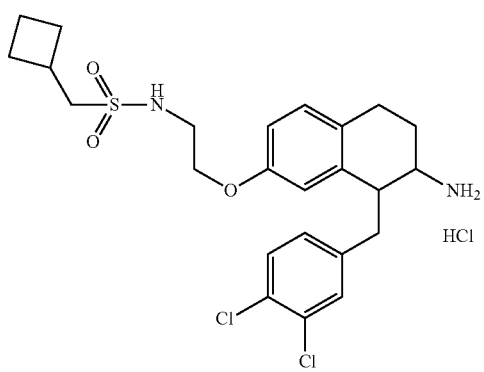 [SMILES: NC1CCc2ccc(OCCNS(=O)(=O)CC3CCC3)cc2C1Cc1ccc(Cl)c(Cl)c1 ; Cl]

N-{2-[7-Amino-8-(3,4-dichloro-benzyl)-5,6,7,8-tetrahydro-naphthalen-2-yloxy]-ethyl}-Ccyclobutyl-methanesulfonamide hydrochloride was prepared in analogy to example 3.

ESI-MS [M+H$^+$]=497 Calculated for $C_{24}H_{30}Cl_2N_2O_3S$=496

Example 107

Propane-1-sulfonic acid {2-[7-amino-8-(3-fluoro-benzyl)-5,6,7,8-tetrahydro-naphthalen-2-yloxy]-ethyl}-amide hydrochloride

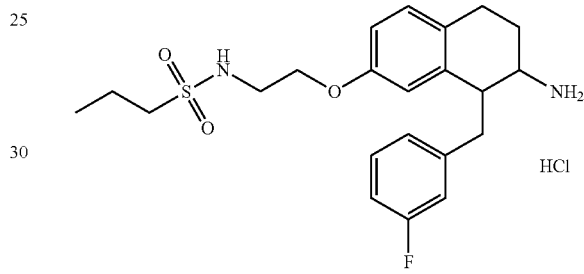

Propane-1-sulfonic acid {2-[7-amino-8-(3-fluoro-benzyl)-5,6,7,8-tetrahydro-naphthalen-2-yloxy]-ethyl}-amide hydrochloride was prepared in analogy to example 3.

ESI-MS [M+H$^+$]=421 Calculated for $C_{22}H_{29}FN_2O_3S$=420

Example 108

N-{2-[7-Amino-8-(3,4-dichloro-benzyl)-5,6,7,8-tetrahydro-naphthalen-2-yloxy]-ethyl}-C-cyclopropyl-N-methyl-methanesulfonamide hydrochloride

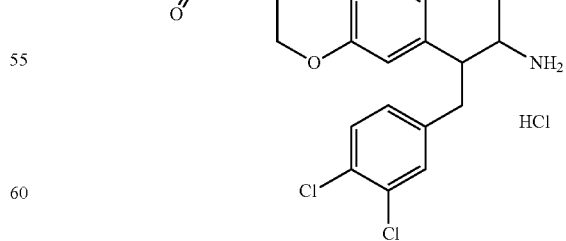

N-{2-[7-Amino-8-(3,4-dichloro-benzyl)-5,6,7,8-tetrahydro-naphthalen-2-yloxy]-ethyl}-C-cyclopropyl-N-methyl-methanesulfonamide hydrochloride was prepared in analogy to example 11.

ESI-MS [M+H$^+$]=497 Calculated for C$_{24}$H$_{30}$Cl$_2$N$_2$O$_3$S=496

Example 109

1-Methyl-1H-pyrazole-4-sulfonic acid [2-(7-amino-8-benzyl-5,6,7,8-tetrahydro-naphthalen-2-yloxy)-ethyl]-methyl-amide

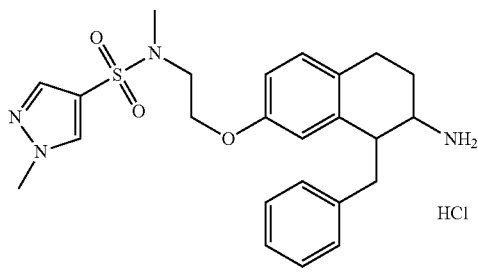 [SMILES: CN(CCOc1ccc2c(c1)C(Cc1ccccc1)C(N)CC2)S(=O)(=O)c1cnn(C)c1 ; Cl]

1-Methyl-1H-pyrazole-4-sulfonic acid [2-(7-amino-8-benzyl-5,6,7,8-tetrahydro-naphthalen-2-yloxy)-ethyl]-methyl-amide was prepared in analogy to example 3 and 89.

ESI-MS [M+H$^+$]=455 Calculated for C$_{24}$H$_{30}$N$_4$O$_3$S=454

Example 110

N-(2-(7-Amino-8-(3,4-dichlorobenzyl)-5,6,7,8-tetrahydronaphthalen-2-yloxy)ethyl)-N-ethyl-1-methyl-1H-pyrazole-4-sulfonamide

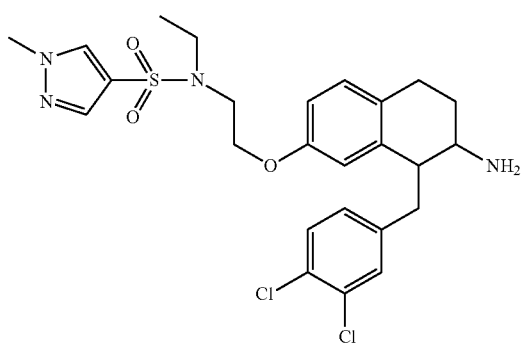 [SMILES: CCN(CCOc1ccc2c(c1)C(Cc1ccc(Cl)c(Cl)c1)C(N)CC2)S(=O)(=O)c1cnn(C)c1]

N-(2-(7-Amino-8-(3,4-dichlorobenzyl)-5,6,7,8-tetrahydronaphthalen-2-yloxy)ethyl)-N-ethyl-1-methyl-1H-pyrazole-4-sulfonamide was prepared in analogy to example 11.

ESI-MS [M+H$^+$]=537 Calculated for C$_{25}$H$_{30}$Cl$_2$N$_4$O$_3$S=536

Example 111

1-Methyl-1H-pyrazole-4-sulfonic acid [2-(8-benzyl-7-pyrrolidin-1-yl-5,6,7,8-tetrahydronaphthalen-2-yloxy)-ethyl]-methyl-amide hydrochloride

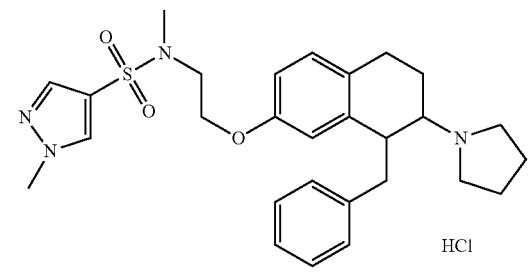 [SMILES: CN(CCOc1ccc2c(c1)C(Cc1ccccc1)C(N1CCCC1)CC2)S(=O)(=O)c1cnn(C)c1 ; Cl]

1-Methyl-1H-pyrazole-4-sulfonic acid [2-(8-benzyl-7-pyrrolidin-1-yl-5,6,7,8-tetrahydronaphthalen-2-yloxy)-ethyl]-methyl-amide hydrochloride was prepared in analogy to example 50.

ESI-MS [M+H$^+$]=509 Calculated for C$_{28}$H$_{36}$N$_4$O$_3$S=508

Example 112

1-Methyl-1H-pyrazole-4-sulfonic acid [2-(7-azetidin-1-yl-8-benzyl-5,6,7,8-tetrahydronaphthalen-2-yloxy)-ethyl]-methyl-amide hydrochloride

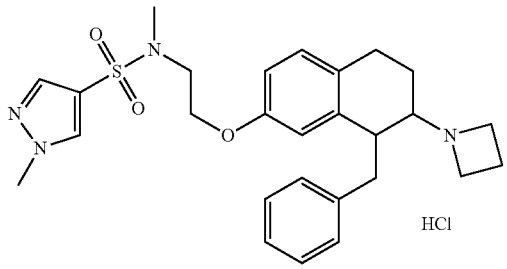 [SMILES: CN(CCOc1ccc2c(c1)C(Cc1ccccc1)C(N1CCC1)CC2)S(=O)(=O)c1cnn(C)c1 ; Cl]

1-Methyl-1H-pyrazole-4-sulfonic acid [2-(7-azetidin-1-yl-8-benzyl-5,6,7,8-tetrahydronaphthalen-2-yloxy)-ethyl]-methyl-amide hydrochloride was prepared in analogy to example 50.

ESI-MS [M+H$^+$]=495 Calculated for C$_{27}$H$_{34}$N$_4$O$_3$S=494

Example 113

N-(2-(7-Amino-8-benzyl-5,6,7,8-tetrahydronaphthalen-2-yloxy)ethyl)-N-ethyl-1-methyl-1H-pyrazole-4-sulfonamide hydrochloride

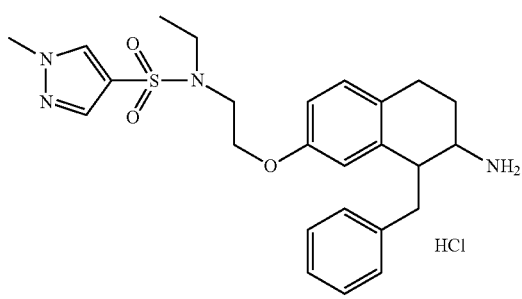 [SMILES: CCN(CCOc1ccc2c(c1)C(Cc1ccccc1)C(N)CC2)S(=O)(=O)c1cnn(C)c1 ; Cl]

N-(2-(7-Amino-8-benzyl-5,6,7,8-tetrahydronaphthalen-2-yloxy)ethyl)-N-ethyl-1-methyl-1H-pyrazole-4-sulfonamide hydrochloride was prepared in analogy to example 3 and 89.

ESI-MS [M+H$^+$]=469 Calculated for $C_{25}H_{32}N_4O_3S$=468

Example 114

N-(2-(7-Amino-8-(3,4-dichlorobenzyl)-5,6,7,8-tetrahydronaphthalen-2-yloxy)ethyl)pentane-1-sulfonamide hydrochloride

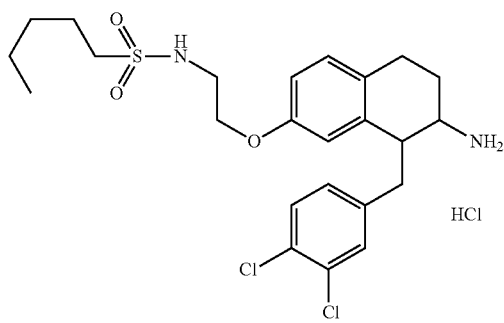 [SMILES: CCCCCS(=O)(=O)NCCOc1ccc2c(c1)C(Cc1ccc(Cl)c(Cl)c1)C(N)CC2 ; Cl]

N-(2-(7-Amino-8-(3,4-dichlorobenzyl)-5,6,7,8-tetrahydronaphthalen-2-yloxy)ethyl)pentane-1-sulfonamide hydrochloride was prepared in analogy to example 3.

ESI-MS [M+H$^+$]=499 Calculated for $C_{24}H_{32}Cl_2N_2O_3S$=498

Example 115

N-(2-(8-(3,4-Dichlorobenzyl)-7-(pyrrolidin-1-yl)-5,6,7,8-tetrahydronaphthalen-2-yloxy)ethyl)-1-methyl-1H-imidazole-4-sulfonamide hydrochloride

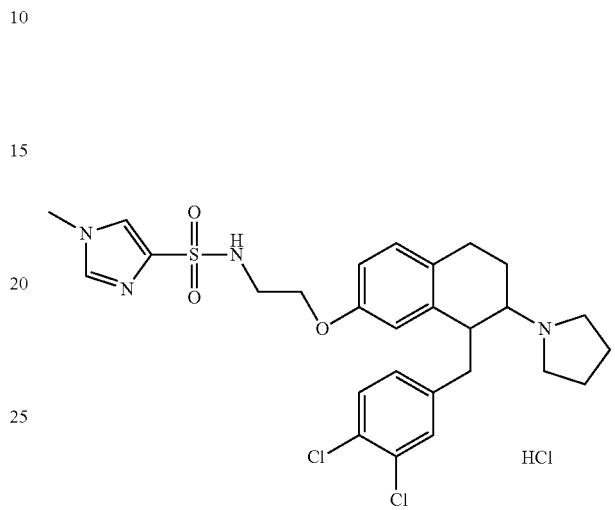

N-(2-(8-(3,4-Dichlorobenzyl)-7-(pyrrolidin-1-yl)-5,6,7,8-tetrahydronaphthalen-2-yloxy)ethyl)-1-methyl-1H-imidazole-4-sulfonamide hydrochloride was synthesized in analogy to example 88.

ESI-MS [M+H$^+$]=536 Calculated for $C_{27}H_{32}Cl_2N_4O_3S$=535

Example 116

N-(2-(8-Benzyl-7-(pyrrolidin-1-yl)-5,6,7,8-tetrahydronaphthalen-2-yloxy)ethyl)-1-methyl-1H-imidazole-4-sulfonamide hydrochloride

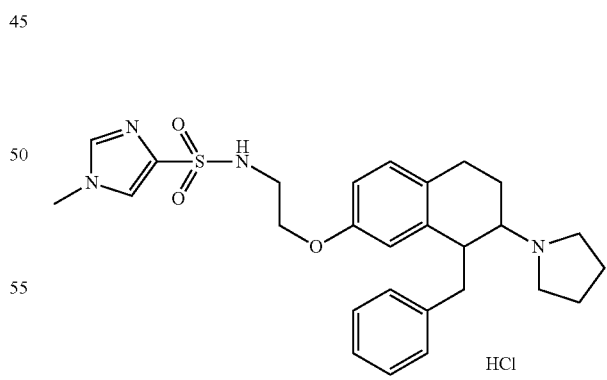

N-(2-(8-Benzyl-7-(pyrrolidin-1-yl)-5,6,7,8-tetrahydronaphthalen-2-yloxy)ethyl)-1-methyl-1H-imidazole-4-sulfonamide hydrochloride was prepared from N-(2-(8-(3,4-dichlorobenzyl)-7-(pyrrolidin-1-yl)-5,6,7,8-tetrahydronaphthalen-2-yloxy)ethyl)-1-methyl-1H-imidazole-4-sulfonamide (example 115) in analogy to 97.

ESI-MS [M+H$^+$]=495 Calculated for $C_{27}H_{34}N_4O_3S$=494

Example 117, 118

Enantiomere 1 and 2 of 116

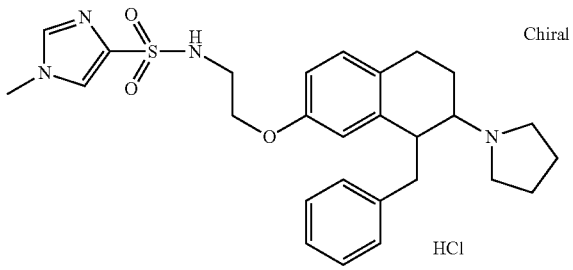 [SMILES: Cn1cnc(S(=O)(=O)NCCOc2ccc3c(c2)C(Cc2ccccc2)C(N2CCCC2)CC3)c1 ; Cl]

The racemate of N-(2-(8-benzyl-7-(pyrrolidin-1-yl)-5,6,7,8-tetrahydronaphthalen-2-yloxy)ethyl)-1-methyl-1H-imidazole-4-sulfonamide hydrochloride (ex. 116) was separated by chiral chromatography on Chiracel AD (n-heptane/ethanol 35:65, 0.1% TEA, 9 ml/min) to deliver (after transfer to the salt form) (−)-N-(2-(8-benzyl-7-(pyrrolidin-1-yl)-5,6,7,8-tetrahydronaphthalen-2-yloxy)ethyl)-1-methyl-1H-imidazole-4-sulfonamide hydrochloride ([α]=−76.0° in MeOH, c=1.040 g/100 ml [ex. 117] and (+)-N-(2-(8-benzyl-7-(pyrrolidin-1-yl)-5,6,7,8-tetrahydronaphthalen-2-yloxy)ethyl)-1-methyl-1H-imidazole-4-sulfonamide hydrochloride ([α]=−77.7° in MeOH, c=0.382 g/100 ml ex. 118]).

ESI-MS [M+H$^+$]=495 Calculated for $C_{27}H_{34}N_4O_3S$=494

Example 119

N-(2-(8-Benzyl-7-(pyrrolidin-1-yl)-5,6,7,8-tetrahydronaphthalen-2-yloxy)ethyl)-1-methyl-1H-pyrazole-4-sulfonamide hydrochloride

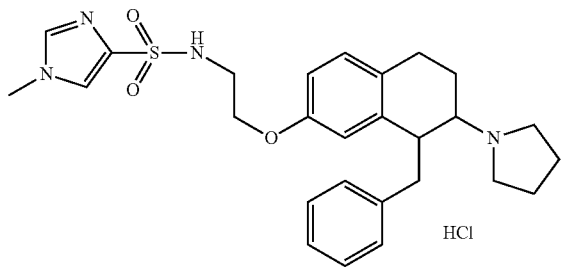 [SMILES: Cn1cnc(S(=O)(=O)NCCOc2ccc3c(c2)C(Cc2ccccc2)C(N2CCCC2)CC3)c1 ; Cl]

N-(2-(8-Benzyl-7-(pyrrolidin-1-yl)-5,6,7,8-tetrahydronaphthalen-2-yloxy)ethyl)-1-methyl-1H-pyrazole-4-sulfonamide hydrochloride was prepared from N-(2-(8-(3,4-dichlorobenzyl)-7-(pyrrolidin-1-yl)-5,6,7,8-tetrahydronaphthalen-2-yloxy)ethyl)-1-methyl-1H-pyrazole-4-sulfonamide (example 114) in analogy to 97.

ESI-MS [M+H$^+$]=495 Calculated for $C_{27}H_{34}N_4O_3S$=494

Example 120

N-(2-{[7-Amino-8-(3-chloro-4-fluorobenzyl)-5,6,7,8-tetrahydronaphthalen-2-yl]oxy}ethyl)propane-1-sulfonamide hydrochloride

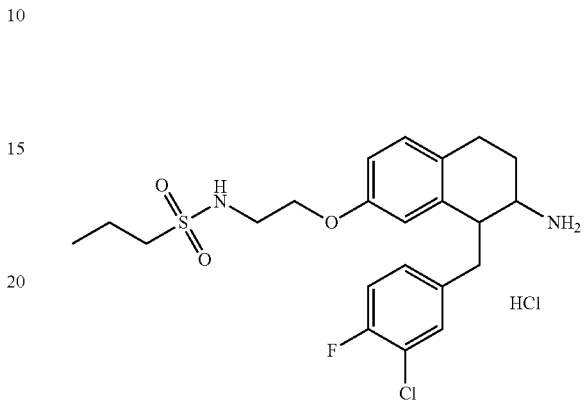

N-(2-{[7-Amino-8-(3-chloro-4-fluorobenzyl)-5,6,7,8-tetrahydronaphthalen-2-yl]oxy}ethyl)propane-1-sulfonamide hydrochloride was prepared in analogy to example 3.

ESI-MS [M+H$^+$]=455 Calculated for $C_{22}H_{28}ClFN_2O_3S$=454

Example 121

N-(2-{[7-Amino-8-benzyl-5,6,7,8-tetrahydronaphthalen-2-yl]oxy}ethyl)-1-cyclopropylmethanesulfonamide hydrochloride

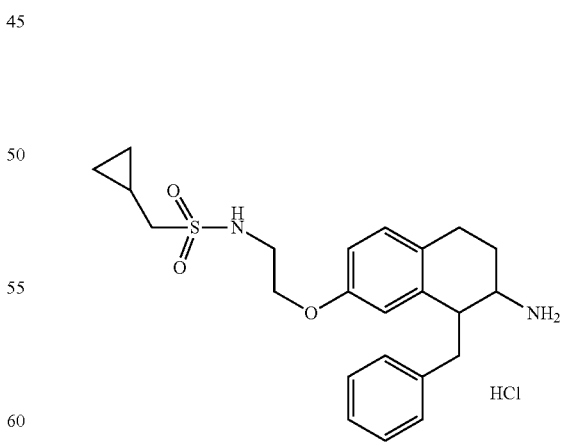

N-(2-{[7-Amino-8-benzyl-5,6,7,8-tetrahydronaphthalen-2-yl]oxy}ethyl)-1-cyclopropylmethanesulfonamide hydrochloride was prepared in analogy to example 3.

ESI-MS [M+H$^+$]=415 Calculated for $C_{23}H_{30}N_2O_3S$=414

Example 122

N-(2-{[7-Amino-8-(3,4-dichlorobenzyl)-5,6,7,8-tetrahydronaphthalen-2-yl]oxy}ethyl)-2-cyclopropylacetamide hydrochloride

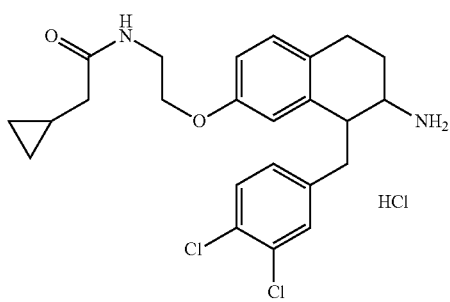 [SMILES: NC1CCc2ccc(OCCNC(=O)CC3CC3)cc2C1Cc1ccc(Cl)c(Cl)c1 ; Cl]

N-(2-{[7-Amino-8-(3,4-dichlorobenzyl)-5,6,7,8-tetrahydronaphthalen-2-yl]oxy}ethyl)-2-cyclopropylacetamide hydrochloride was synthesized in analogy to example 103.

ESI-MS [M+H$^+$]=447 Calculated for C$_{24}$H$_{28}$Cl$_2$N$_2$O$_2$=446

Example 123

N-(2-{[7-Amino-8-(3,4-dichlorobenzyl)-5,6,7,8-tetrahydronaphthalen-2-yl]oxy}ethyl)benzamide hydrochloride

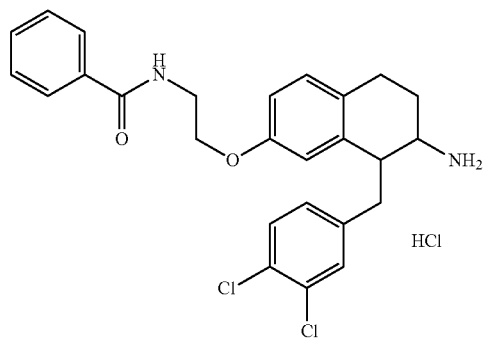 [SMILES: NC1CCc2ccc(OCCNC(=O)c3ccccc3)cc2C1Cc1ccc(Cl)c(Cl)c1 ; Cl]

N-(2-{[7-Amino-8-(3,4-dichlorobenzyl)-5,6,7,8-tetrahydronaphthalen-2-yl]oxy}ethyl)benzamide hydrochloride was synthesized in analogy to example 103.

ESI-MS [M+H$^+$]=469 Calculated for C$_{26}$H$_{26}$Cl$_2$N$_2$O$_2$=468

Example 124

N-(2-{[8-Benzyl-7-(pyrrolidin-1-yl)-5,6,7,8-tetrahydronaphthalen-2-yl]oxy}ethyl)-N-ethyl-1-methyl-1H-pyrazole-4-sulfonamide hydrochloride

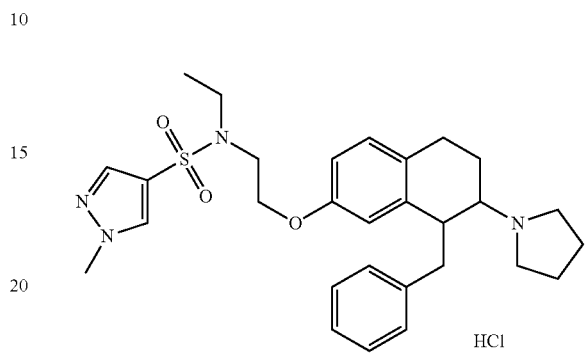

N-(2-{[8-Benzyl-7-(pyrrolidin-1-yl)-5,6,7,8-tetrahydronaphthalen-2-yl]oxy}ethyl)-N-ethyl-1-methyl-1H-pyrazole-4-sulfonamide hydrochloride was synthesized from N-(2-(7-amino-8-benzyl-5,6,7,8-tetrahydronaphthalen-2-yloxy)ethyl)-N-ethyl-1-methyl-1H-pyrazole-4-sulfonamide hydrochloride (example 113) in analogy to example 97.

ESI-MS [M+H$^+$]=523 Calculated for C$_{29}$H$_{38}$N$_4$O$_3$S=522

Example 125

N-(2-{[7-Amino-8-(3,4-dichlorobenzyl)-5,6,7,8-tetrahydronaphthalen-2-yl]oxy}ethyl)-2-cyclopropylethanesulfonamide hydrochloride

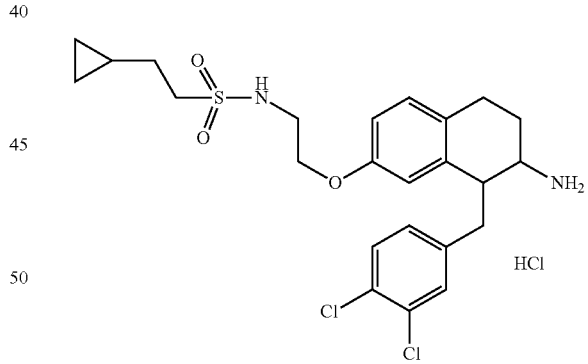

N-(2-{[7-Amino-8-(3,4-dichlorobenzyl)-5,6,7,8-tetrahydronaphthalen-2-yl]oxy}ethyl)-2-cyclopropylethanesulfonamide hydrochloride was prepared in analogy to example 3.

ESI-MS [M+H$^+$]=497 Calculated for C$_{24}$H$_{30}$Cl$_2$N$_2$O$_3$S=496

Example 126

C-Cyclopropyl-N-{2-[8-(3,4-dichloro-benzyl)-7-pyrrolidin-1-yl-5,6,7,8-tetrahydronaphthalen-2-yloxy]-ethyl}-N-methyl-methanesulfonamide hydrochloride

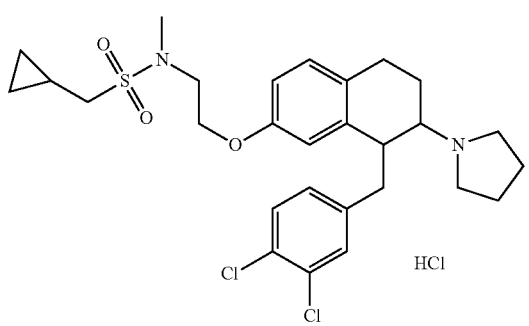 [SMILES: CN(CCOc1ccc2c(c1)C(Cc1ccc(Cl)c(Cl)c1)C(N1CCCC1)CC2)S(=O)(=O)CC1CC1 ; Cl]

C-Cyclopropyl-N-{2-[8-(3,4-dichloro-benzyl)-7-pyrrolidin-1-yl-5,6,7,8-tetrahydronaphthalen-2-yloxy]-ethyl}-N-methyl-methanesulfonamide hydrochloride was synthesized in analogy to examples 89, 97, 101.

ESI-MS [M+H$^+$]=551 Calculated for C$_{28}$H$_{36}$Cl$_2$N$_2$O$_3$S=550

Example 127

N-(2-{[8-Benzyl-7-(pyrrolidin-1-yl)-5,6,7,8-tetrahydronaphthalen-2-yl]oxy}ethyl)-1-cyclopropyl-N-methylmethanesulfonamide hydrochloride

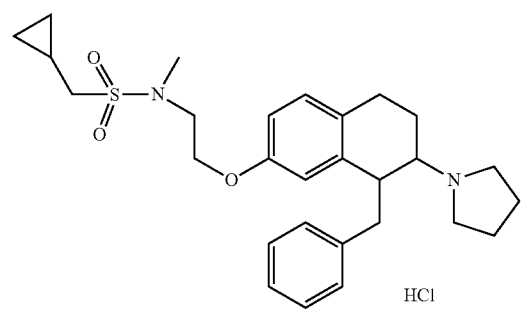 [SMILES: CN(CCOc1ccc2c(c1)C(Cc1ccccc1)C(N1CCCC1)CC2)S(=O)(=O)CC1CC1 ; Cl]

N-(2-{[8-Benzyl-7-(pyrrolidin-1-yl)-5,6,7,8-tetrahydronaphthalen-2-yl]oxy}ethyl)-1-cyclopropyl-N-methyl-methanesulfonamide hydrochloride was synthesized from 1-cyclopropyl-N-(2-{[8-(3,4-dichlorobenzyl)-7-(pyrrolidin-1-yl)-5,6,7,8-tetrahydronaphthalen-2-yl]oxy}ethyl)-N-methylmethanesulfonamide hydrochloride in analogy to example 97.

ESI-MS [M+H$^+$]=483 Calculated for C$_{28}$H$_{38}$N$_2$O$_3$S=482

Example 128

N-(2-{[7-Amino-8-(4-chlorobenzyl)-5,6,7,8-tetrahydronaphthalen-2-yl]oxy}ethyl)-1-cyclopropyl-methanesulfonamide hydrochloride

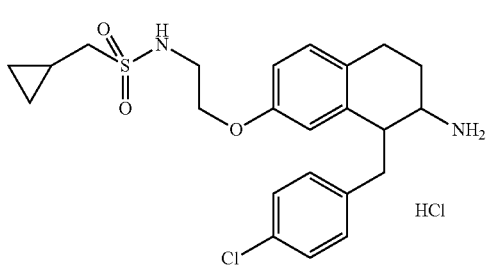 [SMILES: NC1CCc2ccc(OCCNS(=O)(=O)CC3CC3)cc2C1Cc1ccc(Cl)cc1 ; Cl]

N-(2-{[7-Amino-8-(4-chlorobenzyl)-5,6,7,8-tetrahydronaphthalen-2-yl]oxy}ethyl)-1-cyclopropylmethanesulfonamide hydrochloride was prepared in analogy to example 3.

ESI-MS [M+H$^+$]=449 Calculated for C$_{23}$H$_{29}$ClN$_2$O$_3$S=448

Example 129

N-(2-{[7-Amino-8-(4-chlorobenzyl)-5,6,7,8-tetrahydronaphthalen-2-yl]oxy}ethyl)-1-cyclopropyl-N-methylmethanesulfonamide hydrochloride

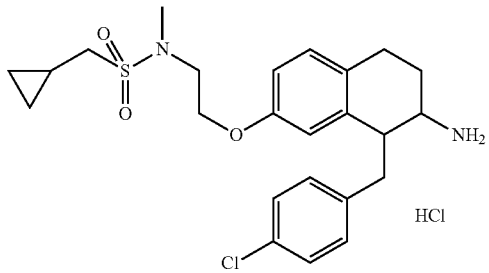 [SMILES: CN(CCOc1ccc2c(c1)C(Cc1ccc(Cl)cc1)C(N)CC2)S(=O)(=O)CC1CC1 ; Cl]

N-(2-{[7-Amino-8-(4-chlorobenzyl)-5,6,7,8-tetrahydronaphthalen-2-yl]oxy}ethyl)-1-cyclopropyl-N-methylmethanesulfonamide hydrochloride was prepared in analogy to example 3, N-methylation was performed according to 89.

ESI-MS [M+H$^+$]=463 Calculated for C$_{24}$H$_{31}$ClN$_2$O$_3$S=462

Example 130

N-[2-(7-Amino-8-benzyl-5,6,7,8-tetrahydro-naphthalen-2-yloxy)-ethyl]-C-cyclopropyl-Nmethyl-methanesulfonamide hydrochloride

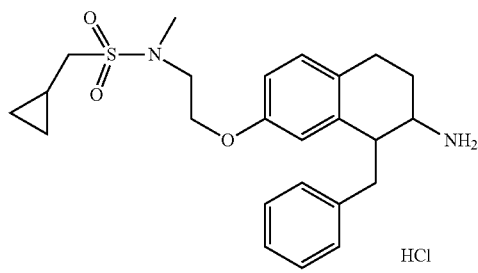 [SMILES: CN(CCOc1ccc2c(c1)C(Cc1ccccc1)C(N)CC2)S(=O)(=O)CC1CC1 ; Cl]

N-[2-(7-Amino-8-benzyl-5,6,7,8-tetrahydro-naphthalen-2-yloxy)-ethyl]-C-cyclopropyl-Nmethyl-methanesulfonamide hydrochloride was prepared from N-(2-{[7-amino-8-(3,4-dichlorobenzyl)-5,6,7,8-tetrahydronaphthalen-2-yl]oxy}ethyl)-1-cyclopropyl-N-methylmethanesulfonamide hydrochloride (example 108) in analogy to example 97.

ESI-MS [M+H$^+$]=429 Calculated for C$_{24}$H$_{32}$N$_2$O$_3$S=428

Example 131

N-(2-{[7-Amino-8-(3,4-difluorobenzyl)-5,6,7,8-tetrahydronaphthalen-2-yl]oxy}ethyl)-1-cyclopropyl-methanesulfonamide hydrochloride

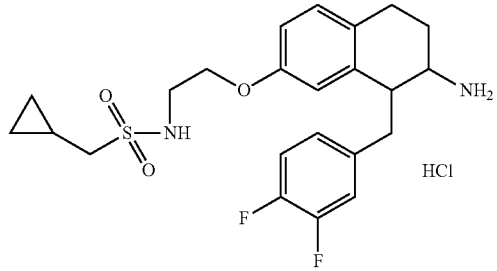 [SMILES: NC1CCc2ccc(OCCNS(=O)(=O)CC3CC3)cc2C1Cc1ccc(F)c(F)c1 ; Cl]

N-(2-{[7-Amino-8-(3,4-difluorobenzyl)-5,6,7,8-tetrahydronaphthalen-2-yl]oxy}ethyl)-1-cyclopropylmethanesulfonamide hydrochloride was prepared in analogy to example 3.

ESI-MS [M+H$^+$]=451 Calculated for C$_{23}$H$_{28}$F$_2$N$_2$O$_3$S=450

Example 132

C-Cyclopropyl-N-{2-[8-(3,4-dichloro-benzyl)-7-pyrrolidin-1-yl-5,6,7,8-tetrahydronaphthalen-2-yloxy]-ethyl}-methanesulfonamide hydrochloride

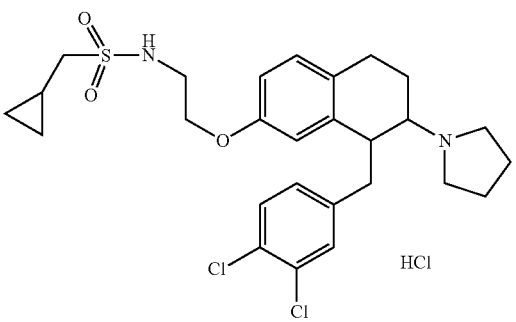 [SMILES: O=S(=O)(CC1CC1)NCCOc1ccc2c(c1)C(Cc1ccc(Cl)c(Cl)c1)C(N1CCCC1)CC2 ; Cl]

C-Cyclopropyl-N-{2-[8-(3,4-dichloro-benzyl)-7-pyrrolidin-1-yl-5,6,7,8-tetrahydronaphthalen-2-yloxy]-ethyl}-methanesulfonamide hydrochloride was prepared in analogy to example 88.

ESI-MS [M+H$^+$]=537 Calculated for C$_{27}$H$_{34}$Cl$_2$N$_2$O$_3$S=536

Example 133

N-(2-{[8-Benzyl-7-(pyrrolidin-1-yl)-5,6,7,8-tetrahydronaphthalen-2-yl]oxy}ethyl)-1-cyclopropyl-methanesulfonamide hydrochloride

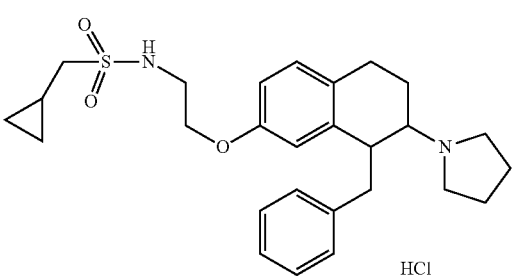 [SMILES: O=S(=O)(CC1CC1)NCCOc1ccc2c(c1)C(Cc1ccccc1)C(N1CCCC1)CC2 ; Cl]

N-(2-{[8-Benzyl-7-(pyrrolidin-1-yl)-5,6,7,8-tetrahydronaphthalen-2-yl]oxy}ethyl)-1-cyclopropylmethanesulfonamide hydrochloride was prepared from C-cyclopropyl-N-{2-[8-(3,4-dichloro-benzyl)-7-pyrrolidin-1-yl-5,6,7,8-tetrahydro-naphthalen-2-yloxy]-ethyl}-methanesulfonamide hydrochloride (example 132) in analogy to example 97

ESI-MS [M+H$^+$]=469 Calculated for C$_{27}$H$_{36}$N$_2$O$_3$S=468.

Example 134

1-Cyclopropyl-N-[2-({8-(3,4-dichlorobenzyl)-7-[3-fluoropyrrolidin-1-yl]-5,6,7,8-tetrahydronaphthalen-2-yl}oxy)ethyl]methanesulfonamide

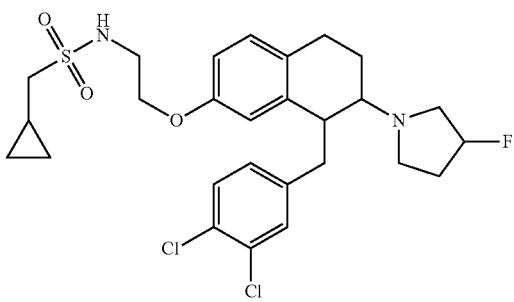 [SMILES: O=S(=O)(CC1CC1)NCCOc1ccc2c(c1)C(Cc1ccc(Cl)c(Cl)c1)C(N1CCC(F)C1)CC2]

7-Amino-8-(3,4-dichlorobenzyl)-5,6,7,8-tetrahydronaphthalen-2-ol (691 mg, 2.146 mmol, example 34), 2 eq of 1,4-dibromo-2-fluorobutane, and 3 eq of triethylamine were dissolved in acetonitrile (10 ml) and heated in the microwave for 2 h. Addition of water with ethylacetate, washing of the organic phase with saturated $NaHCO_3$, NaCl, drying over $Na_2SO_4$ and flash chromatography (silica gel, $CH_2Cl_2$/MeOH 95:5) gave 8-(3,4-dichlorobenzyl)-7-(3-fluoropyrrolidin-1-yl)-5,6,7,8-tetrahydronaphthalen-2-ol (330 mg, 39%). The ethylene sulfonamide side chain was added in analogy to examples 1, 7, 8 to give 1-cyclopropyl-N-[2-({8-(3,4-dichlorobenzyl)-7-[3-fluoropyrrolidin-1-yl]-5,6,7,8-tetrahydronaphthalen-2-yl}oxy)ethyl]methanesulfonamide.

ESI-MS $[M+H^+]+=555$ Calculated for $C_{27}H_{33}Cl_2FN_2O_3S=554$

Example 135

N-(2-{[7-(Azetidin-1-yl)-8-(3,4-dichlorobenzyl)-5,6,7,8-tetrahydronaphthalen-2-yl]oxy}ethyl)-1-cyclopropylmethanesulfonamide

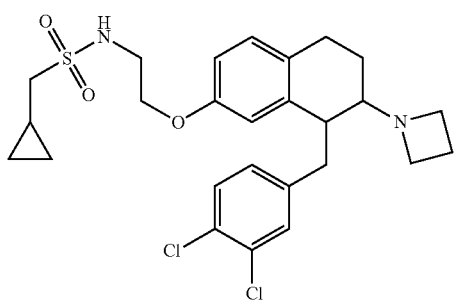 [SMILES: O=S(=O)(CC1CC1)NCCOc1ccc2c(c1)C(Cc1ccc(Cl)c(Cl)c1)C(N1CCC1)CC2]

N-(2-{[7-(Azetidin-1-yl)-8-(3,4-dichlorobenzyl)-5,6,7,8-tetrahydronaphthalen-2-yl]oxy}ethyl)-1-cyclopropylmethanesulfonamide was prepared in analogy to example 320.

ESI-MS $[M+H^+]=523$ Calculated for $C_{26}H_{32}Cl_2N_2O_3S=522$

Example 136

N-[2-({8-Benzyl-7-[3-fluoropyrrolidin-1-yl]-5,6,7,8-tetrahydronaphthalen-2-yl}oxy)ethyl]-1-cyclopropyl-methanesulfonamide hydrochloride

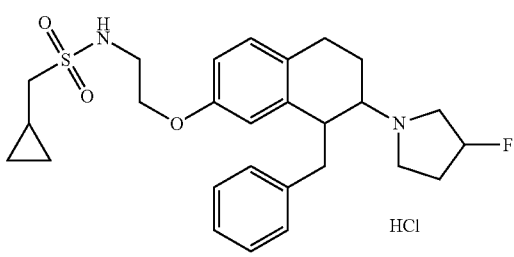 [SMILES: O=S(=O)(CC1CC1)NCCOc1ccc2c(c1)C(Cc1ccccc1)C(N1CCC(F)C1)CC2 ; Cl]

N-[2-({8-Benzyl-7-[3-fluoropyrrolidin-1-yl]-5,6,7,8-tetrahydronaphthalen-2-yl}oxy)ethyl]-1-cyclopropylmethanesulfonamide hydrochloride was synthesized from 1-cyclopropyl-N-[2-({8-(3,4-dichlorobenzyl)-7-[3-fluoropyrrolidin-1-yl]-5,6,7,8-tetrahydronaphthalen-2-yl}oxy)ethyl]methanesulfonamide (example 134) in analogy to 97.

ESI-MS $[M+H^+]=487$ Calculated for $C_{27}H_{35}FN_2O_3S=486$

Example 137

N-(2-{[8-Benzyl-7-(methylamino)-5,6,7,8-tetrahydronaphthalen-2-yl]oxy}ethyl)-1-cyclopropyl-methanesulfonamide hydrochloride

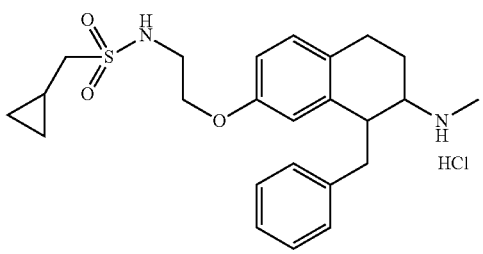 [SMILES: CNC1CCc2ccc(OCCNS(=O)(=O)CC3CC3)cc2C1Cc1ccccc1 ; Cl]

The synthesis was performed starting from ethyl 1-benzyl-7-(2-(cyclopropylmethylsulfonamido)ethoxy)-1,2,3,4-tetrahydronaphthalen-2-ylcarbamate (synthesized in analogy to example 3), which was dissolved in THF (50 ml), after which $LiAlH_4$ was added at room temperature and the mixture was stirred for 8 h under reflux. Addition of 2N aqueous NaOH, extraction with $CH_2Cl_2$, washing of the organic layers with saturated $NaHCO_3$ solution and saturated NaCl solution and evaporation of the solvent gave a residue that was treated with iPrOH/HCl after which the product precipitated. After filtration a white salt (287 mg, 58%) were obtained.

ESI-MS $[M+H^+]=429$ Calculated for $C_{24}H_{32}N_2O_3S=428$

Example 138

1-Cyclopropyl-N-(2-{[8-(3-fluorobenzyl)-7-(pyrrolidin-1-yl)-5,6,7,8-tetrahydronaphthalen-2-yl]oxy}ethyl)methanesulfonamide hydrochloride

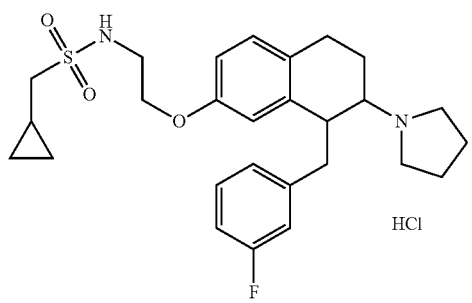 [SMILES: O=S(=O)(CC1CC1)NCCOc1ccc2c(c1)C(Cc1cccc(F)c1)C(N1CCCC1)CC2 ; Cl]

1-Cyclopropyl-N-(2-{[8-(3-fluorobenzyl)-7-(pyrrolidin-1-yl)-5,6,7,8-tetrahydronaphthalen-2-yl]oxy}ethyl)methanesulfonamide hydrochloride was synthesized in analogy to examples 264/88.

ESI-MS [M+H$^+$]=487 C$_{27}$H$_{35}$FN$_2$O$_3$S=486

Example 139

N-(2-{[7-(Azetidin-1-yl)-8-(3-fluorobenzyl)-5,6,7,8-tetrahydronaphthalen-2-yl]oxy}ethyl)-1-cyclopropyl-methanesulfonamide hydrochloride

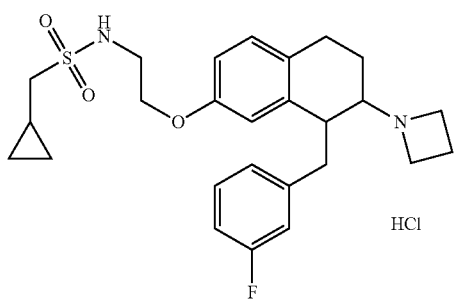 [SMILES: O=S(=O)(CC1CC1)NCCOc1ccc2c(c1)C(Cc1cccc(F)c1)C(N1CCC1)CC2 ; Cl]

N-(2-{[7-(Azetidin-1-yl)-8-(3-fluorobenzyl)-5,6,7,8-tetrahydronaphthalen-2-yl]oxy}ethyl)-1-cyclopropylmethanesulfonamide hydrochloride was synthesized in analogy to example 320.

ESI-MS [M+H$^+$]=473 C$_{26}$H$_{33}$FN$_2$O$_3$S=472

Example 140

N-(2-{[8-(3-Fluorobenzyl)-7-(pyrrolidin-1-yl)-5,6,7,8-tetrahydronaphthalen-2-yl]oxy}ethyl)-1-methyl-1H-imidazole-4-sulfonamide hydrochloride

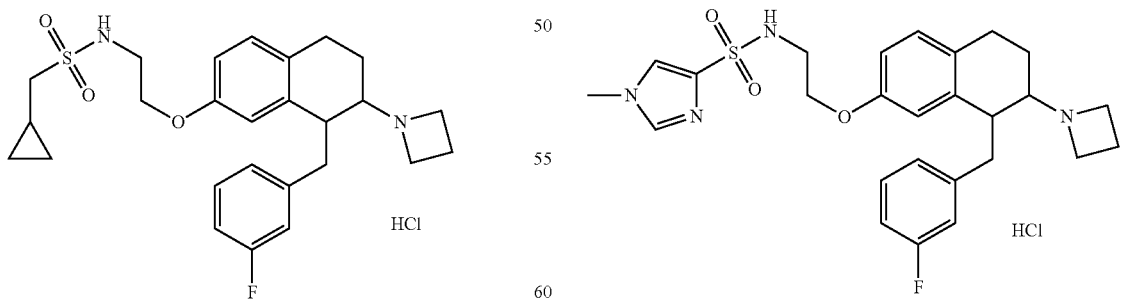

N-(2-{[8-(3-Fluorobenzyl)-7-(pyrrolidin-1-yl)-5,6,7,8-tetrahydronaphthalen-2-yl]oxy}ethyl)-1-methyl-1H-imidazole-4-sulfonamide hydrochloride was synthesized in analogy to examples 264/88

ESI-MS [M+H$^+$]=513 C$_{27}$H$_{33}$FN$_4$O$_3$S=512

Example 141

N-(2-{[7-(Azetidin-1-yl)-8-(3-fluorobenzyl)-5,6,7,8-tetrahydronaphthalen-2-yl]oxy}ethyl)-1-methyl-1H-imidazole-4-sulfonamide hydrochloride N-(2-{[7-(Azetidin-1-yl)-8-(3-fluorobenzyl)-5,6,7,8-tetrahydronaphthalen-2-yl]oxy}ethyl)-1-methyl-1H-imidazole-4-sulfonamide hydrochloride was synthesized in analogy to example 320.

ESI-MS [M+H$^+$]=499 C$_{26}$H$_{31}$FN$_4$O$_3$S=498

Example 142

N-(2-{[7-(Azetidin-1-yl)-8-benzyl-5,6,7,8-tetrahydronaphthalen-2-yl]oxy}ethyl)-1-cyclopropylmethanesulfonamide hydrochloride

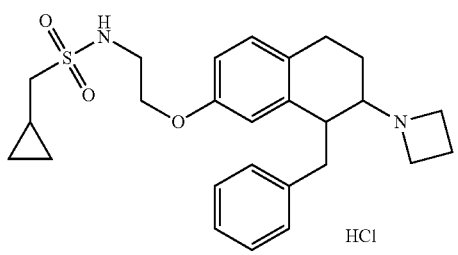 [SMILES: O=S(=O)(CC1CC1)NCCOc1ccc2c(c1)C(Cc1ccccc1)C(N1CCC1)CC2 ; Cl]

N-(2-{[7-(Azetidin-1-yl)-8-benzyl-5,6,7,8-tetrahydronaphthalen-2-yl]oxy}ethyl)-1-cyclopropylmethanesulfonamide hydrochloride was synthesized in analogy to example 320.

ESI-MS [M+H$^+$]=455 $C_{26}H_{34}N_2O_3S$=454

Examples 143, 144

Enantiomeres 1 and 2 of example 142

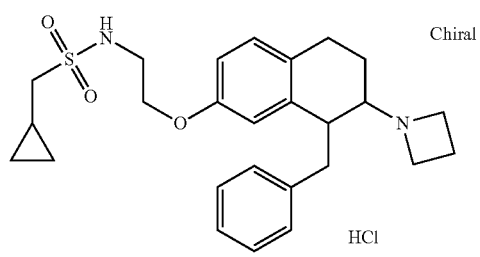 [SMILES: O=S(=O)(CC1CC1)NCCOc1ccc2c(c1)C(Cc1ccccc1)C(N1CCC1)CC2 ; Cl]

The racemate of N-(2-{[7-(azetidin-1-yl)-8-benzyl-5,6,7,8-tetrahydronaphthalen-2-yl]oxy}ethyl)-1-cyclopropylmethanesulfonamide hydrochloride (example 142) was separated by chiral chromatography on Chiracel AD (n-heptane/ethanol 35:65, 0.1% TEA, 9 ml/min) to deliver (after transfer to salt form) (−)-N-(2-(7-(azetidin-1-yl)-8-benzyl-5,6,7,8-tetrahydronaphthalen-2-yloxy)ethyl)-1-cyclopropylmethanesulfonamide ([α]=−103.0° in MeOH, c=0.461 g/100 ml [example 143]) and (+)-N-(2-(7-(azetidin-1-yl)-8-benzyl-5,6,7,8-tetrahydronaphthalen-2-yloxy)ethyl)-1-cyclopropylmethanesulfonamide succinate ([α]=+57.0° in MeOH, c=0.508 g/100 ml [example 144])

ESI-MS [M+H$^+$]=455 $C_{26}H_{34}N_2O_3S$=454

Example 145

N-(2-{[7-(Azetidin-1-yl)-8-benzyl-5,6,7,8-tetrahydronaphthalen-2-yl]oxy}ethyl)-1-methyl-1H-imidazole-4-sulfonamide

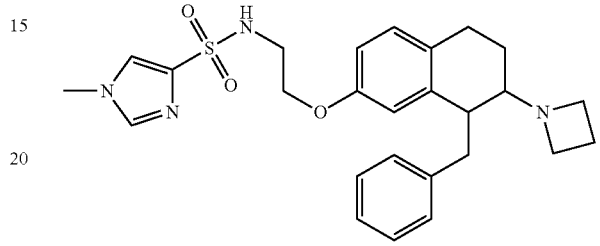

N-(2-{[7-(Azetidin-1-yl)-8-benzyl-5,6,7,8-tetrahydronaphthalen-2-yl]oxy}ethyl)-1-methyl-1H-imidazole-4-sulfonamide was synthesized in analogy to example 320.

ESI-MS [M+H$^+$]=481 $C_{26}H_{32}N_4O_3S$=480

Example 146

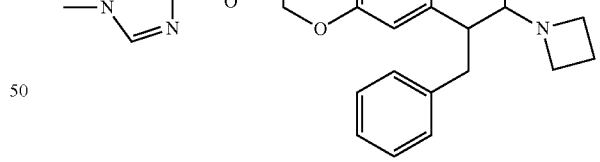

The racemate of N-(2-{[7-(azetidin-1-yl)-8-benzyl-5,6,7,8-tetrahydronaphthalen-2-yl]oxy}ethyl)-1-methyl-1H-imidazole-4-sulfonamide (145) can be separated by chiral chromatography to deliver (after transfer to the salt form) (−)-N-(2-((7S,8R)-7-(azetidin-1-yl)-8-benzyl-5,6,7,8-tetrahydronaphthalen-2-yloxy)ethyl)-1-methyl-1H-imidazole-4-sulfonamide fumarate ([α]=−81.4° in MeOH, c=0.409 g/100 ml).

ESI-MS [M+H$^+$]=481 Calculated for $C_{27}H_{34}N_4O_3S$=480

Example 147

N-(2-{[7-(Azetidin-1-yl)-8-benzyl-5,6,7,8-tetrahydronaphthalen-2-yl]oxy}ethyl)cyclobutanesulfonamide

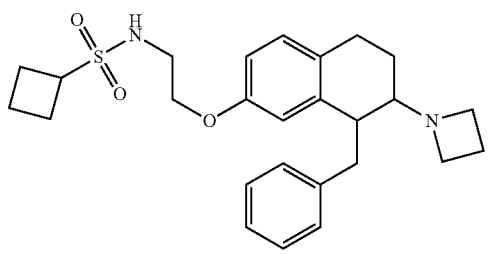 [SMILES: O=S(=O)(NCCOc1ccc2c(c1)C(Cc1ccccc1)C(N1CCC1)CC2)C1CCC1]

N-(2-{[7-(Azetidin-1-yl)-8-benzyl-5,6,7,8-tetrahydronaphthalen-2-yl]oxy}ethyl)cyclobutanesulfonamide was synthesized in analogy to example 320.

ESI-MS [M+H$^+$]=455 C$_{26}$H$_{34}$N$_2$O$_3$S=454

Example 148

Propane-1-sulfonic acid [2-(7-azetidin-1-yl-8-benzyl-5,6,7,8-tetrahydro-naphthalen-2-yloxy)-ethyl]-amide

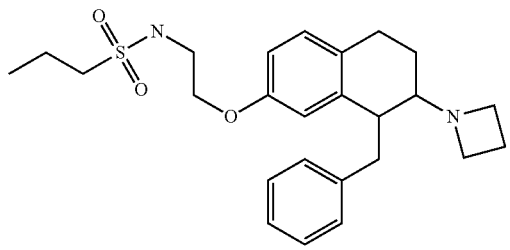 [SMILES: CCCS(=O)(=O)NCCOc1ccc2c(c1)C(Cc1ccccc1)C(N1CCC1)CC2]

Propane-1-sulfonic acid [2-(7-azetidin-1-yl-8-benzyl-5,6,7,8-tetrahydro-naphthalen-2-yloxy)-ethyl]-amide was synthesized in analogy to example 320.

ESI-MS [M+H$^+$]=443 C$_{25}$H$_{34}$N$_2$O$_3$S=442

Example 149

N-(2-{[8-(3-Fluorobenzyl)-7-(pyrrolidin-1-yl)-5,6,7,8-tetrahydronaphthalen-2-yl]oxy}ethyl)-1-methyl-1H-pyrrole-3-sulfonamide hydrochloride N-(2-{[8-(3-Fluorobenzyl)-7-(pyrrolidin-1-yl)-5,6,7,8-tetrahydronaphthalen-2-yl]oxy}ethyl)-1-methyl-1H-pyrrole-3-sulfonamide hydrochloride was synthesized in analogy to examples 264/88.

ESI-MS [M+H$^+$]=512 C$_{28}$H$_{34}$FN$_3$O$_3$S=511

Example 150

N-(2-{[7-Amino-8-(3-chloro-5-fluorobenzyl)-5,6,7,8-tetrahydronaphthalen-2-yl]oxy}ethyl)-1-cyclopropylmethanesulfonamide hydrochloride N-(2-{[7-Amino-8-(3-chloro-5-fluorobenzyl)-5,6,7,8-tetrahydronaphthalen-2-yl]oxy}ethyl)-1-cyclopropylmethanesulfonamide hydrochloride was synthesized in analogy to example 3.

ESI-MS [M+H$^+$]=467 C$_{23}$H$_{28}$ClFN$_2$O$_3$S=466

Example 151

N-(2-{[7-Amino-8-(3-chloro-5-fluorobenzyl)-5,6,7,8-tetrahydronaphthalen-2-yl]oxy}ethyl)-1-methyl-1H-imidazole-4-sulfonamide hydrochloride

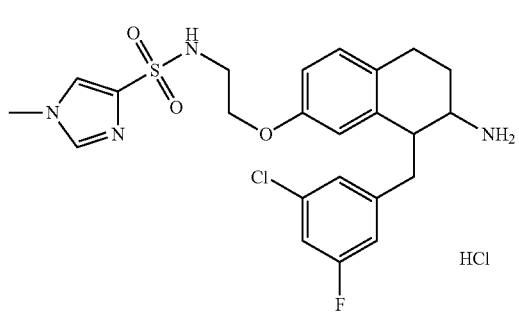 [SMILES: Cn1cnc(S(=O)(=O)NCCOc2ccc3c(c2)C(Cc2cc(F)cc(Cl)c2)C(N)CC3)c1 ; Cl]

N-(2-{[7-Amino-8-(3-chloro-5-fluorobenzyl)-5,6,7,8-tetrahydronaphthalen-2-yl]oxy}ethyl)-1-methyl-1H-imidazole-4-sulfonamide hydrochloride was synthesized in analogy to example 3.

ESI-MS [M+H$^+$]=493 C$_{23}$H$_{26}$ClFN$_4$O$_3$S=492

Example 152

N-[2-({8-Benzyl-7-[3-fluoropyrrolidin-1-yl]-5,6,7,8-tetrahydronaphthalen-2-yl}oxy)ethyl]-1-methyl-1H-imidazole-4-sulfonamide hydrochloride

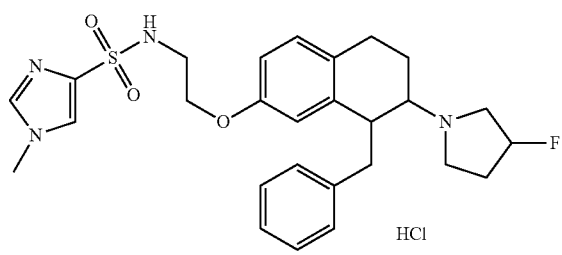 [SMILES: Cn1cnc(S(=O)(=O)NCCOc2ccc3c(c2)C(Cc2ccccc2)C(N2CCC(F)C2)CC3)c1 ; Cl]

N-[2-({8-Benzyl-7-[3-fluoropyrrolidin-1-yl]-5,6,7,8-tetrahydronaphthalen-2-yl}oxy)ethyl]-1-methyl-1H-imidazole-4-sulfonamide hydrochloride was synthesized in analogy to 264/88.

ESI-MS [M+H$^+$]=513 C$_{27}$H$_{33}$FN$_4$O$_3$S=512

Example 153

N-(2-{[8-(3-Cyanobenzyl)-7-(pyrrolidin-1-yl)-5,6,7,8-tetrahydronaphthalen-2-yl]oxy}ethyl)-1-methyl-1H-imidazole-4-sulfonamide

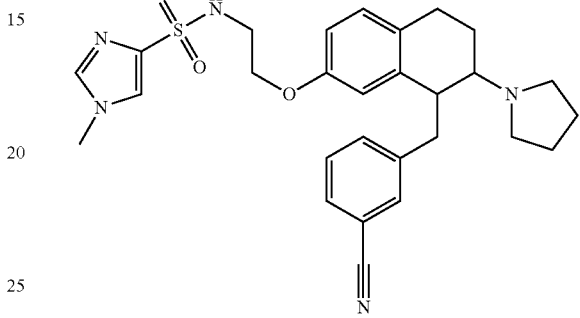

N-(2-{[8-(3-Cyanobenzyl)-7-(pyrrolidin-1-yl)-5,6,7,8-tetrahydronaphthalen-2-yl]oxy}ethyl)-1-methyl-1H-imidazole-4-sulfonamide was synthesized in analogy to 264/88.

ESI-MS [M+H$^+$]=520 C$_{28}$H$_{33}$N$_5$O$_3$S=519

Example 154

N-(2-{[8-(3-Cyanobenzyl)-7-(propan-2-ylamino)-5,6,7,8-tetrahydronaphthalen-2-yl]oxy}ethyl)-1-methyl-1H-imidazole-4-sulfonamide hydrochloride

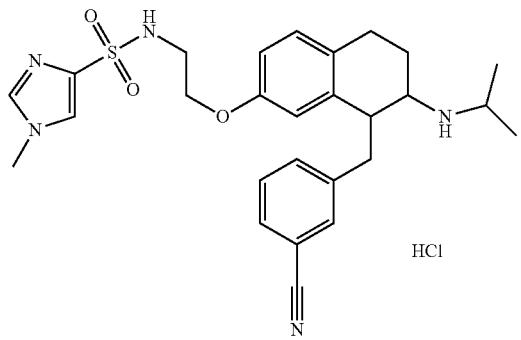 [SMILES: CC(C)NC1CCc2ccc(OCCNS(=O)(=O)c3cn(C)cn3)cc2C1Cc1cccc(C#N)c1 ; Cl]

N-(2-{[8-(3-Cyanobenzyl)-7-(propan-2-ylamino)-5,6,7,8-tetrahydronaphthalen-2-yl]oxy}ethyl)-1-methyl-1H-imidazole-4-sulfonamide hydrochloride was synthesized in analogy to example 88.

ESI-MS [M+H$^+$]+=508 C$_{27}$H$_{33}$N$_5$O$_3$S=507

Example 155

N-(2-{[8-(3-Cyanobenzyl)-7-(pyrrolidin-1-yl)-5,6,7,8-tetrahydronaphthalen-2-yl]oxy}ethyl)-1-cyclopropylmethanesulfonamide hydrochloride

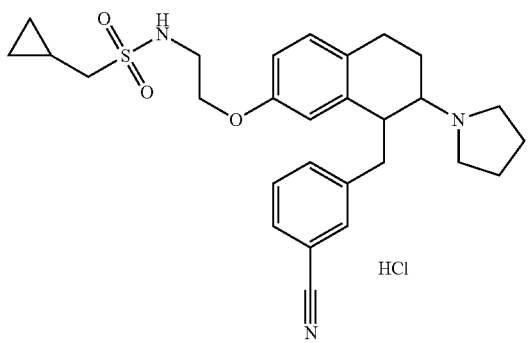 [SMILES: N#Cc1cccc(CC2c3cc(OCCNS(=O)(=O)CC4CC4)ccc3CCC2N2CCCC2)c1 ; Cl]

N-(2-{[8-(3-Cyanobenzyl)-7-(pyrrolidin-1-yl)-5,6,7,8-tetrahydronaphthalen-2-yl]oxy}ethyl)-1-cyclopropylmethanesulfonamide hydrochloride was synthesized in analogy to examples 264/88.

ESI-MS [M+H$^+$]=494 C$_{28}$H$_{35}$N$_3$O$_3$S=493

Example 156

N-(2-{[8-(3-Cyanobenzyl)-7-(propan-2-ylamino)-5,6,7,8-tetrahydronaphthalen-2-yl]oxy}ethyl)-1-cyclopropylmethanesulfonamide hydrochloride

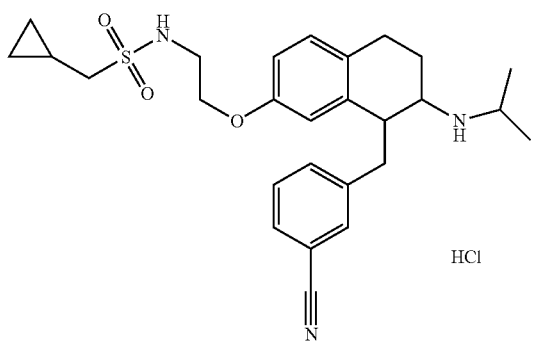 [SMILES: CC(C)NC1CCc2ccc(OCCNS(=O)(=O)CC3CC3)cc2C1Cc1cccc(C#N)c1 ; Cl]

N-(2-{[8-(3-Cyanobenzyl)-7-(propan-2-ylamino)-5,6,7,8-tetrahydronaphthalen-2-yl]oxy}ethyl)-1-cyclopropylmethanesulfonamide hydrochloride was synthesized in analogy to example 88.

ESI-MS [M+H$^+$]=482 C$_{27}$H$_{35}$N$_3$O$_3$S=481

Example 157

N-(2-{[7-Amino-8-benzyl-5,6,7,8-tetrahydronaphthalen-2-yl]oxy}ethyl)propane-1-sulfonamide hydrochloride

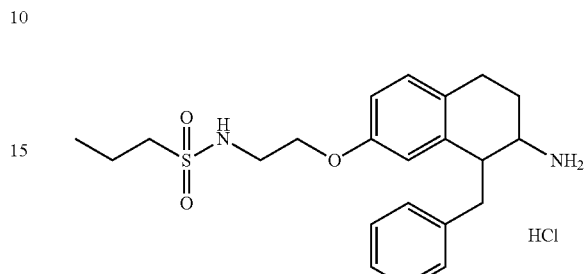

N-(2-{[7-Amino-8-benzyl-5,6,7,8-tetrahydronaphthalen-2-yl]oxy}ethyl)propane-1-sulfonamide hydrochloride was synthesized from Propane-1-sulfonic acid {2-[7-amino-8-(3,4-dichloro-benzyl)-5,6,7,8-tetrahydro-naphthalen-2-yloxy]-ethyl}-amide hydrochloride (example 8) in analogy to example 97.

ESI-MS [M+H$^+$]=403 C$_{22}$H$_{30}$N$_2$O$_3$S=402

Example 158

N-(2-{[8-(3-Chloro-5-fluorobenzyl)-7-(methylamino)-5,6,7,8-tetrahydronaphthalen-2-yl]oxy}ethyl)-1-cyclopropylmethanesulfonamide hydrochloride

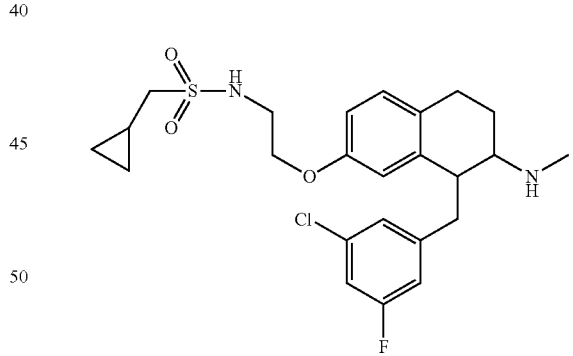

The synthesis was performed starting from ethyl 1-(3-chloro-5-fluorobenzyl)-7-(2-(cyclopropylmethylsulfonamido)ethoxy)-1,2,3,4-tetrahydronaphthalen-2-ylcarbamate (synthesized in analogy to example 3), which was dissolved in THF (50 ml), after which LiAlH$_4$ was added at room temperature and the mixture was stirred for 8 h under reflux. Addition of 2N aqueous NaOH, extraction with CH$_2$Cl$_2$, washing of the organic layers with saturated NaHCO$_3$ solution and saturated NaCl solution and evaporation of the solvent gave a residue that was treated with iPrOH/HCl after which the product precipitated. After filtration a white salt (134 mg, 39%) was obtained.

ESI-MS [M+H⁺]=481 Calculated for $C_{24}H_{30}ClFN_2O_3S$=480

Example 159

N-(2-{[7-(Azetidin-1-yl)-8-(3-chloro-5-fluorobenzyl)-5,6,7,8-tetrahydronaphthalen-2-yl]oxy}ethyl)-1-cyclopropylmethanesulfonamide (2E)-but-2-enedioate

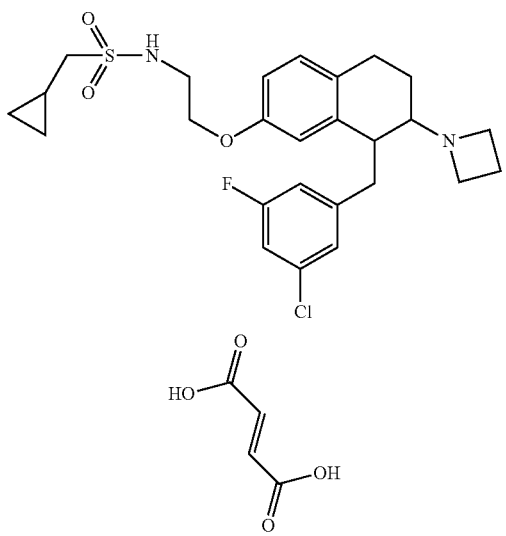

N-(2-{[7-(Azetidin-1-yl)-8-(3-chloro-5-fluorobenzyl)-5,6,7,8-tetrahydronaphthalen-2-yl]oxy}ethyl)-1-cyclopropylmethanesulfonamide(2E)-but-2-enedioate was synthesized in analogy to example 320.

ESI-MS [M+H⁺]=507 $C_{26}H_{32}ClFN_2O_3S$=506

Example 160

N-(2-{[7-(Azetidin-1-yl)-8-(3-chloro-5-fluorobenzyl)-5,6,7,8-tetrahydronaphthalen-2-yl]oxy}ethyl)-1-methyl-1H-imidazole-4-sulfonamide(2E)-but-2-enedioate

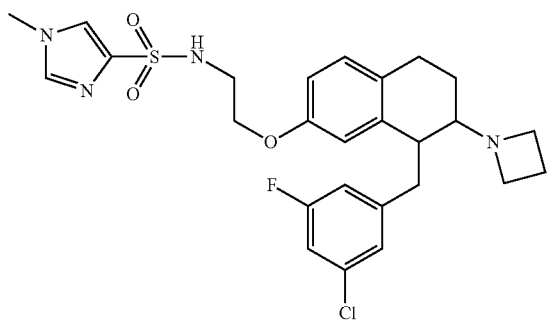

-continued

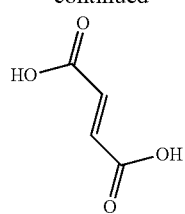

N-(2-{[7-(Azetidin-1-yl)-8-(3-chloro-5-fluorobenzyl)-5,6,7,8-tetrahydronaphthalen-2-yl]oxy}ethyl)-1-methyl-1H-imidazole-4-sulfonamide(2E)-but-2-enedioate was synthesized in analogy to example 320.

ESI-MS [M+H⁺]+=533 $C_{26}H_{30}ClFN_4O_3S$=532

Example 161

1-Cyclopropyl-N-(2-{[8-(4-fluorobenzyl)-7-(methylamino)-5,6,7,8-tetrahydronaphthalen-2-yl]oxy}ethyl)methanesulfonamide

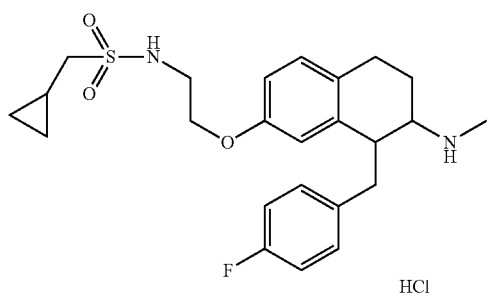 [SMILES: CNC1CCc2ccc(OCCNS(=O)(=O)CC3CC3)cc2C1Cc1ccc(F)cc1 ; Cl]

The synthesis was performed starting from ethyl 7-(2-(cyclopropylmethylsulfonamido)ethoxy)-1-(4-fluorobenzyl)-1,2,3,4-tetrahydronaphthalen-2-ylcarbamate (synthesized in analogy to example 3), which was dissolved in THF (50 ml), after which LiAlH₄ was added at room temperature and the mixture was stirred for 8 h under reflux. Addition of 2N aqueous NaOH, extraction with CH₂Cl₂, washing of the organic layers with saturated NaHCO₃ solution and saturated NaCl solution and evaporation of the solvent gave a residue that was treated with iPrOH/HCl after which the product precipitated. After filtration a white salt (89 mg, 76%) was obtained.

ESI-MS [M+H⁺]=447 $C_{24}H_{31}FN_2O_3S$=446

Example 162

(−)-N-(2-(8-Benzyl-7-(pyrrolidin-1-yl)-5,6,7,8-tetrahydronaphthalen-2-yloxy)ethyl)-1-methyl-1H-imidazole-4-sulfonamide hydrochloride

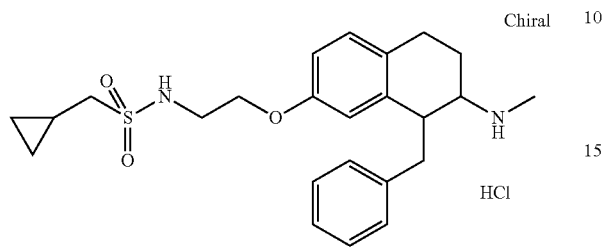

The synthesis was performed starting from (−)-ethyl 1-benzyl-7-(2-(cyclopropylmethylsulfonamido)ethoxy)-1,2,3,4-tetrahydronaphthalen-2-ylcarbamate (137), which was dissolved in THF (50 ml), after which LiAlH$_4$ was added at room temperature and the mixture was stirred for 8 h under reflux. Addition of 2N aqueous NaOH, extraction with CH$_2$Cl$_2$, washing of the organic layers with saturated NaHCO$_3$ solution and saturated NaCl solution and evaporation of the solvent gave a residue that was treated with iPrOH/HCl after which the product precipitated. After filtration a white salt (102 mg, 79%) was obtained. The racemate was separated by chiral chromatography on Chiracel AD (n-heptane/ethanol/tert-butanol 800:150:50) to deliver (after transfer to the salt form) (−)-N-(2-(8-benzyl-7-(pyrrolidin-1-yl)-5,6,7,8-tetrahydronaphthalen-2-yloxy)ethyl)-1-methyl-1H-imidazole-4-sulfonamide hydrochloride ([α]=−80.5° in MeOH, c=0.191 g/100 ml)

ESI-MS [M+H$^+$]=429 C$_{24}$H$_{32}$N$_2$O$_3$S=428

Example 163

1-Methyl-N-(2-{[8-(3-methylbenzyl)-7-(pyrrolidin-1-yl)-5,6,7,8-tetrahydronaphthalen-2-yl]oxy}ethyl)-1H-imidazole-4-sulfonamide

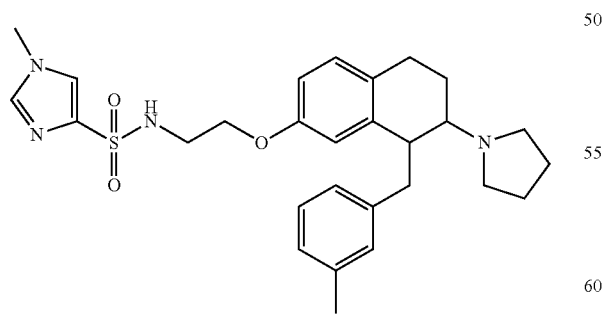

1-Methyl-N-(2-{[8-(3-methylbenzyl)-7-(pyrrolidin-1-yl)-5,6,7,8-tetrahydronaphthalen-2-yl]oxy}ethyl)-1H-imidazole-4-sulfonamide was synthesized in analogy to 264/88

ESI-MS [M+H$^+$]=509 C$_{28}$H$_{36}$N$_4$O$_3$S=508.

Example 164

N-(2-{[8-(3-Methoxybenzyl)-7-(pyrrolidin-1-yl)-5,6,7,8-tetrahydronaphthalen-2-yl]oxy}ethyl)-1-methyl-1H-imidazole-4-sulfonamide hydrochloride

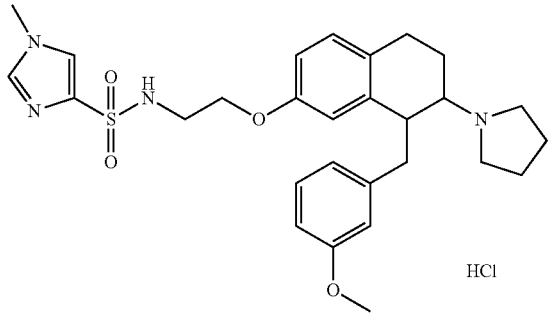 [SMILES: COc1cccc(CC2c3cc(OCCNS(=O)(=O)c4cn(C)cn4)ccc3CCC2N2CCCC2)c1 ; Cl]

N-(2-{[8-(3-Methoxybenzyl)-7-(pyrrolidin-1-yl)-5,6,7,8-tetrahydronaphthalen-2-yl]oxy}ethyl)-1-methyl-1H-imidazole-4-sulfonamide hydrochloride was synthesized in analogy to examples 264/88.

ESI-MS [M+H$^+$]=525 C$_{28}$H$_{36}$N$_4$O$_4$S=524

Example 165

1-Methyl-1H-imidazole-4-sulfonic acid {2-[7-amino-8-(3-trifluoromethyl-benzyl)-5,6,7,8-tetrahydro-naphthalen-2-yloxy]-ethyl}-amide hydrochloride

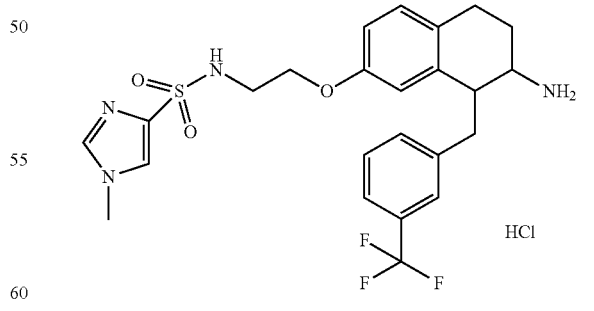

1-Methyl-1H-imidazole-4-sulfonic acid {2-[7-amino-8-(3-trifluoromethyl-benzyl)-5,6,7,8-tetrahydro-naphthalen-2-yloxy]-ethyl}-amide hydrochloride was synthesized in analogy to example 3.

ESI-MS [M+H$^+$]+=509 C$_{24}$H$_{27}$F$_3$N$_4$O$_3$S=508

The following examples were prepared in analogy to example 40:

Example 166

N-{[7-Amino-8-(3-chlorobenzyl)-5,6,7,8-tetrahydronaphthalen-2-yl]methyl}propane-1-sulfonamide hydrochloride

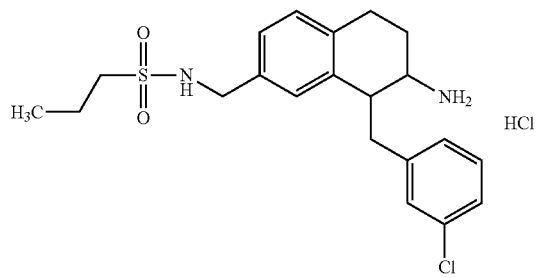 [SMILES: CCCS(=O)(=O)NCc1ccc2c(c1)C(Cc1cccc(Cl)c1)C(N)CC2 ; Cl]

ESI-MS [M+H⁺]=407 Calculated for $C_{21}H_{27}ClN_2O_2S$=406

Example 167

N-[(7-Amino-8-benzyl-5,6,7,8-tetrahydronaphthalen-2-ylmethyl]methanesulfonamide hydrochloride

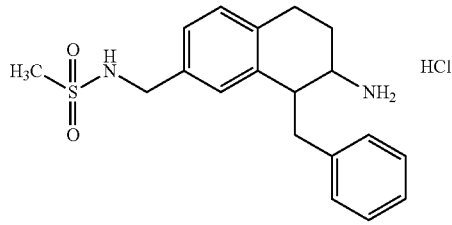 [SMILES: CS(=O)(=O)NCc1ccc2c(c1)C(Cc1ccccc1)C(N)CC2 ; Cl]

ESI-MS [M+H⁺]=345 Calculated for $C_{19}H_{24}N_2O_2S$=344

Example 168

N-[(7-Amino-8-benzyl-5,6,7,8-tetrahydronaphthalen-2-yl)methyl]benzenesulfonamide hydrochloride

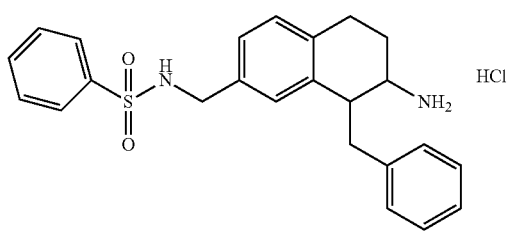 [SMILES: NC1CCc2ccc(CNS(=O)(=O)c3ccccc3)cc2C1Cc1ccccc1 ; Cl]

ESI-MS [M+H⁺]=407 Calculated for $C_{24}H_{26}N_2O_2S$=406

Example 169

Enantiomer 2 of N-{[7-Amino-8-benzyl-5,6,7,8-tetrahydronaphthalen-2-yl]methyl}propane-1-sulfonamide hydrochloride

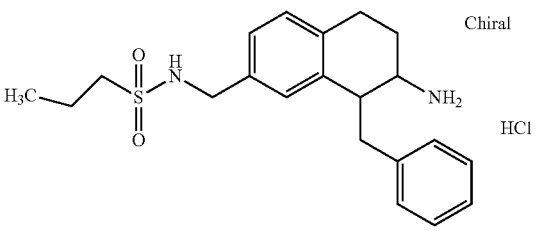 [SMILES: CCCS(=O)(=O)NCc1ccc2c(c1)C(Cc1ccccc1)C(N)CC2 ; Cl]

The compound was obtained by chiral chromatography (Chiralpak AD-H 30 mm ID×250 mm, n-hexane/EtOH/MeOH/diethylamine=20/40/40/0.1) from the racemic compound (example 42) as the first eluting peak. Optical rotation=−50° (589 nm, 25° C., c=0.1 in methanol).

ESI-MS [M+H⁺]=373 Calculated for $C_{21}H_{28}N_2O_2S$=372

Example 170

Enantiomer 1 of N-{[7-amino-8-benzyl-5,6,7,8-tetrahydronaphthalen-2-yl]methyl}propane-1-sulfonamide hydrochloride

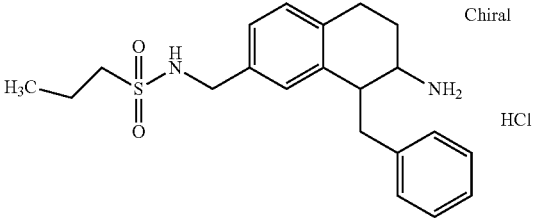 [SMILES: CCCS(=O)(=O)NCc1ccc2c(c1)C(Cc1ccccc1)C(N)CC2 ; Cl]

The compound was obtained by chiral chromatography (Chiralpak AD-H 30 mm ID×250 mm, n-hexane/EtOH/MeOH/diethylamine=20/40/40/0.1) from the racemic compound (example 42) as the second eluting peak. Optical rotation=+49° (589 nm, 25° C., c=0.1 in methanol).

ESI-MS [M+H⁺]=373 Calculated for $C_{21}H_{28}N_2O_2S$=372

Example 171

N-{[7-Amino-8-(3-fluorobenzyl)-5,6,7,8-tetrahydronaphthalen-2-yl]methyl}propane-1-sulfonamide hydrochloride

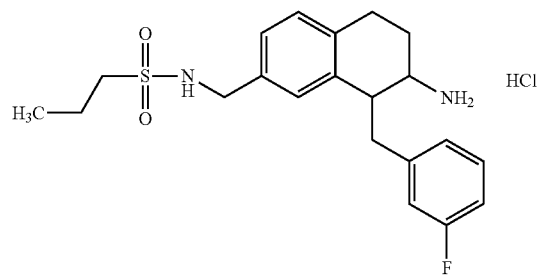 [SMILES: CCCS(=O)(=O)NCc1ccc2c(c1)C(Cc1cccc(F)c1)C(N)CC2 ; Cl]

ESI-MS [M+H$^+$]=391 Calculated for C$_{21}$H$_{27}$FN$_2$O$_2$S=390

Example 172

N-[(7-Amino-8-benzyl-5,6,7,8-tetrahydronaphthalen-2-yl)methyl]-1-methyl-1H-pyrazole-4-sulfonamide hydrochloride

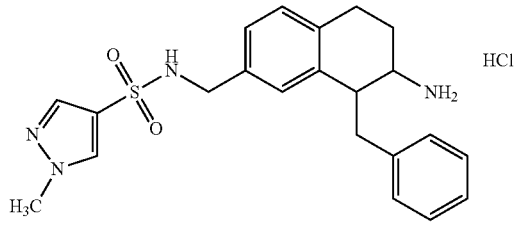 [SMILES: Cn1cc(S(=O)(=O)NCc2ccc3c(c2)C(Cc2ccccc2)C(N)CC3)cn1 ; Cl]

ESI-MS [M+H$^+$]=411 Calculated for C$_{22}$H$_{26}$N$_4$O$_2$S=410

Example 173

N-[(7-Amino-8-benzyl-5,6,7,8-tetrahydronaphthalen-2-yl)methyl]-1-methyl-1H-imidazole-4-sulfonamide hydrochloride

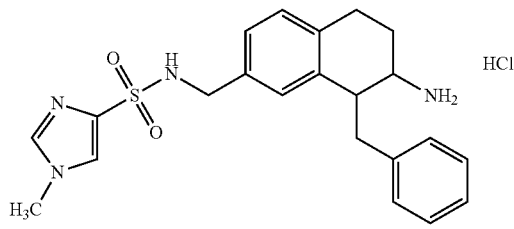 [SMILES: Cn1cnc(S(=O)(=O)NCc2ccc3c(c2)C(Cc2ccccc2)C(N)CC3)c1 ; Cl]

ESI-MS [M+H$^+$]=411 Calculated for C$_{22}$H$_{26}$N$_4$O$_2$S=410

Example 174

N-{[7-Amino-8-(4-fluorobenzyl)-5,6,7,8-tetrahydronaphthalen-2-yl]methyl}cyclobutanesulfonamide hydrochloride

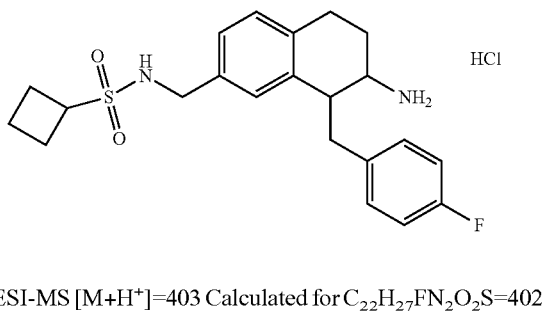

ESI-MS [M+H$^+$]=403 Calculated for C$_{22}$H$_{27}$FN$_2$O$_2$S=402

Example 175

N-{[7-Amino-8-(4-fluorobenzyl)-5,6,7,8-tetrahydronaphthalen-2-yl]methyl}propane-1-sulfonamide hydrochloride

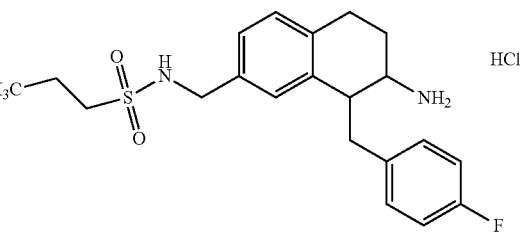

ESI-MS [M+H$^+$]=391 Calculated for C$_{21}$H$_{27}$FN$_2$O$_2$S=390

Example 176

N-{[7-Amino-8-(4-fluorobenzyl)-5,6,7,8-tetrahydronaphthalen-2-yl]methyl}-1-methyl-1H-imidazole-4-sulfonamide hydrochloride

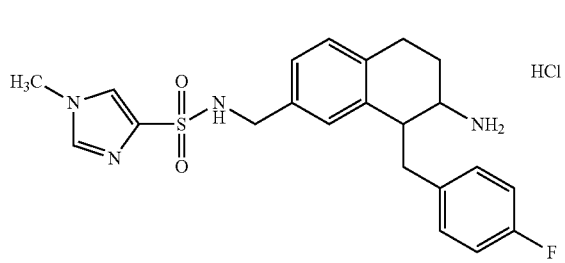 [SMILES: Cn1cnc(S(=O)(=O)NCc2ccc3c(c2)C(Cc2ccc(F)cc2)C(N)CC3)c1 ; Cl]

ESI-MS [M+H$^+$]=429 Calculated for C$_{22}$H$_{25}$FN$_4$O$_2$S=428

Example 177

N-{[7-Amino-8-(3-fluorobenzyl)-5,6,7,8-tetrahydronaphthalen-2-yl]methyl}-1-methyl-1H-imidazole-4-sulfonamide hydrochloride

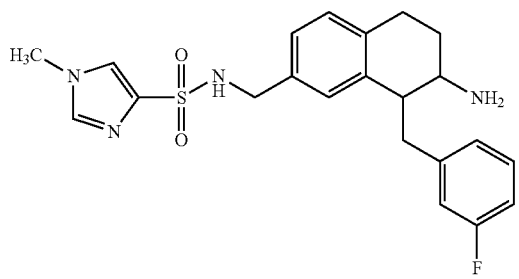

ESI-MS [M+H$^+$]=429 Calculated for $C_{22}H_{25}FN_4O_2S$=428

Example 178

N-{[7-Amino-8-(3-fluorobenzyl)-5,6,7,8-tetrahydronaphthalen-2-yl]methyl}-1-methyl-1H-pyrazole-4-sulfonamide hydrochloride

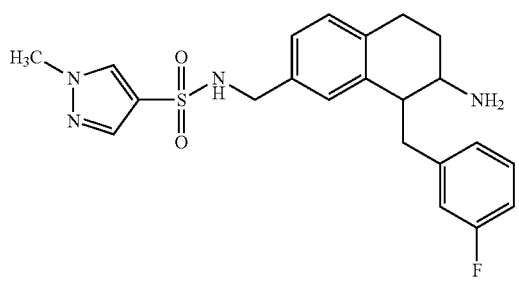

ESI-MS [M+H$^+$]=429 Calculated for $C_{22}H_{25}FN_4O_2S$=428

Example 179

N-{[7-Amino-8-benzyl-5,6,7,8-tetrahydronaphthalen-2-yl]methyl}-3-methylbenzenesulfonamide hydrochloride

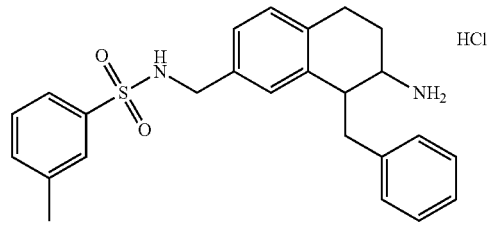 [SMILES: Cc1cccc(S(=O)(=O)NCc2ccc3c(c2)C(Cc2ccccc2)C(N)CC3)c1 ; Cl]

ESI-MS [M+H$^+$]=421 Calculated for $C_{25}H_{28}N_2O_2S$=420

Example 180

N-{[7-Amino-8-benzyl-5,6,7,8-tetrahydronaphthalen-2-yl]methyl}-1-methyl-1H-pyrrole-3-sulfonamide hydrochloride

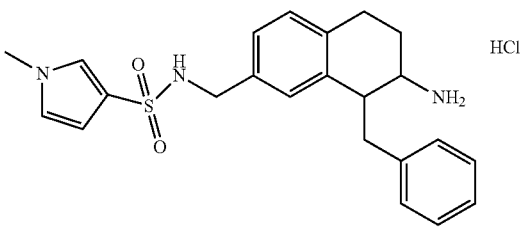 [SMILES: Cn1ccc(S(=O)(=O)NCc2ccc3c(c2)C(Cc2ccccc2)C(N)CC3)c1 ; Cl]

ESI-MS [M+H$^+$]=410 Calculated for $C_{23}H_{27}N_3O_2S$=409

Example 181

N-{[7-Amino-8-benzyl-5,6,7,8-tetrahydronaphthalen-2-yl]methyl}pyridine-3-sulfonamide dihydrochloride

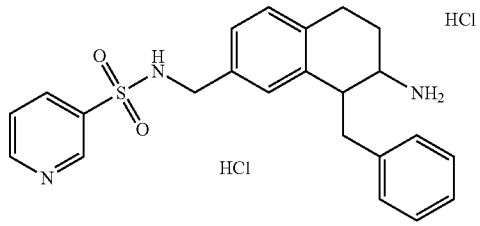 [SMILES: NC1CCc2ccc(CNS(=O)(=O)c3cccnc3)cc2C1Cc1ccccc1 ; Cl ; Cl]

ESI-MS [M+H$^+$]=408 Calculated for $C_{23}H_{25}N_3O_2S$=407

Example 182

N-{[7-Amino-8-benzyl-5,6,7,8-tetrahydronaphthalen-2-yl]methyl}-1-methyl-3-(trifluoromethyl)-1H-pyrazole-4-sulfonamide hydrochloride

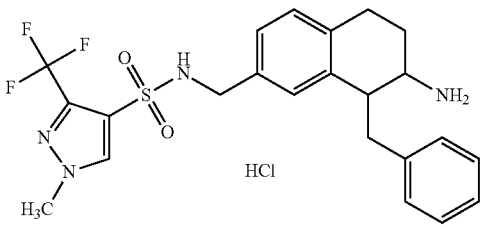 [SMILES: Cn1cc(S(=O)(=O)NCc2ccc3c(c2)C(Cc2ccccc2)C(N)CC3)c(C(F)(F)F)n1 ; Cl]

ESI-MS [M+H⁺]=479 Calculated for $C_{23}H_{25}F_3N_4O_2S$=478

Example 183

N-{[7-Amino-8-benzyl-5,6,7,8-tetrahydronaphthalen-2-yl]methyl}-1-methyl-1H-pyrazole-3-sulfonamide hydrochloride

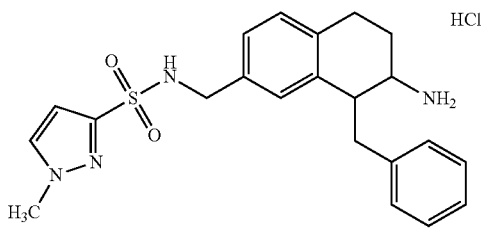 [SMILES: Cn1ccc(S(=O)(=O)NCc2ccc3c(c2)C(Cc2ccccc2)C(N)CC3)n1 ; Cl]

Example 184

N-{[7-Amino-8-(3-fluorobenzyl)-5,6,7,8-tetrahydronaphthalen-2-yl]methyl}cyclobutanesulfonamide hydrochloride

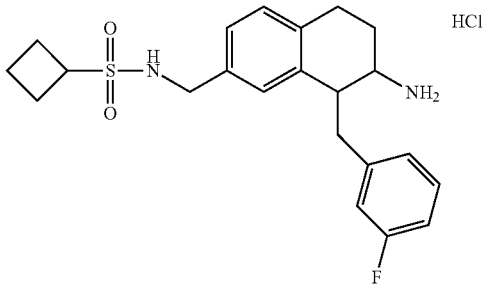 [SMILES: NC1CCc2ccc(CNS(=O)(=O)C3CCC3)cc2C1Cc1cccc(F)c1 ; Cl]

ESI-MS [M+H⁺]=403 Calculated for $C_{22}H_{27}FN_2O_2S$=402

Example 185

N-{[7-Amino-8-(3,4-difluorobenzyl)-5,6,7,8-tetrahydronaphthalen-2-yl]methyl}-1-cyclopropylmethanesulfonamide hydrochloride

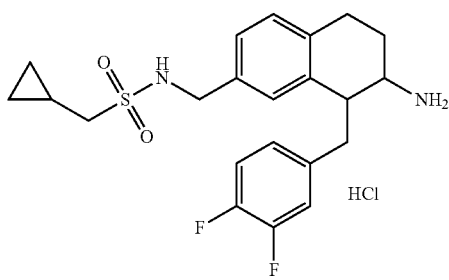 [SMILES: NC1CCc2ccc(CNS(=O)(=O)CC3CC3)cc2C1Cc1ccc(F)c(F)c1 ; Cl]

ESI-MS [M+H⁺]=421 Calculated for $C_{22}H_{26}F_2N_2O_2S$=420

Example 186

N-{[7-Amino-8-(3,4-difluorobenzyl)-5,6,7,8-tetrahydronaphthalen-2-yl]methyl}cyclobutanesulfonamide hydrochloride

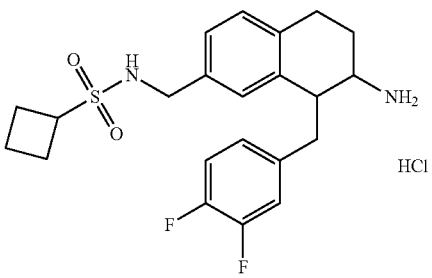 [SMILES: NC1CCc2ccc(CNS(=O)(=O)C3CCC3)cc2C1Cc1ccc(F)c(F)c1 ; Cl]

ESI-MS [M+H⁺]=421 Calculated for $C_{22}H_{26}F_2N_2O_2S$=420

Example 187

N-{[8-Benzyl-7-(methylamino)-5,6,7,8-tetrahydronaphthalen-2-yl]methyl}propane-1-sulfonamide hydrochloride

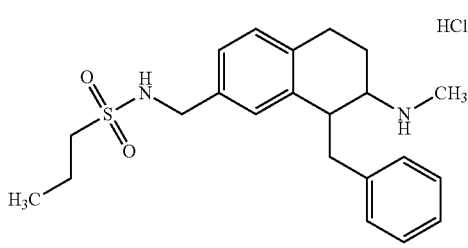 [SMILES: Cl ; CCCS(=O)(=O)NCc1ccc2c(c1)C(Cc1ccccc1)C(NC)CC2]

tert-Butyl[1-benzyl-7-{[(propylsulfonyl)amino]methyl}-1,2,3,4-tetrahydronaphthalen-2-yl]carbamate prepared in analogy to example 39 (1240 mg, 2.62 mmol) was dissolved in tetrahydrofuran (50 mL). A solution of lithium aluminium hydride (1 M in tetrahydrofuran, 7.87 mL, 7.87 mmol) was added dropwise at room temperature. The reaction mixture was then heated to 60° C. for 1 h. Aqueous work-up, purification of the extracted product by flash chromatography (silica gel, dichloromethane, methanol) and treatment with 1.25 M hydrochloric acid in ethanol followed by concentration in vacuo gave the desired product.

Yield: 590 mg (1.4 mmol, 53%).

ESI-MS [M+H⁺]=425 Calculated for $C_{22}H_{30}N_2O_2S$=424

In analogy to example 187 the following examples were prepared:

Example 188

N-{[8-Benzyl-7-(methylamino)-5,6,7,8-tetrahydronaphthalen-2-yl]methyl}cyclobutanesulfonamide hydrochloride

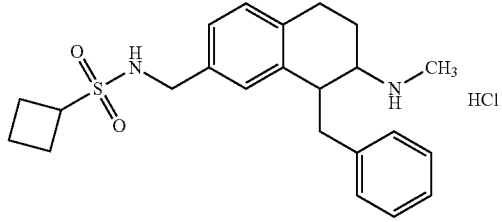 [SMILES: CNC1CCc2ccc(CNS(=O)(=O)C3CCC3)cc2C1Cc1ccccc1 ; Cl]

ESI-MS [M+H$^+$]=400 Calculated for $C_{23}H_{30}N_2O_2S$=399

Example 189

N-{[8-Benzyl-7-(methylamino)-5,6,7,8-tetrahydronaphthalen-2-yl]methyl}-3-methylbenzenesulfonamide hydrochloride

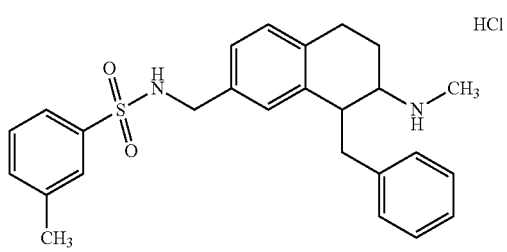 [SMILES: Cl ; CNC1CCc2ccc(CNS(=O)(=O)c3cccc(C)c3)cc2C1Cc1ccccc1]

ESI-MS [M+H$^+$]=435 Calculated for $C_{26}H_{30}N_2O_2S$=434

Example 190

N-{[8-Benzyl-7-(methylamino)-5,6,7,8-tetrahydronaphthalen-2-yl]methyl}-1-methyl-1H-pyrrole-3-sulfonamide hydrochloride

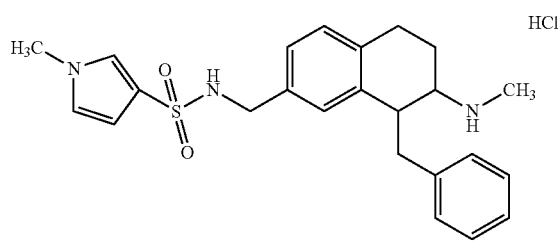

ESI-MS [M+H$^+$]=424 Calculated for $C_{24}H_{29}N_3O_2S$=423

Example 191

N-{[8-Benzyl-7-(methylamino)-5,6,7,8-tetrahydronaphthalen-2-yl]methyl}-1-methyl-1H-pyrazole-3-sulfonamide hydrochloride

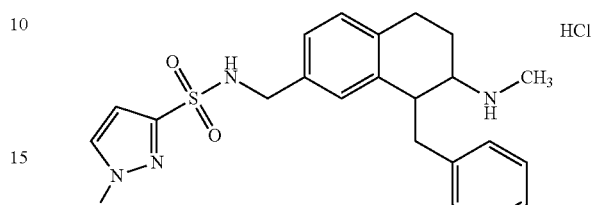

ESI-MS [M+H$^+$]=425 Calculated for $C_{23}H_{28}N_4O_2S$=424

Example 192

Enantiomer 1 of N-{[8-benzyl-7-(methylamino)-5,6,7,8-tetrahydronaphthalen-2-yl]methyl}propane-1-sulfonamide hydrochloride

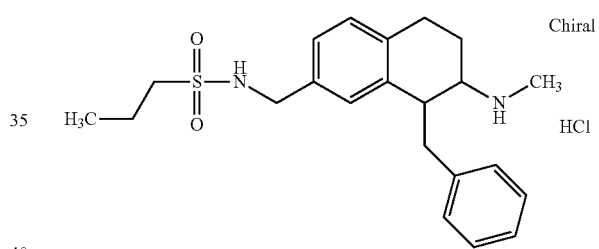

A chiral building block, i.e. an enantiomer of tert-butyl (1-benzyl-7-cyano-1,2,3,4-tetrahydronaphthalen-2-yl)carbamate

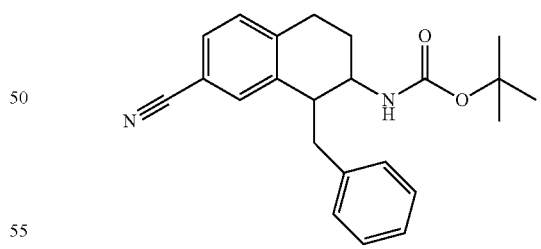

was used for the synthesis.

tert-Butyl (1-benzyl-7-cyano-1,2,3,4-tetrahydronaphthalen-2-yl)carbamate can be prepared in analogy to the dichloroderivative described in example 34. The cis-isomer can be separated into the enantiomers by chiral chromatography (Daicel, Chiralpak IC, 250×4.6 mm ID, 5µ, n-heptane/ethanol=1/9 with 0.1% triethylamine). The enantiomer eluting second was used in the syntheses described above.

ESI-MS [M+H$^+$]=387 Calculated for $C_{22}H_{30}N_2O_2S$=386

Example 193

Enantiomer 1 of N-{[8-benzyl-7-(methylamino)-5,6,7,8-tetrahydronaphthalen-2-yl]methyl}cyclobutanesulfonamide hydrochloride

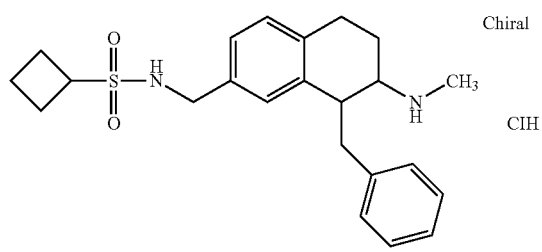

The enantiomer of tert-butyl (1-benzyl-7-cyano-1,2,3,4-tetrahydronaphthalen-2-yl)carbamate described in example 192 was as chiral building block for the synthesis.
ESI-MS [M+H$^+$]+=399 Calculated for $C_{23}H_{30}N_2O_2S$=398

Example 194

N-{[trans-8-Benzyl-7-(methylamino)-5,6,7,8-tetrahydronaphthalen-2-yl]methyl}propane-1-sulfonamide hydrochloride

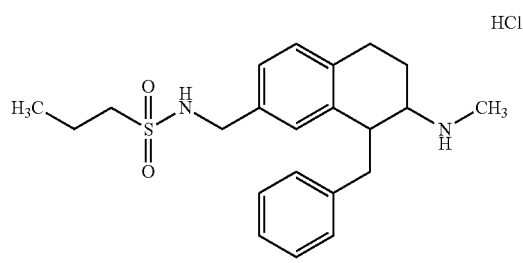 [SMILES: Cl ; CCCS(=O)(=O)NCc1ccc2c(c1)C(Cc1ccccc1)C(NC)CC2]

Prepared from the trans derivative obtained as a by-product in the recrystallization of

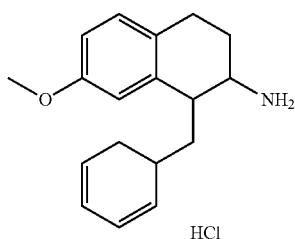 [SMILES: COc1ccc2c(c1)C(CC1C=CC=CC1)C(N)CC2 ; Cl]

(cf. example 1).
ESI-MS [M+H$^+$]=387 Calculated for $C_{22}H_{30}N_2O_2S$=386

Example 195

N-{[8-Benzyl-7-(methylamino)-5,6,7,8-tetrahydronaphthalen-2-yl]methyl}-1-methyl-1H-imidazole-4-sulfonamide hydrochloride

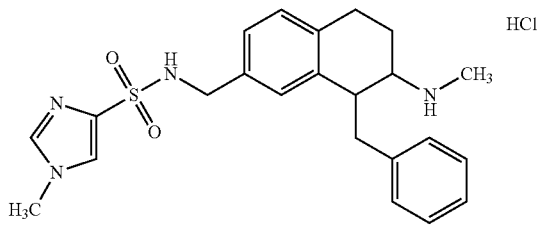 [SMILES: CNC1CCc2ccc(CNS(=O)(=O)c3cn(C)cn3)cc2C1Cc1ccccc1 ; Cl]

ESI-MS [M+H$^+$]=425 Calculated for $C_{23}H_{28}N_4O_2S$=424

Example 196

N-(1-Benzyl-7-{[(propylsulfonyl)amino]methyl}-1,2,3,4-tetrahydronaphthalen-2-yl)acetamide

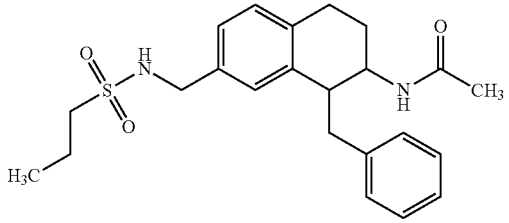 [SMILES: CCCS(=O)(=O)NCc1ccc2c(c1)C(Cc1ccccc1)C(NC(C)=O)CC2]

N-{[7-Amino-8-benzyl-5,6,7,8-tetrahydronaphthalen-2-yl]methyl}propane-1-sulfonamide (cf. example 42) was acetylated in dichloromethane with acetyl chloride in the presence of ethyldiisopropylamine at room temperature.
ESI-MS [M+H$^+$]=415 Calculated for $C_{23}H_{30}N_2O_3S$=414

Example 197

N-[(1-(4-Fluorobenzyl)-7-({[(1-methyl-1H-imidazol-4-yl)sulfonyl]amino}methyl)-1,2,3,4-tetrahydronaphthalen-2-yl]acetamide

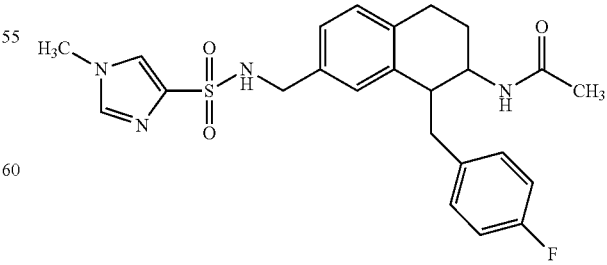

This compound was prepared in analogy to example 196.
ESI-MS [M+H$^+$]=471 Calculated for $C_{24}H_{27}FN_4O_3S$=470

Example 198

N-{[8-Benzyl-7-(ethylamino)-5,6,7,8-tetrahydronaphthalen-2-yl]methyl}propane-1-sulfonamide hydrochloride

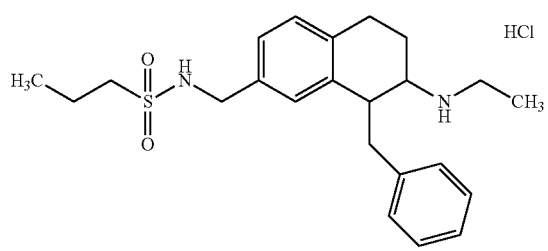 [SMILES: CCCS(=O)(=O)NCc1ccc2c(c1)C(Cc1ccccc1)C(NCC)CC2 ; Cl]

N-(1-Benzyl-7-{[(propylsulfonyl)amino]methyl}-1,2,3,4-tetrahydronaphthalen-2-yl)acetamide (example 196, 153 mg, 0.37 mmol) was dissolved in tetrahydrofuran (5 mL). 1 M Boran dimethylsulfide complex solution in tetrahydrofuran (852 µL, 8.52 mmol) was added and the reaction mixture stirred at room temperature over night. Water was added and the mixture extracted with dichloromethane (three times). The combined organic extracts were dried (MgSO$_4$) and concentrated in vacuo. The crude product was purified by flash chromatography (silica gel, dichloromethane, methanol). Excess 6 M hydrochloric acid in isopropanol was added. The solvent was evaporated and the product dried in vacuo. Yield: 70 mg (0.16 mmol, 36%).

ESI-MS [M+H$^+$]=401 Calculated for C$_{23}$H$_{32}$N$_2$O$_2$S=400

The following examples were prepared in analogy to example 198:

Example 199

1-Methyl-1H-imidazole-4-sulfonic acid [7-ethylamino-8-(4-fluoro-benzyl)-5,6,7,8-tetrahydro-naphthalen-2-ylmethyl]-amide hydrochloride

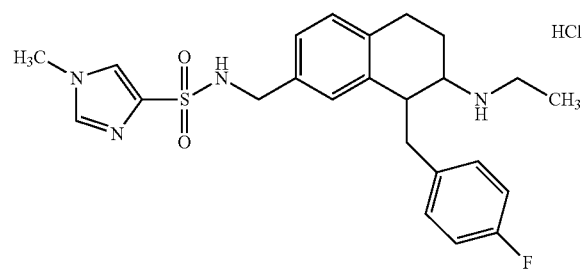 [SMILES: CCNC1CCc2ccc(CNS(=O)(=O)c3cn(C)cn3)cc2C1Cc1ccc(F)cc1 ; Cl]

ESI-MS [M+H$^+$]=457 Calculated for C$_{24}$H$_{29}$FN$_4$O$_2$S=456

Example 200

1-Methyl-1H-pyrazole-4-sulfonic acid [7-ethylamino-8-(3-fluoro-benzyl)-5,6,7,8-tetrahydronaphthalen-2-ylmethyl]-amide hydrochloride

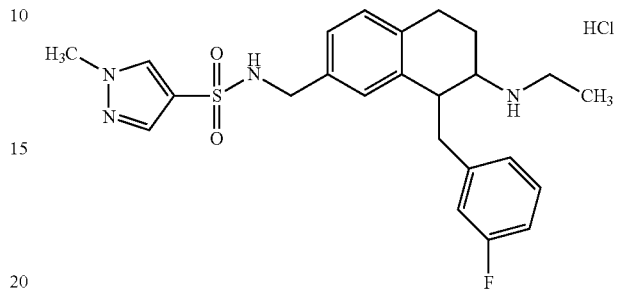

ESI-MS [M+H$^+$]=457 Calculated for C$_{24}$H$_{29}$FN$_4$O$_2$S=456

Example 201

N-{3-[7-Amino-8-(4-chlorobenzyl)-5,6,7,8-tetrahydronaphthalen-2-yl]propyl}propane-1-sulfonamide hydrochloride 201.1 tert-Butyl[1-(4-chlorobenzyl)-7-{3-[(propylsulfonyl)amino]propyl}-1,2,3,4-tetrahydronaphthalen-2-yl]carbamate

To a solution of 9-BBN (0.5 M in tetrahydrofuran, 8.85 mL, 4.42 mmol) was added dropwise a solution N-allylpropane-1-sulfonamide (1152 mg, 7.06 mmol) in tetrahydrofuran (1 mL) a 0° C. After stirring at 0° C. to 5° C. for 3.5 hours dioxane (25 mL) was added followed by 7-(tert-butoxycarbonylamino)-8-(4-chlorobenzyl)-5,6,7,8-tetrahydronaphthalen-2-yl trifluoromethanesulfonate (1000 mg, 1.923 mmol, prepared analogously to example 34.3), palladium acetate (43.2 mg, 0.192 mmol), triphenylphosphine (101 mg, 0.385 mmol) and cesium carbonate (1253 mg, 3.85 mmol). The yellow reaction mixture was heated under reflux for 3 hours. The reaction mixture was diluted with ethyl acetate (60 mL) and washed with water (2×40 mL). The organic layer was dried and concentrated in vacuo. The crude product was purified by flash chromatography (silica gel, dichloro methane, methanol).

Yield: 854 mg (1.596 mmol, 83%).

201. 2N-{3-[7-Amino-8-(4-chlorobenzyl)-5,6,7,8-tetrahydronaphthalen-2-yl]propyl}propane-1-sulfonamide hydrochloride

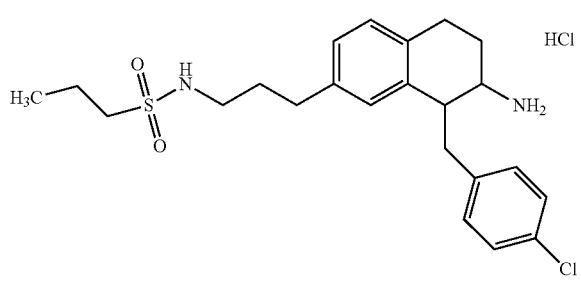 [SMILES: CCCS(=O)(=O)NCCCc1ccc2c(c1)C(Cc1ccc(Cl)cc1)C(N)CC2 ; Cl]

tert-Butyl[1-(4-chlorobenzyl)-7-{3-[(propylsulfonyl)amino]propyl}-1,2,3,4-tetrahydronaphthalen-2-yl]carbamate (150 mg, 0.281 mmol) was dissolved in dichloromethane (3 mL) and a solution of hydrochloric acid (0.5 mL, 5 M in isopropanol) was added. After stirring at room temperature for 2 hours the solvent was removed in vacuo. Water was added (15 mL) and the pH was adjusted to 9 with aqueous saturated sodium bicarbonate and the mixture was extracted with dichloromethane (3×15 mL). The combined organic extracts were dried and concentrated in vacuo. The crude product was purified by flash chromatography (silica gel, dichloromethane, methanol). The product was dissolved in dichloromethane (2 mL) and a solution of hydrochloric acid in ethanol (1.25 M) was added. The solvent was removed in vacuo. Yield: 31.4 mg (0.187 mmol, 36%).

ESI-MS [M+H$^+$]=435 Calculated for $C_{23}H_{31}ClN_2O_2S$=434

The following examples were prepared in analogy to example 201:

Example 202

N-{3-[7-Amino-8-(4-chlorobenzyl)-5,6,7,8-tetrahydronaphthalen-2-yl]propyl}-1-cyclopropylmethanesulfonamide hydrochloride

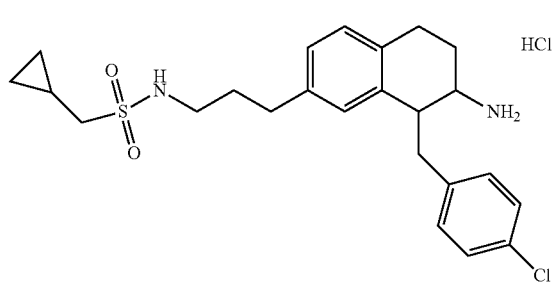 [SMILES: NC1CCc2ccc(CCCNS(=O)(=O)CC3CC3)cc2C1Cc1ccc(Cl)cc1 ; Cl]

ESI-MS [M+H$^+$]=447 Calculated for $C_{24}H_{31}ClN_2O_2S$=446

Example 203

N-{3-[7-Amino-8-(3,4-dichlorobenzyl)-5,6,7,8-tetrahydronaphthalen-2-yl]propyl}propane-1-sulfonamide hydrochloride

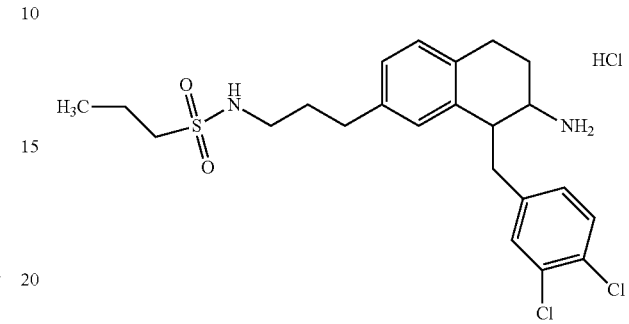

ESI-MS [M+H$^+$]=469 Calculated for $C_{23}H_{30}Cl_2N_2O_2S$=468

Example 204

N-{3-[7-Amino-8-(3,4-difluoro-benzyl)-5,6,7,8-tetrahydro-naphthalen-2-yl]-propyl}-C-cyclopropyl-methanesulfonamide hydrochloride

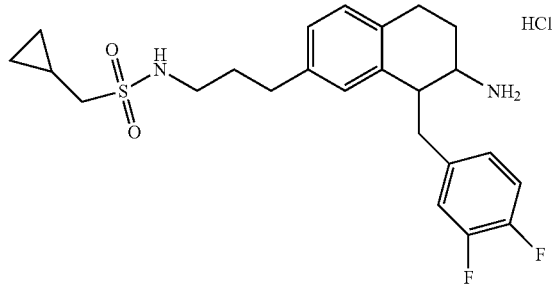 [SMILES: NC1CCc2ccc(CCCNS(=O)(=O)CC3CC3)cc2C1Cc1ccc(F)c(F)c1 ; Cl]

ESI-MS [M+H$^+$]=449 Calculated for $C_{24}H_{30}F_2N_2O_2S$=448

Example 205

N-{3-[7-Amino-8-benzyl-5,6,7,8-tetrahydronaphthalen-2-yl]propyl}propane-1-sulfonamide hydrochloride

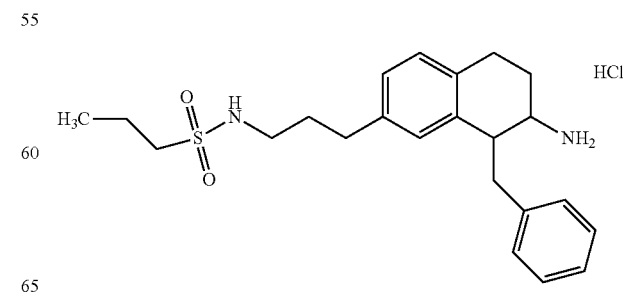

ESI-MS [M+H$^+$]=401 Calculated for $C_{23}H_{32}N_2O_2S$=400

Example 206

N-{3-[7-Amino-8-(3,4-difluoro-benzyl)-5,6,7,8-tetrahydronaphthalen-2-yl]propyl}propane-1-sulfonamide hydrochloride

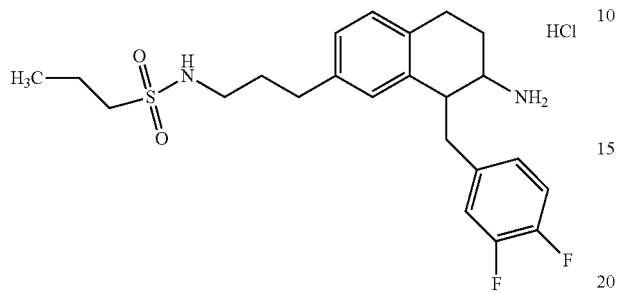

ESI-MS [M+H$^+$]=437 Calculated for C$_{23}$H$_{30}$F$_2$N$_2$O$_2$S=436

Example 207

N-{3-[7-Amino-8-benzyl-5,6,7,8-tetrahydronaphthalen-2-yl]propyl}-1-cyclopropylmethanesulfonamide trifluoroacetate

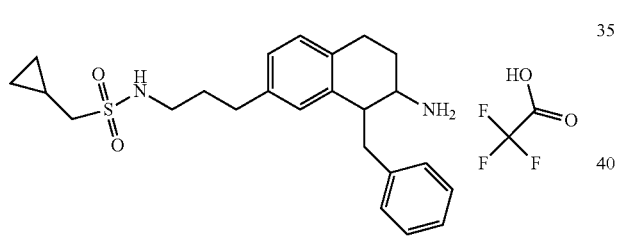

ESI-MS [M+H$^+$]=413 Calculated for C$_{24}$H$_{32}$N$_2$O$_2$S=412

Example 208

N-{3-[7-Amino-8-(4-fluorobenzyl)-5,6,7,8-tetrahydronaphthalen-2-yl]propyl}-1-cyclopropylmethanesulfonamide hydrochloride

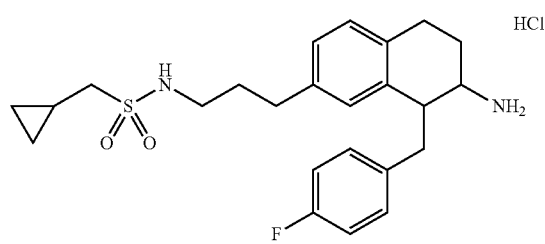 [SMILES: NC1CCc2ccc(CCCNS(=O)(=O)CC3CC3)cc2C1Cc1ccc(F)cc1 ; Cl]

ESI-MS [M+H$^+$]=431 Calculated for C$_{24}$H$_{31}$FN$_2$O$_2$S=430

Example 209

N-{3-[7-Amino-8-(3-fluorobenzyl)-5,6,7,8-tetrahydronaphthalen-2-yl]propyl}propane-1-sulfonamide hydrochloride

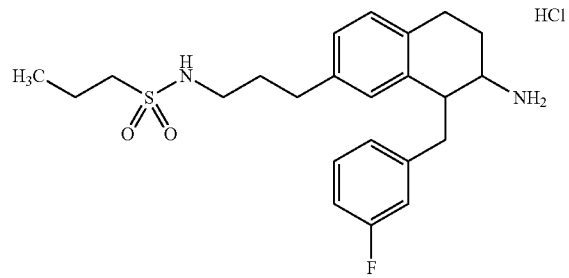 [SMILES: CCCS(=O)(=O)NCCCc1ccc2c(c1)C(Cc1cccc(F)c1)C(N)CC2 ; Cl]

ESI-MS [M+H$^+$]=419 Calculated for C$_{23}$H$_{31}$FN$_2$O$_2$S=418

Example 210

N-{3-[7-Amino-8-(3-fluorobenzyl)-5,6,7,8-tetrahydronaphthalen-2-yl]propyl}-1-cyclopropylmethanesulfonamide hydrochloride

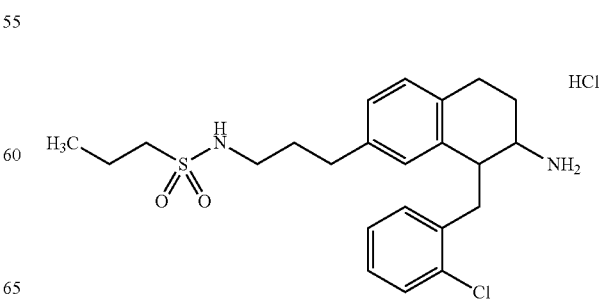

ESI-MS [M+H$^+$]=431 Calculated for C$_{24}$H$_{31}$FN$_2$O$_2$S=430

Example 211

N-{3-[7-Amino-8-(2-chlorobenzyl)-5,6,7,8-tetrahydronaphthalen-2-yl]propyl}propane-1-sulfonamide hydrochloride ESI-MS [M+H$^+$]=435 Calculated for C$_{23}$H$_{31}$ClN$_2$O$_2$S=434

Example 212

N-{3-[7-Amino-8-(2-chloro-benzyl)-5,6,7,8-tetrahydro-naphthalen-2-yl]-propyl}-C-cyclopropyl-methanesulfonamide hydrochloride

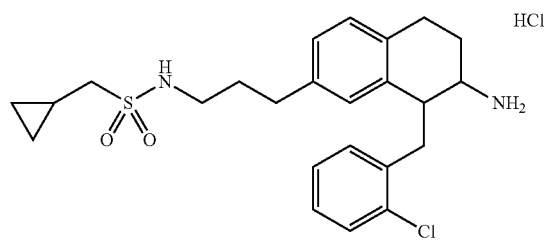 [SMILES: NC1CCc2ccc(CCCNS(=O)(=O)CC3CC3)cc2C1Cc1ccccc1Cl ; Cl]

ESI-MS [M+H$^+$]=447 Calculated for C$_{24}$H$_{31}$ClN$_2$O$_2$S=446

Example 213

N-{3-[7-Amino-8-(4-fluorobenzyl)-5,6,7,8-tetrahydronaphthalen-2-yl]propyl}propane-1-sulfonamide hydrochloride

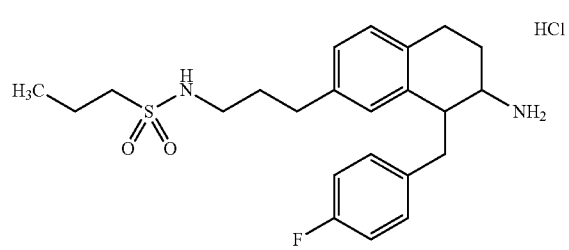 [SMILES: CCCS(=O)(=O)NCCCc1ccc2c(c1)C(Cc1ccc(F)cc1)C(N)CC2 ; Cl]

ESI-MS [M+H$^+$]=419 Calculated for C$_{23}$H$_{31}$FN$_2$O$_2$S=418

Example 214

N-[1-(3-Fluorobenzyl)-7-{3-[(propylsulfonyl)amino]propyl}-1,2,3,4-tetrahydronaphthalen-2-yl]acetamide

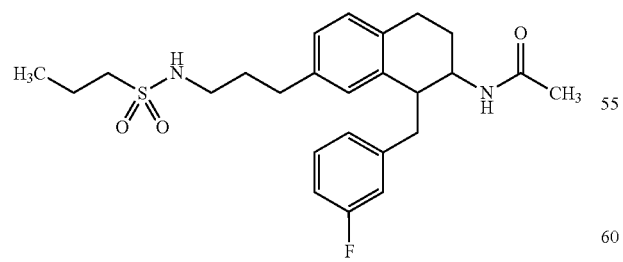

N-(3-(7-Amino-8-(3-fluorobenzyl)-5,6,7,8-tetrahydronaphthalen-2-yl)propyl)propane-1-sulfonamide (cf. example 209: 45 mg, 0.108 mmol) and triethylamine (15 µL, 0.108 mmol) were dissolved in dichloromethane (2 mL). Acetylchloride (7.64 µL, 0.108 mmol) were added. The reaction mixture was stirred for 12 hours at room temperature. The reaction mixture was diluted with dichloromethane and successively washed with hydrochloric acid, water and saturated sodium chloride solution. The organic layer was dried and concentrated in vacuo. The crude product was purified by flash-chromatography (silica gel, dichloromethane, methanol). Yield: 37 mg (0.08 mmol, 75%).

ESI-MS [M+H$^+$]=461 Calculated for C$_{25}$H$_{33}$FN$_2$O$_3$S=460

In analogy to example 214 the following examples were prepared:

Example 215

N-[1-(4-Fluorobenzyl)-7-{3-[(propylsulfonyl)amino]propyl}-1,2,3,4-tetrahydronaphthalen-2-yl]acetamide

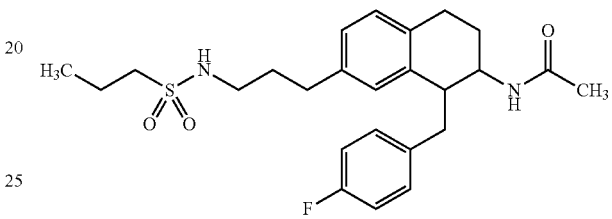

ESI-MS [M+H$^+$]=461 Calculated for C$_{25}$H$_{33}$FN$_2$O$_3$S=460

Example 216

N-[1-Benzyl-7-(3-{[(cyclopropylmethyl)sulfonyl]amino}propyl)-1,2,3,4-tetrahydronaphthalen-2-yl]acetamide

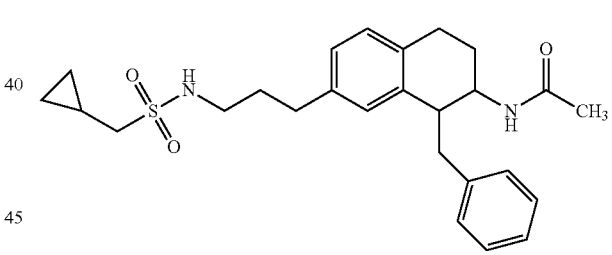

ESI-MS [M+H$^+$]=455 Calculated for C$_{26}$H$_{34}$N$_2$O$_3$S=454

Example 217

N-[1-Benzyl-7-{3-[(propylsulfonyl)amino]propyl}-1,2,3,4-tetrahydronaphthalen-2-yl]acetamide

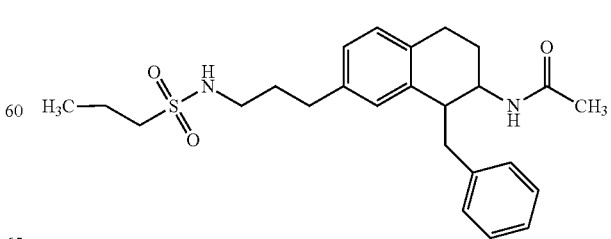

ESI-MS [M+H$^+$]=443 Calculated for C$_{25}$H$_{34}$N$_2$O$_3$S=442

Example 218

N-[7-(3-{[(Cyclopropylmethyl)sulfonyl]amino}propyl)-1-(3-fluorobenzyl)-1,2,3,4-tetrahydronaphthalen-2-yl]acetamide

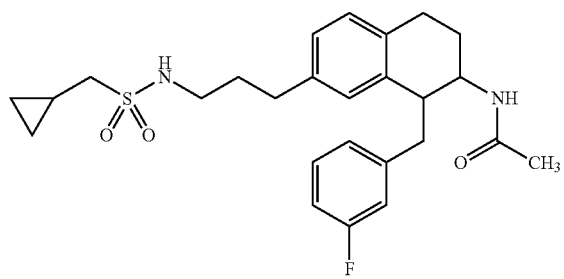 [SMILES: CC(=O)NC1CCc2ccc(CCCNS(=O)(=O)CC3CC3)cc2C1Cc1cccc(F)c1]

ESI-MS [M+H⁺]=473 Calculated for $C_{26}H_{33}FN_2O_3S$=472

Example 219

Propane-1-sulfonic acid {3-[7-ethylamino-8-(3-fluoro-benzyl)-5,6,7,8-tetrahydronaphthalen-2-yl]-propyl}-amide hydrochloride

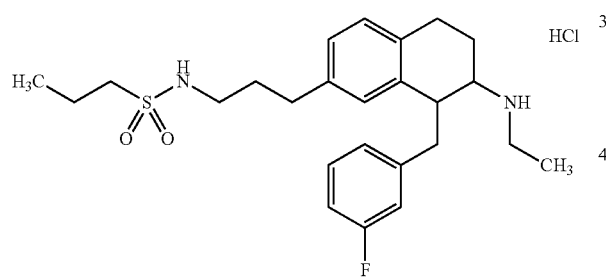

N-(1-(3-Fluorobenzyl)-7-(3-(propylsulfonamido)propyl)-1,2,3,4-tetrahydronaphthalen-2-yl)acetamide (cf. example 214, 19.5 mg, 0.042 mmol) was dissolved in tetrahydrofuran (1 mL) and borane dimethylsulfide (106 µL, 0.212 mmol) was added. The reaction mixture was stirred for 5 hours at 50° C. After cooling to room temperature aqueous hydrochloric acid was added. The mixture was made alkaline by the addition of sodium bicarbonate and extracted several times with dichloromethane. The combined organic extracts were dried (MgSO₄), concentrated in vacuo and the crude product purified by flash-chromatography (silica gel, dichloromethane, methanol). An excess of 1 M hydrochloric acid in ether was added to the purified product and the ether distilled off. Yield: 7 mg (0.016 mmol, 37%).

ESI-MS [M+H⁺]+=447 Calculated for $C_{25}H_{35}FN_2O_2S$=446

The following examples were prepared in analogy to example 219:

Example 220

N-{3-[7-(Ethylamino)-8-(4-fluorobenzyl)-5,6,7,8-tetrahydronaphthalen-2-yl]propyl}propane-1-sulfonamide hydrochloride

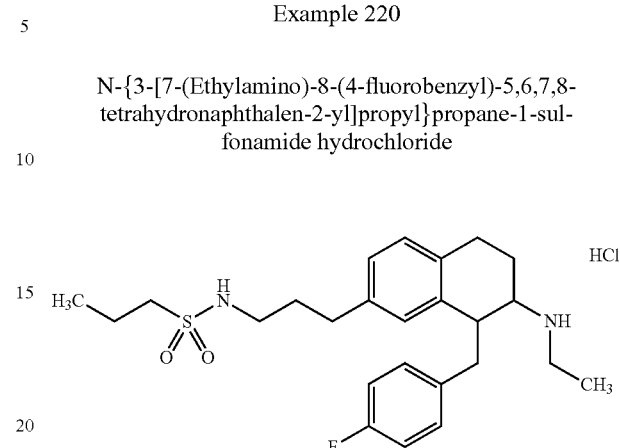

ESI-MS [M+H⁺]=447 Calculated for $C_{25}H_{35}FN_2O_2S$=446

Example 221

C-Cyclopropyl-N-{3-[7-ethylamino-8-(3-fluoro-benzyl)-5,6,7,8-tetrahydro-naphthalen-2-yl]-propyl}-methanesulfonamide hydrochloride

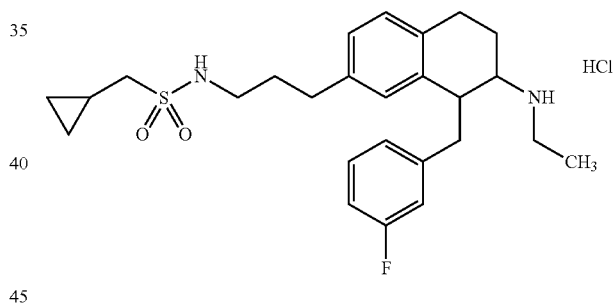

ESI-MS [M+H⁺]=459 Calculated for $C_{26}H_{35}FN_2O_2S$=458

Example 222

Propane-1-sulfonic acid {3-[8-(2-chloro-benzyl)-7-ethylamino-5,6,7,8-tetrahydronaphthalen-2-yl]-propyl}-amide hydrochloride

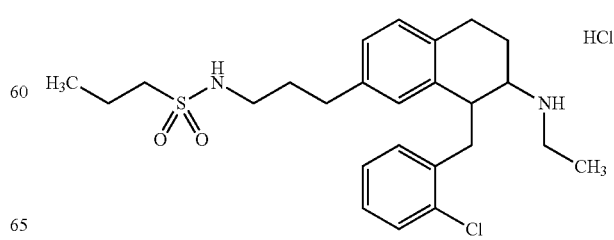

ESI-MS [M+H⁺]=463 Calculated for $C_{25}H_{35}ClN_2O_2S$=462

Example 223

N-{3-[8-Benzyl-7-(ethylamino)-5,6,7,8-tetrahydronaphthalen-2-yl]propyl}propane-1-sulfonamide hydrochloride

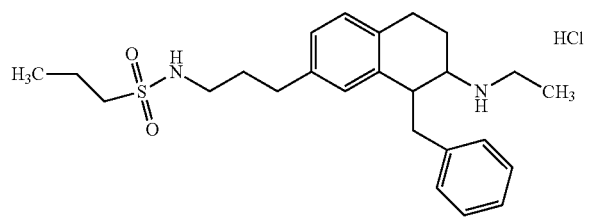 [SMILES: CCCS(=O)(=O)NCCCc1ccc2c(c1)C(Cc1ccccc1)C(NCC)CC2 ; Cl]

ESI-MS [M+H⁺]=429 Calculated for $C_{25}H_{36}N_2O_2S$=428

Example 224

N-{3-[8-Benzyl-7-(ethylamino)-5,6,7,8-tetrahydronaphthalen-2-yl]propyl}-1-cyclopropylmethanesulfonamide hydrochloride

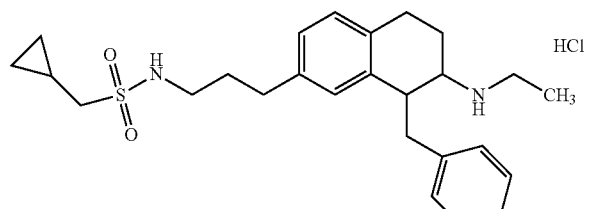

ESI-MS [M+H⁺]=441 Calculated for $C_{26}H_{36}N_2O_2S$=440

Example 225

N-{3-[8-(3,4-Difluorobenzyl)-7-(ethylamino)-5,6,7,8-tetrahydronaphthalen-2-yl]propyl}propane-1-sulfonamide trifluoroacetate

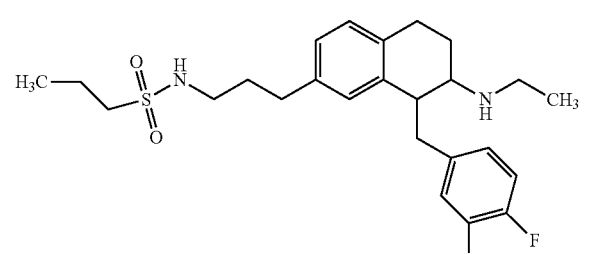

ESI-MS [M+H⁺]=465 Calculated for $C_{26}H_{34}F_2N_2O_2S$=464

Example 226

1-Cyclopropyl-N-{3-[8-(3,4-difluorobenzyl)-7-(ethylamino)-5,6,7,8-tetrahydronaphthalen-2-yl]propyl}methanesulfonamide trifluoroacetate

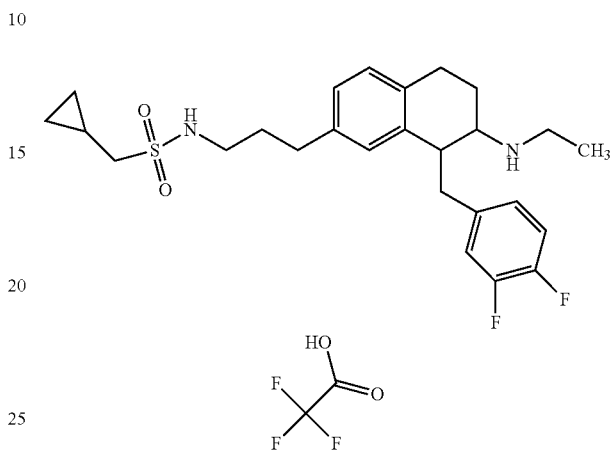

ESI-MS [M+H⁺]=477 Calculated for $C_{26}H_{34}F_2N_2O_2S$=476

Example 227

N-{3-[7-Amino-8-(3-fluorobenzyl)-5,6,7,8-tetrahydronaphthalen-2-yl]propyl}-N-methylpropane-1-sulfonamide hydrochloride

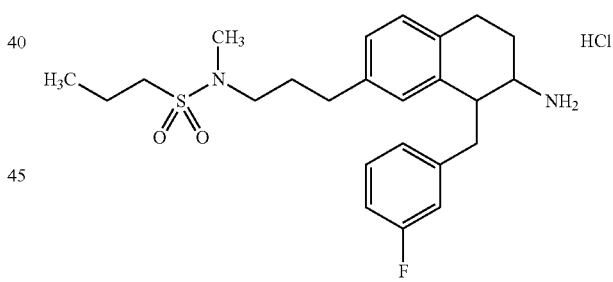

tert-Butyl (1-(3-fluorobenzyl)-7-(3-(propylsulfonamido)propyl)-1,2,3,4-tetrahydronaphthalen-2-ylcarbamate (cf. 209 and 201a, 65 mg, 0.125 mmol) was dissolved in acetonitrile (800 μL) and methyl iodide (24 μL, 0.376 mmol) and cesium carbonate (0.102 g, 0.313 mmol) was added. The reaction mixture was heated for 24 hours in a sealed vessel to 80° C. The reaction mixture was diluted with ethyl acetate. The ethyl acetate solution was successively washed with water and saturated sodium chloride solution. The organic phase was dried (MgSO₄) and concentrated in vacuo. The crude product was purified by preparative thin-layer chromatography (silica gel, dichloromethane, methanol). The obtained tert-butyl 1-(3-fluorobenzyl)-7-(3-(N-methylpropylsulfonamido)propyl)-1,2,3,4-tetrahydronaphthalen-2-ylcarbamate (65 mg, 0.122 mmol) was dissolved in 4 M hydrochloric acid in isopropanol and stirred at room temperature for 4 hours. The solvent was removed in vacuo. Diethyl ether was added and the precipitate removed by filtration and dried. Yield: 22 mg (0.047 mmol, 38%).

ESI-MS [M+H$^+$]=433 Calculated for C$_{24}$H$_{33}$FN$_2$O$_2$S=432

The following examples were prepared in analogy to example 227:

Example 228

N-{3-[7-Amino-8-(2-chloro-benzyl)-5,6,7,8-tetrahydro-naphthalen-2-yl]-propyl}-C-cyclopropyl-N-methyl-methanesulfonamide hydrochloride

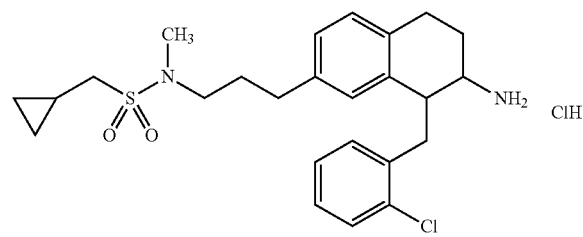 [SMILES: CN(CCCc1ccc2c(c1)C(Cc1ccccc1Cl)C(N)CC2)S(=O)(=O)CC1CC1 ; Cl]

ESI-MS [M+H$^+$]=461 Calculated for C$_{25}$H$_{33}$ClN$_2$O$_2$S=460

Example 229

Propane-1-sulfonic acid {3-[7-amino-8-(2-chlorobenzyl)-5,6,7,8-tetrahydro-naphthalen-2-yl]-propyl}-methyl-amide hydrochloride

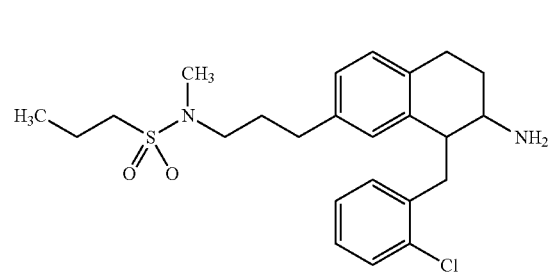

ESI-MS [M+H$^+$]=449 Calculated for C$_{24}$H$_{33}$ClN$_2$O$_2$S=448

Example 230

N-{3-[7-Amino-8-(3-fluorobenzyl)-5,6,7,8-tetrahydronaphthalen-2-yl]propyl}-1-cyclopropylN-methyl-methanesulfonamide hydrochloride

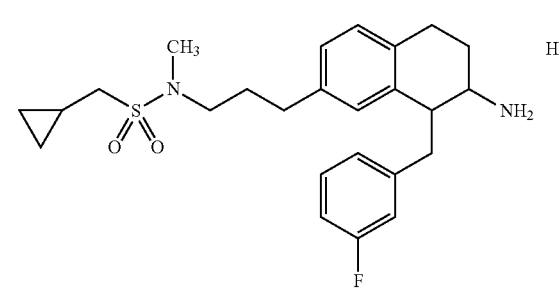

ESI-MS [M+H$^+$]=445 Calculated for C$_{25}$H$_{33}$FN$_2$O$_2$S=444

Example 231

N-{3-[7-Amino-8-(4-fluorobenzyl)-5,6,7,8-tetrahydronaphthalen-2-yl]propyl}-1-cyclopropylN-methyl-methanesulfonamide hydrochloride

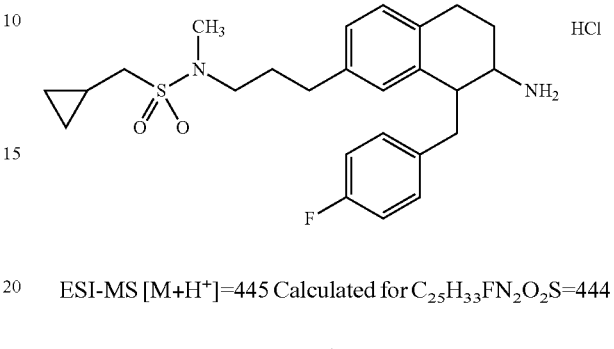

ESI-MS [M+H$^+$]=445 Calculated for C$_{25}$H$_{33}$FN$_2$O$_2$S=444

Example 232

N-{3-[7-Amino-8-(4-fluorobenzyl)-5,6,7,8-tetrahydronaphthalen-2-yl]propyl}-N-methylpropane-1-sulfonamide hydrochloride

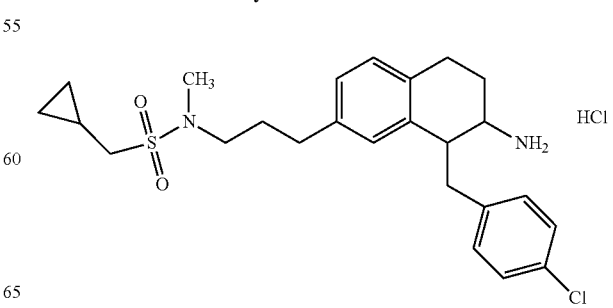

ESI-MS [M+H$^+$]=433 Calculated for C$_{24}$H$_{33}$FN$_2$O$_2$S=432

Example 233

N-{3-[7-Amino-8-(4-chlorobenzyl)-5,6,7,8-tetrahydronaphthalen-2-yl]propyl}-1-cyclopropylN-methyl-methanesulfonamide hydrochloride ESI-MS [M+H⁺]=461 Calculated for $C_{25}H_{33}ClN_2O_2S$=460

Example 234

N-{3-[7-Amino-8-(4-chlorobenzyl)-5,6,7,8-tetrahydronaphthalen-2-yl]propyl}-N-methylpropane-1-sulfonamide hydrochloride

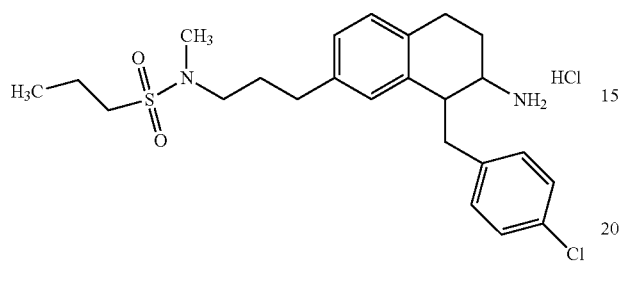

ESI-MS [M+H⁺]=449 Calculated for $C_{24}H_{33}ClN_2O_2S$=448

Example 235 was prepared in analogy to example 47:

N-(2-{[7-Amino-8-(3-fluorobenzyl)-5,6,7,8-tetrahydronaphthalen-2-yl]oxy}ethyl)-1-cyclopropyl-methanesulfonamide hydrochloride

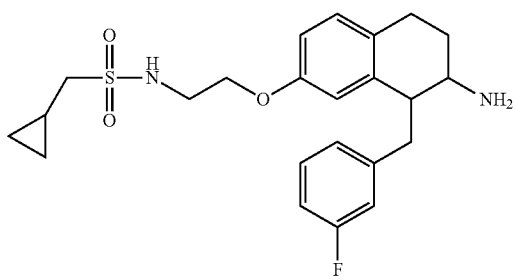

ESI-MS [M+H⁺]=433 Calculated for $C_{23}H_{29}FN_2O_3S$=432

The following examples were prepared in analogy to example 46:

Example 236

Ethyl[1-(3,5-difluorobenzyl)-7-(2-{[(1-methyl-1H-pyrrol-3-yl)sulfonyl]amino}ethoxy)-1,2,3,4-tetrahydronaphthalen-2-yl]carbamate

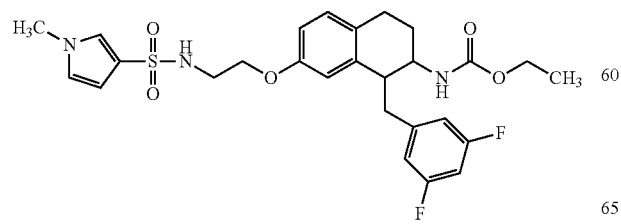

ESI-MS [M+H⁺]=548 Calculated for $C_{27}H_{31}F_2N_3O_5S$=547

Example 237

Ethyl [7-(2-{[(cyclopropylmethyl)sulfonyl]amino}ethoxy)-1-(3,5-difluorobenzyl)-1,2,3,4-tetrahydronaphthalen-2-yl]carbamate

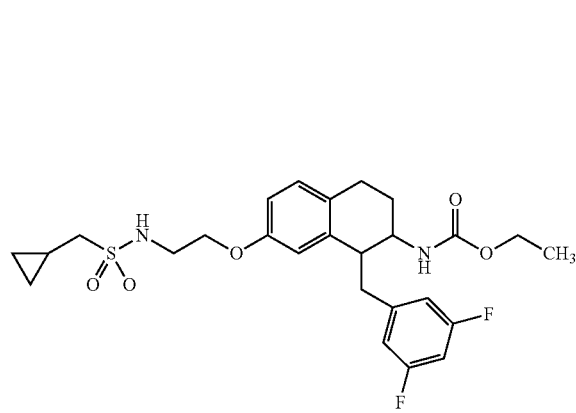

ESI-MS [M+H⁺]=523 Calculated for $C_{26}H_{32}F_2N_2O_5S$=522

Example 238 was prepared in analogy to example 47:

Enantiomer 1 of N-(2-{[7-amino-8-benzyl-5,6,7,8-tetrahydronaphthalen-2-yl]oxy}ethyl)-1-methyl-1H-imidazole-4-sulfonamide hydrochloride

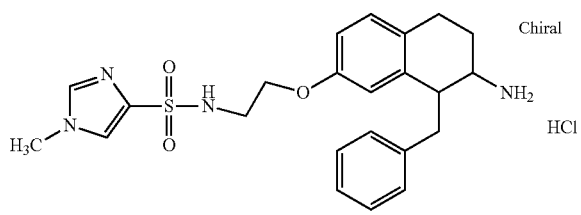 [SMILES: Cn1cnc(S(=O)(=O)NCCOc2ccc3c(c2)C(Cc2ccccc2)C(N)CC3)c1 ; Cl]

Could be separated by chiral chromatography of the final compound or an intermediate.

ESI-MS [M+H⁺]=441 Calculated for $C_{23}H_{28}N_4O_3S$=440

The following examples were prepared in analogy to example 137:

Example 239

Enantiomer 2 of C-cyclopropyl-N-{2-[8-(3-fluoro-benzyl)-7-methylamino-5,6,7,8-tetrahydronaphthalen-2-yloxy]-ethyl}-methanesulfonamide hydrochloride

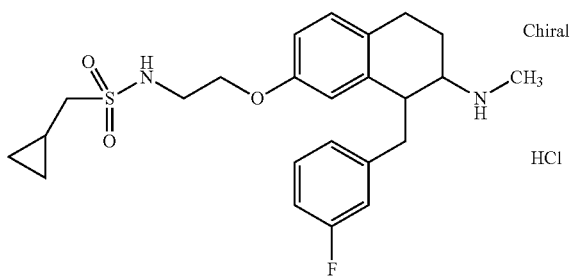 [SMILES: CNC1CCc2ccc(OCCNS(=O)(=O)CC3CC3)cc2C1Cc1cccc(F)c1 ; Cl]

C-Cyclopropyl-N-{2-[8-(3-fluoro-benzyl)-7-methylamino-5,6,7,8-tetrahydro-naphthalen-2-yloxy]-ethyl}-methanesulfonamide (Daicel, Chiralpak IC, 250×4.6 mm ID, 4l, methyl t-butyl ether/dichloromethane/methanol/triethylamine=900/50/50/1). The second eluting enantiomer was used for synthesis of the final compound.

ESI-MS [M+H$^+$]=447 Calculated for $C_{24}H_{31}FN_2O_3S$=446

Example 240

Enantiomer 1 of 1-cyclopropyl-N-(2-{[8-(3-fluorobenzyl)-7-(methylamino)-5,6,7,8-tetrahydronaphthalen-2-yl]oxy}ethyl)methanesulfonamide hydrochloride

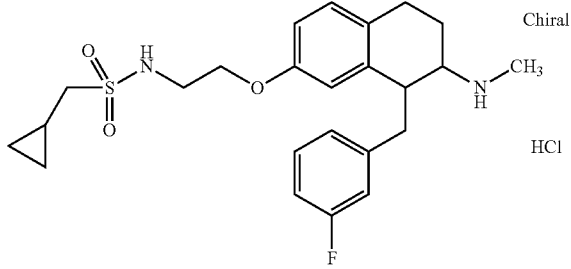 [SMILES: CNC1CCc2ccc(OCCNS(=O)(=O)CC3CC3)cc2C1Cc1cccc(F)c1 ; Cl]

Ethyl 7-(2-(cyclopropylmethylsulfonamido)ethoxy)-1-(3-fluorobenzyl)-1,2,3,4-tetrahydronaphthalen-2-ylcarbamate was separated by chiral chromatography (Daicel, Chiralpak IC, 250×4.6 mm ID, methyl t-butyl ether/dichloromethane/methanol/triethylamine=900/50/50/1). The first eluting enantiomer was used for synthesis of the final compound.

ESI-MS [M+H$^+$]=447 Calculated for $C_{24}H_{31}FN_2O_3S$=446

Example 241

Enantiomer 1 of N-(2-{[8-(3,5-difluorobenzyl)-7-(methylamino)-5,6,7,8-tetrahydronaphthalen-2-yl]oxy}ethyl)-1-methyl-1H-pyrrole-3-sulfonamide hydrochloride

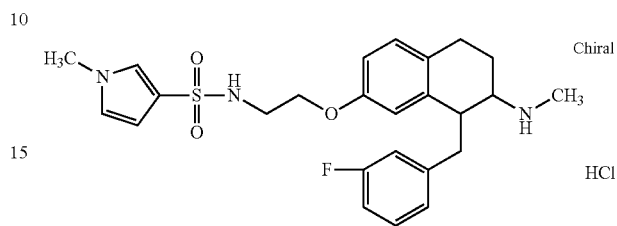

Ethyl 1-(3,5-difluorobenzyl)-7-(2-(1-methyl-1H-pyrrole-3-sulfonamido)ethoxy)-1,2,3,4-tetrahydronaphthalen-2-ylcarbamate was separated by chiral chromatography (Daicel, Chiralpak AD, 250×20 mm ID, 10μ, n-heptane/ethanol/triethylamine=35/65/1). The second eluting enantiomer was used for synthesis of the final compound. Can be separated by chiral chromatography of the final compound or an intermediate.

ESI-MS [M+H$^+$]=490 Calculated for $C_{25}H_{29}F_2N_3O_3S$=489

Example 242

Enantiomer 2 of N-(2-{[8-(3,5-difluorobenzyl)-7-(methylamino)-5,6,7,8-tetrahydronaphthalen-2-yl]oxy}ethyl)-1-methyl-1H-pyrrole-3-sulfonamide hydrochloride

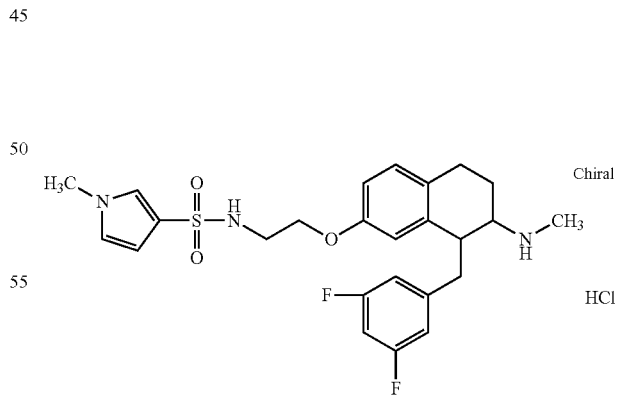

Ethyl 1-(3,5-difluorobenzyl)-7-(2-(1-methyl-1H-pyrrole-3-sulfonamido)ethoxy)-1,2,3,4-tetrahydronaphthalen-2-yl-carbamate was separated by chiral chromatography (Daicel, Chiralpak AD, 250×20 mm ID, 10μ, n-heptane/ethanol/triethylamine=35/65/1). The first eluting enantiomer was used for synthesis of the final compound.

ESI-MS [M+H⁺]=490 Calculated for C$_{25}$H$_{29}$F$_2$N$_3$O$_3$S=489

Example 243

1-Cyclopropyl-N-(2-{[8-(3,5-difluorobenzyl)-7-(methylamino)-5,6,7,8-tetrahydronaphthalen-2-yl]oxy}ethylmethanesulfonamide hydrochloride

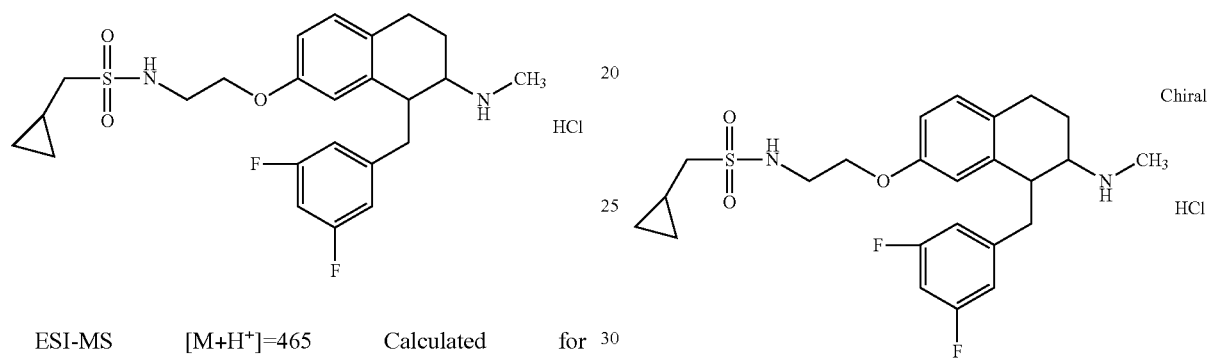

ESI-MS [M+H⁺]=465 Calculated for C$_{24}$H$_{30}$F$_2$N$_2$O$_3$S=464

Example 244

Enantiomer 2 of 1-cyclopropyl-N-(2-{[8-(3,5-difluorobenzyl)-7-(methylamino)-5,6,7,8-tetrahydronaphthalen-2-yl]oxy}ethylmethanesulfonamide hydrochloride

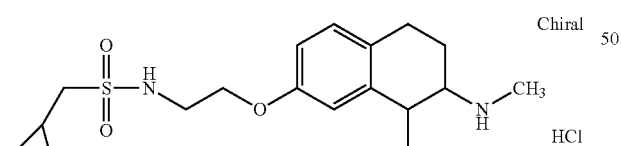

Ethyl 7-(2-(cyclopropylmethylsulfonamido)ethoxy)-1-(3,5-difluorobenzyl)-1,2,3,4-tetrahydronaphthalen-2-ylcarbamate was separated by chiral chromatography (Daicel, Chiralpak AD, 250×20 mm ID, 10μ, n-heptane/ethanol/t-butanol=800/150/50). The first eluting enantiomer was used for synthesis of the final compound.

ESI-MS [M+H⁺]=465 Calculated for C$_{24}$H$_{30}$F$_2$N$_2$O$_3$S=464

Example 245

Enantiomer 1 of 1-cyclopropyl-N-(2-{[8-(3,5-difluorobenzyl)-7-(methylamino)-5,6,7,8-tetrahydronaphthalen-2-yl]oxy}ethyl)methanesulfonamide hydrochloride Ethyl 7-(2-(cyclopropylmethylsulfonamido)ethoxy)-1-(3,5-difluorobenzyl)-1,2,3,4-tetrahydronaphthalen-2-ylcarbamate was separated by chiral chromatography (Daicel, Chiralpak AD, 250×20 mm ID, 10μ, n-heptane/ethanol/t-butanol=800/150/50). The sec- and eluting enantiomer was used for synthesis of the final compound.

ESI-MS [M+H⁺]=465 Calculated for C$_{24}$H$_{30}$F$_2$N$_2$O$_3$S=464

Example 246

N-(2-{[8-(3,5-Difluorobenzyl)-7-(methylamino)-5,6,7,8-tetrahydronaphthalen-2-yl]oxy}ethyl)-1-methyl-1H-pyrrole-3-sulfonamide hydrochloride

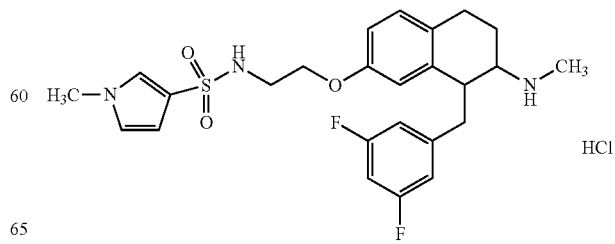

Example 247

1-Cyclopropyl-N-(2-{[8-(3-fluorobenzyl)-7-(methylamino)-5,6,7,8-tetrahydronaphthalen-2-yl]oxy}ethyl)methanesulfonamide hydrochloride

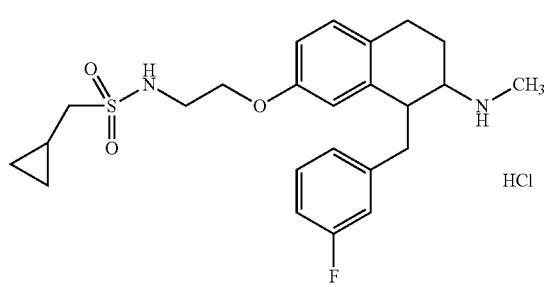 [SMILES: CNC1CCc2ccc(OCCNS(=O)(=O)CC3CC3)cc2C1Cc1cccc(F)c1 ; Cl]

ESI-MS [M+H$^+$]=447 Calculated for C$_{24}$H$_{31}$FN$_2$O$_3$S=446

Example 248

N-{[7-(Azetidin-1-yl)-8-benzyl-5,6,7,8-tetrahydronaphthalen-2-yl]methyl}-1-methyl-1H-imidazole-4-sulfonamide

248.1 7-Amino-8-benzyl-5,6,7,8-tetrahydronaphthalene-2-carbonitrile

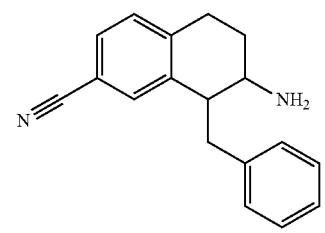 [SMILES: N#Cc1ccc2c(c1)C(Cc1ccccc1)C(N)CC2]

Tert-butyl 1-benzyl-7-cyano-1,2,3,4-tetrahydronaphthalen-2-ylcarbamate (1.1 g, 3.03 mmol) was dissolved in dichloromethane (20 mL) and 5 M hydrochloric acid in isopropanol (2 mL) was added. The reaction mixture was stirred at room temperature for 12 h followed by 4 h at 35° C. The solvent was evaporated in vacuo. Water (30 mL) was added and the pH was adjusted to pH 9 using aqueous saturated sodium bicarbonate solution. The aqueous layer was extracted with dichloromethane. The combined extracts were dried (MgSO$_4$) and the solvent was evaporated in vacuo. Yield: 790 mg (3.03 mmol, 100%).

248.2 7-(Azetidin-1-yl)-8-benzyl-5,6,7,8-tetrahydronaphthalene-2-carbonitrile

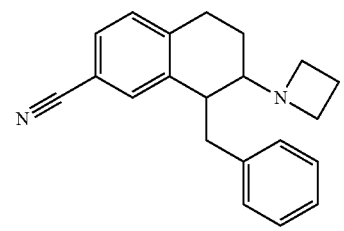 [SMILES: N#Cc1ccc2c(c1)C(Cc1ccccc1)C(N1CCC1)CC2]

7-Amino-8-benzyl-5,6,7,8-tetrahydronaphthalene-2-carbonitrile (790 mg, 3.03 mmol), 1,3-dibromopropane (0.4 mL, 3.93 mmol) and triethylamine (0.914 mL, 6.56 mmol) were dissolved in acetonitrile (8 mL) and the reaction mixture heated to 120° C. in the microwave for 2 h. The solvent was evaporated in vacuo. Water (30 mL) and ethyl acetate (40 mL) were added. The layers were separated and the aqueous layer extracted with ethyl acetate. The combined organic extracts were dried (MgSO$_4$) and the solvent evaporated in vacuo. The crude product was purified by flash chromatography (silica gel, dichloromethane, methanol). Yield: 346 mg (1.14 mmol, 37.6%).

248.3 1-[7-(Azetidin-1-yl)-8-benzyl-5,6,7,8-tetrahydronaphthalen-2-yl]methanamine

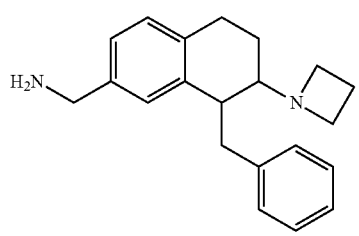 [SMILES: NCc1ccc2c(c1)C(Cc1ccccc1)C(N1CCC1)CC2]

7-(Azetidin-1-yl)-8-benzyl-5,6,7,8-tetrahydronaphthalene-2-carbonitrile (340 mg, 1.12 mmol) was dissolved in dry methanol (20 mL) under a nitrogen atmosphere. Raney nickel (900 mg, 3.36 mmol) was added under nitrogen and the reaction mixture stirred at room temperature for 48 h under an atmosphere of hydrogen. Methanol (20 mL) and dichloromethane (30 mL) were added. After stirring at room temperature for 20 minutes the catalyst was removed by filtration and the solvent evaporated in vacuo. Yield: 338 mg (1.10 mmol, 98%).

248.4 N-{[7-(Azetidin-1-yl)-8-benzyl-5,6,7,8-tetrahydronaphthalen-2-yl]methyl}-1-methyl-1H-imidazole-4-sulfonamide

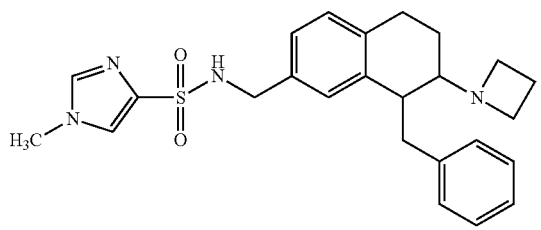 [SMILES: Cn1cnc(S(=O)(=O)NCc2ccc3c(c2)C(Cc2ccccc2)C(N2CCC2)CC3)c1]

(7-(Azetidin-1-yl)-8-benzyl-5,6,7,8-tetrahydronaphthalen-2-yl)methanamine (250 mg, 0.816 mmol) and N,N-dimethyl-4-aminopyridine (199 mg, 1.632 mmol) were dissolved in dichloromethane (18 mL). 1-Methyl-1H-imidazole-4-sulfonyl chloride (147 mg, 0.816 mmol) dissolved in dichloromethane (2 mL) was added dropwise. The reaction mixture was stirred at room temperature for 12 h. The reaction mixture was diluted with dichloromethane (20 mL) and washed successively with saturated ammonium chloride (3×15 mL) and water (2×10 mL). The organic phase was dried (MgSO₄) and the solvent was evaporated in vacuo. The crude product was purified by flash chromatography (silica gel, dichloromethane, methanol). Yield: 64 mg (0.142 mmol, 17%).

ESI-MS [M+H⁺]=451 Calculated for $C_{25}H_{30}N_4O_2S$=450

The following examples were prepared in analogy to 248:

Example 249

N-{[7-(Azetidin-1-yl)-8-benzyl-5,6,7,8-tetrahydronaphthalen-2-yl]methyl}propane-1-sulfonamide

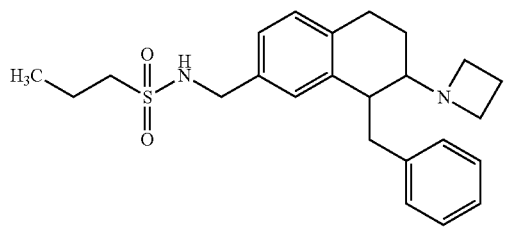 [SMILES: CCCS(=O)(=O)NCc1ccc2c(c1)C(Cc1ccccc1)C(N1CCC1)CC2]

ESI-MS [M+H⁺]=413 Calculated for $C_{24}H_{32}N_2O_2S$=412

Example 250

N-{[7-(Azetidin-1-yl)-8-benzyl-5,6,7,8-tetrahydronaphthalen-2-yl]methyl}-1-methyl-1H-pyrazole-4-sulfonamide

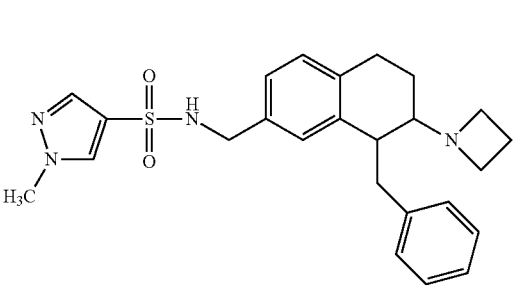 [SMILES: Cn1cc(S(=O)(=O)NCc2ccc3c(c2)C(Cc2ccccc2)C(N2CCC2)CC3)cn1]

ESI-MS [M+H⁺]=451 Calculated for $C_{25}H_{30}N_4O_2S$=450

Example 251

N-{[7-(Azetidin-1-yl)-8-benzyl-5,6,7,8-tetrahydronaphthalen-2-yl]methyl}-1-methyl-1H-pyrrole-3-sulfonamide trifluoroacetate

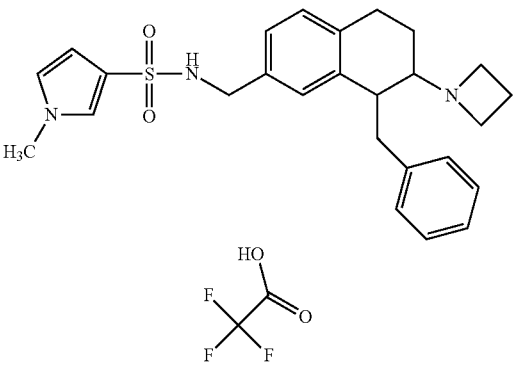

ESI-MS [M+H⁺]=450 Calculated for $C_{26}H_{31}N_3O_2S$=449

Example 252

Enantiomer 1 of N-{[7-(azetidin-1-yl)-8-benzyl-5,6,7,8-tetrahydronaphthalen-2-yl]methyl}-1-methyl-1H-imidazole-4-sulfonamide

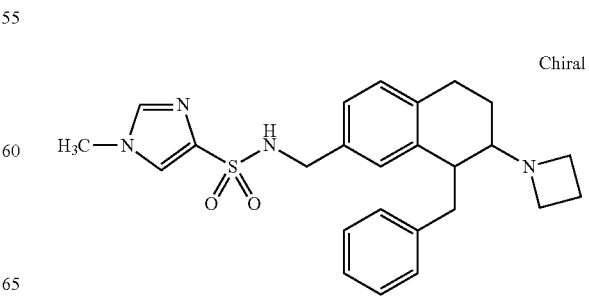

The enantiomer of tert-butyl (1-benzyl-7-cyano-1,2,3,4-tetrahydronaphthalen-2-yl)carbamate described in example 192 was used as chiral building block for the synthesis.
ESI-MS [M+H$^+$]=451 Calculated for C$_{26}$H$_{30}$N$_4$O$_2$S=450

Example 253

Enantiomer 1 of N-{[7-(azetidin-1-yl)-8-benzyl-5,6,7,8-tetrahydronaphthalen-2-yl]methyl}pyridine-2-sulfonamide

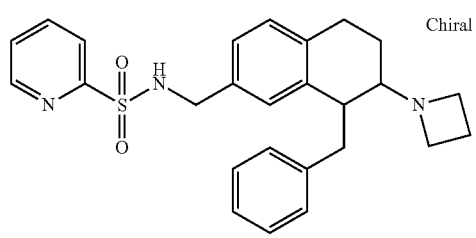 [SMILES: O=S(=O)(NCc1ccc2c(c1)C(Cc1ccccc1)C(N1CCC1)CC2)c1ccccn1]

The enantiomer of tert-butyl (1-benzyl-7-cyano-1,2,3,4-tetrahydronaphthalen-2-yl)carbamate described in example 192 was used as chiral building block for the synthesis.
ESI-MS [M+H$^+$]=448 Calculated for C$_{26}$H$_{29}$N$_3$O$_2$S=447

Example 254

Enantiomer 1 of N-{[7-(azetidin-1-yl)-8-benzyl-5,6,7,8-tetrahydronaphthalen-2-yl]methyl}-1-methyl-1H-pyrazole-4-sulfonamide

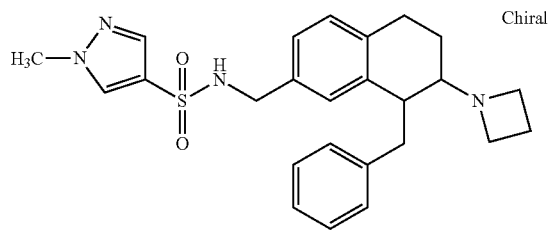 [SMILES: Cn1cc(S(=O)(=O)NCc2ccc3c(c2)C(Cc2ccccc2)C(N2CCC2)CC3)cn1]

The enantiomer of tert-butyl (1-benzyl-7-cyano-1,2,3,4-tetrahydronaphthalen-2-yl)carbamate described in example 192 was as chiral building block for the synthesis.
ESI-MS [M+H$^+$]=451 Calculated for C$_{25}$H$_{30}$N$_4$O$_2$S=450

Example 255

Enantiomer 1 of N-{[7-(azetidin-1-yl)-8-benzyl-5,6,7,8-tetrahydronaphthalen-2-yl]methyl}thiophene-2-sulfonamide

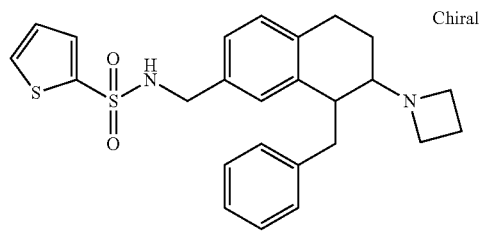 [SMILES: O=S(=O)(NCc1ccc2c(c1)C(Cc1ccccc1)C(N1CCC1)CC2)c1cccs1]

The enantiomer of tert-butyl (1-benzyl-7-cyano-1,2,3,4-tetrahydronaphthalen-2-yl)carbamate described in example 192 was used as chiral building block for the synthesis.
ESI-MS [M+H$^+$]=453 Calculated for C$_{25}$H$_{28}$N$_2$O$_2$S$_2$=452

Example 256

N-{[7-(Azetidin-1-yl)-8-(3-fluorobenzyl)-5,6,7,8-tetrahydronaphthalen-2-yl]methyl}-1-methyl-1H-imidazole-4-sulfonamide hydrochloride

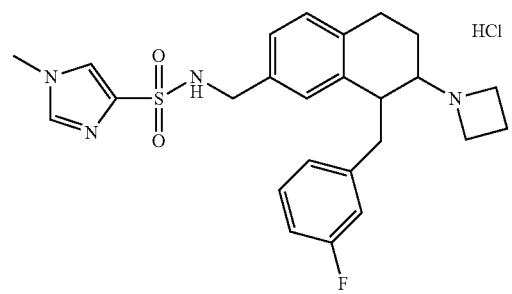 [SMILES: Cn1cnc(S(=O)(=O)NCc2ccc3c(c2)C(Cc2cccc(F)c2)C(N2CCC2)CC3)c1 ; Cl]

ESI-MS [M+H$^+$]=469 Calculated for C$_{25}$H$_{29}$FN$_4$O$_2$S=468

Example 257

N-{[8-Benzyl-7-(morpholin-4-yl)-5,6,7,8-tetrahydronaphthalen-2-yl]methyl}-1-methyl-1H-imidazole-4-sulfonamide

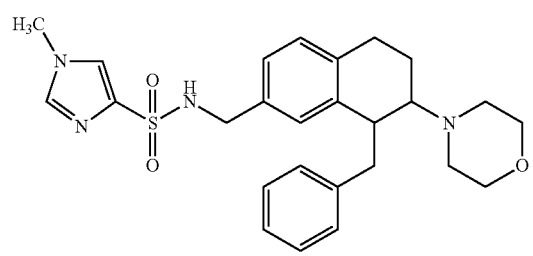 [SMILES: Cn1cnc(S(=O)(=O)NCc2ccc3c(c2)C(Cc2ccccc2)C(N2CCOCC2)CC3)c1]

This compound was prepared in analogy to example 248 using 1-bromo-2-(2-bromoethoxy)ethane in place of 1,3-dibromopropane.
ESI-MS [M+H$^+$]=481 Calculated for C$_{26}$H$_{32}$N$_4$O$_3$S=480

The following examples were prepared in analogy to 257:

Example 258

N-{[8-Benzyl-7-(morpholin-4-yl)-5,6,7,8-tetrahydronaphthalen-2-yl]methyl}-1-methyl-1H-pyrazole-4-sulfonamide

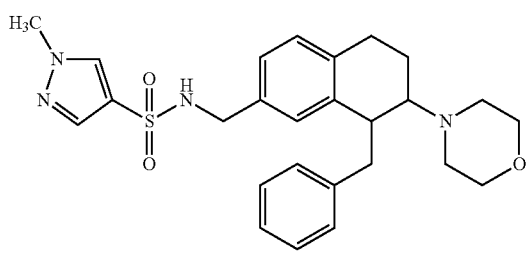 [SMILES: Cn1cc(S(=O)(=O)NCc2ccc3c(c2)C(Cc2ccccc2)C(N2CCOCC2)CC3)cn1]

ESI-MS [M+H$^+$]=481 Calculated for $C_{26}H_{32}N_4O_3S$=480

Example 259

N-{[8-Benzyl-7-(morpholin-4-yl)-5,6,7,8-tetrahydronaphthalen-2-yl]methyl}-1-cyclopropylmethanesulfonamide

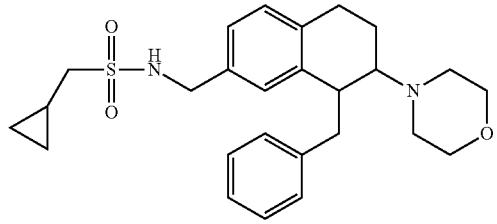 [SMILES: O=S(=O)(CC1CC1)NCc1ccc2c(c1)C(Cc1ccccc1)C(N1CCOCC1)CC2]

ESI-MS [M+H$^+$]=455 Calculated for $C_{26}H_{34}N_2O_3S$=454

Example 260

N-{[8-Benzyl-7-(morpholin-4-yl)-5,6,7,8-tetrahydronaphthalen-2-yl]methyl}propane-1-sulfonamide

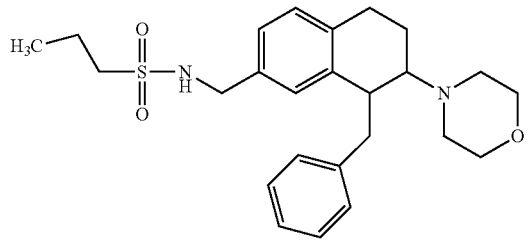 [SMILES: CCCS(=O)(=O)NCc1ccc2c(c1)C(Cc1ccccc1)C(N1CCOCC1)CC2]

ESI-MS [M+H$^+$]=443 Calculated for $C_{25}H_{34}N_2O_3S$=442

Example 261

N-{[8-Benzyl-7-(morpholin-4-yl)-5,6,7,8-tetrahydronaphthalen-2-yl]methyl}cyclobutanesulfonamide

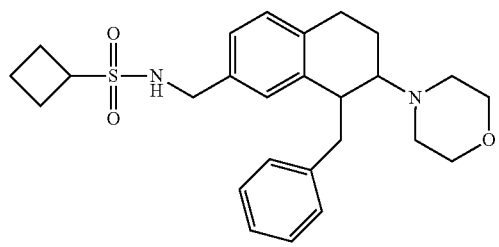 [SMILES: O=S(=O)(NCc1ccc2c(c1)C(Cc1ccccc1)C(N1CCOCC1)CC2)C1CCC1]

ESI-MS [M+H$^+$]=455 Calculated for $C_{26}H_{34}N_2O_3S$=454

Example 262

N-{[8-Benzyl-7-(pyrrolidin-1-yl)-5,6,7,8-tetrahydronaphthalen-2-yl]methyl}-1-methyl-1H-imidazole-4-sulfonamide

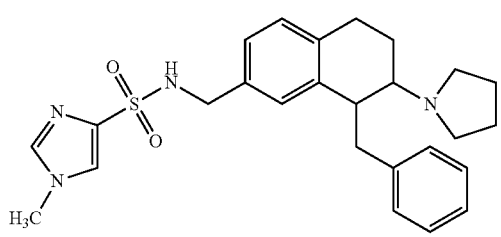 [SMILES: Cn1cnc(S(=O)(=O)NCc2ccc3c(c2)C(Cc2ccccc2)C(N2CCCC2)CC3)c1]

This compound was prepared in analogy to example 248 using 1,4-dibromobutane in place of 1,3-dibromopropane.
ESI-MS [M+H$^+$]=465 Calculated for $C_{26}H_{32}N_4O_2S$=464

Example 263

N-{[8-Benzyl-7-(2-oxopyrrolidin-1-yl)-5,6,7,8-tetrahydronaphthalen-2-yl]methyl}-1-methyl-1H-imidazole-4-sulfonamide

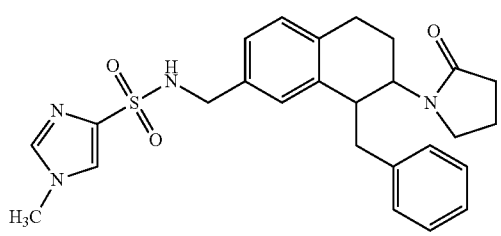 [SMILES: Cn1cnc(S(=O)(=O)NCc2ccc3c(c2)C(Cc2ccccc2)C(N2CCCC2=O)CC3)c1]

N-((7-Amino-8-benzyl-5,6,7,8-tetrahydronaphthalen-2-ylmethyl)-1-methyl-1H-imidazole-4-sulfonamide (271 mg, 0.66 mmol, cf. 173) was dissolved in dichloromethane (10 mL). Pyridine (0.191 mL, 2.357 mmol) was added. 4-Chlorobutanoyl chloride (0.116 mL, 1.038 mmol) was added dropwise. After 2 h N,N-dimethyl-4-aminopyridine (46 mg, 0.378 mmol) was added and stirring was continued over night. 1 N sodium hydroxide solution was added and the mixture extracted with dichloromethane. The combined organic extracts were dried (MgSO₄) and concentrated in vacuo. The crude product was suspended in dry tetrahydrofuran and a suspension of sodium hydride (60% in oil, 179 mg, washed twice with pentane prior to addition) in tetrahydrofuran (3 mL) was added. The reaction mixture was heated to 45° C. for 1 h. Water was added and the mixture was extracted with dichloromethane (3×20 mL). The combined organic extracts were dried (MgSO₄) and concentrated in vacuo. The crude product was purified by flash chromatography (silica gel, dichloromethane, methanol). Yield: 98 mg (0.205 mmol, 46%).

ESI-MS [M+H⁺]=479 Calculated for $C_{26}H_{30}N_4O_3S$=478

Example 264

N-{3-[8-(3-Chlorobenzyl)-7-(pyrrolidin-1-yl)-5,6,7,8-tetrahydronaphthalen-2-yl]propyl}propane-1-sulfonamide hydrochloride 264.1 1-[1-(3-Chlorobenzyl)-7-methoxy-1,2,3,4-tetrahydronaphthalen-2-yl]pyrrolidine

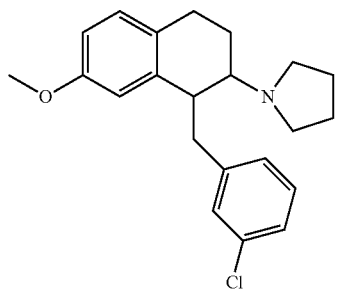 [SMILES: COc1ccc2c(c1)C(Cc1cccc(Cl)c1)C(N1CCCC1)CC2]

1-(3-Chlorobenzyl)-7-methoxy-1,2,3,4-tetrahydronaphthalen-2-amine (6 g, 19.88 mmol) was dissolved in acetonitrile (150 mL). 1,4-Dibromobutane (2.61 mL, 21.87 mmol) and triethylamine (6.1 mL, 43.7 mmol) were added and the reaction mixture heated under reflux for 3 h. The reaction mixture was poured on ice and extracted with dichloromethane. The combined organic extracts were successively washed with water and brine, dried (MgSO₄) and the solvent was evaporated in vacuo. The crude product (6.6 g) was used for the next step without further purification.

264.2 8-(3-Chlorobenzyl)-7-(pyrrolidin-1-yl)-5,6,7,8-tetrahydronaphthalen-2-ol

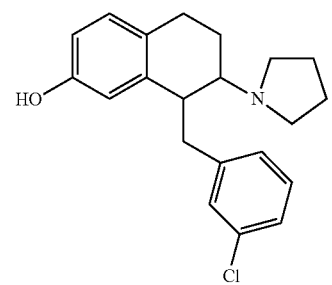 [SMILES: Oc1ccc2c(c1)C(Cc1cccc(Cl)c1)C(N1CCCC1)CC2]

1-(1-(3-Chlorobenzyl)-7-methoxy-1,2,3,4-tetrahydronaphthalen-2-yl)pyrrolidine (6.6 g, 18.54 mmol) was dissolved in dichloromethane (100 mL). A 1 M solution of bortribromide in dichloromethane (55.6 mL, 55.6 mmol) was added dropwise under cooling maintaining the reaction mixture at room temperature. The reaction mixture was stirred at room temperature for 2 h. The reaction was poured on ice, made alkaline with sodium hydroxide. The aqueous phase was extracted with ethyl acetate and the combined organic extracts were washed successively with sodium bicarbonate and brine. The combined extracts were dried (MgSO₄) and the solvent was evaporated in vacuo. The crude product (5.5 g) was used for the next step without further purification.

264.3 8-(3-Chlorobenzyl)-7-(pyrrolidin-1-yl)-5,6,7,8-tetrahydronaphthalen-2-yl trifluoromethanesulfonate

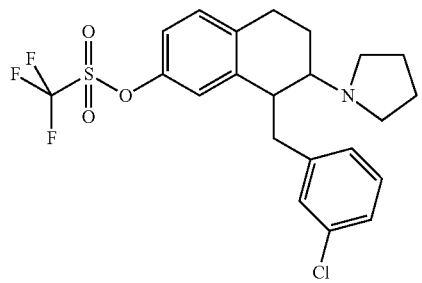 [SMILES: O=S(=O)(Oc1ccc2c(c1)C(Cc1cccc(Cl)c1)C(N1CCCC1)CC2)C(F)(F)F]

8-(3-Chlorobenzyl)-7-(pyrrolidin-1-yl)-5,6,7,8-tetrahydronaphthalen-2-ol (5.5 g, 16.09 mmol) was dissolved in dichloromethane (150 mL). 1,1,1-trifluoro-N-phenyl-N-(trifluoromethylsulfonyl)methanesulfonamide (6.9 g, 19.31 mmol) was added at 0° C. followed by the addition of a solution of triethylamine (4.48 mL, 32.2 mmol) in dichloromethane (50 mL). The reaction mixture was allowed to warm to room temperature and stirring was continued over night. The reaction was poured on ice and extracted with dichloromethane. The combined extracts were washed successively with ammonium chloride solution, water and brine. The extracts were dried (Na₂SO₄) and the solvent was evaporated in vacuo. The crude product was purified by flash chromatography (silica gel, dichloromethane, methanol). Yield: 6.33 g (13.36 mmol, 83%).

264.4 N-{3-[8-(3-Chlorobenzyl)-7-(pyrrolidin-1-yl)-5,6,7,8-tetrahydronaphthalen-2-yl]propyl}propane-1-sulfonamide hydrochloride

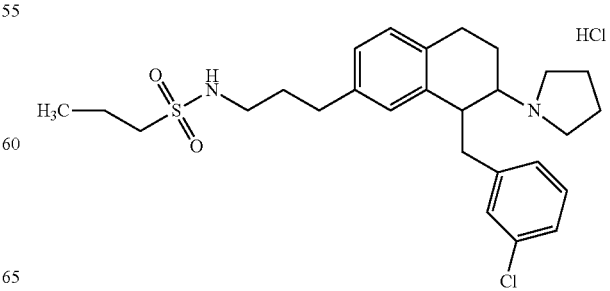

N-allylpropane-1-sulfonamide (0.238 g, 1.456 mmol) is added to a solution of 9-borabicyclo[3.3.1]nonane (0.185 g, 1.519 mmol) in tetrahydrofuran (4 mL). The reaction mixture was stirred for 2 h at room temperature. (7R,8S)-8-(3-chlorobenzyl)-7-(pyrrolidin-1-yl)-5,6,7,8-tetrahydronaphthalen-2-yl trifluoromethanesulfonate (0.3 g, 0.633 mmol) dissolved in tetrahydrofuran (2 mL), sodium hydroxide (0.063 g, 1.582 mmol in 0.06 mL water) and palladium tetrakistriphenylphosphine (0.073 g, 0.063 mmol) were added. The reaction mixture was heated under reflux over night. The reaction mixture was diluted with ethyl acetate and washed with 1 M sodium hydroxide solution. The aqueous phase was extracted two more times with ethyl acetate. The combined organic extracts were washed with brine, dried (MgSO$_4$) and the solvent was evaporated in vacuo. The crude product was purified by preparative thin-layer-chromatography (silica gel, dichloromethane, methanol). The product was dissolved in dichloromethane. Excess 5N hydrochloric acid in ethanol was added. The solvent was evaporated and the product dried in vacuo. Yield: 53 mg (0.108 mmol, 17%).

ESI-MS [M+H$^+$]=489 Calculated for C$_{27}$H$_{37}$ClN$_2$O$_2$S=488

The following examples were prepared in analogy to 264:

Example 265

Propane-1-sulfonic acid [3-(8-benzyl-7-pyrrolidin-1-yl-5,6,7,8-tetrahydro-naphthalen-2-yl)propyl]-amide hydrochloride

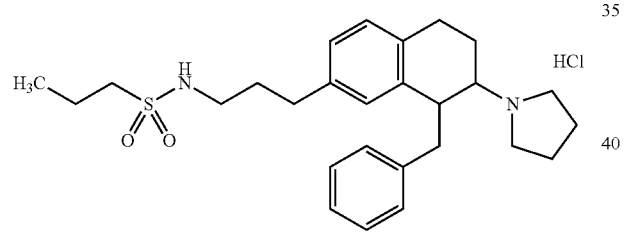

ESI-MS [M+H$^+$]=455 Calculated for C$_{27}$H$_{38}$N$_2$O$_2$S=454

Example 266

N-{3-[8-Benzyl-7-(pyrrolidin-1-yl)-5,6,7,8-tetrahydronaphthalen-2-yl]propyl}-1-cyclopropylmethanesulfonamide hydrochloride

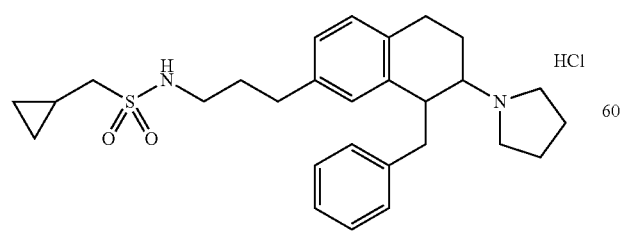

ESI-MS [M+H$^+$]=467 Calculated for C$_{28}$H$_{38}$N$_2$O$_2$S=466

Example 267

N-(2-{[8-(3-Fluorobenzyl)-7-(pyrrolidin-1-yl)-5,6,7,8-tetrahydronaphthalen-2-yl]oxy}ethyl)-1-methyl-1H-pyrrole-3-sulfonamide 267.1 8-(3-Fluorobenzyl)-7-(pyrrolidin-1-yl)-5,6,7,8-tetrahydronaphthalen-2-ol

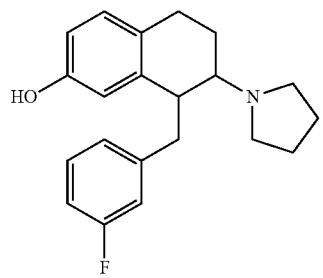 [SMILES: Oc1ccc2c(c1)C(Cc1cccc(F)c1)C(N1CCCC1)CC2]

8-(3-Fluorobenzyl)-7-(pyrrolidin-1-yl)-5,6,7,8-tetrahydronaphthalen-2-ol was prepared in analogy to 8-(3-chlorobenzyl)-7-(pyrrolidin-1-yl)-5,6,7,8-tetrahydronaphthalen-2-ol (cf. 264).

267.2 2-{[8-(3-Fluorobenzyl)-7-(pyrrolidin-1-yl)-5,6,7,8-tetrahydronaphthalen-2-yl]oxy}ethanamine

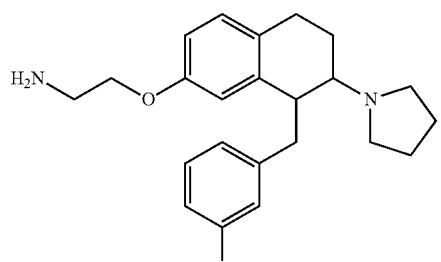

2-{[8-(3-Fluorobenzyl)-7-(pyrrolidin-1-yl)-5,6,7,8-tetrahydronaphthalen-2-yl]oxy}ethanamine was prepared in analogy to example 1 and 2 from 8-(3-fluorobenzyl)-7-(pyrrolidin-1-yl)-5,6,7,8-tetrahydronaphthalen-2-ol.

267.3 N-(2-{[8-(3-fluorobenzyl)-7-(pyrrolidin-1-yl)-5,6,7,8-tetrahydronaphthalen-2-yl]oxy}ethyl)-1-methyl-1H-pyrrole-3-sulfonamide

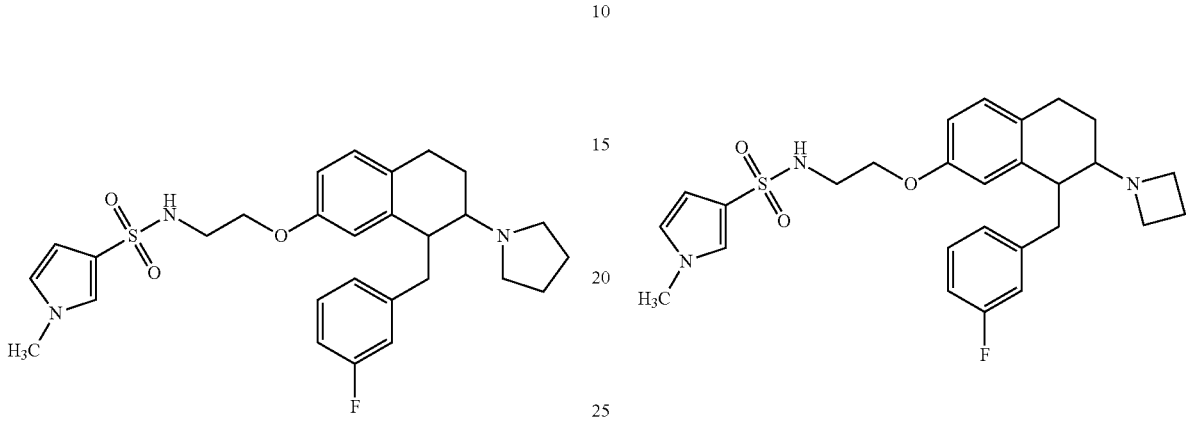

2-(8-(3-Fluorobenzyl)-7-(pyrrolidin-1-yl)-5,6,7,8-tetrahydronaphthalen-2-yloxy)ethanamine (50 mg, 0.136 mmol) was dissolved in dichloromethane (2 mL). N,N-Dimethyl-4-aminopyridine (49.7 mg, 0.407 mmol) and 1-methyl-1H-pyrrole-3-sulfonyl chloride (24.4 mg, 0.136 mmol) were added successively. The reaction mixture was stirred at room temperature over night. The reaction was diluted with dichloromethane and washed with water. The organic phase was dried (MgSO$_4$) and the solvent was evaporated in vacuo. The crude product was purified by flash chromatography (silica gel, dichloromethane, methanol). Yield: 31 mg (0.061 mmol, 45%).

ESI-MS [M+H$^+$]=512 Calculated for $C_{28}H_{34}FN_3O_3S$=511

The following examples were prepared in analogy to 267:

Example 268

N-(2-{[7-(Azetidin-1-yl)-8-benzyl-5,6,7,8-tetrahydronaphthalen-2-yl]oxy}ethyl)-1-methyl-1H-pyrrole-3-sulfonamide

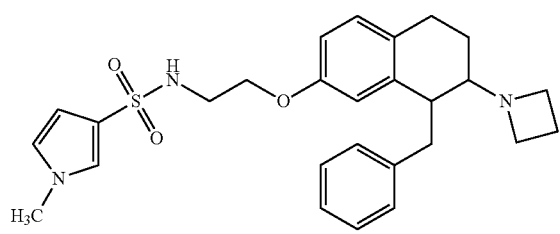 [SMILES: Cn1ccc(S(=O)(=O)NCCOc2ccc3c(c2)C(Cc2ccccc2)C(N2CCC2)CC3)c1]

ESI-MS [M+H$^+$]=480 Calculated for $C_{27}H_{33}N_3O_3S$=479

Example 269

1-Methyl-1H-pyrrole-3-sulfonic acid {2-[7-azetidin-1-yl-8-(3-fluoro-benzyl)-5,6,7,8-tetrahydro-naphthalen-2-yloxy]-ethyl}-amide

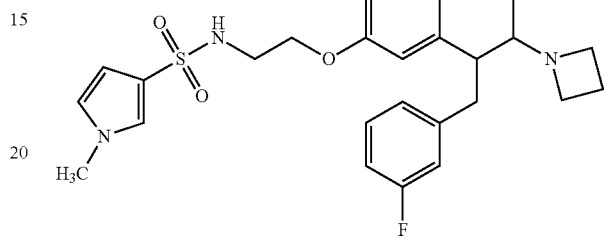

ESI-MS [M+H$^+$]=498 Calculated for $C_{27}H_{32}FN_3O_3S$=497

Example 270

Enantiomer 1 of N-{1-benzyl-7-[2-(1-methyl-1H-imidazole-4-sulfonylamino)-ethoxy]-1,2,3,4-tetrahydro-naphthalen-2-yl}-propionamide

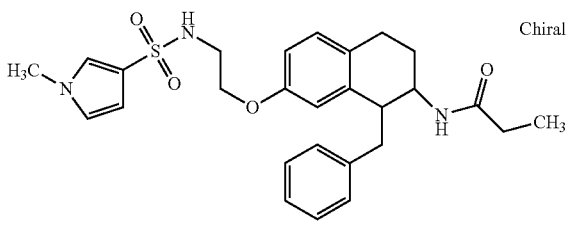 [SMILES: CCC(=O)NC1CCc2ccc(OCCNS(=O)(=O)c3ccn(C)c3)cc2C1Cc1ccccc1]

N-{1-Benzyl-7-[2-(1-methyl-1H-imidazole-4-sulfonylamino)-ethoxy]-1,2,3,4-tetrahydronaphthalen-2-yl}-propionamide was prepared in analogy to example 2 using propionyl chloride in place of ethyl chloroformate.

Could be separated by chiral chromatography of the final compound or an intermediate.

ESI-MS [M+H$^+$]=497 Calculated for $C_{26}H_{32}N_4O_4S$=496

Example 271

N-(2-{[8-(3,5-Difluorobenzyl)-7-(formylamino)-5,6,7,8-tetrahydronaphthalen-2-yl]oxy}ethyl)-1-methyl-1H-pyrrole-3-sulfonamide

271.1 Ethyl[1-(3,5-difluorobenzyl)-7-(2-{[(1-methyl-1H-pyrrol-3-yl)sulfonyl]amino}ethoxy)-1,2,3,4-tetrahydronaphthalen-2-yl]carbamate

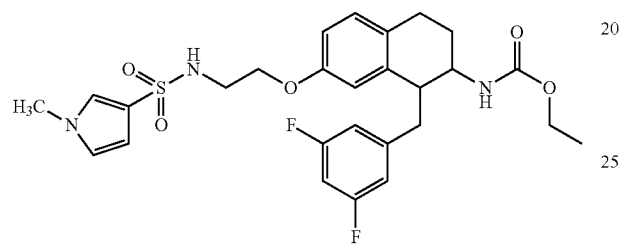

Ethyl[1-(3,5-difluorobenzyl)-7-(2-{[(1-methyl-1H-pyrrol-3-yl)sulfonyl]amino}ethoxy)-1,2,3,4-tetrahydronaphthalen-2-yl]carbamate was prepared in analogy to example 2.

271.2 N-(2-{[8-(3,5-Difluorobenzyl)-7-(formylamino)-5,6,7,8-tetrahydronaphthalen-2-yl]oxy}ethyl)-1-methyl-1H-pyrrole-3-sulfonamide

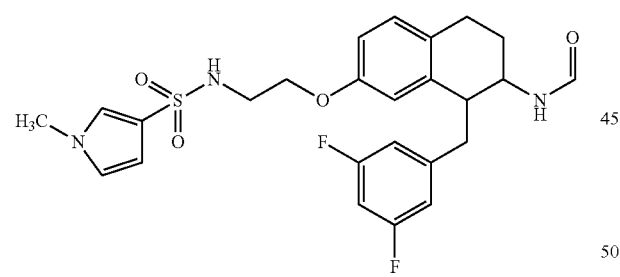

Ethyl[1-(3,5-difluorobenzyl)-7-(2-{[(1-methyl-1H-pyrrol-3-yl)sulfonyl]amino}ethoxy)-1,2,3,4-tetrahydronaphthalen-2-yl]carbamate (200 mg, 0.365 mmol) was dissolved in tetrahydrofuran (16 mL). A 1 M solution of lithium aluminium hydride in tetrahydrofuran (0.73 mL, 0.73 mmol) was added dropwise at room temperature. The reaction mixture was heated to 50° C. for 2 h. Under cooling 2N sodium hydroxide solution (3 mL) was added dropwise. Water (30 mL) and ethyl acetate (30 mL) were added. The aqueous phase was extracted twice with ethyl acetate. The combined extracts were dried (MgSO$_4$) and the solvent was evaporated in vacuo. The crude product was purified by flash chromatography (silica gel, dichloromethane, methanol). Yield: 61 mg (0.116 mmol, 32%).

ESI-MS [M+H$^+$]=504 Calculated for C$_{25}$H$_{27}$F$_2$N$_3$O$_4$S=503

Example 272

N-{3-[8-(3,4-Dichlorobenzyl)-7-(propan-2-ylamino)-5,6,7,8-tetrahydronaphthalen-2-yl]propyl}propane-1-sulfonamide

272.1 1-(3,4-Dichlorobenzyl)-7-methoxy-N-(propan-2-yl)-1,2,3,4-tetrahydronaphthalen-2-amine

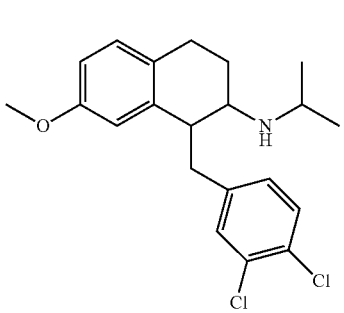 [SMILES: COc1ccc2c(c1)C(Cc1ccc(Cl)c(Cl)c1)C(NC(C)C)CC2]

1-(3,4-Dichlorobenzyl)-7-methoxy-N-(propan-2-yl)-1,2,3,4-tetrahydronaphthalen-2-amine was isolated as a minor by-product in the recrystallization of 1-(3,4-dichlorobenzyl)-7-methoxy-1,2,3,4-tetrahydronaphthalen-2-amine hydrochloride from isopropanol.

272.2 N-{3-[8-(3,4-Dichlorobenzyl)-7-(propan-2-ylamino)-5,6,7,8-tetrahydronaphthalen-2-yl]propyl}propane-1-sulfonamide

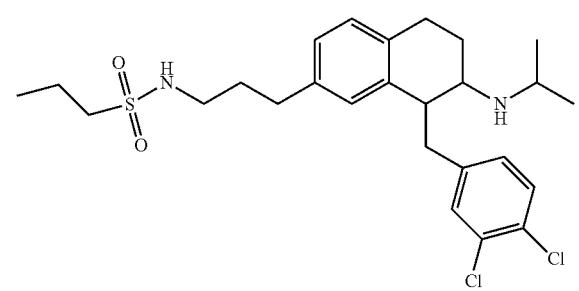 [SMILES: CCCS(=O)(=O)NCCCc1ccc2c(c1)C(Cc1ccc(Cl)c(Cl)c1)C(NC(C)C)CC2]

N-{3-[8-(3,4-Dichlorobenzyl)-7-(propan-2-ylamino)-5,6,7,8-tetrahydronaphthalen-2-yl]propyl}propane-1-sulfonamide was prepared in analogy to example 264 using 1-(3,4-dichlorobenzyl)-7-methoxy-N-(propan-2-yl)-1,2,3,4-tetrahydronaphthalen-2-amine in place of 1-[1-(3-chlorobenzyl)-7-methoxy-1,2,3,4-tetrahydronaphthalen-2-yl]pyrrolidine.

ESI-MS [M+H⁺]=511 Calculated for C$_{25}$H$_{32}$Cl$_2$N$_2$O$_3$S=510

Example 273

N-{3-[8-Benzyl-7-(propan-2-ylamino)-5,6,7,8-tetrahydronaphthalen-2-yl]propyl}propane-1-sulfonamide hydrochloride

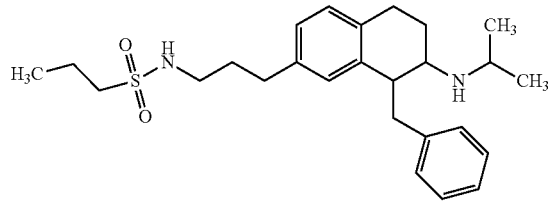

N-{3-[8-(3,4-Dichlorobenzyl)-7-(propan-2-ylamino)-5,6,7,8-tetrahydronaphthalen-2-yl]propyl}propane-1-sulfonamide (70 mg, 0.137 mmol) was dissolved in methanol (1.5 mL) and palladium hydroxide (30 mg, 0.214 mmol) was added. The reaction mixture was heated under reflux in an atmosphere of hydrogen for 6 h. The catalyst was removed by filtration and the crude product was purified by flash chromatography (silica gel, dichloromethane, methanol). The obtained amine was dissolved in dichloromethane (2 mL) and 5 N hydrochloric acid in isopropanol (0.3 mL) was added. The solvent was evaporated and the product dried in vacuo. Yield: 30 mg (0.63 mmol, 46%).

ESI-MS [M+H⁺]=443 Calculated for C$_{26}$H$_{38}$N$_2$O$_2$S=442

Example 274

N-{3-[8-(4-Chlorobenzyl)-7-(diethylamino)-5,6,7,8-tetrahydronaphthalen-2-yl]propyl}-1-cyclopropylmethanesulfonamide hydrochloride 274.1 N-{3-[7-Amino-8-(4-chlorobenzyl)-5,6,7,8-tetrahydronaphthalen-2-yl]propyl}-1-cyclopropylmethanesulfonamide

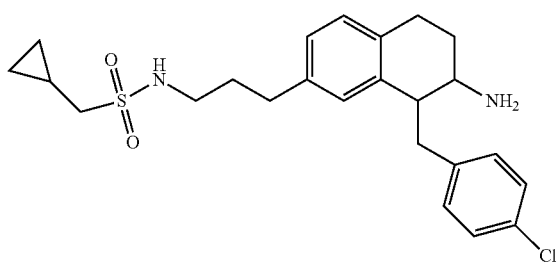 [SMILES: NC1CCc2ccc(CCCNS(=O)(=O)CC3CC3)cc2C1Cc1ccc(Cl)cc1]

N-{3-[7-Amino-8-(4-chlorobenzyl)-5,6,7,8-tetrahydronaphthalen-2-yl]propyl}-1-cyclopropylmethanesulfonamide (cf. 202).

274.2 N-{3-[8-(4-Chlorobenzyl)-7-(diethylamino)-5,6,7,8-tetrahydronaphthalen-2-yl]propyl}-1-cyclopropylmethanesulfonamide hydrochloride

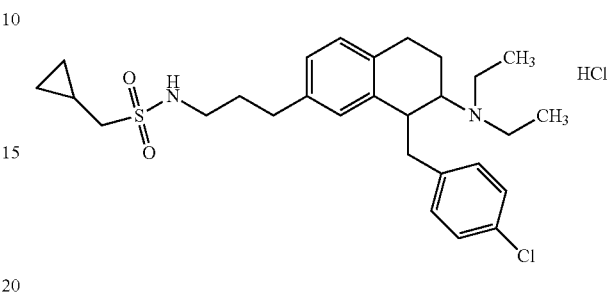

N-(3-(7-Amino-8-(4-chlorobenzyl)-5,6,7,8-tetrahydronaphthalen-2-yl)propyl)-1-cyclopropylmethanesulfonamide (49 mg, 0.11 mmol) was dissolved in dichloromethane (2 mL). Acetic acid (7 μL, 0.11 mmol) was added followed by acetaldehyde (18 μL, 0.322 mmol) in dichloromethane (2 mL) and sodium triacetoxyborohydride (34 mg, 0.16 mmol). The reaction mixture was stirred at room temperature for 2 h. The reaction mixture was diluted with dichloromethane (20 mL) and washed with water (2×10 mL). The organic layer was dried (MgSO$_4$) and the solvent was evaporated in vacuo. The crude product was purified by flash chromatography (silica gel, dichloromethane, methanol). The amine was dissolved in dichloromethane (3 mL) and excess hydrochloric acid in ethanol was added. The solvents were evaporated and the product dried in vacuo. Yield: 22 mg (0.041 mmol, 38%).

ESI-MS [M+H⁺]=503 Calculated for C$_{28}$H$_{39}$ClN$_2$O$_2$S=502

Example 275

N-{[8-Benzyl-7-(methylamino)-5,6,7,8-tetrahydronaphthalen-2-yl]methyl}-N-methylpropane-1-sulfonamide trifluoroacetate

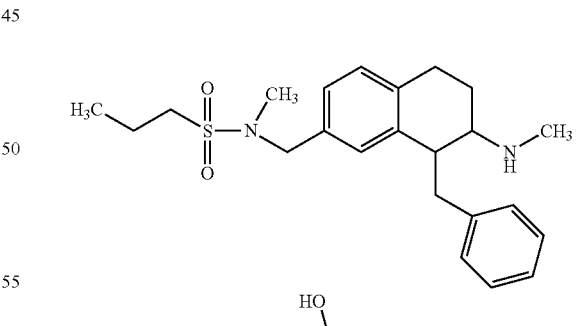

This compound could be prepared in analogy to example 227 using tert-butyl[(1S,2R)-1-benzyl-7-{[(propylsulfonyl)amino]methyl}-1,2,3,4-tetrahydronaphthalen-2-yl]carbamate in place of tert-butyl 1-(3-fluorobenzyl)-7-(3-(propylsulfonamido)propyl)-1,2,3,4-tetrahydronaphthalen-2-ylcarbamate (alkylation of sulfonamide). The tert-butyl

Example 276

N-[1-Benzyl-7-{3-[(propylsulfonyl)amino]prop-1-yn-1-yl}-1,2,3,4-tetrahydronaphthalen-2-yl]acetamide

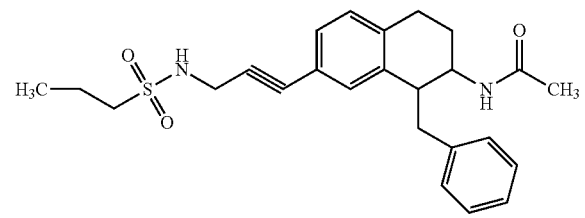 [SMILES: CCCS(=O)(=O)NCC#Cc1ccc2c(c1)C(Cc1ccccc1)C(NC(C)=O)CC2]

7-Acetamido-8-benzyl-5,6,7,8-tetrahydronaphthalen-2-yl trifluoromethanesulfonate (100 mg, 0.234 mmol; prepared in analogy to 8-(3,4-dichlorobenzyl)-7-[(ethoxycarbonyl)amino]-5,6,7,8-tetrahydronaphthalen-2-yl trifluoromethanesulfonate, example 29), N-(prop-2-ynyl)propane-1-sulfonamide (75 mg, 0.468 mmol), palladium tetrakistriphenylphosphine (54 mg, 0.047 mmol), copper(I) iodide (35.6 mg, 0.187 mmol) and triethylamine (65 µL, 0.468 mmol) in dioxane (3 mL) were heated under reflux for 16 h. Water (15 mL) was added and the mixture extracted with dichloromethane (3×20 mL). The combined organic extracts were dried (MgSO$_4$) and the solvent was evaporated in vacuo. The crude product was purified by flash chromatography (silica gel, dichloromethane, methanol). Yield: 56 mg (0.132 mmol, 57%).

ESI-MS [M+H$^+$]=439 Calculated for C$_{25}$H$_{30}$N$_2$O$_3$S=438

Example 277

N-(2-(8-Benzyl-7-(oxetan-3-ylamino)-5,6,7,8-tetrahydronaphthalen-2-yloxy)ethyl)-1-cyclopropyl-methanesulfonamide

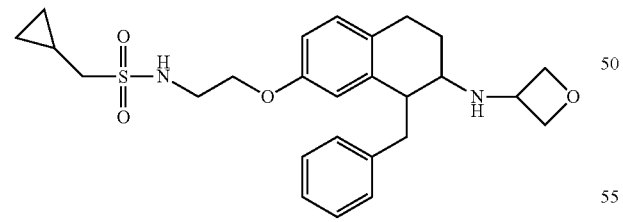

N-(2-(7-Amino-8-benzyl-5,6,7,8-tetrahydronaphthalen-2-yloxy)ethyl)-1-cyclopropylmethanesulfonamide (50 mg, 0.121 mmol) was dissolved in methanol. Oxetan-3-one (87 mg, 1.21 mmol), zinc chloride (66 mg, 0.482 mmol) and sodium cyanoborohydride (23 mg, 0.362 mmol) were added at 0° C. The reaction mixture was then heated to 40° C. for 5 h. Aqueous ammonium chloride solution was added and the aqueous layer was extracted with ethyl acetate. The combined organic extracts were washed with brine, dried (MgSO$_4$) and concentrated in vacuo. The crude product was purified by flash chromatography (silica gel, dichloromethane, methanol). Yield: 3 mg (6.4 µmol, 5%).

ESI-MS [M+H$^+$]+=471 Calculated for C$_{26}$H$_{34}$N$_2$O$_4$S=470

Example 278

Propane-1-sulfonic acid (8-benzyl-7-cyclopropylamino-5,6,7,8-tetrahydro-naphthalen-2-ylmethyl)-amide hydrochloride

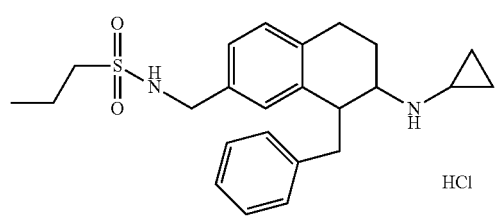 [SMILES: CCCS(=O)(=O)NCc1ccc2c(c1)C(Cc1ccccc1)C(NC1CC1)CC2 ; Cl]

N-((7-Amino-8-benzyl-5,6,7,8-tetrahydronaphthalen-2-yl)methyl)propane-1-sulfonamide (51 mg, 0.137 mmol), (1-ethoxycyclopropoxy)trimethylsilane (26 mg, 0.151 mmol), acetic acid (0.078 mL, 1.37 mmol), sodium cyanoborohydride (26 mg, 0.411 mmol) and molecular sieve (50 mg) in methanol (1.5 mL) were heated in the microwave at 100° C. for 25 min. The solvent was evaporated and the crude product purified by flash chromatography (silica gel, dichloromethane, methanol) and converted into the hydrochloride. Yield: 18 mg (0.04 mmol, 29%).

ESI-MS [M+H$^+$]=413 Calculated for C$_{24}$H$_{32}$N$_2$O$_2$S=412

Example 279

(1-(4-Chloro-benzyl)-7-{2-[methyl-(propane-1-sulfonyl)-amino]-ethoxy}-1,2,3,4-tetrahydronaphthalen-2-yl)-carbamic acid ethyl ester 279.1 Propane-1-sulfonic acid cyclopropyl amide

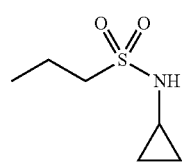

To a solution of cyclopropylamine (1.2 ml, 17.5 mmol) in 100 ml CH$_2$Cl$_2$ and DMAP (2.4 g, 17.5 mmol) was added dropwise a solution of propane-1-sulfonyl chloride (2.3 ml, 19.2 mmol) in 50 ml CH$_2$Cl$_2$. The resulting mixture was stirred at room temperature over night and diluted with 50 ml of CH$_2$Cl$_2$. The mixture was extracted subsequently with water, 1 M HCl, and brine, tried over Na$_2$SO$_4$, filtered and the solvent evaporated to obtain 2.8 g of product (oil) which was used in the next step without further purification.

279.2 Acetic acid 2-[cyclopropyl-(propane-1-sulfonyl)-amino]ethyl ester

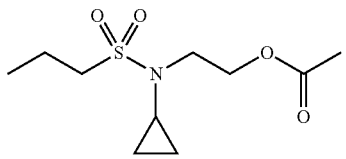 [SMILES: CCCS(=O)(=O)N(CCOC(C)=O)C1CC1]

A mixture of propane-1-sulfonic acid cyclopropyl amide (1.3 g, 8 mmol), K2CO3 (2.4 g, 14.4 mmol) and acetic acid 2-bromo-ethyl ester (9.5 g, 16 mmol) mmol) in 10 ml acetone was heated for 6 h to 120° C. in the microwave (Biotage). After cooling the mixture was filtered and the solvent evaporated to obtain 1.7 g of product as an oil which was used without further purification in the next step.

279.3 Propane-1-sulfonic acid cyclopropyl-(2-hydroxy-ethyl)-amide

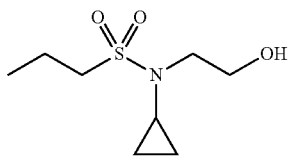

A mixture of acetic acid 2-[cyclopropyl-(propane-1-sulfonyl)-amino]ethyl ester (1.7 g, 6.8 mmol) and KOH (0.57 g, 10.2 mmol) in 30 ml Methanol was stirred over night at room temperature. The solvent was evaporated the residue dissolved in ethyl acetate and subsequently extracted with water and 1 M KOH, dried over $Na_2SO_4$ and the solvent evaporated to obtain 0.46 g of product which was used purified by chromatography (253.5 mg of colorless oil)

279.4 Propane-1-sulfonic acid 2-[cyclopropyl-(propane-1-sulfonyl)-amino]ethyl ester

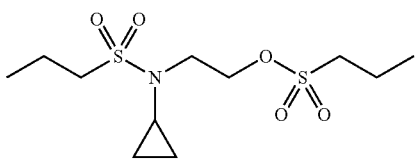 [SMILES: CCCS(=O)(=O)OCCN(C1CC1)S(=O)(=O)CCC]

To a solution of propane-1-sulfonic acid cyclopropyl-(2-hydroxy-ethyl)-amide (150 mg, 0.8 mmol) in $CH_2Cl_2$ and DMAP (97 mg, 0.8 mmol) was added dropwise a solution of propane-1-sulfonyl chloride (97 mg, 0.8 mmol) in $CH_2Cl_2$. The resulting mixture was stirred at room temperature over night, diluted with 50 ml of $CH_2Cl_2$, extracted subsequently with water, 1 M HCl, and brine, tried over $Na_2SO_4$, filtered and the solvent evaporated to obtain 197.5 mg of product which was used in the next step without further purification.

279.5 1-(3-Chloro-benzyl)-7-{2-[cyclopropyl-(propane-1-sulfonyl)-amino]-ethoxy}-1,2,3,4-tetrahydro-naphthalen-2-yl)-carbamic acid ethyl ester

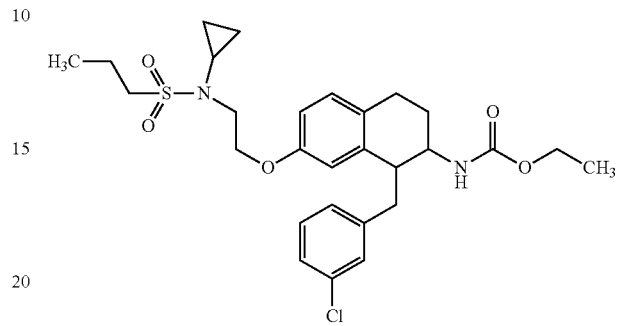

Prepared in one step from ethyl 1-(3-chlorobenzyl)-7-hydroxy-1,2,3,4-tetrahydronaphthalen-2-ylcarbamate (prepared in analogy to example 1d) and propane-1-sulfonic acid 2-[cyclopropyl-(propane-1-sulfonyl)-amino]ethyl ester in analogy to example 76.

ESI-MS [M+H$^+$]=549 Calculated for $C_{28}H_{37}ClN_2O_5S$=548

Example 280

1-Benzyl-7-{2-[cyclopropyl-(propane-1-sulfonyl)-amino]-ethoxy}-1,2,3,4-tetrahydronaphthalen-2-yl)-carbamic acid ethyl ester

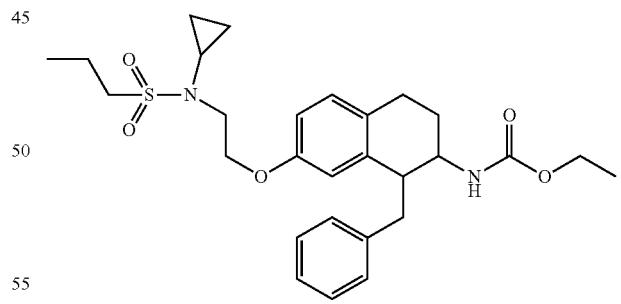

Prepared in one step from ethyl 1-benzyl-7-hydroxy-1,2,3,4-tetrahydronaphthalen-2-ylcarbamate (prepared in analogy to example 1d) and propane-1-sulfonic acid 2-[cyclopropyl-(propane-1-sulfonyl)-amino]-ethyl ester in analogy to example 76.

ESI-MS [M+H$^+$]=515 Calculated for $C_{28}H_{38}N_2O_5S$=514

Example 281

Propane-1-sulfonic acid {2-[7-amino-8-(3-chloro-benzyl)-5,6,7,8-tetrahydro-naphthalen-2-yloxy]-ethyl}-cyclopropyl-amide hydrochloride

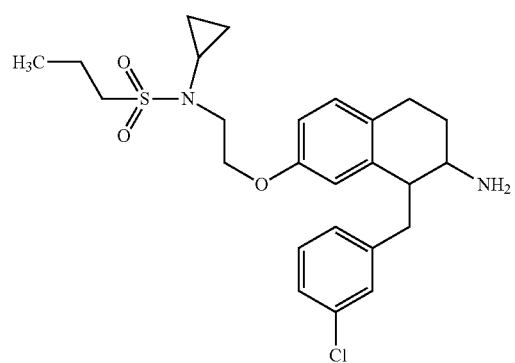

Prepared in one step from 1-(3-Chloro-benzyl)-7-{2-[cyclopropyl-(propane-1-sulfonyl)amino]-ethoxy}-1,2,3,4-tetrahydro-naphthalen-2-yl)-carbamic acid ethyl ester (example 279) example in analogy to example 3.

ESI-MS [M+H⁺]=477 Calculated for C$_{25}$H$_{33}$ClN$_2$O$_3$S=476

Example 282

Propane-1-sulfonic acid [2-(7-amino-8-benzyl-5,6,7,8-tetrahydro-naphthalen-2-yloxy)ethyl]-cyclopropyl-amide hydrochloride

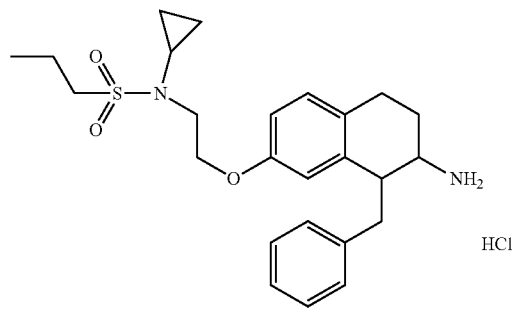 [SMILES: CCCS(=O)(=O)N(CCOc1ccc2c(c1)C(Cc1ccccc1)C(N)CC2)C1CC1 ; Cl]

Prepared in one step from 1-Benzyl-7-{2-[cyclopropyl-(propane-1-sulfonyl)-amino]-ethoxy}-1,2,3,4-tetrahydro-naphthalen-2-yl)-carbamic acid ethyl ester (example 280) in analogy to example 3.

ESI-MS [M+H⁺]=443 Calculated for C$_{25}$H$_{34}$N$_2$O$_3$S=442

Example 283

1-(3-Chloro-benzyl)-7-[1-(propane-1-sulfonyl)-azetidin-3-yl]-1,2,3,4-tetrahydro-naphthalen-2-ylamine hydrochloride

283.1 3-[8-(3-Chloro-benzyl)-7-ethoxycarbonylamino-5,6,7,8-tetrahydro-naphthalen-2-yl]-azetidine-1-carboxylic acid tert-butyl ester

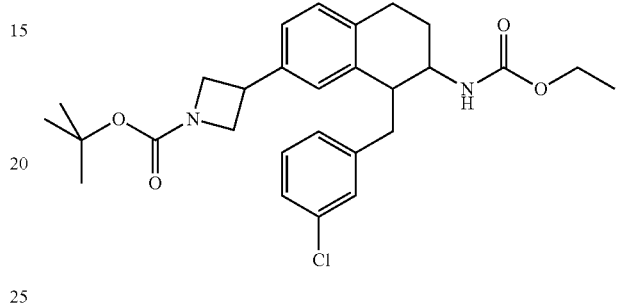

A suspension of zinc powder (152 mg, 2.3 mmol) in 1 ml of DMA in a dry flask was heated under N$_2$ to 65-70° C. A mixture of TMS-Cl (28 mg, 0.26 mmol) and 1,2-dibromoethane (49 mg, 0.26 mmol) was added dropwise, stirred for 30 min, followed by slow (15 min) addition of 3-iodo-azetidine-1-carboxylic acid tert-butyl ester (510 mg, 1.8 mmol) in 1 ml DMA. The reaction was cooled slowly (3 h) to room temperature, added to a mixture of 8-(3,4-chlorobenzyl)-7-[(ethoxycarbonyl)amino]-5,6,7,8-tetrahydronaphthalen-2-yl trifluoromethanesulfonate (633 mg, 1.3 mmol, prepared in analogy to example 29), CuI (74 mg, 0.39 mmol) and PdCl$_2$(dppf) (63 mg, 0.08 mmol) in 4 ml DMA preheated to 70° C. and stirred for 7 h at 70° C. Water and MTB (1:1 20 ml) were added and the resulting mixture filtered. The organic layer was separated, dried (Na$_2$SO$_4$) and the solvent evaporated. Purification by chromatography afforded 560 mg of product (white foam).

283.2 1-(3-Chloro-benzyl)-7-[1-(propane-1-sulfonyl)-azetidin-3-yl]-1,2,3,4-tetrahydronaphthalen-2-ylamine hydrochloride

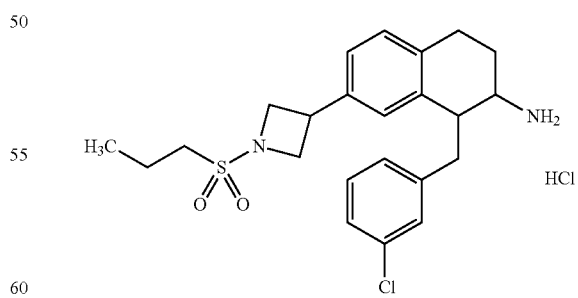

Prepared in three steps from 3-[8-(3-chloro-benzyl)-7-ethoxycarbonylamino-5,6,7,8-tetrahydro-naphthalen-2-yl] azetidine-1-carboxylic acid tert-butyl ester in analogy to example 46/47.

Cleavage of Boc-group was done in formic acid.

ESI-MS [M+H⁺]=433 Calculated for $C_{23}H_{29}ClN_2O_2S$=432

Example 284

1-Benzyl-7-[1-(propane-1-sulfonyl)-azetidin-3-yl]-1,2,3,4-tetrahydro-naphthalen-2-ylamine hydrochloride

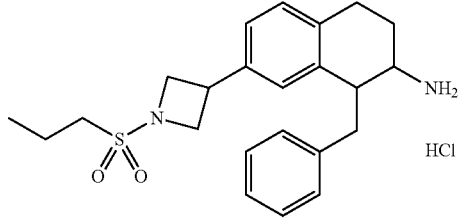 [SMILES: CCCS(=O)(=O)N1CC(c2ccc3c(c2)C(Cc2ccccc2)C(N)CC3)C1 ; Cl]

Prepared in analogy to example 283.
ESI-MS [M+H⁺]+=399 Calculated for $C_{23}H_{30}N_2O_2S$=398

Example 285

{1-(3-Chloro-benzyl)-7-[1-(propane-1-sulfonyl)-azetidin-3-ylmethoxy]-1,2,3,4-tetrahydronaphthalen-2-yl}-carbamic acid ethyl ester

285.1 1-(Propane-1-sulfonyl)-azetidine-3-carboxylic acid methyl ester

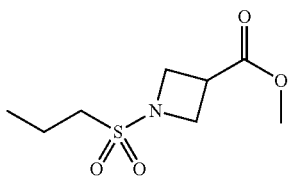

Prepared by standard procedure from azetidine-3-carboxylic acid methyl ester and propane-1-sulfonyl chloride (e.g. example 279).

285.2 [1-(Propane-1-sulfonyl)-azetidin-3-yl]methanol

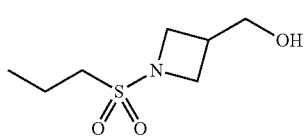

Prepared by reduction of 1-(propane-1-sulfonyl)-azetidine-3-carboxylic acid methyl with LiAlH₄ in THF at room temperature to 50° C. (e.g. example 300).

285.3 Methanesulfonic acid 1-(propane-1-sulfonyl)-azetidin-3-ylmethyl ester

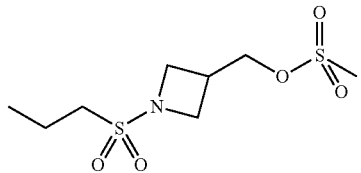 [SMILES: CCCS(=O)(=O)N1CC(COS(C)(=O)=O)C1]

Prepared by standard procedure from [1-(propane-1-sulfonyl)-azetidin-3-yl]methanol and methan-1-sulfonyl chloride (e.g. example 40)

285.4 {1-(3-Chloro-benzyl)-7-[1-(propane-1-sulfonyl)-azetidin-3-ylmethoxy]-1,2,3,4-tetrahydronaphthalen-2-yl}-carbamic acid ethyl ester

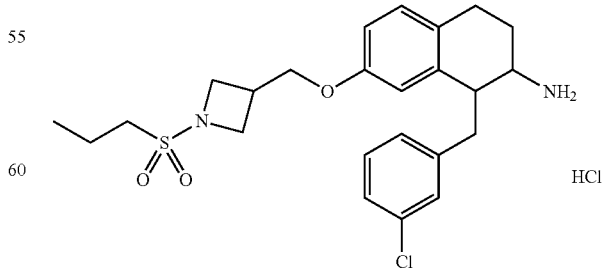

Prepared from 1-(3-chlorobenzyl)-7-hydroxy-1,2,3,4-tetrahydronaphthalen-2-ylcarbamate and methanesulfonic acid 1-(propane-1-sulfonyl)-azetidin-3-ylmethyl ester in analogy to example 315.
ESI-MS [M+H⁺]=536 Calculated for $C_{27}H_{35}ClN_2O_5S$=535

Example 286

1-(3-Chloro-benzyl)-7-[1-(propane-1-sulfonyl)-azetidin-3-ylmethoxy]-1,2,3,4-tetrahydronaphthalen-2-ylamine hydrochloride Prepared from {1-(3-chloro-benzyl)-7-[1-(propane-1-sulfonyl)-azetidin-3-ylmethoxy]-1,2,3,4-tetrahydronaphthalen- 2-yl}-carbamic acid ethyl ester in analogy to example 3. ESI-MS [M+H⁺]=463 Calculated for $C_{24}H_{31}ClN_2O_3S$=462

Example 287

[1-(3-Chloro-benzyl)-7-(2-cyclopropylmethanesulfonylamino-ethoxy)-1,2,3,4-tetrahydronaphthalen-2-yl]-carbamic acid ethyl ester

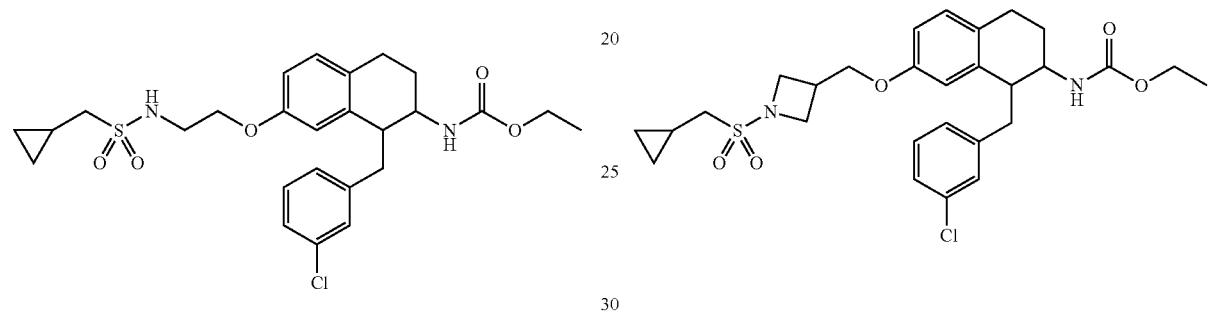

Prepared in analogy to example 3.
ESI-MS [M+H⁺]=521 Calculated for $C_{26}H_{33}ClN_2O_5S$=520

Example 288

N-{2-[7-Amino-8-(3-chloro-benzyl)-5,6,7,8-tetrahydro-naphthalen-2-yloxy]-ethyl}-C-cyclopropyl-methanesulfonamide hydrochloride

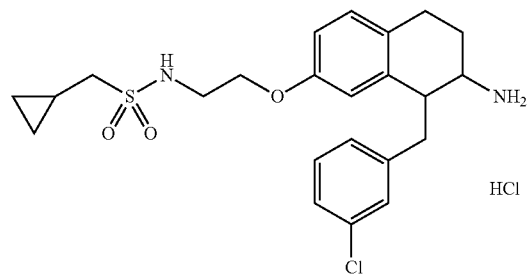 [SMILES: NC1CCc2ccc(OCCNS(=O)(=O)CC3CC3)cc2C1Cc1cccc(Cl)c1 ; Cl]

Prepared from [1-(3-chloro-benzyl)-7-(2-cyclopropyl-methanesulfonylamino-ethoxy)-1,2,3,4-tetrahydro-naphthalen-2-yl]-carbamic acid ethyl ester in analogy to example 3.

ESI-MS [M+H⁺]=449 Calculated for $C_{23}H_{29}ClN_2O_3S$=448

Example 289

[1-(3-Chloro-benzyl)-7-(1-cyclopropylmethanesulfonyl-azetidin-3-ylmethoxy)-1,2,3,4-tetrahydro-naphthalen-2-yl]-carbamic acid ethyl ester

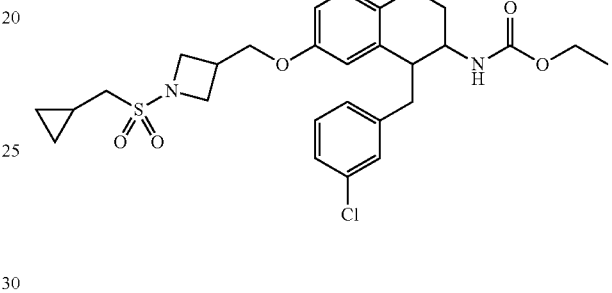

Prepared from 1-(3-chlorobenzyl)-7-hydroxy-1,2,3,4-tetrahydronaphthalen-2-ylcarbamate and methanesulfonic acid Methanesulfonic acid 1-cyclopropylmethanesulfonyl-azetidin-3-yl methylester (prepared in analogy to example 285) in analogy to example 315.
ESI-MS [M+H⁺]=547 Calculated for $C_{28}H_{35}ClN_2O_5S$=546

Example 290

{1-(3-Chloro-benzyl)-7-[2-(cyclopropylmethane-sulfonyl-methyl-amino)-ethoxy]-1,2,3,4-tetrahydro-naphthalen-2-yl}-carbamic acid ethyl ester

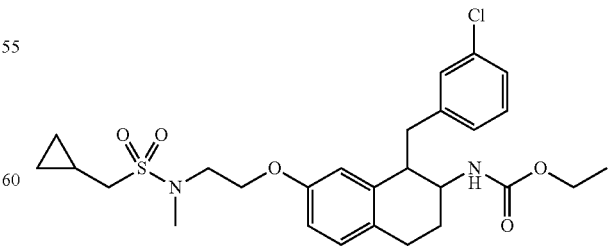

Prepared from [1-(3-chloro-benzyl)-7-(2-cyclopropyl-methanesulfonylamino-ethoxy)-1,2,3,4-tetrahydro-naphthalen-2-yl]carbamic acid ethyl ester in analogy to example 45.

ESI-MS [M+H⁺]+=535 Calculated for C$_{27}$H$_{35}$ClN$_2$O$_5$S=534

Example 291

N-{2-[7-Amino-8-(3-chloro-benzyl)-5,6,7,8-tetrahydro-naphthalen-2-yloxy]-ethyl}-C-cyclopropyl-N-methyl-methanesulfonamide

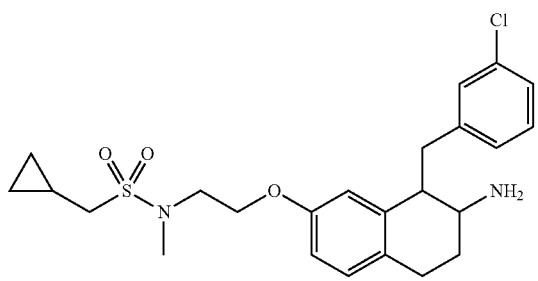 [SMILES: CN(CCOc1ccc2c(c1)C(Cc1cccc(Cl)c1)C(N)CC2)S(=O)(=O)CC1CC1]

{1-(3-Chloro-benzyl)-7-[2-(cyclopropylmethanesulfonyl-methyl-amino)-ethoxy]-1,2,3,4-tetrahydro-naphthalen-2-yl}-carbamic acid ethyl ester in analogy to example 3.
ESI-MS [M+H⁺]=463 Calculated for C$_{24}$H$_{31}$ClN$_2$O$_3$S=462

Example 292

1-Benzyl-7-[1-(propane-1-sulfonyl)-azetidin-3-yl-methoxy]-1,2,3,4-tetrahydro-naphthalen-2-ylamine hydrochloride

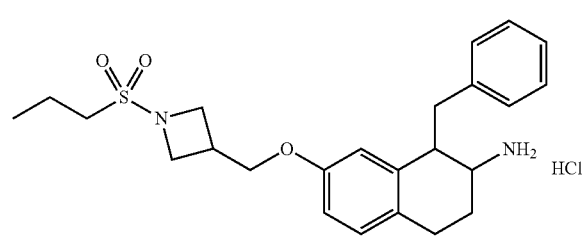 [SMILES: CCCS(=O)(=O)N1CC(COc2ccc3c(c2)C(Cc2ccccc2)C(N)CC3)C1 ; Cl]

Prepared in analogy to example 46.
ESI-MS [M+H⁺]=429 Calculated for C$_{24}$H$_{31}$ClN$_2$O$_3$S=428

Example 293

Propane-1-sulfonic acid {2-[7-amino-8-(2-chloro-benzyl)-5,6,7,8-tetrahydro-naphthalen-2-yloxy]-ethyl}-amide hydrochloride

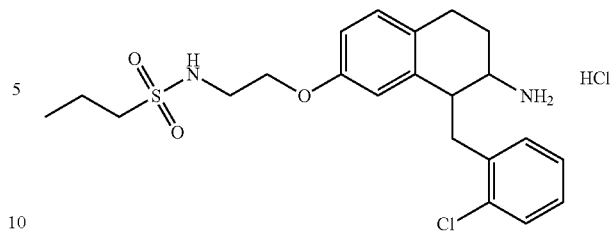

Prepared in analogy to example 3.
ESI-MS [M+H⁺]=437 Calculated for C$_{22}$H$_{29}$ClN$_2$O$_3$S=436

Example 294

Cyclopropanesulfonic acid {2-[7-amino-8-(2-chloro-benzyl)-5,6,7,8-tetrahydro-naphthalen-2-yloxyl]-ethyl}-amide hydrochloride

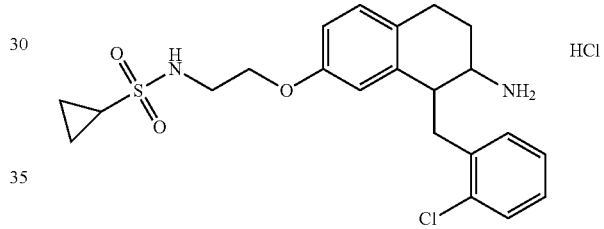

Prepared in analogy to example 3.
ESI-MS [M+H⁺]=435 Calculated for C$_{22}$H$_{27}$ClN$_2$O$_3$S=434

Example 295

N-{2-[7-Amino-8-(2-chloro-benzyl)-5,6,7,8-tetrahydro-naphthalen-2-yloxy]-ethyl}-C-cyclopropyl-methanesulfonamide hydrochloride

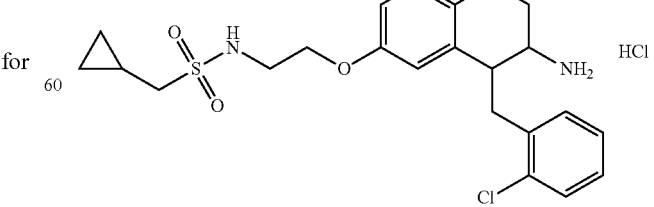

Prepared in analogy to example 3.

ESI-MS [M+H$^+$]=449 Calculated for C$_{23}$H$_{29}$ClN$_2$O$_3$S=448

Example 296

N-{3-[7-Amino-8-(3-chloro-benzyl)-5,6,7,8-tetrahydro-naphthalen-2-yl]-propyl}-C-cyclopropyl-methanesulfonamide hydrochloride 296.1 [7-(3-tert-Butoxycarbonylamino-propyl)-1-(3-chloro-benzyl)-1,2,3,4-tetrahydronaphthalen-2-yl]-carbamic acid ethyl ester

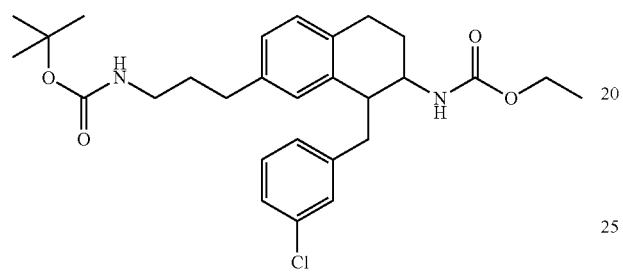

A solution of tert-butyl allylcarbamate (297 mg, 1.9 mmol) in dry THF under nitrogen was added dropwise at 0° C. to 9-BBN dissolved in THF (0.5 M, 2.3 ml, 1.2 mmol) and stirred for 4 h. This mixture was subsequently treated with 8-(3,4-chlorobenzyl)-7-[(ethoxycarbonyl)amino]-5,6,7,8-tetrahydronaphthalen-2-yl trifluoromethanesulfonate (250 mg, 0.5 mmol), palladium(11)acetate (11.5 mg, 0.05 mmol), triphenylphosphine (27 mg, 0.1 mmol) and cesium carbonate (333 mg, 1 mmol) after which the mixture was heated to reflux for 2 h.

The solvent was evaporated the residue dissolved in ethylacetate, extracted with water, dried (Na$_2$SO$_4$). Evaporation of solvent gave 0.51 g of a brown oil which was treated with diisopropyl ether to afford 91 mg of a brownish powder.

296.2 N-{3-[7-Amino-8-(3-chloro-benzyl)-5,6,7,8-tetrahydro-naphthalen-2-yl]-propyl}-C-cyclopropyl-methanesulfonamide hydrochloride

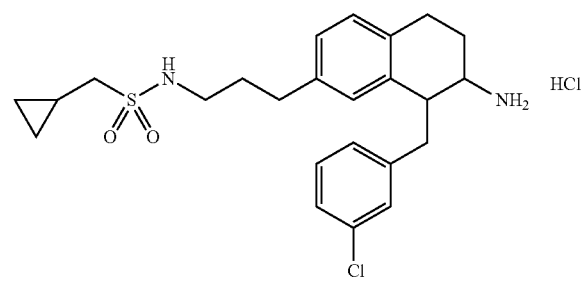 [SMILES: NC1CCc2ccc(CCCNS(=O)(=O)CC3CC3)cc2C1Cc1cccc(Cl)c1 ; Cl]

Prepared from [7-(3-tert-butoxycarbonylamino-propyl)-1-(3-chloro-benzyl)-1,2,3,4-tetrahydro-naphthalen-2-yl]-carbamic acid ethyl ester in analogy to example 3.
ESI-MS [M+H$^+$]=447 Calculated for C$_{24}$H$_{31}$ClN$_2$O$_2$S=446

Example 297

Propane-1-sulfonic acid {3-[7-amino-8-(3-chloro-benzyl)-5,6,7,8-tetrahydro-naphthalen-2-yl]-propyl}-amide hydrochloride

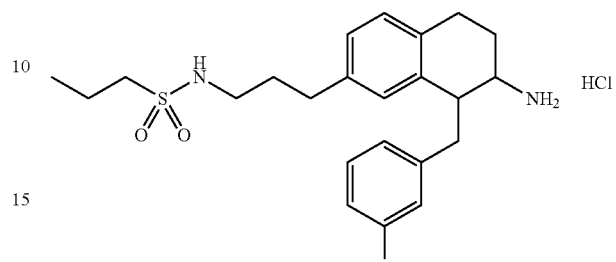

Prepared in analogy to example 296.
ESI-MS [M+H$^+$]=435 Calculated for C$_{23}$H$_{31}$ClN$_2$O$_2$S=434

Example 298

{1-(2-Chloro-benzyl)-7-[2-(1-methyl-1H-imidazole-4-sulfonylamino)-ethoxy]-1,2,3,4-tetrahydro-naphthalen-2-yl}-carbamic acid ethyl ester

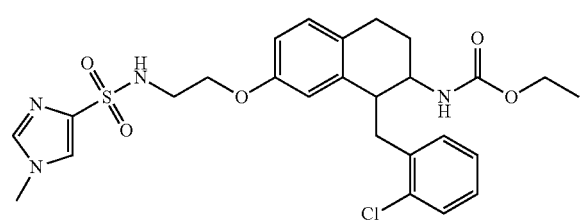 [SMILES: CCOC(=O)NC1CCc2ccc(OCCNS(=O)(=O)c3cn(C)cn3)cc2C1Cc1ccccc1Cl]

Prepared in analogy to example 3.
ESI-MS [M+H$^+$]=547 Calculated for C$_{26}$H$_{31}$ClN$_4$O$_5$S=546

Example 299

{1-(2-Chloro-benzyl)-7-[2-(1-methyl-1H-pyrazole-4-sulfonylamino)-ethoxy]-1,2,3,4-tetrahydro-naphthalen-2-yl}-carbamic acid ethyl ester

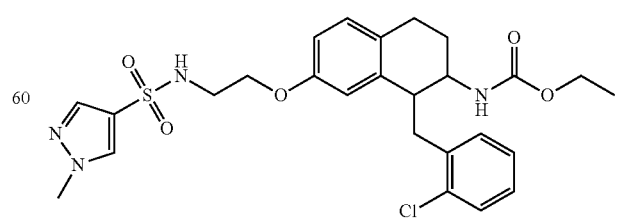

Prepared in analogy to example 3.

ESI-MS [M+H⁺]=547 Calculated for C$_{26}$H$_{31}$ClN$_4$O$_5$S=546

Example 300

N-{2-[8-(3-Chloro-benzyl)-7-methylamino-5,6,7,8-tetrahydro-naphthalen-2-yloxy]-ethyl}-C-cyclopropyl-methanesulfonamide hydrochloride

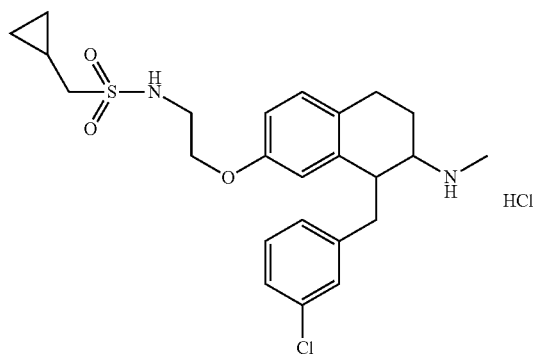 [SMILES: CNC1CCc2ccc(OCCNS(=O)(=O)CC3CC3)cc2C1Cc1cccc(Cl)c1 ; Cl]

A solution of LiAlH$_4$ in THF (1 M, 1.5 ml, 1.5 mmol) was added dropwise to [1-(3-chlorobenzyl)-7-(2-cyclopropyl-methanesulfonylamino-ethoxy)-1,2,3,4-tetrahydro-naphthalen-2-yl]-carbamic acid ethyl ester (523 mg, 1 mmol, example 287) dissolved in 100 ml of dry THF. The mixture was heated to reflux for 1 h, treated with 2N NaOH, and extracted with CH$_2$Cl$_2$. The organic layer was extracted with sat. NaHCO$_3$ and brine, dried (Na$_2$SO$_4$) filtered and the solvent evaporated. Purification by chromatography afforded 324 mg of product as colorless oil which was transformed to the hydrochloride in a mixture of HCl in isopropanol. (325 mg, white powder) ESI-MS [M+H⁺]=463 Calculated for C$_{24}$H$_{31}$ClN$_2$O$_3$S=462

Example 301

1-Methyl-1H-pyrazole-4-sulfonic acid {2-[7-amino-8-(2-chloro-benzyl)-5,6,7,8-tetrahydronaphthalen-2-yloxy]-ethyl}-amide hydrochloride

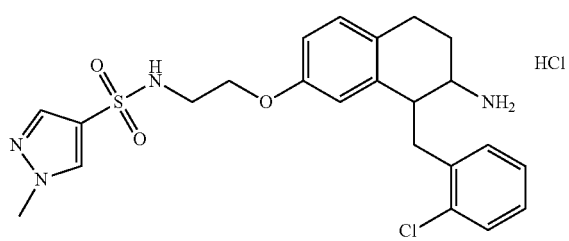 [SMILES: Cn1cc(S(=O)(=O)NCCOc2ccc3c(c2)C(Cc2ccccc2Cl)C(N)CC3)cn1 ; Cl]

Prepared in analogy to example 3.

ESI-MS [M+H⁺]=475 Calculated for C$_{23}$H$_{27}$ClN$_4$O$_3$S=474

Example 302

1-Methyl-1H-pyrazole-4-sulfonic acid {2-[8-(2-chloro-benzyl)-7-methylamino-5,6,7,8-tetrahydro-naphthalen-2-yloxy]-ethyl}-amide hydrochloride

Prepared in analogy to example 3/300.

ESI-MS [M+H⁺]=489 Calculated for C$_{24}$H$_{29}$ClN$_4$O$_3$S=488

Example 303

1-Methyl-1H-imidazole-4-sulfonic acid {2-[8-(2-chloro-benzyl)-7-methylamino-5,6,7,8-tetrahydro-naphthalen-2-yloxy]-ethyl}-amide hydrochloride

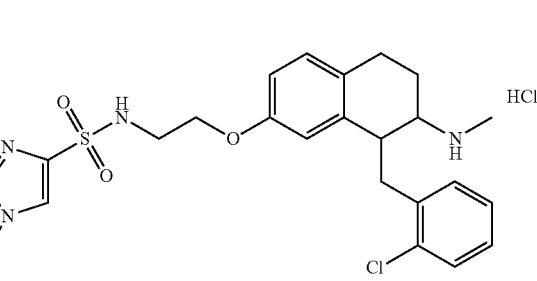

Prepared in analogy to example 3/300.

ESI-MS [M+H$^+$]=489 Calculated for C$_{24}$H$_{29}$ClN$_4$O$_3$S=488

Example 304

Propane-1-sulfonic acid {2-[7-amino-8-(3-chloro-benzyl)-5,6,7,8-tetrahydro-naphthalen-2-yl]-ethyl}-amide hydrochloride

304.1 [7-(2-Benzyloxycarbonylamino-ethyl)-1-(3-chloro-benzyl)-1,2,3,4-tetrahydronaphthalen-2-yl]-carbamic acid ethyl ester

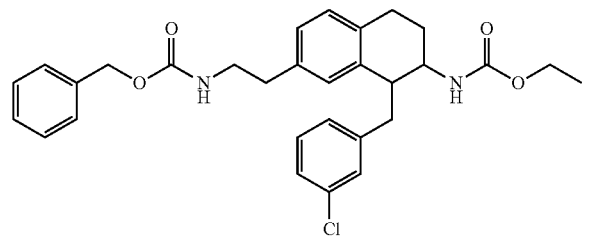 [SMILES: CCOC(=O)NC1CCc2ccc(CCNC(=O)OCc3ccccc3)cc2C1Cc1cccc(Cl)c1]

A mixture of potassium (2-(benzyloxycarbonylamino)ethyl)trifluoroborate (1,130 g, 3.96 mmol), cesium carbonate (2.58 g, 7.93 mmol), 8-(3-chlorobenzyl)-7-(ethoxycarbonylamino)-5,6,7,8-tetrahydronaphthalen-2-yl trifluoromethanesulfonate (1.3 g, 2.64 mmol), Pd(OAc)$_2$ (0.030 g, 0.132 mmol) and 2-dicyclohexyphosphino-2',6'-di-1-propoxy-1,1'-biphenyl (0.130 g, 0.264 mmol) under N$_2$ in toluene/water 3:1 (15 ml) was heated to refluxed for 13 h. The reaction was filtered, the solvent evaporated and the residue purified by chromatography to afford 1.04 g of product as colorless oil.

304.2 [7-(2-Amino-ethyl)-1-(3-chloro-benzyl)-1,2,3,4-tetrahydro-naphthalen-2-yl]-carbamic acid ethyl ester

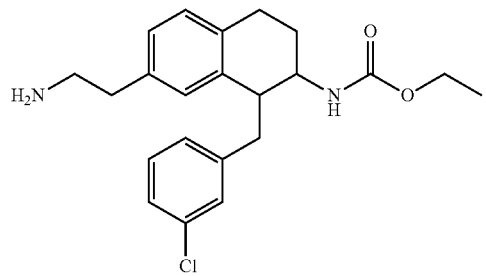 [SMILES: CCOC(=O)NC1CCc2ccc(CCN)cc2C1Cc1cccc(Cl)c1]

To [7-(2-benzyloxycarbonylamino-ethyl)-1-(3-chlorobenzyl)-1,2,3,4-tetrahydronaphthalen-2-yl]-carbamic acid ethyl ester (500 mg, 0.960 mmol) was added at room temperature 8 ml of 33% HBr in acetic acid. After 2 h the mixture was diluted with CH$_2$Cl$_2$, washed twice with NaHCO$_3$, dried and filtered. The solvent was evaporated to obtain the product as a yellow oil (392 mg), which was used without further purification.

304.3 Propane-1-sulfonic acid {2-[7-amino-8-(3-chloro-benzyl)-5,6,7,8-tetrahydronaphthalen-2-yl]-ethyl}-amide hydrochloride

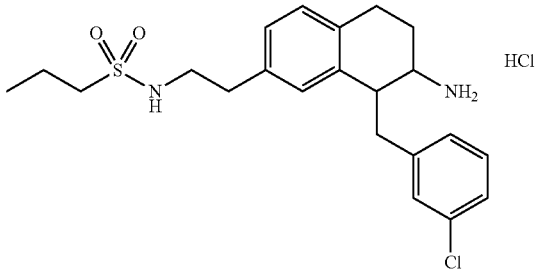 [SMILES: CCCS(=O)(=O)NCCc1ccc2c(c1)C(Cc1cccc(Cl)c1)C(N)CC2 ; Cl]

Prepared from [7-(2-amino-ethyl)-1-(3-chloro-benzyl)-1,2,3,4-tetrahydro-naphthalen-2-yl]-carbamic acid ethyl ester in analogy to example 3.

ESI-MS [M+H$^+$]=421 Calculated for C$_{22}$H$_{29}$ClN$_2$O$_2$S=420

Example 305

1-Methyl-1H-imidazole-4-sulfonic acid {2-[7-amino-8-(2-chloro-benzyl)-5,6,7,8-tetrahydronaphthalen-2-yloxy]-ethyl}-amide hydrochloride

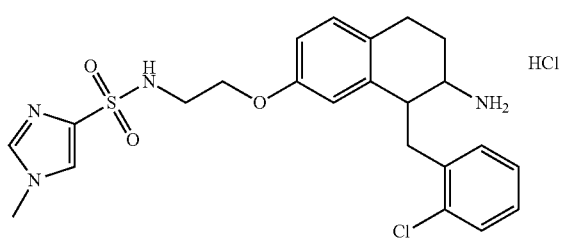 [SMILES: Cn1cnc(S(=O)(=O)NCCOc2ccc3c(c2)C(Cc2ccccc2Cl)C(N)CC3)c1 ; Cl]

Prepared in analogy to example 3.

ESI-MS [M+H⁺]=475 Calculated for $C_{23}H_{27}ClN_4O_3S$=474

Example 306

N-[1-(3-Chloro-benzyl)-7-(2-cyclopropylmethane-sulfonylamino-ethoxy)-1,2,3,4-tetrahydronaphthalen-2-yl]-acetamide

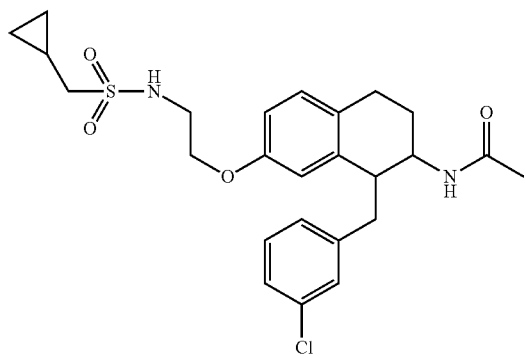 [SMILES: CC(=O)NC1CCc2ccc(OCCNS(=O)(=O)CC3CC3)cc2C1Cc1cccc(Cl)c1]

Prepared in analogy to example 214.
ESI-MS [M+H⁺]=491 Calculated for $C_{25}H_{31}ClN_2O_4S$=490

Example 307

N-{2-[8-(3-Chloro-benzyl)-7-ethylamino-5,6,7,8-tetrahydro-naphthalen-2-yloxy]-ethyl}-C-cyclopropyl-methanesulfonamide hydrochloride

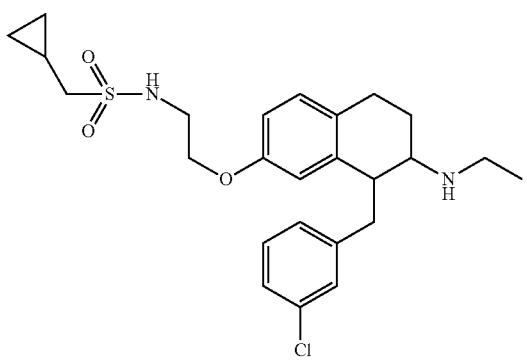

Prepared in analogy to example 300.

ESI-MS [M+H⁺]=477 Calculated for $C_{25}H_{33}ClN_2O_3S$=476

Example 308

Propane-1-sulfonic acid {3-[8-(3-chloro-benzyl)-7-methylamino-5,6,7,8-tetrahydronaphthalen-2-yl]-propyl}-amide hydrochloride

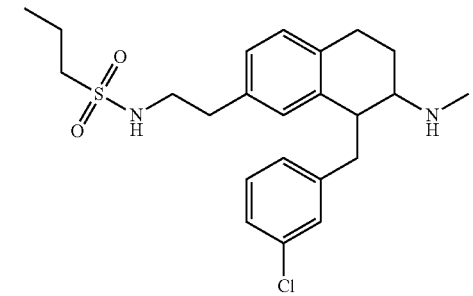 [SMILES: CCCS(=O)(=O)NCCc1ccc2c(c1)C(Cc1cccc(Cl)c1)C(NC)CC2]

Prepared in analogy to examples 297/300.
ESI-MS [M+H⁺]=449 Calculated for $C_{24}H_{33}ClN_2O_2S$=448

Example 309

Propane-1-sulfonic acid {2-[8-(3-chloro-benzyl)-7-methylamino-5,6,7,8-tetrahydronaphthalen-2-yl]-ethyl}-amide Prepared in analogy to examples 304/300.
ESI-MS [M+H⁺]=435 Calculated for $C_{23}H_{31}ClN_2O_2S$=434

Example 310

N-{2-[7-Amino-8-(3-chloro-benzyl)-5,6,7,8-tetrahydro-naphthalen-2-yl]-ethyl}-C-cyclopropyl-methanesulfonamide hydrochloride

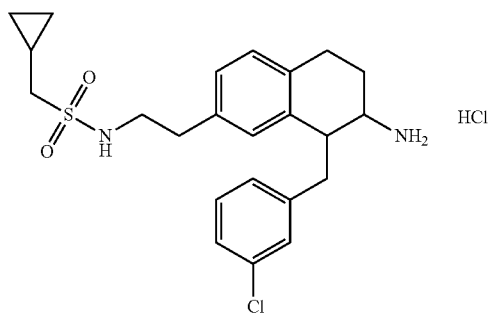 [SMILES: NC1CCc2ccc(CCNS(=O)(=O)CC3CC3)cc2C1Cc1cccc(Cl)c1 ; Cl]

Prepared in analogy to example 304.
ESI-MS [M+H$^+$]=433 Calculated for C$_{23}$H$_{29}$ClN$_2$O$_2$S=432

Example 311

Propane-1-sulfonic acid {2-[8-(2-fluoro-benzyl)-7-methylamino-5,6,7,8-tetrahydronaphthalen-2-yloxy]-ethyl}-amide hydrochloride

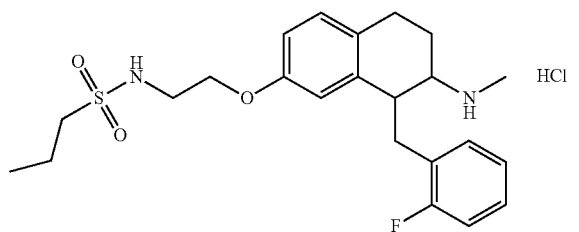 [SMILES: CCCS(=O)(=O)NCCOc1ccc2c(c1)C(Cc1ccccc1F)C(NC)CC2 ; Cl]

Prepared in analogy to examples 3/300.
ESI-MS [M+H$^+$]=435 Calculated for C$_{23}$H$_{31}$FN$_2$O$_3$=434

Example 312

C-Cyclopropyl-N-{2-[8-(2-fluoro-benzyl)-7-methylamino-5,6,7,8-tetrahydro-naphthalen-2-yloxy]-ethyl}-methanesulfonamide hydrochloride

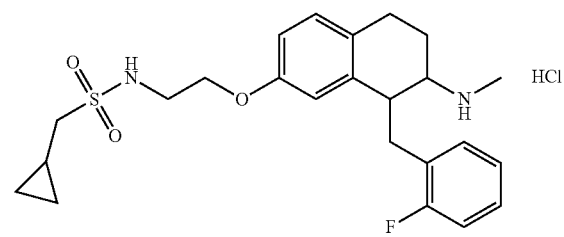 [SMILES: CNC1CCc2ccc(OCCNS(=O)(=O)CC3CC3)cc2C1Cc1ccccc1F ; Cl]

Prepared in analogy to examples 3/300.
ESI-MS [M+H$^+$]=447 Calculated for C$_{24}$H$_{31}$FN$_2$O$_3$S=446

Example 313

1-Methyl-1H-imidazole-4-sulfonic acid {2-[8-(3-chloro-benzyl)-7-methylamino-5,6,7,8-tetrahydro-naphthalen-2-yl]-ethyl}-amide

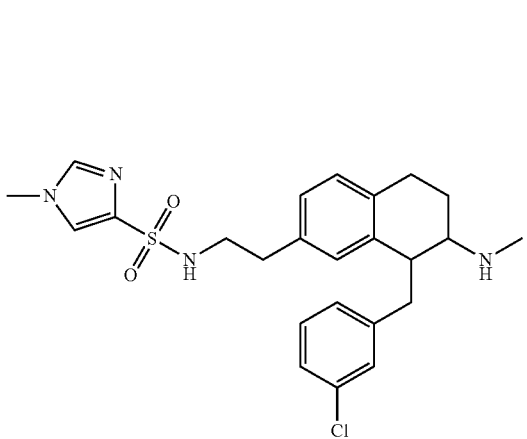

Prepared in analogy to examples 304/300.
ESI-MS [M+H$^+$]=473 Calculated for C$_{24}$H$_{29}$ClN$_4$O$_2$S=472

Example 314

Propane-1-sulfonic acid [2-(8-cyclohexylmethyl-7-methylamino-5,6,7,8-tetrahydronaphthalen-2-yloxy)-ethyl]-amide trifluoroacetate

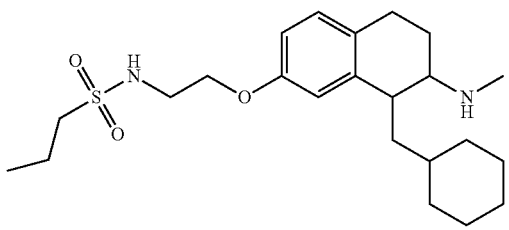

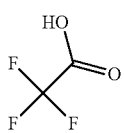

Prepared in analogy to examples 3/300.
ESI-MS [M+H$^+$]=423 Calculated for C$_{23}$H$_{38}$N$_2$O$_3$S=422

Example 315

1-Methyl-1H-imidazole-4-sulfonic acid {2-[8-(2-chloro-benzyl)-7-pyrrolidin-1-yl-5,6,7,8-tetrahydro-naphthalen-2-yloxy]-ethyl}-amide hydrochloride 315.1 1-Methyl-1H-imidazole-4-sulfonic acid {2-[8-(2-chloro-benzyl)-7-(2-oxopyrrolidin-1-yl)-5,6,7,8-tetrahydro-naphthalen-2-yloxy]-ethyl}-amide

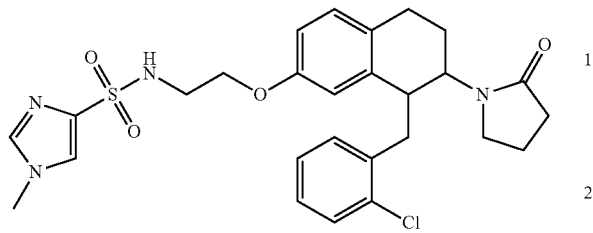

Prepared in analogy to example 263.

315.2 1-Methyl-1H-imidazole-4-sulfonic acid {2-[8-(2-chloro-benzyl)-7-pyrrolidin-1-yl-5,6,7,8-tetrahydro-naphthalen-2-yloxy]-ethyl}-amide hydrochloride

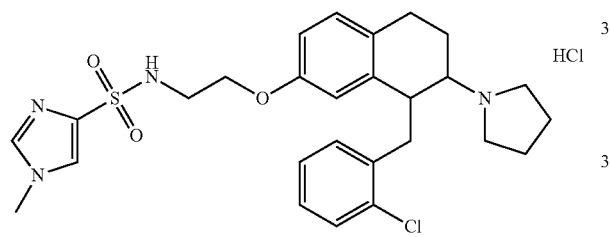

Prepared from compound of previous step by reduction with LiAlH$_4$ in analogy to 300.
ESI-MS [M+H$^+$]=529 Calculated for C$_{27}$H$_{33}$ClN$_4$O$_3$S=528

Example 316

1,2-Dimethyl-1H-imidazole-4-sulfonic acid {2-[7-amino-8-(3-chloro-benzyl)-5,6,7,8-tetrahydro-naphthalen-2-yloxy]-ethyl}-amide hydrochloride

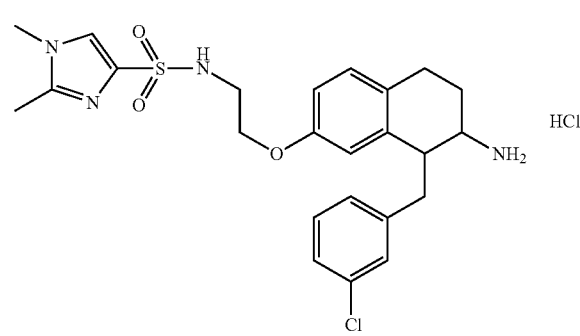 [SMILES: Cc1nc(S(=O)(=O)NCCOc2ccc3c(c2)C(Cc2cccc(Cl)c2)C(N)CC3)cn1C ; Cl]

Prepared in analogy to example 3.

ESI-MS [M+H$^+$]=489 Calculated for C$_{24}$H$_{29}$ClN$_4$O$_3$S=488

Example 317

N-{2-[8-(3-Chloro-benzyl)-7-pyrrolidin-1-yl-5,6,7,8-tetrahydro-naphthalen-2-yloxy]-ethyl}-C-cyclopropyl-methanesulfonamide hydrochloride

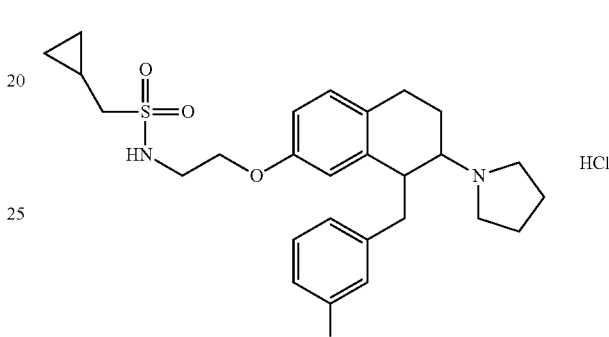

Prepared in analogy to examples 264/88.
ESI-MS [M+H$^+$]=503 Calculated for C$_{27}$H$_{35}$ClN$_2$O$_3$S=502

Example 318

1-Methyl-1H-pyrazole-4-sulfonic acid {2-[8-(3-chloro-benzyl)-7-pyrrolidin-1-yl-5,6,7,8-tetrahydro-naphthalen-2-yloxy]-ethyl}-amide hydrochloride

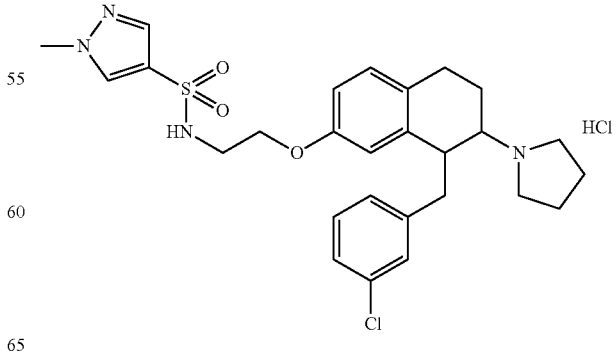

Prepared in analogy to examples 264/88.

ESI-MS [M+H⁺]=529 Calculated for C₂₇H₃₃ClN₄O₃S=528

Example 319

1-Methyl-1H-imidazole-4-sulfonic acid {2-[8-(3-chloro-benzyl)-7-pyrrolidin-1-yl-5,6,7,8-tetrahydro-naphthalen-2-yloxy]-ethyl}-amide hydrochloride

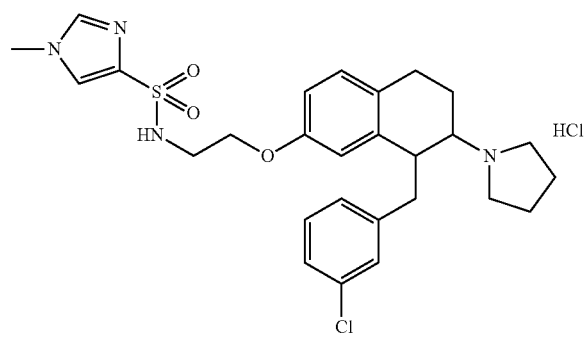 [SMILES: Cn1cnc(S(=O)(=O)NCCOc2ccc3c(c2)C(Cc2cccc(Cl)c2)C(N2CCCC2)CC3)c1 ; Cl]

Prepared in analogy to examples 264/88.
ESI-MS [M+H⁺]=529 Calculated for C₂₇H₃₃ClN₄O₃S=528

Example 320

N-{2-[7-Azetidin-1-yl-8-(3-chloro-benzyl)-5,6,7,8-tetrahydro-naphthalen-2-yloxy]-ethyl}-C-cyclopropyl-methanesulfonamide 320.1 1-[1-(3-Chloro-benzyl)-7-methoxy-1,2,3,4-tetrahydro-naphthalen-2-yl]-azetidine

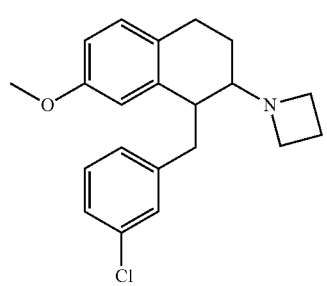 [SMILES: COc1ccc2c(c1)C(Cc1cccc(Cl)c1)C(N1CCC1)CC2]

Prepared in analogy to example 264 using 1,3-dibromopropane instead of 1,4-dibromobutane.

320.2 N-{2-[7-Azetidin-1-yl-8-(3-chloro-benzyl)-5,6,7,8-tetrahydro-naphthalen-2-yloxy]-ethyl}-C-cyclopropyl-methanesulfonamide

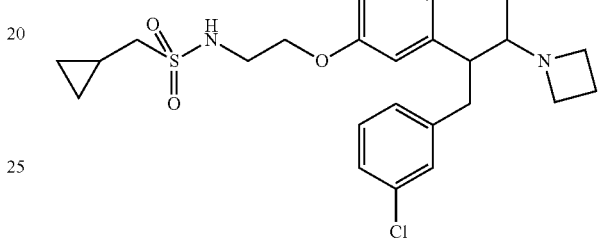

Prepared from compound of previous step in analogy to example 88.
ESI-MS [M+H⁺]=489 Calculated for C₂₆H₃₃ClN₂O₃S=488

Example 321

1-Methyl-1H-imidazole-4-sulfonic acid {2-[7-azetidin-1-yl-8-(3-chloro-benzyl)-5,6,7,8-tetrahydro-naphthalen-2-yloxy]-ethyl}-amide hydrochloride

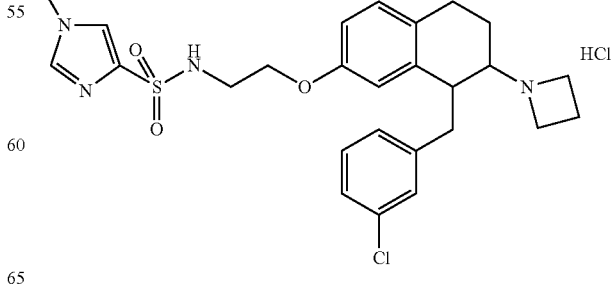

Prepared in analogy to example 320.

ESI-MS [M+H⁺]=515 Calculated for C$_{26}$H$_{31}$ClN$_4$O$_3$S=514

Example 322

1-Methyl-1H-pyrazole-4-sulfonic acid {2-[7-azetidin-1-yl-8-(3-chloro-benzyl)-5,6,7,8-tetrahydronaphthalen-2-yloxy]-ethyl}-amide hydrochloride

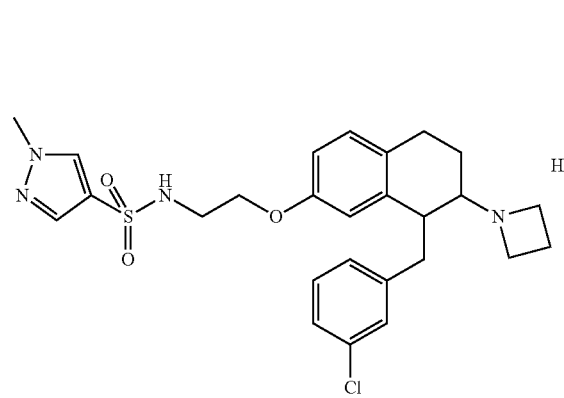

Prepared in analogy to example 320.
ESI-MS [M+H⁺]=515 Calculated for C$_{26}$H$_{31}$ClN$_4$O$_3$S=514

Example 323

Propane-1-sulfonic acid {2-[8-(3-chloro-benzyl)-7-pyrrolidin-1-yl-5,6,7,8-tetrahydronaphthalen-2-yloxy]-ethyl}-amide hydrochloride

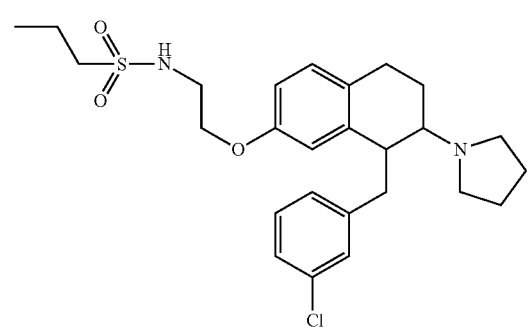

Prepared in analogy to examples 264/88.

ESI-MS [M+H⁺]=491 Calculated for C$_{26}$H$_{35}$ClN$_2$O$_3$S=490

Example 324

1-Methyl-1H-pyrazole-4-sulfonic acid [2-(7-azetidin-1-yl-8-benzyl-5,6,7,8-tetrahydronaphthalen-2-yloxy)-ethyl]amide hydrochloride

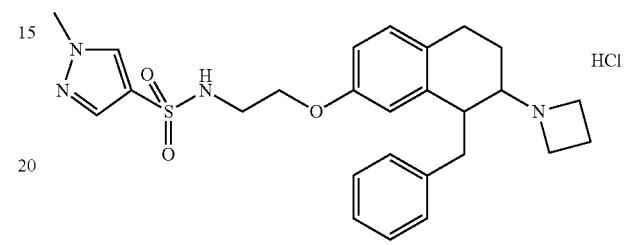

Prepared in analogy to example 320.
ESI-MS [M+H⁺]=481 Calculated for C$_{26}$H$_{32}$N$_4$O$_3$S=480

Example 325

1-Benzyl-7-[2-(propane-1-sulfonyl)-ethyl]-1,2,3,4-tetrahydro-naphthalen-2-ylamine hydrochloride 325.1 [1-(3-Chloro-benzyl)-7-vinyl-1,2,3,4-tetrahydro-naphthalen-2-yl]-carbamic acid ethyl ester

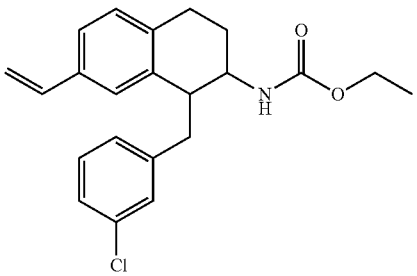 [SMILES: C=Cc1ccc2c(c1)C(Cc1cccc(Cl)c1)C(NC(=O)OCC)CC2]

Synthesis performed in analogy to: Organic Letters; 2002, Vol 4; p. 107-109.

A solution of potassium trifluoro(vinyl)borate (1,000 g, 7.46 mmol), PdCl$_2$(dppf)-CH$_2$Cl$_2$ adduct (0.102 g, 0.124 mmol), 8-(3-chlorobenzyl)-7-(ethoxycarbonylamino)-5,6,7,8-tetrahydronaphthalen-2-yl trifluoromethanesulfonate (3.06 g, 6.22 mmol) and triethylamine (0.867 ml, 6.22 mmol) in 100 ml n-BuOH was stirred under N$_2$ at 85-90° C. for 4 h and then cooled to room temperature.

Water was added, followed by extraction with ether. The ethereal solution was washed with brine, dried, filtered and evaporated to obtain a brown oil. Chromatography afforded 1.55 g of product as a pale yellow solid.

325.2 [1-(3-Chloro-benzyl)-7-(2-hydroxy-ethyl)-1,2,3,4-tetrahydro-naphthalen-2-yl]-carbamic acid ethyl ester

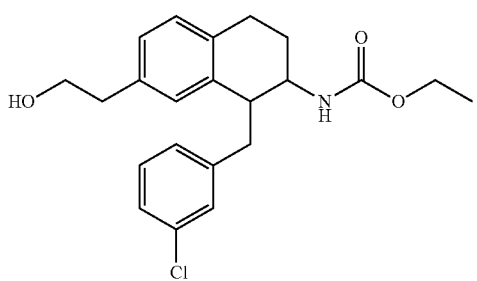 [SMILES: CCOC(=O)NC1CCc2ccc(CCO)cc2C1Cc1cccc(Cl)c1]

BH$_3$.DMS (1 M in THF, 0.838 ml, 0.838 mmol) was added a solution of ethyl 1-(3-chlorobenzyl)-7-vinyl-1,2,3,4-tetrahydronaphthalen-2-ylcarbamate (1.55 g, 4.19 mmol) in 20 ml dry THF. The reaction was stirred at 60° C. for 1 h and cooled to room temperature.

Some water was added to destroy the excess of borane complex and the resulting mixture refluxed for 1 h with 30% H$_2$O$_2$ (8.56 ml, 84 mmol) and 2N NaOH (9.74 ml, 19.49 mmol). The reaction mixture was extracted with CH$_2$Cl$_2$, washed with water and brine, dried, filtered and the solvent evaporated to obtain a pale brown solid (1.7 g), which was purified by chromatography to afford 854 mg of product as a white solid.

325.3 [7-(2-Bromo-ethyl)-1-(3-chloro-benzyl)-1,2,3,4-tetrahydro-naphthalen-2-yl]-carbamic acid ethyl ester

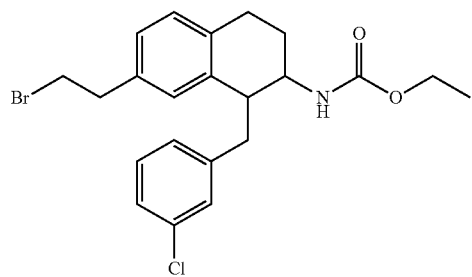 [SMILES: CCOC(=O)NC1CCc2ccc(CCBr)cc2C1Cc1cccc(Cl)c1]

To a solution of [1-(3-chloro-benzyl)-7-(2-hydroxy-ethyl)-1,2,3,4-tetrahydro-naphthalen-2-yl]-carbamic acid ethyl ester (554 mg, 1.428 mmol) in 15 ml dry CH$_2$Cl$_2$ cooled to 0° C. was added triphenylphosphine (562 mg, 2.142 mmol) and carbon tetrabromide (0.208 ml, 2.142 mmol). The mixture was stirred for 1 h, after which solvents were evaporated. The residue was purified by chromatography to obtain 277 mg of product as a white solid.

325.4 [1-(3-Chloro-benzyl)-7-(2-propylsulfanyl-ethyl)-1,2,3,4-tetrahydro-naphthalen-2-yl]-carbamic acid ethyl ester

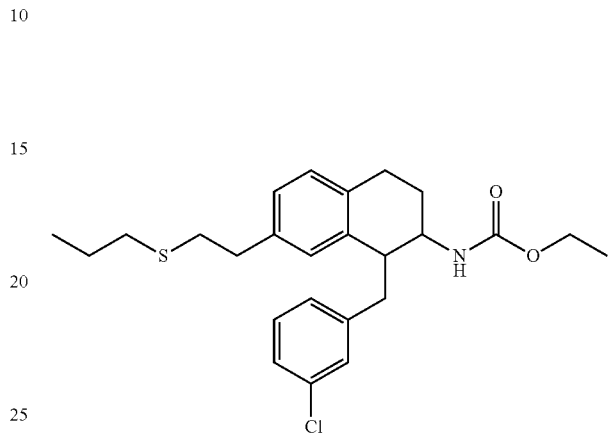

To a suspension of NaH (4.73 mg, 0.177 mmol) in 3 ml dry DMF under N$_2$ was added 1-propanthiol (0.012 ml, 0.133 mmol, dissolved in 1 ml dry DMF). The reaction was stirred at room temperature for 2 h, followed by addition of triethylamine (0.019 ml, 0.133 mmol) and ethyl 7-(2-bromoethyl)-1-(3-chlorobenzyl)-1,2,3,4-tetrahydronaphthalen-2-ylcarbamate (40 mg, 0.089 mmol, dissolved in 2 ml dry DMF). The mixture was stirred at room temperature over night, the solvent evaporated, the residue re-dissolved in ethyl acetate, washed with water, citric acid, NaHCO$_3$ and brine and filtered. The solvent was evaporated to obtain 31 mg of an off white solid which was used without further purification.

325.5 {1-(3-Chloro-benzyl)-7-[2-(propane-1-sulfonyl)-ethyl]-1,2,3,4-tetrahydronaphthalen-2-yl}-carbamic acid ethyl ester

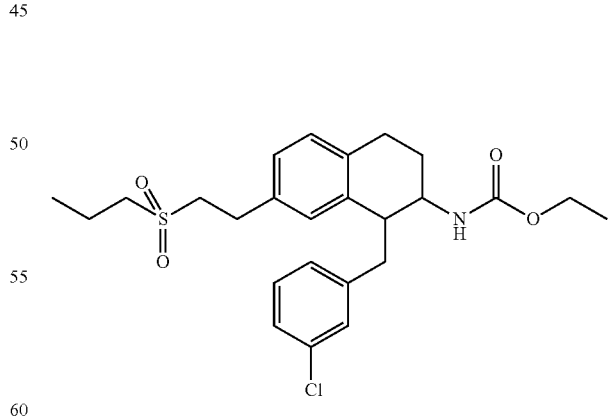

To a cooled mixture (0° C.) of ethyl 1-(3-chlorobenzyl)-7-(2-(propylthio)ethyl)-1,2,3,4-tetrahydronaphthalen-2-ylcarbamate (31.4 mg, 0.070 mmol) in 2 ml ethyl acetate was added m-CPBA (33.4 mg, 0.155 mmol). The reaction was stirred for 2 h allowing warming up to room temperature. The mixture was diluted with ethyl acetate, washed with NaHCO$_3$, water and brine, dried, filtered and the solvent evaporated to obtain a white solid, which was purified by chromatography (27 mg).

325.6 [1-Benzyl-7-(2-propylsulfanyl-ethyl)-1,2,3,4-tetrahydro-naphthalen-2-yl]-carbamic acid ethyl ester

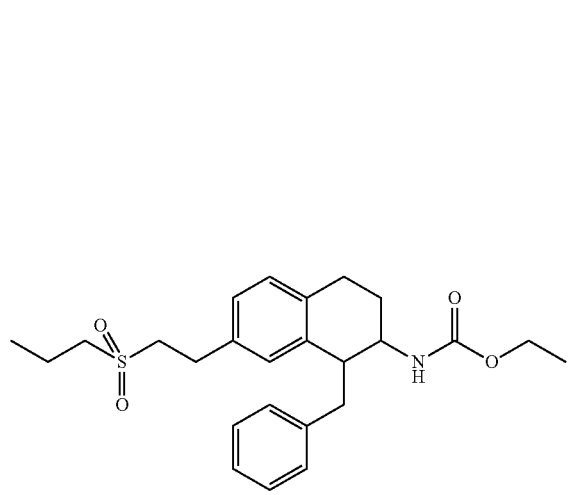 [SMILES: CCCS(=O)(=O)CCc1ccc2c(c1)C(Cc1ccccc1)C(NC(=O)OCC)CC2]

Ethyl 1-(3-chlorobenzyl)-7-(2-(propylsulfonyl)ethyl)-1,2,3,4-tetrahydronaphthalen-2-ylcarbamate (27.1 mg, 0.057 mmol) and ammonium formate (71.5 mg, 1.134 mmol) were dissolved in 5 ml MeOH. Pd/C (0.845 mg, 7.94 µmol) was added and stirred at 80° C. for 4 h. The mixture was filtered, the solvent evaporated, the residue re-dissolved in ethyl acetate, which was subsequently washed with water, NaHCO$_3$ and brine, dried, filtered. Solvent was evaporated to obtain white solid which was purified by chromatography affording 12.7 mg of product as a white solid.

325.7 1-Benzyl-7-[2-(propane-1-sulfonyl)-ethyl]-1,2,3,4-tetrahydro-naphthalen-2-ylamine hydrochloride

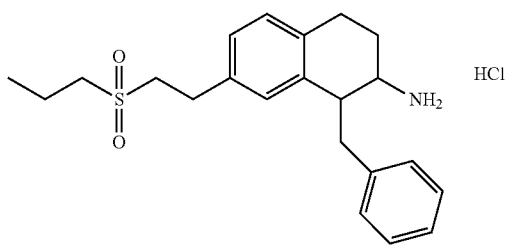 [SMILES: CCCS(=O)(=O)CCc1ccc2c(c1)C(Cc1ccccc1)C(N)CC2 ; Cl]

Prepared in analogy to example 3 [1-Benzyl-7-(2-propylsulfanyl-ethyl)-1,2,3,4-tetrahydronaphthalen-2-yl]-carbamic acid ethyl ester.
ESI-MS [M+H$^+$]=372 Calculated for C$_{22}$H$_{29}$NO$_2$S=371

Example 326

1-(3-Chloro-benzyl)-7-[2-(propane-1-sulfonyl)-ethyl]-1,2,3,4-tetrahydro-naphthalen-2-ylamine hydrochloride

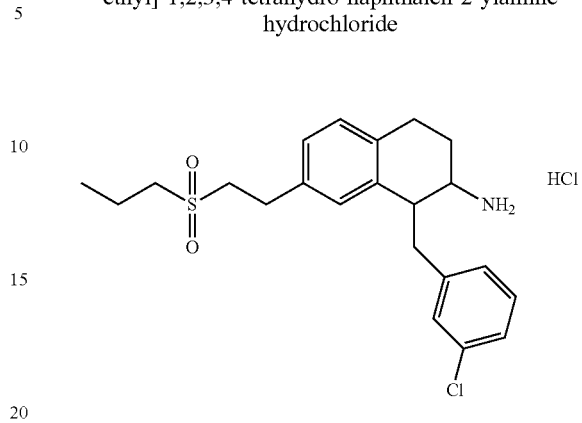

Prepared in analogy to example 325 leaving out the de-chlorination step.
ESI-MS [M+H$^+$]=406 Calculated for C$_{22}$H$_{29}$ClNO$_2$S=405

Biological Testing

1. [$^3$H]-Glycine uptake into recombinant CHO cells expressing human GlyT1: Human GlyT1c expressing recombinant hGlyT1c_5_CHO cells were plated at 20,000 cells per well in 96 well Cytostar-T scintillation microplates (Amersham Biosciences) and cultured to sub-confluency for 24 h. For glycine uptake assays the culture medium was aspirated and the cells were washed once with 100 µl HBSS (Gibco BRL, #14025-050) with 5 mM L-Alanine (Merck #1007). 80 µl HBSS buffer were added, followed by 10 µl inhibitor or vehicle (10% DMSO) and 10 µl [$^3$H]-glycine (TRK71, Amersham Biosciences) to a final concentration of 200 nM for initiation of glycine uptake. The plates were placed in a Wallac Microbeta (PerkinElmer) and continuously counted by solid phase scintillation spectrometry during up to 3 hours. Nonspecific uptake was determined in the presence of 10 µM Org24598. IC$_{50}$ calculations were made by four-parametric logistic nonlinear regression analysis (GraphPad Prism) using determinations within the range of linear increase of [$^3$H]-glycine incorporation between 60 and 120 min.

2. Radioligand binding assays using recombinant CHO cell membranes expressing human GlyT1:
Radioligand binding to human GlyT1c transporter-expressing membranes was carried out as described in Mezler et al., Molecular Pharmacology 74:1705-1715, 2008.

The following results were obtained with the compounds disclosed in the examples:

TABLE 1

| Example | Glycine uptake IC$_{50}$ [µmol] | radioligand binding K$_{iapp}$ [µmol] |
|---|---|---|
| 1 | ≤1000 | ≤10 |
| 2 | ≤1 | ≤0.1 |
| 3 | ≤0.01 | ≤0.01 |
| 4 | ≤0.01 | ≤0.01 |
| 5 | ≤1 | ≤1 |
| 6 | ≤1 | ≤0.1 |
| 7 | ≤10 | ≤10 |
| 8 | ≤0.1 | ≤0.1 |

TABLE 1-continued

| Example | Glycine uptake IC$_{50}$ [μmol] | radioligand binding K$_{iapp}$ [μmol] |
|---|---|---|
| 9 | ≤1 | ≤1 |
| 10 | ≤100 | ≤10 |
| 11 | ≤1 | ≤0.1 |
| 12 | ≤100 | ≥10 |
| 13 | ≤1000 | ≤100 |
| 14 | ≤1000 | ≤100 |
| 15 | ≤1 | ≤1 |
| 16 | ≤10 | ≤10 |
| 17 | ≤10 | ≤1 |
| 18 | ≤0.1 | ≤0.01 |
| 19 | ≤100 | ≤10 |
| 20 | ≤0.1 | ≤0.01 |
| 21 | ≤1000 | ≤100 |
| 22 | ≤1000 | ≤10 |
| 23 | ≤100 | ≤10 |
| 24 | ≤10 | ≤0.1 |
| 25 | ≤1 | ≤0.1 |
| 26 | ≤1000 | ≤10 |
| 27 | ≤0.01 | ≤0.01 |
| 28 | ≤0.01 | ≤0.01 |
| 29 | ≤100 | ≤10 |
| 30 | ≤100 | ≤100 |
| 31 | ≤1 | ≤0.1 |
| 32 | ≤100 | ≤10 |
| 33 | ≤1 | ≤1 |
| 34 | ≤1000 | ≤10 |
| 35 | ≤100 | ≥100 |
| 36 | ≤10 | ≤100 |
| 37 | ≤100 | ≤10 |
| 38 | ≤100 | ≤100 |
| 39 | ≤1000 | ≤10 |
| 40 | ≤100 | ≤10 |
| 41 | ≤100 | ≤10 |
| 42 | ≤0.1 | ≤0.1 |
| 43 | ≤1 | ≤0.1 |
| 44 | ≤0.1 | ≤0.1 |
| 45 | ≤0.1 | ≤0.1 |
| 46 | ≤1 | ≤1 |
| 47 | ≤0.01 | ≤0.01 |
| 48 | ≤0.01 | ≤0.01 |
| 49 | ≤100 | ≤100 |
| 50 | ≤10 | ≤1 |
| 51 | ≤1000 | ≤100 |
| 52 | ≤10 | ≤10 |
| 53 | ≤1000 | ≤10 |
| 54 | ≥100 | ≤10 |
| 55 | ≤0.1 | ≤0.01 |
| 56 | ≤1 | ≤0.1 |
| 57 | ≤10 | ≤1 |
| 58 | ≤10 | ≤1 |
| 59 | ≤10 | ≤1 |
| 60 | ≥100 | ≤10 |
| 61 | ≤1000 | ≤10 |
| 62 | ≤1000 | ≤10 |
| 63 | ≥100 | ≤10 |
| 64 | ≤1000 | ≤10 |
| 65 | ≤100 | ≥10 |
| 66 | ≤1 | ≤0.1 |
| 67 | ≤1 | ≤0.1 |
| 68 | ≤10 | ≤1 |
| 69 | ≤10 | ≤1 |
| 70 | ≤1 | ≤0.1 |
| 71 | ≤0.1 | ≤0.01 |
| 72 | ≤10 | ≤10 |
| 73 | ≤10 | ≤1 |
| 74 | ≤100 | ≥10 |
| 75 | ≤10 | ≤1 |
| 76 | ≤1000 | ≤100 |
| 77 | ≤1 | ≤0.1 |
| 78 | ≤10 | ≤10 |
| 79 | ≤1 | ≤0.1 |
| 80 | ≤1 | ≤1 |
| 81 | ≥1000 | ≤10 |
| 82 | ≤1 | ≤0.1 |
| 83 | ≤10 | ≤1 |
| 84 | ≤10 | ≤10 |
| 85 | — | ≤1 |
| 86 | — | ≤10 |
| 87 | — | ≤10 |
| 88 | — | ≤0.1 |
| 89 | — | ≤0.1 |
| 90 | — | ≤1 |
| 91 | — | ≤0.1 |
| 92 | — | — |
| 93 | — | ≤1 |
| 94 | — | ≤0.1 |
| 95 | — | ≤0.01 |
| 967 | — | ≤1 |
| 98 | — | ≤1 |
| 99 | — | ≤0.1 |
| 100 | — | ≤1 |
| 100 | — | ≤10 |
| 101 | — | ≤0.1 |
| 102 | — | ≤1 |
| 103 | — | ≤10 |
| 104 | — | ≤1 |
| 105 | — | ≤0.1 |
| 106 | — | ≤1 |
| 107 | — | ≤0.1 |
| 108 | — | ≤0.01 |
| 109 | — | ≤0.1 |
| 110 | — | ≤1 |
| 111 | — | ≤0.1 |
| 112 | — | ≤0.1 |
| 113 | — | ≤0.1 |
| 114 | — | ≤1 |
| 115 | — | — |
| 116 | — | ≤0.01 |
| 117 | — | ≤0.01 |
| 118 | — | ≤0.1 |
| 119 | — | ≤0.01 |
| 120 | — | ≤0.1 |
| 121 | — | ≤0.01 |
| 122 | — | ≤10 |
| 123 | — | ≤10 |
| 124 | — | ≤1 |
| 125 | — | ≤1 |
| 126 | — | ≤0.01 |
| 127 | — | ≤0.1 |
| 128 | — | ≤0.1 |
| 129 | — | ≤0.01 |
| 130 | — | ≤0.01 |
| 131 | — | ≤0.1 |
| 132 | — | ≤0.1 |
| 133 | — | ≤0.1 |
| 134 | — | ≤1 |
| 135 | — | ≤0.1 |
| 136 | — | ≤0.1 |
| 137 | — | ≤0.01 |
| 138 | — | ≤0.01 |
| 139 | — | ≤0.01 |
| 140 | — | ≤0.01 |
| 141 | — | ≤0.01 |
| 142 | — | ≤0.1 |
| 143 | — | ≤0.01 |
| 144 | — | ≤1 |
| 145 | — | ≤0.01 |
| 146 | — | ≤0.01 |
| 147 | — | ≤0.1 |
| 148 | — | ≤0.1 |
| 149 | — | ≤0.1 |
| 150 | — | ≤0.01 |
| 151 | — | ≤0.01 |
| 152 | — | ≤0.01 |
| 153 | — | ≤0.1 |
| 154 | — | ≤0.01 |
| 155 | — | ≤1 |
| 156 | — | ≤1 |
| 157 | — | ≤0.1 |
| 158 | — | ≤0.01 |
| 159 | — | ≤0.1 |
| 160 | — | ≤0.01 |
| 161 | — | ≤0.01 |
| 162 | — | ≤0.01 |

TABLE 1-continued

| Example | Glycine uptake IC$_{50}$ [μmol] | radioligand binding K$_{iapp}$ [μmol] |
|---|---|---|
| 163 | — | ≤0.01 |
| 164 | — | ≤0.01 |
| 165 | — | ≤0.01 |
| 166 | — | ≤0.1 |
| 167 | — | ≤10 |
| 168 | — | ≤10 |
| 169 | — | ≤0.01 |
| 170 | — | >10 |
| 171 | — | ≤0.1 |
| 172 | — | ≤0.01 |
| 173 | — | ≤0.01 |
| 174 | — | ≤1 |
| 175 | — | ≤1 |
| 176 | — | ≤0.1 |
| 177 | — | ≤0.01 |
| 178 | — | ≤0.01 |
| 179 | — | ≤1 |
| 180 | — | ≤0.01 |
| 181 | — | ≤0.1 |
| 182 | — | ≤0.1 |
| 183 | — | ≤1 |
| 184 | — | ≤0.1 |
| 185 | — | ≤1 |
| 186 | — | ≤1 |
| 187 | — | ≤0.01 |
| 188 | — | ≤0.1 |
| 189 | — | ≤10 |
| 190 | — | ≤0.01 |
| 191 | — | ≤1 |
| 192 | — | — |
| 193 | — | ≤0.01 |
| 194 | — | — |
| 195 | — | — |
| 196 | — | ≤10 |
| 197 | — | ≤10 |
| 198 | — | ≤0.1 |
| 199 | — | ≤0.1 |
| 200 | — | ≤0.1 |
| 201 | — | ≤0.1 |
| 202 | — | ≤0.1 |
| 203 | — | ≤0.01 |
| 204 | — | ≤0.1 |
| 205 | — | ≤0.1 |
| 206 | — | ≤0.1 |
| 207 | — | ≤0.1 |
| 208 | — | ≤0.1 |
| 209 | — | ≤0.1 |
| 210 | — | ≤0.1 |
| 211 | — | ≤1 |
| 212 | — | ≤1 |
| 213 | — | ≤0.1 |
| 214 | — | ≤10 |
| 215 | — | ≤10 |
| 216 | — | ≤10 |
| 217 | — | ≤10 |
| 218 | — | ≤10 |
| 219 | — | ≤0.1 |
| 220 | — | ≤1 |
| 221 | — | ≤0.1 |
| 222 | — | ≤1 |
| 223 | — | ≤0.1 |
| 224 | — | ≤0.1 |
| 225 | — | ≤0.1 |
| 226 | — | ≤0.1 |
| 227 | — | ≤0.1 |
| 228 | — | ≤0.1 |
| 229 | — | ≤1 |
| 230 | — | ≤0.01 |
| 231 | — | ≤0.01 |
| 232 | — | ≤0.1 |
| 233 | — | ≤0.1 |
| 234 | — | ≤0.1 |
| 235 | — | ≤0.01 |
| 236 | — | ≤1 |
| 237 | — | ≤10 |
| 238 | — | ≤0.01 |
| 239 | — | ≤1 |
| 240 | — | ≤0.01 |
| 241 | — | ≤0.1 |
| 242 | — | ≤0.01 |
| 243 | — | ≤0.01 |
| 244 | — | ≤0.01 |
| 245 | — | ≤1 |
| 246 | — | ≤0.01 |
| 247 | — | ≤0.01 |
| 248 | — | ≤0.01 |
| 249 | — | ≤0.1 |
| 250 | — | ≤0.01 |
| 251 | — | ≤0.1 |
| 252 | — | ≤0.01 |
| 253 | — | ≤1 |
| 254 | — | ≤0.01 |
| 255 | — | ≤1 |
| 256 | — | ≤0.1 |
| 257 | — | ≤0.1 |
| 258 | — | ≤0.1 |
| 259 | — | ≤1 |
| 260 | — | ≤1 |
| 261 | — | ≤1 |
| 262 | — | ≤0.1 |
| 263 | — | ≤1 |
| 264 | — | ≤1 |
| 265 | — | ≤1 |
| 266 | — | ≤1 |
| 267 | — | ≤0.1 |
| 268 | — | ≤0.01 |
| 269 | — | ≤0.01 |
| 270 | — | ≤0.1 |
| 271 | — | ≤0.1 |
| 272 | — | ≤0.1 |
| 273 | — | ≤1 |
| 274 | — | ≤0.1 |
| 275 | — | ≤0.1 |
| 276 | — | ≤10 |
| 277 | — | |
| 278 | — | |
| 279 | — | ≤10 |
| 280 | — | ≤10 |
| 281 | — | ≤0.1 |
| 282 | — | ≤0.1 |
| 283 | — | ≤1 |
| 284 | — | ≤1 |
| 285 | — | ≤10 |
| 286 | — | ≤10 |
| 287 | — | ≤10 |
| 288 | — | ≤0.01 |
| 289 | — | >10 |
| 290 | — | ≤10 |
| 291 | — | ≤0.01 |
| 292 | — | ≤1 |
| 293 | — | ≤1 |
| 294 | — | ≤10 |
| 295 | — | ≤1 |
| 296 | — | ≤0.1 |
| 297 | — | ≤0.1 |
| 298 | — | ≤10 |
| 299 | — | >10 |
| 300 | — | ≤0.01 |
| 301 | — | ≤0.01 |
| 302 | — | ≤0.1 |
| 303 | — | ≤0.1 |
| 304 | — | ≤1 |
| 305 | — | ≤0.1 |
| 306 | — | ≤0.1 |
| 307 | — | ≤0.01 |
| 308 | — | ≤0.01 |
| 309 | — | ≤0.1 |
| 310 | — | ≤1 |
| 311 | — | ≤0.1 |
| 312 | — | ≤0.1 |
| 313 | — | ≤0.1 |
| 314 | — | ≤1 |
| 315 | — | ≤1 |
| 316 | — | ≤1 |

TABLE 1-continued

| Example | Glycine uptake IC$_{50}$ [µmol] | radioligand binding K$_{iapp}$ [µmol] |
|---|---|---|
| 317 | — | ≤0.1 |
| 318 | — | ≤0.01 |
| 319 | — | ≤0.1 |
| 320 | — | ≤0.1 |
| 321 | — | ≤0.01 |
| 322 | — | ≤0.01 |
| 323 | — | ≤1 |
| 324 | — | ≤0.01 |
| 325 | — | ≤1 |
| 326 | — | ≤1 |

We claim:

1. An aminotetraline derivative of the formula (I)

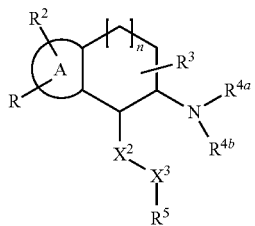

wherein
A is a 5- or 6-membered ring;
R is $R^1$—W-$A^1$-Q-Y-$A^2$-$X^1$—;
$R^1$ is hydrogen, $C_1$-$C_6$-alkyl, $C_3$-$C_{12}$-cycloalkyl-$C_1$-$C_4$-alkyl, halogenated $C_1$-$C_6$-alkyl, tri-($C_1$-$C_4$-alkyl)-silyl-$C_1$-$C_4$-alkyl, hydroxy-$C_1$-$C_4$-alkyl, $C_1$-$C_6$-alkoxy-$C_1$-$C_4$-alkyl, amino-$C_1$-$C_4$-alkyl, $C_1$-$C_6$-alkylamino-$C_1$-$C_4$-alkyl, di-$C_1$-$C_6$-alkylamino-$C_1$-$C_4$-alkyl, $C_1$-$C_6$-alkylcarbonylamino-$C_1$-$C_4$-alkyl, $C_1$-$C_6$-alkyloxycarbonylamino-$C_1$-$C_4$-alkyl, $C_1$-$C_6$-alkylaminocarbonylamino-$C_1$-$C_4$-alkyl, di-$C_1$-$C_6$-alkylaminocarbonylamino-$C_1$-$C_4$-alkyl, $C_1$-$C_6$-alkylsulfonylamino-$C_1$-$C_4$-alkyl, (optionally substituted $C_6$-$C_{12}$-aryl-$C_1$-$C_6$-alkyl)amino-$C_1$-$C_4$-alkyl, optionally substituted $C_6$-$C_{12}$-aryl-$C_1$-$C_4$-alkyl, optionally substituted $C_3$-$C_{12}$-heterocyclyl-$C_1$-$C_4$-alkyl, $C_3$-$C_{12}$-cycloalkyl, $C_1$-$C_6$-alkylcarbonyl, $C_1$-$C_6$-alkoxycarbonyl, halogenated $C_1$-$C_6$-alkoxycarbonyl, $C_6$-$C_{12}$-aryloxycarbonyl, aminocarbonyl, $C_1$-$C_6$-alkylaminocarbonyl, (halogenated $C_1$-$C_4$-alkyl) aminocarbonyl, $C_6$-$C_{12}$-arylaminocarbonyl, $C_2$-$C_6$-alkenyl, $C_2$-$C_6$-alkynyl, optionally substituted $C_6$-$C_{12}$-aryl, hydroxy, $C_1$-$C_6$-alkoxy, halogenated $C_1$-$C_6$-alkoxy, $C_1$-$C_6$-hydroxyalkoxy, $C_1$-$C_6$-alkoxy-$C_1$-$C_4$-alkoxy, amino-$C_1$-$C_4$-alkoxy, $C_1$-$C_6$-alkylamino-$C_1$-$C_4$-alkoxy, di-$C_1$-$C_6$-alkylamino-$C_1$-$C_4$-alkoxy, $C_1$-$C_6$-alkylcarbonylamino-$C_1$-$C_4$-alkoxy, $C_6$-$C_{12}$-arylcarbonylamino-$C_1$-$C_4$-alkoxy, $C_1$-$C_6$-alkoxycarbonylamino-$C_1$-$C_4$-alkoxy, $C_6$-$C_{12}$-aryl-$C_1$-$C_4$-alkoxy, $C_1$-$C_6$-alkylsulfonylamino-$C_1$-$C_4$-alkoxy, (halogenated $C_1$-$C_6$-alkyl)sulfonylamino-$C_1$-$C_4$-alkoxy, $C_6$-$C_{12}$-arylsulfonylamino-$C_1$-$C_4$-alkoxy, ($C_6$-$C_{12}$-aryl-$C_1$-$C_6$-alkyl)sulfonylamino-$C_1$-$C_4$-alkoxy, $C_3$-$C_{12}$-heterocyclylsulfonylamino-$C_1$-$C_4$-alkoxy, $C_3$-$C_{12}$-heterocyclyl-$C_1$-$C_4$-alkoxy, $C_6$-$C_{12}$-aryloxy, $C_3$-$C_{12}$-heterocyclyloxy, $C_1$-$C_6$-alkylthio, halogenated $C_1$-$C_6$-alkylthio, $C_1$-$C_6$-alkylamino, (halogenated $C_1$-$C_6$-alkyl)amino, di-$C_1$-$C_6$-alkylamino, di-(halogenated $C_1$-$C_6$-alkyl)amino, $C_1$-$C_6$-alkylcarbonylamino, (halogenated $C_1$-$C_6$-alkyl)carbonylamino, $C_6$-$C_{12}$ arylcarbonylamino, $C_1$-$C_6$-alkylsulfonylamino, (halogenated $C_1$-$C_6$-alkyl)sulfonylamino, $C_6$-$C_{12}$-arylsulfonylamino or optionally substituted $C_3$-$C_{12}$-heterocyclyl;

W is —$NR^8$— or a bond;
$A^1$ is optionally substituted $C_1$-$C_4$-alkylene or a bond;
Q is —S(O)$_2$— or —C(O)—;
Y is —$NR^9$— or a bond;
$A^2$ is optionally substituted $C_1$-$C_4$-alkylene, $C_1$-$C_4$-alkylene-CO—, —CO—$C_1$-$C_4$-alkylene, $C_1$-$C_4$-alkylene-O—$C_1$-$C_4$-alkylene, $C_1$-$C_4$-alkylene-$NR^{10}$—$C_1$-$C_4$-alkylene, optionally substituted $C_2$-$C_4$-alkenylen, optionally substituted $C_2$-$C_4$-alkynylene, optionally substituted $C_6$-$C_{12}$-arylene, optionally substituted $C_6$-$C_{12}$ heteroarylene or a bond;
$X^1$ is —O—, —$NR^{11}$—, —S—, optionally substituted $C_1$-$C_4$-alkylene, optionally substituted $C_2$-$C_4$-alkenylen, or optionally substituted $C_2$-$C_4$-alkynylene;
$R^2$ is hydrogen, halogen, $C_1$-$C_6$-alkyl, halogenated $C_1$-$C_4$-alkyl, hydroxy-$C_1$-$C_4$-alkyl, —CN, $C_2$-$C_6$-alkenyl, $C_2$-$C_6$-alkynyl, optionally substituted $C_6$-$C_{12}$-aryl, hydroxy, $C_1$-$C_6$-alkoxy, halogenated $C_1$-$C_6$-alkoxy, $C_1$-$C_6$-alkoxycarbonyl, $C_2$-$C_6$-alkenyloxy, $C_6$-$C_{12}$-aryl-$C_1$-$C_4$-alkoxy, $C_1$-$C_6$-alkylcarbonyloxy, $C_1$-$C_6$-alkylthio, $C_1$-$C_6$-alkylsulfinyl, $C_1$-$C_6$-alkylsulfonyl, aminosulfonyl, amino, $C_1$-$C_6$-alkylamino, $C_2$-$C_6$-alkenylamino, nitro or optionally substituted $C_3$-$C_{12}$-heterocyclyl, or two radicals $R^2$ together with the ring atoms of A to which they are bound form a 5- or 6 membered ring;
$R^3$ is hydrogen, halogen, $C_1$-$C_6$-alkyl or $C_1$-$C_6$-alkoxy, or two radicals $R^3$ together with the carbon atom to which they are attached form a carbonyl group;
$R^{4a}$ is hydrogen, $C_1$-$C_6$-alkyl, $C_3$-$C_{12}$-cycloalkyl-$C_1$-$C_4$-alkyl, halogenated $C_1$-$C_4$-alkyl, hydroxy-$C_1$-$C_4$-alkyl, $C_1$-$C_6$-alkoxy-$C_1$-$C_4$-alkyl, amino-$C_1$-$C_4$-alkyl, CH$_2$CN, —CHO, $C_1$-$C_4$-alkylcarbonyl, (halogenated $C_1$-$C_4$-alkyl)carbonyl, $C_6$-$C_{12}$-arylcarbonyl, $C_1$-$C_4$-alkoxycarbonyl, $C_6$-$C_{12}$-aryloxycarbonyl, $C_1$-$C_6$-alkylaminocarbonyl, $C_2$-$C_6$-alkenyl, —C(=NH)NH$_2$, —C(=NH)NHCN, $C_1$-$C_6$-alkylsulfonyl, $C_6$-$C_{12}$-arylsulfonyl, amino, —NO or $C_3$-$C_{12}$-heterocyclyl;
$R^{4b}$ is hydrogen, $C_1$-$C_6$-alkyl, halogenated $C_1$-$C_4$-alkyl, hydroxy-$C_1$-$C_4$-alkyl, $C_1$-$C_6$-alkoxy-$C_1$-$C_4$-alkyl, amino-$C_1$-$C_4$-alkyl, CH$_2$CN, —CHO, $C_1$-$C_4$-alkylcarbonyl, (halogenated $C_1$-$C_4$-alkyl)carbonyl, $C_6$-$C_{12}$-arylcarbonyl, $C_1$-$C_4$-alkoxycarbonyl, $C_6$-$C_{12}$-aryloxycarbonyl, $C_1$-$C_6$-alkylaminocarbonyl, $C_2$-$C_6$-alkenyl, —C(=NH)NH$_2$, —C(=NH)NHCN, $C_1$-$C_6$-alkylsulfonyl, $C_6$-$C_{12}$-arylsulfonyl, amino, —NO or $C_3$-$C_{12}$-heterocyclyl; or
$R^{4a}$, $R^{4b}$
together are optionally substituted $C_1$-$C_6$-alkylene, wherein one —CH$_2$— of $C_1$-$C_4$-alkylene may be replaced by an oxygen atom or —$NR^{16}$;
$X^2$ is —O—, —S—, >$CR^{12a}R^{12b}$ or a bond;
$X^3$ is —O—, —S—, >$CR^{13a}R^{13b}$ or a bond;
$R^5$ is optionally substituted $C_6$-$C_{12}$-aryl, optionally substituted $C_3$-$C_{12}$-cycloalkyl or optionally substituted $C_3$-$C_{12}$-heterocyclyl;
n is 0, 1 or 2;
$R^6$ is hydrogen or $C_1$-$C_6$-alkyl;
$R^7$ is hydrogen or $C_1$-$C_6$-alkyl;
$R^8$ is hydrogen or $C_1$-$C_6$-alkyl;

R⁹ is hydrogen, $C_1$-$C_6$-alkyl, $C_3$-$C_{12}$-cycloalkyl, amino-$C_1$-$C_6$-alkyl, optionally substituted $C_6$-$C_{12}$-aryl-$C_1$-$C_4$-alkyl or $C_3$-$C_{12}$-heterocyclyl; or R⁹, R¹
 together are $C_1$-$C_4$-alkylene; or R⁹ is $C_1$-$C_4$-alkylene that is bound to a carbon atom in A² and A² is $C_1$-$C_4$-alkylene or to a carbon atom in X¹ and X¹ is $C_1$-$C_4$-alkylene;

R¹⁰ is hydrogen, $C_1$-$C_6$-alkyl or $C_1$-$C_6$-alkylsulfonyl;

R¹¹ is hydrogen or $C_1$-$C_6$-alkyl, or

R⁹, R¹¹
 together are $C_1$-$C_4$-alkylene,

R¹²ᵃ is hydrogen, optionally substituted $C_1$-$C_6$-alkyl, $C_1$-$C_6$-alkylamino-$C_1$-$C_4$-alkyl, di-$C_1$-$C_6$-alkylamino-$C_1$-$C_4$-alkyl, $C_3$-$C_{12}$-heterocyclyl-$C_1$-$C_6$-alkyl, optionally substituted $C_6$-$C_{12}$-aryl or hydroxy;

R¹²ᵇ is hydrogen or $C_1$-$C_6$-alkyl, or

R¹²ᵃ, R¹²ᵇ
 together are carbonyl or optionally substituted $C_1$-$C_4$-alkylene, wherein one —CH₂— of $C_1$-$C_4$-alkylene may be replaced by an oxygen atom or —NR¹⁴—;

R¹³ᵃ is hydrogen, optionally substituted $C_1$-$C_6$-alkyl, $C_1$-$C_6$-alkylamino-$C_1$-$C_4$-alkyl, di-$C_1$-$C_6$-alkylamino-$C_1$-$C_4$-alkyl, $C_3$-$C_{12}$-heterocyclyl-$C_1$-$C_6$-alkyl, optionally substituted $C_6$-$C_{12}$-aryl or hydroxy;

R¹³ᵇ is hydrogen or $C_1$-$C_6$-alkyl, or

R¹³ᵃ, R¹³ᵇ
 together are carbonyl or optionally substituted $C_1$-$C_4$-alkylene, wherein one —CH₂— of $C_1$-$C_4$-alkylene may be replaced by an oxygen atom or —NR¹⁵—;

R¹⁴ is hydrogen or $C_1$-$C_6$-alkyl;
R¹⁵ is hydrogen or $C_1$-$C_6$-alkyl; and
R¹⁶ is hydrogen or $C_1$-$C_6$-alkyl,
or a physiologically tolerated salt thereof.

2. A method for inhibiting the glycine transporter GlyT1 in a mammal in need thereof which comprises the administration of an effective amount of a compound of claim 1.

3. A method for treating a neurologic or psychiatric disorder or pain in a mammalian patient in need thereof which comprises administering to the patient a therapeutically effective amount of a compound of claim 1, wherein the neurologic disorder is selected from the group consisting of dementia, cognitive impairment, and attention deficit disorder, wherein the psychiatric disorder is selected from the group consisting of anxiety disorder, depression, bipolar disorder, schizophrenia, and psychosis.

4. The method as claimed in claim 3, wherein the attention deficit disorder is an attention deficit disorder with hyperactivity.

5. The method of claim 3, wherein the compound of formula (I) is selected from the group consisting of:
[7-(2-tert-Butoxycarbonylamino-ethoxy)-1-(3,4-dichloro-benzyl)-1,2,3,4-tetrahydro-naphthalen-2-yl]-carbamic acid ethyl ester;
Ethyl 1-(3,4-dichlorobenzyl)-7-(2-(1-methyl-1H-imidazole-4-sulfonamido)ethoxy)-1,2,3,4-tetrahydronaphthalen-2-ylcarbamate;
N-(2-(7-Amino-8-(3,4-dichlorobenzyl)-5,6,7,8-tetrahydronaphthalen-2-yloxy)ethyl)-1-methyl-1H-imidazole-4-sulfonamide;
1-Methyl-1H-pyrazole-4-sulfonic acid {2-[7-amino-8-(3,4-dichloro-benzyl)-5,6,7,8-tetrahydro-naphthalen-2-yloxy]-ethyl}-amide;
Pyridine-3-sulfonic acid {2-[7-amino-8-(3,4-dichloro-benzyl)-5,6,7,8-tetrahydro-naphthalen-2-yloxy]-ethyl}-amide;
Propane-1-sulfonic acid {2-[8-(3,4-dichloro-benzyl)-7-dimethylamino-5,6,7,8-tetrahydro-naphthalen-2-yloxy]-ethyl}-amide;
1-(3,4-Dichloro-benzyl)-7-[2-(propane-1-sulfonylamino)-ethoxy]-1,2,3,4-tetrahydro-naphthalen-2-yl}-carbamic acid ethyl ester;
Propane-1-sulfonic acid {2-[7-amino-8-(3,4-dichloro-benzyl)-5,6,7,8-tetrahydro-naphthalen-2-yloxy]-ethyl}-amide;
{1-(3,4-Dichloro-benzyl)-7-[2-(1-methyl-1H-pyrazole-4-sulfonylamino)-ethoxy]-1,2,3,4-tetrahydro-naphthalen-2-yl}-carbamic acid ethyl ester;
{1-(3,4-Dichloro-benzyl)-7-[2-(pyridine-3-sulfonylamino)-ethoxy]-1,2,3,4-tetrahydro-naphthalen-2-yl}-carbamic acid ethyl ester;
N-(2-(7-Amino-8-(3,4-dichlorobenzyl)-5,6,7,8-tetrahydronaphthalen-2-yloxy)ethyl)-N-methylpropane-1-sulfonamide;
[1-(3,4-Dichloro-benzyl)-7-(2-methanesulfonylamino-ethoxy)-1,2,3,4-tetrahydro-naphthalen-2-yl]-carbamic acid ethyl ester;
[7-(2-Benzenesulfonylamino-ethoxy)-1-(3,4-dichloro-benzyl)-1,2,3,4-tetrahydro-naphthalen-2-yl]-carbamic acid ethyl ester;
{1-(3,4-Dichloro-benzyl)-7-[2-(thiophene-2-sulfonylamino)-ethoxy]-1,2,3,4-tetrahydro-naphthalen-2-yl}-carbamic acid ethyl ester;
N-{2-[7-Amino-8-(3,4-dichloro-benzyl)-5,6,7,8-tetrahydro-naphthalen-2-yloxy]-ethyl}-methanesulfonamide;
N-{2-[7-Amino-8-(3,4-dichloro-benzyl)-5,6,7,8-tetrahydro-naphthalen-2-yloxy]-ethyl}-benzenesulfonamide;
Thiophene-2-sulfonic acid {2-[7-amino-8-(3,4-dichloro-benzyl)-5,6,7,8-tetrahydro-naphthalen-2-yloxy]-ethyl}-amide;
N-{1-(3,4-Dichloro-benzyl)-7-[2-(1-methyl-1H-imidazole-4-sulfonylamino)-ethoxy]-1,2,3,4-tetrahydro-naphthalen-2-yl}-2,2,2-trifluoro-acetamide;
Pyrrolidine-3-sulfonic acid {2-[7-amino-8-(3,4-dichloro-benzyl)-5,6,7,8-tetrahydro-naphthalen-2-yloxy]-ethyl}-amide;
1-Methyl-1H-imidazole-4-sulfonic acid {2-[8-(3,4-dichloro-benzyl)-7-formylamino-5,6,7,8-tetrahydro-naphthalen-2-yloxy]-ethyl}-amide;
1-(3,4-Dichloro-benzyl)-7-[2-(4-methyl-thiophene-2-sulfonylamino)-ethoxy]-1,2,3,4-tetrahydro-naphthalen-2-yl}-carbamic acid ethyl ester;
{1-(3,4-Dichloro-benzyl)-7-[2-(3-fluoro-propane-1-sulfonylamino)-ethoxy]-1,2,3,4-tetrahydro-naphthalen-2-yl}-carbamic acid ethyl ester;
1-Methyl-1H-imidazole-4-sulfonic acid {2-[8-(3,4-dichloro-benzyl)-7-ethylamino-5,6,7,8-tetrahydro-naphthalen-2-yloxy]-ethyl}-amide;
4-Methyl-thiophene-2-sulfonic acid {2-[7-amino-8-(3,4-dichloro-benzyl)-5,6,7,8-tetrahydro-naphthalen-2-yloxy]-ethyl}-amide;
N'-(2-{[7-amino-8-(3,4-dichlorobenzyl)-5,6,7,8-tetrahydronaphthalen-2-yl]oxy}ethyl)-N,N-dimethylsulfuric diamide;
{1-(3,4-Dichloro-benzyl)-7-[2-(3,3,3-trifluoro-propane-1-sulfonylamino)-ethoxy]-1,2,3,4-tetrahydro-naphthalen-2-yl}-carbamic acid ethyl ester;
1-Methyl-1H-imidazole-4-sulfonic acid {2-[7-amino-8-(4-chloro-benzyl)-5,6,7,8-tetrahydro-naphthalen-2-yloxy]-ethyl}-amide;
1-Methyl-1H-pyrazole-4-sulfonic acid {2-[7-amino-8-(4-chloro-benzyl)-5,6,7,8-tetrahydro-naphthalen-2-yloxy]-ethyl}-amide;

N-[(7-Amino-8-benzyl-5,6,7,8-tetrahydronaphthalen-2-yl)methyl]-3-fluoropropane-1-sulfonamide;

1-(3-Chlorobenzyl)-7-[2-(1,1-dioxidoisothiazolidin-2-yl)ethoxy]-1,2,3,4-tetrahydronaphthalen-2-amine;

tert-Butyl[1-(3,4-dichlorobenzyl)-7-{[(propylsulfonyl)amino]methyl}-1,2,3,4-tetrahydronaphthalen-2-yl]carbamate;

N-{[7-Amino-8-(3,4-dichlorobenzyl)-5,6,7,8-tetrahydronaphthalen-2-yl]methyl}propane-1-sulfonamide;

N-{[7-Amino-8-(3,4-dichlorobenzyl)-5,6,7,8-tetrahydronaphthalen-2-yl]methyl}-3-fluoropropane-1-sulfonamide;

N-{[7-Amino-8-benzyl-5,6,7,8-tetrahydronaphthalen-2-yl]methyl}propane-1-sulfonamide;

N-{[cis-7-Amino-8-benzyl-5,6,7,8-tetrahydronaphthalen-2-yl]methyl}cyclobutanesulfonamide;

N-{[cis-7-Amino-8-benzyl-5,6,7,8-tetrahydronaphthalen-2-yl]methyl}-1-cyclopropylmethanesulfonamide;

N-{[cis-7-amino-8-benzyl-5,6,7,8-tetrahydronaphthalen-2-yl]methyl}-N-methylpropane-1-sulfonamide;

{1-(3-Chloro-benzyl)-7-[2-(1-methyl-1H-pyrazole-4-sulfonylamino)-ethoxy]-1,2,3,4-tetrahydro-naphthalen-2-yl}-carbamic acid ethyl ester;

1-Methyl-1H-pyrazole-4-sulfonic acid {2-[7-amino-8-(3-chloro-benzyl)-5,6,7,8-tetrahydro-naphthalen-2-yloxy]-ethyl}-amide;

1-Methyl-1H-imidazole-4-sulfonic acid {2-[7-amino-8-(3-chloro-benzyl)-5,6,7,8-tetrahydro-naphthalen-2-yloxy]-ethyl}-amide;

{1-(3-Chloro-benzyl)-7-[2-(2,4-dimethyl-thiazole-5-sulfonylamino)-ethoxy]-1,2,3,4-tetrahydro-naphthalen-2-yl}-carbamic acid ethyl ester;

{1-(3-Chloro-benzyl)-7-[2-(thiophene-2-sulfonylamino)-ethoxy]-1,2,3,4-tetrahydro-naphthalen-2-yl}-carbamic acid ethyl ester;

{1-(3-Chloro-benzyl)-7-[2-(5-chloro-thiophene-2-sulfonylamino)-ethoxy]-1,2,3,4-tetrahydro-naphthalen-2-yl}-carbamic acid ethyl ester;

{1-(3-Chloro-benzyl)-7-[2-(2-methyl-3H-imidazole-4-sulfonylamino)-ethoxy]-1,2,3,4-tetrahydro-naphthalen-2-yl}-carbamic acid ethyl ester;

{1-(3-Chloro-benzyl)-7-[2-(5-methyl-thiophene-2-sulfonylamino)-ethoxy]-1,2,3,4-tetrahydro-naphthalen-2-yl}-carbamic acid ethyl ester;

{1-(3-Chloro-benzyl)-7-[2-(4-methyl-thiophene-2-sulfonylamino)-ethoxy]-1,2,3,4-tetrahydro-naphthalen-2-yl}-carbamic acid ethyl ester;

Propane-1-sulfonic acid {2-[7-amino-8-(3-chloro-benzyl)-5,6,7,8-tetrahydro-naphthalen-2-yloxy]-ethyl}-amide;

Thiophene-2-sulfonic acid {2-[7-amino-8-(3-chloro-benzyl)-5,6,7,8-tetrahydro-naphthalen-2-yloxy]-ethyl}-amide;

2,4-Dimethyl-thiazole-5-sulfonic acid {2-[7-amino-8-(3-chloro-benzyl)-5,6,7,8-tetrahydro-naphthalen-2-yloxy]-ethyl}-amide;

2-Methyl-3H-imidazole-4-sulfonic acid {2-[7-amino-8-(3-chloro-benzyl)-5,6,7,8-tetrahydro-naphthalen-2-yloxy]-ethyl}-amide;

5-Chloro-thiophene-2-sulfonic acid {2-[7-amino-8-(3-chloro-benzyl)-5,6,7,8-tetrahydro-naphthalen-2-yloxy]-ethyl}-amide;

{1-(3-Chloro-benzyl)-7-[2-(2,5-dimethyl-thiophene-3-sulfonylamino)-ethoxy]-1,2,3,4-tetrahydro-naphthalen-2-yl}-carbamic acid ethyl ester;

{1-(3-Chloro-benzyl)-7-[2-(1-ethyl-1H-pyrazole-4-sulfonylamino)-ethoxy]-1,2,3,4-tetrahydro-naphthalen-2-yl}-carbamic acid ethyl ester;

{1-(2,4-Dichloro-benzyl)-7-[2-(1-methyl-1H-pyrazole-4-sulfonylamino)-ethoxy]-1,2,3,4-tetrahydro-naphthalen-2-yl}-carbamic acid ethyl ester;

{1-(2,4-Dichloro-benzyl)-7-[2-(thiophene-2-sulfonylamino)-ethoxy]-1,2,3,4-tetrahydro-naphthalen-2-yl}-carbamic acid ethyl ester;

{1-(2,4-Dichloro-benzyl)-7-[2-(5-methyl-thiophene-2-sulfonylamino)-ethoxy]-1,2,3,4-tetrahydro-naphthalen-2-yl}-carbamic acid ethyl ester;

[1-(3-Chloro-benzyl)-7-(2-ethanesulfonylamino-ethoxy)-1,2,3,4-tetrahydro-naphthalen-2-yl]-carbamic acid ethyl ester;

1-Ethyl-1H-pyrazole-4-sulfonic acid {2-[7-amino-8-(3-chloro-benzyl)-5,6,7,8-tetrahydro-naphthalen-2-yloxy]-ethyl}-amide;

4-Methyl-thiophene-2-sulfonic acid {2-[7-amino-8-(3-chloro-benzyl)-5,6,7,8-tetrahydro-naphthalen-2-yloxy]-ethyl}-amide;

5-Methyl-thiophene-2-sulfonic acid {2-[7-amino-8-(3-chloro-benzyl)-5,6,7,8-tetrahydro-naphthalen-2-yloxy]-ethyl}-amide;

2,5-Dimethyl-thiophene-3-sulfonic acid {2-[7-amino-8-(3-chloro-benzyl)-5,6,7,8-tetrahydro-naphthalen-2-yloxy]-ethyl}-amide;

Ethanesulfonic acid {2-[7-amino-8-(3-chloro-benzyl)-5,6,7,8-tetrahydro-naphthalen-2-yloxy]-ethyl}-amide;

1-Methyl-1H-pyrazole-4-sulfonic acid {2-[7-amino-8-(2,4-dichloro-benzyl)-5,6,7,8-tetrahydro-naphthalen-2-yloxy]-ethyl}-amide;

Thiophene-2-sulfonic acid {2-[7-amino-8-(2,4-dichloro-benzyl)-5,6,7,8-tetrahydro-naphthalen-2-yloxy]-ethyl}-amide;

5-Methyl-thiophene-2-sulfonic acid {2-[7-amino-8-(2,4-dichloro-benzyl)-5,6,7,8-tetrahydro-naphthalen-2-yloxy]-ethyl}-amide;

{1-(2,4-Dichloro-benzyl)-7-[2-(propane-1-sulfonylamino)-ethoxy]-1,2,3,4-tetrahydro-naphthalen-2-yl}-carbamic acid ethyl ester;

Propane-1-sulfonic acid {2-[7-amino-8-(2,4-dichloro-benzyl)-5,6,7,8-tetrahydro-naphthalen-2-yloxy]-ethyl}-amide;

(1-(4-Chloro-benzyl)-7-{2-[methyl-(propane-1-sulfonyl)-amino]-ethoxy}-1,2,3,4-tetrahydro-naphthalen-2-yl)-carbamic acid ethyl ester;

Propane-1-sulfonic acid {2-[7-amino-8-(4-chloro-benzyl)-5,6,7,8-tetrahydro-naphthalen-2-yloxy]-ethyl}-methyl-amide;

(1-(3-Chloro-benzyl)-7-{2-[methyl-(propane-1-sulfonyl)-amino]-ethoxy}-1,2,3,4-tetrahydro-naphthalen-2-yl)-carbamic acid ethyl ester;

Propane-1-sulfonic acid {2-[7-amino-8-(3-chloro-benzyl)-5,6,7,8-tetrahydro naphthalen-2-yloxy]-ethyl}-methyl-amide;

{1-(3-Chloro-benzyl)-7-[2-(1-methyl-1H-imidazole-4-sulfonylamino)-ethoxy]-1,2,3,4-tetrahydro-naphthalen-2-yl}-carbamic acid ethyl ester;

{1-(3-Chloro-benzyl)-7-[2-(1-difluoromethyl-1H-pyrazole-4-sulfonylamino)-ethoxy]-1,2,3,4-tetrahydro-naphthalen-2-yl}-carbamic acid ethyl ester;

1-(3-Chloro-benzyl)-7-[(R)-1-(propane-1-sulfonyl)-pyrrolidin-2-ylmethoxy]-1,2,3,4-tetrahydro-naphthalen-2-ylamine;

1-(3-Chloro-benzyl)-7-[1-(propane-1-sulfonyl)-azetidin-3-yloxy]-1,2,3,4-tetrahydro-naphthalen-2-ylamine;

1-(3-Chloro-benzyl)-7-(3-ethanesulfonyl-propoxy)-1,2,3,4-tetrahydro-naphthalen-2-ylamine;
Cyclohexanesulfonic acid {2-[7-amino-8-(3,4-dichloro-benzyl)-5,6,7,8-tetrahydro-naphthalen-2-yloxy]-ethyl}-amide;
2-Trimethylsilanyl-ethanesulfonic acid {2-[7-amino-8-(3,4-dichloro-benzyl)-5,6,7,8-tetrahydro-naphthalen-2-yloxy]-ethyl}-amide;
N-{2-[7-Amino-8-(3,4-dichloro-benzyl)-5,6,7,8-tetrahydro-naphthalen-2-yloxy]-ethyl}-C-(5-methyl-isoxazol-3-yl)-methanesulfonamide;
Cyclobutanesulfonic acid {2-[8-(3,4-dichloro-benzyl)-7-pyrrolidin-1-yl-5,6,7,8-tetrahydro-naphthalen-2-yloxy]-ethyl}-amide;
1-Methyl-1H-pyrazole-4-sulfonic acid {2-[8-(3,4-dichloro-benzyl)-7-pyrrolidin-1-yl-5,6,7,8-tetrahydro-naphthalen-2-yloxy]-ethyl}-methyl-amide;
Butane-1-sulfonic acid {2-[7-amino-8-(3,4-dichloro-benzyl)-5,6,7,8-tetrahydro-naphthalen-2-yloxy]-ethyl}-amide;
Propane-2-sulfonic acid {2-[7-amino-8-(3,4-dichloro-benzyl)-5,6,7,8-tetrahydro-naphthalen-2-yloxy]-ethyl}-amide;
1-Methyl-1H-pyrazole-4-sulfonic acid {2-[8-(3,4-dichloro-benzyl)-7-pyrrolidin-1-yl-5,6,7,8-tetrahydro-naphthalen-2-yloxy]-ethyl}-amide;
2-Ethoxy-ethanesulfonic acid {2-[7-amino-8-(3,4-dichloro-benzyl)-5,6,7,8-tetrahydro-naphthalen-2-yloxy]-ethyl}-amide;
Cyclobutanesulfonic acid {2-[8-(3,4-dichloro-benzyl)-7-pyrrolidin-1-yl-5,6,7,8-tetrahydro-naphthalen-2-yloxy]-ethyl}-methyl-amide;
N-{2-[7-Amino-8-(3,4-dichloro-benzyl)-5,6,7,8-tetrahydro-naphthalen-2-yloxy]-ethyl}-C-cyclopropyl-methanesulfonamide;
Propane-1-sulfonic acid {2-[7-amino-8-(4-methoxy-benzyl)-5,6,7,8-tetrahydro-naphthalen-2-yloxy]-ethyl}-amide;
N-[2-(7-Amino-8-benzyl-5,6,7,8-tetrahydro-naphthalen-2-yloxy)-ethyl]-methanesulfonamide;
1-Methyl-1H-imidazole-4-sulfonic acid [2-(7-amino-8-benzyl-5,6,7,8-tetrahydro-naphthalen-2-yloxy)-ethyl]-methyl-amide;
N-[2-(7-Amino-8-benzyl-5,6,7,8-tetrahydro-naphthalen-2-yloxy)-ethyl]-benzenesulfonamide;
3,3,3-Trifluoro-propane-1-sulfonic acid [2-(7-amino-8-benzyl-5,6,7,8-tetrahydro-naphthalen-2-yloxy)-ethyl]-amide;
1-Methyl-1H-imidazole-4-sulfonic acid [2-(8-benzyl-7-pyrrolidin-1-yl-5,6,7,8-tetrahydronaphthalen-2-yloxy)-ethyl]-methyl-amide;
Cyclopropanesulfonic acid [2-(7-amino-8-benzyl-5,6,7,8-tetrahydro-naphthalen-2-yloxy)-ethyl]-amide;
N-[2-(7-Amino-8-benzyl-5,6,7,8-tetrahydro-naphthalen-2-yloxy)-ethyl]-propionamide;
1-Methyl-1H-[1,2,4]triazole-3-sulfonic acid {2-[7-amino-8-(3,4-dichloro-benzyl)-5,6,7,8-tetrahydro-naphthalen-2-yloxy]-ethyl}-amide;
1-Methyl-1H-imidazole-4-sulfonic acid [2-(7-azetidin-1-yl-8-benzyl-5,6,7,8-tetrahydro-naphthalen-2-yloxy)-ethyl]-methyl-amide;
N-{2-[7-Amino-8-(3,4-dichloro-benzyl)-5,6,7,8-tetrahydro-naphthalen-2-yloxy]-ethyl}-C-cyclobutyl-methanesulfonamide;
Propane-1-sulfonic acid {2-[7-amino-8-(3-fluoro-benzyl)-5,6,7,8-tetrahydro-naphthalen-2-yloxy]-ethyl}-amide;
N-{2-[7-Amino-8-(3,4-dichloro-benzyl)-5,6,7,8-tetrahydro-naphthalen-2-yloxy]-ethyl}-C-cyclopropyl-N-methyl-methanesulfonamide;
1-Methyl-1H-pyrazole-4-sulfonic acid [2-(7-amino-8-benzyl-5,6,7,8-tetrahydro-naphthalen-2-yloxy)-ethyl]-methyl-amide;
N-(2-(7-Amino-8-(3,4-dichlorobenzyl)-5,6,7,8-tetrahydronaphthalen-2-yloxy)ethyl)-N-ethyl-1-methyl-1H-pyrazole-4-sulfonamide;
1-Methyl-1H-pyrazole-4-sulfonic acid [2-(8-benzyl-7-pyrrolidin-1-yl-5,6,7,8-tetrahydro-naphthalen-2-yloxy)-ethyl]-methyl-amide;
1-Methyl-1H-pyrazole-4-sulfonic acid [2-(7-azetidin-1-yl-8-benzyl-5,6,7,8-tetrahydro-naphthalen-2-yloxy)-ethyl]-methyl-amide;
N-(2-(7-Amino-8-benzyl-5,6,7,8-tetrahydronaphthalen-2-yloxy)ethyl)-N-ethyl-1-methyl-1H-pyrazole-4-sulfonamide;
N-(2-(7-Amino-8-(3,4-dichlorobenzyl)-5,6,7,8-tetrahydronaphthalen-2-yloxy)ethyl)pentane-1-sulfonamide;
N-(2-(8-(3,4-Dichlorobenzyl)-7-(pyrrolidin-1-yl)-5,6,7,8-tetrahydronaphthalen-2-yloxy)ethyl)-1-methyl-1H-imidazole-4-sulfonamide;
N-(2-(8-Benzyl-7-(pyrrolidin-1-yl)-5,6,7,8-tetrahydronaphthalen-2-yloxy)ethyl)-1-methyl-1H-imidazole-4-sulfonamide;
N-(2-(8-Benzyl-7-(pyrrolidin-1-yl)-5,6,7,8-tetrahydronaphthalen-2-yloxy)ethyl)-1-methyl-1H-pyrazole-4-sulfonamide;
N-(2-{[7-Amino-8-(3-chloro-4-fluorobenzyl)-5,6,7,8-tetrahydronaphthalen-2-yl]oxy}ethyl)propane-1-sulfonamide;
N-(2-{[7-Amino-8-benzyl-5,6,7,8-tetrahydronaphthalen-2-yl]oxy}ethyl)-1-cyclopropylmethanesulfonamide;
N-(2-{[7-Amino-8-(3,4-dichlorobenzyl)-5,6,7,8-tetrahydronaphthalen-2-yl]oxy}ethyl)-2-cyclopropylacetamide;
N-(2-{[7-Amino-8-(3,4-dichlorobenzyl)-5,6,7,8-tetrahydronaphthalen-2-yl]oxy}ethyl)benzamide;
N-(2-{[8-Benzyl-7-(pyrrolidin-1-yl)-5,6,7,8-tetrahydronaphthalen-2-yl]oxy}ethyl)-N-ethyl-1-methyl-1H-pyrazole-4-sulfonamide;
N-(2-{[7-Amino-8-(3,4-dichlorobenzyl)-5,6,7,8-tetrahydronaphthalen-2-yl]oxy}ethyl)-2-cyclopropylethanesulfonamide;
C-Cyclopropyl-N-{2-[8-(3,4-dichloro-benzyl)-7-pyrrolidin-1-yl-5,6,7,8-tetrahydro-naphthalen-2-yloxy]-ethyl}-N-methyl-methanesulfonamide;
N-(2-{[8-Benzyl-7-(pyrrolidin-1-yl)-5,6,7,8-tetrahydronaphthalen-2-yl]oxy}ethyl)-1-cyclopropyl-N-methylmethanesulfonamide;
N-(2-{[7-Amino-8-(4-chlorobenzyl)-5,6,7,8-tetrahydronaphthalen-2-yl]oxy}ethyl)-1-cyclopropylmethanesulfonamide;
N-(2-{[7-Amino-8-(4-chlorobenzyl)-5,6,7,8-tetrahydronaphthalen-2-yl]oxy}ethyl)-1-cyclopropyl-N-methylmethanesulfonamide;
N-[2-(7-Amino-8-benzyl-5,6,7,8-tetrahydro-naphthalen-2-yloxy)-ethyl]-C-cyclopropyl-N-methyl-methanesulfonamide;
N-(2-{[7-Amino-8-(3,4-difluorobenzyl)-5,6,7,8-tetrahydronaphthalen-2-yl]oxy}ethyl)-1-cyclopropylmethanesulfonamide;
C-Cyclopropyl-N-{2-[8-(3,4-dichloro-benzyl)-7-pyrrolidin-1-yl-5,6,7,8-tetrahydro-naphthalen-2-yloxy]-ethyl}-methanesulfonamide;

N-(2-{[8-Benzyl-7-(pyrrolidin-1-yl)-5,6,7,8-tetrahydronaphthalen-2-yl]oxy}ethyl)-1-cyclopropylmethanesulfonamide;

1-Cyclopropyl-N-[2-({8-(3,4-dichlorobenzyl)-7-[3-fluoropyrrolidin-1-yl]-5,6,7,8-tetrahydronaphthalen-2-yl}oxy)ethyl]methanesulfonamide;

N-(2-{[7-(Azetidin-1-yl)-8-(3,4-dichlorobenzyl)-5,6,7,8-tetrahydronaphthalen-2-yl]oxy}ethyl)-1-cyclopropylmethanesulfonamide;

N-[2-({8-Benzyl-7-[3-fluoropyrrolidin-1-yl]-5,6,7,8-tetrahydronaphthalen-2-yl}oxy)ethyl]-1-cyclopropylmethanesulfonamide;

N-(2-{[8-Benzyl-7-(methylamino)-5,6,7,8-tetrahydronaphthalen-2-yl]oxy}ethyl)-1-cyclopropylmethanesulfonamide;

1-Cyclopropyl-N-(2-{[8-(3-fluorobenzyl)-7-(pyrrolidin-1-yl)-5,6,7,8-tetrahydronaphthalen-2-yl]oxy}ethyl)methanesulfonamide;

N-(2-{[7-(Azetidin-1-yl)-8-(3-fluorobenzyl)-5,6,7,8-tetrahydronaphthalen-2-yl]oxy}ethyl)-1-cyclopropylmethanesulfonamide;

N-(2-{[8-(3-Fluorobenzyl)-7-(pyrrolidin-1-yl)-5,6,7,8-tetrahydronaphthalen-2-yl]oxy}ethyl)-1-methyl-1H-imidazole-4-sulfonamide;

N-(2-{[7-(Azetidin-1-yl)-8-(3-fluorobenzyl)-5,6,7,8-tetrahydronaphthalen-2-yl]oxy}ethyl)-1-methyl-1H-imidazole-4-sulfonamide;

N-(2-{[7-(Azetidin-1-yl)-8-benzyl-5,6,7,8-tetrahydronaphthalen-2-yl]oxy}ethyl)-1-cyclopropylmethanesulfonamide;

N-(2-{[7-(Azetidin-1-yl)-8-benzyl-5,6,7,8-tetrahydronaphthalen-2-yl]oxy}ethyl)-1-methyl-1H-imidazole-4-sulfonamide;

N-(2-{[7-(Azetidin-1-yl)-8-benzyl-5,6,7,8-tetrahydronaphthalen-2-yl]oxy}ethyl)cyclobutanesulfonamide;

Propane-1-sulfonic acid [2-(7-azetidin-1-yl-8-benzyl-5,6,7,8-tetrahydro-naphthalen-2-yloxy)-ethyl]-amide;

N-(2-{[8-(3-Fluorobenzyl)-7-(pyrrolidin-1-yl)-5,6,7,8-tetrahydronaphthalen-2-yl]oxy}ethyl)-1-methyl-1H-pyrrole-3-sulfonamide;

N-(2-{[7-Amino-8-(3-chloro-5-fluorobenzyl)-5,6,7,8-tetrahydronaphthalen-2-yl]oxy}ethyl)-1-cyclopropylmethanesulfonamide;

N-(2-{[7-Amino-8-(3-chloro-5-fluorobenzyl)-5,6,7,8-tetrahydronaphthalen-2-yl]oxy}ethyl)-1-methyl-1H-imidazole-4-sulfonamide;

N-[2-({8-Benzyl-7-[3-fluoropyrrolidin-1-yl]-5,6,7,8-tetrahydronaphthalen-2-yl}oxy)ethyl]-1-methyl-1H-imidazole-4-sulfonamide;

N-(2-{[8-(3-Cyanobenzyl)-7-(pyrrolidin-1-yl)-5,6,7,8-tetrahydronaphthalen-2-yl]oxy}ethyl)-1-methyl-1H-imidazole-4-sulfonamide;

N-(2-{[8-(3-Cyanobenzyl)-7-(propan-2-ylamino)-5,6,7,8-tetrahydronaphthalen-2-yl]oxy}ethyl)-1-methyl-1H-imidazole-4-sulfonamide;

N-(2-{[8-(3-Cyanobenzyl)-7-(pyrrolidin-1-yl)-5,6,7,8-tetrahydronaphthalen-2-yl]oxy}ethyl)-1-cyclopropylmethanesulfonamide;

N-(2-{[8-(3-Cyanobenzyl)-7-(propan-2-ylamino)-5,6,7,8-tetrahydronaphthalen-2-yl]oxy}ethyl)-1-cyclopropylmethanesulfonamide;

N-(2-{[7-Amino-8-benzyl-5,6,7,8-tetrahydronaphthalen-2-yl]oxy}ethyl)propane-1-sulfonamide;

N-(2-{[8-(3-Chloro-5-fluorobenzyl)-7-(methylamino)-5,6,7,8-tetrahydronaphthalen-2-yl]oxy}ethyl)-1-cyclopropylmethanesulfonamide;

N-(2-{[7-(Azetidin-1-yl)-8-(3-chloro-5-fluorobenzyl)-5,6,7,8-tetrahydronaphthalen-2-yl]oxy}ethyl)-1-cyclopropylmethanesulfonamide;

N-(2-{[7-(Azetidin-1-yl)-8-(3-chloro-5-fluorobenzyl)-5,6,7,8-tetrahydronaphthalen-2-yl]oxy}ethyl)-1-methyl-1H-imidazole-4-sulfonamide;

1-Cyclopropyl-N-(2-{[8-(4-fluorobenzyl)-7-(methylamino)-5,6,7,8-tetrahydronaphthalen-2-yl]oxy}ethyl)methanesulfonamide;

(−)-N-(2-(8-Benzyl-7-(pyrrolidin-1-yl)-5,6,7,8-tetrahydronaphthalen-2-yloxy)ethyl)-1-methyl-1H-imidazole-4-sulfonamide;

1-Methyl-N-(2-{[8-(3-methylbenzyl)-7-(pyrrolidin-1-yl)-5,6,7,8-tetrahydronaphthalen-2-yl]oxy}ethyl)-1H-imidazole-4-sulfonamide;

N-(2-{[8-(3-Methoxybenzyl)-7-(pyrrolidin-1-yl)-5,6,7,8-tetrahydronaphthalen-2-yl]oxy}ethyl)-1-methyl-1H-imidazole-4-sulfonamide;

1-Methyl-1H-imidazole-4-sulfonic acid {2-[amino-8-(3-trifluoromethyl-benzyl)-5,6,7,8-tetrahydro-naphthalen-2-yloxy]-ethyl}-amide;

N-{[7-Amino-8-(3-chlorobenzyl)-5,6,7,8-tetrahydronaphthalen-2-yl]methyl}propane-1-sulfonamide;

N-[(7-Amino-8-benzyl-5,6,7,8-tetrahydronaphthalen-2-yl)methyl]methanesulfonamide;

N-[(7-Amino-8-benzyl-5,6,7,8-tetrahydronaphthalen-2-yl)methyl]benzenesulfonamide;

N-{[7-Amino-8-benzyl-5,6,7,8-tetrahydronaphthalen-2-yl]methyl}propane-1-sulfonamide;

N-{[7-amino-8-benzyl-5,6,7,8-tetrahydronaphthalen-2-yl]methyl}propane-1-sulfonamide;

N-{[7-Amino-8-(3-fluorobenzyl)-5,6,7,8-tetrahydronaphthalen-2-yl]methyl}propane-1-sulfonamide;

N-[(7-Amino-8-benzyl-5,6,7,8-tetrahydronaphthalen-2-yl)methyl]-1-methyl-1H-pyrazole-4-sulfonamide;

N-[(7-Amino-8-benzyl-5,6,7,8-tetrahydronaphthalen-2-yl)methyl]-1-methyl-1H-imidazole-4-sulfonamide;

N-{[7-Amino-8-(4-fluorobenzyl)-5,6,7,8-tetrahydronaphthalen-2-yl]methyl}cyclobutanesulfonamide;

N-{[7-Amino-8-(4-fluorobenzyl)-5,6,7,8-tetrahydronaphthalen-2-yl]methyl}propane-1-sulfonamide;

N-{[7-Amino-8-(4-fluorobenzyl)-5,6,7,8-tetrahydronaphthalen-2-yl]methyl}-1-methyl-1H-imidazole-4-sulfonamide;

N-{[7-Amino-8-(3-fluorobenzyl)-5,6,7,8-tetrahydronaphthalen-2-yl]methyl}-1-methyl-1H-imidazole-4-sulfonamide;

N-{[7-Amino-8-(3-fluorobenzyl)-5,6,7,8-tetrahydronaphthalen-2-yl]methyl}-1-methyl-1H-pyrazole-4-sulfonamide;

N-{[7-Amino-8-benzyl-5,6,7,8-tetrahydronaphthalen-2-yl]methyl}-3-methylbenzenesulfonamide;

N-{[7-Amino-8-benzyl-5,6,7,8-tetrahydronaphthalen-2-yl]methyl}-1-methyl-1H-pyrrole-3-sulfonamide;

N-{[7-Amino-8-benzyl-5,6,7,8-tetrahydronaphthalen-2-yl]methyl}pyridine-3-sulfonamide;

N-{[7-Amino-8-benzyl-5,6,7,8-tetrahydronaphthalen-2-yl]methyl}-1-methyl-3-(trifluoromethyl)-1H-pyrazole-4-sulfonamide;

N-{[7-Amino-8-benzyl-5,6,7,8-tetrahydronaphthalen-2-yl]methyl}-1-methyl-1H-pyrazole-3-sulfonamide;

N-{[7-Amino-8-(3-fluorobenzyl)-5,6,7,8-tetrahydronaphthalen-2-yl]methyl}cyclobutanesulfonamide;

N-{[7-Amino-8-(3,4-difluorobenzyl)-5,6,7,8-tetrahydronaphthalen-2-yl]methyl}-1-cyclopropylmethanesulfonamide;

N-{[7-Amino-8-(3,4-difluorobenzyl)-5,6,7,8-tetrahydronaphthalen-2-yl]methyl}cyclobutanesulfonamide;
N-{[8-Benzyl-7-(methylamino)-5,6,7,8-tetrahydronaphthalen-2-yl]methyl}propane-1-sulfonamide;
N-{[8-Benzyl-7-(methylamino)-5,6,7,8-tetrahydronaphthalen-2-yl]methyl}cyclobutanesulfonamide;
N-{[8-Benzyl-7-(methylamino)-5,6,7,8-tetrahydronaphthalen-2-yl]methyl}-3-methylbenzenesulfonamide;
N-{[8-Benzyl-7-(methylamino)-5,6,7,8-tetrahydronaphthalen-2-yl]methyl}-1-methyl-1H-pyrrole-3-sulfonamide;
N-{[8-Benzyl-7-(methylamino)-5,6,7,8-tetrahydronaphthalen-2-yl]methyl}-1-methyl-1H-pyrazole-3-sulfonamide;
N-{[8-Benzyl-7-(methylamino)-5,6,7,8-tetrahydronaphthalen-2-yl]methyl}-1-methyl-1H-imidazole-4-sulfonamide;
N-(1-Benzyl-7-{[(propylsulfonyl)amino]methyl}-1,2,3,4-tetrahydronaphthalen-2-yl) acetamide;
N-[(1-(4-Fluorobenzyl)-7-({[(1-methyl-1H-imidazol-4-yl)sulfonyl]amino}methyl)-1,2,3,4-tetrahydronaphthalen-2-yl]acetamide;
N-{[8-Benzyl-7-(ethylamino)-5,6,7,8-tetrahydronaphthalen-2-yl]methyl}propane-1-sulfonamide;
1-Methyl-1H-imidazole-4-sulfonic acid [7-ethylamino-8-(4-fluoro-benzyl)-5,6,7,8-tetrahydro-naphthalen-2-ylmethyl]-amide;
1-Methyl-1H-pyrazole-4-sulfonic acid [7-ethylamino-8-(3-fluoro-benzyl)-5,6,7,8-tetrahydro-naphthalen-2-ylmethyl]-amide;
N-{3-[7-Amino-8-(4-chlorobenzyl)-5,6,7,8-tetrahydronaphthalen-2-yl]propyl}propane-1-sulfonamide;
N-{3-[7-Amino-8-(4-chlorobenzyl)-5,6,7,8-tetrahydronaphthalen-2-yl]propyl}-1-cyclopropylmethanesulfonamide;
N-{3-[7-Amino-8-(3,4-dichlorobenzyl)-5,6,7,8-tetrahydronaphthalen-2-yl]propyl}propane-1-sulfonamide;
N-{3-[7-Amino-8-(3,4-difluoro-benzyl)-5,6,7,8-tetrahydro-naphthalen-2-yl]-propyl}-C-cyclopropyl-methanesulfonamide;
N-{3-[7-Amino-8-benzyl-5,6,7,8-tetrahydronaphthalen-2-yl]propyl}propane-1-sulfonamide;
N-{3-[7-Amino-8-(3,4-difluoro-benzyl)-5,6,7,8-tetrahydronaphthalen-2-yl]propyl}propane-1-sulfonamide;
N-{3-[7-Amino-8-benzyl-5,6,7,8-tetrahydronaphthalen-2-yl]propyl}-1-cyclopropylmethanesulfonamide;
N-{3-[7-Amino-8-(4-fluorobenzyl)-5,6,7,8-tetrahydronaphthalen-2-yl]propyl}-1-cyclopropylmethanesulfonamide;
N-{3-[7-Amino-8-(3-fluorobenzyl)-5,6,7,8-tetrahydronaphthalen-2-yl]propyl}propane-1-sulfonamide;
N-{3-[7-Amino-8-(3-fluorobenzyl)-5,6,7,8-tetrahydronaphthalen-2-yl]propyl}-1-cyclopropylmethanesulfonamide;
N-{3-[7-Amino-8-(2-chlorobenzyl)-5,6,7,8-tetrahydronaphthalen-2-yl]propyl}propane-1-sulfonamide;
N-{3-[7-Amino-8-(2-chloro-benzyl)-5,6,7,8-tetrahydro-naphthalen-2-yl]-propyl}-C-cyclopropyl-methanesulfonamide;
N-{3-[7-Amino-8-(4-fluorobenzyl)-5,6,7,8-tetrahydronaphthalen-2-yl]propyl}propane-1-sulfonamide;
N-[1-(3-Fluorobenzyl)-7-{3-[(propylsulfonyl)amino]propyl}-1,2,3,4-tetrahydronaphthalen-2-yl]acetamide;
N-[1-(4-Fluorobenzyl)-7-{3-[(propylsulfonyl)amino]propyl}-1,2,3,4-tetrahydronaphthalen-2-yl]acetamide;
N-[1-Benzyl-7-(3-{[(cyclopropylmethyl) sulfonyl]amino}propyl)-1,2,3,4-tetrahydronaphthalen-2-yl]acetamide;
N-[1-Benzyl-7-{3-[(propylsulfonyl)amino]propyl}-1,2,3,4-tetrahydronaphthalen-2-yl]acetamide;
N-[7-(3-{[(Cyclopropylmethyl)sulfonyl]amino}propyl)-1-(3-fluorobenzyl)-1,2,3,4-tetrahydronaphthalen-2-yl]acetamide;
Propane-1-sulfonic acid {3-[7-ethylamino-8-(3-fluoro-benzyl)-5,6,7,8-tetrahydro-naphthalen-2-yl]-propyl}-amide;
N-{3-[7-(Ethylamino)-8-(4-fluorobenzyl)-5,6,7,8-tetrahydronaphthalen-2-yl]propyl}propane-1-sulfonamide;
C-Cyclopropyl-N-{3-[7-ethylamino-8-(3-fluoro-benzyl)-5,6,7,8-tetrahydro-naphthalen-2-yl]-propyl}-methanesulfonamide;
Propane-1-sulfonic acid {3-[8-(2-chloro-benzyl)-7-ethylamino-5,6,7,8-tetrahydro-naphthalen-2-yl]-propyl}-amide;
N-{3-[8-Benzyl-7-(ethylamino)-5,6,7,8-tetrahydronaphthalen-2-yl]propyl}propane-1-sulfonamide;
N-{3-[8-Benzyl-7-(ethylamino)-5,6,7,8-tetrahydronaphthalen-2-yl]propyl}-1-cyclopropylmethanesulfonamide;
N-{3-[8-(3,4-Difluorobenzyl)-7-(ethylamino)-5,6,7,8-tetrahydronaphthalen-2-yl]propyl}propane-1-sulfonamide;
1-Cyclopropyl-N-{3-[8-(3,4-difluorobenzyl)-7-(ethylamino)-5,6,7,8-tetrahydronaphthalen-2-yl]propyl}methanesulfonamide;
N-{3-[7-Amino-8-(3-fluorobenzyl)-5,6,7,8-tetrahydronaphthalen-2-yl]propyl}-N-methylpropane-1-sulfonamide;
N-{3-[7-Amino-8-(2-chloro-benzyl)-5,6,7,8-tetrahydro-naphthalen-2-yl]-propyl}-C-cyclopropyl-N-methyl-methanesulfonamide;
Propane-1-sulfonic acid {3-[7-amino-8-(2-chloro-benzyl)-5,6,7,8-tetrahydro-naphthalen-2-yl]-propyl}-methyl-amide;
N-{3-[7-Amino-8-(3-fluorobenzyl)-5,6,7,8-tetrahydronaphthalen-2-yl]propyl}-1-cyclopropyl-N-methylmethanesulfonamide;
N-{3-[7-Amino-8-(4-fluorobenzyl)-5,6,7,8-tetrahydronaphthalen-2-yl]propyl}-1-cyclopropyl-N-methylmethanesulfonamide;
N-{3-[7-Amino-8-(4-fluorobenzyl)-5,6,7,8-tetrahydronaphthalen-2-yl]propyl}-N-methylpropane-1-sulfonamide;
N-{3-[7-Amino-8-(4-chlorobenzyl)-5,6,7,8-tetrahydronaphthalen-2-yl]propyl}-1-cyclopropyl-N-methylmethanesulfonamide;
N-{3-[7-Amino-8-(4-chlorobenzyl)-5,6,7,8-tetrahydronaphthalen-2-yl]propyl}-N-methylpropane-1-sulfonamide;
N-(2-{[7-Amino-8-(3-fluorobenzyl)-5,6,7,8-tetrahydronaphthalen-2-yl]oxy}ethyl)-1-cyclopropylmethanesulfonamide;
Ethyl [1-(3,5-difluorobenzyl)-7-(2-{[(1-methyl-1H-pyrrol-3-yl)sulfonyl]amino}ethoxy)-1,2,3,4-tetrahydronaphthalen-2-yl]carbamate;
Ethyl [7-(2-{[(cyclopropylmethyl)sulfonyl]amino}ethoxy)-1-(3,5-difluorobenzyl)-1,2,3,4-tetrahydronaphthalen-2-yl]carbamate;
N-(2-{[7-amino-8-benzyl-5,6,7,8-tetrahydronaphthalen-2-yl]oxy}ethyl)-1-methyl-1H-imidazole-4-sulfonamide;

C-cyclopropyl-N-{2-[8-(3-fluoro-benzyl)-7-methylamino-5,6,7,8-tetrahydro-naphthalen-2-yloxy]-ethyl}-methanesulfonamide;
1-Cyclopropyl-N-(2-{[8-(3-fluorobenzyl)-7-(methylamino)-5,6,7,8-tetrahydronaphthalen-2-yl]oxy}ethyl)methanesulfonamide;
N-(2-{[8-(3,5-difluorobenzyl)-7-(methylamino)-5,6,7,8-tetrahydronaphthalen-2-yl]oxy}ethyl)-1-methyl-1H-pyrrole-3-sulfonamide;
N-(2-{[8-(3,5-difluorobenzyl)-7-(methylamino)-5,6,7,8-tetrahydronaphthalen-2-yl]oxy}ethyl)-1-methyl-1H-pyrrole-3-sulfonamide;
1-Cyclopropyl-N-(2-{[8-(3,5-difluorobenzyl)-7-(methylamino)-5,6,7,8-tetrahydronaphthalen-2-yl]oxy}ethyl)methanesulfonamide;
N-(2-{[8-(3,5-Difluorobenzyl)-7-(methylamino)-5,6,7,8-tetrahydronaphthalen-2-yl]oxy}ethyl)-1-methyl-1H-pyrrole-3-sulfonamide;
1-Cyclopropyl-N-(2-{[8-(3-fluorobenzyl)-7-(methylamino)-5,6,7,8-tetrahydronaphthalen-2-yl]oxy}ethyl)methanesulfonamide;
N-{[7-(Azetidin-1-yl)-8-benzyl-5,6,7,8-tetrahydronaphthalen-2-yl]methyl}-1-methyl-1H-imidazole-4-sulfonamide;
N-{[7-(Azetidin-1-yl)-8-benzyl-5,6,7,8-tetrahydronaphthalen-2-yl]methyl}propane-1-sulfonamide;
N-{[7-(Azetidin-1-yl)-8-benzyl-5,6,7,8-tetrahydronaphthalen-2-yl]methyl}-1-methyl-1H-pyrazole-4-sulfonamide;
N-{[7-(Azetidin-1-yl)-8-benzyl-5,6,7,8-tetrahydronaphthalen-2-yl]methyl}-1-methyl-1H-pyrrole-3-sulfonamide;
N-{[7-(azetidin-1-yl)-8-benzyl-5,6,7,8-tetrahydronaphthalen-2-yl]methyl}pyridine-2-sulfonamide;
N-{[7-(azetidin-1-yl)-8-benzyl-5,6,7,8-tetrahydronaphthalen-2-yl]methyl}thiophene-2-sulfonamide;
N-{[7-(Azetidin-1-yl)-8-(3-fluorobenzyl)-5,6,7,8-tetrahydronaphthalen-2-yl]methyl}-1-methyl-1H-imidazole-4-sulfonamide;
N-{[8-Benzyl-7-(morpholin-4-yl)-5,6,7,8-tetrahydronaphthalen-2-yl]methyl}-1-methyl-1H-imidazole-4-sulfonamide;
N-{[8-Benzyl-7-(morpholin-4-yl)-5,6,7,8-tetrahydronaphthalen-2-yl]methyl}-1-methyl-1H-pyrazole-4-sulfonamide;
N-{[8-Benzyl-7-(morpholin-4-yl)-5,6,7,8-tetrahydronaphthalen-2-yl]methyl}-1-cyclopropylmethanesulfonamide;
N-{[8-Benzyl-7-(morpholin-4-yl)-5,6,7,8-tetrahydronaphthalen-2-yl]methyl}propane-1-sulfonamide;
N-{[8-Benzyl-7-(morpholin-4-yl)-5,6,7,8-tetrahydronaphthalen-2-yl]methyl}cyclobutanesulfonamide;
N-{[8-Benzyl-7-(pyrrolidin-1-yl)-5,6,7,8-tetrahydronaphthalen-2-yl]methyl}-1-methyl-1H-imidazole-4-sulfonamide;
N-{[8-Benzyl-7-(2-oxopyrrolidin-1-yl)-5,6,7,8-tetrahydronaphthalen-2-yl]methyl}-1-methyl-1H-imidazole-4-sulfonamide;
N-{3-[8-(3-Chlorobenzyl)-7-(pyrrolidin-1-yl)-5,6,7,8-tetrahydronaphthalen-2-yl]propyl}propane-1-sulfonamide;
Propane-1-sulfonic acid [3-(8-benzyl-7-pyrrolidin-1-yl-5,6,7,8-tetrahydro-naphthalen-2-yl)-propyl]-amide;
N-{3-[8-Benzyl-7-(pyrrolidin-1-yl)-5,6,7,8-tetrahydronaphthalen-2-yl]propyl}-1-cyclopropylmethanesulfonamide;
N-(2-{[8-(3-Fluorobenzyl)-7-(pyrrolidin-1-yl)-5,6,7,8-tetrahydronaphthalen-2-yl]oxy}ethyl)-1-methyl-1H-pyrrole-3-sulfonamide;
N-(2-{[7-(Azetidin-1-yl)-8-benzyl-5,6,7,8-tetrahydronaphthalen-2-yl]oxy}ethyl)-1-methyl-1H-pyrrole-3-sulfonamide;
1-Methyl-1H-pyrrole-3-sulfonic acid {2-[7-azetidin-1-yl-8-(3-fluoro-benzyl)-5,6,7,8-tetrahydro-naphthalen-2-yloxy]-ethyl}-amide;
N-{1-benzyl-7-[2-(1-methyl-1H-imidazole-4-sulfonylamino)-ethoxy]-1,2,3,4-tetrahydro-naphthalen-2-yl}-propionamide;
N-(2-{[8-(3,5-Difluorobenzyl)-7-(formylamino)-5,6,7,8-tetrahydronaphthalen-2-yl]oxy}ethyl)-1-methyl-1H-pyrrole-3-sulfonamide;
N-{3-[8-(3,4-Dichlorobenzyl)-7-(propan-2-ylamino)-5,6,7,8-tetrahydronaphthalen-2-yl]propyl}propane-1-sulfonamide;
N-{3-[8-Benzyl-7-(propan-2-ylamino)-5,6,7,8-tetrahydronaphthalen-2-yl]propyl}propane-1-sulfonamide;
N-{3-[8-(4-Chlorobenzyl)-7-(diethylamino)-5,6,7,8-tetrahydronaphthalen-2-yl]propyl}-1-cyclopropylmethanesulfonamide;
N-{[8-Benzyl-7-(methylamino)-5,6,7,8-tetrahydronaphthalen-2-yl]methyl}-N-methylpropane-1-sulfonamide;
N-[1-Benzyl-7-{3-[(propylsulfonyl)amino]prop-1-yn-1-yl}-1,2,3,4-tetrahydronaphthalen-2-yl]acetamide;
N-(2-(8-Benzyl-7-(oxetan-3-ylamino)-5,6,7,8-tetrahydronaphthalen-2-yloxy)ethyl)-1-cyclopropylmethanesulfonamide;
Propane-1-sulfonic acid (8-benzyl-7-cyclopropylamino-5,6,7,8-tetrahydro-naphthalen-2-ylmethyl)-amide;
(1-(4-Chloro-benzyl)-7-{2-[methyl-(propane-1-sulfonyl)-amino]-ethoxy}-1,2,3,4-tetrahydro-naphthalen-2-yl)-carbamic acid ethyl ester;
1-Benzyl-7-{2-[cyclopropyl-(propane-1-sulfonyl)-amino]-ethoxy}-1,2,3,4-tetrahydro-naphthalen-2-yl)-carbamic acid ethyl ester;
Propane-1-sulfonic acid {2-[7-amino-8-(3-chloro-benzyl)-5,6,7,8-tetrahydro-naphthalen-2-yloxy]-ethyl}-cyclopropyl-amide;
Propane-1-sulfonic acid [2-(7-amino-8-benzyl-5,6,7,8-tetrahydro-naphthalen-2-yloxy)-ethyl]-cyclopropyl-amide;
1-(3-Chloro-benzyl)-7-[1-(propane-1-sulfonyl)-azetidin-3-yl]-1,2,3,4-tetrahydro-naphthalen-2-ylamine;
1-Benzyl-7-[1-(propane-1-sulfonyl)-azetidin-3-yl]-1,2,3,4-tetrahydro-naphthalen-2-ylamine;
{1-(3-Chloro-benzyl)-7-[1-(propane-1-sulfonyl)-azetidin-3-ylmethoxy]-1,2,3,4-tetrahydronaphthalen-2-yl}-carbamic acid ethyl ester;
1-(3-Chloro-benzyl)-7-[1-(propane-1-sulfonyl)-azetidin-3-ylmethoxy]-1,2,3,4-tetrahydro-naphthalen-2-ylamine;
[1-(3-Chloro-benzyl)-7-(2-cyclopropylmethanesulfonylamino-ethoxy)-1,2,3,4-tetrahydro-naphthalen-2-yl]-carbamic acid ethyl ester;
N-{2-[7-Amino-8-(3-chloro-benzyl)-5,6,7,8-tetrahydronaphthalen-2-yloxy]-ethyl}-C-cyclopropyl-methanesulfonamide;
[1-(3-Chloro-benzyl)-7-(1-cyclopropylmethanesulfonylazetidin-3-ylmethoxy)-1,2,3,4-tetrahydro-naphthalen-2-yl]-carbamic acid ethyl ester;
{1-(3-Chloro-benzyl)-7-[2-(cyclopropylmethanesulfonylmethyl-amino)-ethoxy]-1,2,3,4-tetrahydro-naphthalen-2-yl}-carbamic acid ethyl ester;

N-{2-[7-Amino-8-(3-chloro-benzyl)-5,6,7,8-tetrahydro-naphthalen-2-yloxy]-ethyl}-C-cyclopropyl-N-methyl-methanesulfonamide;

1-Benzyl-7-[1-(propane-1-sulfonyl)-azetidin-3-yl-methoxy]-1,2,3,4-tetrahydro-naphthalen-2-ylamine;

Propane-1-sulfonic acid {2-[7-amino-8-(2-chloro-benzyl)-5,6,7,8-tetrahydro-naphthalen-2-yloxy]-ethyl}-amide;

Cyclopropanesulfonic acid {2-[7-amino-8-(2-chloro-benzyl)-5,6,7,8-tetrahydro-naphthalen-2-yloxy]-ethyl}-amide;

N-{2-[7-Amino-8-(2-chloro-benzyl)-5,6,7,8-tetrahydro-naphthalen-2-yloxy]-ethyl}-C-cyclopropyl-methane-sulfonamide;

N-{3-[7-Amino-8-(3-chloro-benzyl)-5,6,7,8-tetrahydro-naphthalen-2-yl]-propyl}-C-cyclopropyl-methane-sulfonamide;

Propane-1-sulfonic acid {3-[7-amino-8-(3-chloro-benzyl)-5,6,7,8-tetrahydro-naphthalen-2-yl]-propyl}-amide;

{1-(2-Chloro-benzyl)-7-[2-(1-methyl-1H-imidazole-4-sulfonylamino)-ethoxy]-1,2,3,4-tetrahydro-naphthalen-2-yl}-carbamic acid ethyl ester;

{1-(2-Chloro-benzyl)-7-[2-(1-methyl-1H-pyrazole-4-sulfonylamino)-ethoxy]-1,2,3,4-tetrahydro-naphthalen-2-yl}-carbamic acid ethyl ester;

N-{2-[8-(3-Chloro-benzyl)-7-methylamino-5,6,7,8-tetrahydro-naphthalen-2-yloxy]-ethyl}-C-cyclopropyl-methanesulfonamide;

1-Methyl-1H-pyrazole-4-sulfonic acid {2-[7-amino-8-(2-chloro-benzyl)-5,6,7,8-tetrahydro-naphthalen-2-yloxy]-ethyl}-amide;

1-Methyl-1H-pyrazole-4-sulfonic acid {2-[8-(2-chloro-benzyl)-7-methylamino-5,6,7,8-tetrahydro-naphthalen-2-yloxy]-ethyl}-amide;

1-Methyl-1H-imidazole-4-sulfonic acid {2-[8-(2-chloro-benzyl)-7-methylamino-5,6,7,8-tetrahydro-naphthalen-2-yloxy]-ethyl}-amide;

Propane-1-sulfonic acid {2-[7-amino-8-(3-chloro-benzyl)-5,6,7,8-tetrahydro-naphthalen-2-yl]-ethyl}-amide;

1-Methyl-1H-imidazole-4-sulfonic acid {2-[7-amino-8-(2-chloro-benzyl)-5,6,7,8-tetrahydro-naphthalen-2-yloxy]-ethyl}-amide;

N-[1-(3-Chloro-benzyl)-7-(2-cyclopropylmethanesulfonylamino-ethoxy)-1,2,3,4-tetrahydro-naphthalen-2-yl]-acetamide;

N-{2-[8-(3-Chloro-benzyl)-7-ethylamino-5,6,7,8-tetrahydro-naphthalen-2-yloxy]-ethyl}-C-cyclopropyl-methanesulfonamide;

Propane-1-sulfonic acid {3-[8-(3-chloro-benzyl)-7-methylamino-5,6,7,8-tetrahydro-naphthalen-2-yl]-propyl}-amide;

Propane-1-sulfonic acid {2-[8-(3-chloro-benzyl)-7-methylamino-5,6,7,8-tetrahydro-naphthalen-2-yl]-ethyl}-amide;

N-{2-[7-Amino-8-(3-chloro-benzyl)-5,6,7,8-tetrahydro-naphthalen-2-yl]-ethyl}-C-cyclopropyl-methane-sulfonamide;

Propane-1-sulfonic acid {2-[8-(2-fluoro-benzyl)-7-methylamino-5,6,7,8-tetrahydro-naphthalen-2-yloxy]-ethyl}-amide;

C-Cyclopropyl-N-{2-[8-(2-fluoro-benzyl)-7-methylamino-5,6,7,8-tetrahydro-naphthalen-2-yloxy]-ethyl}-methanesulfonamide;

1-Methyl-1H-imidazole-4-sulfonic acid {2-[8-(3-chloro-benzyl)-7-methylamino-5,6,7,8-tetrahydro-naphthalen-2-yl]-ethyl}-amide;

Propane-1-sulfonic acid [2-(8-cyclohexylmethyl-7-methylamino-5,6,7,8-tetrahydro-naphthalen-2-yloxy)-ethyl]-amide;

1-Methyl-1H-imidazole-4-sulfonic acid {2-[8-(2-chloro-benzyl)-7-pyrrolidin-1-yl-5,6,7,8-tetrahydro-naphthalen-2-yloxy]-ethyl}-amide;

1,2-Dimethyl-1H-imidazole-4-sulfonic acid {2-[7-amino-8-(3-chloro-benzyl)-5,6,7,8-tetrahydro-naphthalen-2-yloxy]-ethyl}-amide;

N-{2-[8-(3-Chloro-benzyl)-7-pyrrolidin-1-yl-5,6,7,8-tetrahydro-naphthalen-2-yloxy]-ethyl}-C-cyclopropyl-methanesulfonamide;

1-Methyl-1H-pyrazole-4-sulfonic acid {2-[8-(3-chloro-benzyl)-7-pyrrolidin-1-yl-5,6,7,8-tetrahydro-naphthalen-2-yloxy]-ethyl}-amide;

1-Methyl-1H-imidazole-4-sulfonic acid {2-[8-(3-chloro-benzyl)-7-pyrrolidin-1-yl-5,6,7,8-tetrahydro-naphthalen-2-yloxy]-ethyl}-amide;

N-{2-[7-Azetidin-1-yl-8-(3-chloro-benzyl)-5,6,7,8-tetrahydro-naphthalen-2-yloxy]-ethyl}-C-cyclopropyl-methanesulfonamide;

1-Methyl-1H-imidazole-4-sulfonic acid {2-[7-azetidin-1-yl-8-(3-chloro-benzyl)-5,6,7,8-tetrahydro-naphthalen-2-yloxy]-ethyl}-amide;

1-Methyl-1H-pyrazole-4-sulfonic acid {2-[7-azetidin-1-yl-8-(3-chloro-benzyl)-5,6,7,8-tetrahydro-naphthalen-2-yloxy]-ethyl}-amide;

Propane-1-sulfonic acid {2-[8-(3-chloro-benzyl)-7-pyrrolidin-1-yl-5,6,7,8-tetrahydro-naphthalen-2-yloxy]-ethyl}-amide;

1-Methyl-1H-pyrazole-4-sulfonic acid [2-(7-azetidin-1-yl-8-benzyl-5,6,7,8-tetrahydro-naphthalen-2-yloxy)-ethyl]-amide;

1-Benzyl-7-[2-(propane-1-sulfonyl)-ethyl]-1,2,3,4-tetrahydro-naphthalen-2-ylamine; and 1-(3-Chloro-benzyl)-7-[2-(propane-1-sulfonyl)-ethyl]-1,2,3,4-tetrahydro-naphthalen-2-ylamine, or a physiologically tolerated salt thereof.

6. The method of claim 3, wherein the compound of formula (I) is (−)-N-(2-((7S,8R)-7-(azetidin-1-yl)-8-benzyl-5,6,7,8-tetrahydronaphthalen-2-yloxy)ethyl)-1-methyl-1H-imidazole-4-sulfonamide, or a physiologically tolerated salt thereof.

* * * * *